(12) United States Patent
Cheong et al.

(10) Patent No.: US 10,534,900 B2
(45) Date of Patent: Jan. 14, 2020

(54) ELECTRONIC DEVICE

(71) Applicant: Samsung Electronics Co., Ltd., Suwon-si, Gyeonggi-do (KR)

(72) Inventors: Cheol-Ho Cheong, Seoul (KR); Hyuk Kang, Yongin-si (KR); Dong-Hyun Kim, Yongin-si (KR); Yang-Su Kim, Suwon-si (KR); Hyun-Soo Kim, Hwaseong-si (KR); Bo-Yeon Na, Yongin-si (KR); Byoung-Tack Roh, Suwon-si (KR); Jeong-Min Park, Suwon-si (KR); Ji-Hyun Park, Seongnam-si (KR); Tae-Gun Park, Yongin-si (KR); Kwang-Sub Son, Suwon-si (KR); Dong-Il Son, Hwaseong-si (KR); Sung-Ho Son, Daegu (KR); Sung-Hyuk Shin, Seongnam-si (KR); Hyun-Seok Shin, Seongnam-si (KR); Jin-gil Yang, Suwon-si (KR); Jae-Yung Yeo, Seongnam-si (KR); Jae-Bong Yoo, Seongnam-si (KR); Su-Ha Yoon, Seoul (KR); Seung-Young Jeon, Suwon-si (KR); Kyung-Soo Lim, Yongin-si (KR); Eui-Chang Jung, Seoul (KR); In-Ji Jin, Bucheon-si (KR); Jong-Ho Choi, Suwon-si (KR); Duk-Ki Hong, Seoul (KR); Moo-Hyun Baek, Gumi-si (KR); Sang-Youp Seok, Gumi-si (KR); Byoung-Uk Yoon, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 206 days.

(21) Appl. No.: 15/120,687

(22) PCT Filed: Feb. 11, 2015

(86) PCT No.: PCT/KR2015/001391
§ 371 (c)(1),
(2) Date: Aug. 22, 2016

(87) PCT Pub. No.: WO2015/126095
PCT Pub. Date: Aug. 27, 2015

(65) Prior Publication Data
US 2017/0011210 A1 Jan. 12, 2017

Related U.S. Application Data

(60) Provisional application No. 61/943,004, filed on Feb. 21, 2014.

(51) Int. Cl.
*G06F 21/32* (2013.01)
*H04W 12/06* (2009.01)
(Continued)

(52) U.S. Cl.
CPC ............ *G06F 21/32* (2013.01); *A61B 5/0022* (2013.01); *A61B 5/02055* (2013.01);
(Continued)

(58) Field of Classification Search
CPC .............................. G06F 21/32; H04L 63/0861
USPC ........................................... 726/7; 340/573.1
See application file for complete search history.

(56) References Cited

U.S. PATENT DOCUMENTS

| 8,947,239 B1* | 2/2015 | Park ................... G06K 7/10237 340/573.1 |
| 2003/0179229 A1* | 9/2003 | Van Erlach ........... G06F 1/1626 715/744 |

(Continued)

FOREIGN PATENT DOCUMENTS

| KR | 10-2009-0019365 A | 2/2009 |
| KR | 10-2010-0001681 A | 1/2010 |

(Continued)

*Primary Examiner* — David J Pearson
(74) *Attorney, Agent, or Firm* — Jefferson IP Law, LLP

(57) ABSTRACT

A method for providing a service by an electronic device according to various embodiments may comprise the steps of: obtaining biometric information of a user; determining at least one service associated with the biometric information out of a plurality of services that the electronic device supports; and providing the determined at least one service.

22 Claims, 171 Drawing Sheets

(51) Int. Cl.
*H04W 4/00* (2018.01)
*G06F 1/16* (2006.01)
*G06F 21/34* (2013.01)
*A61B 5/00* (2006.01)
*A61B 5/0205* (2006.01)
*G06F 3/01* (2006.01)
*G16H 10/00* (2018.01)
*G16H 20/30* (2018.01)
*H04W 88/02* (2009.01)
*H04L 29/06* (2006.01)
*A61B 5/021* (2006.01)
*A61B 5/024* (2006.01)
*A61B 5/0402* (2006.01)

(52) U.S. Cl.
CPC .............. *A61B 5/681* (2013.01); *G06F 1/163* (2013.01); *G06F 1/1632* (2013.01); *G06F 1/1652* (2013.01); *G06F 3/017* (2013.01); *G06F 21/34* (2013.01); *G16H 10/00* (2018.01); *G16H 20/30* (2018.01); *H04W 4/00* (2013.01); *H04W 12/06* (2013.01); *A61B 5/021* (2013.01); *A61B 5/02416* (2013.01); *A61B 5/0402* (2013.01); *G06F 2221/2153* (2013.01); *H04L 63/0861* (2013.01); *H04W 88/02* (2013.01)

(56) References Cited

U.S. PATENT DOCUMENTS

| | | | | |
|---|---|---|---|---|
| 2004/0133787 | A1* | 7/2004 | Doughty | G06Q 20/327 713/186 |
| 2006/0184800 | A1* | 8/2006 | Rosenberg | G06F 21/32 713/186 |
| 2008/0113787 | A1* | 5/2008 | Alderucci | G06F 21/31 463/29 |
| 2008/0216171 | A1* | 9/2008 | Sano | H04L 9/32 726/19 |
| 2009/0193519 | A1 | 7/2009 | Tamkhane et al. | |
| 2009/0260078 | A1* | 10/2009 | Nakazawa | G06F 21/31 726/19 |
| 2011/0169603 | A1* | 7/2011 | Fithian | G06Q 10/00 340/5.52 |
| 2011/0275940 | A1 | 11/2011 | Nims et al. | |
| 2012/0105200 | A1 | 5/2012 | Yoo et al. | |
| 2012/0317024 | A1* | 12/2012 | Rahman | G01K 13/002 705/42 |
| 2013/0278414 | A1* | 10/2013 | Sprigg | G08B 21/0453 340/539.12 |
| 2014/0107493 | A1* | 4/2014 | Yuen | A61B 5/0205 600/473 |
| 2015/0338236 | A1 | 11/2015 | Hoffman et al. | |
| 2016/0234204 | A1* | 8/2016 | Rishi | G06F 21/31 |

FOREIGN PATENT DOCUMENTS

| | | |
|---|---|---|
| KR | 10-2010-0019084 A | 2/2010 |
| KR | 10-2010-0114110 A | 10/2010 |
| KR | 10-2012-0045921 A | 5/2012 |
| KR | 10-2012-0098854 A | 9/2012 |
| KR | 10-2013-0095326 A | 8/2013 |
| KR | 10-2013-0111570 A | 10/2013 |

* cited by examiner

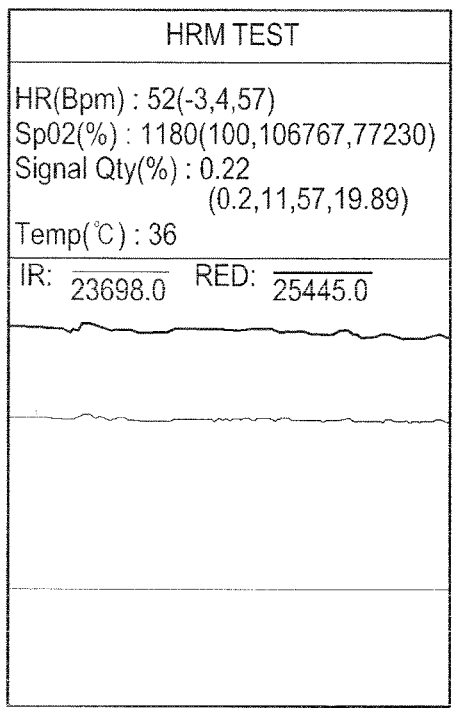
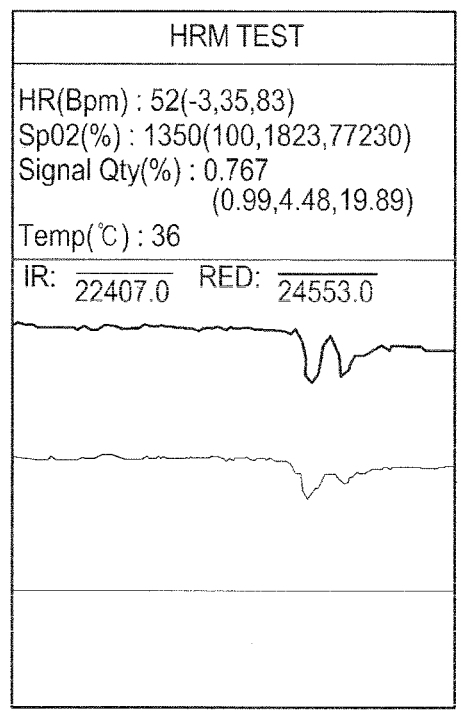
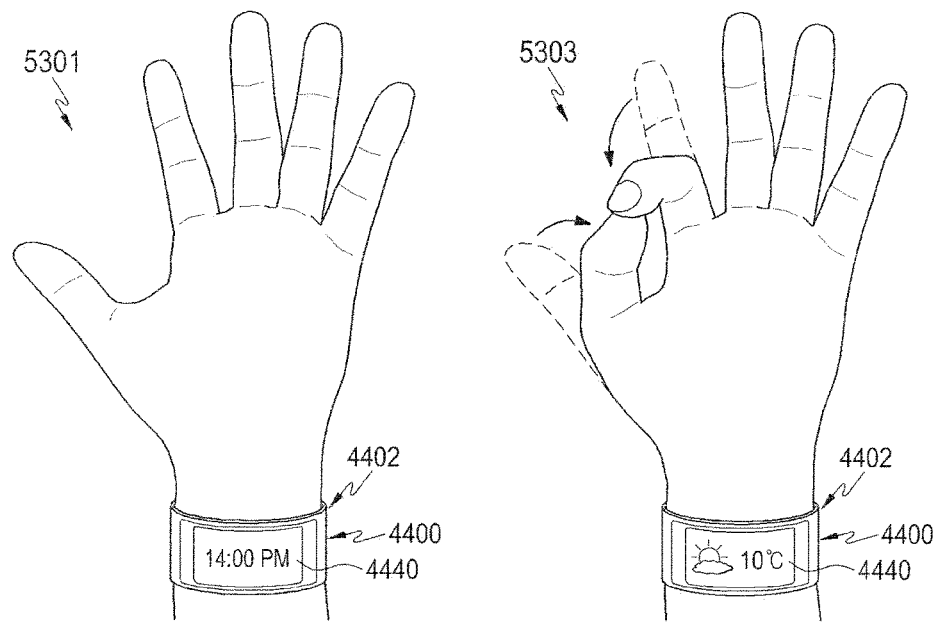
FIG.103

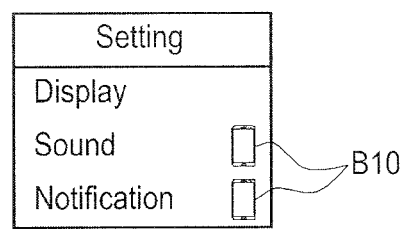
FIG.159A
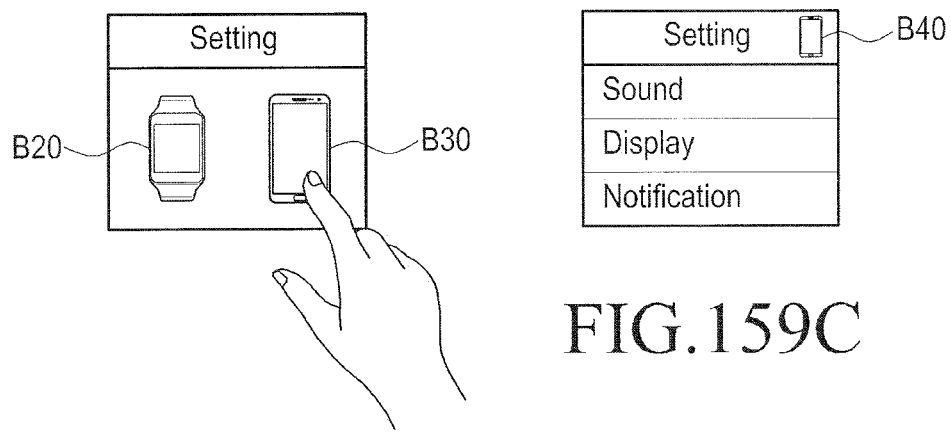
FIG.159B
FIG.159C

| SENSOR | EXTERNAL DEVICE | ELECTRONIC DEVICE |
|---|---|---|
| GPS | ON | OFF |
| ACC | OFF | OFF |
| GYRO | OFF | OFF |
| ⋮ | ⋮ | ⋮ |
| | | |

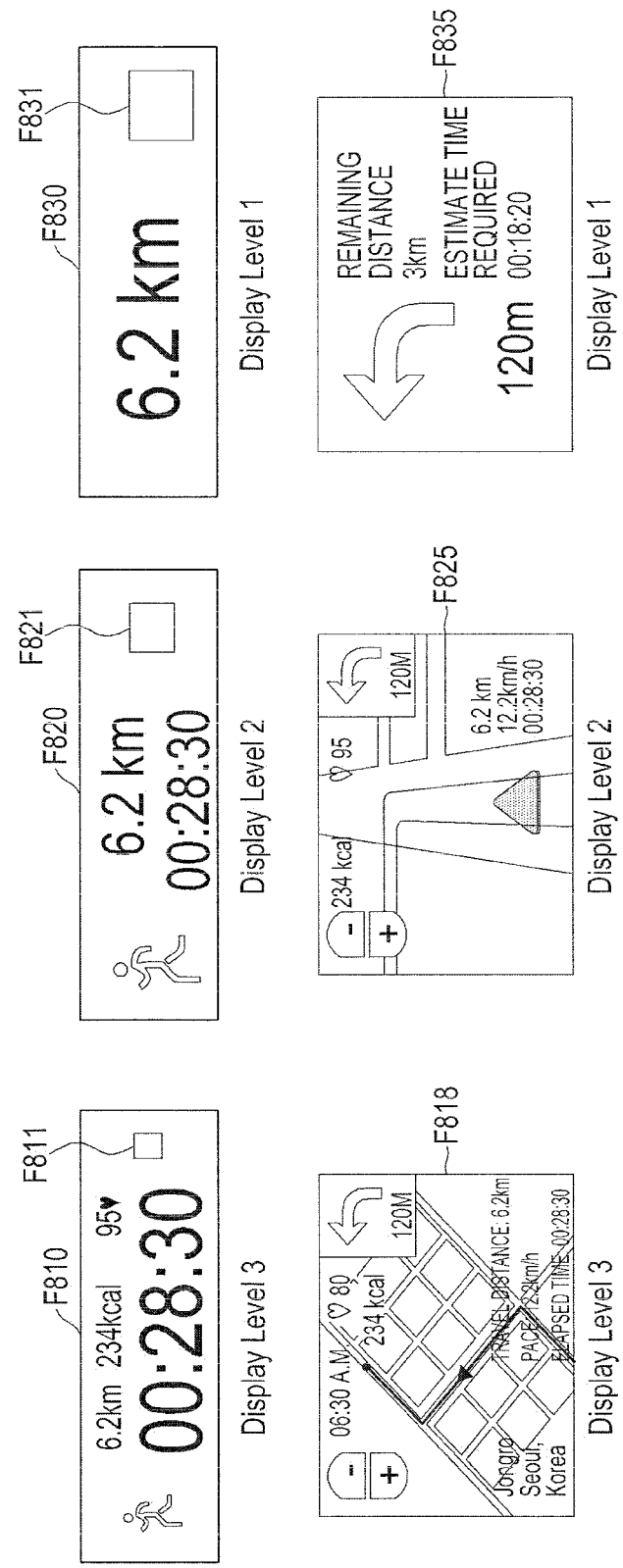

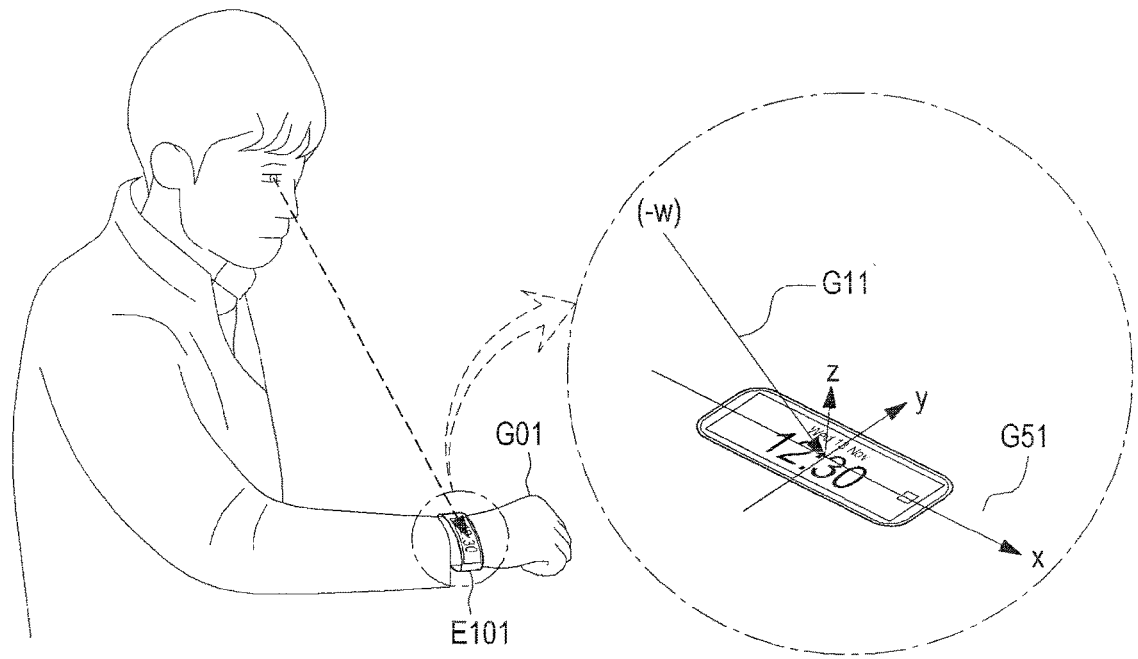
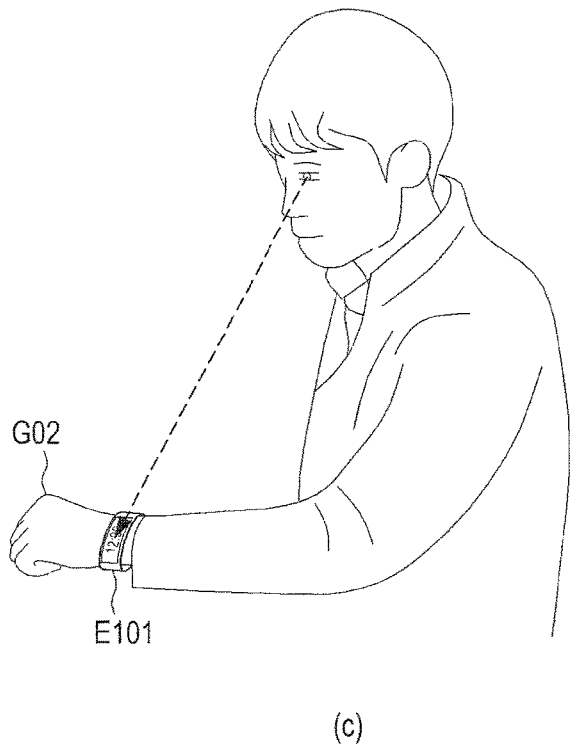
FIG.203A

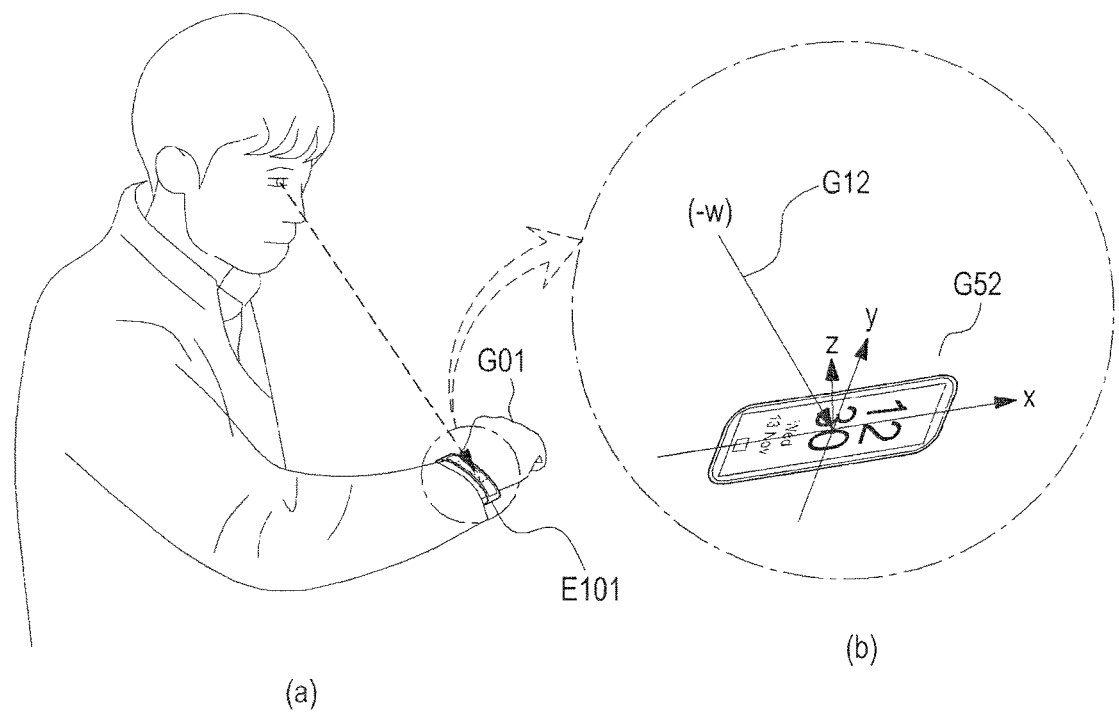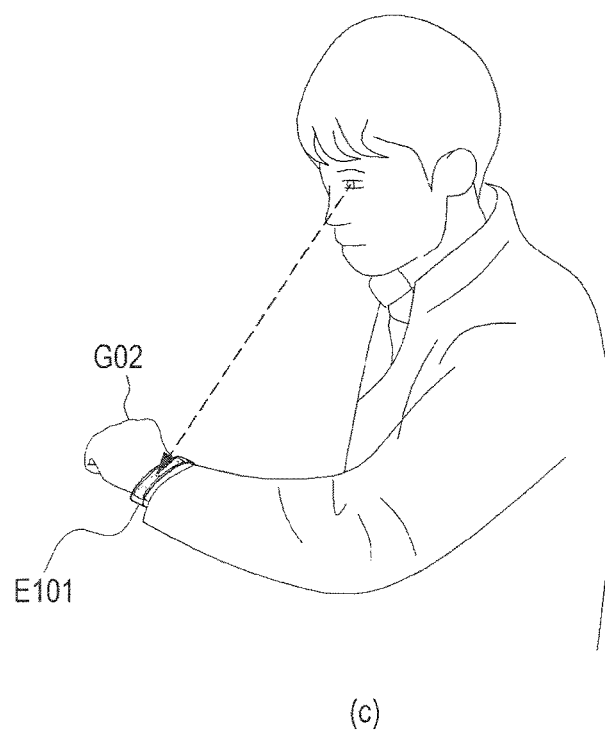
FIG.203B

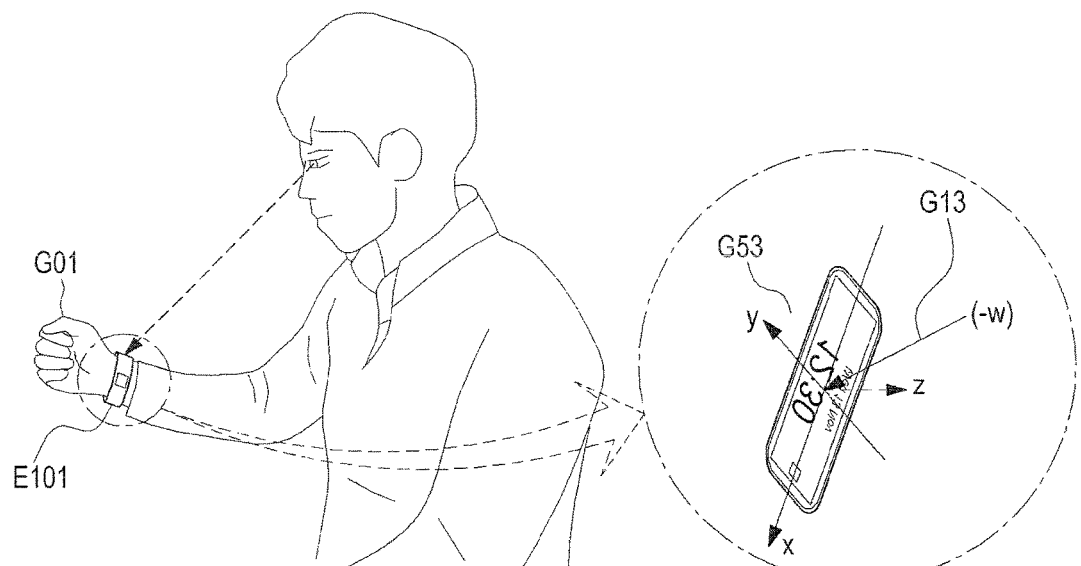
(a) (b)
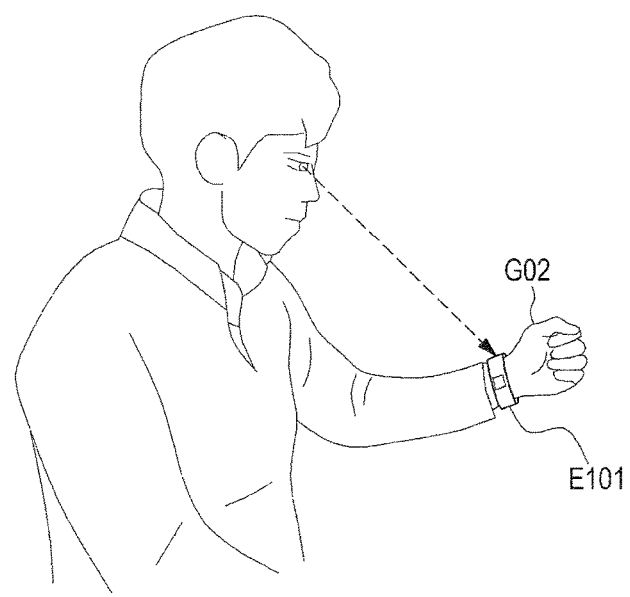
(c)
FIG.203C

ELECTRONIC DEVICE

PRIORITY

This application is a National Phase Entry of PCT International Application No. PCT/KR2015/001391, which was filed on Feb. 11, 2015, and claims a priority to U.S. Patent Application No. 61/943,004, which was filed on Feb. 21, 2014, the contents of which are incorporated herein by reference.

TECHNICAL FIELD

Various embodiments relate to electronic devices.

BACKGROUND ART

Electronic devices may carry out various functions in an integrated manner. For example, smartphones or other portable terminals are advancing to allow users more convenience with better performance.

Functions using sensors are among various functions offered by electronic devices. Such sensors may gather information related to an electronic device, an outside of the electronic device, and the user.

An electronic device may include one or more sensors and may provide various services using information gathered through the sensors.

DISCLOSURE

Technical Problem

Various embodiments may provide various services using bio information gathered through various sensors.

Various embodiments may provide an electronic device with comfortable wearability on the human body and an outer appearance for smoothly implementing functionality.

Various embodiments may provide an electronic device allowing electronic parts efficiently arranged in an inner space thereof while providing comfortable human body wearability.

Various embodiments may provide an electronic device allowing for easy exchanging of wearing portions depending on the user's preference or his body features (e.g., the curvature of his wrist).

Various embodiments may provide an electronic device providing comfortable wearability fitting the user's body features and allowing the bio signal sensor mounted in the body part to come in tight contact with the user's body.

Technical Solution

According to an embodiment, an electronic device may include a wearing portion extending in a direction and having an opening and a main body detachably provided to the opening. The wearing portion may be fastened to the user's body to allow the main body to be worn on the user's body.

According to an embodiment, a method for providing a service by an electronic device may include the operation of obtaining a user's bio information, the operation of determining at least one service related to the bio information of a plurality of services supported by the electronic device, and the operation of providing the determined at least one service.

According to an embodiment, an electronic device may include at least one sensor and a processor configured to obtain a user's bio information using the at least one sensor or a communication module of the electronic device, determine at least one service associated with the bio information among a plurality of services supported by the electronic device, and provide the determined at least one service.

According to an embodiment, a method for providing a service by the electronic device may include the operation of detecting an event, the operation of determining the bio information corresponding to the event, the operation of determining at least one service corresponding to the determined bio information among a plurality of services associated with the event supported by the electronic device, and the operation of providing the determined at least one service.

According to an embodiment, an electronic device may include a memory and a processor configured to detect an event, determine the bio information corresponding to the event, determine at least one service corresponding to the determined bio information among a plurality of services associated with the event supported by the electronic device, and provide the determined at least one service.

According to an embodiment, a method for providing a route direction by an electronic device may include the operation of obtaining information on a plurality of points, the operation of determining at least one reference point based on the obtained information, and the operation of providing a route direction including the information on the reference point.

According to an embodiment, an electronic device may include an input/output interface for obtaining at least one destination information, a memory for storing the information on a plurality of reference points, and a processing module determining some of the plurality of reference points as reference points to be provided as route direction based on at least destination information, and the processing module may be configured to provide the route direction including the information on the determined reference point.

According to an embodiment, a method for connecting communication by a first electronic device may include the operation of obtaining first bio information, the operation of obtaining pairing information for communication connection with the second electronic device based on the first bio information, and the operation of establishing the communication connection with the second electronic device using the pairing information.

According to an embodiment, the first electronic device may include at least one sensor, a communication module, and a processor configured to obtaining first bio information using the communication module of the electronic device or the at least one sensor, obtain pairing information for communication connection with the second electronic device through the communication module based on the first bio information, and establish the communication connection with the second electronic device through the communication module using the pairing information.

According to an embodiment, a method for connecting communication by a server device may include the operation of receiving first bio information from a first electronic device, the operation of determining a second electronic device to be connected via communication with the first electronic device based on the first bio information, and the operation of transmitting pairing information for communication connection of the first electronic device and the second electronic device to at least one of the first electronic device and the second electronic device.

According to an embodiment, a server device may include a communication module and a processor configured to receive first bio information from a first electronic device through the communication module, determine a second electronic device to be connected via communication with the first electronic device based on the first bio information, and transmit pairing information for communication connection of the first electronic device and the second electronic device to at least one of the first electronic device and the second electronic device through the communication module.

According to an embodiment, a method for syncing bio information by an electronic device may include the operation of obtaining a plurality of bio information on a user, the operation of determining update periods or targets for each of the plurality of obtained bio information, and the operation of transmitting the plurality of obtained bio information to at least one external device at different times according to the determined update periods or targets.

According to an embodiment, an electronic device may include a memory and a processor configured to obtain a plurality of bio information on a user, store the plurality of obtained bio information in the memory, determine update periods or targets for each of the plurality of stored bio information, and transmit the plurality of obtained bio information to at least one external device at different times through the communication module of the electronic device according to the determined update periods or targets.

According to an embodiment, a method for displaying an item by an electronic device may include the operation of displaying the item on at least a portion of a display of the electronic device, the operation of detecting a movement of the electronic device, and the operation of moving or transforming the item based on the size or direction of the movement of the electronic device.

According to an embodiment, an electronic device may include a display and a processor configured to display an item on at least a portion of the display, detect a movement through a sensor of the electronic device, and move or transform and display the item on the display based on the size or direction of the movement of the electronic device.

According to an embodiment, a method for alarming by an electronic device may include the operation of receiving an alarm condition, the operation of determining a preliminary condition corresponding to the alarm condition, the operation of determining whether the preliminary condition is met, and the operation of outputting a first alarm signal before the alarm condition is met according to whether the preliminary condition is met.

According to an embodiment, an electronic device may include a memory and a processor configured to receive an alarm condition, store the received alarm condition in the memory, determine a preliminary condition corresponding to the alarm condition, store the determined printed layer in the memory, determine whether the printed layer is met, and output a first alarm signal before the alarm condition is met according to whether the preliminary condition is met.

According to an embodiment, an image capturing method by an electronic device may include the operation of displaying an image, the operation of transmitting image capturing-related information to an external device, the operation of receiving the image capturing-related control information from the external device, and the operation of processing the control information.

According to an embodiment, an electronic device may include a communication module, a display displaying an image, and a processor configured to transmit the image capturing-related information to an external device through the communication module, receive image capturing-related control information from the external device through the communication module, and process the control information.

According to an embodiment, a method for operating haptic information according to an embodiment may set the operation of performing at least one of screen information analysis, input information analysis, or execution information analysis, the operation of assigning at least one haptic information according to the result of the analysis, and the operation of outputting the haptic feedback corresponding to the haptic information corresponding to the occurrence of the event.

According to an embodiment, an electronic device may include a haptic support module performing at least one of screen information analysis, input information analysis, or execution information analysis and assigning at least one haptic information according to the result of the analysis, and a haptic module outputting the haptic feedback corresponding to the haptic information corresponding to the occurrence of the event.

According to an embodiment, a wearable electronic device may include an input module receiving a user's manipulation varying a setting value of a main electronic device and a communication module transmitting a control signal varying the setting value to the main electronic device.

According to an embodiment, a control method by a wearable electronic device may include the operation of receiving a user's manipulation varying a setting value of a main electronic device and the operation of transmitting a control signal varying the setting value to the main electronic device.

According to an embodiment, a system may include a wearable electronic device that, upon receiving a user's manipulation varying a setting value of a main electronic device, transmits the varied setting value to the electronic device, and the main electronic device varying the setting value according to the setting value received from the wearable electronic device.

According to an embodiment, an electronic device may include a receiving module for receiving a user's bio signal on the electronic device, an identifying module for identifying the attachment or detachment state of the electronic device on the user at least based on the bio signal, and an input/output control module for independently controlling each of a plurality of input/output devices functionally connected with the electronic device at least based on the attachment/detachment state.

According to an embodiment, a method may include the operation of receiving a user's bio signal by the electronic device, the operation of identifying the attachment or detachment state of the electronic device on the user at least based on the bio signal, and the operation of independently controlling each of a plurality of input/output devices functionally connected with the electronic device at least based on the attachment/detachment state.

According to an embodiment, an electronic device may include a sensor module gathering a signal, a module generating bio information at least based on a portion of the gathered signal, a module generating proximity information at least based on a portion of the gathered signal, a module generating illuminance information at least based on a portion of the gathered signal, and a module determining a state of the electronic device at least based on the bio information, the proximity information, or the illuminance information.

According to an embodiment, a method for operating an electronic device may include the operation of gathering a sensor module-based signal and the operation of determining a state of the electronic device using at least one of bio information at least based on a portion of the gathered signal, proximity information at least based on a portion of the gathered signal, and illuminance information at least based on a portion of the gathered signal.

According to an embodiment, an electronic device may include a control module performing control to activate the sensor corresponding to the request information, upon receiving the request information requesting to activate the sensor in relation to running the function of the external device and the communication interface forming the communication channel with the external device.

According to an embodiment, a method for operating an electronic device may include the operation of forming a communication channel with the external device, the operation of receiving request information requesting to activate the sensor in relation with running the function of the external device, and the operation of controlling to activate the sensor corresponding to the request information.

According to an embodiment, a method for controlling an electronic device according to request information may include the operation of receiving request information to be activated from the external device connected via communication, the operation of activating the sensor based on the received request information, the operation of transmitting data generated based on the activated sensor to the external device, and the operation of deactivating the activated sensor in case the communication connection with the external device is released or the battery runs out.

According to an embodiment, a method for operating an electronic device may include the operation of determining movement information of the electronic device based on sensing data measured by a sensor module, the operation of determining bio information on a user by analyzing one or more bio signals, and the operation of controlling an operation of the electronic device according to the movement information and the bio information.

According to an embodiment, an operation method by an electronic device may include the operation of determining whether a communication module communicating with an external device is connected with the external device and the operation of controlling an operation of the electronic device according to the state of the connection with the electronic device.

According to an embodiment, an operation method by an electronic device may include the operation of pairing with one or more external devices, the operation of determining movement information of the electronic device using a motion sensor, the operation of determining bio information on a user by analyzing one or more bio signals, the operation of determining a service providable to the user from the electronic device based on the bio information or the movement information and the operation of providing the service to the user using the external devices.

According to an embodiment, a method for displaying content by an electronic device may include the operation of obtaining sensing data, the operation of determining a user's current state based on the sensing data, the operation of determining a content to be displayed on a display based on the current state, and the operation of displaying the content on the display.

According to an embodiment, a method for displaying content by an electronic device may include the operation of obtaining sensing data for determining a direction of a screen, the operation of determining the direction of the screen based on the sensing data, the operation of determining the direction of display of the content according to the direction of the screen, and the operation of displaying the content on the screen.

According to an embodiment, an electronic device may include a display including a screen displaying a content and a control module controlling the display to obtain sensing data, determine a user's current state based on the sensing data, determine a content to be displayed on the screen based on the current state, and display the content on the screen.

Effects of the Invention

According to various embodiments, the electronic device may allow for easier exchange of wearing portions depending on the user's preference or the curvature of his wrist to provide comfortable wearability while allowing the user to pursue his individuality. Further, in case a bio signal sensor is disposed in the main body, the bio signal sensor may be brought in tight contact with the user's body, allowing it to be utilized as an assistant medical device. Further, the main body and the wearing portion may be securely coupled, while the wearing portion may be easily exchanged, and the main body may be prevented from escaping from the wearing portion while being worn, enabling a stable wearing state.

Various embodiments may provide various services using bio information gathered through various sensors.

BRIEF DESCRIPTION OF THE DRAWINGS

FIG. 103 illustrates a graph related to function running control of an electronic device according to an embodiment;

FIG. 123 is a flowchart illustrating an operation of a first electronic device according to an embodiment;

FIG. 124 illustrates an interworking environment between a plurality of electronic devices according to an embodiment;

FIG. 125 illustrates an environment showing a control method of a wearable electronic device according to an embodiment;

FIG. 126 is a block diagram illustrating a haptic supporting module of an electronic device according to an embodiment;

FIG. 127 illustrates a haptic information operation method according to an embodiment;

FIG. 128 illustrates an operation method of object-based haptic information among screen information according to an embodiment;

FIG. 129 illustrates a haptic information operation method based on the type of an input object according to an embodiment;

FIG. 130 illustrates an execution information condition-based haptic information operation method according to an embodiment;

FIG. 131 is a view illustrating an example of a screen for describing a per-object haptic information operation according to an embodiment;

FIG. 132 is a view illustrating an example of a screen for describing a per-composite object haptic information operation according to an embodiment;

FIG. 133 illustrates a screen interface related to a one-hand input-related haptic information operation according to an embodiment;

FIG. 134 illustrates a screen interface related to a direction-related haptic information operation according to an embodiment;

Figure 135:
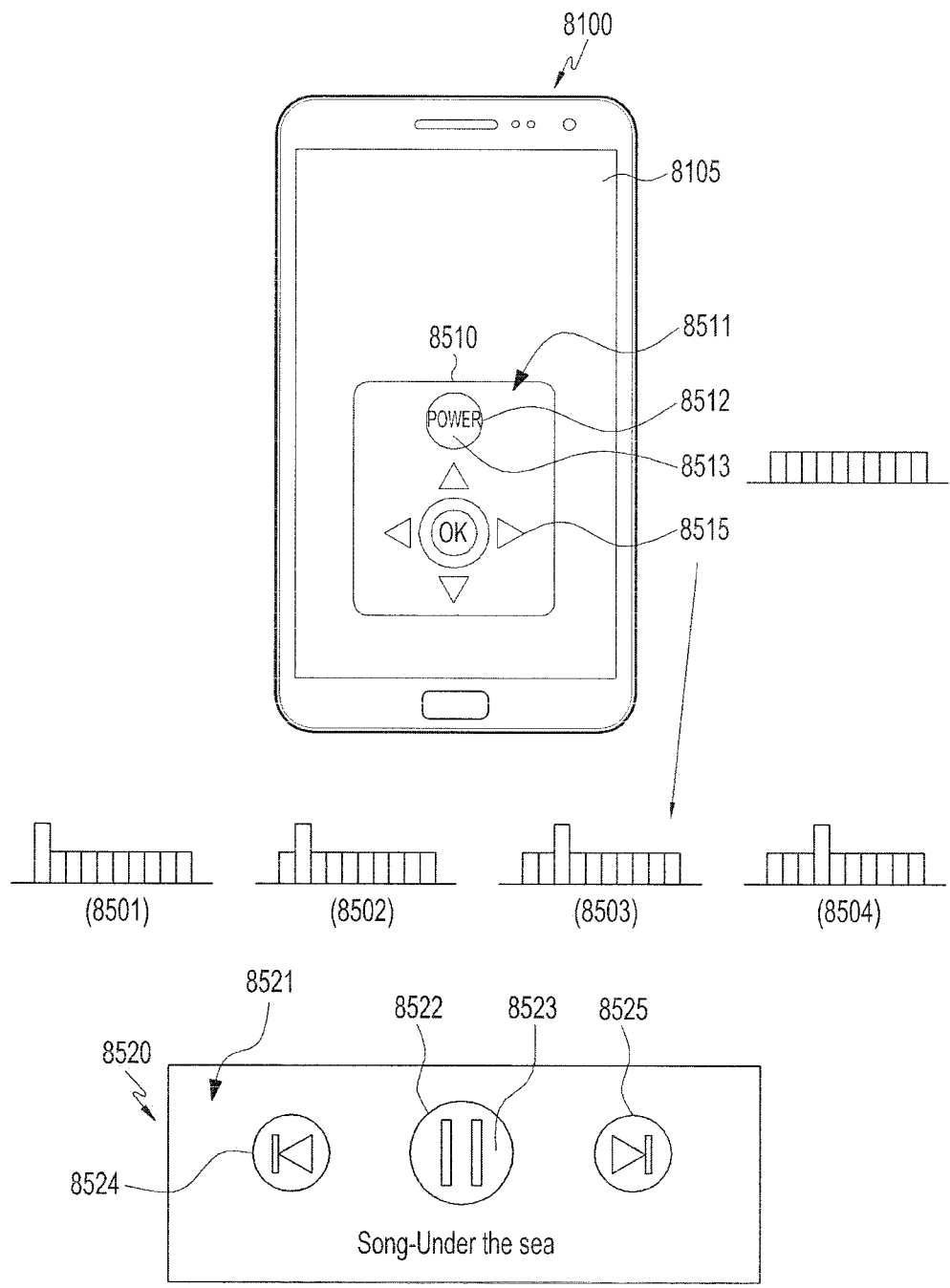
Figure 136:
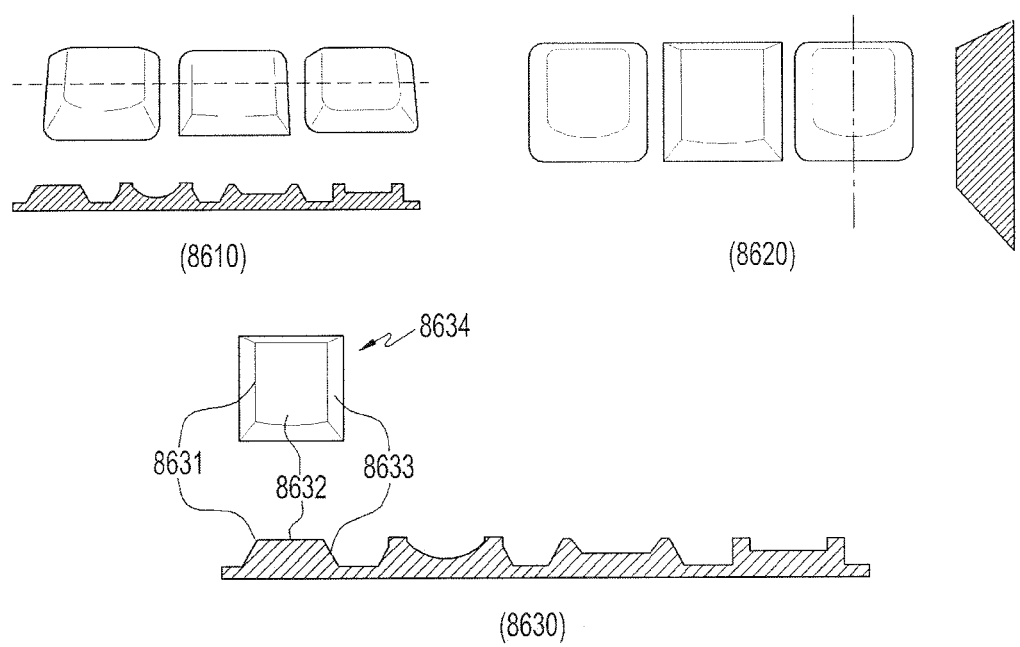
Figure 137:
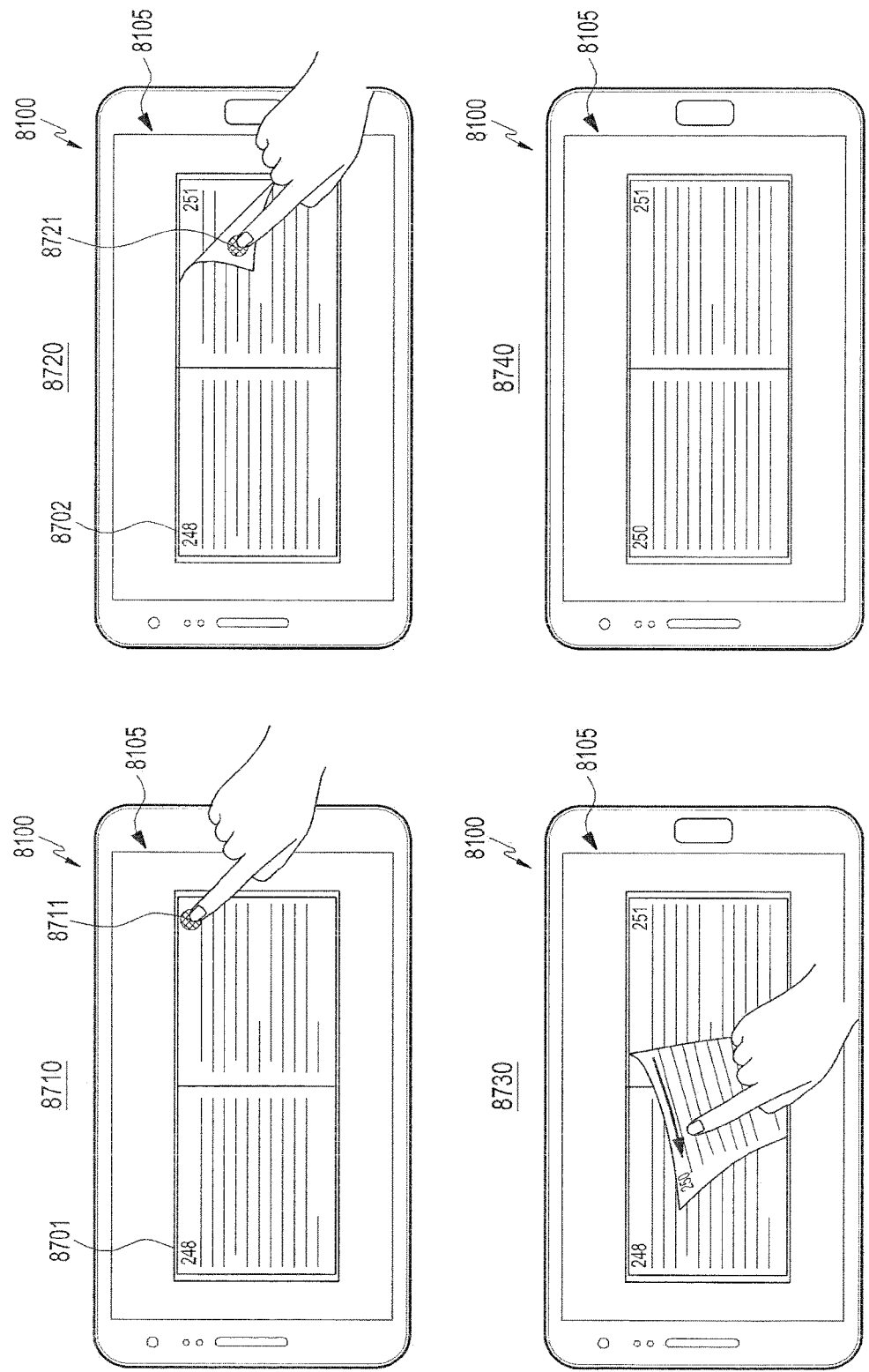
Figure 138:
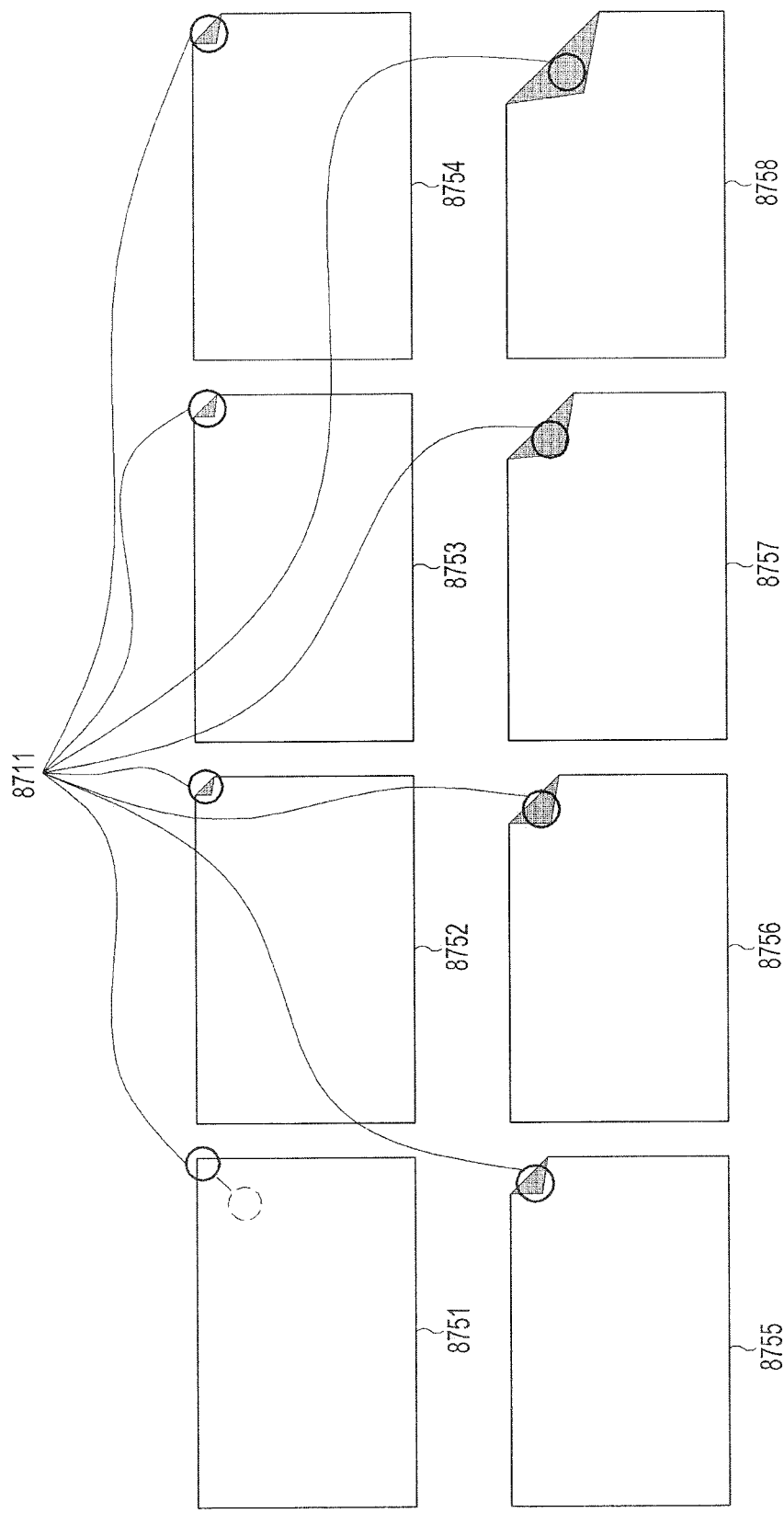
Figure 139:
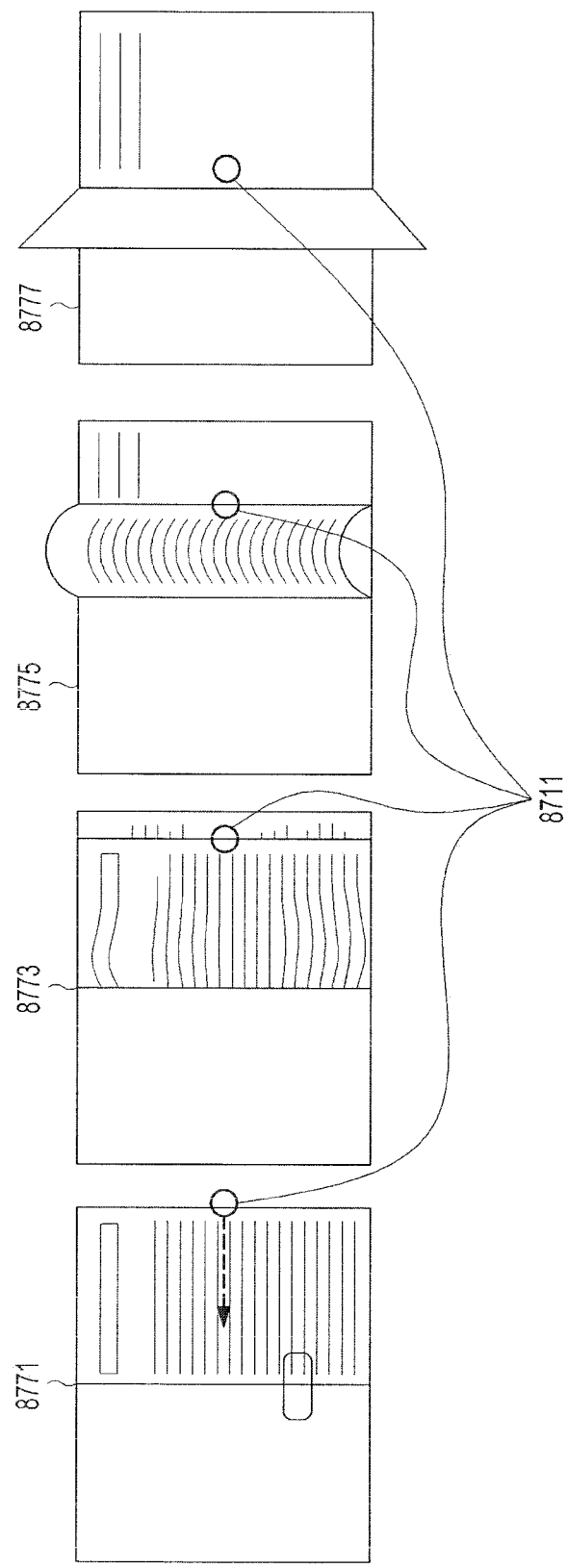
Figure 140:
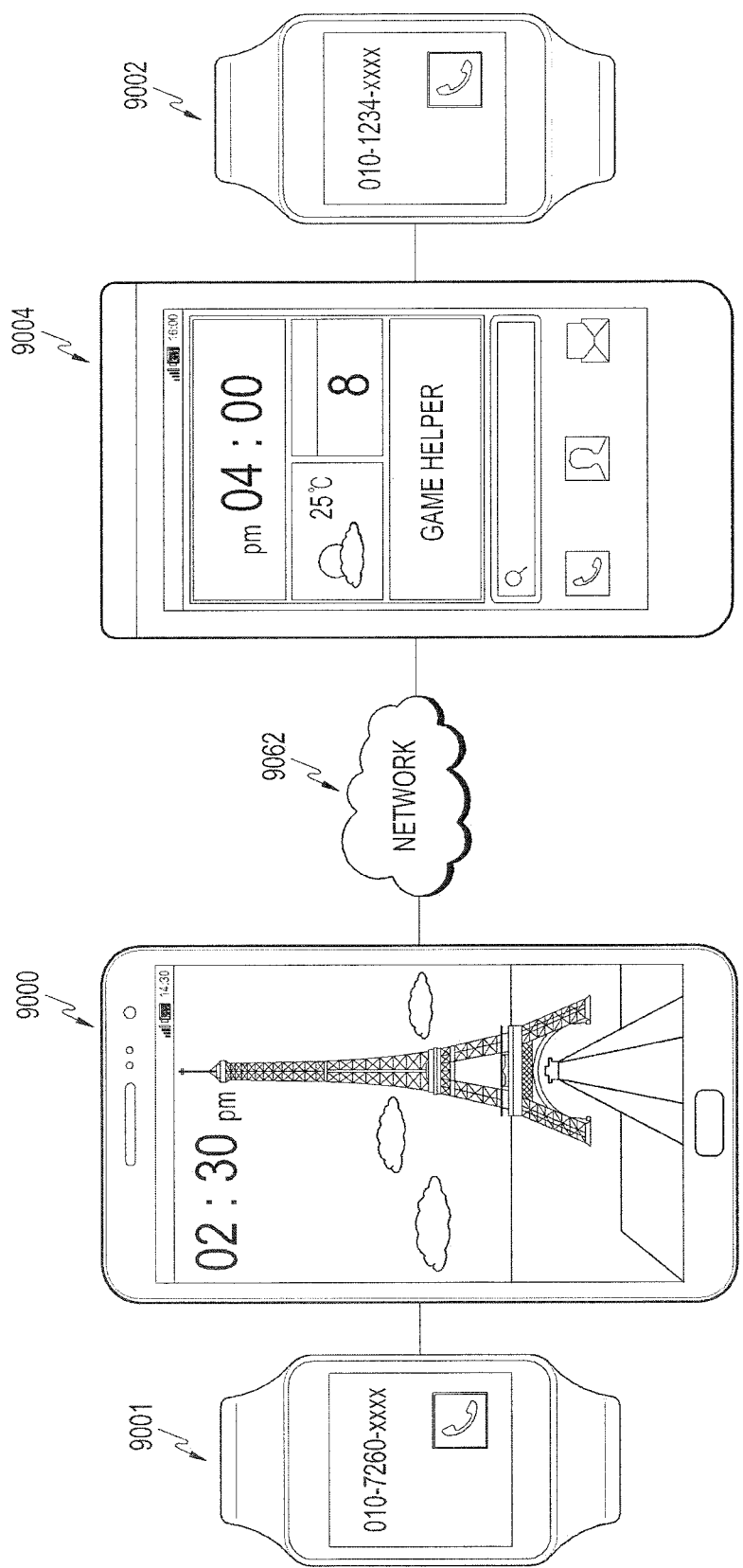
Figure 141:
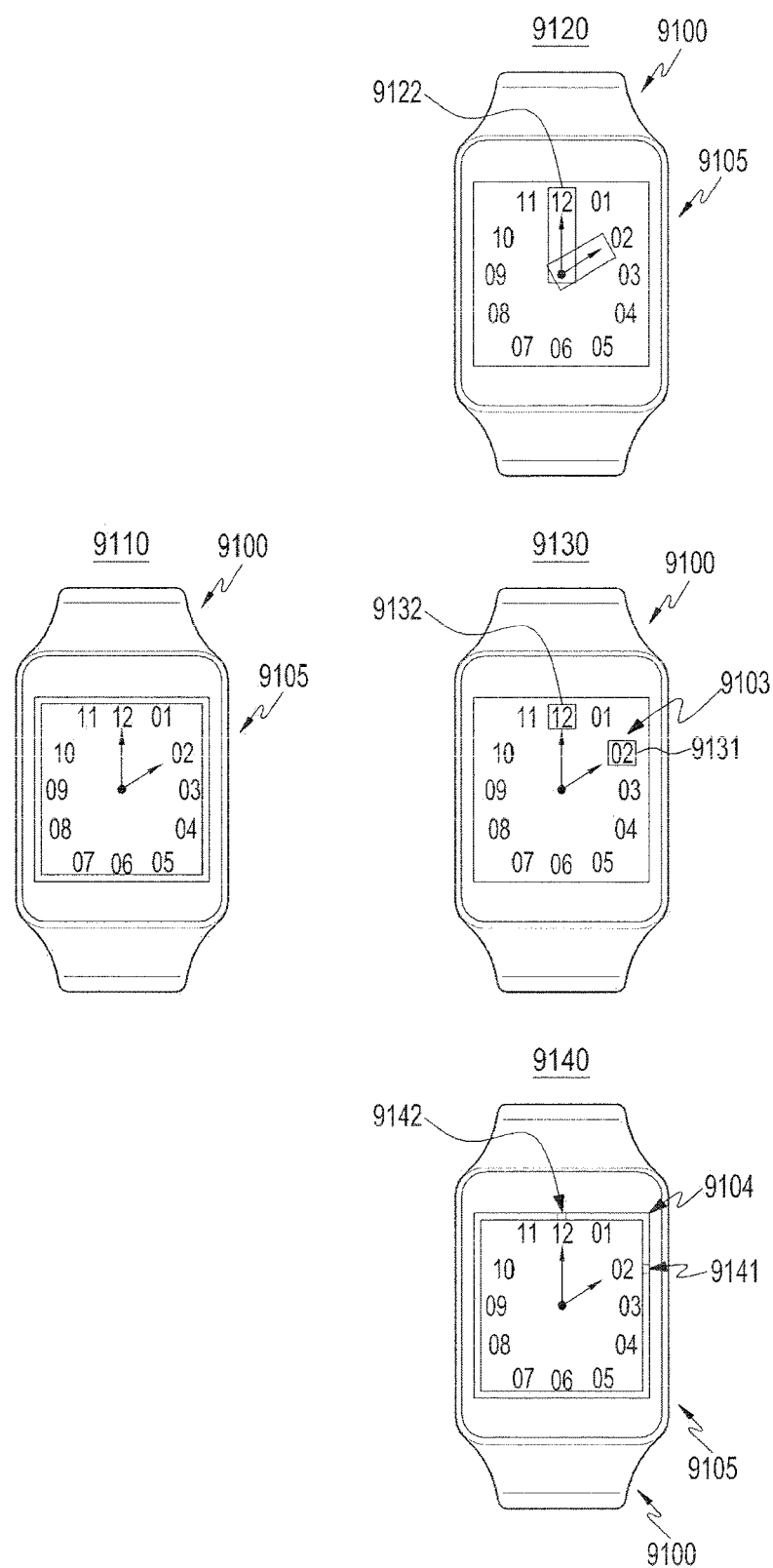
Figure 142:
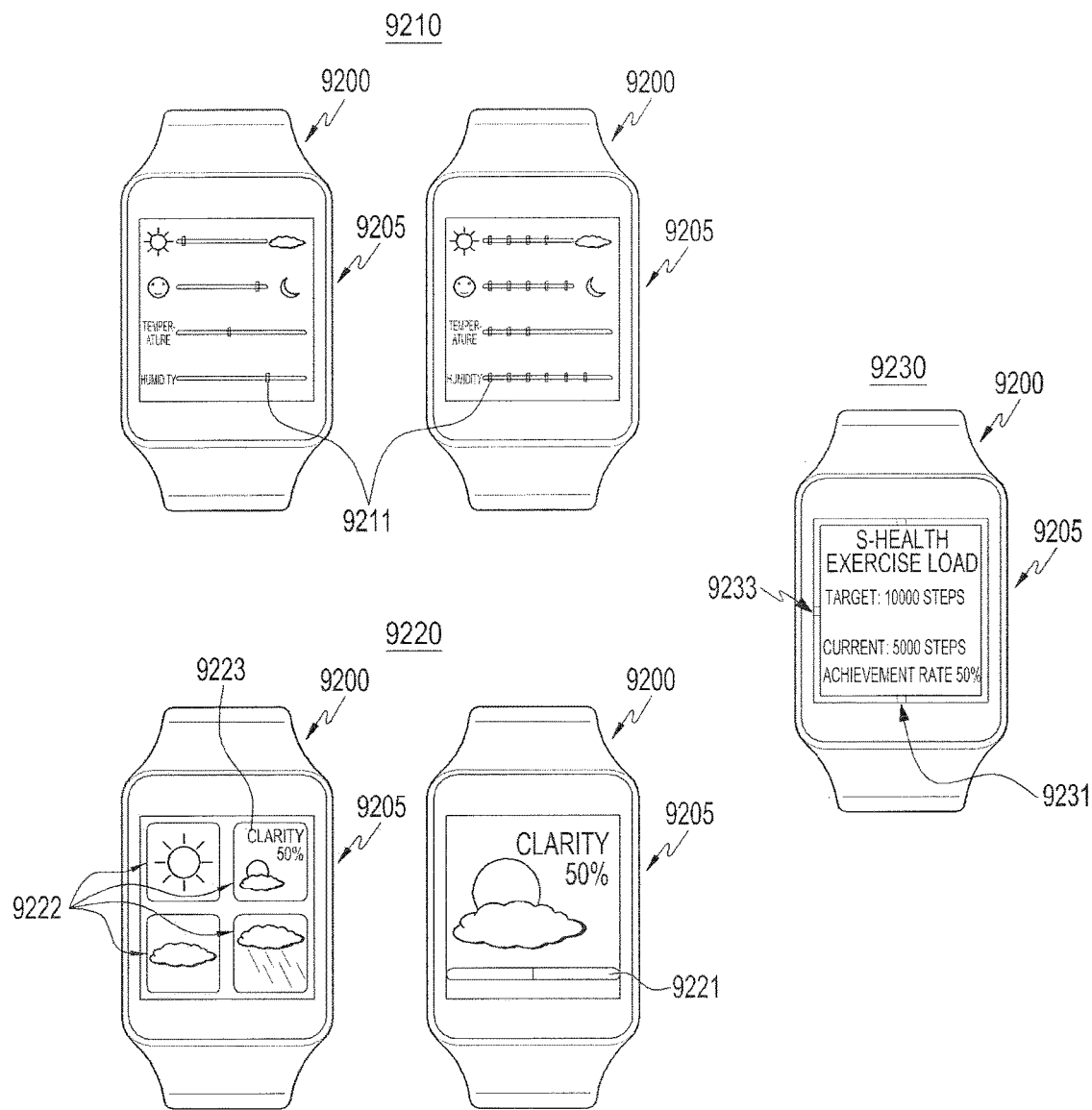
Figure 143:
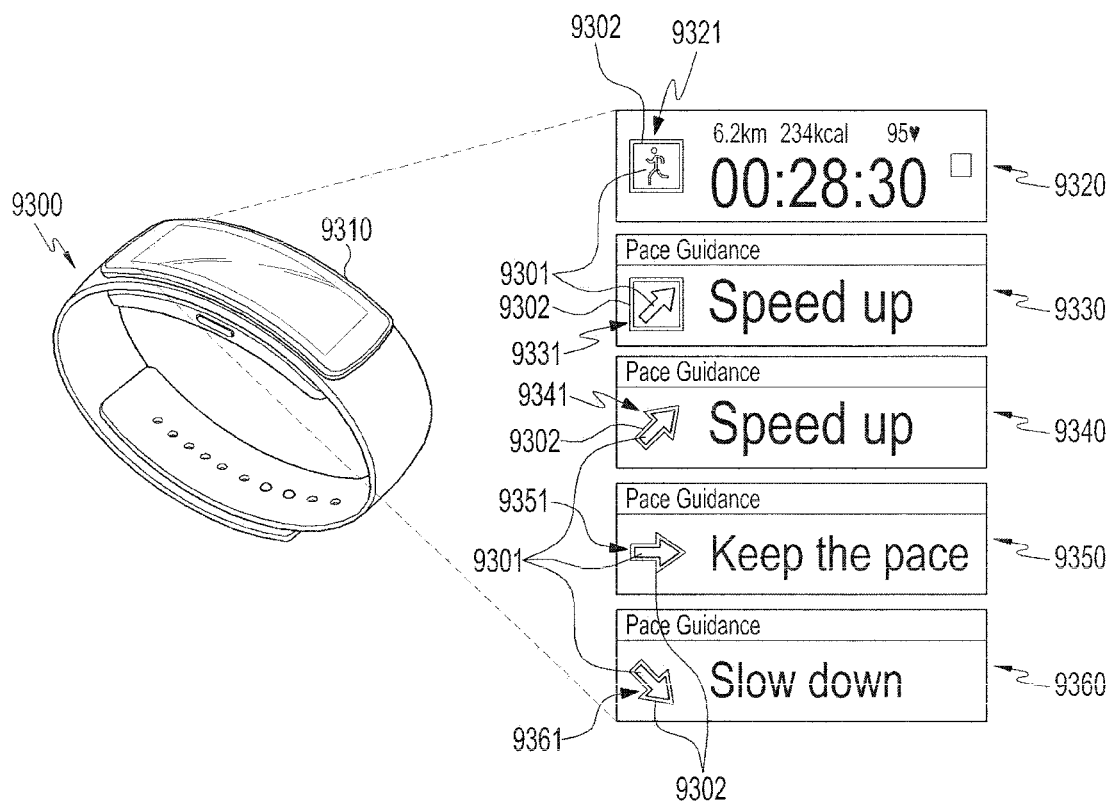
Figure 144:
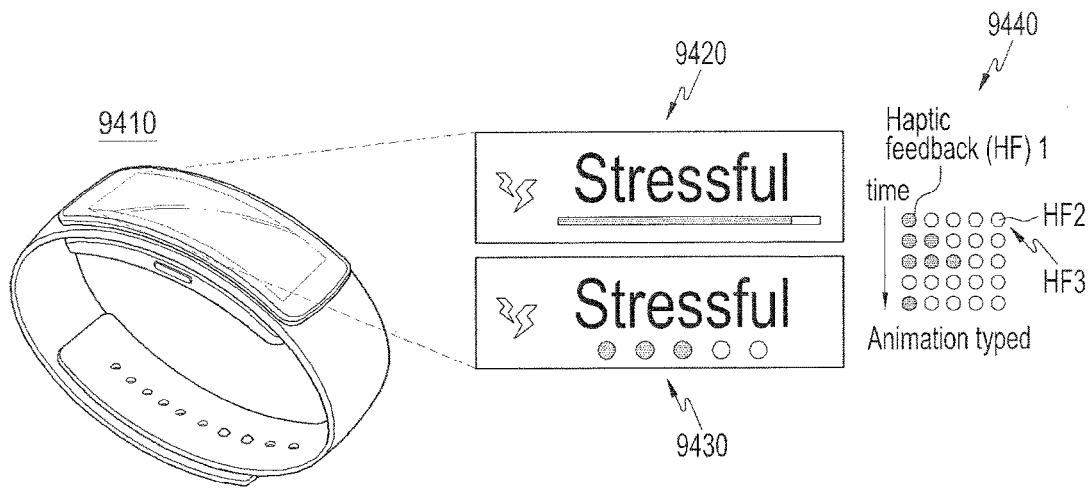
Figure 145:
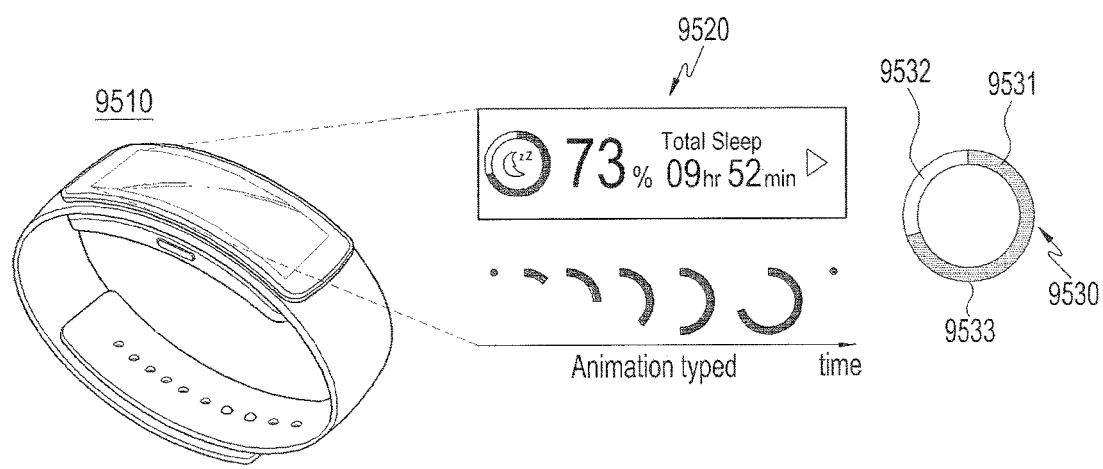
Figure 146:
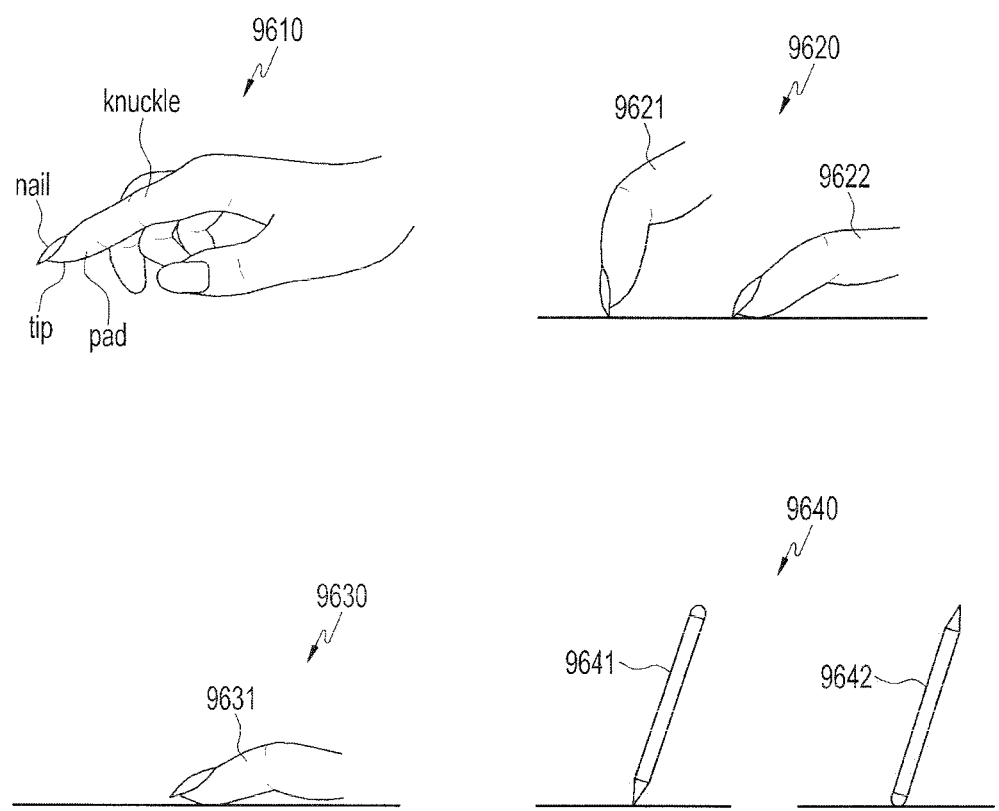
Figure 147:
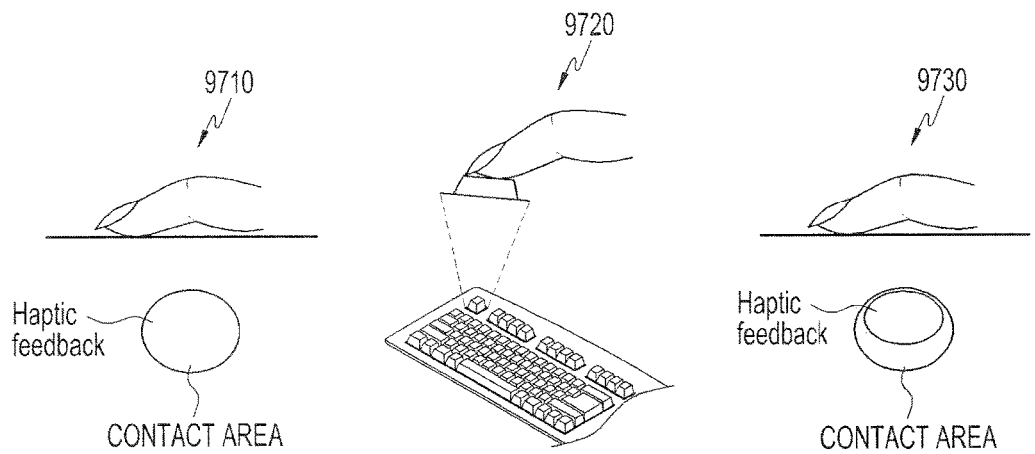
Figure 148:
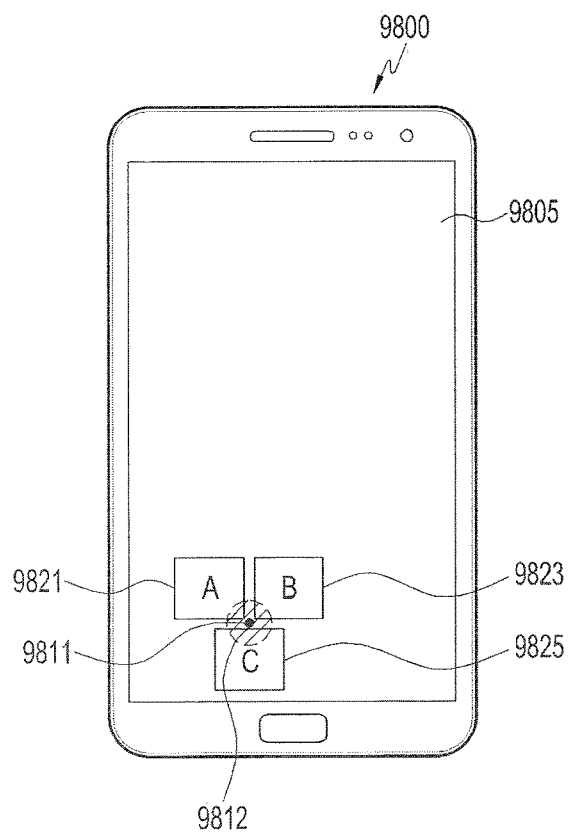
Figure 149:
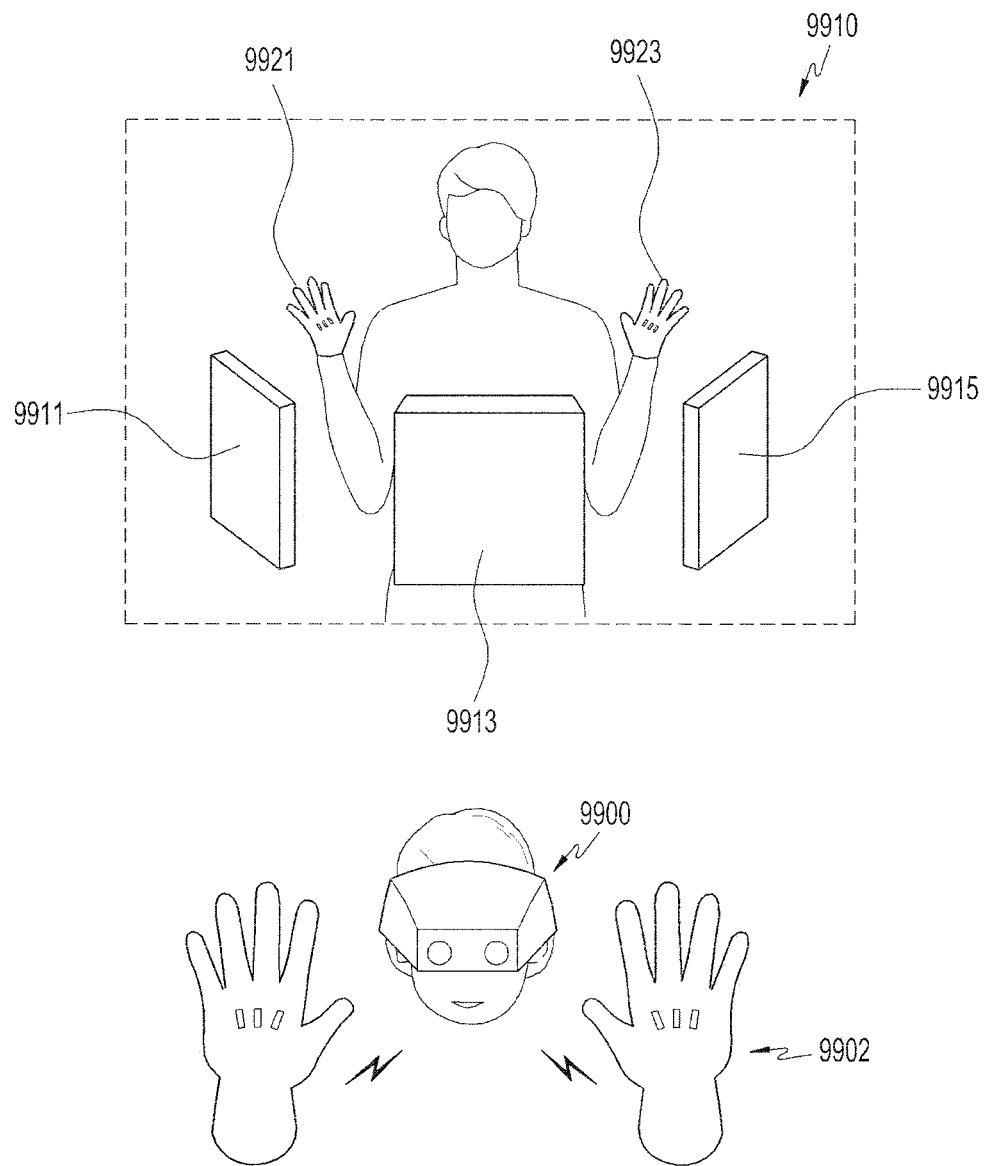
Figure 150:
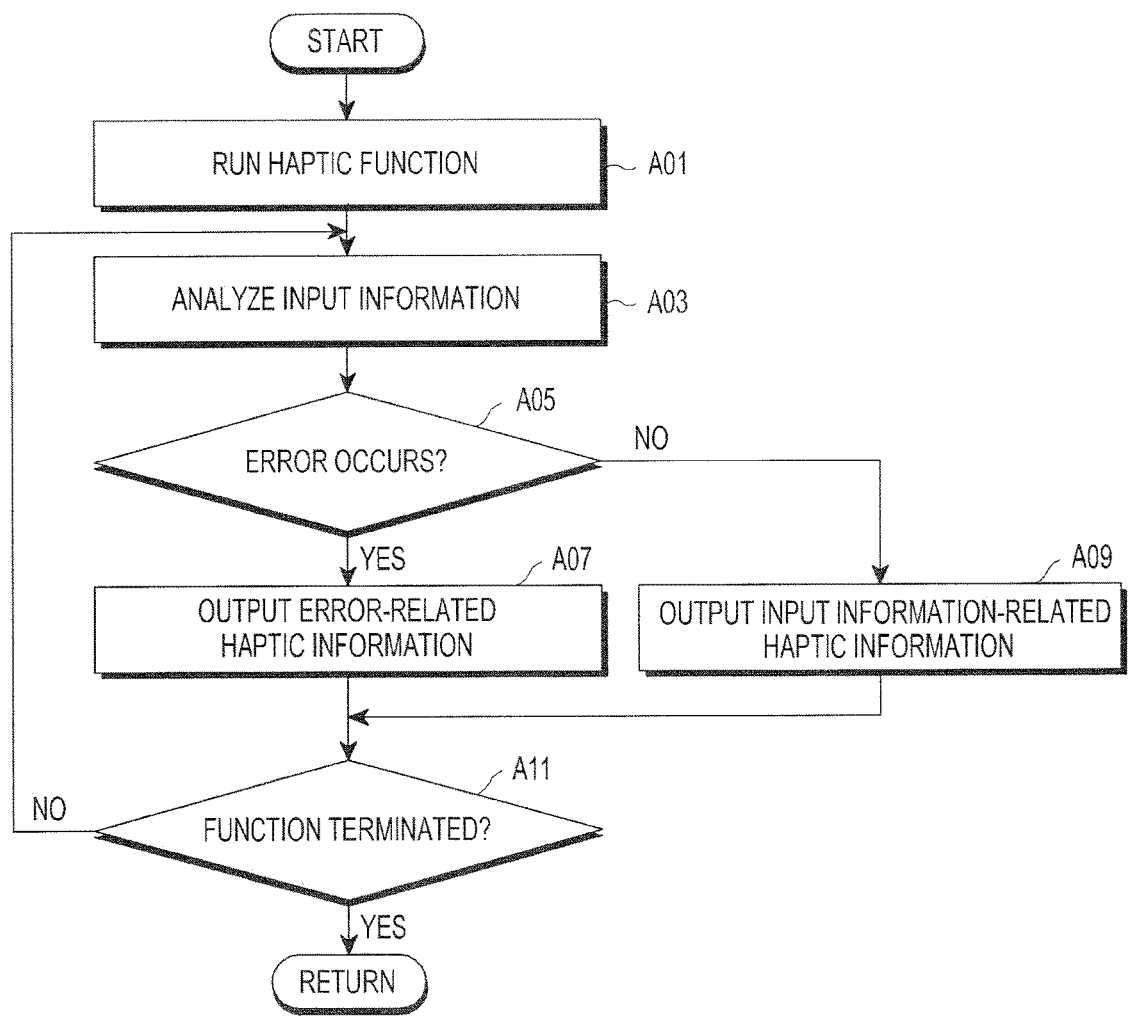
Figure 151:
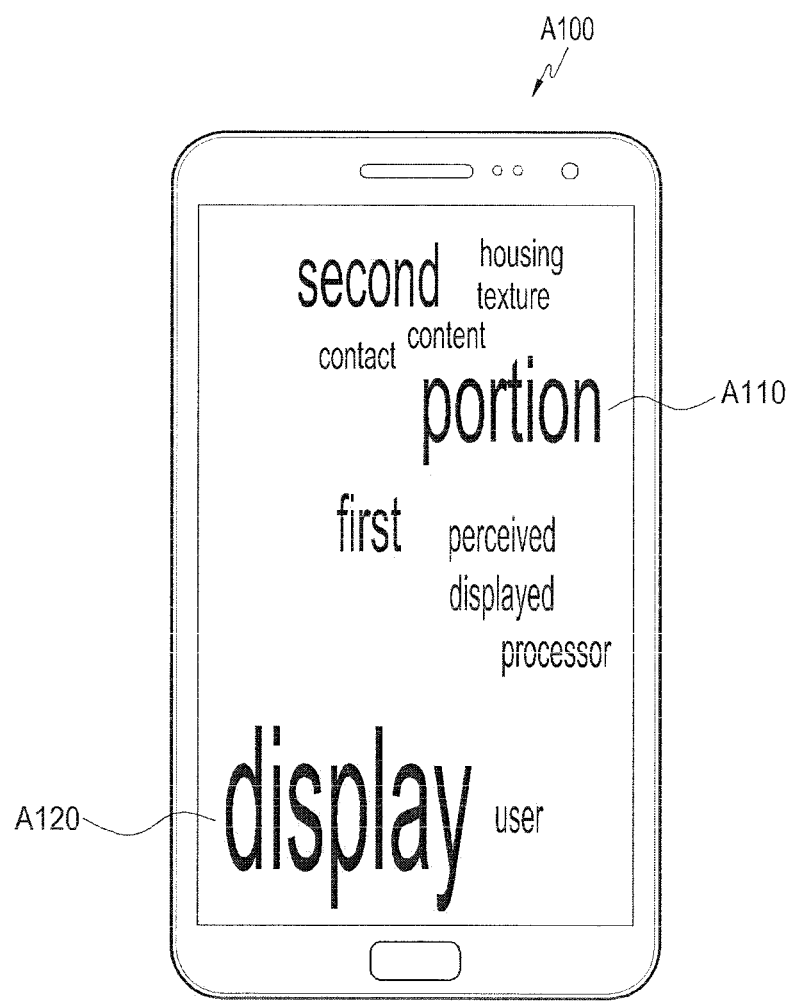
Figure 152:
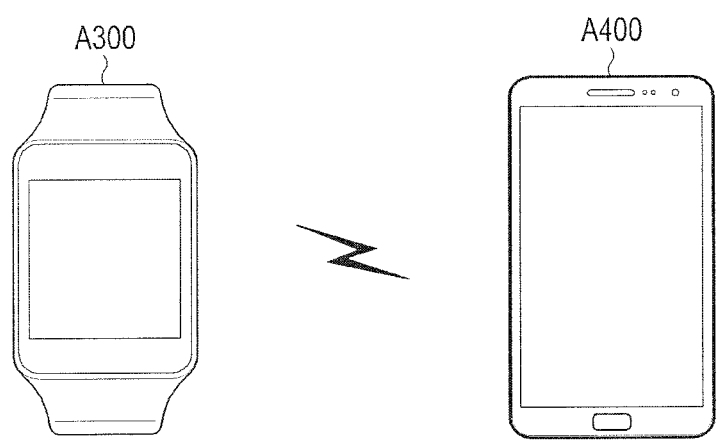
Figure 153:
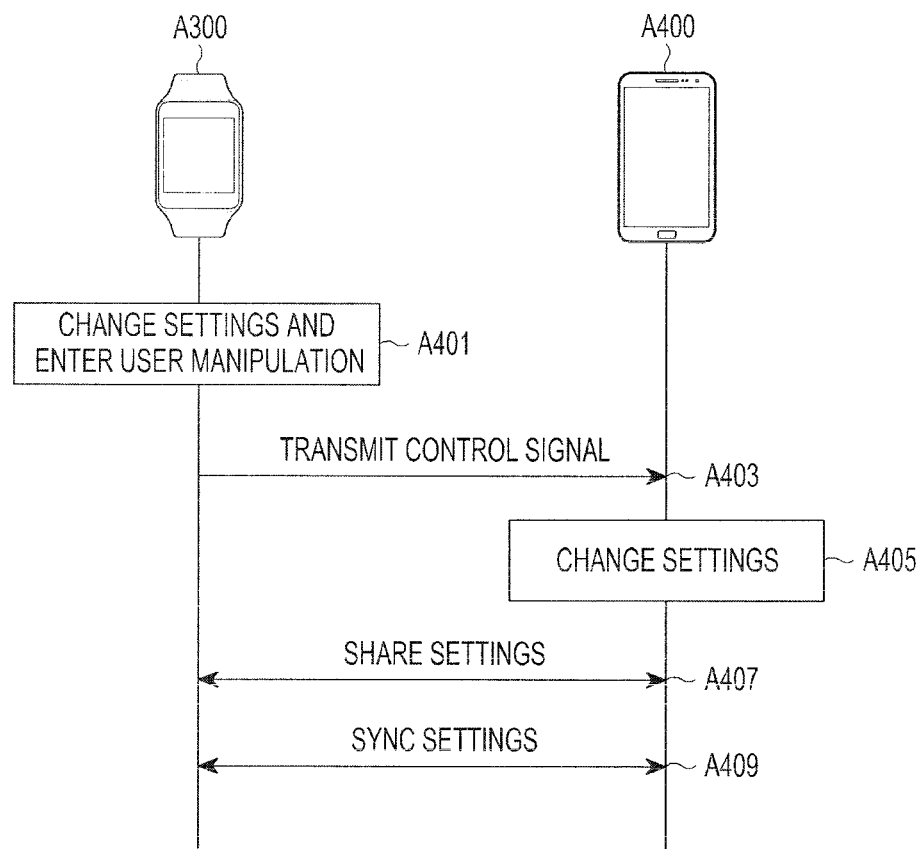
Figure 154:
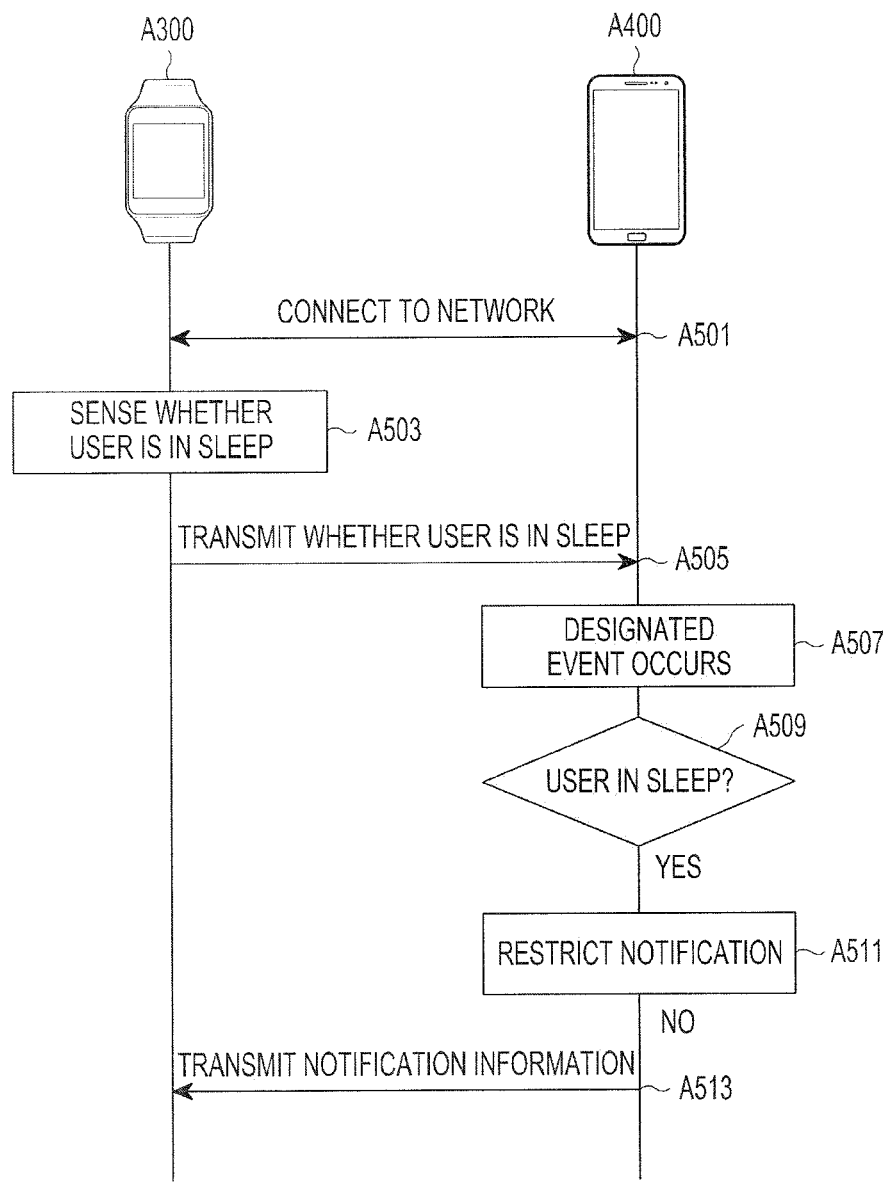
Figure 155:
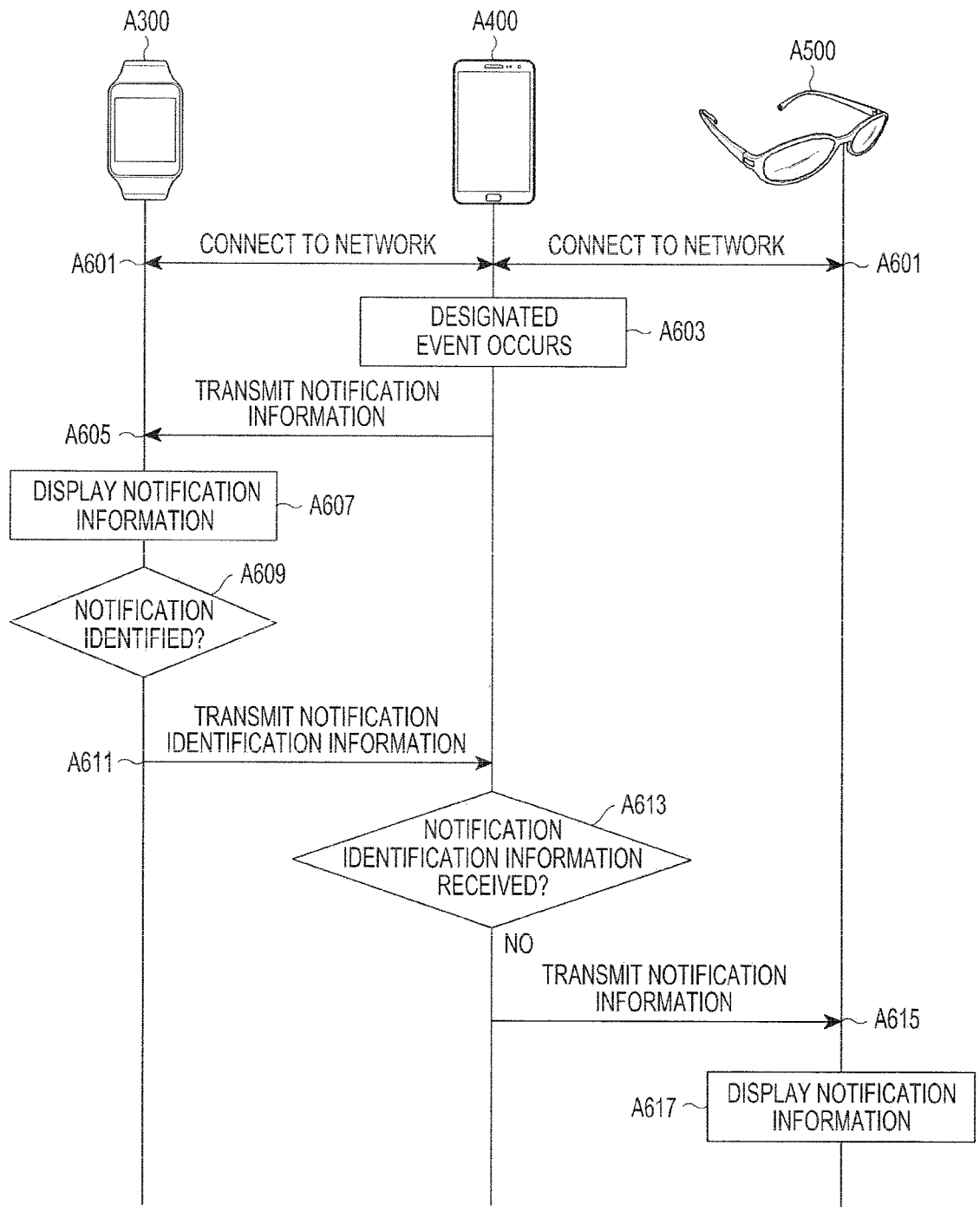
Figure 156:
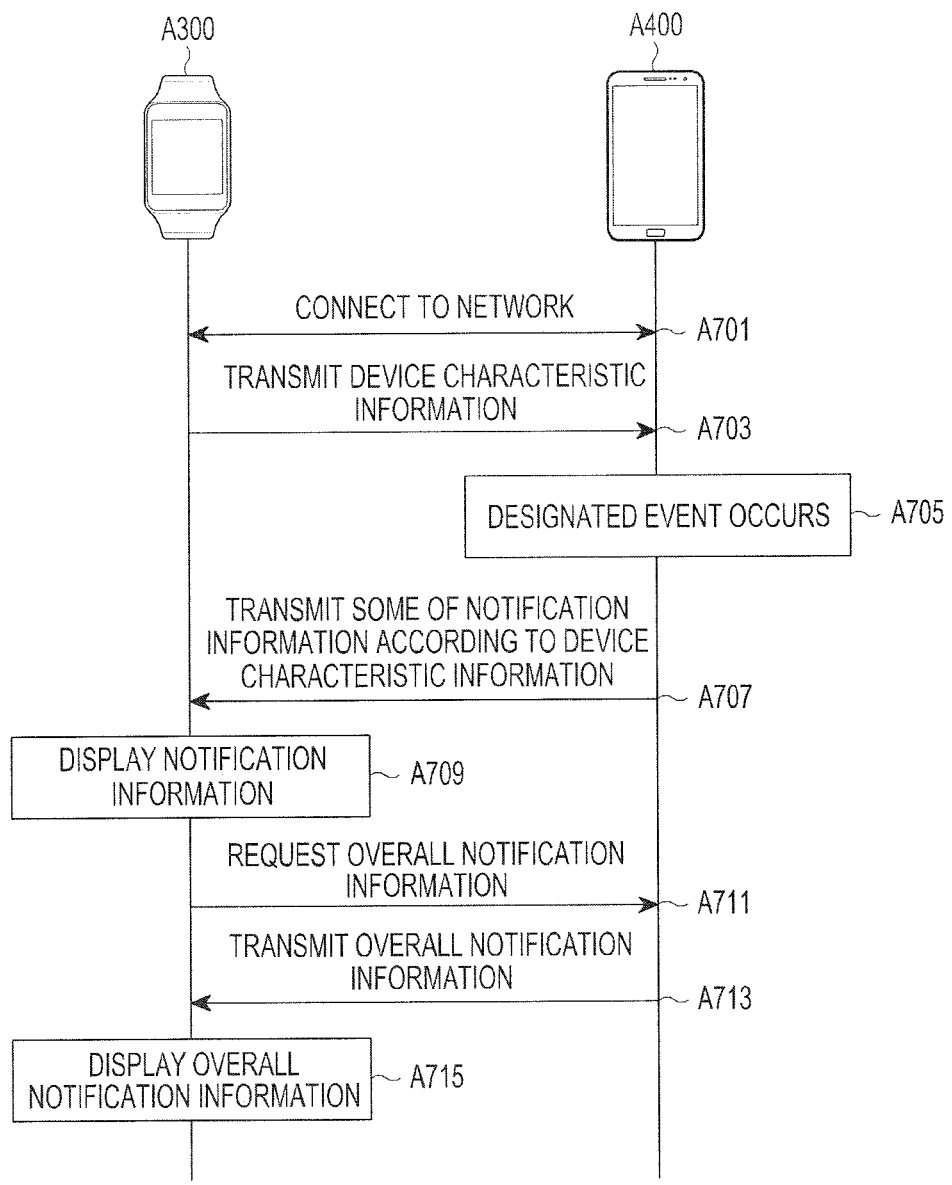
Figure 157:
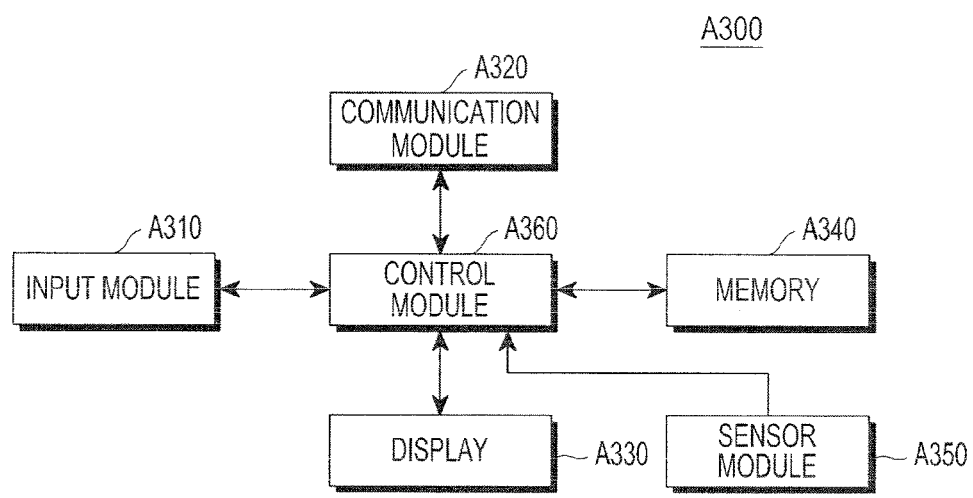
Figure 158:
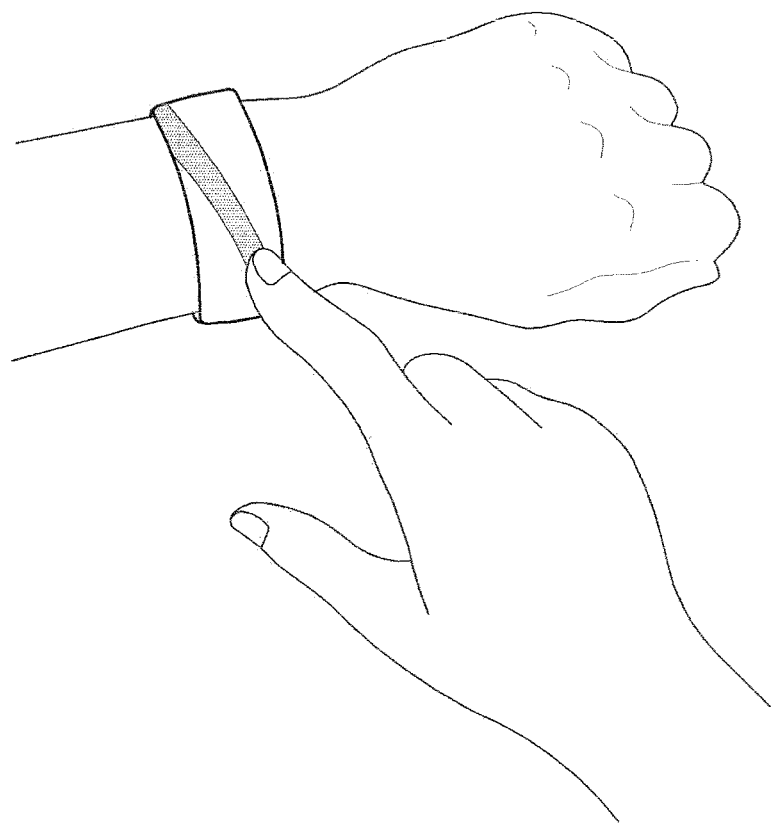
Figure 160:
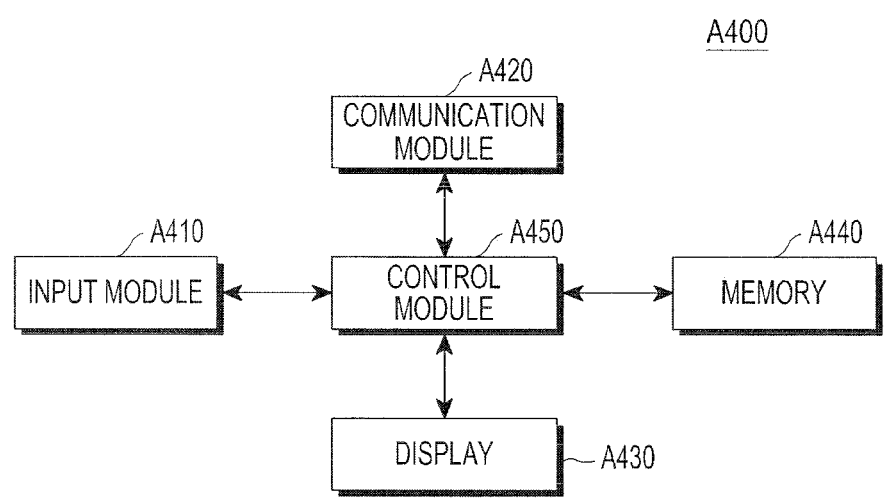
Figure 162:
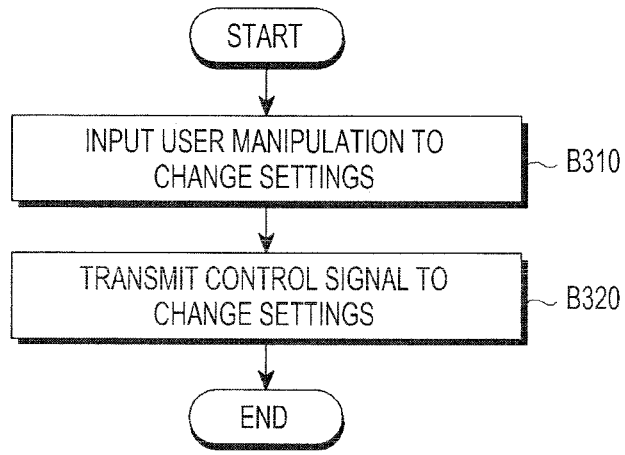
Figure 163:
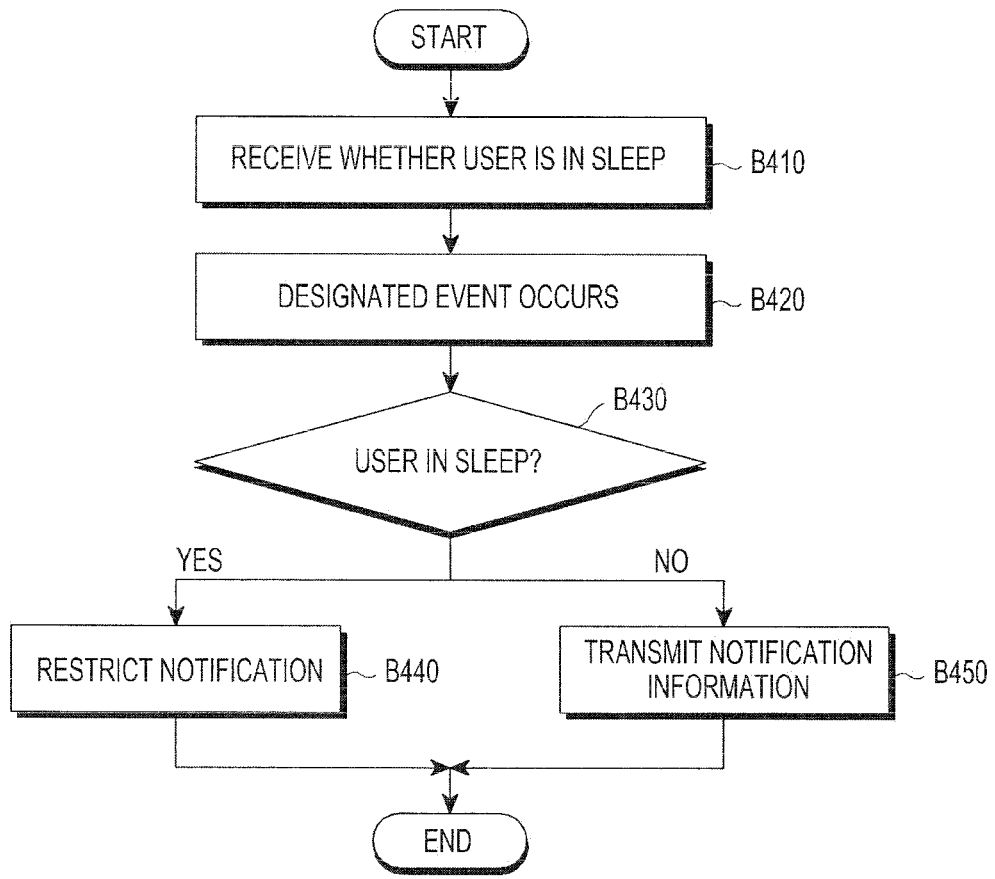
Figure 164:
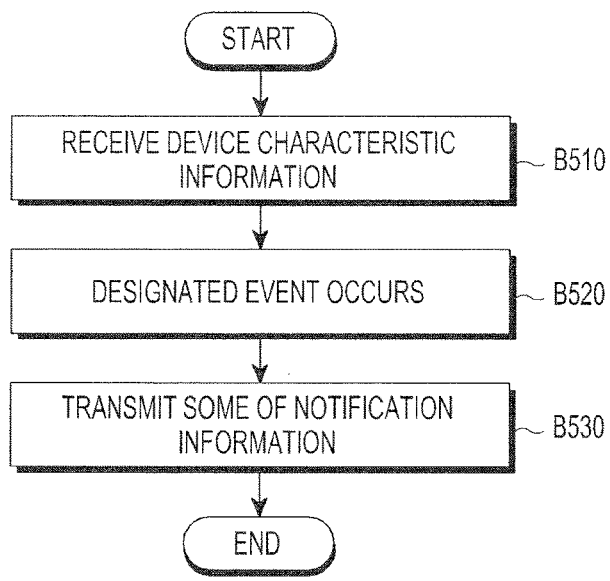
Figure 165:
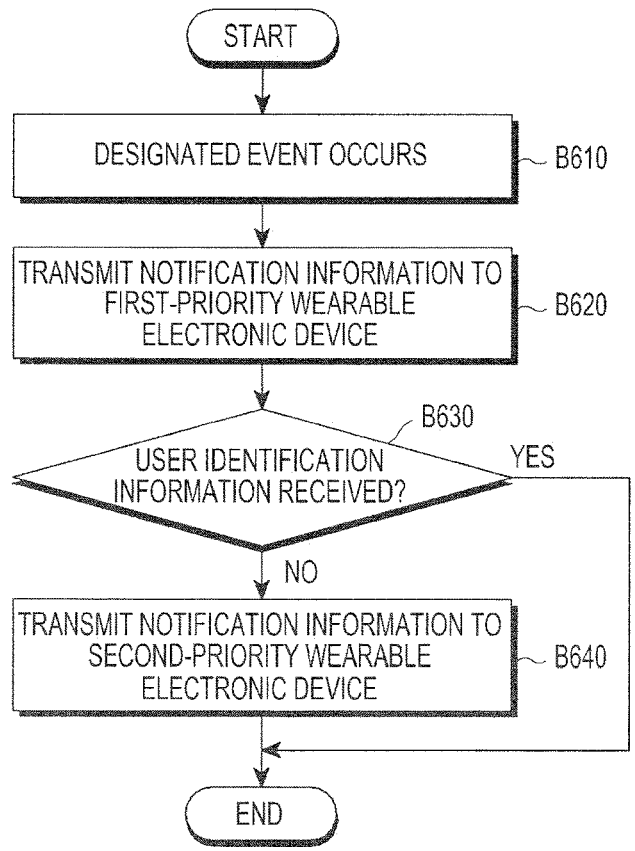
Figure 166:
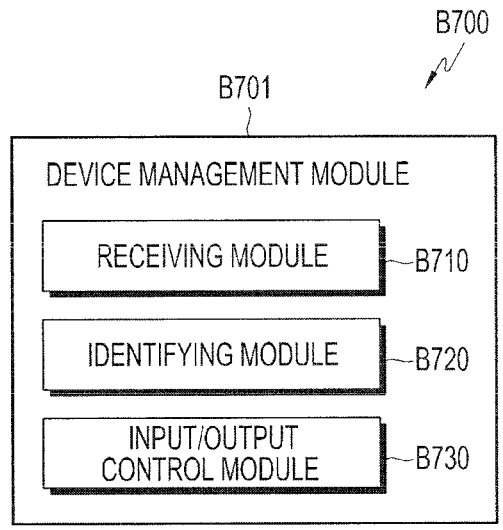
Figure 167:
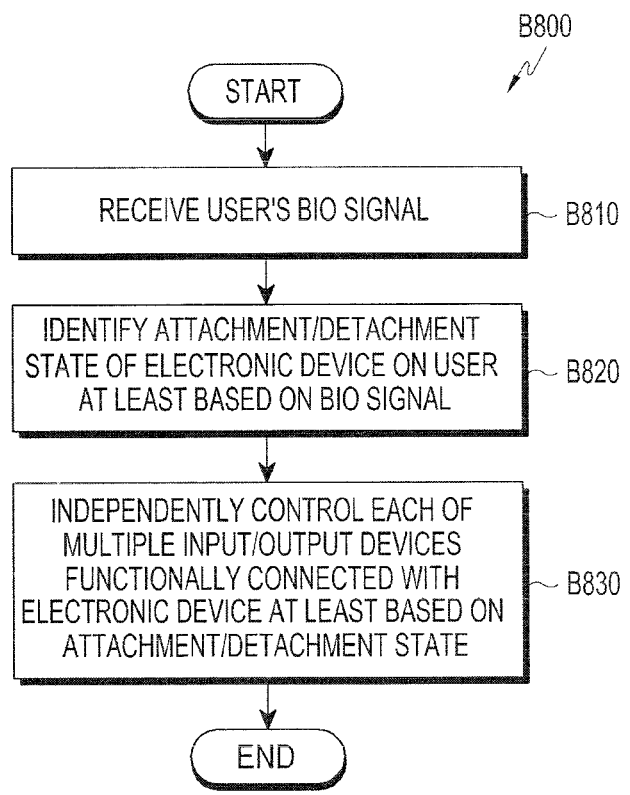
Figure 168:
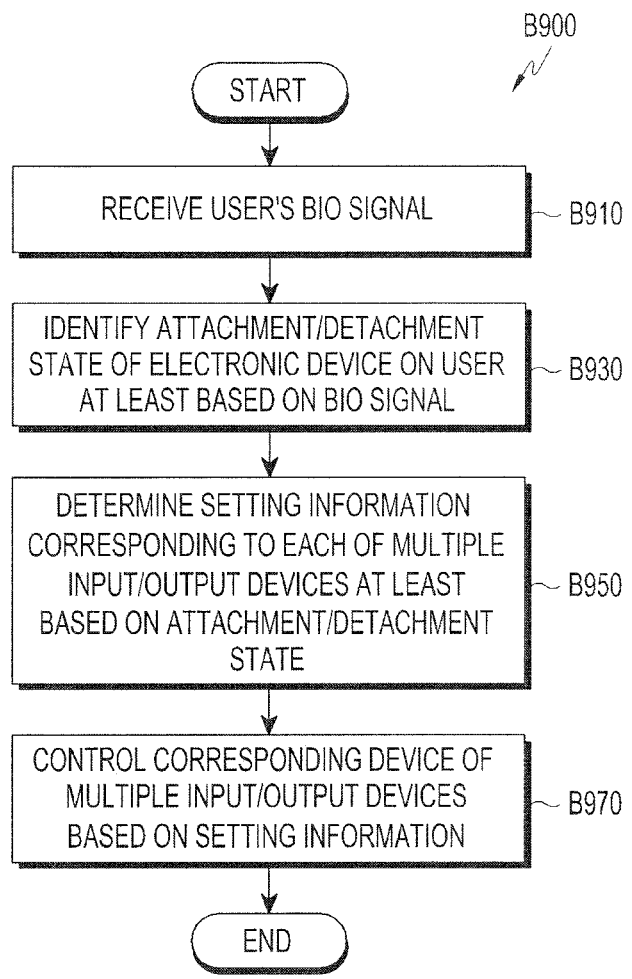
Figure 169:
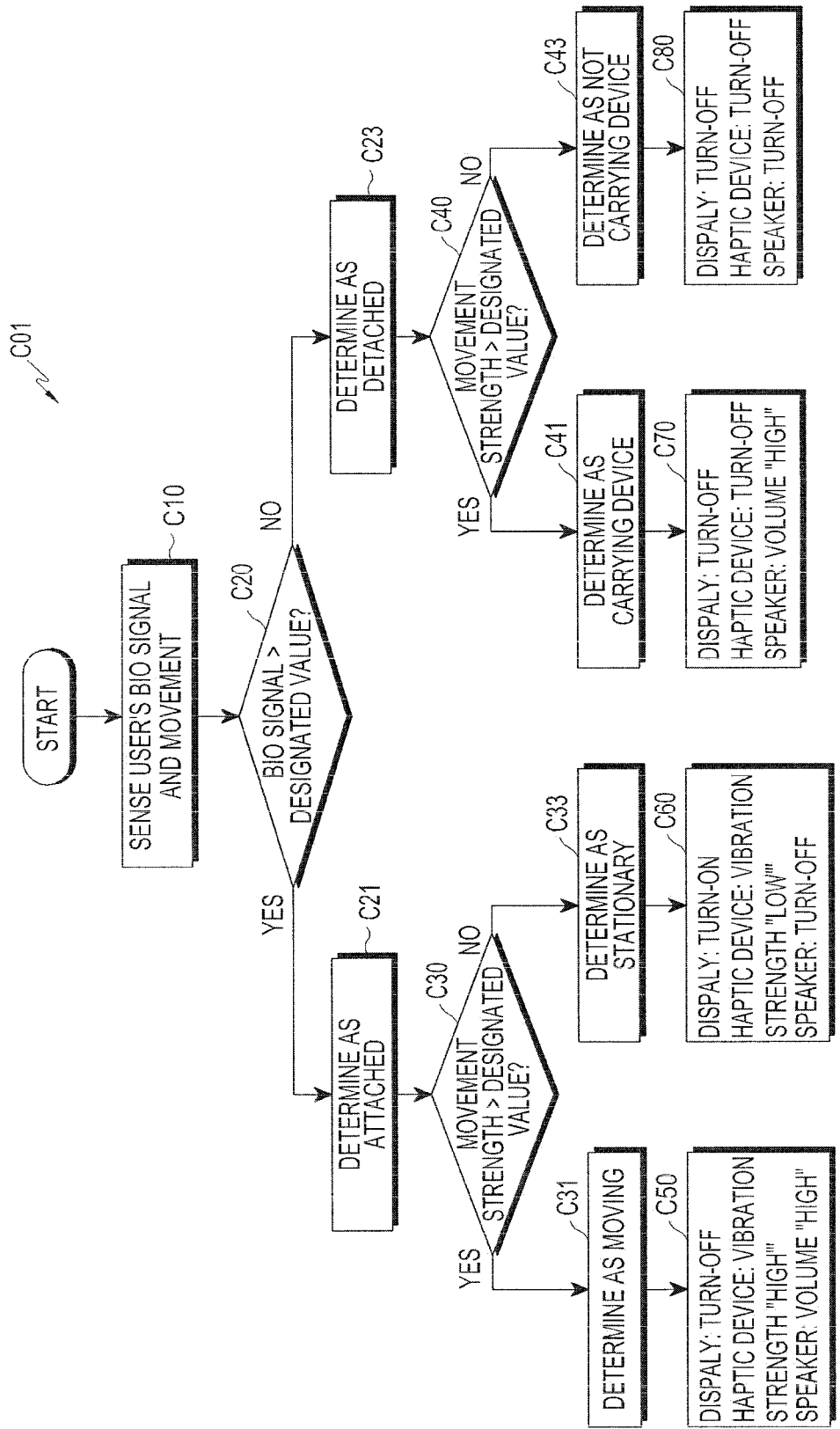
Figure 170:
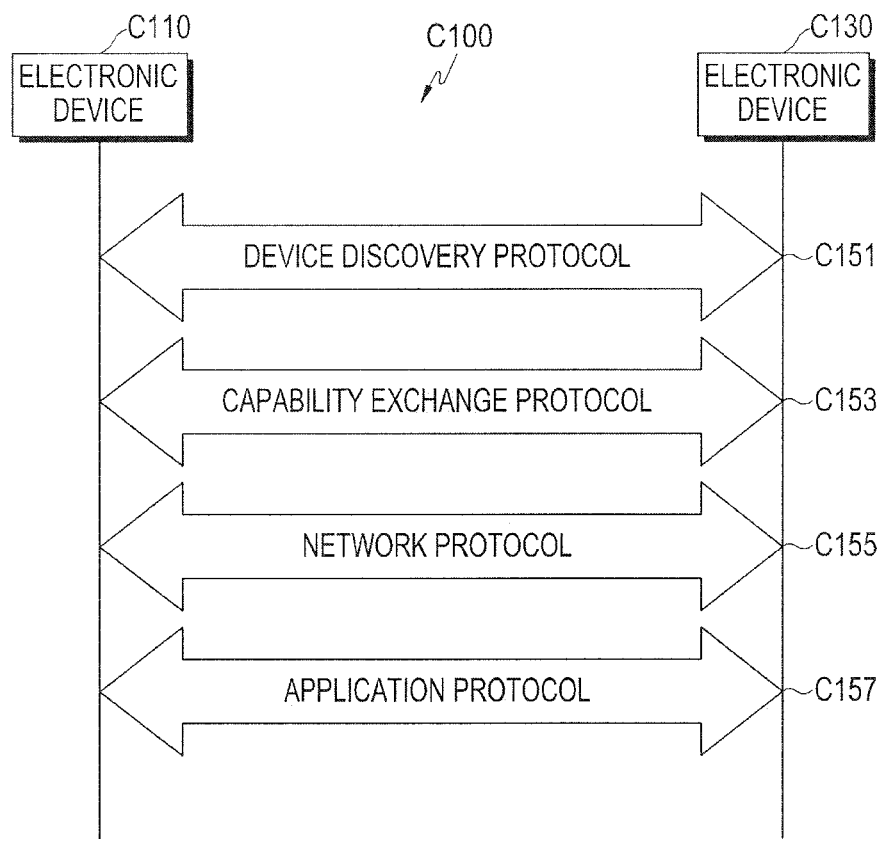
Figures 171, 172:
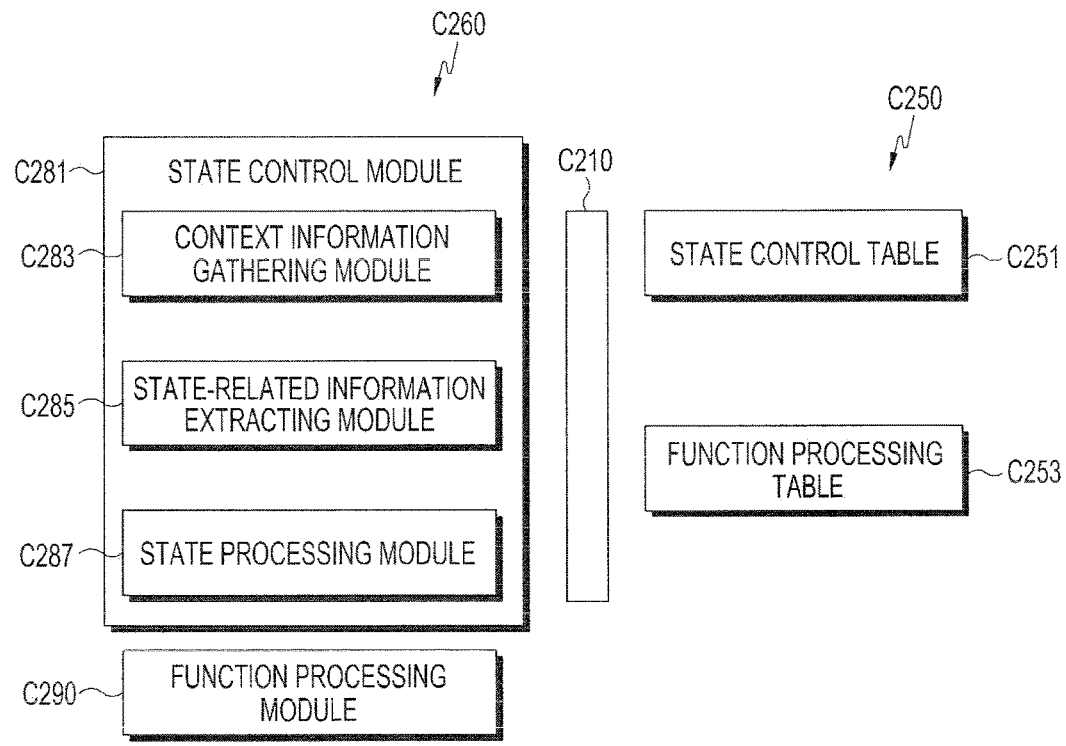
Figure 173:
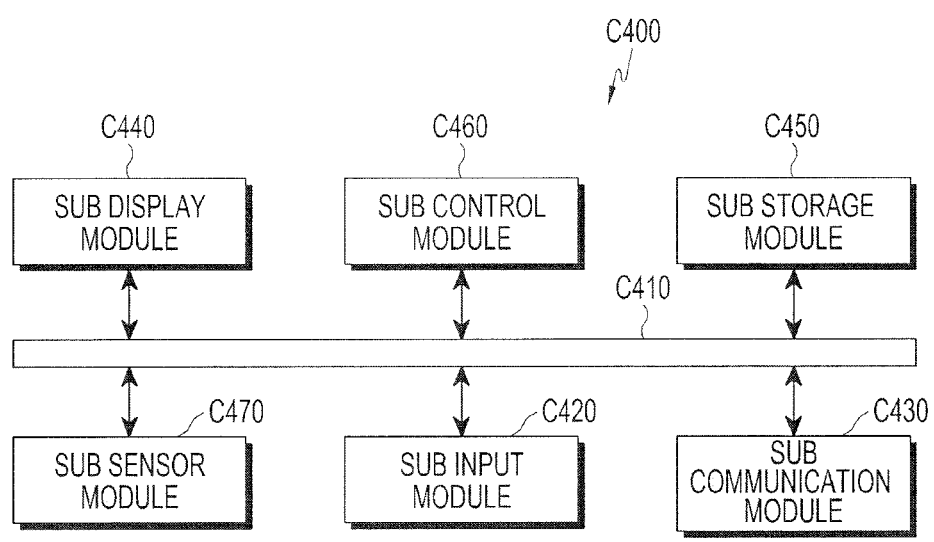
Figure 174:
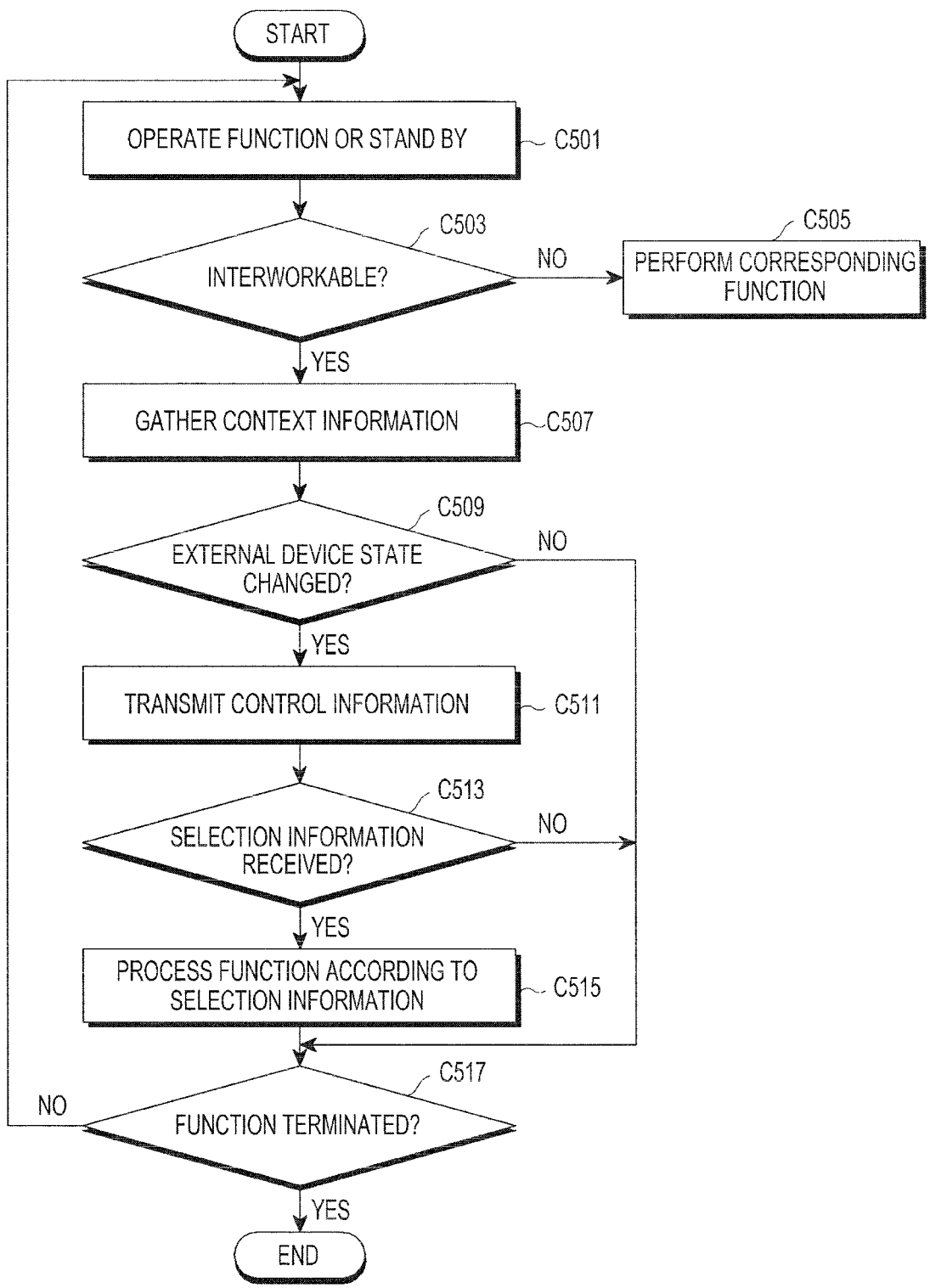
Figure 175:
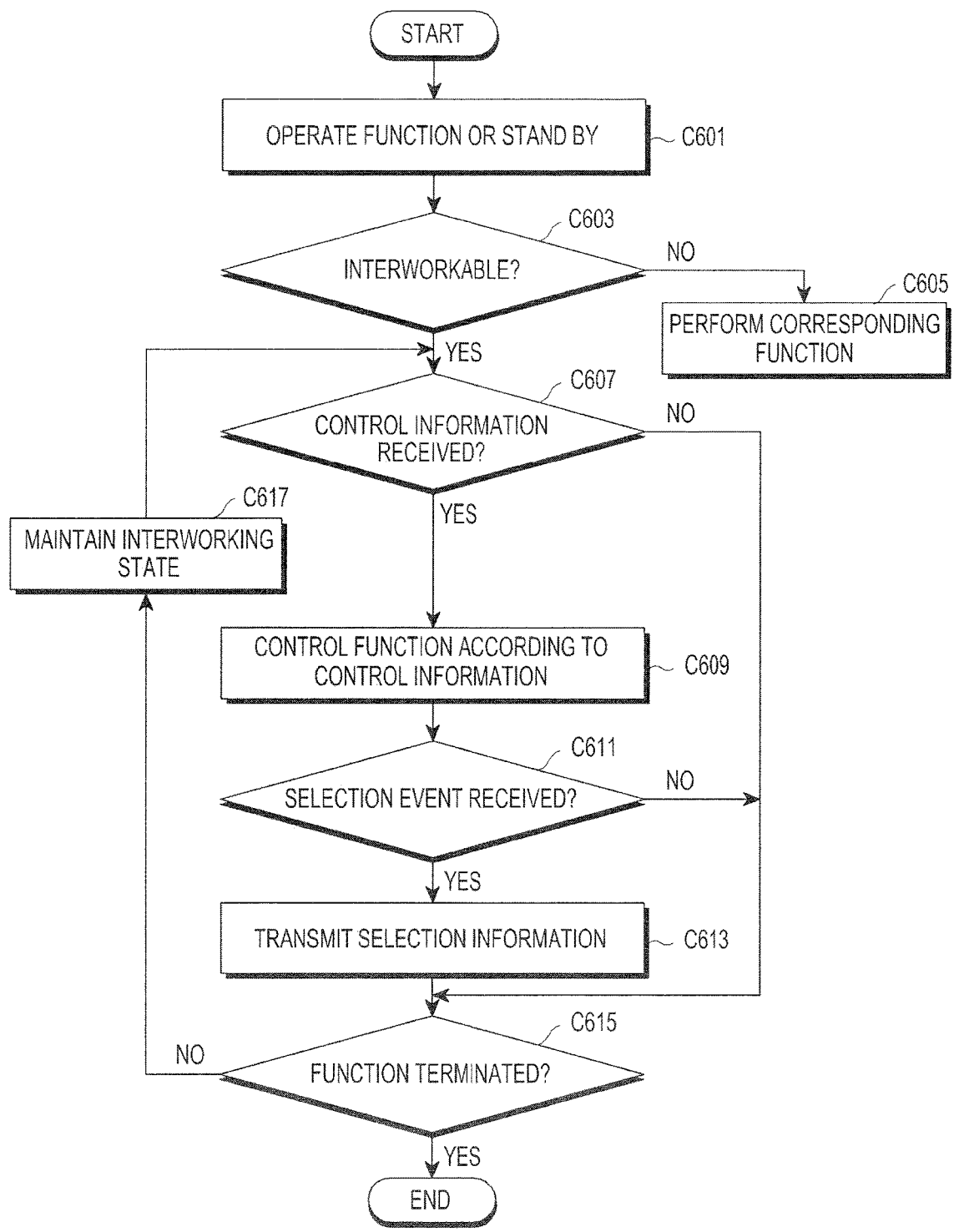
Figure 176:
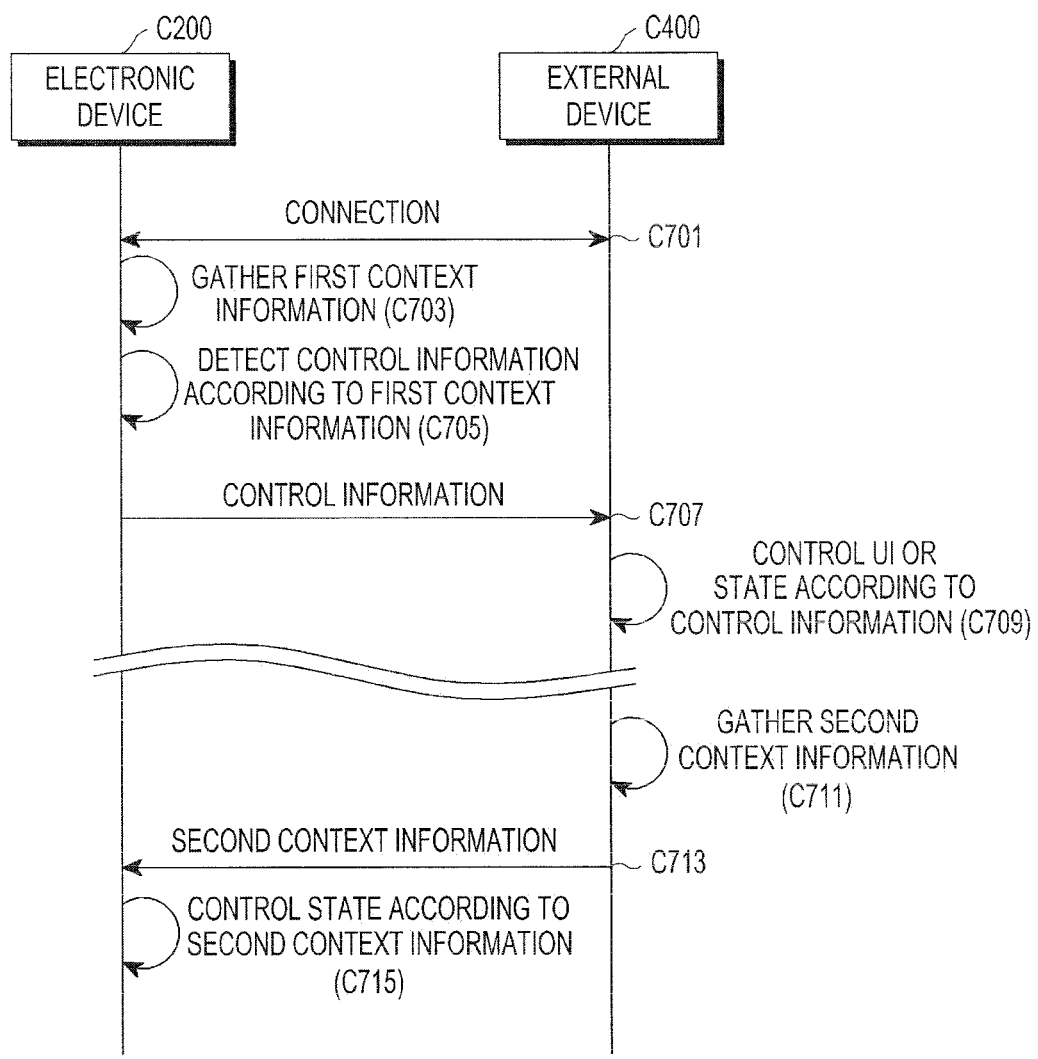
Figure 177:
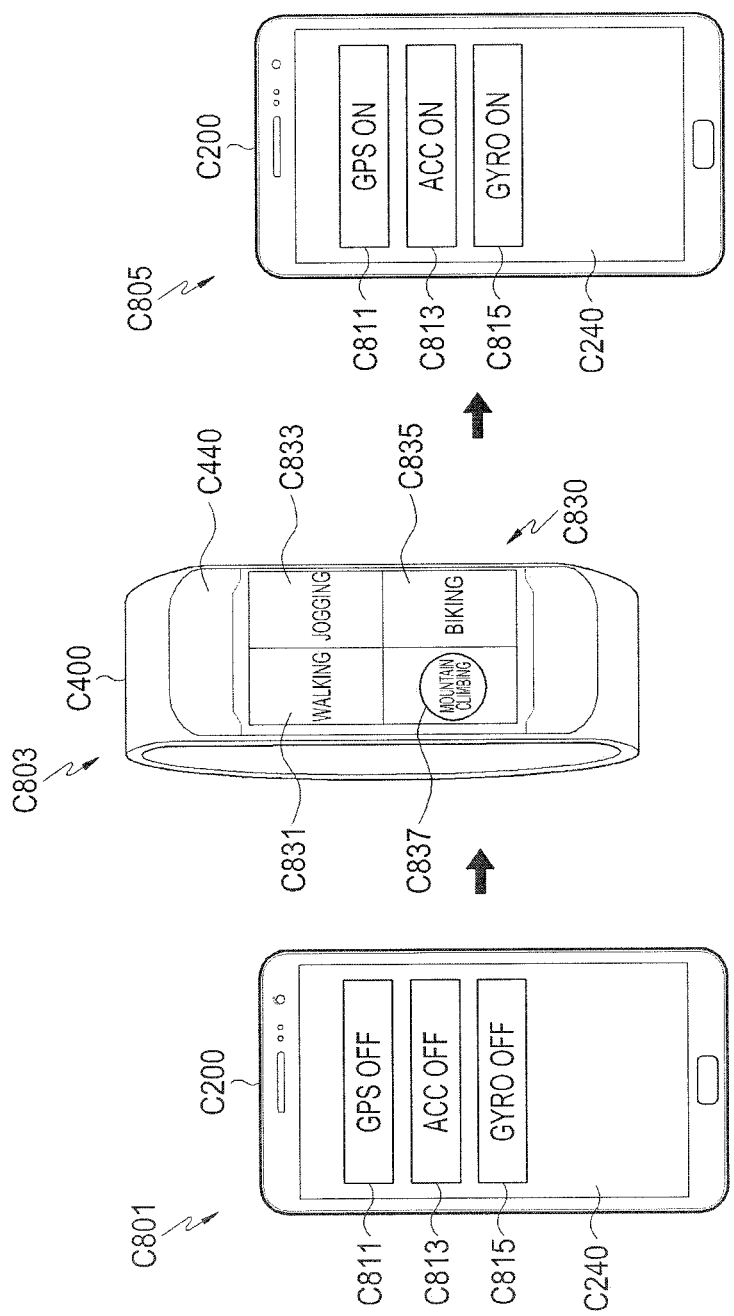
Figure 178:
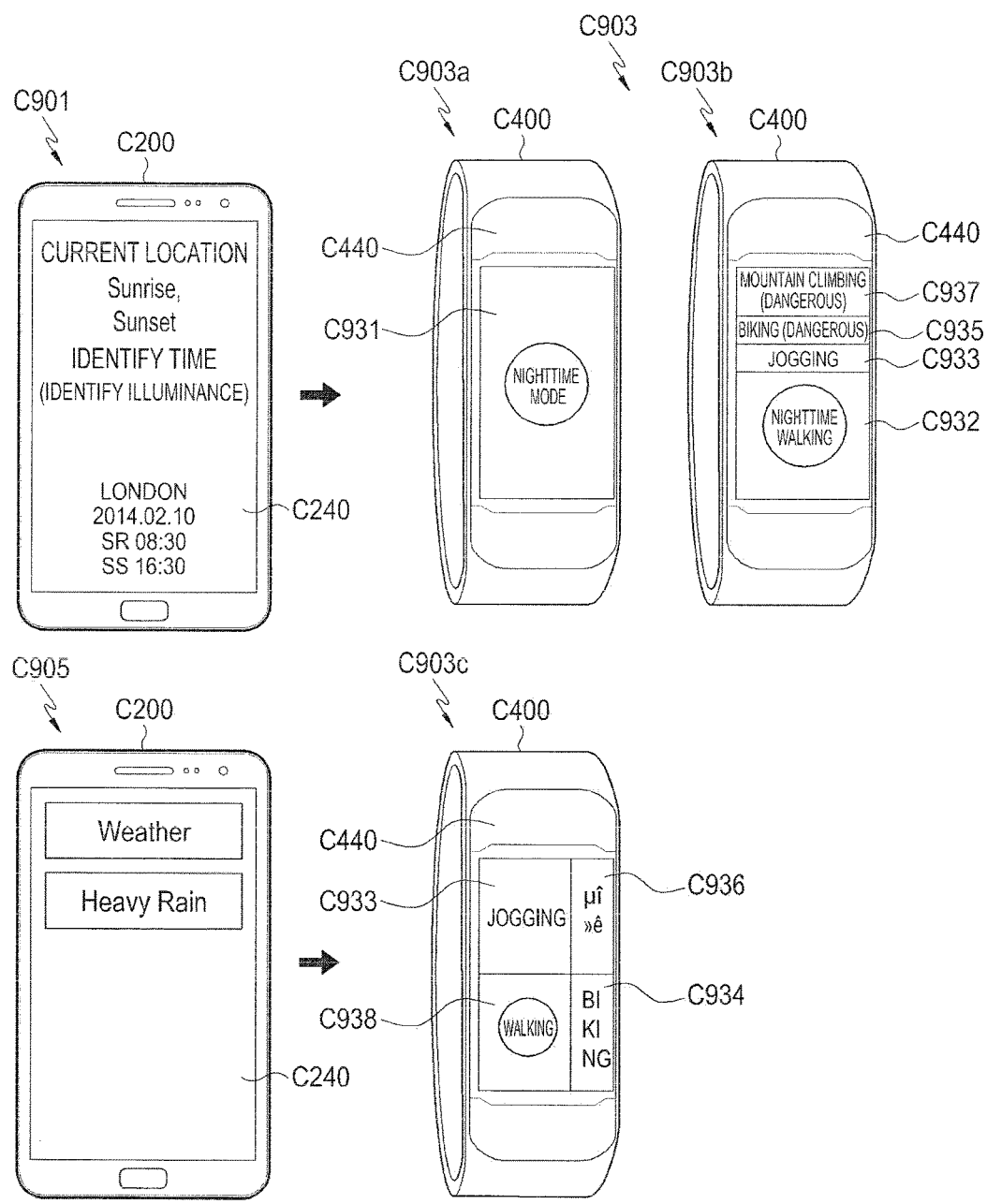
Figure 179:
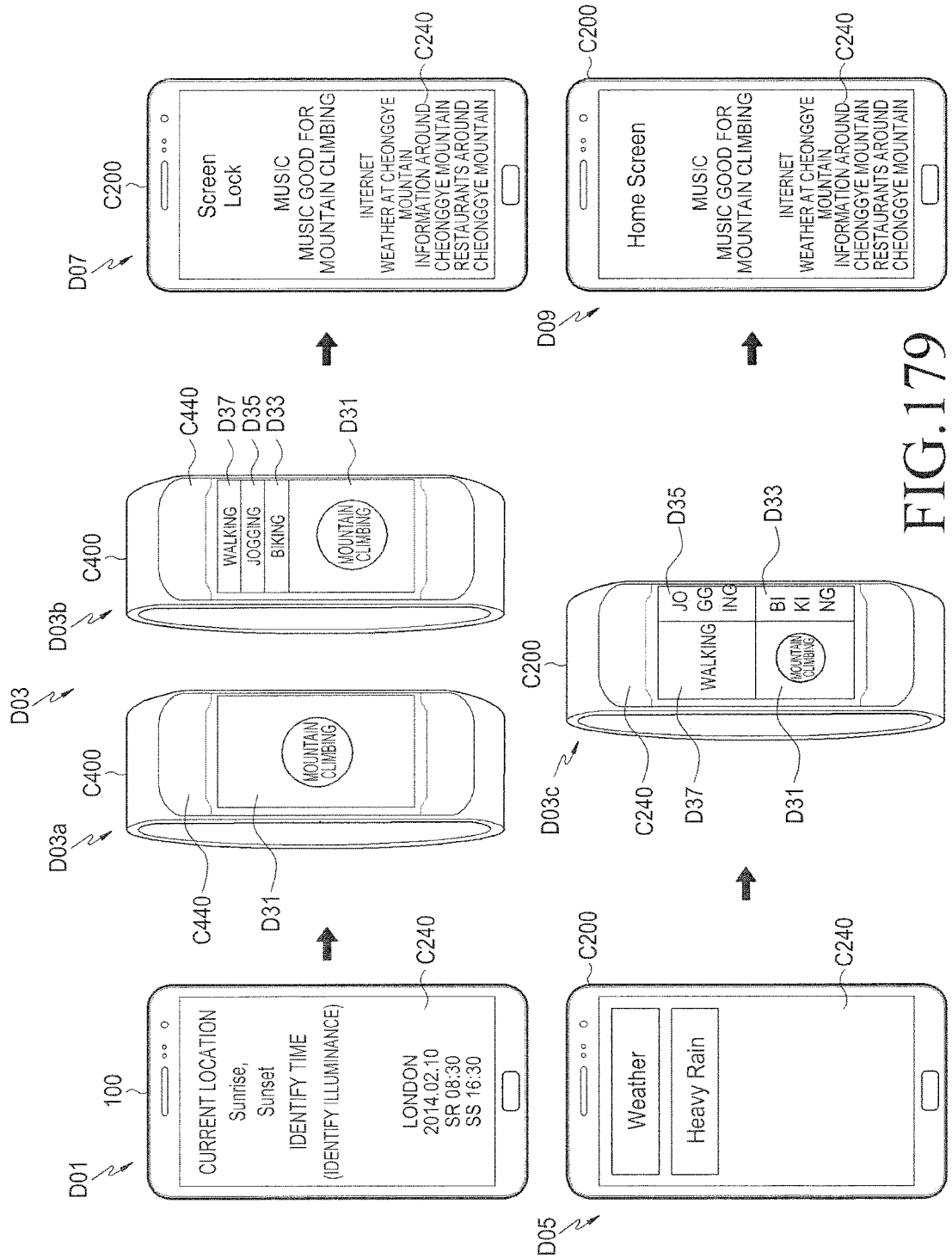
Figure 180:
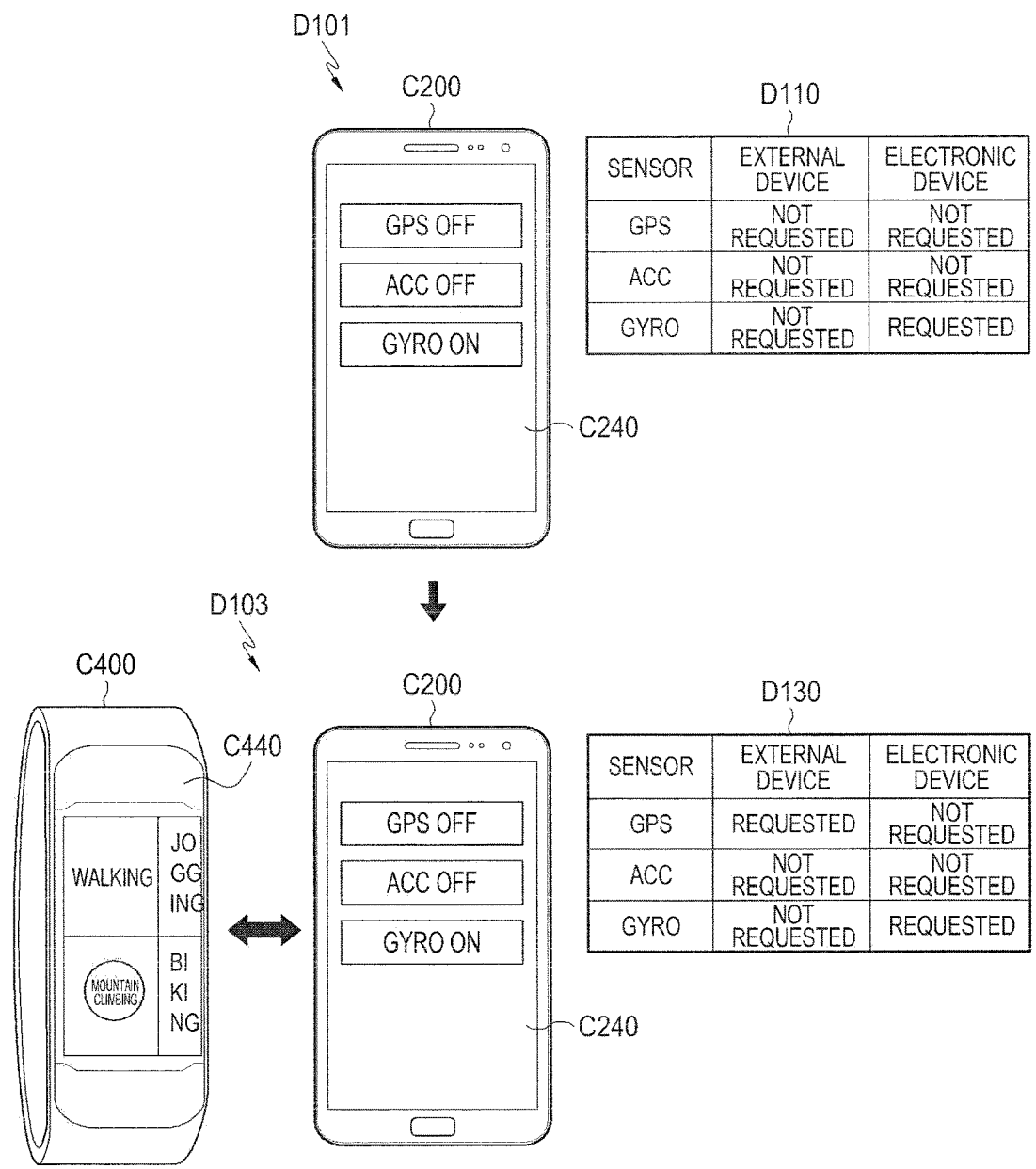
Figure 181:
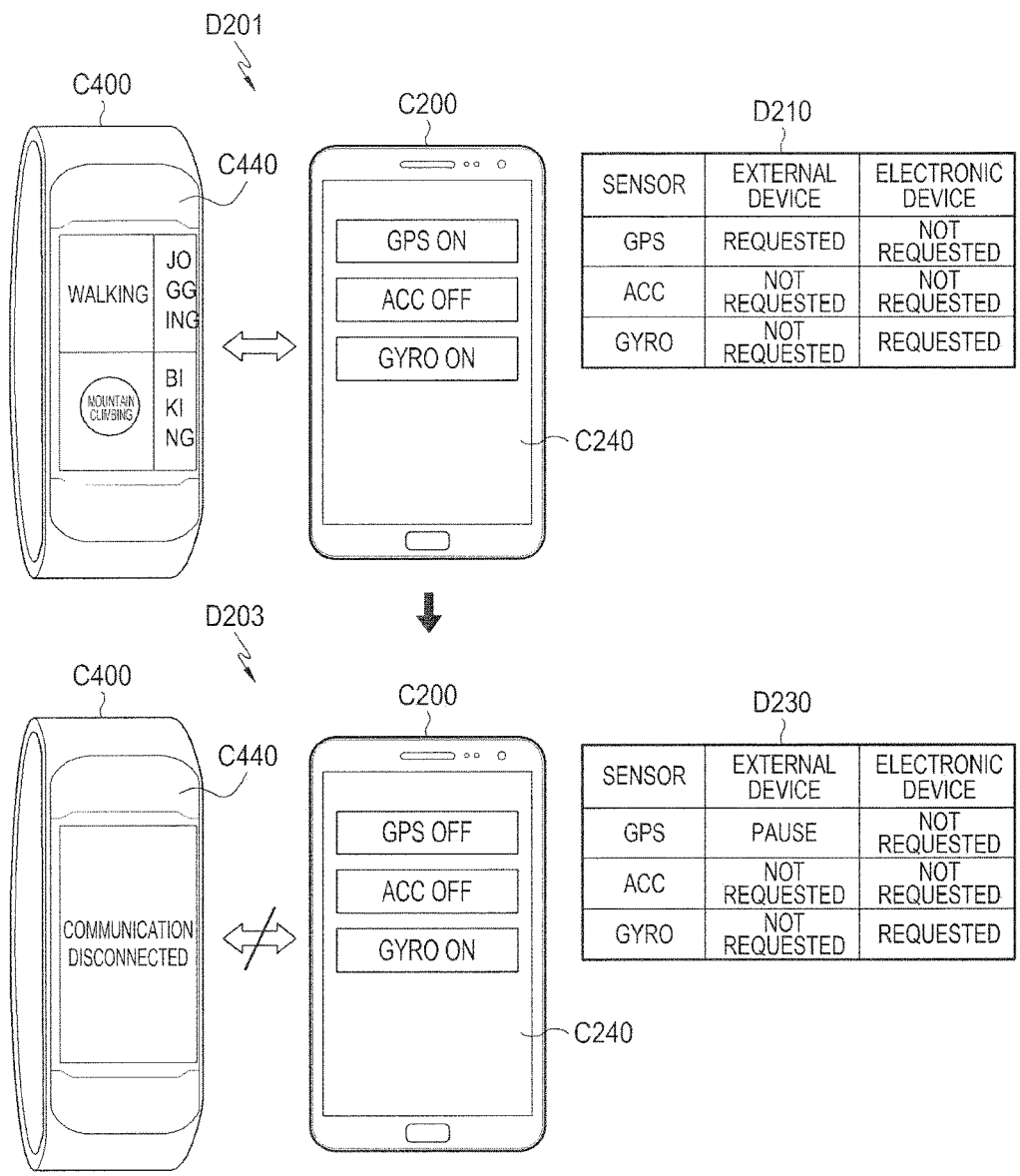
Figure 182:
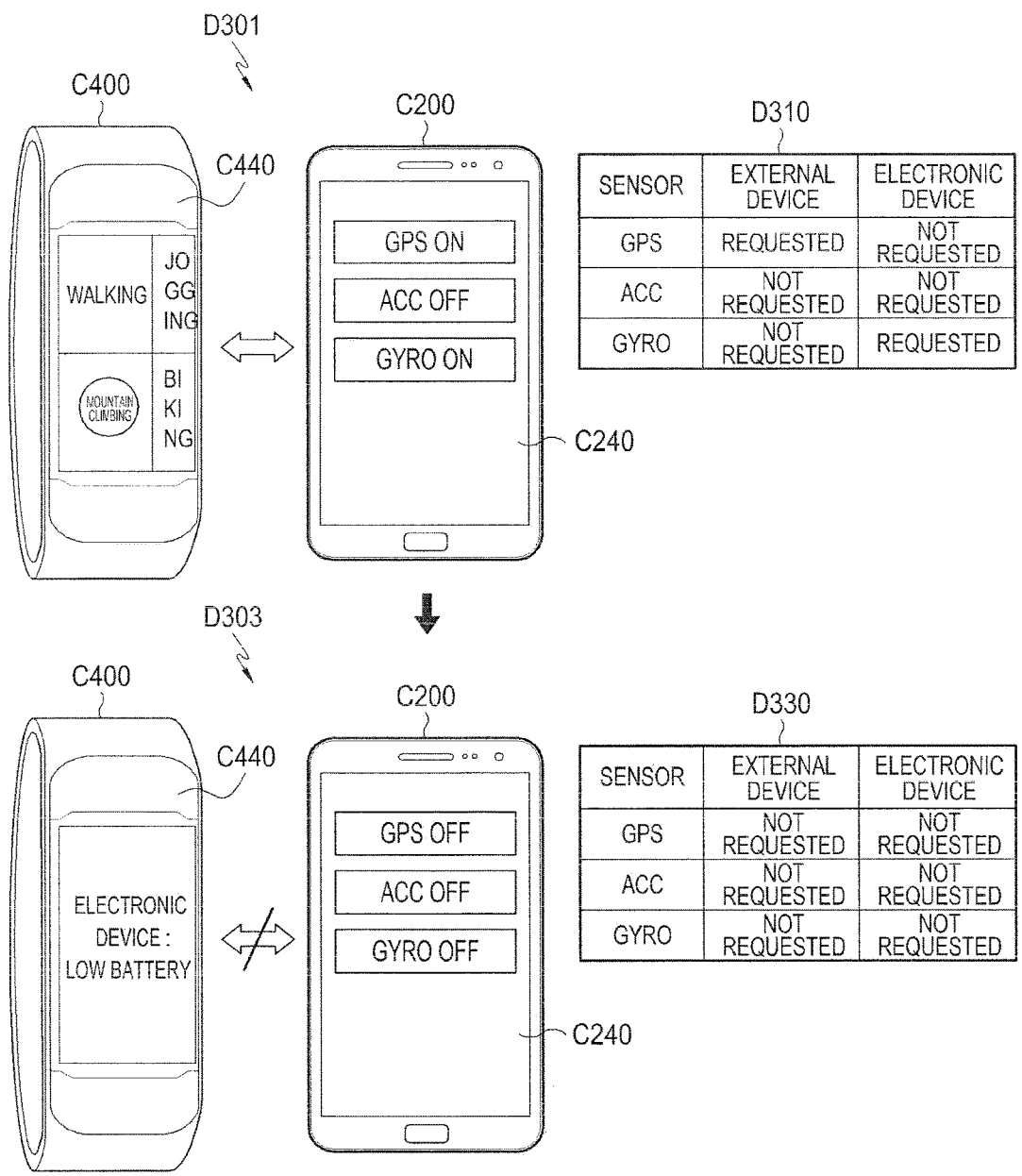
Figure 183:
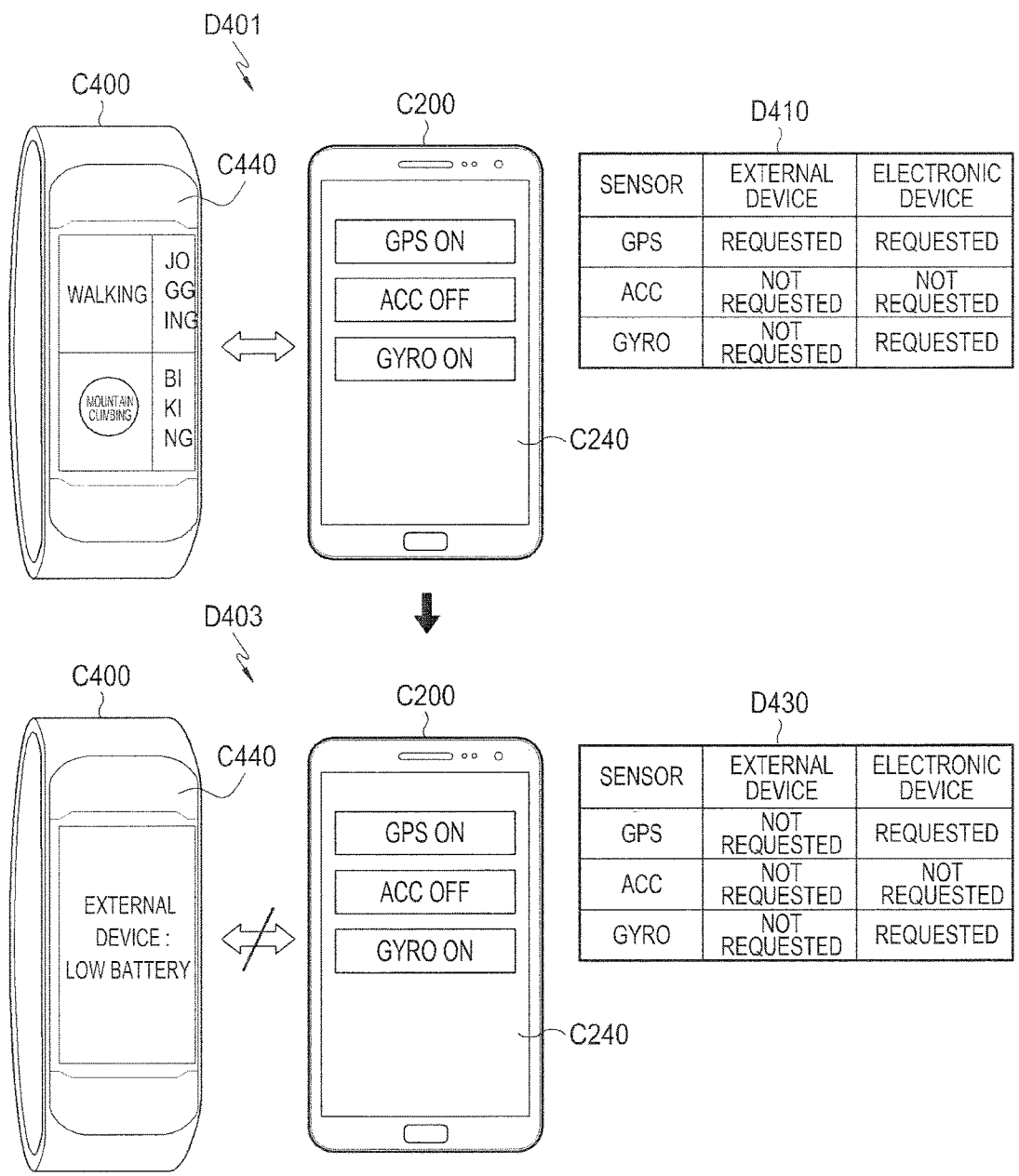
Figure 184:
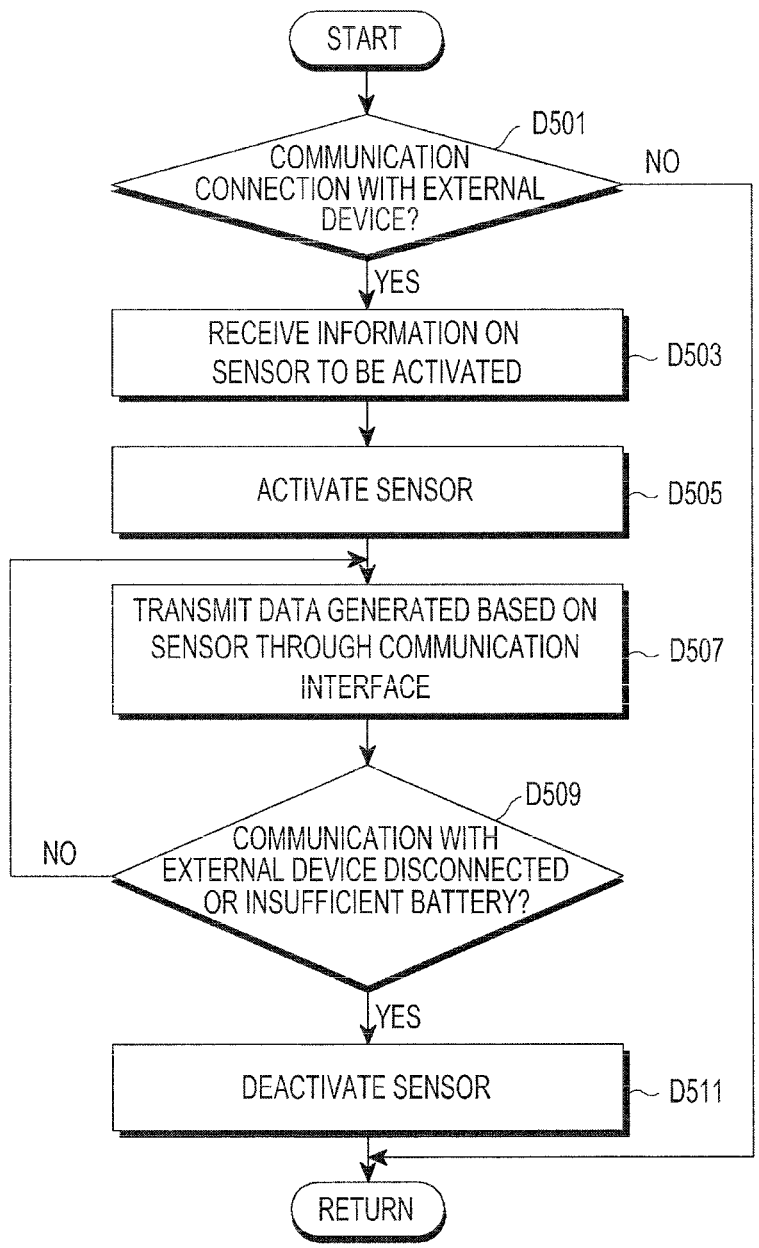
Figure 185:
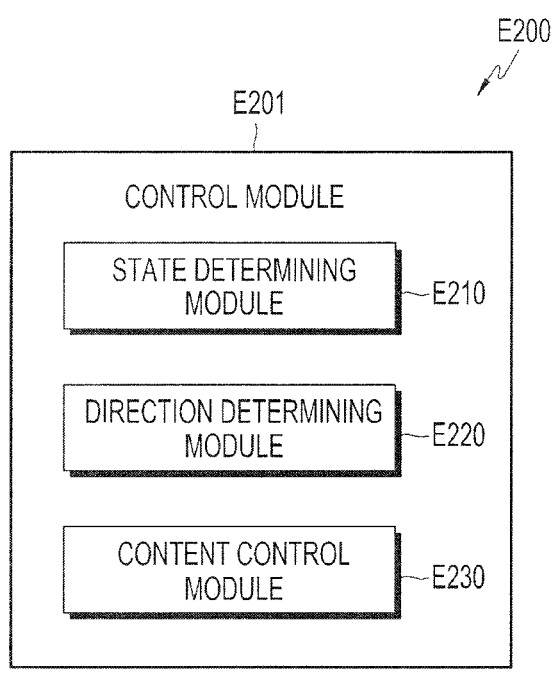
Figure 186:
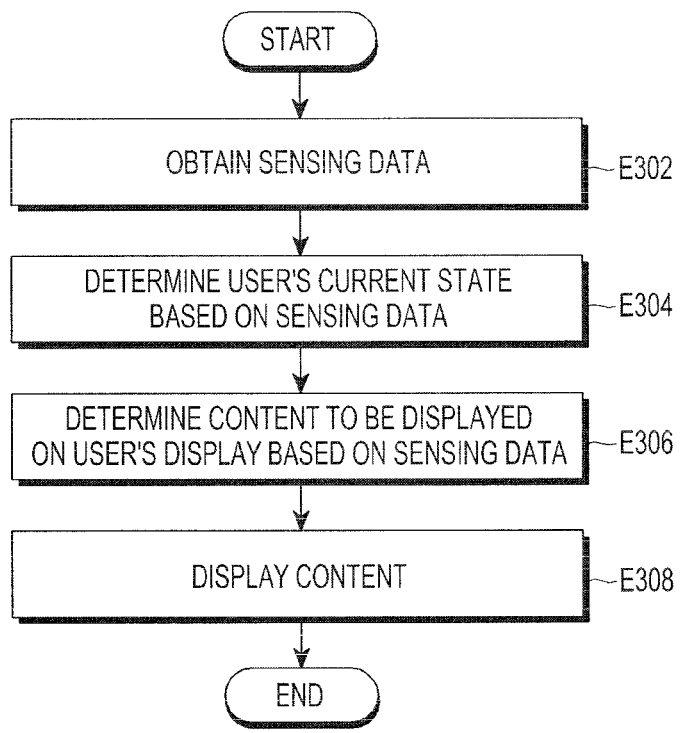
Figure 187:
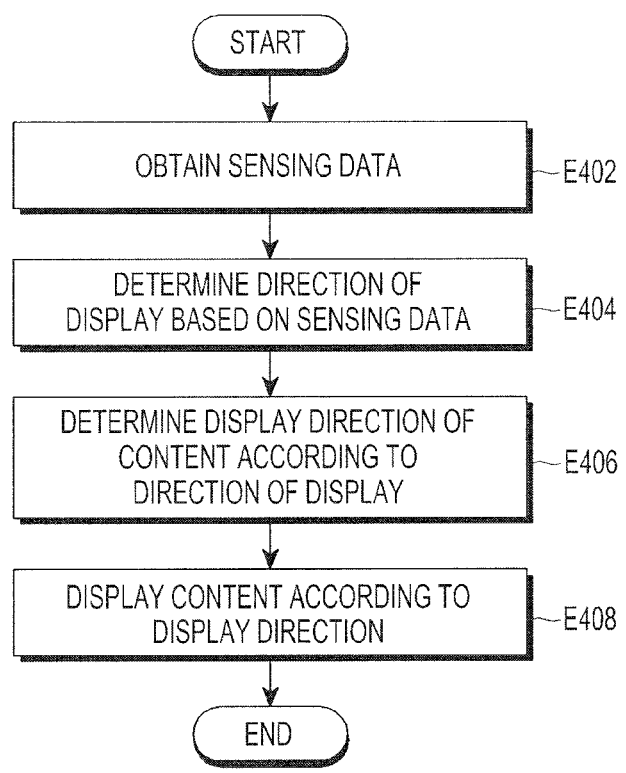
Figure 188:
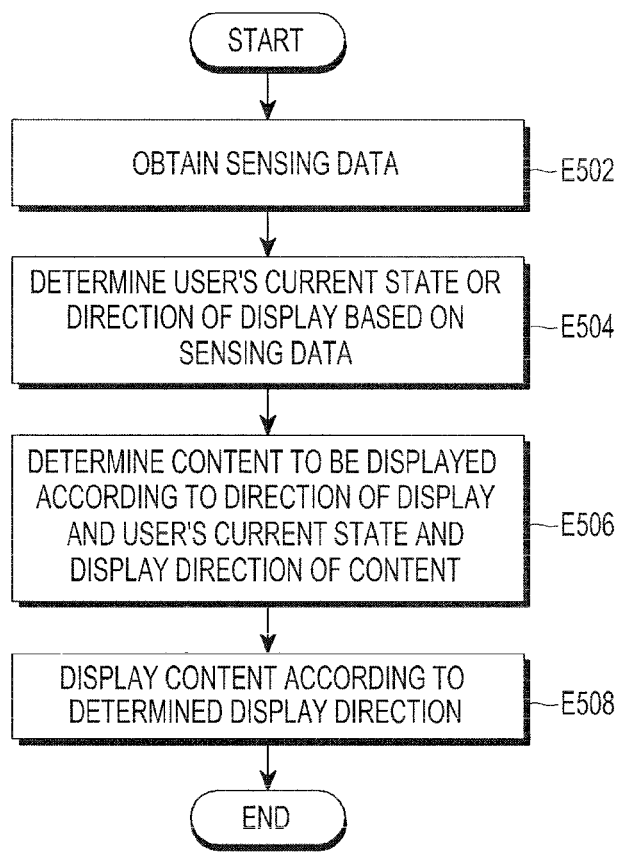
Figure 189:
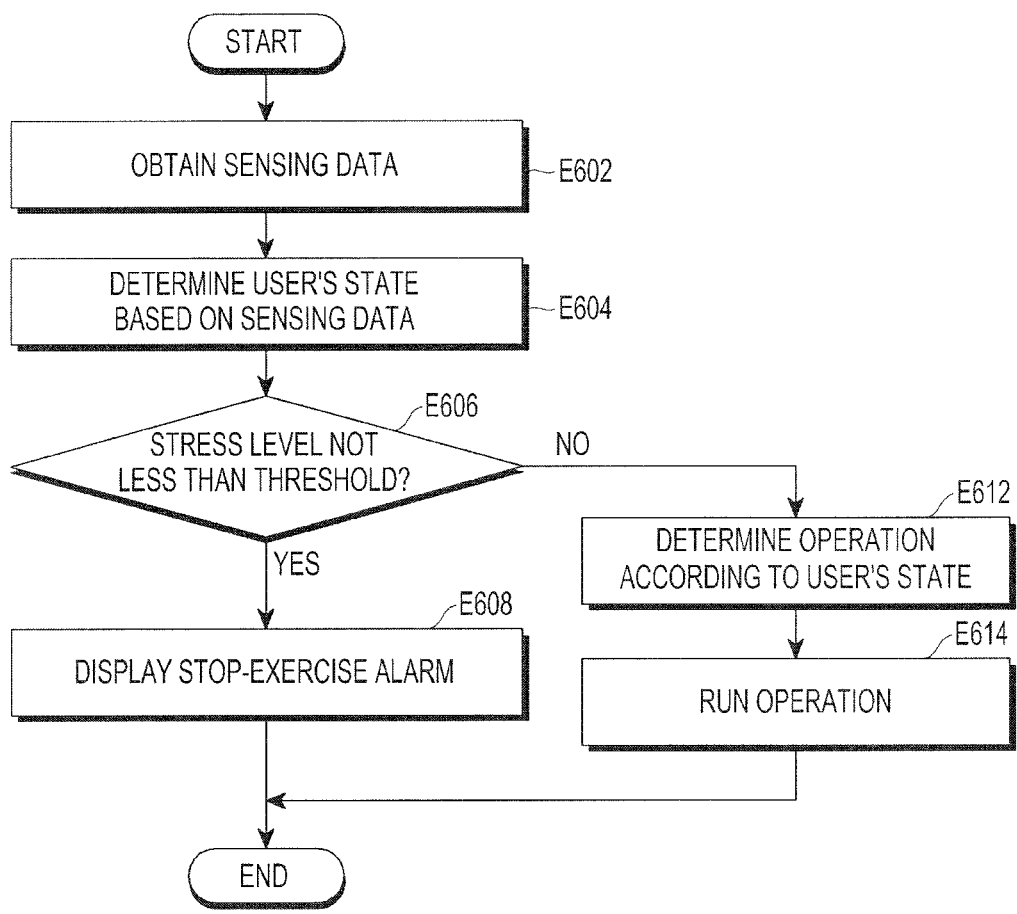
Figure 195A:
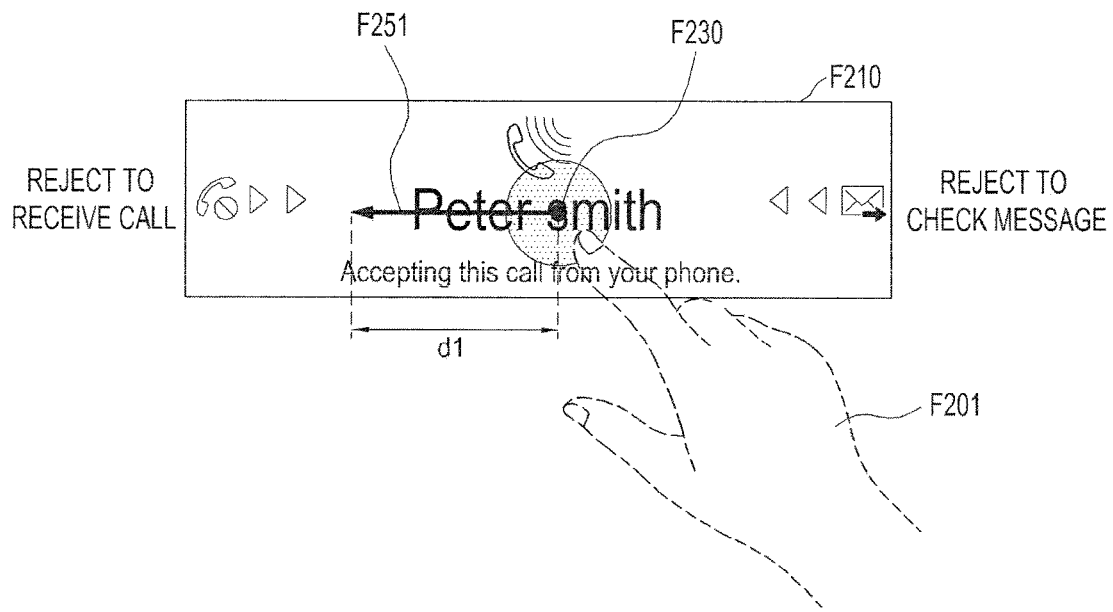
Figure 195B:
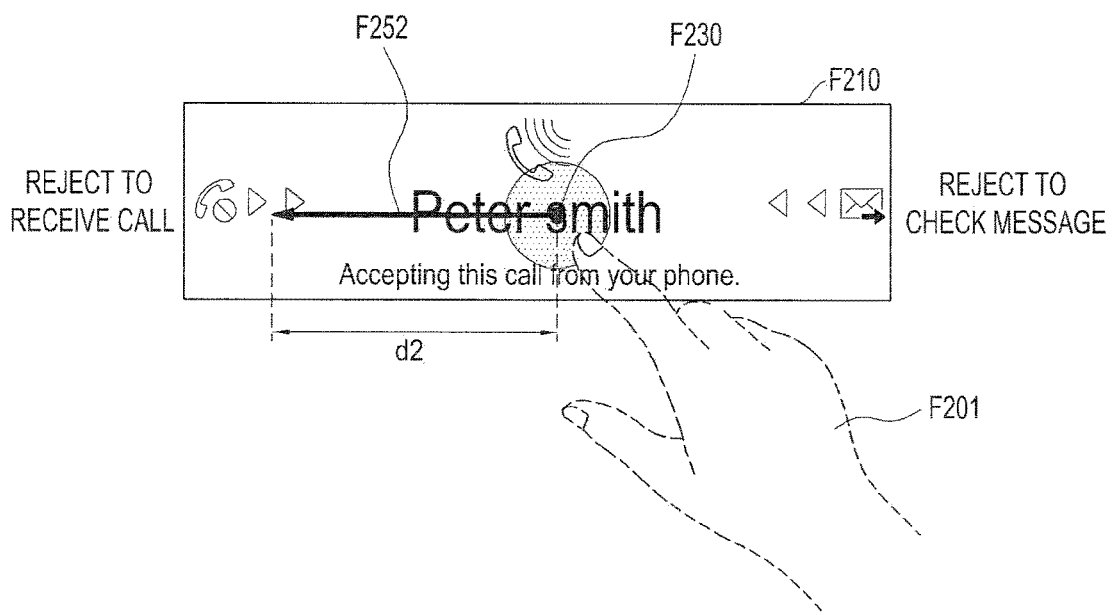
Figure 196:
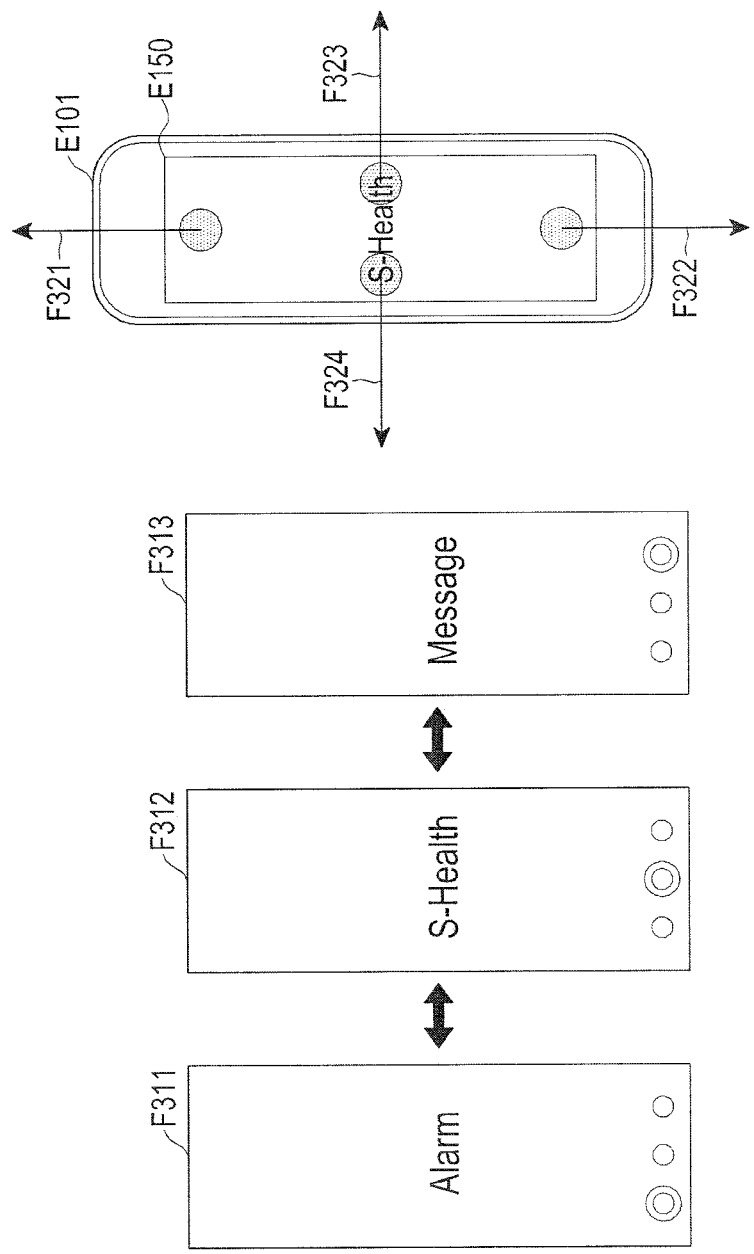
Figure 197:
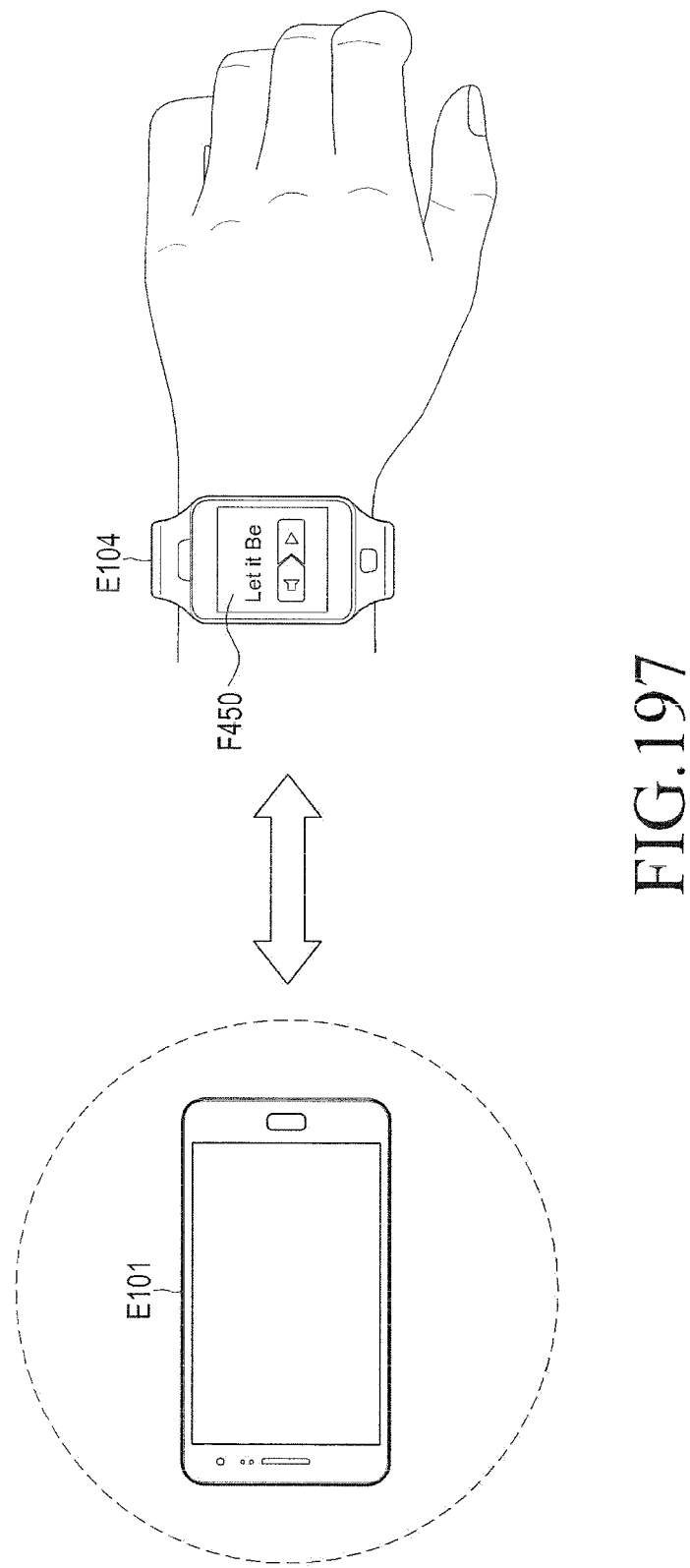
Figure 198:
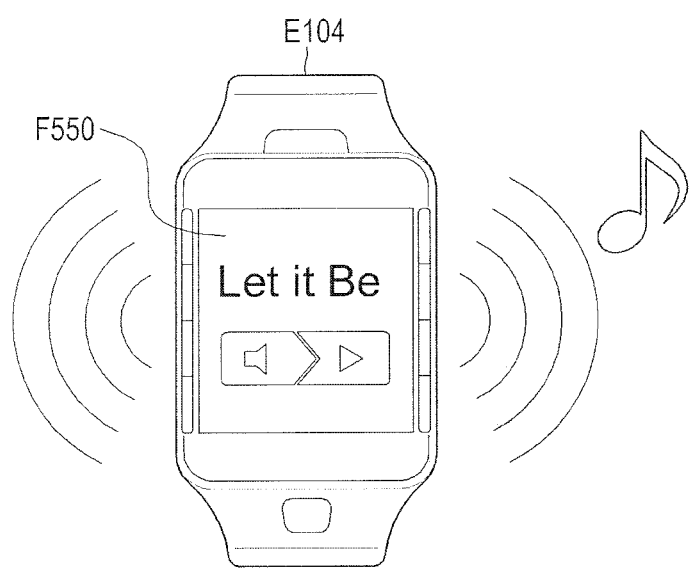
Figure 199:
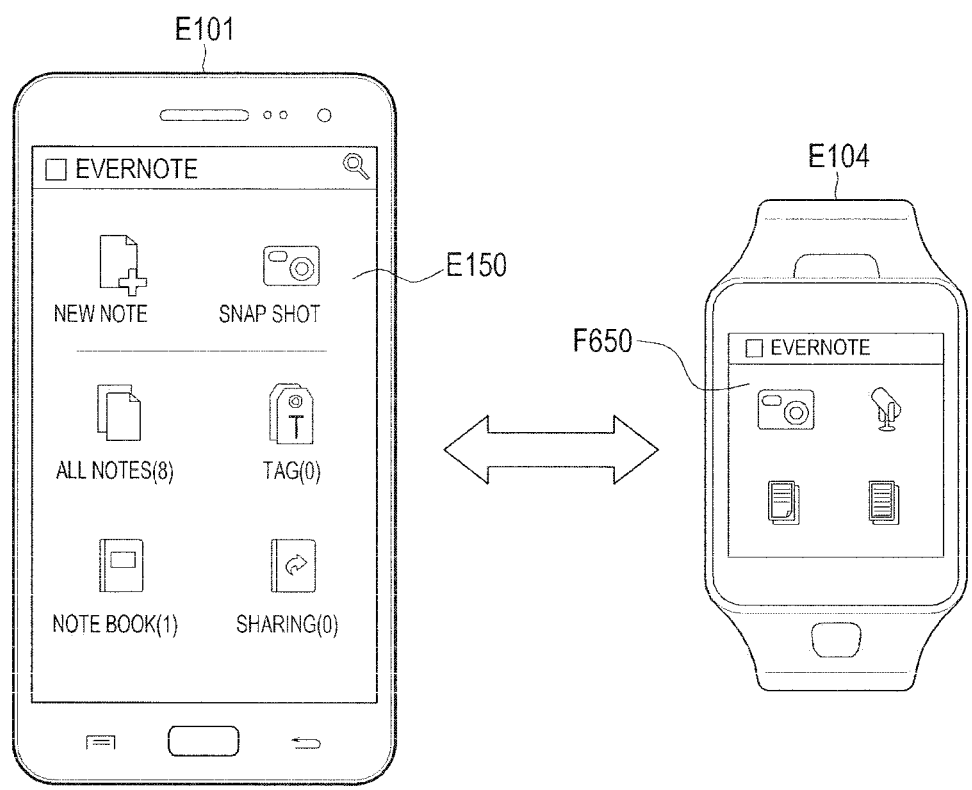
Figure 202:
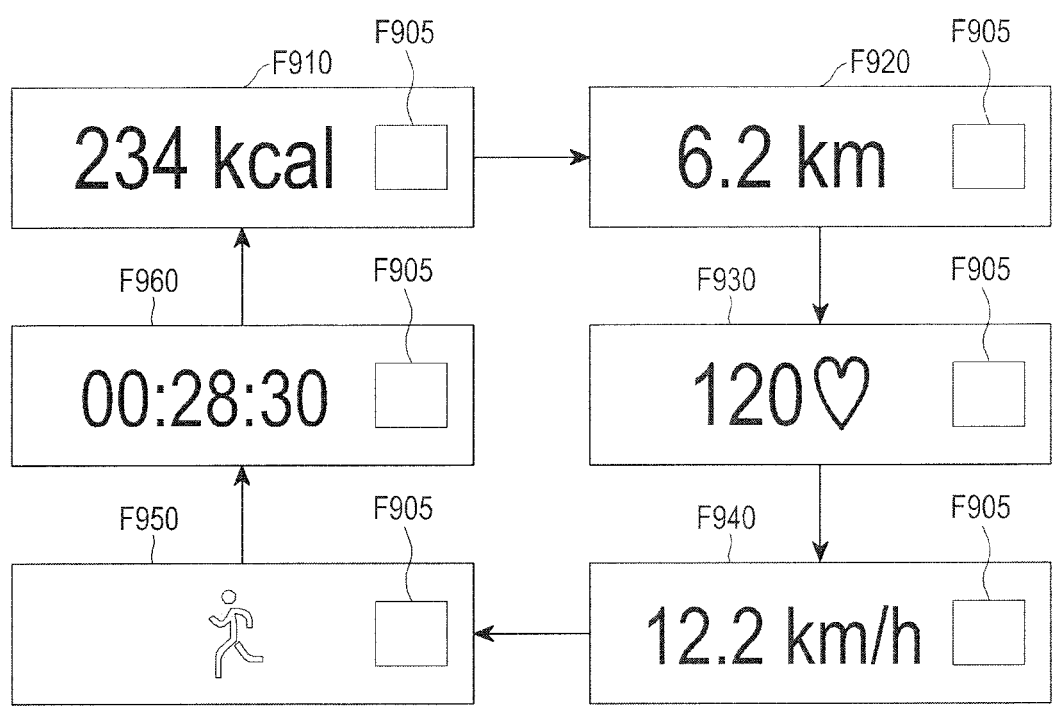
Figure 204A:
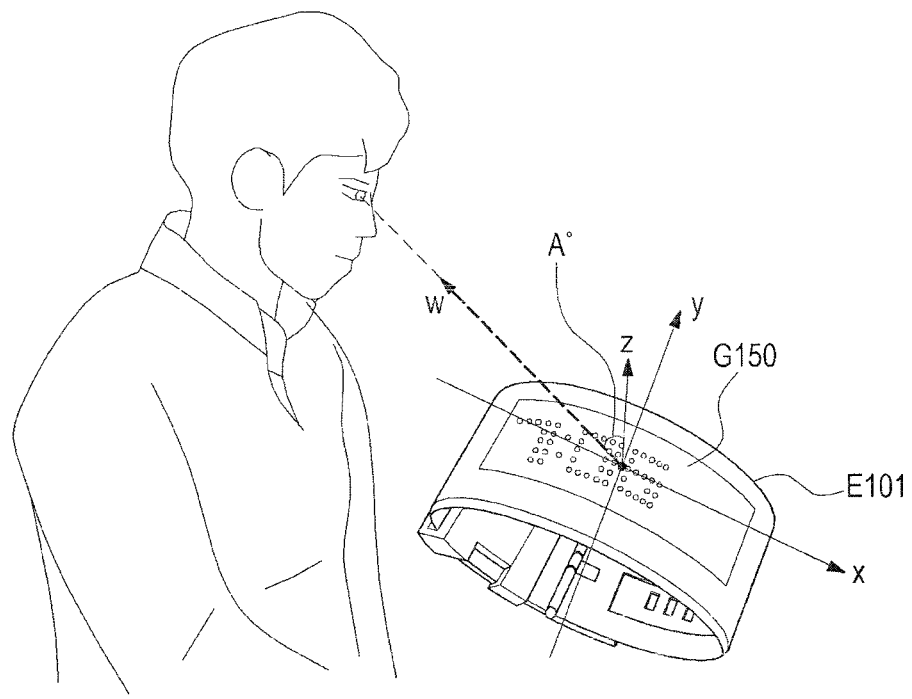
Figure 204B:
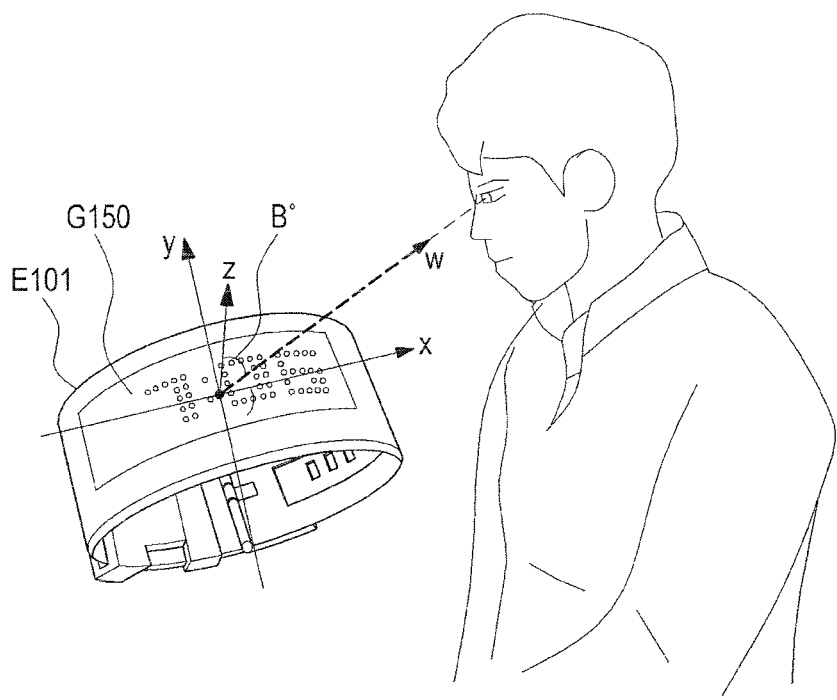
Figure 206:
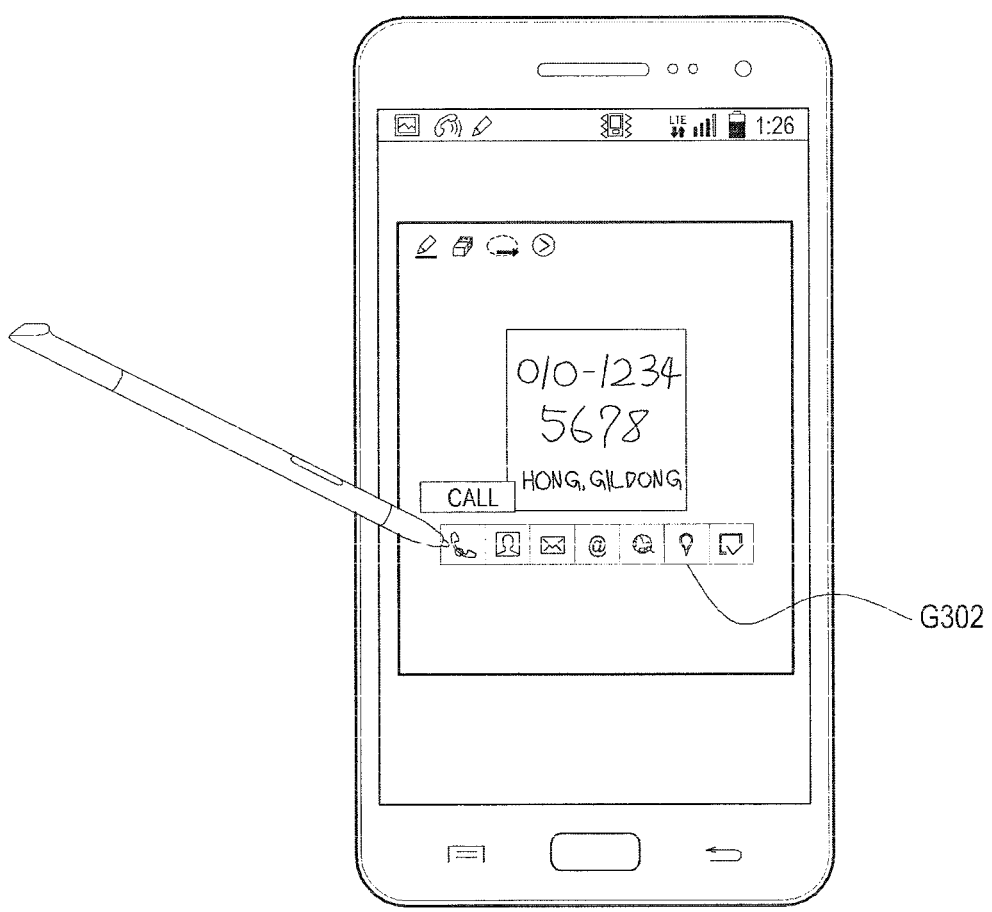
Figure 207:
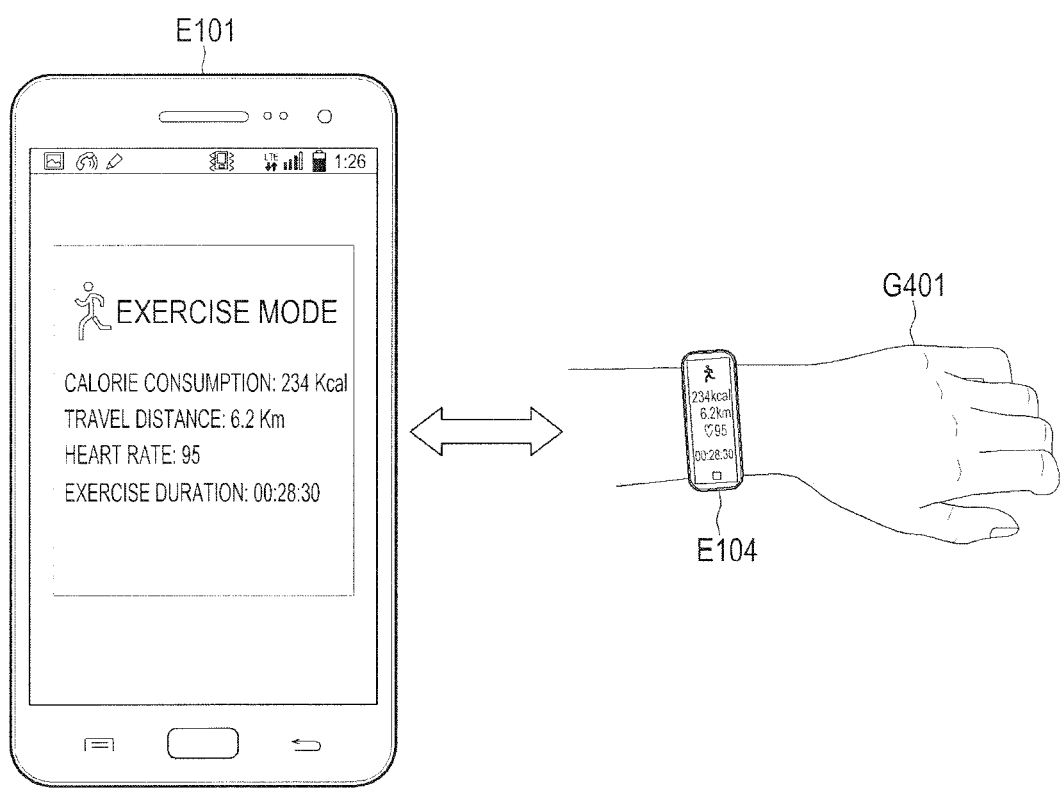

FIG. 135 illustrates a screen interface related to a remote control-related haptic information operation according to an embodiment;

FIG. 136 is a view related to a virtual key button-related haptic information operation according to an embodiment;

FIG. 137 is a view illustrating a page shifting-related haptic information operation according to an embodiment;

FIG. 138 is a view illustrating a page edge folding-related haptic information operation according to an embodiment;

FIG. 139 is a view illustrating a page flipping-related haptic information operation according to an embodiment;

FIG. 140 is a view related to a haptic information operation according to input information according to an embodiment;

FIG. 141 is a view related to a haptic information operation according to clock function execution information according to an embodiment;

FIG. 142 is a view related to an external environment and per-healthcare function-related execution information haptic information operation;

FIG. 143 illustrates a per exercise speed-related execution information haptic information operation among health coaching functions according to an embodiment;

FIG. 144 illustrates a per-stress-related execution information haptic information operation according to an embodiment;

FIG. 145 illustrates a per-deep sleep degree-related execution information haptic information operation according to an embodiment;

FIG. 146 is a view related to a per-input object haptic information operation according to an embodiment;

FIG. 147 is a view related to a per-touch area haptic information operation according to an embodiment;

FIG. 148 is a view related to detecting a touch area and a haptic information operation according to the same according to an embodiment;

FIG. 149 is a view related to a haptic information operation in virtual reality according to an embodiment;

FIG. 150 illustrates a haptic information operation method related to input error correction according to an embodiment;

FIG. 151 illustrates a screen information-related haptic information operation according to an embodiment;

FIG. 152 is a view illustrating a configuration of a system according to an embodiment;

FIG. 153 is a view illustrating a method of controlling a system according to an embodiment;

FIG. 154 is a view illustrating a method of controlling a system according to an embodiment;

FIG. 155 is a view illustrating a method of controlling a system according to an embodiment;

FIG. 156 is a view illustrating a method of controlling a system according to an embodiment;

FIG. 157 is a block diagram illustrating a configuration of a wearable electronic device according to an embodiment;

FIG. 158 is a view illustrating an example of receiving a touch input;

FIG. 159 is a view illustrating a UI displayed on a wearable electronic device according to an embodiment;

FIG. 160 is a block diagram illustrating a configuration of a main electronic device according to an embodiment;

FIG. 161 is a view illustrating a UI displayed on a main electronic device according to an embodiment;

FIG. 162 is a flowchart illustrating a method of controlling a wearable electronic device according to an embodiment;

FIG. 163 is a flowchart illustrating a method of controlling a main electronic device according to an embodiment;

FIG. 164 is a flowchart illustrating a method of controlling a main electronic device according to an embodiment;

FIG. 165 is a flowchart illustrating a method of controlling a main electronic device according to an embodiment;

FIG. 166 is a block diagram illustrating a device management module of an electronic device according to an embodiment;

FIG. 167 is a flowchart illustrating a method of controlling a plurality of input/output devices by an electronic device according to an embodiment;

FIG. 168 is a flowchart illustrating a method of controlling a plurality of input/output devices by an electronic device according to an embodiment;

FIG. 169 is a flowchart illustrating a method of controlling a plurality of input/output devices by an electronic device according to an embodiment;

FIG. 170 illustrates a communication protocol between a plurality of electronic devices according to an embodiment;

FIG. 171 is a block diagram illustrating a device control module of an electronic device according to an embodiment;

FIG. 172 illustrates a device state table according to an embodiment;

FIG. 173 illustrates an external device according to an embodiment;

FIG. 174 illustrates an electronic device operation method according to an embodiment;

FIG. 175 illustrates an external device operation method according to an embodiment;

FIG. 176 is a signal flowchart of a request information operation system according to an embodiment;

FIG. 177 illustrates function mode-related control according to an embodiment;

FIG. 178 illustrates an operation as per a surrounding environment of an electronic device according to an embodiment;

FIG. 179 illustrates a schedule-related operation according to an embodiment;

FIG. 180 illustrates a state control table operation related to forming a communication channel according to an embodiment;

FIG. 181 illustrates a state control table operation related to disconnection according to an embodiment;

FIG. 182 illustrates a state control table operation related to a low battery status of an electronic device according to an embodiment;

FIG. 183 illustrates a state control table operation related to a low battery status of an external device according to an embodiment;

FIG. 184 illustrates a device operation method according to an embodiment;

FIG. 185 is a view illustrating an electronic device (e.g., a block diagram of a control module of the electronic device) according to an embodiment;

FIG. 186 is a flowchart illustrating an example of a method of displaying content by an electronic device according to an embodiment;

FIG. 187 is a flowchart illustrating another example of a method of displaying content by an electronic device according to an embodiment;

FIG. 188 is a flowchart illustrating another example of a method of displaying content by an electronic device according to an embodiment;

FIG. 189 is a flowchart illustrating another example of a method of displaying content by an electronic device according to an embodiment;

FIG. 190 is a view illustrating an example of a method of displaying content by an electronic device according to an embodiment;

FIG. 191 is a view illustrating another example of a method of displaying content by an electronic device according to an embodiment;

FIG. 192 is a view illustrating another example of a method of displaying content by an electronic device according to an embodiment;

FIG. 193 is a view illustrating another example of a method of displaying content by an electronic device according to an embodiment;

FIG. 194 is a view illustrating another example of a method of displaying content by an electronic device according to an embodiment;

FIGS. 195a and 195b are views illustrating another example of a method of displaying content by an electronic device according to an embodiment;

FIG. 196 is a view illustrating another example of a method of displaying content by an electronic device according to an embodiment;

FIG. 197 is a view illustrating another example of a method of displaying content by an electronic device according to an embodiment;

FIG. 198 is a view illustrating another example of a method of displaying content by an electronic device according to an embodiment;

FIG. 199 is a view illustrating another example of a method of displaying content by an electronic device according to an embodiment;

FIG. 200 is a view illustrating another example of a method of displaying content by an electronic device according to an embodiment;

FIG. 201 is a view illustrating another example of a method of displaying content by an electronic device according to an embodiment;

FIG. 202 is a view illustrating another example of a method of displaying content by an electronic device according to an embodiment;

FIGS. 203a to 203d are views illustrating another example of a method of displaying content by an electronic device according to an embodiment;

FIGS. 204a and 204b are views illustrating another example of a method of displaying content by an electronic device according to an embodiment;

FIG. 205 is a view illustrating another example of a method of displaying content by an electronic device according to an embodiment;

FIG. 206 is a view illustrating another example of a method of displaying content by an electronic device according to an embodiment; and FIG. 207 is a view illustrating an example of a method of displaying content by a plurality of electronic devices according to an embodiment.

MODE FOR CARRYING OUT THE INVENTION

Hereinafter, various embodiments are described with reference to the accompanying drawings. Various changes may be made to the present invention, and the present invention may come with a diversity of embodiments. Some embodiments of the present invention are shown and described in connection with the drawings. However, it should be appreciated that the present invention is not limited to the embodiments, and all changes and/or equivalents or replacements thereto also belong to the scope of the present invention. The same or similar reference denotations are used to refer to the same or similar elements throughout the specification and the drawings.

The terms "comprise" and/or "comprising" as herein used specify the presence of disclosed functions, operations, or components, but do not preclude the presence or addition of one or more other functions, operations, or components. It will be further understood that the terms "comprise" and/or "have," when used in this specification, specify the presence of stated features, integers, steps, operations, elements, and/or components, but do not preclude the presence or addition of one or more other features, integers, steps, operations, elements, components, and/or groups thereof.

As used herein, the term "and/or" includes any and all combinations of one or more of the associated listed items. For examples, "A or B" may include A, or include B, or include both A and B.

Ordinal numbers as herein used, such as "first", "second", etc., may modify various components of various embodiments, but do not limit those components. For example, these terms do not limit the order and/or importance of the components. These terms are only used to distinguish one component from another. For example, a first user device and a second user device are different user devices from each other. For example, a first component may be denoted a second component, and vice versa without departing from the scope of the present disclosure.

When a component is "connected to" or "coupled to" another component, the component may be directly connected or coupled to the other component, or other component(s) may intervene therebetween. In contrast, when a component is "directly connected to" or "directly coupled to" another component, no other intervening components may intervene therebetween.

The terms as used herein are provided merely to describe some embodiments thereof, but not to limit the present invention. It is to be understood that the singular forms "a," "an," and "the" include plural references unless the context clearly dictates otherwise.

Unless otherwise defined, all terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to various embodiments, the electronic device may be a device including a communication function. Examples of the electronic device according to embodiments of the present invention may include at least one of a smartphone, a tablet personal computer (PC), a mobile phone, a video phone, an e-book reader, a desktop PC, a laptop computer, a netbook computer, a personal digital assistant (PDA), a portable multimedia player (PMP), an MP3 player, a mobile medical device, a camera, or a wearable device (e.g., a head-mounted device (HMD), such as smart glasses, electronic clothes, an electronic bracelet, an electronic necklace, an electronic appcessory, an electronic tattoo, or a smart watch).

According to an embodiment, the electronic device may be a smart home appliance with a communication functionality. For example, examples of the smart home appliance may include, but is not limited to, a television, a digital video disk (DVD) player, an audio player, a refrigerator, an air conditioner, a vacuum cleaner, an oven, a microwave oven, a washer, a drier, an air cleaner, a set-top box, a TV box (e.g., Samsung HomeSync™, Apple TV™, or Google TV™), a gaming console, an electronic dictionary, a camcorder, or an electronic picture frame.

According to an embodiment, examples of the electronic device may include, but is not limited to, various medical devices (e.g., magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, an sailing electronic device (e.g., a sailing navigation device, a gyroscope, or a compass), avionics, security devices, vehicular head units, industrial or home robots, automatic teller machines (ATMs), or point of sales (POS) devices.

According to various embodiments of the disclosure, examples of the electronic device may at least one of part of a piece of furniture or building/structure with a communication functionality, an electronic board, an electronic signature input device, a projector, or various measurement devices (e.g., devices for measuring water, electricity, gas, or electromagnetic waves). According to an embodiment, the electronic device may be one or a combination of the above-listed devices. According to an embodiment, the electronic device may be a flexible device. According to an embodiment, the electronic device is not limited to the above-listed devices or appliances.

Various embodiments of the present invention are now described with reference to the accompanying drawings. As used herein, the term "user" may denote a human or another device using the electronic device.

According to an embodiment, the electronic device may include a wearing portion extending in a direction and having an opening and a main body detachably provided to the opening. The wearing portion may be fastened to the user's body to allow the main body to be worn on the user's body.

The opening is provided so that its four inner walls each form at least a portion of an edge of a rectangle and that two adjacent inner walls may be connected via a curved surface.

In an embodiment, the wearing portion may include a first wearing member extending from a portion of a surrounding edge of the opening to a side and a second wearing member extending from another portion of the surrounding edge of the opening to an opposite side. The first and second wearing members are coupled together so that the wearing portion forms a looped curve allowing it to be coupled to the user's body.

In another embodiment, the wearing portion may further include at least one coupling member provided in an inner wall of the opening, and the coupling member may be fastened to the surrounding edge of the main body.

The above coupling member may be shaped as a looped curve facing the surrounding edge of the main body or at least a pair of coupling members may be continuously arranged along the inner wall of the opening.

In another embodiment, the coupling member may be electrically connected with the main body.

In another embodiment, the electronic device may further include a magnetic body provided in the coupling member and a hall sensor provided in the main body to recognize the magnetic body. As the hall sensor recognizes the magnetic body while the main body is mounted on the wearing portion, the main body may detect a mounting direction to the wearing portion.

The electronic device may further include a fastening member provided in the first wearing member and fastening holes formed in the second wearing member and arranged along the extending direction of the second wearing member. The fastening member may be engaged to at least one of the fastening holes to keep the wearing portion in the looped curve shape.

In some embodiment, the electronic device may further include a second fastening member provided in the second wearing member. The second fastening member may be provided to face at least a portion of the surrounding edge of the first wearing member.

The fastening member may include at least one fastening protrusion formed on an inner surface. The fastening protrusion may be engaged to one of the fastening holes.

In one embodiment, the fastening member may further include a fixing part fixed to an outer surface of the first wearing member. The fastening protrusion may extend from the fixing part to pass through the first wearing member.

The electronic device may further include a second opening formed in the wearing portion and a second main body detachably provided to the second opening.

In another embodiment, the main body may include a curved display device or flexible display device mounted on the front surface.

In the above electronic device, the main body may include a fastening groove formed in the periphery of a side surface, and a portion of the wearing portion may be engaged to the fastening groove.

In some embodiment, the fastening groove may be shaped as a looped curve along the side surface of the main body.

In the above electronic device, the fastening groove may include a first inner wall positioned adjacent to the front surface of the main body, a second inner wall positioned adjacent to the rear surface of the main body, and a bottom connecting the first and second inner walls. The first inner wall may be formed to be away from the rear surface of the main body as it becomes distant from the bottom.

In one embodiment, the width of the main body between the fastening groove and the front surface of the main body may be set to be smaller than the width of the main body between the fastening groove and the rear surface of the main body.

In another embodiment, the main body may include a front surface and a rear surface contacting the user's body while worn. The width of the main body in the front surface may be formed to be smaller than the width of the main body in the rear surface.

In another embodiment, the main body may include a front surface and a rear surface contacting the user's body while worn. The front surface and the rear surface may be formed of curved surfaces with different curvatures.

In the above electronic device, the main body may include a sensor portion installed on the rear surface, and the rear surface of the main body may contact the user's body while the electronic device is worn on the user's body.

In one embodiment, the main body may further include a through hole formed in the rear surface. The sensor portion may include a bio signal sensor disposed on the through hole.

In another embodiment, the main body may further include a recessed portion formed to be stepped on the rear surface at the periphery of the through hole, and the interface window edge of the bio signal sensor may be accommodated in the recessed portion.

In another embodiment, the main body may further include a sealing member interposed between the recessed portion and the interface window at the periphery of the through hole.

In the above electronic device, the sensor portion may include a bio signal sensor detecting at least one of the user's photo plethysmo graph (PPG), sleep period, skin temperature, or heart rate.

According to an embodiment, the electronic device may further include a battery pack embedded in the main body and a bracket provided to face at least a portion of the battery pack.

In one embodiment, the electronic device may further include a second bracket embedded in the main body, and the battery pack may be interposed between the bracket and the second bracket.

The electronic device may further include a first circuit board at least partially facing the bracket. The first circuit board may be disposed to face the battery pack.

In another embodiment, the electronic device may further include the second bracket interposed between the battery pack and the first circuit board.

In another embodiment, the electronic device may further include a second circuit board disposed to be inclined with respect to the first circuit board at a side of the first circuit board.

In another embodiment, the electronic device may further include a vibration module disposed at another side of the first circuit board. The vibration module may be disposed, at least partially, in parallel with the battery pack inside the main body.

According to an embodiment, the electronic device may further include a display device supported to a surface of the bracket. The display device may be installed on the front surface of the main body.

According to an embodiment, the electronic device may further include a mount. The main body separated from the wearing portion may be detachably placed on the mount.

In one embodiment, the main body may include a connecting member disposed on a surface (e.g., rear surface) thereof, and the main body may be electrically connected to the mount via the connecting member.

In another embodiment, the mount may include a seating surface facing at least a portion of a surface (e.g., rear surface) of the main body and fixing surfaces facing each other and extending from the seating surface. The fixing surfaces may be provided to face at least a portion of another surface (e.g., side surface) of the main body.

In another embodiment, the main body may include a fixing hole formed in a surface (e.g., side surface), and the mount may include a fixing protrusion formed in the fixing surface. The fixing protrusion may be engaged to the fixing hole to fix the main body to the mount.

In another embodiment, the mount may include an interface connector.

The electronic device may further include a fixing device connected to the mount. The fixing device may be implemented as a clip, snap button, magnet body, or Velcro tape.

In another embodiment, the electronic device may further include a connecting portion formed of a soft material to connect the mount to the fixing device.

Figure 1:
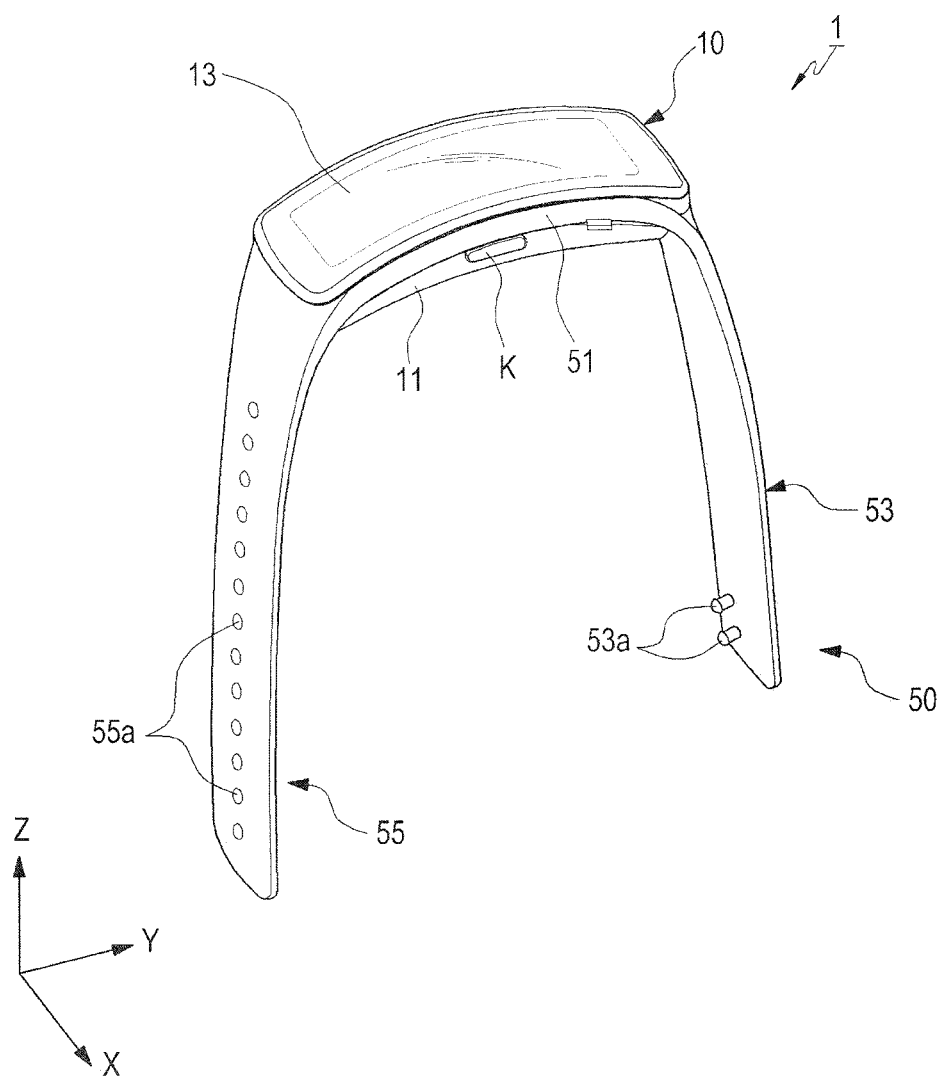
FIG. 1 is a perspective view illustrating an electronic device according to an embodiment.
Figure 2:
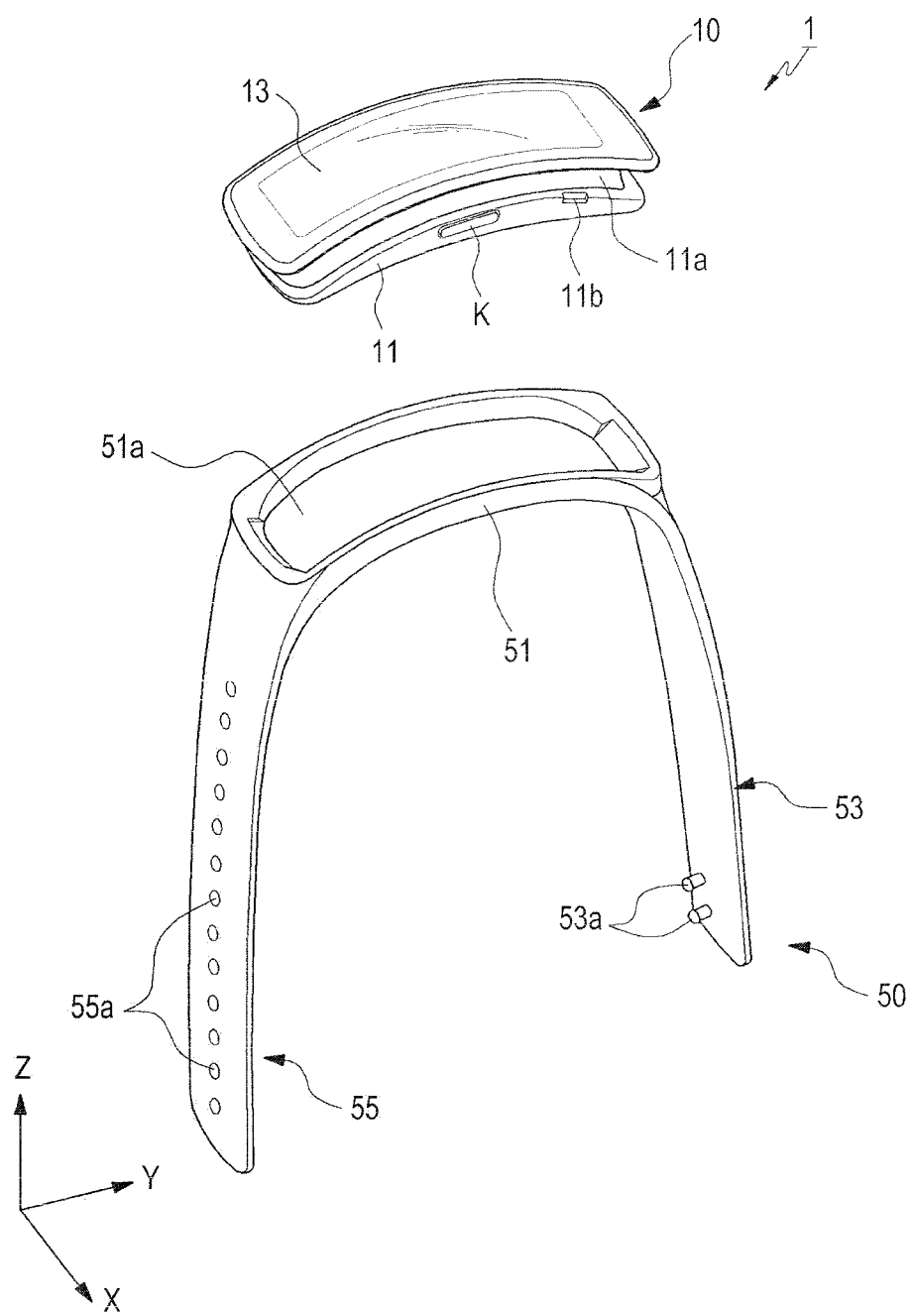
FIG. 2 is a perspective view illustrating an example in which a main body is separated from a wearing portion in an electronic device according to an embodiment.
Figure 3:
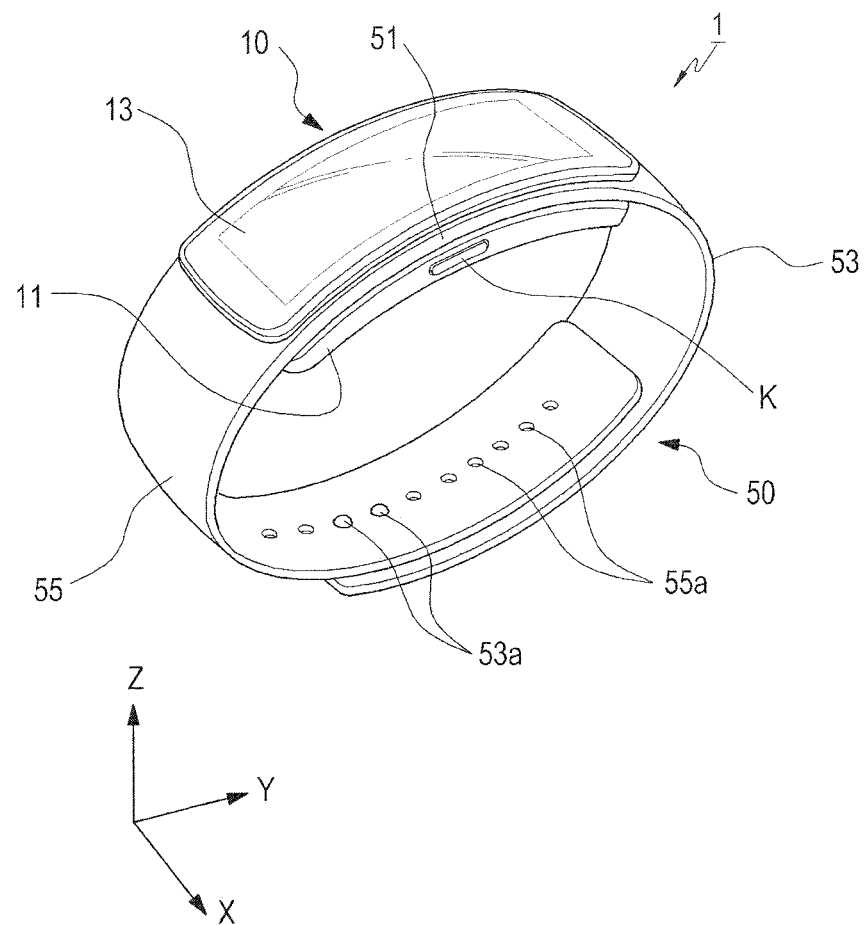
FIG. 3 is a perspective view illustrating a state where an electronic device is worn according to an embodiment.
Figure 4:
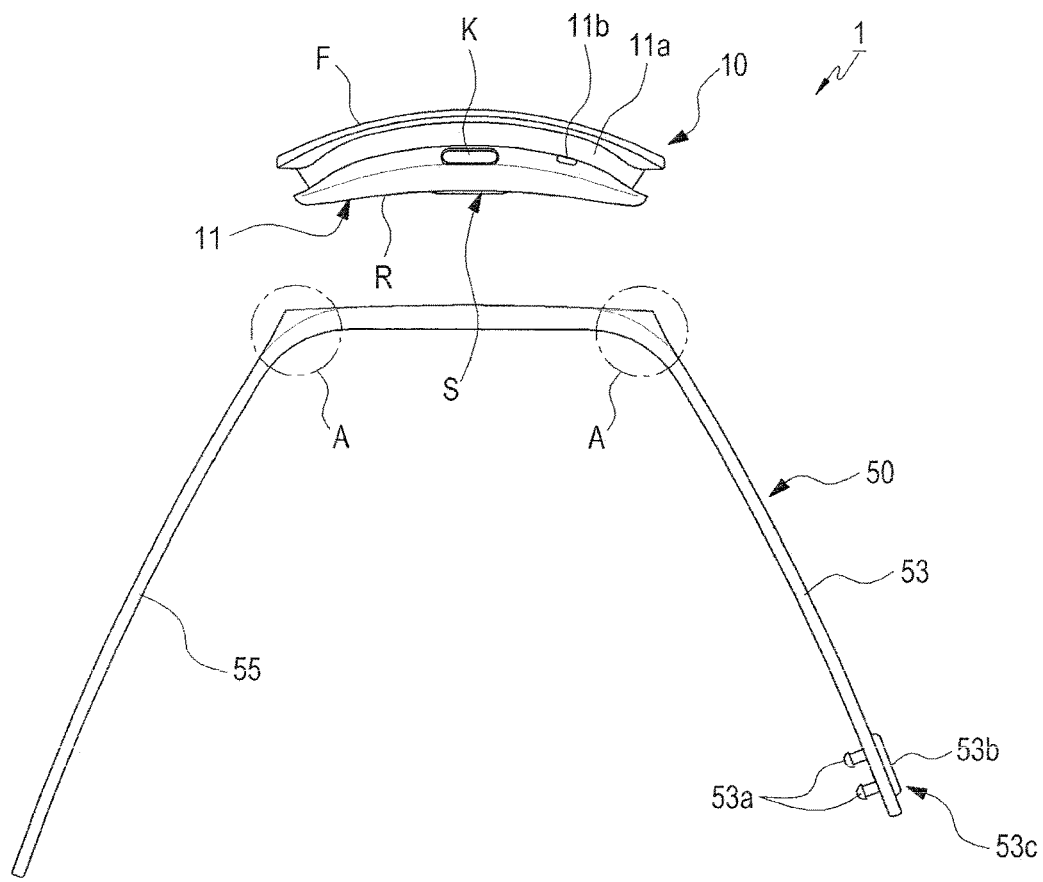
FIG. 4 is a side view illustrating an electronic device according to an embodiment.
Figure 5:
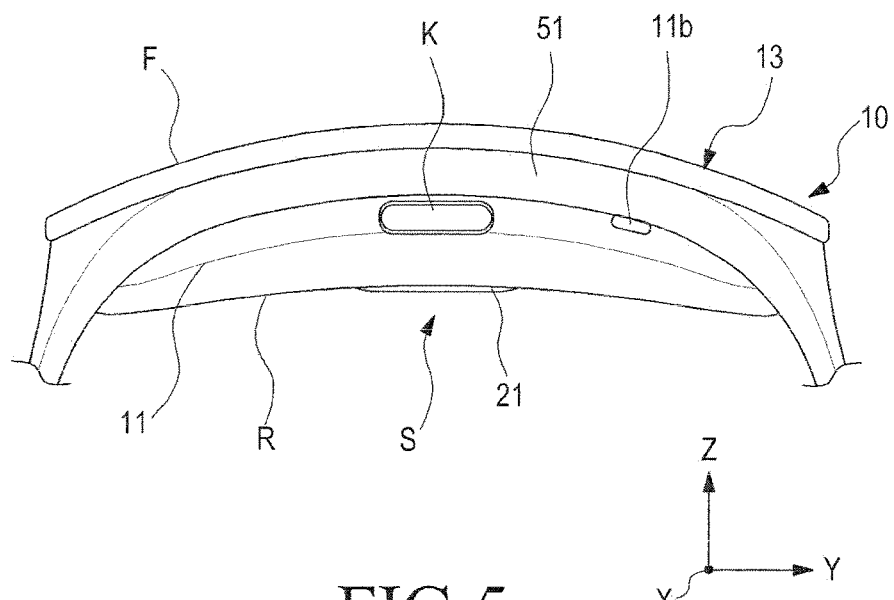
FIG. 5 is an expanded side view illustrating a portion of an electronic device according to an embodiment.

FIG. 1 is a perspective view illustrating an electronic device according to an embodiment. FIG. 2 is a perspective view illustrating an example in which a main body is separated from a wearing portion in an electronic device according to an embodiment. FIG. 3 is a perspective view illustrating a state where an electronic device is worn according to an embodiment. FIG. 4 is a side view illustrating an electronic device according to an embodiment. FIG. 5 is an expanded side view illustrating a portion of an electronic device according to an embodiment.

Referring to FIGS. 1 to 5, a three-dimensional X/Y/Z orthogonal coordinate system is shown. The "Z" axis refers to an upper-lower direction (thickness direction) of the main body 10 of the electronic device 1, the "X axis" a horizontal direction of the main body 10, and the "Y axis" a vertical direction of the main body 10.

In the instant embodiment, as the electronic device 1, a wearable electronic device, e.g., an electronic device that may be put on the user's wrist, such as a wristwatch or bracelet, is exemplified. Various embodiments are not limited thereto, and according to embodiments, the electronic device may be implemented as various communication devices or assistant medical devices. Further, according to an embodiment, the electronic device may apply to a curved part of the user's body in a diversified manner. The curved part of the user's body may be, e.g., a wrist or ankle. According to an embodiment, the electronic device may be easily put on various parts of the user's body depending on the configuration of a wearing unit.

According to an embodiment, the electronic device 1 may include the main body 10 (a function device portion) and a wearing portion 50 including a wearing member (e.g., a band or strap). The main body 10 may be detachably coupled to the wearing portion 50. On the main body 10 may be arranged a display device 13 to display various types of information, a pressing key (e.g., a side key K) to enter various types of information, a sensor portion S (e.g., a bio signal sensor), or a touch input unit. The main body 10 may include a front surface F and a rear surface R contacting the user's body when the electronic device is worn on the user). The display device 13 may be positioned on the front surface F of the main body 10, and the sensor portion S may be positioned on the rear surface R of the main body 10.

The main body 10 may be shaped as a bar and may at least partially have a curvature corresponding to the user's body. For example, the main body 10 may be shaped substantially as a rectangle extending in the vertical direction (the Y axis direction) with a curvature. The main body 10 may have a connecting hole 11*a* on its side for coupling with the wearing portion 50. A plurality of connecting holes 11*a* may be formed in the side surface of the main body 10, or the connecting hole 11*a* may be shaped as a looped curve extending along the periphery of the main body 10.

The wearing portion 50 may be formed of an elastic material and enables the main body 10 to be stably worn on the user's body. As necessary, the wearing portion 320 may bring the main body 10 in tight contact with the user's skin. The main body 10 may be detachably coupled to the wearing portion 50. Accordingly, the wearing portion 50 may be replaced by the user's taste or preference. According to an embodiment, the portion (e.g., seating portion 51) of the wearing portion 50 that is coupled to the main body 10 may be configured to be elastically transformed, and the worn surface (e.g., the inner surface of the first and second wearing members 53 and 55) brought in tight contact with the user's body might not be formed of an elastic material. The wearing portion 50 may have an opening 51a extending in a direction thereof and where the main body 10 is fitted or removed. The seating portion 51 may be formed to surround the periphery of the opening 51a, and, at least, the seating portion 51 of the wearing portion 50 may be formed of an elastic material. When the main body 10 is coupled to the wearing portion 50, at least a portion of the seating portion 51 may be inserted into the connecting hole 11a along a side surface of the main body 10.

The opening 51a is an open space where the main body 10 is inserted and is shaped to be surrounded by the seating portion 51. According to this embodiment, the opening 51a may be shaped as a rectangle having substantially a thickness. As viewed from above, the opening 51a may be shaped as a rectangle which is longer in the vertical direction Y than in the horizontal direction X. Further, the wearing portion 50 may include a linear portion surrounding the opening 51a, e.g., the seating portion 51. The first and second wearing members 53 and 55 may extend away from each other along the vertical direction Y of the main body 10 at the periphery of the opening 51a, e.g., at least, a portion of the seating portion 51. However, the first and second wearing members 53 and 55 may have a shape curved along the thickness direction (Z) of the main body 10 with respect to the seating portion 51 considering that the electronic device 1 is worn on the user's body.

The wearing portion 50 may include a means to together couple the first and second wearing members 53 and 55. For example, the first wearing member 53 may have a fastening means 53c, and the second wearing member 55 may include multiple fastening holes 55a. The fastening holes 55a may be arrayed along the extending direction of the second wearing member 55 and may be engaged with the first fastening member 53c. As the first fastening member 53c is engaged with one of the fastening holes 55a to fasten together the first and second wearing members 53 and 55, allowing the wearing portion 50 to maintain its looped curve shape.

The first fastening member 53c may include a fastening protrusion 53a projecting to an internal surface of the first wearing member 53. The fastening protrusion 53a may be formed as a single body with the first wearing member 53 or may be produced as a separate part to be assembled in the first wearing member 53. For example, the first fastening member 53c may include a fixing portion 53b fixed to an outer surface of the first wearing member 53. The fastening protrusion 53a may extend from the fixing portion 53b to pass through the first wearing member 53. When wearing the electronic device 1, the user may select the position of the fastening hole 55a engaged with the first fastening member 53c, e.g., the fastening protrusion 53a, considering, e.g., the size and curvature of where the electronic device 1 is to be worn.

The above-described fastening structure is merely an example and may be replaced with other various structures (e.g., a buckle or hook-type fastening structure) depending on the material and structure of the first and second wearing members 53 and 55.

The electronic device 1 may include a connecting hole 11a formed along the periphery of a side surface, among surfaces of the body housing 11 constituting the main body 10, and a seating portion 51 formed at the periphery of the opening 51a of the wearing portion 50 to fit into the connecting hole 11a. The electronic device 1 may further include a coupling member that, after the main body 10 is inserted into the wearing portion 50, may more securely fasten the main body 10 to the wearing portion 50. Such coupling member is described below in greater detail.

The main body 10, e.g., the body housing 11, may have a shape with a curvature. Since the seating portion 51 is formed of an elastic material and may thus be elastically deformed, the seating portion 51 may be deformed to fit the shape of the main body, e.g., the shape of the connecting hole 11a, and coupled thereto. The wearing portion 50, because of having an exchangeable structure, may be implemented to have various designs or colors and may be replaced by the user's taste. That is, the wearing portion 50 may be utilized as a fashion accessory to represent the user's individuality. Further, the main body 10 has a shape (e.g., substantially rectangular) corresponding to the seating portion 51 (or the opening 51a), and the electronic device 1 may activate various functions depending on directions of coupling the main body 10 to the wearing portion 50. Activation of different functions depending on the coupling direction of the main body 10 is described below in greater detail.

Generally, users have different wrist sizes, e.g., curvatures. Since individual users have different wrist curvatures, the users have different feelings when wearing the same shape of electronic device. For example, since a woman has a thinner wrist than a man, it may be difficult to provide all users with comfortable wearability when wearing the same wearable electronic device. However, according to an embodiment, the electronic device 1 has a structure in which the main body 10 and the wearing portion 50 are attached or detached, and the user may select a wearing portion 50 appropriate for his body feature to have comfortable wearability.

Referring to FIG. 4, comfortable wearability may be provided depending on various users' body shape by allowing the wearing portion 50 different curvatures in the boundary area A where the seating portion 51 is connected with the first or second wearing member 53 or 55. For example, when the main body 10 is coupled, the seating portion 51 maintains the same curvature as the first curvature (e.g., the curvature of the front surface F) of the main body 10 but may have a different curvature from the first curvature in the boundary area A. Further, the curvature of the fastening groove 11a in the side surface of the main body 10 may be configured to be different from the first curvature in the boundary area A. In case the curvature provided by the fastening groove 11a and the seating portion 51 in the boundary area A is configured to be smaller than the first curvature of the main body 10, the electronic device 1 may provide better wearability to users with a small wrist curvature. In case the curvature provided by the fastening groove 11a and the seating portion 51 in the boundary area A is configured to be larger than the first curvature, the electronic device 1 may provide better wearability to users with a large wrist curvature.

Further, the seating portion 51 has an upper curvature and a lower curvature, and making the upper and lower curvatures different in the boundary area A may allow the user to wear with the main body 10 coupled to the wearing portion appropriate for his body. As such, the curvature of the fastening groove 11a and the seating portion 51 need not be constant, and partially varying the curvature of the fastening groove 11a in the boundary area A or shape (e.g., curvature) of the seating portion 51 may allow it to correspond to users' different body features.

In an embodiment, a fixing hole 11b may be formed in a side surface of the main body 10. The fixing hole 11b is for mounting and fixing the main body 10 to other device (e.g., mount) and this is described below in more detail with reference to FIGS. 31 to 33.

Figure 6:
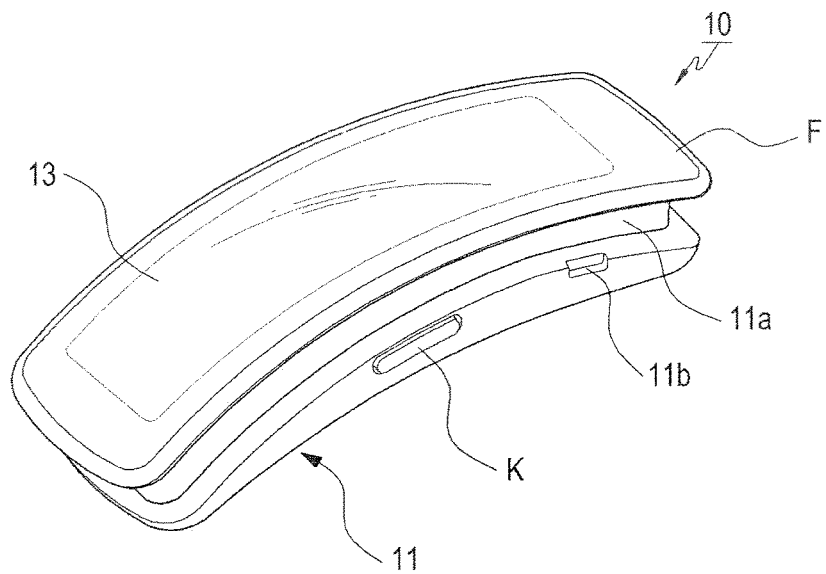
FIG. 6 is a perspective view illustrating a main body of an electronic device according to an embodiment.
Figure 7:
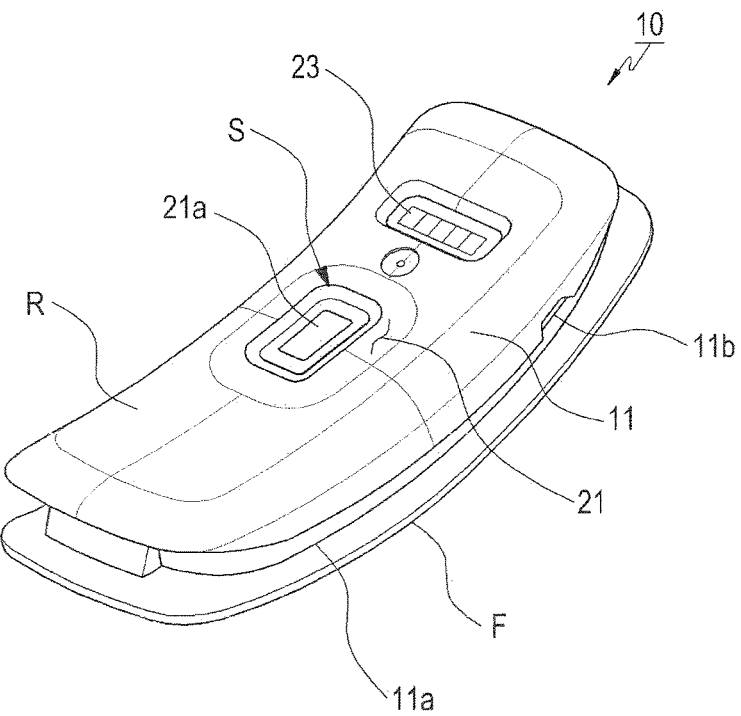
FIG. 7 is a perspective view illustrating a main body of an electronic device as viewed from a different direction according to an embodiment.

FIG. 6 is a perspective view illustrating a main body of an electronic device according to an embodiment. FIG. 7 is a perspective view illustrating a main body of an electronic device as viewed from a different direction according to an embodiment.

According to an embodiment, the main body 10 of the electronic device is shaped as a rectangular bar long in the vertical direction Y and having a curvature, and the main body 10 may include a body housing 11 and a display device 13 mounted in the body housing 11. The body housing 11 may include a front surface F, a rear surface R, and a side surface connecting the front surface F with the rear surface R. The front surface F and the rear surface R each may be configured with a curvature. The front surface F is a surface on which the display device 13 is positioned, and the rear surface R is a surface that contacts the user's body. The front surface F has a first curvature, and the rear surface R has a second curvature. The first and second curvatures may be determined considering the design of the product, the outline of the user' wrist, and the sense of wearing. In the instant embodiment, an example in which the first curvature is smaller than the second curvature is described.

The front surface F of the body housing 11 has the display device 13 disposed thereon and needs to be configured to enable easier screen viewing. The rear surface R of the body housing 311 should be configured to provide a comfortable fit. Since a sensor portion S (e.g., a bio signal sensor) is disposed on the rear surface R, the rear surface R may have a shape to tightly contact the user's wrist.

The main body 10 may be configured to gradually slim down towards both ends from a middle portion thereof along the vertical direction Y. Approximately, the body housing 11 is thick at its center and slims down away from the center along the vertical direction Y. Further, although in the instant embodiment the rear surface R has the second curvature, the rear surface R may alternatively be formed to be flat overall or partially.

The body housing 11 may have a curvature suited for the user's body shape, e.g., the thickness or curvature (e.g., the second curvature) of the wrist, thus bringing up with enhanced wearability and increased compatibility with various customers. The curved display device 13 may be provided on the front surface F of the body housing 11, and the sensor portion S, e.g., a bio signal sensor, may be provided on the rear surface R of the body housing 311. The rear surface R may come in contact with the user's body (e.g., a wrist). As set forth above, the body housing 11 may be shaped to have a curvature considering the user's body shape and allows the sensor portion S to come in tight contact with the user's body. The sensor portion S provided in the main body 10 may be formed as a bio signal sensor detecting at least one of the user's photo plethysmo graph (PPG), sleep period, skin temperature, or heart rate. Although the display device 13 is shown to have a shape reflecting the user's body curvature, the display 315 may alternatively be configured as a flat display (e.g., a liquid crystal display (LCD) or an organic light emitting diode (OLED) display), a curved display, or a flexible display. For example, although in the instant embodiment the main body 10 has a curved display, the main body 310 may alternatively have a flat display or a flexible display.

The sensor portion S may include a sensor interface 21a, e.g., an interface window, disposed on the rear surface R of the main body 11. To place the sensor interface 21a, the protrusion 21 may be formed on the rear surface R. As the sensor interface 21a is disposed on the protrusion 21, the sensor portion S may come in more tight contact with the user's body when sensing a bio signal. Contact members 23, e.g., charging terminals, may be arranged on the rear surface R of the main body 11. The array of the contact members 23 may be positioned adjacent to the sensor portion S. While the user wears the electronic device 1, the contact members 23 may be hidden by the main body 10 or the user's body.

A fastening groove 11a is formed in a side surface of the body housing 11. The fastening groove 11a may extend along the side surface of the body housing 11 to have a looped curve shape, and the side surface positioned to face the horizontal direction X among the side surfaces of the body housing 11 may have a curvature. The fastening groove 11a may be configured with the same curvature as the first curvature of the front surface of the body housing 11. However, because different users have different wrist curvatures, the curvature of the fastening groove 11a may be formed to be smaller than the first curvature. The fastening groove 11a includes an upper curvature and a lower curvature in a portion, and varying the lower curvature may allow it to correspond to the respective different wrist curvatures of the users. The upper curvature and lower curvature of the fastening groove 11a may be formed to be different in the boundary area A depending on the wrist curvature of the wearing user. As such, the curvature of the fastening groove 11a may be set to be the same or different from the first curvature, e.g., the curvature of the front surface of the body housing 11. This may be properly selected considering each user's wearability and the size of actual product.

Figure 8:
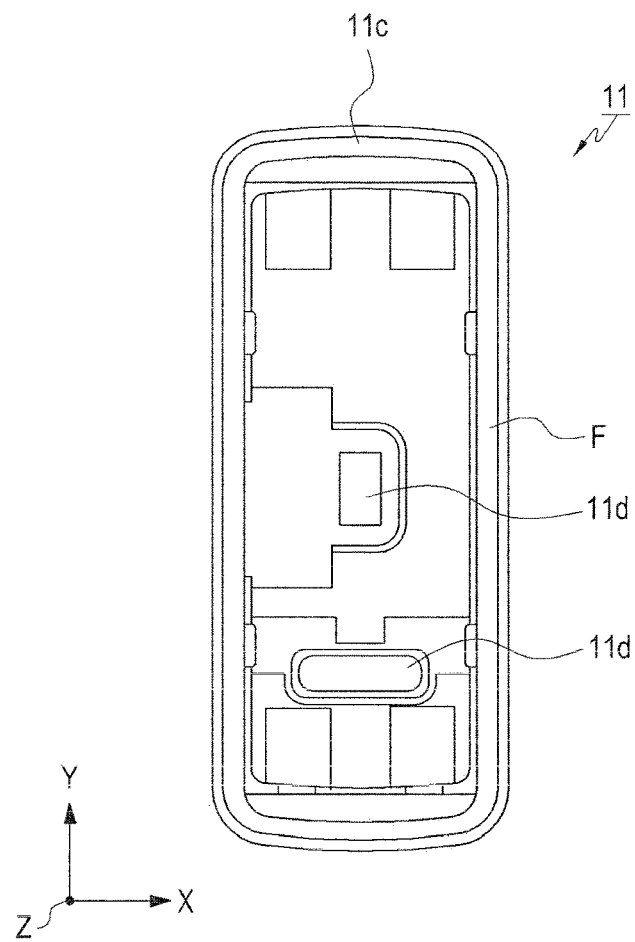
FIG. 8 is a plan view illustrating a housing of an electronic device according to an embodiment.

FIG. 8 is a plan view illustrating a housing of an electronic device according to an embodiment.

In this embodiment, a body housing excluding a screw boss is disclosed. Brackets (e.g., an inner bracket or battery bracket) modularizing electronic parts may be fastened to the body housing 11 by a structure, e.g., hooks or protrusions, and the window of the display device 13 may be attached to the body housing 11 by a waterproof tape. Thus, screw bosses may be excluded from inside the body housing 11, thus allowing for efficient use of the internal mounting space and enhancement in the waterproof capability. In FIG. 8, the reference denotation '11c' refers to a sealing member, e.g., a surface where the waterproof tape is attached, and the reference denotation '11d' refers to openings for arranging the sensor portion S or contact members 23.

Figure 9:
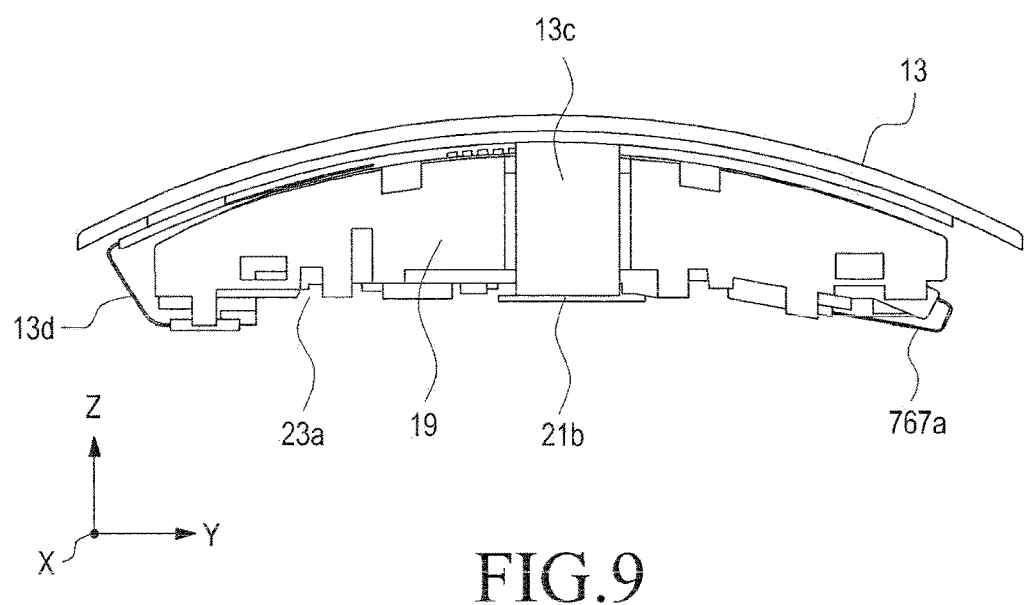
FIG. 9 is a side view illustrating an internal configuration of an electronic device according to an embodiment.
Figure 10:
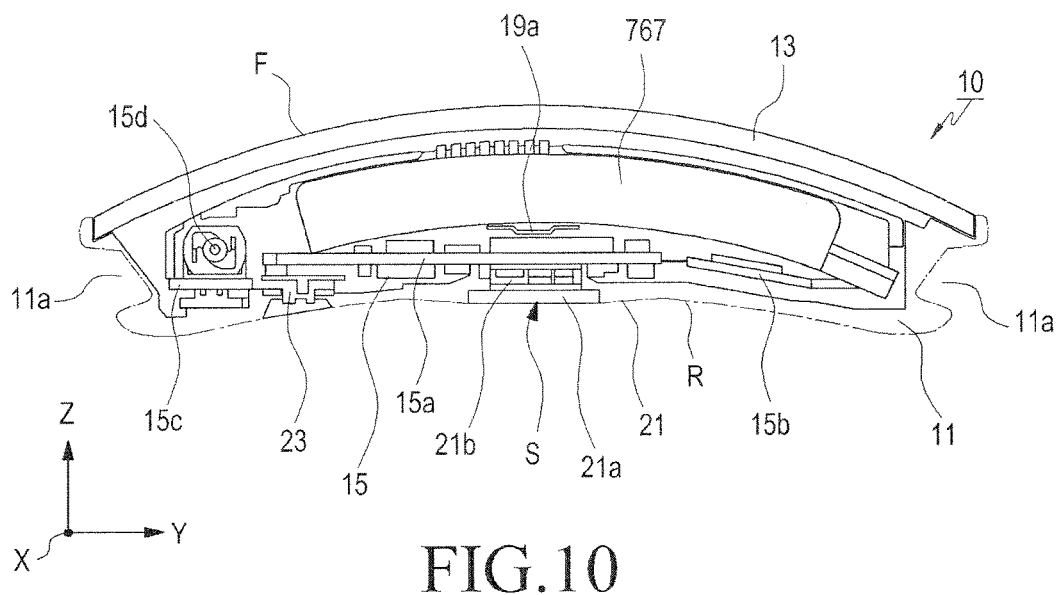
FIG. 10 is a cross-sectional view illustrating an internal configuration of an electronic device according to an embodiment.

FIG. 9 is a side view illustrating an internal configuration of an electronic device according to an embodiment. FIG. 10 is a cross-sectional view illustrating an internal configuration of an electronic device according to an embodiment.

Referring to FIGS. 9 and 10, the electronic parts mounted in the body housing 11 may be modularized by brackets 19 (e.g., the inner bracket or battery bracket). In this embodiment, various electronic parts including a curved battery pack 17 may be mounted in a stacking structure at a lower side of the display device 13, and such an arrangement may be made that the upper-to-lower thickness gradually reduces from the center of the body housing 11 to a side direction (e.g., the vertical direction Y). For example, the body housing 11 may accommodate the electronic parts where the curved display device 13, the curved battery pack 17, and the board assembly 15 are modularized in the upper-to-lower stacking structure.

According to this embodiment, the main body 10 of the electronic device 1 may be designed so that the outer surface (e.g., the display screen) easily viewed to the user has a different curvature from the contact surface (the rear surface of the body housing) tightly contacting the user's skin when the user wears it, thus allowing the internal space of the body housing 11 to be efficiently utilized. According to this embodiment, the display device 13 highly able to be manufactured with a curved surface may be disposed on the outer surface (e.g., the front surface F) having a smaller curvature, and the battery pack 17 may be placed inside the display device 13. Here, the battery pack 17 may have a curved shape and may have the same curvature as the first curvature. The battery pack 17 may be placed with respect to the center of the curved display device 13 and a mounting space may be secured inside the body housing 11 at both ends of the battery pack 17. The above mounting structure may come up with an effect of reducing the thickness at both ends as compared with the center of the body housing 11, allowing for an aesthetic design together with a shape allowing the rear surface R of the body housing 11 to sufficiently come in tight contact with the user's body.

The display device 13, the curved battery pack 17, and at least one board 15a, 15b, and 15c where a plurality of various electronic parts are mounted are arranged in an upper-to-lower stacking structure in the main body 10. According to this embodiment, the battery pack 17 may be disposed in a middle layer between the display device 13 and the boards 15a, 15b, and 15c. This may mean a safety device able to prevent the user's damage, such as damage to the battery pack 17 or low-temperature burn by heat generation.

The main body 10 may include the body housing 11 and the bracket 19. The bracket 11 may be coupled and fastened to the body housing 10, forming a single body. Although the body housing 11 and the bracket 19 have been exemplified to be independently manufactured and coupled together, the bracket 19 may be appreciated as having a configuration that it is included in the body housing 11. The display device 13 is attached and fastened to the front surface F of the body housing 11 by an adhesive tape (double-sided waterproof tape), and the bracket 19 may be received and fastened inside the body housing 11. The display device 13 may be supported by the bracket 19 inside the body housing 11. The bracket 19 may accommodate therein the battery pack 17 stacked at a lower side of the display device 13 and one or more boards 15a, 15b, and 15c arranged between the front surface F and the rear surface R of the body housing 11. The plurality of boards 15a, 15b, and 15c may be formed of a board assembly 15 of a segmented structure.

Hereinafter, various electronic parts mounted in the main body and their arrangement are described below in greater detail further referring to FIGS. 11 to 13.

Figure 11:
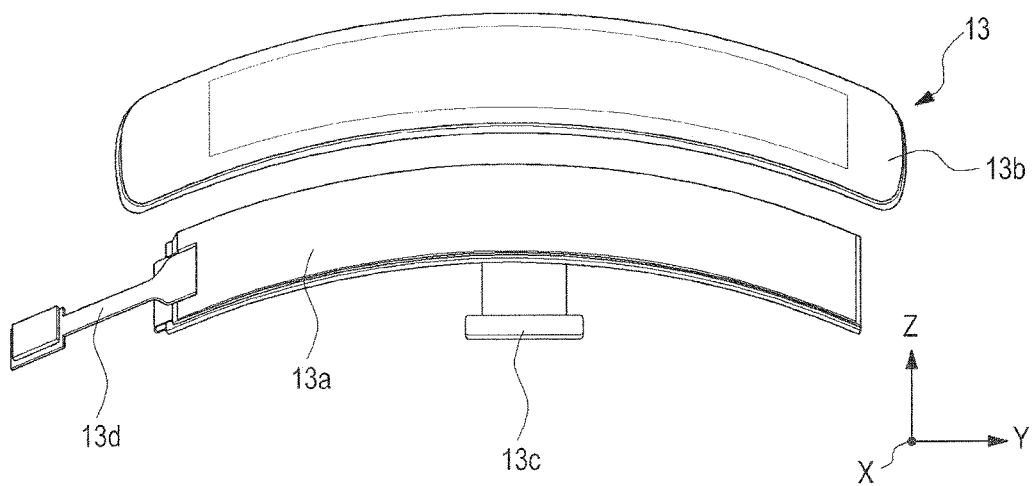
FIG. 11 is an exploded perspective view illustrating a display device of an electronic device according to an embodiment.

FIG. 11 is an exploded perspective view illustrating a display device of an electronic device according to an embodiment.

Referring to FIG. 11, the display device 13 is implemented as a curved display 13a having curvature for realizing a curved design with a curvature and may further include a curved window 13b with the same curvature as the curvature of the curved display 13a. The curved window 13b includes a rigid or flexible layer. In another embodiment, the curved display 13a may be implemented as a flexible display or may be replaced with a flat display depending on the outer appearance of the electronic device. The curved window 13b may be replaced with a window having a shape appropriate for the shape of the display device 13 depending on the shape of the display device 13. The curvature of the curved window 13b may not necessarily be the same as the curvature of the curved display 13a. In another embodiment, even when the curved display 13a is replaced with a flat display, the curved window 13b may have the same curvature as a predetermined curvature, e.g., the first curvature.

The display device 13 may be implemented in a shape considering the curved surface of the user's body, e.g., as a curved display, and the front F design of the main body 10 may be implemented with the curved window 13b disposed on an upper surface of the display device 13. The display device 13 may further include a sensing unit, e.g., a touch panel, sensing, e.g., capacitance or pressure or temperature by the user's touch. The touch panel may be integrated with the curved display 13a. As the sensing unit is equipped in the display device 13, a physical user interface (PUI) optimized for the utilization of various UIs may be provided. In FIG. 11, the reference denotation '13a' may refer to the curved display integrated with the touch panel, '13d' the flexible printed circuit board connected to the touch panel, and '13c' the flexible printed circuit board connected to the curved display. In another embodiment, the touch panel may be integrated with the curved window 13b. The curved window 13b may be formed of glass or ceramic or may include a layer formed of a sheet material, such as PET or PC, to protect the surface.

Figure 12:
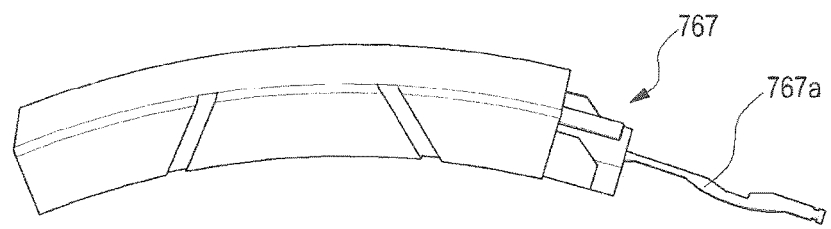
FIG. 12 is a perspective view illustrating a battery pack of an electronic device according to an embodiment.

FIG. 12 is a perspective view illustrating a battery pack of an electronic device according to an embodiment.

Referring to FIG. 12, according to an embodiment, the battery pack 17 of the electronic device 1 may be implemented to be curved to contribute to efficiency of mounting the electronic parts in the main body 10. The battery pack 17 is mounted while curved, and this may lead to implementation of an outer design of the main body 10 and optimized mounting of hardware parts of the wearable electronic device worn on the user's body. As the battery pack 17 has the flexible printed circuit board 17a, it may be connected with one of the boards 15a, 15b, and 15c to provide a power source. The battery pack 17 may be made in a curved shape, giving itself a predetermined curvature. The battery pack 17 may have the same curvature as the display device 13 and may be disposed facing the rear surface of the display device 13. The battery pack 17 may have a mounting space (a concave portion) at the center in its rear surface to accommodate the hardware electronic parts, enhancing the mounting efficiency. In another embodiment, the battery pack 17 may be configured with a different curvature than the curvature of the display device 13 or may be configured in a flat shape. In case the battery pack 17 is configured in a curved shape, the battery pack 17 may be disposed on a lower surface of the boards 15a, 15b, and 15c.

Referring back to FIG. 10, a separate layer part, e.g., the second bracket 19a, may be added between the battery pack 17 and the first circuit board 15a, so that even when the battery pack 17 is swollen while the electronic device 1 operates, the parts of the first circuit board 15a and the battery pack 17 may be prevented from damage. For example, the second bracket 19a may prevent the battery pack 17 from expansion. The second bracket 19a may function as a physical supporting structure, shock-absorbing section for the battery pack 17 and the first circuit board 15a and may serve as a barrier preventing the lower-side electronic parts from being contaminated due to leakage of the battery fluid. The second bracket 19a may be formed of a metal piece or injection-molded piece.

Figure 13:
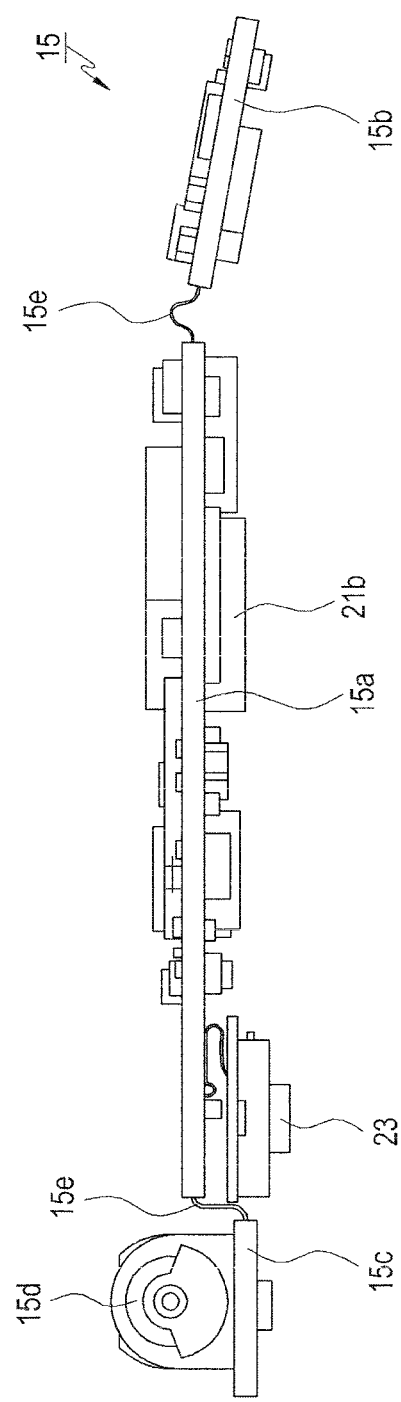
FIG. 13 is a side view illustrating a circuit board structure of an electronic device according to an embodiment.

FIG. 13 is a side view illustrating a circuit board structure of an electronic device according to an embodiment.

Referring to FIGS. 10 and 13, the plurality of boards 15a, 15b, and 15c are arranged in a segmented (joint) structure in the internal space of the body housing 10, e.g., the bracket 19, leading to efficient mounting of the electronic parts. The board assembly 15 arranged in the segmented structure properly may properly place rigid boards (e.g., the boards 15a, 15b, and 15c) and flexible boards 15e in necessary portions, allowing for an arrangement or array fitting the curved design and such arrangement may be made in each segmented portion given, e.g., the working environment of the electronic parts, thus allowing the electronic device an optimized performance.

For example, a part vulnerable to noise and a noise-generating part may be separately placed in different boards, and a part vulnerable to impacts and an impacting part may be separately placed in different boards. Such internal arrangement of the electronic parts may naturally space the noise generating part apart from the noise-vulnerable part and cut off the vibrational impact transferred through the rigid boards in the flexible boards, allowing for a design optimizing the electrical performance and durability of the electronic device. As the technology develops in the future, curved rigid boards or flexible boards, instead of rigid boards, may be applicable. In addition to basic communication, input/output-related parts, contactless sensors, such as gyro, acceleration, or optical sensors, may be further provided in the segmented-structure board assembly 15.

As such, the segmented-structure board assembly 15 may include a plurality of rigid boards (PCBs) 15a, 15b, and 15c and a plurality of flexible boards (PCBs) 15e. The rigid boards 15a, 15b, and 15c are boards having various electronic parts mounted thereon. Electronic parts may be mounted on each of the top and bottom of the board. According to this embodiment, the board assembly 15 includes three rigid boards, respectively denoted as the first circuit board 15a, the second circuit board 15b, and the third circuit board 15c. The first circuit board 15a denotes the board disposed at the middle, the board at the right side of the first circuit board 15a is referred to as the second circuit board 15b, and the board at the left side of the first circuit board 15a is referred to as the third circuit board 15c. Further, the board connecting the first circuit board 15a with the second circuit board 15b or connecting the first circuit board 15a with the third circuit board 15c is referred to as a flexible board 15e. The second and third circuit boards 15b and 15c each are connected to the first circuit board 15a through the flexible boards 15e, allowing the board assembly 15 a segmented structure. Further, in the arrangement of various electronic parts on the first, second, and third circuit boards 15a, 15b, and 15c, noise-vulnerable parts and noise-generating parts may be arranged on different ones of the first, second, and third circuit boards 15a, 15b, and 15c, and impact-vulnerable parts and impacting parts may also be arranged on different circuit boards.

For example, among the electronic parts mounted on the first, second, and third circuit boards 15a, 15b, and 15c, noise-vulnerable parts (e.g., PAM) and noise-generating parts (e.g., AP and CP) may be separately arranged on the first and second circuit boards 15a and 15b, respectively, and impact-vulnerable parts (e.g., BGA parts such as AP or CP) and impacting parts (e.g., a vibrator including a vibrating module) may be separately arranged on the second and third circuit boards 15b and 15c. Such internal arrangement of the electronic parts may naturally space the noise generating part apart from the noise-vulnerable part and cut off the vibrational impact transferred through the rigid boards in the flexible boards, allowing for a design optimizing the electrical performance and durability of the electronic device.

Further, at least one of the first, second, and third circuit boards 15a, 15b, and 15c positioned on the rear surface R of the body housing 11 may be arranged inclined or horizontally. The first circuit board 15a is a board disposed at the center and mounts the sensor portion S, e.g., a bio signal sensor, thereon, and thus, this together with the sensor portion S may be disposed horizontally. The sensor portion S may be disposed to be exposed to the rear surface R of the body housing 11, and this may be disposed horizontally at the position where it may mostly tightly contact the user's body skin, i.e., substantially at the center of the rear surface R of the body housing 11. The sensor portion S may be mounted on the rear surface of the first circuit board 15a and may have a sensor interface portion 21a (e.g., an interface window). Further, even when the circuit board (e.g., the first circuit board 15a) where the sensor portion S is mounted is mounted inclined relative to the outer surface of the body housing 11, it may be balanced using an interposer between the circuit board and the sensor portion S. The sensor portion S may be positioned horizontally while exposing the sensor interface portion 21a (e.g., interface window) to the rear surface R of the body housing 11. The sensor interface portion 21a (e.g., interface window) may be provided in the sensor portion S itself or may be attached to the outer portion of the body housing 11. The sensor portion S may be formed of a bio signal sensor, such as HRM or vein sensor, which may obtain information from the user's skin or body. Such bio signal sensors may transmit light to the body blood vessel using, e.g., a light emitting diode or infrared (IR) diode, or reflect light and detect returning light using a light receiving element (e.g., a photo diode) to detect, e.g., heart rate, blood flow amount, or oxygen saturation.

Additionally, a protrusion 21 may be further provided on the rear surface R of the body housing 11. A portion of the sensor portion S, e.g., the sensor interface portion 21a (e.g., interface window), may be exposed externally on the protrusion 21. As the sensor interface portion 21a is disposed on the protrusion 21, the sensor portion S may further tightly contact the user's skin. The sensor interface portion 21a may be positioned at the center on the protrusion 21, e.g., on a flat surface. In one embodiment, in arranging boards in a segmented structure, a minimum horizontal, flat area (e.g., the area in the body housing 11 where the first circuit board 15a is disposed) may be formed for mounting electronic parts inside the body housing 11.

In another embodiment, the space secured at both ends of the battery pack 17 may be utilized as a mounting space allowing for more efficient use of the mounting space. For example, a relatively thick part, such as the vibration module 15d or connector, may be disposed in the space secured at both ends of the battery pack 17, preventing an increase in the overall thickness of the body housing 11. Although not shown, various mechanisms, such as assistant battery or hook assembly, may be disposed in the secured space.

According to this embodiment, the main body 10 of the electronic device 1 may place the third circuit board 15c in an area at a side (Y-axis direction) of the battery pack 17 at a lower side of the display device 13 while putting the vibration module 15d and the contact member 23 (e.g., a charging terminal) on the third circuit board 15c and the first circuit board 15a, respectively. In another embodiment, the vibration module 15d itself may be mounted and fastened to the bracket 19 or body housing 11, and if a separate flexible printed circuit board is provided to connect the vibration module 15d to the first circuit board 15c, the third circuit board 15c is not necessarily provided. The vibration module 15d may be disposed in parallel with the battery pack 17, and the contact member 23 (e.g., a charging terminal) may also be disposed in parallel with the battery pack 17. The vibration module 15d may be disposed on an upper surface of the third circuit board 15c, and the contact member 23 may be disposed on a lower surface of the first circuit board 15a. The contact member 23 may be exposed to the rear surface R of the body housing 11. The vibration module 15d is a thick or bulky one among the electronic parts mounted, and thus, it may be mounted on the second circuit board 15b or the third circuit board 15c in parallel with the battery pack 17 (not to be layered with the battery pack 17), preventing an increase in the thickness of the main body 10 while increasing mounting efficiency.

Further, an electrical switch interface portion using, e.g., a touch sensor, pressure sensor, and temperature sensor, as other input devices respectively mounted on the first, second, and third circuit boards 15a, 15b, and 15c and a physical switch interface portion, such as Tact or Dome key, may be arranged on a surface of the body housing 11. Such input devices may generate signals that are respectively assigned thereto, by the user's direct manipulation. A charging and interface terminal may be further disposed on the front surface F or rear surface R of the body housing 11 not to deteriorate the outer appearance. In this embodiment, the contact member 23 (e.g., a charging terminal) may be disposed on the rear surface R of the body housing 11, and while worn, it may be hidden by the body housing 11 or the user's body.

Hereinafter, waterproof structures of the electronic device according to embodiments are described with reference to FIGS. 14 to 18.

Figure 14:
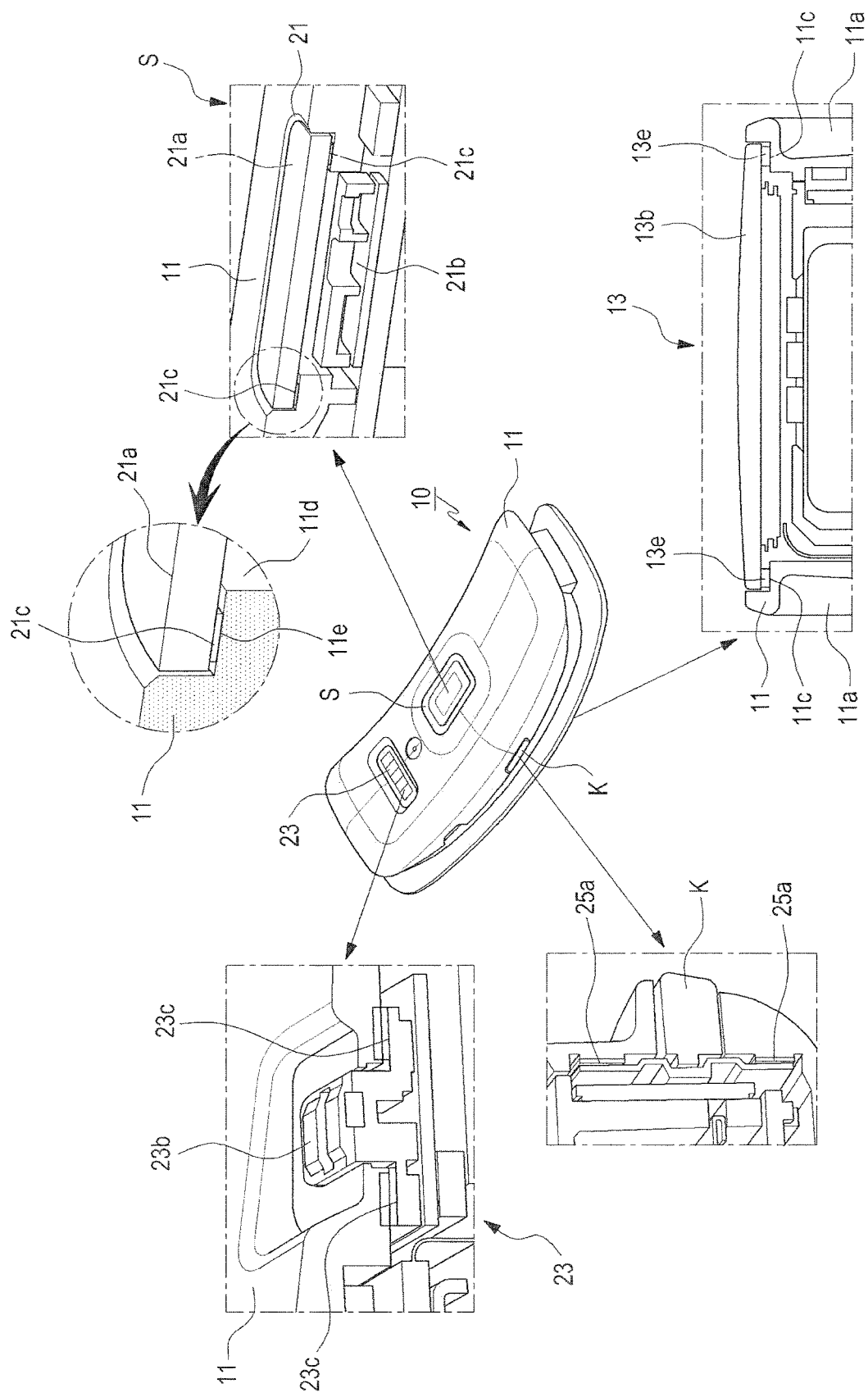
FIG. 14 is a view illustrating a water-proof structure of an electronic device according to an embodiment.
Figure 15:
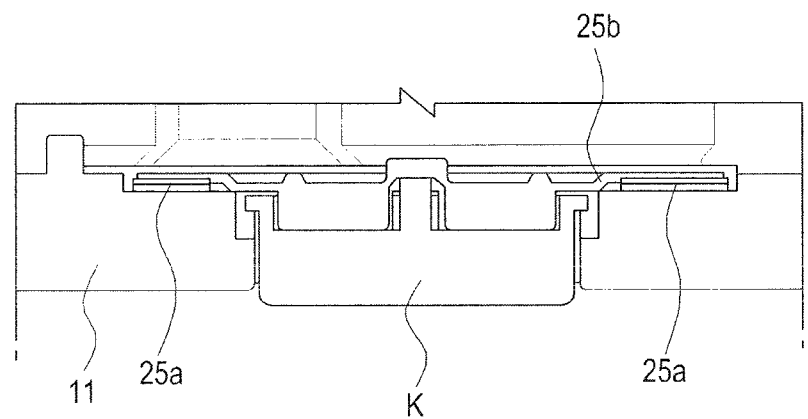
FIG. 15 is a perspective view illustrating an electronic device with a side key partially cut, according to an embodiment.
Figure 16:
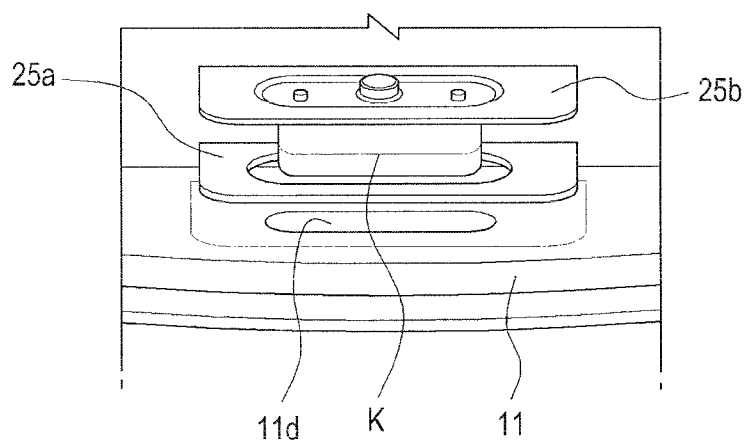
FIG. 16 is an exploded perspective view illustrating a side key of an electronic device according to an embodiment.
Figure 17:
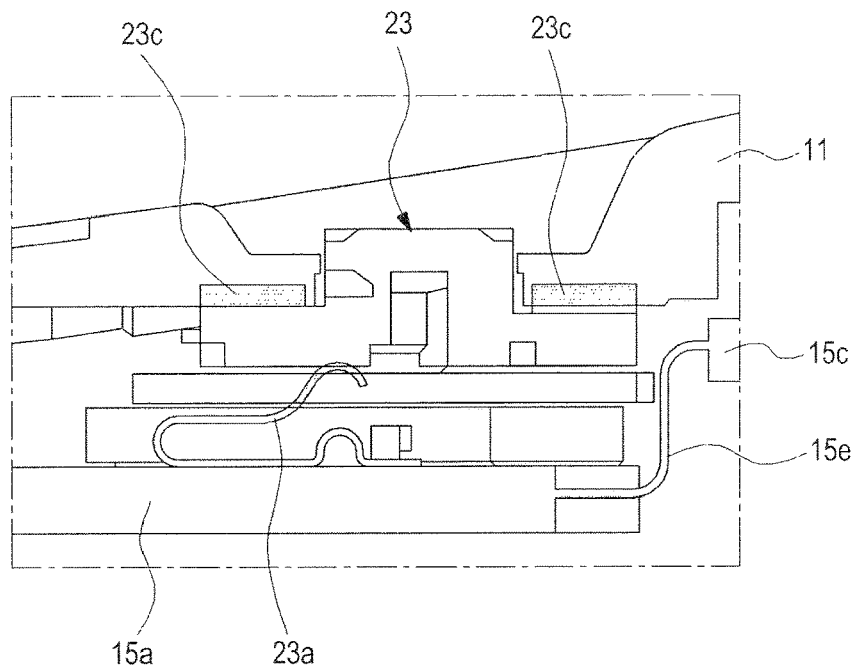
FIG. 17 is a perspective view illustrating an electronic device with a charging terminal portion partially cut, according to an embodiment.
Figure 18:
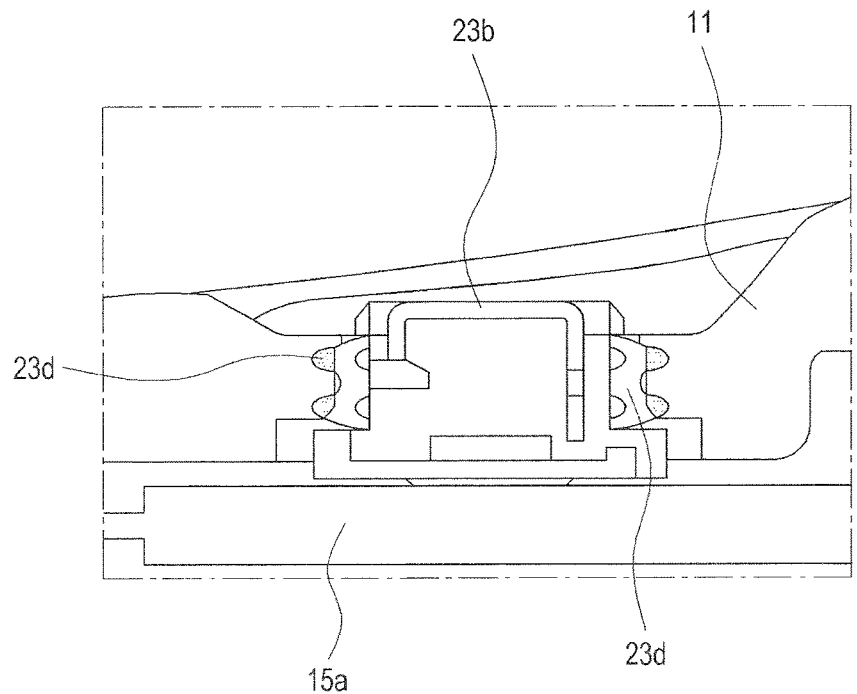
FIG. 18 is a view illustrating a variation to a charging terminal portion of an electronic device according to an embodiment.

FIG. 14 is a view illustrating a water-proof structure of an electronic device according to an embodiment. FIG. 15 is a perspective view illustrating an electronic device with a side key partially cut, according to an embodiment. FIG. 16 is an exploded perspective view illustrating a side key of an electronic device according to an embodiment. FIG. 17 is a perspective view illustrating an electronic device with a charging terminal portion partially cut, according to an embodiment. FIG. 18 is a view illustrating a variation to a charging terminal portion of an electronic device according to an embodiment.

It has been described above that the body housing 11 has a uni-body structure, is shaped to have an opened front surface F for installation of the display device 13, and may include openings 11d for arrangement of a sensor portion S (e.g., a bio signal sensor), side key K, and contact member 23. A waterproof structure may be formed in such opened surface or openings each, preventing influx of moisture into the inside of the main body 10. In this embodiment, the main body 10 of the electronic device 1 may minimize waterproof points by coupling the bracket 19 capable of modularizing various electronic parts to the uni-body body housing 11.

Referring to FIGS. 14 to 18, according to the instant embodiment, where the waterproof structure is applied in the main body 10 of the electronic device 1 may include where the curved window 13b is disposed, where the side key K is disposed, where the sensor portion S is disposed, and where the contact member 23 is disposed.

As the waterproof structure of the curved window 13b mounted on the front surface F of the body housing 11, a sealing member, e.g., a waterproof tape 13e, may be used. The waterproof tape 11e formed on the periphery of the front surface of the body housing 11 may be attached to the edge of the curved window 13b. The waterproof tape 13e may be a double-sided tape, and its upper surface may be attached to the curved window 13b while the lower surface may be attached to the attaching surface 11c. Thus, moisture may be prevented from flowing in the space between the body housing 11 and the curved window 13b.

The waterproof structure of the side key K disposed on a side surface of the body housing 11 may use another sealing member, e.g., a waterproof tape 25a. The waterproof tape 25a may be a double-sided tape and may be provided in a shape surrounding the side key K. A surface of the waterproof tape 25a may be attached onto an inner surface of the body housing 11, and the other surface thereof may be attached to the silicone rubber 25b of the side key K, preventing inflow of water. Further, the silicone rubber 25a may provide a restoration force against the operation of pressing the side key K. Although not shown, waterproof protrusions may be formed along the periphery of the silicone rubber 25a to be brought in tight contact to the inner side of the opening 11d, preventing influx of moisture between the silicone rubber 25a and the body housing 11. For example, the silicone rubber 25a may form a dual-waterproof structure using the waterproof protrusions and sealing member.

A waterproof structure using a waterproof tape 21c may also be applied to the sensor portion S (e.g., a bio signal sensor) disposed on the lower surface of the body housing 11. The sensor portion S may have an interface window (e.g., the sensor interface portion 23a). The waterproof tape 21c may be a double-sided tape, with one surface attached to the body housing 11, and the other surface attached to the lower surface of the interface window. The waterproof tape 21c is attached along the periphery of the lower surface of the interface window. The edge of the interface window may be attached to the rear surface R of the body housing 11 at the periphery of the opening 11d (e.g., a through hole) for disposing the sensor portion S. A recessed portion 11e may be formed at the periphery of the opening 11d to prevent the interface window from projecting to the rear surface R of the body housing 11, and the edge of the interface window may be received in the recessed portion 11e. A sealing member, e.g., the waterproof tape 21c, may be interposed between the recessed portion 11e and the interface window to provide a waterproof structure. The bio signal sensor 21b may be mounted on the first circuit board 15a to be positioned on the opening 11d.

The contact member 23 (e.g., a charging terminal) may have a waterproof tape 23c, such as a double-sided tape, or rubber or silicone high-elasticity waterproof part 23d (shown in FIG. 18) put therein, implementing a waterproof structure. The waterproof tape 23c may be attached to a space between the contact member 23 and the body housing 11 to form a waterproof structure. The waterproof part 23d may be disposed between a side surface of the contact member 23 and an inner wall of the body housing 11, so that the waterproof structure using the waterproof tape 23c or the waterproof part 23d may be replaced with a waterproof structure implemented as, e.g., silicone or other various adhesives. In FIGS. 14, 17, and 18, the reference denotation 23a refers to a c-clip connecting the contact member 23 to the circuit board (e.g., the first circuit board 15a), and the reference denotation 23b refers to a contact pad directly contacting a contact member of another device (e.g., a contact terminal of the mount).

Figure 19:
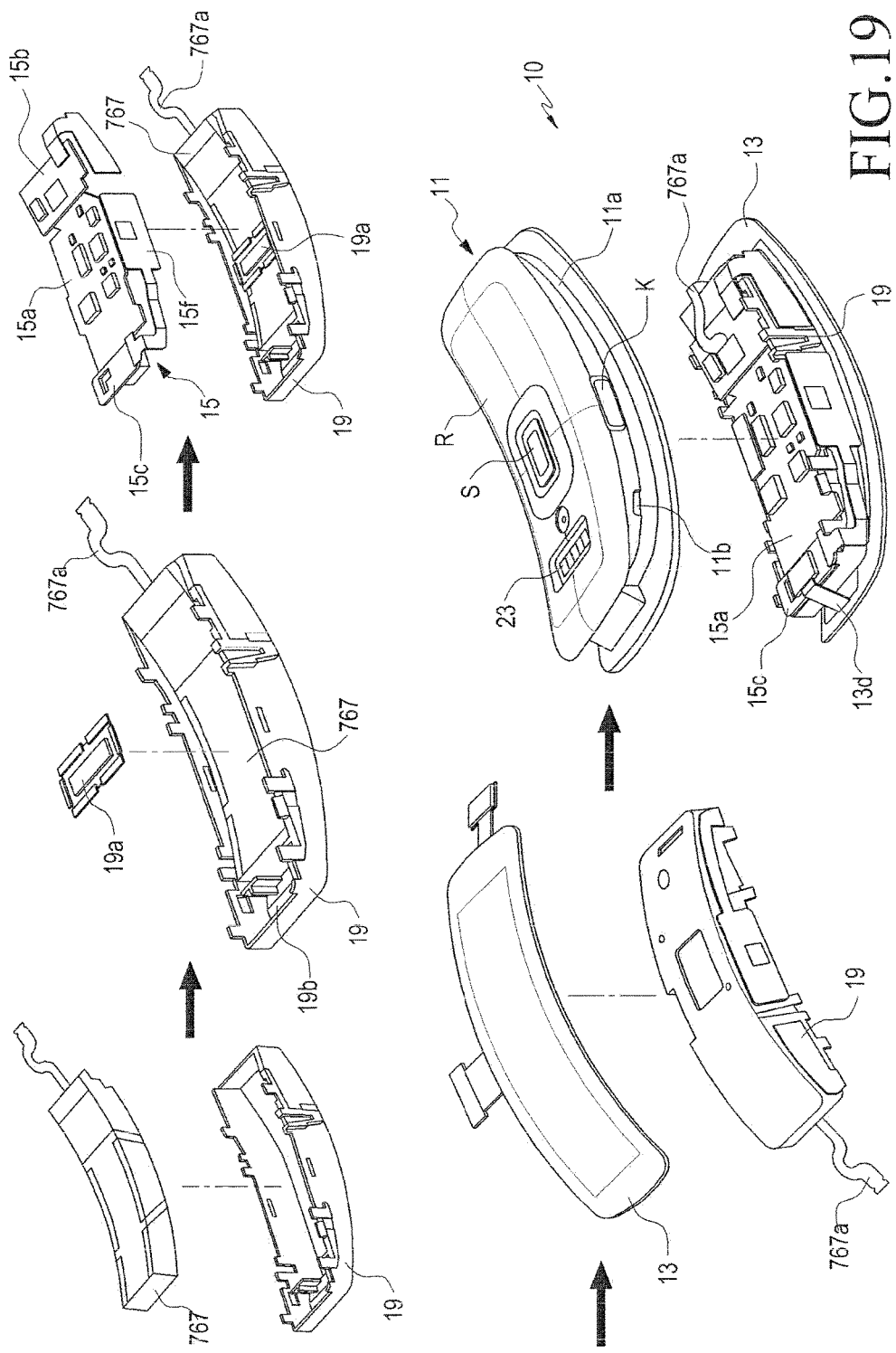
FIG. 19 is a view illustrating a process for assembling a main body of an electronic device according to an embodiment.

FIG. 19 is a view illustrating a process for assembling a main body of an electronic device according to an embodiment.

Referring to FIG. 19, the main body 10 enables various electronic parts to be implemented in a single modular type using the bracket 19 and to be assembled in the body housing 11. The uni-body body housing 11 and the electronic parts may be coupled to the modularized bracket 19 to secure waterproof-fitful assemblability. Further, various electronic parts may be secured to the bracket 19, e.g., by assembly, attachment, fusion, riveting, or a screw structure. By modularizing various electronic parts using the bracket, the electronic parts may be easily assembled even without forming screw bosses on the body housing 11. The bracket 19 modularizing the electronic parts and the uni-body body housing 11 may be fastened by a fastening structure, such as a hook or protrusion, and the gap between the curved window 13b and the body housing 11 may be finished with a waterproof tape, leading to efficient use of the internal mounting space and maximized waterproof capability through elimination of screw bosses.

According to an embodiment, a process for assembling the main body 10 configured as above is described. First, the battery pack 17 is mounted in the bracket 19, and a metal piece (e.g., the second bracket 19a) is fastened to a middle area of the rear surface of the battery pack 17. When the battery pack 17 is mounted in the bracket 19, a mounting space 19b may be formed inside the bracket 19 at, at least, a side of the battery pack 17. Subsequently, a board assembly 15 is assembled to the bracket 19, and the display device 13 is fastened to the bracket 19. The board assembly 15 may further include at least one side board 15f corresponding to, e.g., the side key K. If a bulkier electronic part (e.g., a vibration module) remains mounted in the board assembly 15, it may be accommodated in the mounting space 19b to thereby increase the mounting efficiency of the main body 10. The bracket 19 may be coupled with the display device 13 while supporting the rear surface of the display device 13. Flexible printed circuit boards 13c, 13d, and 17d (or connectors) extending from their respective electronic parts are connected to the board assembly 15, with various electronic parts assembled in the bracket 19. Lastly, as the bracket 19 is accommodated in the body housing 11, the assembly of the main body 10 is complete, and the display device 13, e.g., the curved window 13b, may be attached to the body housing 11, forming a waterproof structure.

Figure 20:
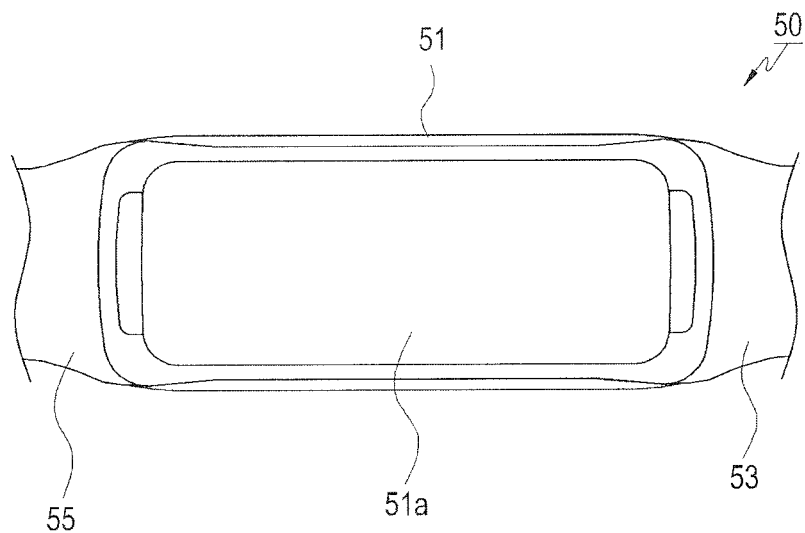
FIG. 20 is a plan view illustrating a wearing portion of an electronic device according to an embodiment.
Figure 21:
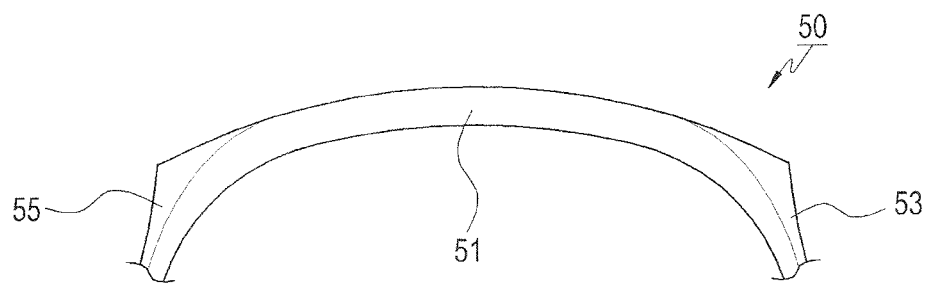
FIG. 21 is a side view illustrating a wearing portion of an electronic device according to an embodiment.

FIG. 20 is a plan view illustrating a wearing portion of an electronic device according to an embodiment. FIG. 21 is a side view illustrating a wearing portion of an electronic device according to an embodiment.

Referring to FIGS. 20 and 21, the wearing portion 50 may include an opening 51a substantially shaped as a rectangle at plan view. For example, four inner walls of the opening 51a are arranged to each form at least a portion of the rectangle, and neighboring ones of the inner walls constituting the opening 51a may be connected via a curved surface. For example, although the opening 51a has substantially a rectangular shape, the two neighboring inner walls do not need to cross each other perpendicularly.

The seating portion 51 surrounding the opening 51a is substantially rectangular at plan view. However, it may be shaped to have a predetermined curvature at side view. The curvature of the seating portion 51 may be set to be the same as the first curvature of the main body 10. However, as described above, the curvature in the boundary area A between the seating portion 51 and the first and second wearing members 53 and 55 may be set to be different from the first curvature. Further, the seating portion 51 may be manufactured as an elastic material to facilitate attachment or detachment of the main body 10 to be deformed corresponding to the shape of the fastening groove 11a, and thus, it should be noted that the curvature need not be limited to a specific value.

Figure 22:
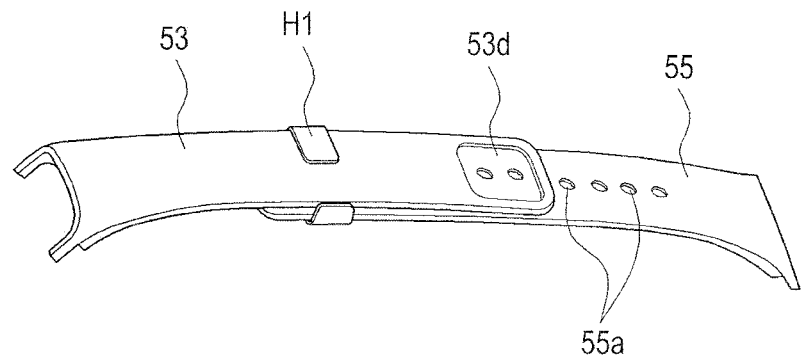
FIG. 22 is a view illustrating a structure of a wearing portion of an electronic device according to an embodiment.
Figure 23:
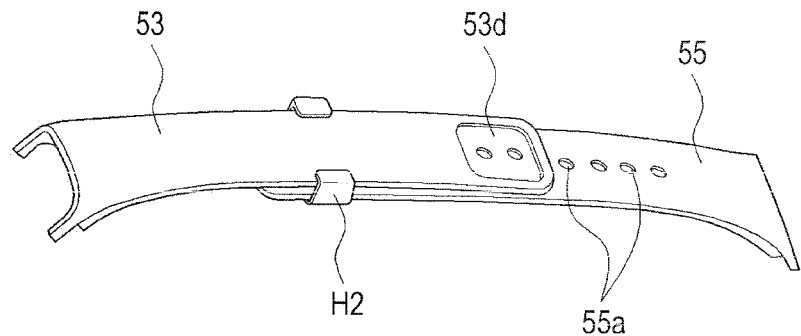
FIG. 23 is a view illustrating a variation to a structure of a wearing portion of an electronic device according to an embodiment.
Figure 24:
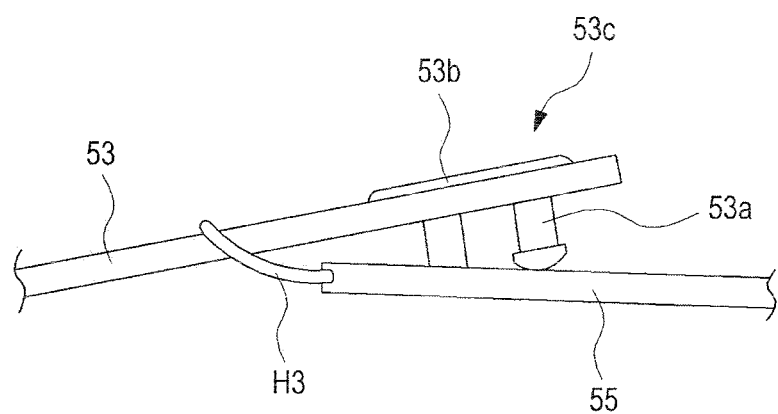
FIG. 24 is a side view illustrating a wearing portion coupling structure of an electronic device according to an embodiment.
Figure 25:
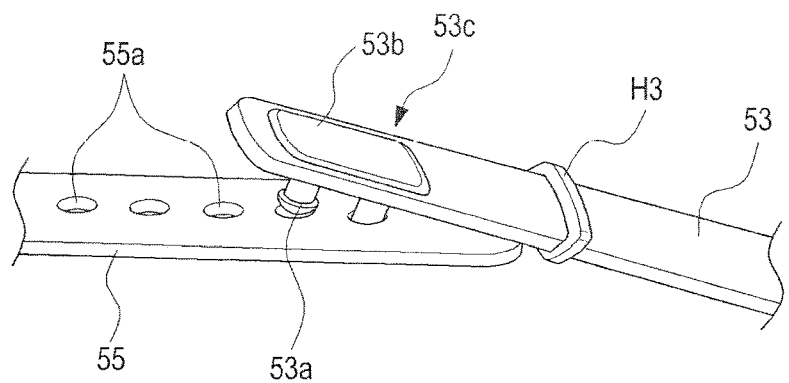
FIG. 25 is a perspective view illustrating a wearing portion coupling structure of an electronic device according to an embodiment.
Figure 26:
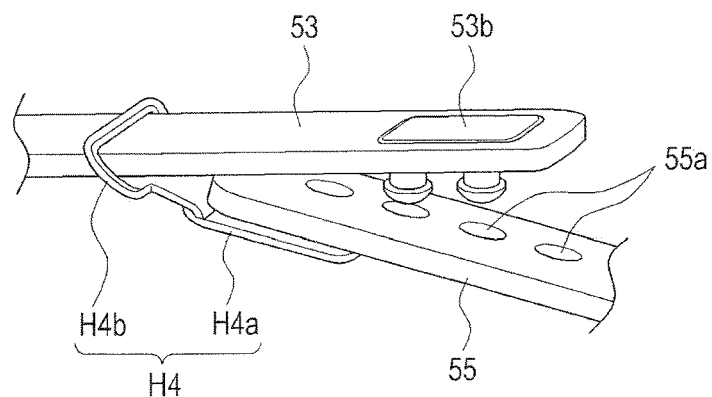
FIG. 26 is a perspective view illustrating a variation to a wearing portion coupling structure of an electronic device according to an embodiment.
Figure 27:
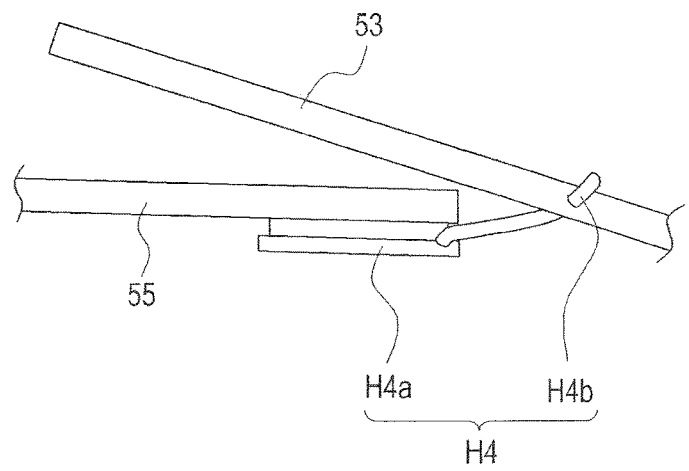
FIG. 27 is a side view illustrating a variation to a wearing portion coupling structure of an electronic device according to an embodiment.

FIG. 22 is a view illustrating a structure of a wearing portion of an electronic device according to an embodiment. FIG. 23 is a view illustrating a variation to a structure of a wearing portion of an electronic device according to an embodiment; FIG. 24 is a side view illustrating a wearing portion coupling structure of an electronic device according to an embodiment; FIG. 25 is a perspective view illustrating a wearing portion coupling structure of an electronic device according to an embodiment; FIG. 26 is a perspective view illustrating a variation to a wearing portion coupling structure of an electronic device according to an embodiment; FIG. 27 is a side view illustrating a variation to a wearing portion coupling structure of an electronic device according to an embodiment.

The wearing portion shown in FIG. 22 may include first and second wearing members 53 and 55 and an area or shape (e.g., a clip H1) arranging the first and second wearing members 53 and 55 in a single body. In case the electronic device 1 is worn on a wrist, the clip H1 may be used to arrange the first and second wearing members 53 and 55 in a single body. The clip H1 is a part fitted into one of the first and second wearing members 53 and 55 and its portion may be shaped to be opened. The first wearing member 53 may have the first fastening member 53c disposed therein as described above, but it should be noted that the first fastening member is not shown in FIG. 22. However, FIG. 22 shows a configuration in which the surface 53d where the fastening portion of the first fastening member is seated is formed on an outer surface of the first wearing member 53. A plurality of fastening holes 55a may be provided in the second wearing member 55 along its longitudinal direction.

The wearing portion shown in FIG. 23 may include first and second wearing members 53 and 55 and an area or shape (e.g., a clip H2) arranging the first and second wearing members 53 and 55 in a single body. When the electronic device 1 is worn on a wrist, the clip H2 may be used to arrange the first and second wearing members 53 and 55 in a single body. The clip H2 is a part fitted into one of the first and second wearing members 53 and 55 and may be formed to be further opened than the clip H1 shown in FIG. 22.

The wearing portions shown in FIGS. 24 and 25 may include areas or shapes (e.g., the second fastening member H3) arranging the first and second wearing members 53 and 55 and the first and second wearing members 53 and 55 in a single body. When the electronic device 1 is worn on a wrist, the second fastening member H3, e.g., a hook, may be used to secure together the first and second wearing members 53 and 55. The second fastening member H3 may be provided as a single body in the second wearing member 55 to at least partially surround the first wearing member 53. The first fastening member 53c may be fastened as a single body to an end of the first wearing member 55, and the fastening protrusion 53a of the first fastening member 53c may be inserted into one of the fastening holes 55a of the second wearing member 55, securing the first and second wearing members 53 and 55 in a single body.

The wearing portions shown in FIGS. 26 and 27 may include another second fastening member H4 arranging the first and second wearing members 53 and 55 and the first and second wearing members 53 and 55 in a single body. When the electronic device 1 is worn on a wrist, the second fastening member H4 may be used to secure together the first and second wearing members 53 and 55. While in the prior embodiment the second fastening member H3 is structured to be formed as a single body in the second wearing member 55, the second fastening member H4 in the instant embodiment may include a second fastening portion H4a fastened to the second wearing member 55 and a coupling portion H4b extending from the second fastening portion H4a, and the second fastening portion H4a may be assembled in the second wearing member 55. As the fastening portion H4b is provided to at least partially surround the first wearing member 53, the first and second wearing members 53 and 55 may be arranged in a single body. Although not shown in FIGS. 26 and 27, it may be easily appreciated from the prior embodiments that the above-described fastening member 53c may be provided at an end of the first wearing member 53 to secure together the first and second wearing members 53 and 55.

The wearing portions shown in FIGS. 22 to 27 may be implemented with various colors or shapes, and the wearing surface contacting the user's body may be configured in a protrusion-and-depression shape (its cross section is shaped as a wave), leading to enhanced wearability. Further, the components disclosed in each embodiment may be selectively combined to configure another shape of wearing portion not disclosed herein.

Figure 28:
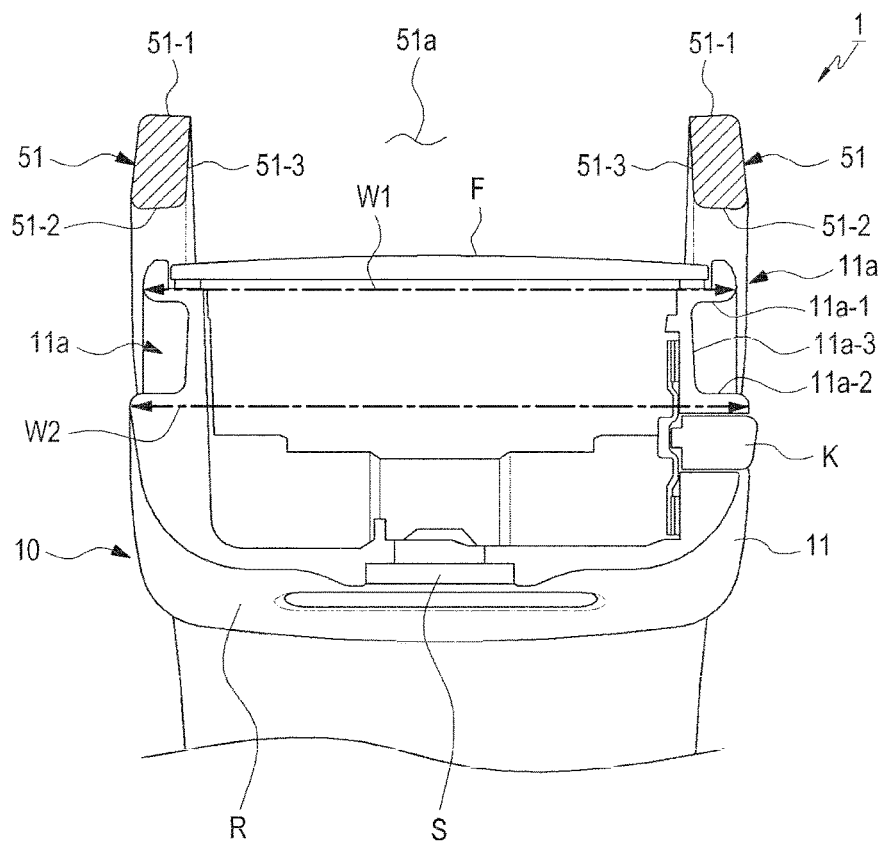
FIG. 28 is a view illustrating a structure in which a main body and wearing portion of an electronic device are fastened together according to an embodiment.
Figure 29:
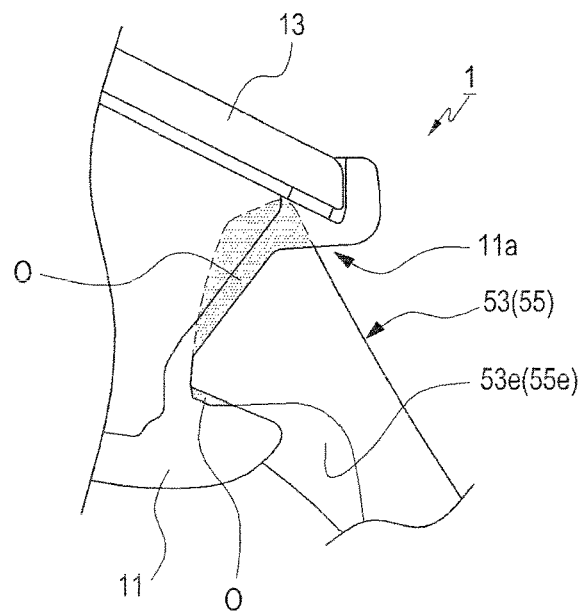
FIG. 29 is a view illustrating a first state in which a main body and wearing portion of an electronic device are fastened together according to an embodiment.
Figure 30:
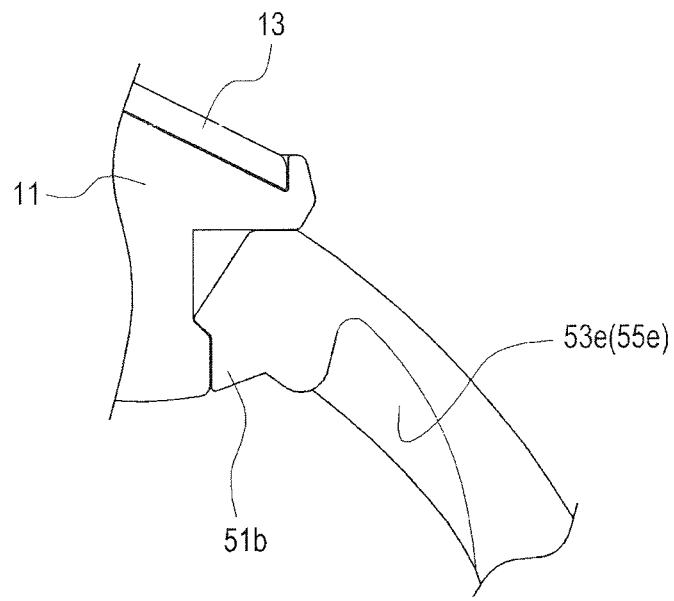
FIG. 30 is a view illustrating a second state in which a main body and wearing portion of an electronic device are fastened together according to an embodiment.

FIG. 28 is a view illustrating a structure in which a main body and wearing portion of an electronic device are fastened together according to an embodiment. FIG. 29 is a view illustrating a first state in which a main body and wearing portion of an electronic device are fastened together according to an embodiment. FIG. 30 is a view illustrating a second state in which a main body and wearing portion of an electronic device are fastened together according to an embodiment.

Referring to FIGS. 28 to 30, unless the shape of the main body 10 complies with the user's body curvature, a forced bend may occur between the main body 10 and the seating portion 51 or in the above-described boundary area A while worn on the user. Such forced bend may cause the main body 10 to escape from the seating portion 51. In order to prevent the main body 10 from escaping from the wearing portion 51, the measure of the seating portion 51 corresponding to the main body 10 may be designed to be small relative to the actual size of the main body 10, e.g., the actual size of the fastening groove 11a, the seating portion 51 may more tightly contact or fasten to a side surface of the main body 10. Further, a separate anti-bend protrusion structure (e.g., a supporting protrusion 51b) may be added to a portion of the seating portion 51 facing the main body 10 for where an excessive bend occurs while worn on the user's body.

Referring to FIG. 28, the main body 10, e.g., the body housing 11, may have a structure of being attached or detached from the seating portion 51, and the main body 10 may be moved up and coupled to the seating portion 51, and while coupled, it may be moved down to be separated from the seating portion 51. In case the main body 10 is coupled to the seating portion 51, the main body 10 may remain in a stable wearing position without escaped from the seating portion 51 while the user wears the electronic device 1.

The curved body housing 11 has the width in the horizontal direction X narrowing from the rear surface R (or a middle portion between the rear surface R and the front surface F) to the front surface F. For example, as shown in FIG. 28, the horizontal (X) width W2 of the middle portion (including a lower surface) of the main body 10 is smaller than the horizontal width (W1) in the front surface F. Such shape of the body housing 11 facilitates to couple the main body 10 from below the seating portion 51 to above the seating portion 51. The side surface of the body housing 11 may include a first portion positioned between the fastening groove 11a and the front surface F and a second portion positioned between the fastening groove 11a and the rear surface R, and the width W1 of the first portion may be configured to be smaller than the width W2 of the second portion when viewed in a cross section cut perpendicularly to the Y direction. Such shape enables the main body 10 to be coupled from below the seating portion 51 to above the seating portion 51 or to be moved and separated while coupled with the seating portion 51. The fastening groove 11a may extend in the shape of a curve with the same curvature as the first curvature along the periphery of the side surface of the body housing 11. The seating portion 51 may tightly be coupled to the fastening groove 11a, firmly securing the body housing 11 to the opening 51a. The seating portion 51 may be formed of an elastic material and may be elastically deformed as the main body 10 is attached or detached, and the opening 51a may be configured to be slightly smaller than the body housing 11 to allow the seating portion 51 to be tightly coupled to the fastening groove 11a. The seating portion 51 may be coupled to the fastening groove at the position extending along the vertical direction Y of the body housing 11 among the side surfaces of the body housing 11, allowing it the same curvature as the first curvature.

The fastening groove 11a may include first and second inner walls 11a-1 and 11a-2 and a bottom 11a-3 connecting together the first and second inner walls 11a-1 and 11a-2. The first inner wall 11a-1 is positioned adjacent to the front surface F of the main body 10, and the second inner wall 11a-2 is positioned adjacent to the rear surface R of the main body 10, and the bottom 11a-3 may be positioned between the first and second inner walls 11a-1 and 11a-2. As the width of the first inner wall 11a-1 of the fastening groove 11a is formed to be smaller than the width of the second inner wall 11a-2, the main body 10 may be easily attached or detached from the seating portion 51 at a lower side of the seating portion 51 while attachment or detachment of the main body 10 from the seating portion 51 may be restricted at an upper side of the seating portion 51.

In another embodiment, the first inner wall 11a-1 may be configured as a horizontal flat surface or substantially horizontal flat surface with respect to the rear surface R of the body housing 11, and the second inner wall 11a-2 may be configured of a horizontal or substantially horizontal flat surface. In another embodiment, the first inner wall 11a-1 may be formed to be away from the rear surface R as it goes away from the bottom 11a-3. As such, the inclined shape of the first inner wall 11a-1 may allow the seating portion 51 to easily escape from the fastening groove 11a when the main body 10 is separated from the seating portion 51.

Further, the inner walls of the seating portion 51 may include first and second outer walls 51-1 and 51-2 and a seating wall 51-3 connecting together the first and second outer walls 51-1 and 51-2. The first outer wall 51-1 may be formed of a flat, curved, or inclined surface corresponding to the first inner wall 11a-1. The second outer wall 51-2 may be formed of a horizontal or substantially horizontal flat surface corresponding to the second inner wall 11a-2. The seating portion 51 may be configured so that the outer-side horizontal width corresponding to the first outer wall 51-1 is larger than the outer-side horizontal width corresponding to the second outer wall 51-2.

As the inner wall of the seating portion 51 is configured in a shape corresponding to the fastening groove 11a, the main body 10 may be safely fastened to the seating portion 51. Further, since the width W2 of the second portion is formed to be larger than the width W1 of the first portion, and the second portion is thus positioned between the seating portion 51 and the user's body while wearing the electronic device 1, the wearing state may be stably maintained. Further, as the width of the main body 10 is configured as above (configured to decrease to the front surface F), the main body 10 may be easily separated from the seating portion 51. Such attaching/detaching structure may prevent unintentional escape (the main body 10 being escaped from the seating portion 51) by the wearing pressure while the user moves his body.

Referring to FIGS. 29 and 30, as the wearing portion 50, e.g., the seating portion 51, is formed of an elastic material, its portion may be deformed (e.g., compressed) when coupled with the main body 10. As the wearing portion 50 deforms, the coupling between the main body 10 and the wearing portion 50 may be reinforced. The area denoted with "O" in FIG. 29 refers to a portion of the seating portion 51 which deforms as the main body 10 and the wearing portion 50 couple together. Since the portion O of the seating portion 51 deforms, the seating portion 51 may be positioned substantially in the fastening groove 11a.

In case the user wears the electronic device 1, a tensile force may act in the boundary area A between the seating portion 51 and the first or second wearing member 53 or 55. In case such tensile force concentrates on a particular position, a crack may arise between the main body 10 and the wearing portion 50. To avoid such crack, as shown in FIGS. 29 and 30, cavity-shaped losing weight portions 53e and 55e may be formed in an inner surface of the wearing portion 50 in the boundary area A, i.e., a portion of the wearing surface contacting the user's body. The losing weight portions 53e and 55e allow a portion of the wearing portion 50 to be relatively smaller in thickness than the rest. Accordingly, upon wearing the electronic device 1, the losing weight portions 53e and 55e are bend relatively further, preventing a crack between the main body 10 and the wearing portion 50.

Further, the wearing portion 50 may have a supporting protrusion 51b. The supporting protrusion 51b may be supported by the body housing 11 inside the fastening groove 11a, further securing the coupling between the seating portion 51 and the body housing 11. The supporting protrusion 51b may induce the losing weight portions 53e and 55e to deform while maintaining the shape of the seating portion 51 even when a tensile force acts to the wearing portion 50 while the user wears the electronic device 1.

Figure 31:
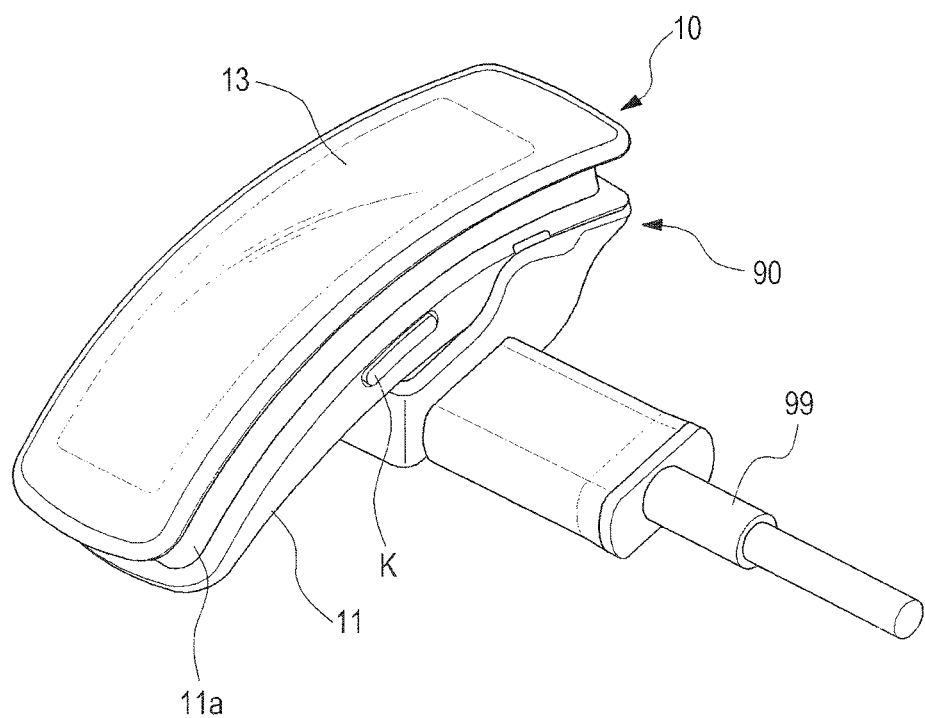
FIG. 31 is a perspective view illustrating an example in which a main body of an electronic device is cradled on a mount according to an embodiment.
Figure 32:
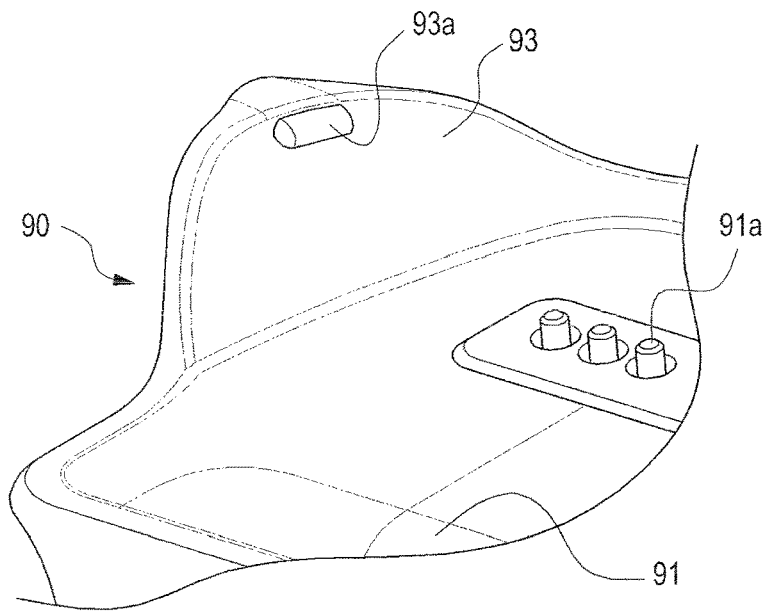
FIG. 32 is a perspective view illustrating a portion of a mount of an electronic device according to an embodiment.
Figure 33:
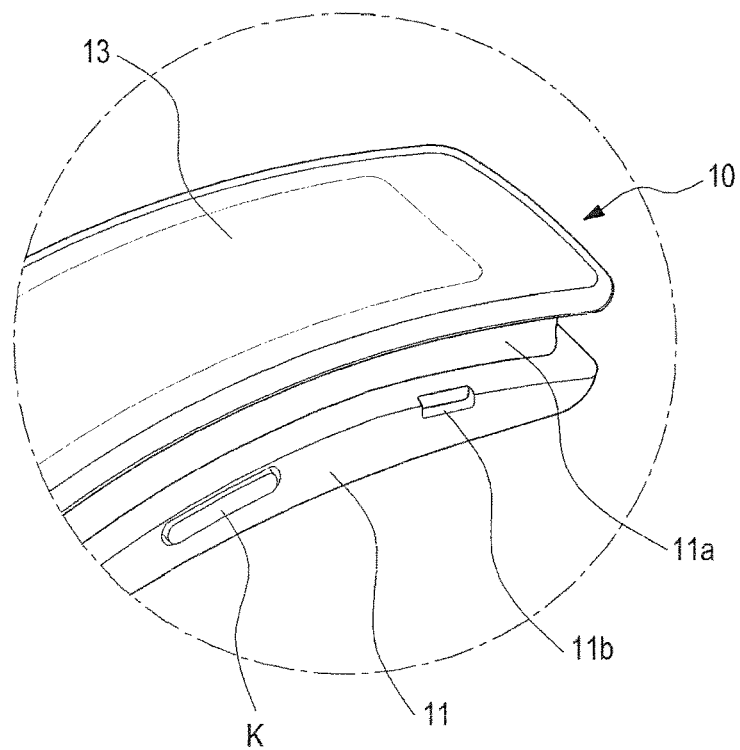
FIG. 33 is a perspective view illustrating a portion of a main body of an electronic device according to an embodiment.

FIG. 31 is a perspective view illustrating an example in which a main body of an electronic device is cradled on a mount according to an embodiment. FIG. 32 is a perspective view illustrating a portion of a mount of an electronic device according to an embodiment. FIG. 33 is a perspective view illustrating a portion of a main body of an electronic device according to an embodiment.

Referring to FIGS. 31 to 33, according to this embodiment, the electronic device 1 may further include an external device, e.g., a mount 90, and may be configured so that the main body 10 separated from the wearing portion 50 may be attached or detached from the mount 90. The mount 90 may provide a means for connection to other electronic device, e.g., a personal computer, as well as the function of charging the battery pack embedded in the main body 10.

The mount 90 may include a seating surface 91 at least partially surrounding the rear surface of the main body 10 and fastening surfaces 93 extending from the seating surface 91 while facing each other. The fastening surfaces 93 may be formed to at least partially cover a side surface of the main body 10. In order to stably fasten the main body 10 to the mount 90, the fastening surfaces 93 may have fastening protrusions 93a. The fastening protrusions 93a may be engaged with the fastening groove 11b formed on the side surface of the main body 10, stably fastening the main body 10 to the mount 90. The fastening protrusions 93a may be formed of an elastomer, such as silicone or rubber or may be configured to be withdrawn from the fastening surface 93.

For electrical connection between the main body 10 and the mount 90, the mount 90 may have second contact members 91a, such as pogo fins. The second contact members 91a may be arranged corresponding to the contact member 23 (e.g., the charging terminal) provided on the rear surface R of the main body 10, providing electrical connection between the main body 10 and the mount 90. Although the contact members 23 are collectively denoted as the charging terminal in describing particular embodiments of the present invention, such contact members are not limited to the charging terminal. For example, the contact members 23 provided on the rear surface R of the main body 10 may be utilized as contact terminals providing data communication with other electronic device, such as a personal computer.

Figure 34:
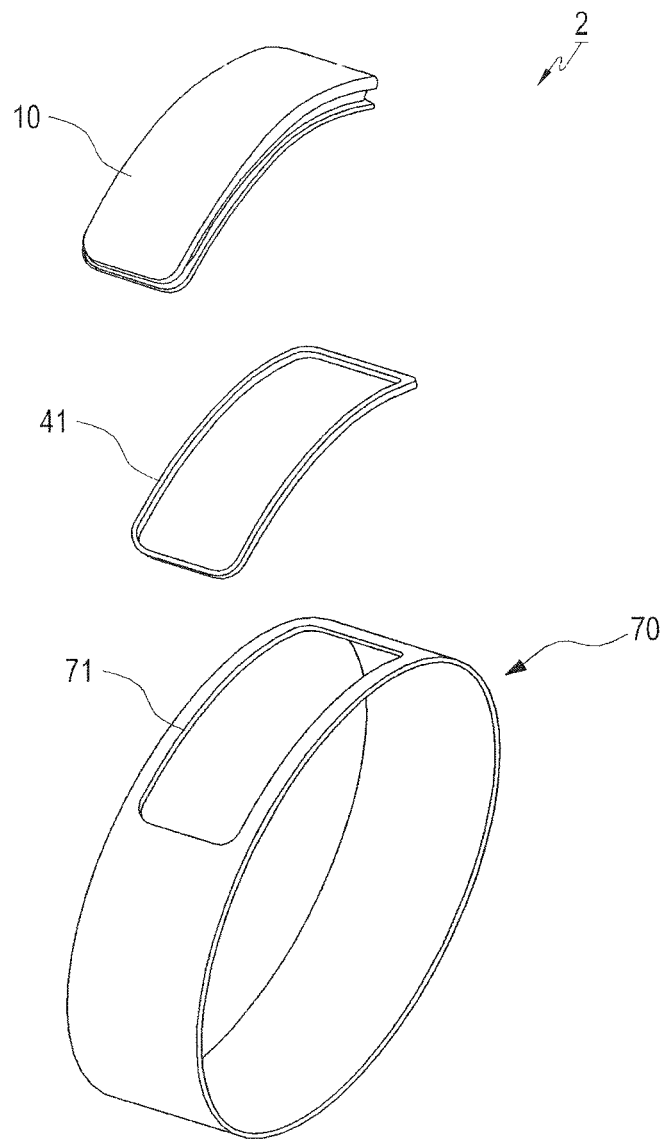
FIG. 34 is a perspective view illustrating an example in which a main body is separated from a wearing portion in an electronic device according to another embodiment.
Figure 35:
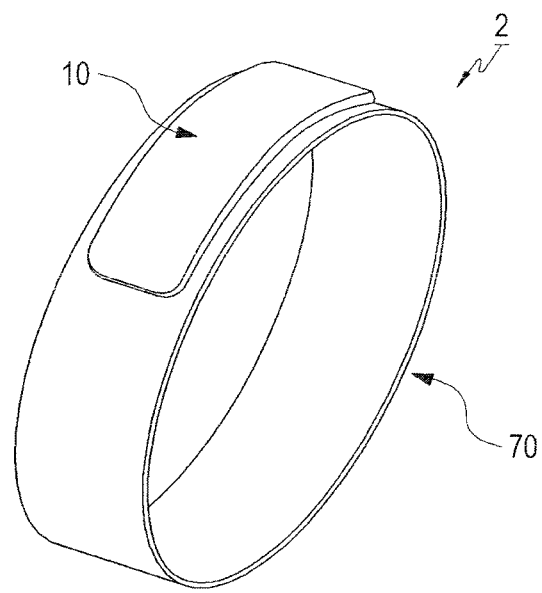
FIG. 35 is a perspective view illustrating a state where an electronic device is worn according to another embodiment.

FIG. 34 is a perspective view illustrating an example in which a main body is separated from a wearing portion in an electronic device according to another embodiment. FIG. 35 is a perspective view illustrating a state where an electronic device is worn according to another embodiment.

In describing the electronic device according to this embodiment, it should be noted that, despite differences in shape, the same components as those in the prior embodiments or components easily appreciated from the prior embodiments are assigned with the same reference numerals or excluded from numbering, and their detailed description is omitted.

Referring to FIGS. 34 and 35, according to this embodiment, the wearing portion 70 of the electronic device 2 may further include a connecting member 41 formed of a different material. The connecting member 41 may be formed of a different material from the seating portion 71 or the wearing band. For example, if the seating portion 71 or wearing band is formed of an elastic material (flexible material), the connecting member 41 may be formed of a more rigid material than the seating portion 71 or the wearing band. For example, the connecting member 41 may be formed of a synthetic resin including polycarbonate or conductive metal. The connecting member 41 may be disposed to an inner surface of the seating portion 71 through assembly, bonding, dual injection molding, or insert injection molding. The connecting member 41 may provide further secure fastening between the seating portion 71 and the main body 10 and may mitigate or prevent wear of the seating portion 71 due to long-term, repetitive attachment or detachment of the main body 10. The connecting member 41 may be fastened to the inner surface of the seating portion 71 by dual injection molding, and when coupled with the main body 10, it may be fully accommodated in the side surface of the main body 10.

In another embodiment, the connecting member may be utilized as a decoration of the electronic device.

Figure 36:
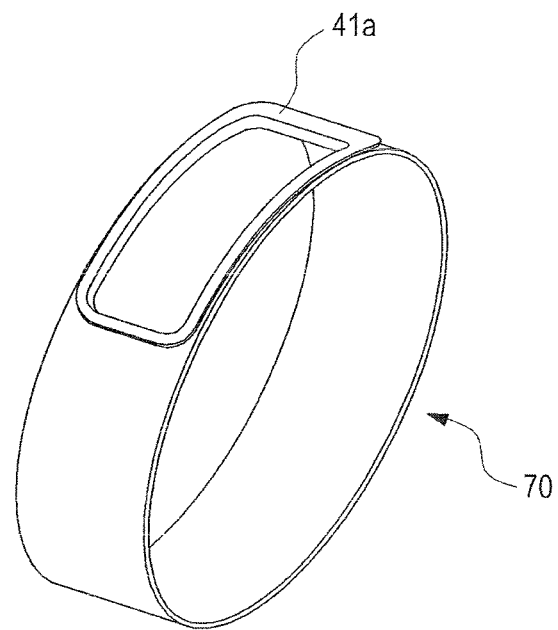
FIG. 36 is a perspective view illustrating a variation to a wearing portion of an electronic device according to another embodiment.
Figure 37:
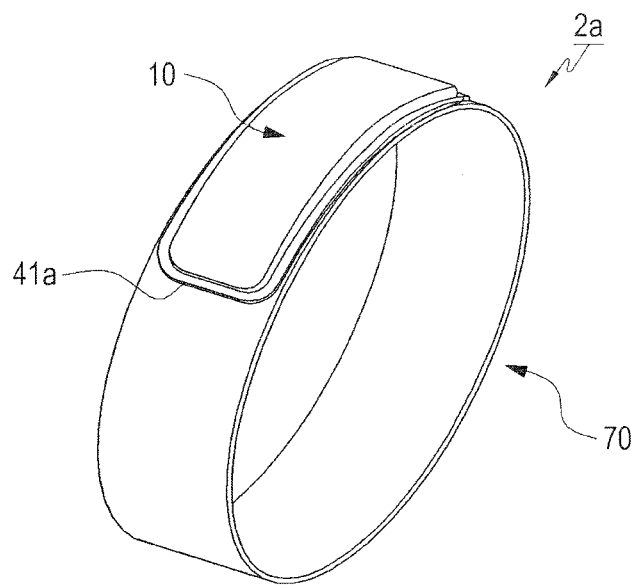
FIG. 37 is a perspective view illustrating a variation to an electronic device according to another embodiment.

FIG. 36 is a perspective view illustrating a variation to a wearing portion of an electronic device according to another embodiment. FIG. 37 is a perspective view illustrating a variation to an electronic device according to another embodiment.

In the prior embodiments, the connecting member 41 is completely received in the main body 10 and is thus not externally exposed. However, as shown in FIGS. 36 and 37, the connecting member 41*a* in the instant embodiment may have its portion exposed to the periphery of the main body 10. Accordingly, the connecting member 41*a* may be utilized as a decoration of the electronic device 2*a* by using its color or shape, forming the connecting member 41*a* with a phosphor-containing synthetic resin, or adding, e.g., a light emitting diode. As such, various decorative effects may be achieved using the connecting member 41*a* depending on the material of the connecting member 41*a* or devices (e.g., a light emitting diode) added to the connecting member 41*a*.

Figure 38:
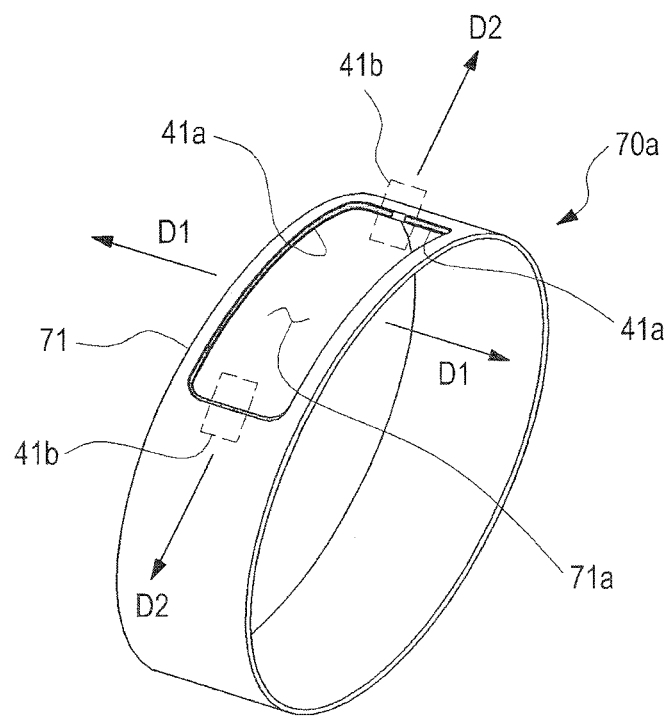
FIG. 38 is a perspective view illustrating another variation to a wearing portion of an electronic device according to another embodiment.

FIG. 38 is a perspective view illustrating another variation to a wearing portion of an electronic device according to another embodiment.

Referring to FIG. 38, at least one pair of connecting members 41*a* may be provided in the wearing portion 70. The plurality of connecting members 41*a* may be arranged along an inner wall of the opening 71*a*. In this embodiment, the wearing portion 70*a* includes a pair of connecting members 41*a*, for example. In arranging the connecting members 41*a*, slits 41*b* may be formed between the connecting members 41*a*. The slits 41*b* respectively may be arranged at both ends of the opening 71*a* in the vertical direction. If the connecting members 41*a* are formed of a rigid material (e.g., polycarbonate or conductive metal), the seating portion 71 may be deformed or its deformation may become smooth by the connecting members 41*a* in only one direction. For example, as shown in FIG. 38, while the seating portion 71 may be deformed against the tensile force D1 acting to the seating portion 71 in the horizontal direction, the deformation of the seating portion 71 against the tensile force D2 acting in the vertical direction may be suppressed by the connecting members 41*a*. Various settings may be made to the direction along which the wearing portion may be deformed by the tensile force depending on the number or position of the slits 41*b* (or depending on the number and position of the connecting members 41*a*).

According to a specific embodiment of the present invention, exemplified is a structure in which the seating portion is not deformed in a defined direction but may be deformed in other directions using the structure where a plurality of connecting members are arranged with the slits disposed therebetween. However, the present invention is not limited thereto. For example, the direction in which the seating portion may be deformed may be restricted by disposing one looped curve-shaped connecting member and making a portion of the connecting member thinner than the rest or by forming a portion of the connecting member with an elastically deformable material.

The arrangement of the connecting members 41*a* and the slits 41*b* shown in FIG. 38 may suppress a deformation of the wearing portion 70 against the tensile force acting while worn, stably maintaining the coupled state of the main body to the wearing portion 70*a*. Further, the user may easily couple or decouple the main body from the wearing portion 70*a* while stretching the wearing portion 70*a* in the horizontal direction.

Figure 39:
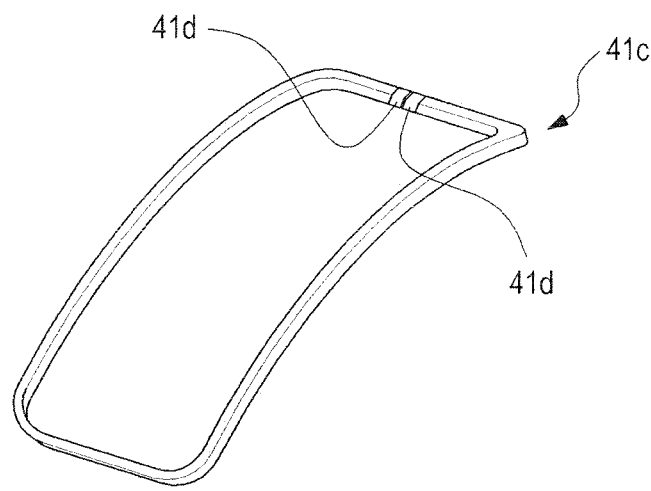
FIG. 39 is a perspective view illustrating an example of a coupling member provided in a wearing portion of an electronic device according to another embodiment.
Figure 40:
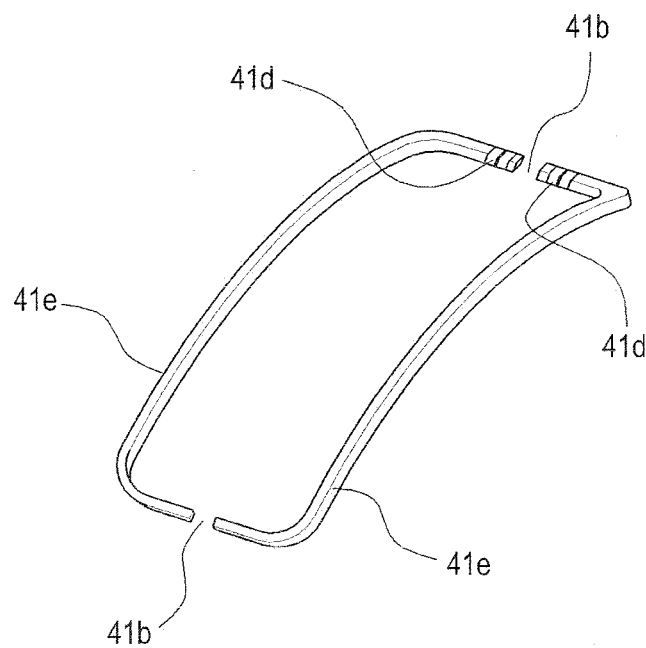
FIG. 40 is a perspective view illustrating another example of a coupling member provided in a wearing portion of an electronic device according to another embodiment.

FIG. 39 is a perspective view illustrating an example of a coupling member provided in a wearing portion of an electronic device according to another embodiment. FIG. 40 is a perspective view illustrating another example of a coupling member provided in a wearing portion of an electronic device according to another embodiment.

The connecting members 41*c* and 41*e* shown in FIGS. 39 and 40 may be each formed of a conductive material and may be electrically connected with the main body. For example, the connecting members 41*c* and 41*e* may be utilized as antenna devices expanding wireless communication functionality. In one embodiment, the connecting members 41*c* and 41*e* respectively may have contact terminals 41*d* or magnetic bodies. The contact terminals 41*d* may provide electrical connection between the main body and the connecting members 41*c* and 41*e*. A configuration of the main body corresponding to the connecting members 41*c* and 41*e* having such contact terminals 41*d* or magnetic bodies is shown in FIG. 41.

Figure 41:
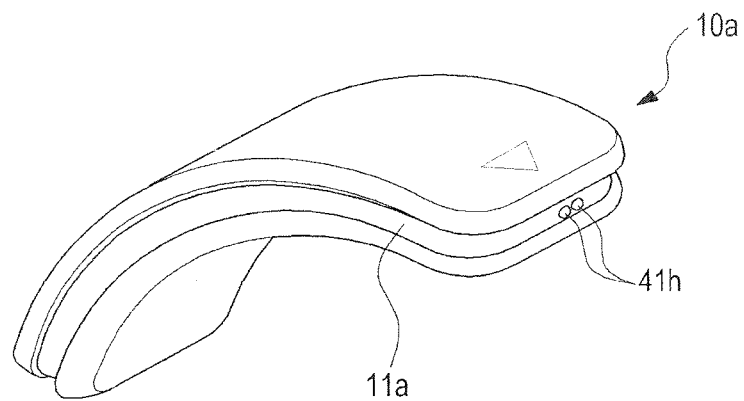
FIG. 41 is a perspective view illustrating another example of a main body of an electronic device according to another embodiment.

FIG. 41 is a perspective view illustrating another example of a main body of an electronic device according to another embodiment.

Referring to FIGS. 39, 40, and 41, the main body 10*a* corresponding to the connecting members 41*c* and 41*e* may have another sensor 41*h* arranged at a side surface of the main body 10*a*, e.g., inside, around, or adjacent to the fastening groove 11*a*. In this embodiment, the sensor 41*h* may be connected with the contact terminals 41*d* to detect whether the main body 10*a* is mounted to the wearing portions 70 and 70*a* or the direction where the main body 10*a* is mounted to the wearing portions 70*a* and 70*a*. For example, if the contact terminals 41*d* are formed of conductive pads, the sensor 41*h* may be formed of at least one electrode electrically connected through the contact terminals 41*d*. If the contact terminals 41*d* are provided in the connecting members 41*c* and 41*e*, but not in the magnetic bodies, the sensor 41*h* may be formed of a hall sensor.

If the connecting members 41*c* and 41*e* are formed of a conductive material, and the sensor 41*h* is formed of an electrode, the connecting members 41*c* and 41*e* may be utilized as an antenna device expanding wireless communication functionality of the main body 10*a*. In such case, upon detecting an electrical connection with the connecting members 41*c* and 41*e* while coupled with the wearing portions 70 and 70*a*, the main body 10*a* may activate a communication mode. If the main body 10*a* is separated from the wearing portions 70 and 70*a* or the main body 10*a* is mounted to the wearing portions 70 and 70*a* in a direction where the sensor 41*h* cannot detect the contact terminals 41*d*, the main body 10*a* may release the communication mode to prevent battery consumption. Other various operation modes may be set considering, e.g., the direction where the main body 10*a* is mounted utilizing the sensor 41*h* and the contact terminal 41*d* (or magnetic body).

Figure 42:
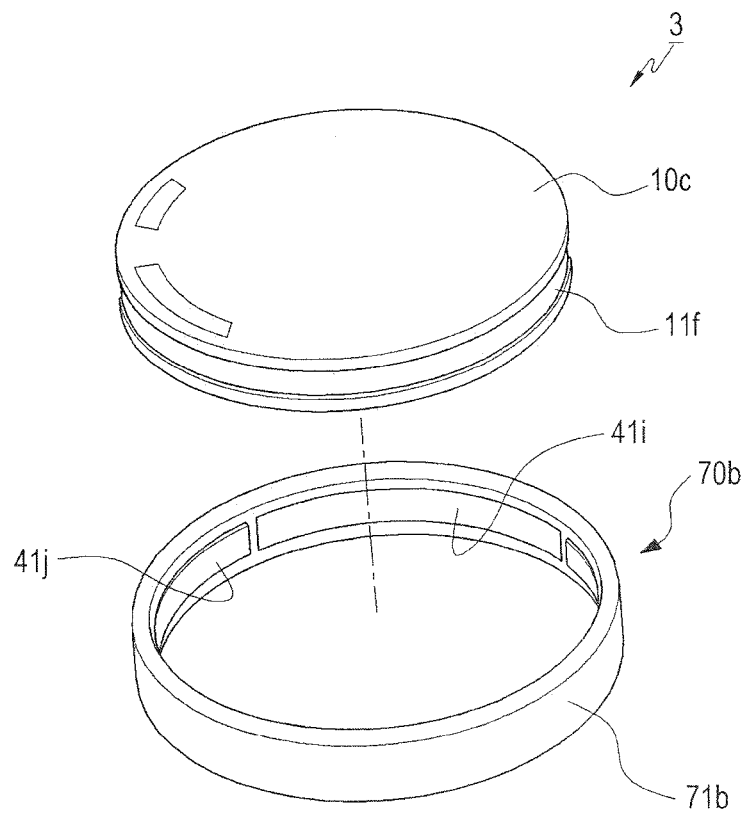
FIG. 42 is a perspective view illustrating an example in which a main body is separated from a wearing portion in an electronic device according to another embodiment.

FIG. 42 is a perspective view illustrating an example in which a main body is separated from a wearing portion in an electronic device according to another embodiment.

According to an embodiment, the wearing portion 70*b* of the electronic device 3 may be implemented in a pendant shape. For example, the seating portion 71*b* of the wearing portion 70*b* may be implemented in an annular shape, and a necklace-shaped wearing member (not shown) may extend from the seating portion 71*b*. Other connecting member(s) 41*i* and 41*j* formed of a different material from the seating portion 71*b* may be arranged on an inner surface of the seating portion 71*b*. If a plurality of connecting members 41*i* and 41*j* are arranged on the inner surface of the seating portion 71*b*, the seating portion 71*b* may be expanded by a tensile force acting in a particular direction but may be suppressed from expansion against tensile force acting in other directions. The main body 10*c* of the electronic device 3 may be shaped as a circular plate wrapped around the seating portion 71*b*. A connecting hole 11*f* may be formed in a side surface of the main body 10*c* to have a shape corresponding to the seating portion 71*b*. Although not shown, if the contact terminals (or magnetic bodies) are arranged in the connecting members 41*i* and 41*j*, and their corresponding sensors are provided in the main body 10c, the operation mode of the main body 10c may be set depending on the position or direction where the main body 10c is coupled.

Figure 43:
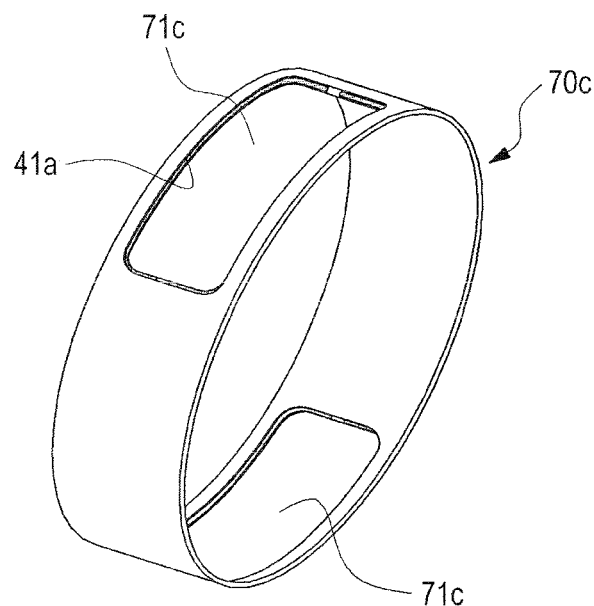
FIG. 43 is a perspective view illustrating a wearing portion of an electronic device according to another embodiment.
Figure 44:
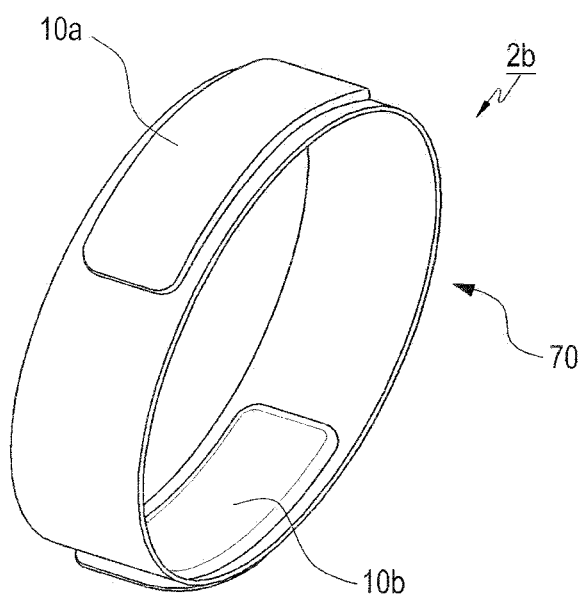
FIG. 44 is a perspective view illustrating an electronic device according to another embodiment.

FIG. 43 is a perspective view illustrating a wearing portion of an electronic device according to another embodiment. FIG. 44 is a perspective view illustrating an electronic device according to another embodiment.

Referring to FIGS. 43 and 44, according to this embodiment, the electronic device 2b may have a plurality of openings 71c in the wearing portion 70c. Accordingly, the electronic device 2b may further include a second main body 10b in addition to the main bodies 10 and 10a. The second main body 10b may be configured identically to the main bodies 10 and 10a or may be configured to have different functions. In the case of being configured identically to the main bodies 10 and 10a, the second main body 10b may expand the memory capacity or display area, and the second main body 10b may interwork with the main bodies 10 and 10b wiredly or wirelessly or operate independently therefrom, allowing various applications to be driven simultaneously. Further, the second main body 10b may expand the computation device or battery capacity or provide an assistant storage device or may add various switches or sensors not mounted in the main bodies 10 and 10a. For example, if the electronic device 2b has a bio signal sensor but is under the environment where it cannot secure a sufficient amount of light required to recognize, e.g., a vein, it may supply the insufficient light using the second main body 10b.

Figure 45:
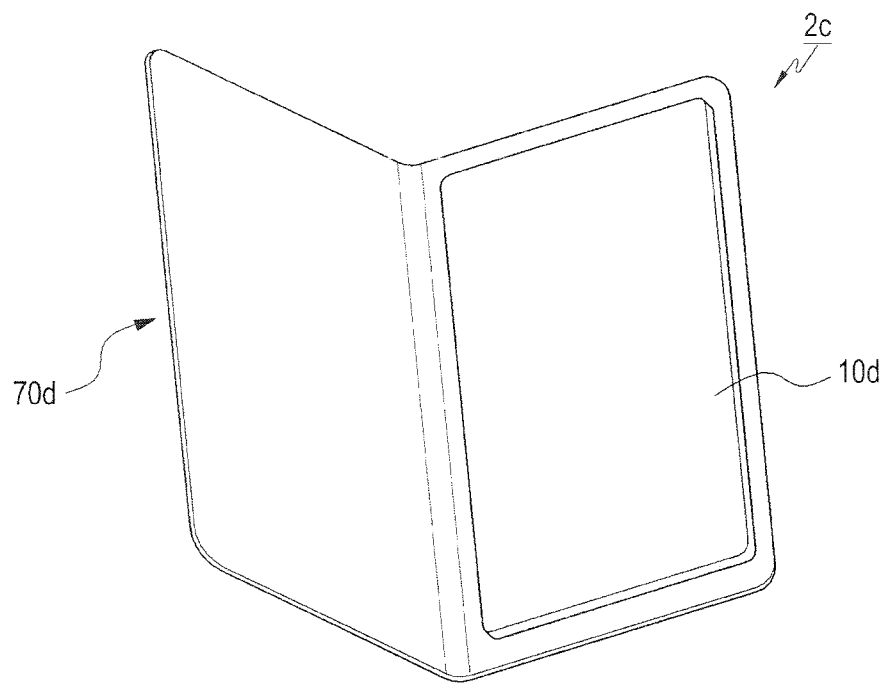
FIG. 45 is a perspective view illustrating an electronic device according to another embodiment.
Figure 46:
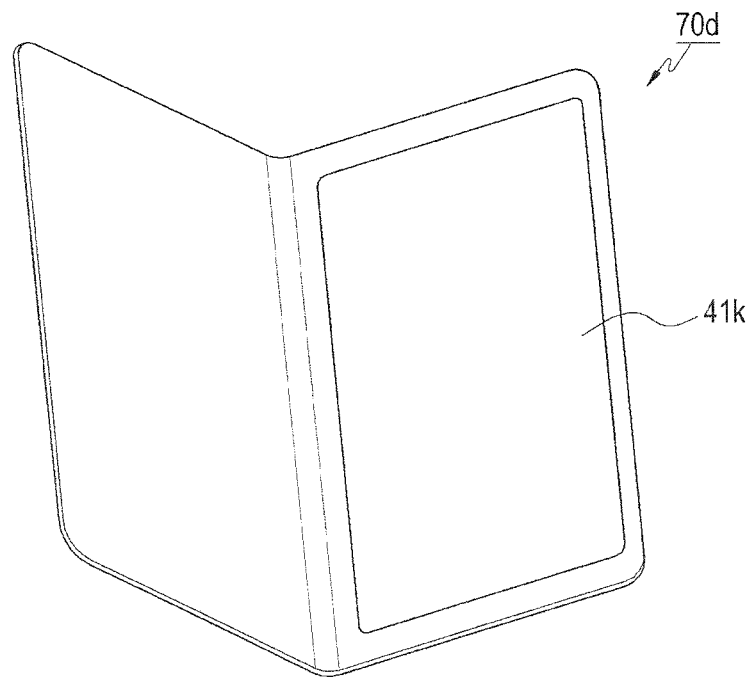
FIG. 46 is a perspective view illustrating a cover part of an electronic device according to another embodiment.
Figure 47:
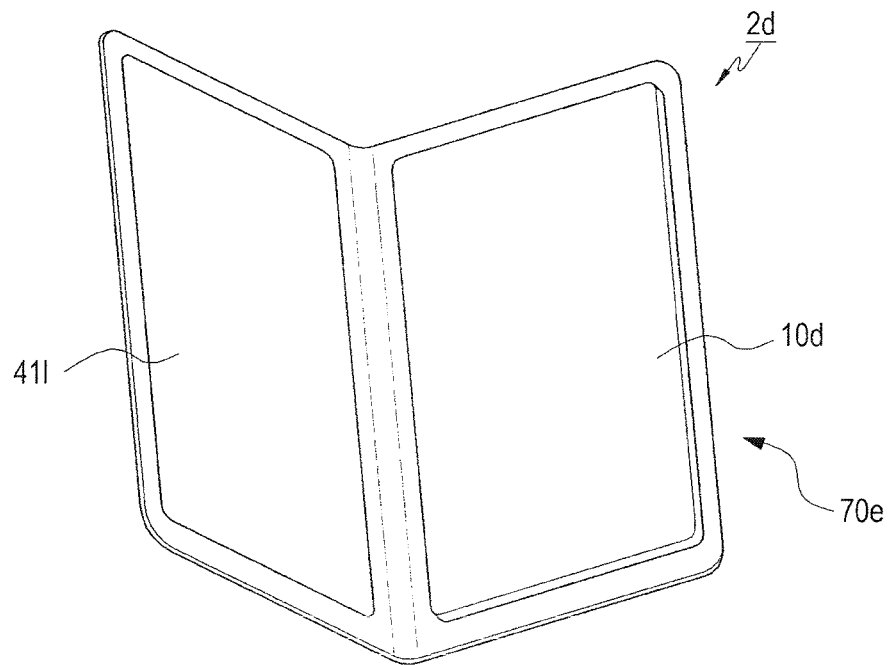
FIG. 47 is a perspective view illustrating a variation to an electronic device according to another embodiment.

FIG. 45 is a perspective view illustrating an electronic device according to another embodiment. FIG. 46 is a perspective view illustrating a cover part of an electronic device according to another embodiment. FIG. 47 is a perspective view illustrating a variation to an electronic device according to another embodiment.

In describing particular embodiments of the present invention, although wearable electronic devices are described as an example in the prior embodiments, the present invention is not limited thereto. For example, various embodiments may also be applicable to commercially available bar-type electronic devices.

Referring to FIGS. 45 to 47, the main body of the electronic device 2c may be implemented in a bar-type mobile communication terminal 10d, and the wearing portion may be formed of covering members 70d and 70e detachably provided in the terminal 10d. The covering members 70d and 70e may be configured to be mounted and fastened to the rear surface of the terminal 10d to open and close the front surface of the terminal 10d. The covering members 70d and 70e may include additional devices 41k and 41l on their internal surfaces, e.g., a first surface attached or detached from the rear surface of the terminal 10d or a second surface opening and closing the front surface of the terminal 10d. The additional devices 41k and 41l may be configured of, e.g., near-field communication (NFC) antennas, assistant batteries, or assistant storage devices. Further, if the covering members 70d and 70e include seating portions fastened to side surfaces of the terminal 10d, the additional devices 41k and 41l may be arranged on the seating portions of the covering members 70d and 70e. As implemented in the prior embodiments, various settings may be made, such as setting different operation modes of the terminal 10d depending on the direction where the terminal 10d is mounted to the covering members 70d and 70e by allowing the assistant devices 41k and 41l to interwork with the terminal 10d.

Figure 48:
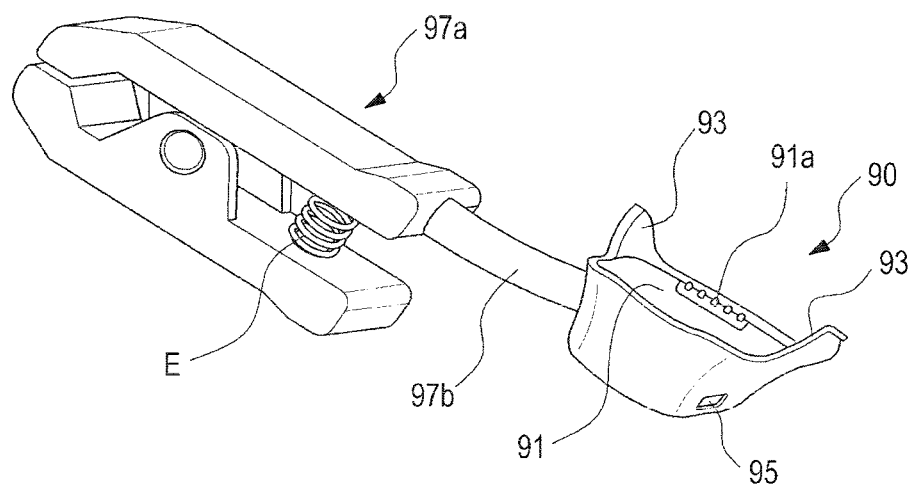
FIG. 48 is a perspective view illustrating a variation to a mount of an electronic device according to an embodiment.
Figure 49:
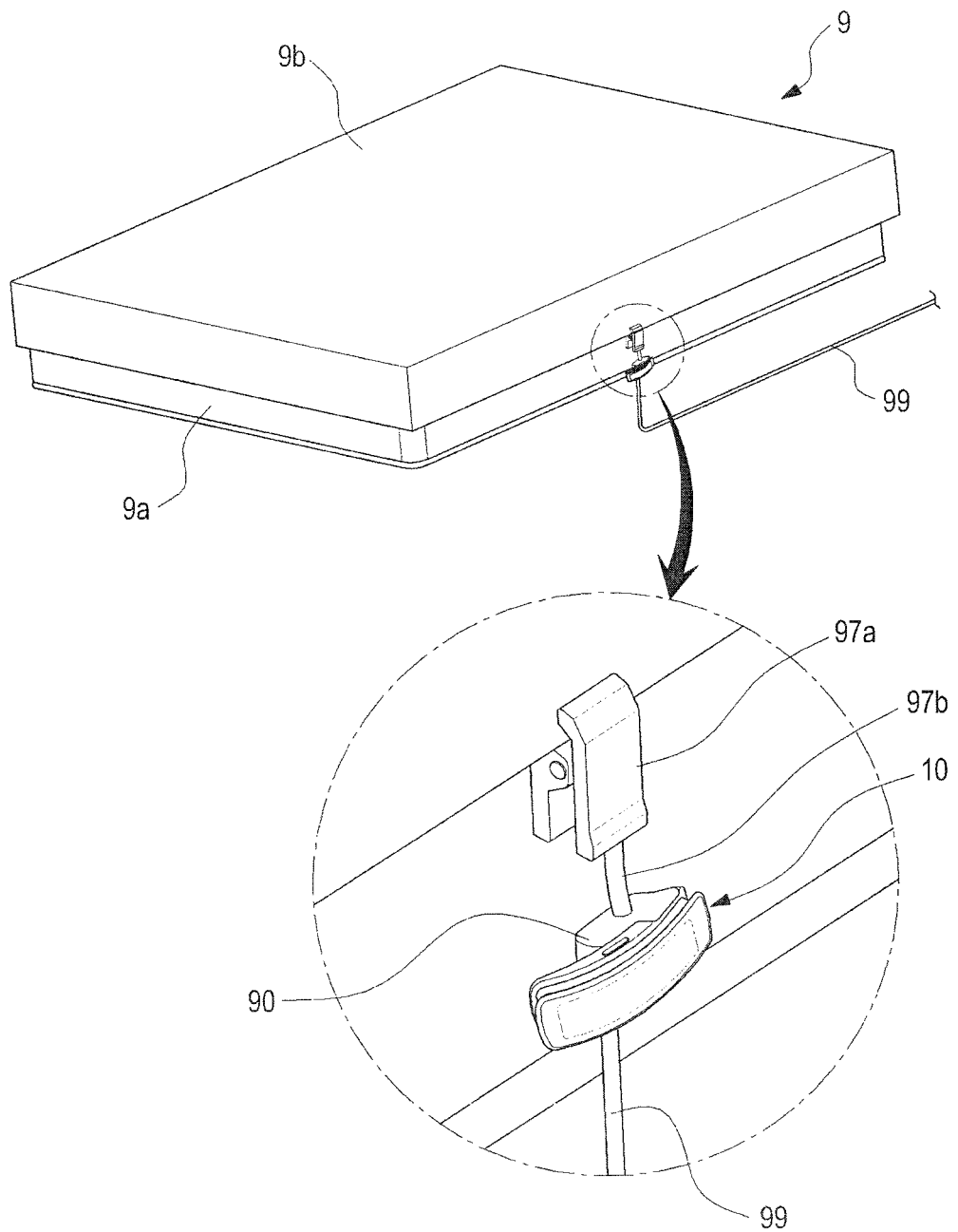
FIG. 49 is a view illustrating an example of using a mount of an electronic device according to another embodiment.
Figure 50:
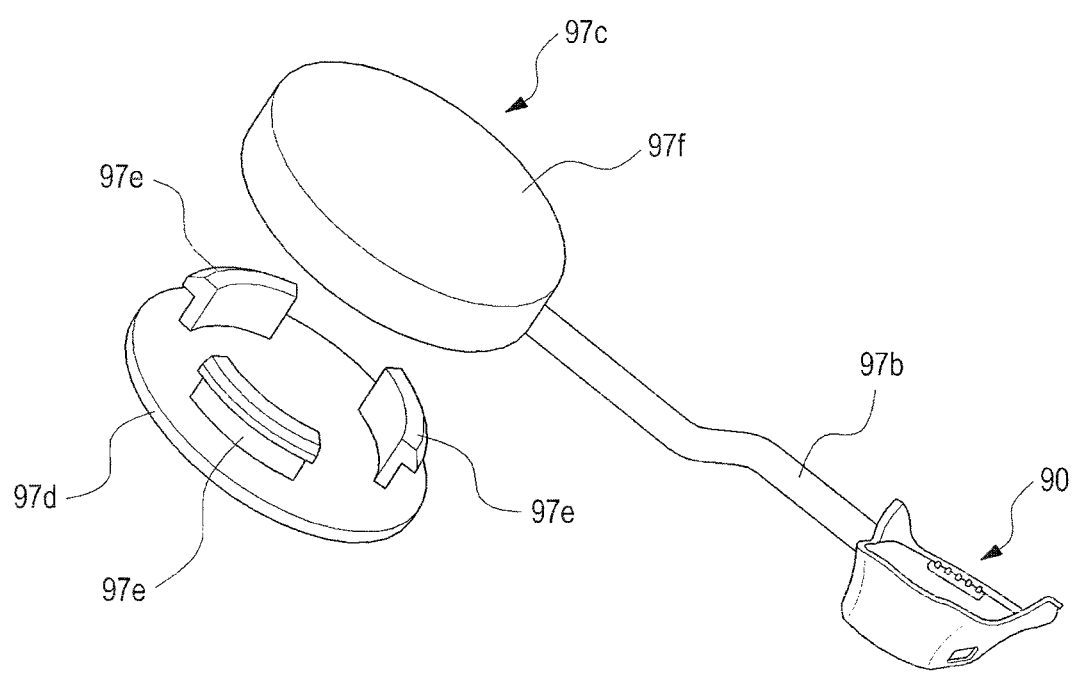
FIG. 50 is a perspective view illustrating another variation to a mount of an electronic device according to an embodiment.

FIG. 48 is a perspective view illustrating a variation to a mount of an electronic device according to an embodiment. FIG. 49 is a view illustrating an example of using a mount of an electronic device according to another embodiment. FIG. 50 is a perspective view illustrating another variation to a mount of an electronic device according to an embodiment.

Referring to FIGS. 48 to 50, according to an embodiment, the electronic device may allow the main body to be mounted on an external device, e.g., the above-described mount, to implement various functions even when not worn on the human body. According to this embodiment, the mount may be equipped in a product used by the user or a piece of furniture, e.g., a bed, allowing for adjustment of a light to a sleep environment or detection of the user's sleep state when the main body of the electronic device is coupled.

According to an embodiment, the electronic device may include fastening devices 97a and 97c connected to the mount 90. The mount 90 and the fastening devices 97a and 97c may be connected together via a connecting portion 97b formed of a soft material. The fastening devices 97a and 97c may be implemented in a clip structure shown in FIG. 48 or in a snap button structure as shown in FIG. 50, and in another embodiment, they may be implemented as magnetic bodies or Velcro tapes. The fastening devices 97a and 97c allow the mount 90 to be mounted on a good or piece of furniture used by the user, e.g., a desk, standing light, wall, or bed.

Referring to FIG. 49, the clip-structure fastening device 97a including an elastic member E may be fastened to a base 9a or mattress 9b of a bed 9. FIG. 50 illustrates an example of the fastening device 97c implemented in a snap button structure. For example, the fastening device 97c may include a fastening plate 97d fastened to the bed mattress and a coupling plate 97f provided in the connecting portion 97b. The coupling plate 97f may be coupled and fastened to the fastening plate 97d by way of multiple hooks 97e formed in the fastening plate 97d, facing the fastening plate 97d, thereby fastening the mount 90 to the bed.

According to an embodiment, if the main body 10 of the electronic device 1 is separated from the wearing portion 50 and is positioned on the mount 90 for, e.g., charging purposes, some functions may be limited. For example, the bio signal sensing function detecting the user's heart rate may be limited. Further, in case the bio signal sensor is used to monitor the user's sleep state or sleep quality while wearing the electronic device 1, it may rather interfere with sleep. According to an embodiment, as the main body 10-coupled mount 90 may be mounted to the bed, e.g., the mattress 9b by way of the fastening devices 97a and 97c, it may monitor the body movement and state such as the user's toss and turn during sleep simultaneously with charging. For example, if the bed shakes due to the user's movement, such movement may be transferred to the main body 10 through the fastening devices 97a and 97c and the connecting portion 97b. The main body mounted in the mount 90 may monitor the user's sleep state through such movement or vibration. If a charging cable 99 is connected to an interface connector 95 provided on a side surface of the mount 90, the battery pack embedded in the main body 10 may be charged while such sleep state is simultaneously monitored. Monitoring the user's sleep state may be performed through a microphone embedded in the main body 10 as well as through such movement or vibration.

In another embodiment, as the main body 10 is coupled to the mount 90, the main body 90 may share information with other electronic devices. Here, the term "other electronic devices" may mean devices connectable to the main body 10 through a network, such as other types of accessories or mobile devices or home network devices (e.g., smart TVs, smart lights, air conditioners, or home network controllers) as well as the above-described wearing portions.

If the user couples the main body 10 to the mount 90, information indicating that the user desires to sleep may be transferred from the main body 10 to the other electronic device to adjust a video/audio device, light, or air conditioner. Further, if a wakeup time is previously scheduled, the main body 10 may operate the video/audio device or light at the scheduled time to inform of the wakeup time. If the user separates the main body 10 from the mount 90 and mounts it to the wearing portion 50, the main body 10 may recognize the coupling with the mount 90 to stop the sleep monitoring function. Further, other various functions may be embodied depending on the operating environment of the main body 10 or user settings.

Figure 51:
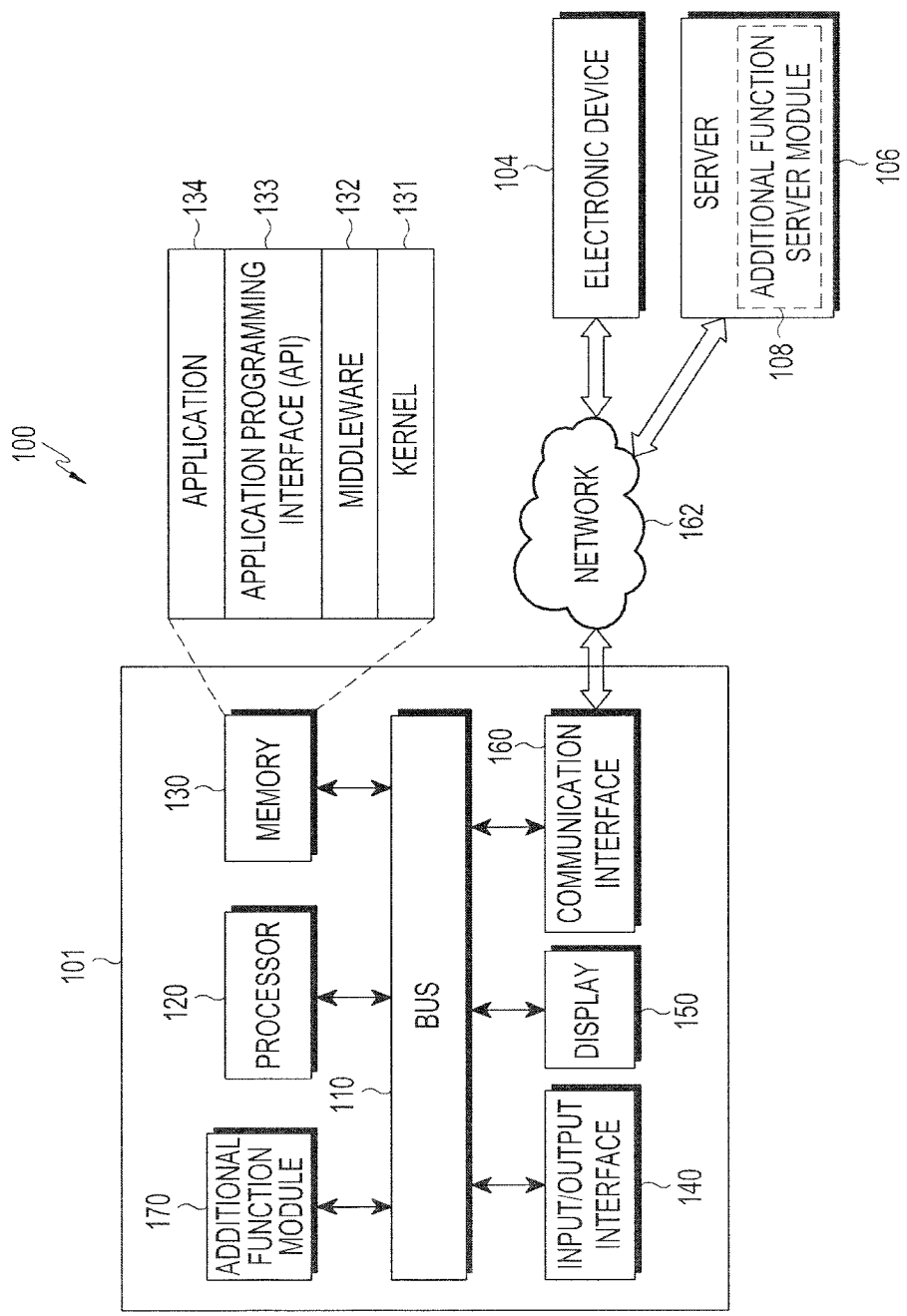
FIG. 51 illustrates a network environment including an electronic device according to an embodiment.

FIG. 51 illustrates a network environment 100 including an electronic device 101 according to an embodiment. Referring to FIG. 51, the electronic device 101 may include a bus 110, a processor 120, a memory 130, an input/output interface 140, a display 150, a communication interface 160, and an additional function module 170.

The bus 110 connects the other components to each other, and the bus 110 may carry communications (e.g., control messages) between the other components.

The processor 120 may receive a command from other component (e.g., at least one of the memory 130, the input/output interface 140, the display 150, the communication interface 160, or the additional function module 170) through, e.g., the bus 110, may interpret the received command, and may execute computation or data processing according to the interpreted command.

The memory 130 may store a command or data received from other component (e.g., at least of the input/output interface 140, the display 150, the communication interface 160, or the additional function module 170) or a command or data generated by the processor 120 or other component. The memory 130 may retain programming modules including, e.g., a kernel 131, middleware 132, an application programming interface (API) 133, or an application 134. The programming modules may be configured in software, firmware, hardware or a combination of two or more thereof.

The kernel 131 may control or manage system resources (e.g., at least one of the bus 110, the processor 120, or the memory 130) used to execute the operation or function implemented in the other programming modules, e.g., the middleware 132, the API 133 or the application 134. The kernel 131 may provide an interface that allows the middleware 132, the API 133, or the application 134 to access the individual components of the electronic device 101 to control or manage the same.

The middleware 132 may function as a relay to allow the API 133 or the application 134 to communicate data with the kernel 131. Further, the middleware 132 may perform control on task requests (e.g., at least one of scheduling or load balancing) using, e.g., a method of assigning priority allowing at least one of the applications 134 to use system resources (e.g., at least one of the bus 110, processor 120, and memory 130) of the electronic device 101 in relation with the task requests received from the applications 134.

The API 133 is an interface allowing the application 134 to control functions provided from the kernel 131 or the middleware 132. For example, the API 133 may include at least one interface or function (e.g., a command) for at least one file control, window control, image processing or text control.

According to an embodiment, the applications 134 may include at least one of a short message service (SMS)/ multimedia messaging service (MMS) application, an email application, a calendar application, an alarm application, a healthcare application (e.g., an application for measuring exercise load or blood sugar), or an environmental information application (e.g., an application providing at least one of air pressure, moisture, or temperature information). Additionally or alternatively, the application 134 may be an application related to information exchange between the electronic device 101 and an external electronic device (e.g., electronic device 104). Examples of the information exchange-related application may include, but is not limited to, a notification relay application for transferring specific information to the external electronic device, or a device management application for managing the external electronic device.

For example, the notification relay application may include a function for relaying notification information generated from other applications of the electronic device 101 (e.g., the SMS/MMS application, email application, health-care application, or environmental information application) to the external electronic device (e.g., the electronic device 104). Additionally or optionally, the notification relay application may receive notification information from, e.g., the external electronic device (e.g., the electronic device 104) and may provide the received notification information to the user. The device management application may perform at least some functions of the external electronic device (e.g., the electronic device 104) communicating with the electronic device 104 (for example, at least one of turning on/off the external electronic device (or some components of the external electronic device) or control of brightness (or resolution) of the display), and the device management application may manage (e.g., at least one of install, delete, or update) an application operating in the external electronic device or a service (e.g., call service or message service) provided from the external electronic device.

According to an embodiment, the application 134 may include an application designated depending on the attribute (e.g., type of electronic device) of the external electronic device (e.g., the electronic device 104). For example, in case the external electronic device is an MPEG audio layer-3 (MP3) player, the application 134 may include an application related to playing music. Similarly, in case the external electronic device is a mobile medical device, the application 134 may include an application related to health-care. According to an embodiment, the application 134 may include an application designated to the electronic device 101 or an application received from an external electronic device (e.g., a server 106 or the electronic device 104).

The input/output interface 140 may transfer commands or data input by the user through an input/output device (e.g., at least one of a sensor, a keyboard or touchscreen) to at least one of the processor 120, the memory 130, the communication interface 160, or the additional function module 170 through, e.g., the bus 110. For example, the input/output interface 140 may provide data regarding the user's touch input through a touchscreen to the processor 120. The input/output interface 140 may output, through the input/ output device (e.g., at least one of a speaker or display), commands or data received from at least one of the processor 120, the memory 130, the communication interface 160, or the additional function module 170 through, e.g., the bus 110. For example, the input/output interface 140 may output voice data processed by the processor 120 to the user through a speaker.

The display 150 may display various types of information (e.g., at least one of multimedia data or text data) to the user.

The communication interface 160 may interface communication between the electronic device 101 and an external electronic device (e.g., the electronic device 104 or the server 106). For example, the communication interface 160 may be wiredly or wirelessly connected with the network 162 to communicate with the external electronic device. The wireless communication may include at least one of, e.g., wireless fidelity (Wi-Fi), Wi-Fi direct, Bluetooth (BT), near field communication (NFC), global positioning system (GPS), or cellular communication (e.g., LTE, LTE-A, CDMA, WCDMA, UMTS, WiBro or GSM). The wired communication may include at least one of, e.g., universal serial bus (USB), high definition multimedia interface (HDMI), recommended standard 232 (RS-232), or plain old telephone service (POTS).

According to an embodiment, the network 162 may be a communication network. The telecommunication network may include a computer network, the Internet, an Internet of things (IoT) network, or a telephone network. According to an embodiment, protocols for communication between the electronic device 101 and the external electronic device (examples of such protocols include, but not limited to, transport layer protocol, data link layer protocol, or physical layer protocol) may be supported by the application 134, the API 133, the middleware 132, the kernel 131, or the communication interface 160.

According to an embodiment, the additional function module 170 may support to drive the electronic device 101 by performing at least one operation of operations (or functions) implemented on the electronic device 101. For example, the server 106 may include an additional function server module 108 able to support the additional function module 170 implemented in the electronic device 101. For example, the additional function server module 108 may include at least one component of the additional function module 170 to perform (or surrogate) at least one of operations performed by the additional function module 170.

The additional function module 170 may process at least part of information obtained from other elements (e.g., at least one of the processor 120, the memory 130, the input/output interface 140, or the communication interface 160) and may use the same in various manners. For example, the additional function module 170 may control at least some functions of the electronic device 101 using the processor 120 or independently from the processor 120 so that the electronic device 101 may interwork with another electronic device (e.g., the electronic device 104 or 104 or the server 106). The additional function module 170 may be integrated with the processor 120 or the communication interface 160. According to an embodiment, at least one configuration of the additional function module 170 may be included in the server 106 (e.g., the additional function server module 108) and may be supported for at least one operation implemented on the additional function module 170 from the server 106.

Figure 52:
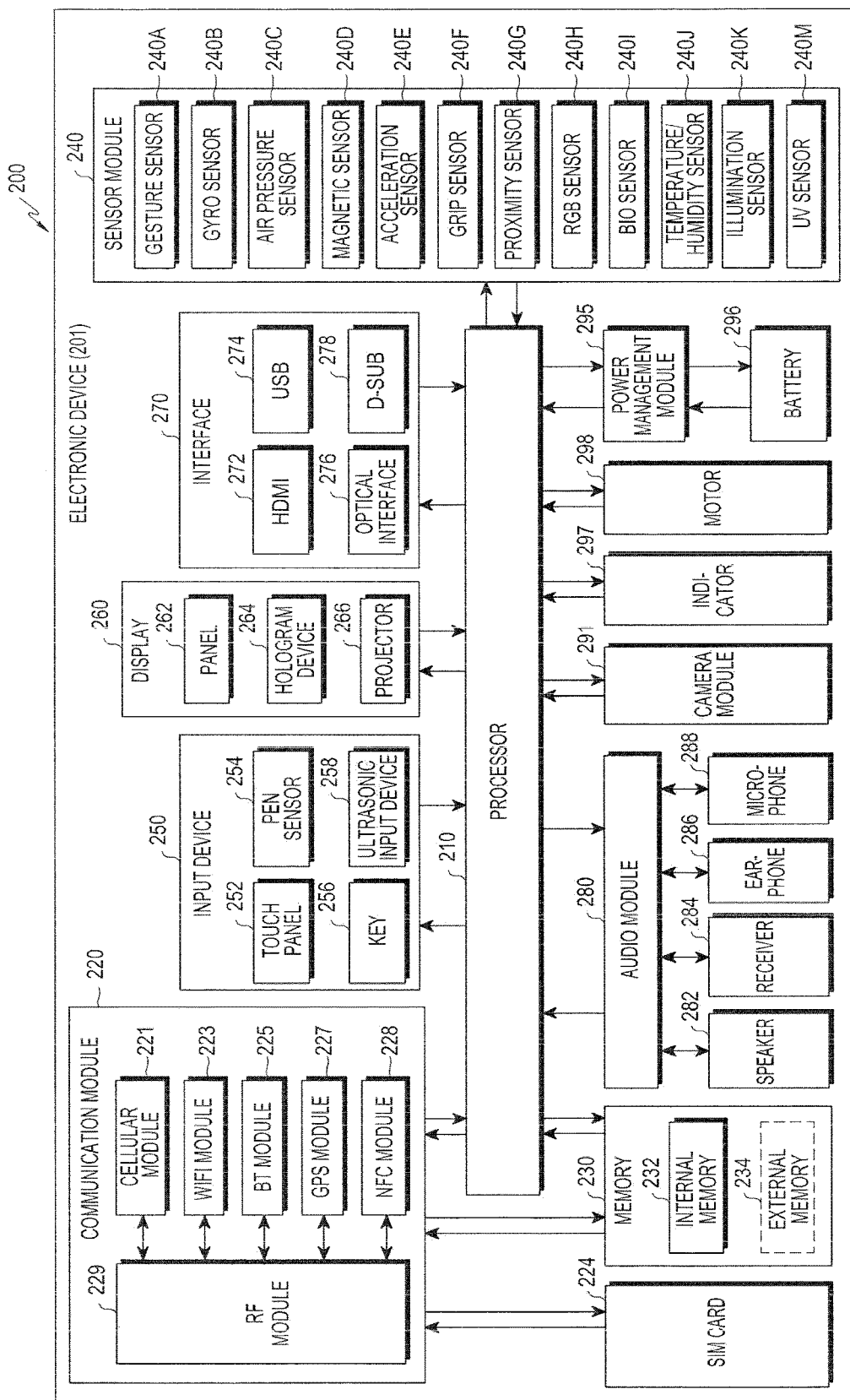
FIG. 52 is a block diagram illustrating an electronic device according to an embodiment.

FIG. 52 is a block diagram illustrating a circuit 200 of an electronic device 201 according to an embodiment. The electronic device 201 may include the whole or part of the configuration of, e.g., the electronic device 101 shown in FIG. 51. Referring to FIG. 52, the electronic device 201 may include at least one of a processor 210 including one or more application processors (APs) and/or one or more communication processor (CPs), a communication module 220, an SIM (subscriber identification module) card 224, a memory 230, a sensor module 240, an input device 250, a display 260, an interface 270, an audio module 280, a camera module 291, a power management module 295, a battery 296, an indicator 297, or a motor 298.

The AP 210 may control multiple hardware and software components connected to the AP 210 by running an operating system or application programs, and the AP 2010 may process and compute various data including multimedia data. The AP 210 may be implemented in, e.g., a system on chip (SoC). According to an embodiment, the AP 210 may further include a graphic processing unit (GPU) (not shown).

The communication module 220 (e.g. the communication interface 160) may perform data communication with other electronic devices (e.g., the electronic device 104 or the server 106) connected with the electronic device 201 via a network. According to an embodiment, the communication module 220 may include at least one of a cellular module 221, a Wi-Fi module 223, a BT module 225, a GPS module 227, an NFC module 228, or a radio frequency (RF) module 229.

The cellular module 221 may provide at least one of voice call, video call, text, or Internet services through a communication network (e.g., an LTE, LTE-A, CDMA, WCDMA, UMTS, WiBro, or GSM network). The cellular module 221 may perform identification and authentication on the electronic device in the communication network using, e.g., a subscriber identification module (e.g., the SIM card 224). According to an embodiment, the cellular module 221 may perform at least some of the functions providable by the AP 210. For example, the cellular module 221 may perform at least some of the multimedia control functions.

According to an embodiment, the communication processor may be included in the cellular module 221. The cellular module 221 may be implemented in, e.g., an SoC. Although in FIG. 52 the cellular module 221 (e.g., a communication processor), the memory 230, or the power management module 295 are provided separately from the AP 210, the AP 210 may be configured to include at least some (e.g., the cellular module 221) of the above-listed components, according to an embodiment.

According to an embodiment, the AP 210 or the cellular module 221 (e.g., a communication processor) may load commands or data received from a non-volatile memory or other component connected thereto and process the loaded commands or data. The AP 210 or the cellular module 221 may store, in the non-volatile memory, data received from other component(s) or data generated by the other component(s).

The Wi-Fi module 223, the BT module 225, the GPS module 227, or the NFC module 228 may include a process for, e.g., processing data communicated through the module. Although in FIG. 52 the cellular module 221, the Wi-Fi module 223, the BT module 225, the GPS module 227, and the NFC module 228 are shown in their respective separate blocks, at least some (e.g., two or more) of the cellular module 221, the Wi-Fi module 223, the BT module 225, the GPS module 227, and the NFC module 228 may be included in a single integrated circuit (IC) or an IC package. For example, at least some of the processors respectively corresponding to the cellular module 221, the Wi-Fi module 223, the BT module 225, the GPS module 227, or the NFC module 228 (e.g., the communication processor corresponding to the cellular module 221 and the Wi-Fi processor corresponding to the Wi-Fi module 223) may be implemented in a single SoC.

The RF module 229 may communicate data, e.g., radio frequency (RF) signals. Although not shown, the RF module 229 may include at least one of, e.g., a transceiver, a power amplifier module (PAM), a frequency filter, or a low noise amplifier (LNA). The RF module 229 may further include at least one of parts (e.g., conductors or wires) for communicating radio waves in a free space upon performing wireless communication. Although in FIG. 52 the cellular module 221, the Wi-Fi module 223, the BT module 225, the GPS module 227, and the NFC module 228 share a single RF module 229, the cellular module 221, the Wi-Fi module 223, the BT module 225, the GPS module 227, or the NFC module 228 may communicate RF signals through a separate RF module(s).

The SIM card 224 may include a subscriber identification module, and the SIM card 2024 may be inserted into a slot formed at a predetermined position of the electronic device. The SIM card 224 may contain unique identification information (e.g., an integrated circuit card identifier (ICCID) or subscriber information (e.g., an international mobile subscriber identity (IMSI)).

The memory 230 (e.g., the memory 130) may include an internal memory 232 or an external memory 234. The internal memory 232 may include, e.g., a volatile memory (e.g., a dynamic RAM (DRAM), a static RAM (SRAM), a synchronous dynamic RAM (SDRAM), etc.) or a non-volatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a NAND flash memory, or a NOR flash memory).

According to an embodiment, the internal memory 232 may be a solid state drive (SSD). The external memory 234 may include at least one of a flash drive, e.g., a compact flash (CF) memory, a secure digital (SD) memory, a micro-SD memory, a min-SD memory, an extreme digital (xD) memory, or a Memory Stick™. The external memory 234 may be functionally connected with the electronic device 201 via various interfaces. According to an embodiment, the electronic device 201 may further include a storage device (or storage medium) such as a hard disk drive.

The sensor module 240 may measure a physical quantity or detect an operational stage of the electronic device 201, and the sensor module 2040 may convert the measured or detected information into an electrical signal. The sensor module 240 may include at least one of, e.g., a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., an Red-Green-Blue (RGB) sensor, a bio sensor 240I, a temperature/humidity sensor 240J, an illumination sensor 240K, or an Ultra Violet (UV) sensor 240M. Additionally or alternatively, the sensor module 240 may include at least one of, e.g., an E-nose sensor, an electromyography (EMG) sensor, an electroencephalogram (EEG) sensor, an electrocardiogram (ECG) sensor, an infrared (IR) sensor, an iris sensor, or a finger print sensor which is not shown in the drawings. The sensor module 240 may further include a control circuit for controlling at least one or more of the sensors included in the sensing module.

The input unit 250 may include a touch panel 252, a (digital) pen sensor 254, a key 256, or an ultrasonic input device 258. The touch panel 252 may recognize touch inputs in at least one of capacitive, resistive, infrared, or ultrasonic methods. The touch panel 252 may further include a control circuit. With the capacitive method, physical contact or proximity detection may be possible. The touch panel 252 may further include a tactile layer. In this regard, the touch panel 252 may provide the user with a tactile response.

The (digital) pen sensor 254 may be implemented in a way identical or similar to e.g., how a touch input of a user is received, or by using a separate sheet for recognition. The key 256 may include e.g., a physical button, optical key or key pad. The ultrasonic input device 258 may use an input tool that generates an ultrasonic signal and enable the electronic device 201 to identify data by sensing the ultrasonic signal to a microphone (e.g., a microphone 288). According to an embodiment, the electronic device 201 may receive the user's input from an external electronic device (e.g., a network, computer, or server) connected with the electronic device 2301 using the communication module 220.

The display 260 (e.g., the display 150) may include a panel 262, a hologram device 264, or a projector 266. The panel 262 may be, e.g., a Liquid Crystal Display (LCD), Active Matrix Organic Light Emitting Diodes (AMOLEDs), or the like. The panel 262 may be implemented to be flexible, transparent, or wearable. The panel 262 may also be incorporated with the touch panel 252 in a module. The hologram device 264 may make three dimensional (3D) images (holograms) in the air by using light interference. The projector 266 may display an image by projecting light onto a screen. The screen may be, for example, located inside or outside of the electronic device 201. In accordance with an embodiment, the display 260 may further include a control circuit to control the panel 262, the hologram device 264, or the projector 266.

The interface 270 may include e.g., a High Definition Multimedia Interface (HDMI) 272, a USB 274, an optical interface 276, or a D-subminiature (D-sub) 278. The interface 270 may be included in e.g., the communication interface 160 shown in FIG. 51. Additionally or alternatively, the interface 270 may include a mobile high-definition link (MHL) interface, a secure digital (SD) card/multimedia card (MMC) interface, or IrDA standard interface.

The audio module 280 may perform various processes (e.g., encoding or decoding) relating to converting a sound wave and audio signal to an electric signal or vice versa. At least a part of the audio module 280 may be included in e.g., the electronic device 101 as shown in FIG. 51. The audio module 280 may process sound information input or output through at least one of e.g., a speaker 282, a receiver 284, an earphone 286, or a microphone 288.

The camera module 291 may be a device for capturing still images and videos, and may include, according to an embodiment, one or more image sensors (e.g., front and back sensors) (not shown), a lens (not shown), an Image Signal Processor (ISP) (not shown), or a flash such as an LED or xenon lamp (not shown).

The power manager module 295 may manage power of the electronic device 201. Although not shown, e.g., a Power Management Integrated Circuit (PMIC), a charger IC, or a battery or fuel gauge is included in the power manager module 295.

The PMIC may be mounted on e.g., an IC or an SOC. A charging method may be divided into wired and wireless charging methods. The charger IC may charge a battery and prevent overvoltage or overcurrent from being induced from a charger. According to an embodiment, the charger IC may be used in at least one of a cable charging scheme and a wireless charging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging.

The battery gauge may measure an amount of remaining power of the battery 296, a voltage, a current, or a temperature while the battery 2096 is being charged. The battery 296 may save or generate electricity, and supply power to the electronic device 201 with the saved or generated electricity. The battery 296 may include, e.g., a rechargeable battery or a solar battery.

The indicator 297 may indicate a particular state of the electronic device 201 or a part of the electronic device (e.g., the AP 210), including e.g., a booting state, a message state, or charging state. The motor 298 may convert an electric signal to a mechanical vibration. Although not shown, a processing unit for supporting mobile TV, such as a GPU may be included in the electronic device 201. The processing unit for supporting mobile TV may process media data conforming to a standard for digital multimedia broadcasting (DMB), digital video broadcasting (DVB), or media flow.

Figure 53:
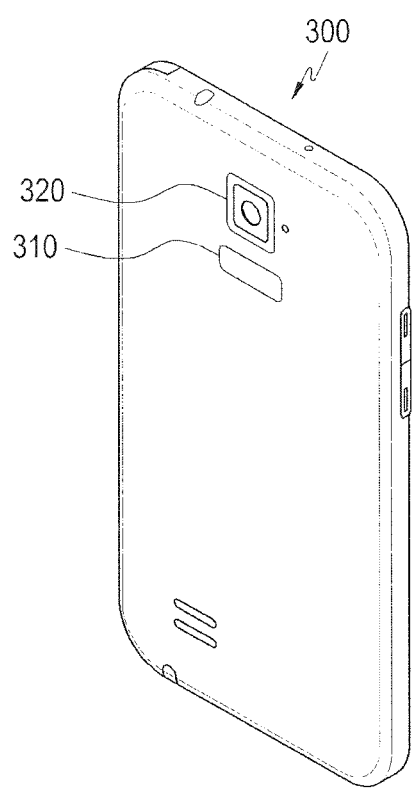
FIG. 53 illustrates an electronic device including a sensor device according to an embodiment.

FIG. 53 illustrates an electronic device including a sensor device 310 according to an embodiment. The electronic device 300 shown in FIG. 53 may be, e.g., the electronic device 101 shown in FIG. 51 or the electronic device 201 shown in FIG. 52. The sensor device 310 shown in FIG. 53 may be, e.g., the sensor device shown in FIG. 52 (e.g., the sensor module 240 or the bio sensor 240I). The sensor device 310 may be positioned adjacent to the camera 320 (e.g., the camera module 291) on the rear surface of the electronic device 300, providing for an assistant light source upon camera capturing through a flash included in the sensor device 310. If at least a portion of the sensor device 310 approaches or contacts a portion of the user's body, the electronic device 300 may recognize bio information through the sensor device 310. The bio information may include at least of, e.g., a pulse, heart rate, oxygen saturation, or blood flow.

According to an embodiment, the electronic device (e.g., the electronic devices 101 and 201) may be equipped with one or more sensors to detect one or more of a physical characteristic, biochemical characteristic, emotional characteristic, body activity, identification information, body information, emotion information, health information, disease information, exercise information, activity information, stress information, or sleep information from the user's body. The electronic device may be one or more portable or wearable electronic devices and may communicate with other electronic devices or peripheral electronic devices. At least one of the electronic device, another electronic device, or peripheral electronic device may include an input/output device (e.g., the input/output interface 140 or input device 250) capable of user input and information search. The electronic device, the other electronic device, or peripheral electronic device may be one of a portable phone, a smartphone, a laptop computer, an electronic book, a wrist watch, a bracelet, an anklet, a strip, a band, an adhesive (Band-Aid type) band, a belt, an in-ear earphone, a headphone, clothes-type, shoe-type, head mounted display (HMD), hat-type, glove-type, finger cap-type, clip-type, arm band-type, a contact lens device capable of checking blood sugar, digital clothes, or a remote controller.

The electronic device (e.g., the electronic devices 101 and 201) may be operated standalone or may be wiredly or wirelessly connected with the other device or peripheral device to provide services to the user. As an example, the electronic device may be connected with an electronic weight meter, an electronic thermometer, a cardiocam mirror, a fitness instrument, a display, a home appliance, an electronic bed mattress, or an electronic blanket through wired or wireless communication to provide various services.

As an example, in case the user's heart rate is measured using a heart rate sensor (hear rate monitor (HRM)), the heart rate sensor-embedded smartphone or wrist watch may measure the user's heart rate on his finger or wrist and display the measured heart rate information on the embedded display. As another example, information measured by an HRM sensor embedded in an ear clip-type wearable device may be transferred wiredly or wirelessly to the smartphone and may be provided to the user in real-time through the display of the smartphone.

According to an embodiment, the electronic device may transmit or store data containing one or more of bio information or personal information to a separate server or remote device. When receiving the bio information or personal information, the server or remote device may analyze, e.g., the received information and may deliver its result (e.g., generating new information by combining the same with information received from another electronic device) to the electronic device.

The body sensor (also referred to as a health sensor) may be a sensor gathering or measuring one or more bio signals from, e.g., the user. The bio sensor may gather basic data (raw data) for measuring one or more of the user's blood pressure, blood flow, heart rate (HRM, HRV), temperature, respiration rate, oxygen saturation, cardiorespiratory sound detection, blood sugar, waist measurement, height, weight, body fat, calorie consumption, brain wave, voice, skin resistance, electromyogram, electrocardiogram, gait, ultrasound image, sleep state, look (face), pupil dilation or blink. According to an embodiment, the electronic device may analyze the bio signal to generate bio information (also referred to as bio characteristic information). As an example, the bio signal may be a pulse signal obtained through a heart rate variability (HRV) sensor. The electronic device may obtain first bio information, such as mean heart rate or heart rate distribution and may process such bio information to obtain second bio information, such as stress state or blood vessel aging degree which is higher dimensional. According to an embodiment, the bio sensor may simply output the gathered user bio signals, and the bio sensor may also analyze the bio signals through an embedded processor and output the bio information. Accordingly, the bio signals gathered through the bio sensor may be delivered to the processor in the bio sensor, the processor of the electronic device embedding the bio sensor, or an external device (e.g., the server 106 or electronic device 104) to be used to produce bio information. According to an embodiment, the user may use an ECG sensor-embedded portable phone or a PPG sensor-embedded wrist watch.

In case the bio sensor-embedded electronic device (e.g., the electronic device 101 or 201) transmits the bio signals to a remote device (e.g., the electronic device 104) or server (e.g., the server 106) through a direct connection or through a wired network or wireless network, the remote device or server receiving the bio signals may process the bio signals to generate bio information. According to an embodiment, if the bio sensor-embedded electronic device (e.g., the electronic device 101 or 201) generates first bio information and transmits the generated bio information to the remote device or server, the second bio information may be generated by the remote device or server.

As an example, bio signals gathered by the HRV sensor embedded in the wrist watch device (an example of wearable device) may be delivered to a smartphone (an example of host or main electronic device) wirelessly connected with the wrist watch device, and the smartphone may analyze the received bio signals to generate bio information. The bio information may be displayed on the display of the smartphone or may be transmitted using a wired or wireless communication means to be displayed on the display of the wrist watch device. The bio information may be displayed or stored in one or more of, e.g., the smartphone or wrist watch device. According to an embodiment, bio signals gathered by the HRV sensor embedded in the ear clip with earphone functionality may be transferred to the wrist watch device or smartphone, and the wrist watch device or smartphone may generate bio information. The generated bio information may be transferred to one or more devices. If the smartphone generates the bio information, the wrist watch device receiving the bio information may display the information, and the ear clip receiving the bio information may provide the same to the user through a voice.

There are a diversity of examples of the bio sensor. For example, various portable devices are present for the blood sugar sensor. Currently, noninvasive measuring sensors are being developed such as ultrasonic noninvasive blood sugar measurers using Raman spectroscopy, e.g., by MIT. For cholesterol sensors, there have been developed devices allowing for simplified cholesterol measurement by a smartphone, such as smartCARD developed by a reach team in Cornell University. In such devices, if the user puts a drop of blood on a test sheet and puts in a measuring device connected with the smartphone, a chemical action occurs, and the electronic device may drive the flash and camera to transmit the result of measurement to an application. The application may analyze the measurement result and show the user specific values and statuses. Such a technique as detects Parkinson's disease by measuring the degree or frequency of sway with a smartphone placed on the wrist or various smartphone diagnostic techniques including detecting salmonellae utilizing microfluidic engineering are being reported to international academic journals. A team led by Professor PARK, Hyun Gyu, Biomolecular Engineering, has published the following research result showing that disease diagnosis may be possible by detecting a variation in capacitance when urine or blood contacts the touchscreen of a smartphone and detecting bio molecules, such as the presence or absence of DNA or its concentration, cells, protein, or nucleic acids.

Byoung Yeon Won, Hyun Gyu Park, A Touchscreen as a Biomolecule Detection Platform, Angewandte Chemie International Edition, DOI, 10.1002/anie.201105986, Volume 51, Issue 3, pages 748-751, Jan. 16, 2012

Blood pressure is also referred to as arteriotony, "B.P.", or hemadynamometer, and high blood pressure is called so when it measures 140 mmHg or higher systolic or 90 mmHg or higher diastolic. Recently, a smartphone is also used as a portable digital measurer connected with a blood pressure meter worn on the user's arm to provide the result of measurement.

Figure 54:
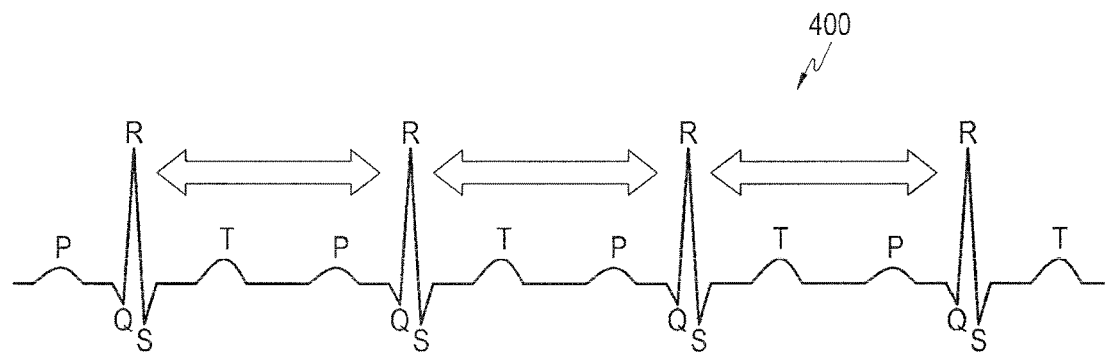
FIG. 54 illustrates an example of an electrocardiogram (ECG) waveform.

FIG. 54 illustrates an example of an electrocardiogram (ECG) waveform 400. In FIG. 54, the horizontal axis denotes the time, and the vertical axis denotes the current or voltage. An electrocardiogram sensor is also referred to as an ECG or EKG and is a sensor detecting the pattern signal of active current of the heart. The electrocardiogram sensor may break down into current ECG and voltage ECG depending on the way of detecting signals. There may also be a portable ECG monitoring device called a portable ECG monitor (PEM), and it allows a bio signal to be detected if the user holds the portable phone case with a rim attached with multiple ECG electrodes. The ECG waveform 400 consists of a P, Q, S, and T wave. Among them, the R wave corresponds to a peak signal and is widely used to analyze bio signals. For example, a heart rate may be measured through the number of R waves generated per unit time, and this is used to measure the overall heart capability and to diagnose cardiac arrhythmia, such as brady cardia or tachycardia.

Hear rate variability (HRV) is a scheme for measuring a variation in time interval (R-R) between R waves (peaks). This scheme may present analysis of activity of autonomic nerves from a tiny variation between heart rates, allowing various bio states to be known. HRV may be used to obtain stress information related to sympathetic nerves or parasympathetic nerves. Stress is related to, e.g., lethargy, nervousness, excitement, rage, concern, fear, autonomic nerve balance, or external environment adaptation. Further, cardiac arrhythmia or heart stroke may be predicted or detected through HRV analysis.

The healthy show a high and complicated HRV, but under disease or stress, the variation complexity is shown to be significantly reduced. In order to measure the inter-heart rate interval by the bio sensor to measure an HRV, the event signal may be received every peak to obtain a difference between the times of occurrence, or heart rates generated for a preset time may be continuously collected to estimate the R-R interval.

Figure 55A:
FIGS. 55a and 55b illustrate an example of comparison between an ECG waveform and a heart rate waveform.
Figure 55B:
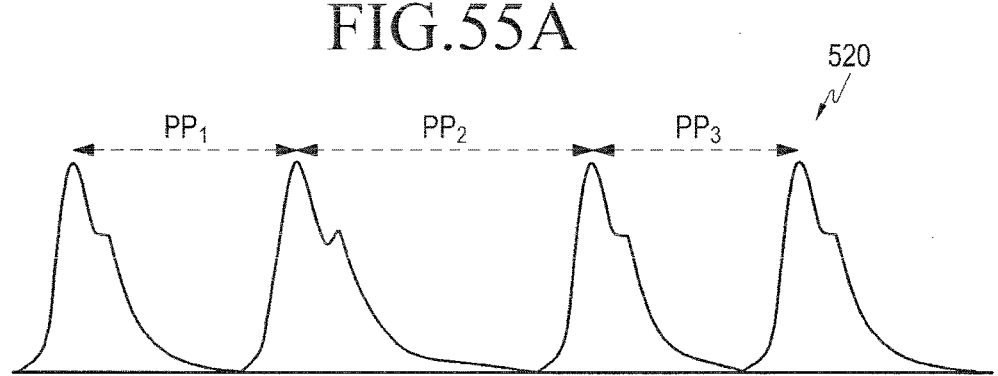

FIGS. 55a and 55b illustrate an example of comparison between an ECG waveform and a heart rate waveform. FIG. 55a shows an ECG waveform 510, and FIG. 55b shows a heart rate waveform 520. Regarding the waveforms shown in FIG. 55, the horizontal axis denotes the time, and the vertical axis denotes the current or voltage. The heart rate sensor is also referred to as a pulse sensor or pulse wave sensor and may include a hear rate monitor (HRM) sensor capable of measuring a heart rate per unit time and a sensor capable of measuring a hear rate variability (HRV) which is a variation in time interval between heart rates. The heart rate or HRV may be obtained through the heart rate sensor as well as the ECG. The heart rate waveform 520, although slightly different from the ECG waveform 510, has also a peak P corresponding to the R wave of the ECG waveform 510. Thus, the peak P may be used to obtain a heart rate or HRV. Although there is a slight time gap between the peak of the ECG waveform 510 and the heart rate waveform 520, the peak distance RR1, RR2, and RR3 of the ECG waveform 510 is shown to be nearly the same as the peak distance PP1, PP2, and PP3 of the heart rate waveform 520. This may be found from a number of documents including the following.

A comparative analysis of heart rate variability of Electrocardiogram and Pulse-wave using time series, Naghwan Kim, et al., Journal of Korean Soc Med Inform. 2000 December, 6(4), 165-173. Korean.

As the heart repeatedly contracts or relaxes, the peripheral blood vessel varies in blood flow and volume. The photoplethysmography (PPG), one of heart rate sensors, is a technique showing in a waveform the heart rate by measuring the amount of transmitted light using an optical sensor and this technique is used to measure a variation in the amount of blood in a blood vessel or to measure oxygen saturation. A heart rate sensor is embedded in, e.g., a clip, wrist watch, necklace, band, or portable phone and measures bio signals by attaching or contacting a body portion (e.g., an ear, wrist, carotid, finger, or ankle). As an example, in case measurement is performed through a finger, the finger is brought in contact with the heart rate sensor consisting of a light emitter and a light receiver and remains contacting for a predetermined time or longer. Then, the heart rate sensor measures such a variation that more blood is gathered in the finger during contraction so that the amount of light transmitted through the finger reduces while the blood escapes from the finger during relaxation so that the amount of light transmitted through the finger increases.

The heart rate sensor may detect the amount of light as a voltage, and the heart rate sensor or electronic device may convert the detected voltage into a digital value to measure the frequency of such variation. The heart rate sensor or electronic device may be aware of the number of pulses generated per second based on the detected voltage and may compute the heart rate or elapsing time between heart rates using the same. In case a PPG sensor is embedded in the wrist watch device, a bio signal may be detected through the radial artery or ulnar artery, and even not with the arteries, a bio signal may be measured through where vessels are distributed. Further, since a signal generated from the heart has a delay in being transferred to each portion of the body, a difference may occur between the ECG signal and the heart rate signal. For example, in case the heart rate sensor is mounted in the wrist watch device or ear clip, a time delay may arise when the signal delivers from the heart to a wrist or ear.

The per-minute heart rate varies depending on ages, and the heart rate pattern differs depending on emotional states. The electronic device (e.g., the electronic device 101 or 201) may measure the vessel elasticity through pulse wave analysis and may determine the aging degree of vessel through the same. That is, the electronic device may analyze the strength of cardiac output, vessel elasticity, or amount of remaining blood through accelerated plethysmo (APG) analysis obtained by performing quadratic differential on the pulse wave signal and may perform an auxiliary test on, e.g., high blood pressure, diabetes, high blood fat, arteriosclerosis, heart disease, or peripheral blood circulatory disturbance by automatically analyzing, e.g., blood vessel elasticity or hardening degree through the same.

Figure 56A:
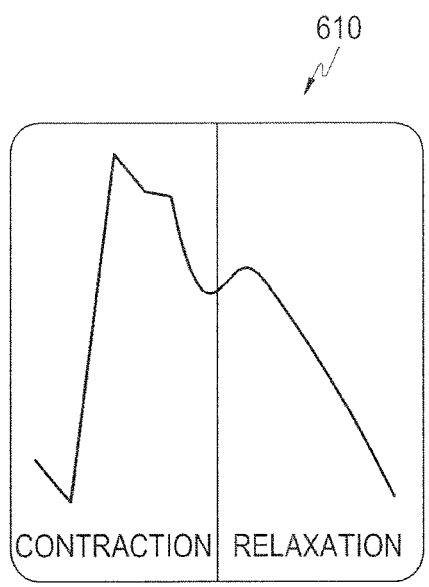
FIGS. 56a and 56b illustrate an example of calculating an accelerated photoplethysmograph using a pulse wave.
Figure 56B:
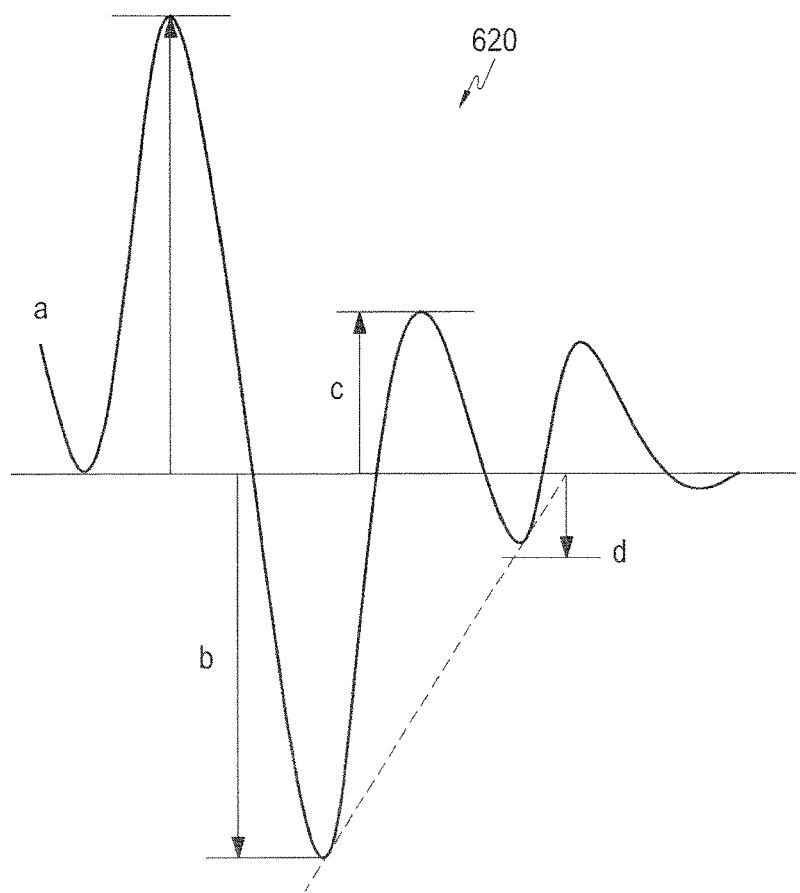

FIGS. 56a and 56b illustrate an example of calculating an accelerated photoplethysmograph using a pulse wave. FIG. 56a shows the pulse waveform 610, and FIG. 56b shows the waveform 620 of accelerated plethysmo. Regarding the waveforms shown in FIG. 56, the horizontal axis denotes the time, and the vertical axis denotes the current or voltage. In the accelerated plethysmo (APG), index a denotes the base value for easier comparison of waveform observance, index b the cardiac output strength, index c the blood vessel elasticity, and index d the amount of remaining blood. Since hand-foot tingling may occur at low cardiac output strength, and the blood vessel elasticity deteriorates as aging or depending on health conditions, they may be used to estimate the age group. If the high blood pressure patient does not take medication, the elasticity may deteriorate, and thus, it may be used for management of medicine administration. The amount of remaining blood is related with blood spurt and extravagated blood (toxins) and represents functional blood vessel hardening information. Such information as blood vessel wall self-hardening, organic hardening, or functional blood vessel hardening may be obtained through comparison between indexes b and d.

Various healthcare-related information and stress state may be identified through time domain analysis on heart rate variations. As an example, the mean heart rate (HR) and heart rate distribution (heart rate variability (HRV) index) may be used. Bio information may be analyzed through the mean heart rate per minute and the probability distribution of heart rates, and in case it is determined through such analysis that there is bradycardia with a preset reference or less, attention needs to be paid to fatigue, dizziness, or hyphothyrosis. By contrast, when determined as pyknocardia, heart disease or hyperthyreosis should be noted.

Information related to anti-stress index, homeostasis, immunity, or auto therapy may be obtained through the standard deviation of normal R-normal R intervals (SDNNs), and this is primarily related to the body fatigue. For example, an SDNN reduction may be used as a reference to determine work stress for shifting workers. The root mean square of SD (RMSSD) is related to the heart's parasympathetic nerve adjustability, and it being higher than a standard range means being healthier, and it reduces during rage, concern, or fear. Thus, a small gap in the overall RR interval may be determined as a low mental stress degree. The ratio (pNN50) for heart rate intervals being 50 ms or higher denotes the diversity of heart rates, and as it reduces within a standard range, it may be determined to be healthier.

Various autonomic nervous system information may be obtained through frequency domain analysis on the HRV. To that end, the power spectrum density (PSD) on the HRV may be obtained, and analysis may be done on the power peak information generated in a 0.01-0.02 Hz VLF (Very Low Frequency), 0.04-0.15 Hz LF (Low Frequency), and 0.16-0.4 Hz HF (High Frequency) band. The PSD may be obtained by, e.g., a correlation function method, fast Fourier transform, or autoregressive (AR) scheme, and a dispersion distribution is represented as a frequency function calculating the time-series data value obtained through the ECG sensor or heart rate sensor. The low frequency (LF) power peak information is influenced by both the sympathetic nerve and parasympathetic nerve, represents a blood pressure variation, and reflects lack of immunity, physical stress, physical fatigue, body energy loss, lack of sleep, or lethargy. As the sympathetic nerve is activated, the heart rate tends to decrease. The high frequency (HF) power peak information related to the parasympathetic nerve is related to the respiratory variation whose peak reduces while nervous and increases while relaxed and this is related with the mental or psychological fatigue or aging chronic stress. For example, it is shown to be low dung rage, concern, or fear and this may also be used to determine the hypofunction of digestive system.

The LF/HF ratio means the degree of balancing in the autonomic nerve and is utilized to determine the type of stress, e.g., acute stress, chronic stress (overwork-type or disease-type), arrhythmia degree, or causing insomnia relevancy. According to medical reports, high-stressful groups present a decreased heart rate variation due to the overreaction of the sympathetic nerve system, and it may be used as an index to predict heart disease. That is, in case a patient who has experienced myocardial infarction shows a decrease in the normal heart rate variation, his degree of danger of death may increase. The following documents may be referenced for the result of stress and medical examination obtainable through the HRV information acquired using the ECG or pulse wave.

Guidelines, Heart rate variability-Standards of measurement, physiological interpretation, and clinical use Task Force of The European Society of Cardiology and The North American Society of Pacing and Electrophysiology, European Heart Journal (1996) 17, 354-381

Job Stress, Heart Rate Variability and Metabolic Syndrome, Sei Jin Chang, et al., Korean J Occup Environ Med, 2003, 16(1), 70-81

The oxygen saturation sensor is a sensor measuring the ratio of hemoglobin saturated oxygen relative to the overall hemoglobin. Different denotations are used for oxygen saturation depending on measuring methods and portions, and pulse oximetry (SpO2) comes in wide use. This measures the amount of absorbed light with a particular wavelength according to the oxygen saturation of blood using an infrared (IR) beam, and this, as a non-invasive scheme, is easy to use or capable of continuous measurement. The PPG sensor technique may also be used as an oxygen saturation sensor, and this radiates two or more wavelengths of light (e.g., a 904 nm IR beam and a 660 nm red beam) to the user's wrist and receives and analyzes the reflected light. The oxygen saturation sensor is frequently use for computation of calorie consumed by the user's activity and is also used to monitor, e.g., dyspnea, consciousness disturbance, shock, physical state of the body during exercise, lung disease, e.g., acute respiratory distress syndrome (ARDS), detection of the danger of hypoxea at an alpine district, gas poisoning, or suffocation.

The sleep sensor is for measuring the human being's sleep state and may measure a sleep state using one or more of an acceleration sensor (accelerometer), gyro sensor, pulse wave measuring sensor, respiratory rate measuring sensor, or blood pressure measuring sensor. Here, one or more sleep state patterns per user may be stored, and the sleep state may be determined based on the similarity between a measured bio signal with a pre-stored sleep state pattern. Here, a sensor for detecting the user's movement, such as an acceleration sensor, and a time sensor may be used as materials to determine the sleep state. For example, in case the user's movement in a particular night time is maintained for a preset time or more as below a preset reference, it may be determined as the sleep state. Sleep passes through several steps from starting sleeping to wake up. Sleep largely comes in rapid eye movement (REM) sleep and non-REM sleep. Upon starting sleeping, non-REM sleep comes first. Non-REM sleep consists of four periods. The first and second periods of non-REM sleep during which sleep starts pass, and about 30 minutes after the start of sleep, sleep goes into a deep sleep state of the third and fourth periods. After such state lasts about one hour, the sleep comes back to the second and first periods, and about 90 minutes after the start of the sleep, the sleep arrives at a first REM sleep. That is, normal sleep repeats the process of the first, second, third, fourth, third, second, first periods, and the REM sleep at the cycle of about 90 minutes. During such REM sleep state, biological activities increase, and blood pressure, heart rate, and respiratory rate sharply grow accordingly, so that the best state for wakeup comes at the time that the REM sleep ends. By contrast, biological activities slow down during the third and fourth periods of the non-REM sleep, rendering wakeup difficult, and wakeup at this stage may cause confusion. Thus, the optimal wakeup time for maintaining the biorhythm is after the REM sleep ends and immediately before entering into the non-REM sleep.

In an embodiment, the bio sensor may be used to measure energy consumption. Basal metabolic rate (BMR) means the minimum energy level necessary for maintaining life during wakeup, and this means the amount of heat generated from the body, i.e., the amount of heat consumed. Such heat consumption is a calorie consumption and is used as important material for a weight adjusting program through a diet and exercise. Conventionally, to measure it, fastening should be started 12 hours before the measurement, followed by 30 minutes of relaxation at a lying position, and then, the oxygen intake for 10 minutes is measured to compute the energy consumption. The typical BMR is about 160-290 ml/min (0.8-1.43 kcal/min). Although the rest metabolic rate (RMR), a value measured, at rest, 3 to 4 hours after a light meal, is slightly higher than the BMR, it may be used instead of the BMR. As aging, the RMR presents a reduction in the order of 2% per 10 years.

1 kg of our body consumes 3.5 ml of oxygen per minute in a relaxing state, such as RMR, and consumes about 1 kcal for one hour. The energy metabolic rate corresponding to such RMR is called metabolic equivalent (MET), which may be used to represent the strength of exercise related to energy consumption and is represented as in the following equation.

$$MET=VO2/3.5(VO2, \text{ oxygen consumption})$$

$$1MET=3.5 \text{ ml/kg/min}=1 \text{ kcal/kg/h}=4.184 \text{ kJ/kg/h}=58.2 \text{ W/m2}$$

Since oxygen is carried by blood, and the amount of circulating blood is proportional to the heart rate, the heart rate is also proportional to the oxygen consumption. Accordingly, the calorie consumption may be estimated by the oxygen consumption or heart rate. This may be used in setting a heart rate (target heart rate), which is an effective exercise strength appropriate for the user, considering per-person, per-age maximum heart rate, and doing exercise while identifying the set heart rate may be useful to calculate the target energy consumption.

MET varies depending on the type of exercise. 5 MET means five times as much exercise strength or oxygen (energy) consumption as it is at relaxation. For example, 5 MET means such exercise as consumes 5 kcal for one hour per 1 kg in weight for one-hour workout. If a 70 kg person does jogging with a METs 7.0 exercise strength for one hour, he consumes 490 kcal (=70 kg*7 MET*1 hour).

An exercise strength may be easily known using a table recording the user's activities and their corresponding METs. For example, use of the following table estimating METs per user activity may estimate his activity and predicted energy consumption.

Compendium of Physical Activities, An update of activity codes and MET intensities. Medicine and Science in Sports and Exercise, 2000, 32 (Suppl), S498-S516

2011 Compendium of Physical Activities, a second update of codes and MET values, Ainsworth B E, Haskell W L, Herrmann S D, Meckes N, Bassett Jr D R, Tudor-Locke C, Greer J L, Vezina J, Whitt-Glover M C, Leon A S., Medicine and Science in Sports and Exercise, 2011, 43(8), 1575-1581, https,//sites.google.com/site/compendiumofphysicalactivities/compendia Since such energy consumption is also related with heart rate, energy consumption may also be estimated through the heart rate sensor. The maximum heart rate (HRmax), although obtainable through the following equation, appears to produce lots of errors.

$$\text{Maximum heart rate (HRma=220-age}$$

A study shows that an equation to estimate the maximum heart rate for women is mean peak HR=206−0.88×age, and it has been known to differ between men and women. Since the accuracy of an individual's maximum heart rate estimation equation depends on his physical strength, exercise practice, or health condition, it is practically preferable that the user obtains his maximum heart rate through continuous sensing on his wearing electronic device.

The strength of exercise should be determined not to overburden the user while giving a stimulus enough to enhance his respiratory functionality. Oftentimes, the exercise strength is determined based on the maximum oxygen consumption reserve (VO2R) or maximum heart rate reserve (HRR), and a recommended exercise strength is about 50 to 85% for the young and healthy and 40 to 50% for the aged or persons with no exercise experience. The VO2R is a value obtained by subtracting the resting oxygen consumption from the maximum oxygen consumption (VO2max), and the maximum HRR is a value obtained by subtracting the resting heart rate from the maximum heart rate. Accordingly, an equation for calculating a target exercise strength is as follows.

Target oxygen consumption=exercise strength (%)× (maximum oxygen consumption−resting oxygen consumption)+resting oxygen consumption Target heart rate=exercise strength (%)×(maximum heart rate−resting heart rate)+resting heart rate For example, an estimated maximum heart rate is 220−60=160 to obtain a target heart rate for a 60 years old man with no exercise experience and a resting heart rate of 70 counts per minute. Here, since 40 to 50% is proper as the recommended exercise strength, the maximum and minimum value of the target heart rate (THR) may be obtained as follows.

Minimum target heart rate, 40%×(160−70)+70=106

Maximum target heart rate, 50%×(160−70)+70=115

Thus, exercise enough to maintain a per-minute heart rate of 106 to 115 may be done, and a heart rate during exercise may be measured in such a way as to measure the pulse rate for 10 seconds on the carotid or radial artery while walking or resting five minutes after the main workout and then multiplying the measured value with six. However, it should be reflected that the heart rate cannot be used as an index for exercise strength under the context influencing the variation in heart rate due to drug administration or pregnancy.

Ratings of perceived exertion (RPE) refers to a subjective, 20-point scale rating technique as to how hard exercise is. In this technique, "comfortable" is rated as zero grade, "cannot be done further" as the highest grade, and "slightly hard" or "normal" as a middle grade. This is measure developed by psychologist Borg, and in the case of 20-point scale, each grade is multiplied with 10 to represent an approximate heart rate. For example, since high strength corresponds to "hard" (15 points), and a middle grade corresponds to slightly hard (13 points), this may be put to use.

Various sensors may be used to measure such energy consumption. For example, the number of steps may be measured through an acceleration sensor (accelerometer) or gyro sensor as functioning as a step counter for measuring a step count, and this may be based to estimate calorie consumption. Or, a traveled distance may be measured using the GPS or indoor positioning technique.

An example of determining exercise strength is as follows.

Sedentary=BMR×1.2 (little exercise or office work)

Lightly active=BMR×1.375 (light exercise or sports are done one to three times per week)

Mod. Lightly active=BMR×1.55 (light exercise or sports are done one to three times per week)

Very active=BMR×1.725 (heavy exercise or sports are done three to five times per week)

Extreme Active=BMR×1.9 (very heavy work or exercise, e.g., marathon or triathlons, is done every day)

The bio signals or bio information measured by the bio sensor or emotional or physical activity information may be transferred to other electronic device. For example, in case a bio signal (or converted bio information) measured by a wearable device (e.g., a smart watch or ear clip-type device) is transmitted to another electronic device (e.g., a connected smartphone or cloud/server), the battery status of the other electronic device, wireless communication means or communication protocol (e.g., Bluetooth low energy (BLE)/BT, Wi-Fi, or cellular), application compatibility and requirements, or user authentication may be taken into account.

Figure 57:
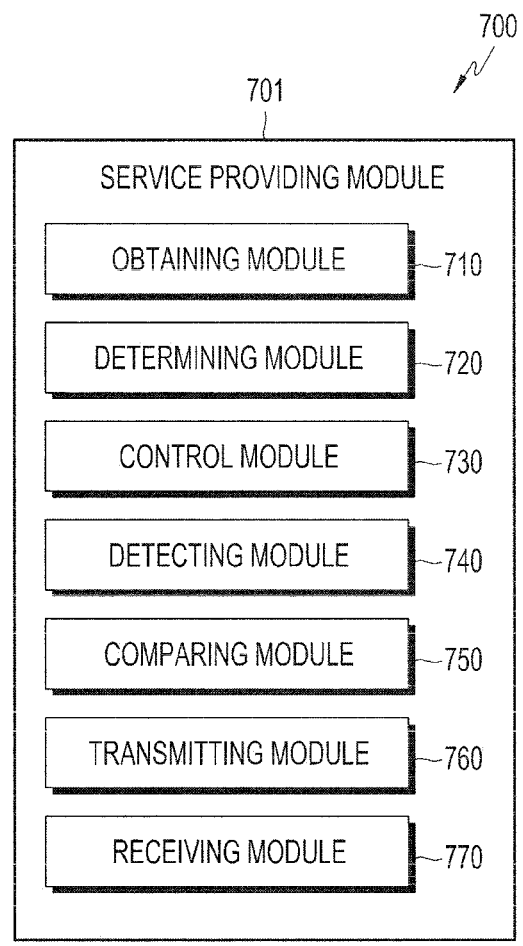
FIG. 57 is a block diagram illustrating a service providing module 701 (e.g., an additional functional module) of an electronic device according to an embodiment.

FIG. 57 is a block diagram 700 illustrating a service providing module 701 (e.g., an additional functional module 170) of an electronic device (e.g., the electronic device 101 or 201) according to an embodiment. The service providing module 701 may be the additional function module 170 shown in FIG. 51. Referring to FIG. 57, the service providing module 701 may include an obtaining module 710, a determining module 720, a control module 730, a detecting module 740, a comparing module 750, a transmitting module 750, and a receiving module 770. The service providing module 701 may be provided separately from a processor (e.g., the processor 120 or 210) or may be fully or partially integrated with the processor.

According to an embodiment, the obtaining module 710 may obtain the user's bio information. The user's bio information may include at least one of the user's identification information, body information, emotion information, health information, disease information, exercise information, stress information, and sleep information. In one embodiment, the obtaining module 710 may measure a bio signal from the user through a sensor module (e.g., the sensor module 240) and may produce bio information indicating the user's mental state or body state from the measured bio signal. In one embodiment, the obtaining module 710 may receive the user's bio signal through a communication device (e.g., the communication interface 160, the communication module 220, the input/output interface 140, and the interface 270) and may produce the user's bio information from the received bio signal. In one embodiment, the obtaining module 710 may receive the user's bio information through the communication device.

The obtaining module 710 may obtain the user association information. The user association information may include at least one of information on the user, information on the electronic device, and information on the ambient environment of the electronic device. The user association information may include at least one of movement information of the user and/or electronic device, location information of the user and/or electronic device, current time/date/day/weather information, user input information, information on the occurrence of a preset event, an image, a video, and an audio. Or, the user association information may include at least one of the identification information of the user/electronic device, body information, emotion information, health information, disease information, exercise information, activity information, stress information, and sleep information. In one embodiment, the obtaining module 710 may obtain the user association information through at least one of a communication device (e.g., the communication interface 160, the communication module 220, the input/output interface 140, or interface 270), an input device (e.g., the input/output interface 140, input device 250, or display 150), a sensor module (e.g., the sensor module 240), and a memory (e.g., the memory 130 or 230). In one embodiment, the obtaining module 710 may receive the user association information through the communication device. In one embodiment, the obtaining module 710 may receive the user association information from the user through the input interface. The obtaining module 710 may obtain the user association information stored in the memory.

According to an embodiment, the determining module 720 may determine at least one service among a plurality of services associated with the bio information supported by the electronic device. In one embodiment, the determining module 720 may determine at least one service corresponding to the user association information and the bio information among the plurality of services associated with the bio information supported by the electronic device.

In one embodiment, the determining module 720 may determine whether a preset condition is met, and the obtaining module 710 may initiate the operation of obtaining the bio information as the preset condition is met. The preset condition may include at least one of a movement of the electronic device exceeding a threshold, a movement of the electronic device according to a preset gesture, a location movement of the electronic device to a preset area, a user input to the electronic device, occurrence of a preset in the electronic device, and switch between a sleep state of the electronic device and a wakeup state.

In one embodiment, the determining module 720 may determine the user association information associated with the bio information of user association information pre-stored in the electronic device and may determine at least one service corresponding to the determined user association information and the bio information among a plurality of services associated with the bio information supported by the electronic device.

In one embodiment, the determining module 720 may determine at least one service corresponding to an event that occurs in the electronic device.

According to an embodiment, the control module 730 may provide the user with at least one service determined by the determining module 720. The at least one determined service may include at least one of changing a user interface (e.g., a visual interface, such as a graphical user interface (GUI), an auditory interface, such as a voice guidance, or a tactile interface, such as a haptic feedback), user authentication, exercise coaching, information recommendation, information provision, information storage, provision of a function or service, restriction or blocking access to a preset content, function, or service, varying the settings of the electronic device, and control of an external device.

According to an embodiment, the detecting module 740 may detect a variation in state of the electronic device. In one embodiment, the detecting module 740 may detect a variation in the state of the electronic device meeting a preset condition, and the obtaining module 710 may obtain the bio information as it detects the state change in the electronic device.

According to an embodiment, the comparing module 750 may compare the bio information with a preset value. In one embodiment, the control module 730 may vary the period of obtaining the bio information depending on the difference between the bio information and the preset value. In one embodiment, the control module 730 may output at least one alarm signal according to the difference between the bio information and the preset value.

According to an embodiment, the transmitting module 760 may transmit the bio information to an external device.

According to an embodiment, the receiving module 770 may receive the information on the period of obtaining the bio information from the external device. In one embodiment, the receiving module 740 may receive the bio information from the external device.

In one embodiment, the obtaining module 710 may obtain the user's bio information after obtaining the user association information, and the determining module 720 may determine at least one service corresponding to the user association information and the bio information among a plurality of services associated with the bio information supported by the electronic device.

In one embodiment, the obtaining module 710 may obtain at least one of the user's movement, the user's location, the current time/date, the user's exercise strength, and the user's activity type. The control module 730 may authenticate the user based on at least one of the user's movement, the user's location, the current time/date, the user's exercise strength, and the user's activity type.

In one embodiment, the comparing module 750 may compare the user's bio information with a preset first value for user authentication. The obtaining module 710 may obtain additional bio information in case the difference between the user's bio information and the preset first value is a threshold or less. The comparing module 750 may compare the additional bio information with a preset second value for user authentication.

In one embodiment, the control module 730 may authenticate the user based on the user's bio information. The detecting module 740 may detect an event after the user authentication. The control module 730 may search for an event identical to the event and the user from a database stored in the electronic device or first external device. The control module 730 may control the electronic device, the first external device, or the second external device based on control information stored in the database corresponding to the searched event.

In one embodiment, the control module 730 may authenticate the user based on the user's bio information. The detecting module 740 may detect an event after the user authentication. The control module 730 may detect the control information of the electronic device associated with the event. The control module 730 may store the information on the control information and the event to the database of the electronic device or the external device.

In one embodiment, the comparing module 750 may compare the user's bio information with a preset value. The obtaining module 710 may obtain the user association information depending on the difference between the user's bio information and the preset value. The control module 730 may store the bio information and the user association information in the database of the electronic device or the external device.

In one embodiment, the determining module 720 may determine the category where the user's bio information belongs among a plurality of preset categories. The control module 730 may store information on the category and content being currently played to the database of the electronic device or the external device.

In one embodiment, the detecting module 740 may detect the event. The determining module 720 may determine the bio information corresponding to the event and determine at least one service corresponding to the determined bio information among a plurality of services associated with the event supported by the electronic device. The control module 730 may provide the at least one determined service to the user.

In one embodiment, the determining module 720 may search for an event identical to the event detected from the database stored in the electronic device or external device and determine that the bio information stored in the database corresponding to the searched event is the bio information corresponding to the detected event.

In one embodiment, the determining module 720 may search for an event identical to the event detected from the database stored in the electronic device or external device and identify the type of bio information stored in the database corresponding to the searched event. The obtaining module 710 may obtain the identified type of bio information from the user.

In one embodiment, the obtaining module 710 may obtain the user's bio information after detecting the event. The control module 730 may store information on the obtained bio information and event in the database of the electronic device or external device.

In one embodiment, the obtaining module 710 may obtain the user's bio information after detecting the event. The comparing module 750 may compare the obtained bio information with a preset value. The control module 730 may store the information associated with the user's bio information and the event in the database of the electronic device or external device depending on the difference between the obtained bio information and the preset value.

In one embodiment, the transmitting module 760 may transmit the determined bio information to the external device. The receiving module 770 may receive information associated with the bio information from the external device. The control module 730 may provide the received information to the user.

In one embodiment, the determining module 720 may determine the control information of the external device corresponding to the determined bio information. The transmitting module 760 may transmit the control information to the external device.

In one embodiment, the determining module 720 may search for an area where the electronic device is located from the database stored in the electronic device or external device and may determine that the bio information stored in the database corresponding to the searched area is the bio information corresponding to the detected event.

Figure 58:
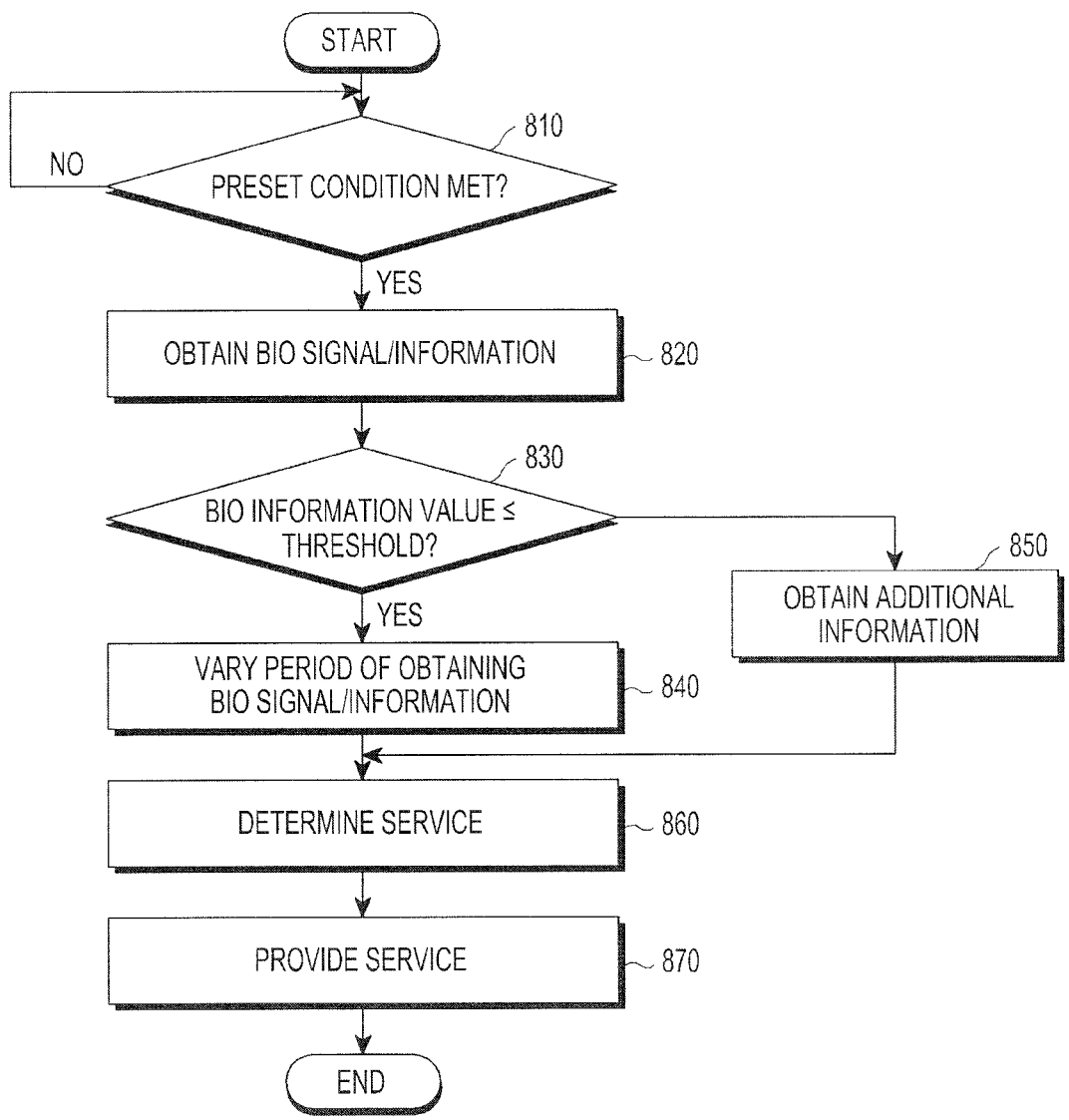
FIG. 58 is a flowchart illustrating a service providing method according to an embodiment.

FIG. 58 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 810 to 870.

In operation 810, whether a preset condition is met may be determined. The electronic device may perform operation 820 in case the preset condition is met and may periodically repeat operation 810 unless the preset condition is met. The preset condition may include at least one of a movement of the electronic device exceeding a threshold, a movement of the electronic device according to a preset gesture, a location movement of the electronic device to a preset area, a user input to the electronic device, occurrence of a preset in the electronic device, and switch between a sleep state of the electronic device and a wakeup state.

For example, whether the state of the electronic device is varied may be determined, and in case the state of the electronic device is varied, the bio sensor may be operated. The preset condition may include one or more of the case where the physical location of the electronic device detected through one or more of a motion sensor or a sensor capable of recognizing location (e.g., one or more of a camera module, gyro sensor, acceleration sensor, GPS sensor, gyro compass, or positioning sensor) is varied, the case where a signal detecting a movement of the electronic device has a strength not less than a threshold, the case where the movement signal shows a preset gesture, the case where a user input occurs through the power button or touch pane, the case where a preset event (e.g., a call, or text) is generated from the electronic device, the case where the AP or CP of the electronic device switches from sleep state to wakeup state, and the case where the AP or CP of the electronic device switches from wakeup state to sleep state.

In operation 820, a bio signal and/or bio information may be obtained. The electronic device may measure the bio signal from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may produce bio information indicating the user's mental state or body state from the measured bio signal. The bio signal may represent an electrical signal (e.g., an ECG signal or pulse wave signal) output from the bio sensor, and the bio information may include at least one of the user's identification information, body information, emotion information, health information, disease information, exercise information, activity information, stress information, or sleep information. In one embodiment, the electronic device may receive the user's bio signal from the external device through a communication device (e.g., the communication interface 160, the communication module 220, the input/output interface 140, or the interface 270) and may produce the user's bio information from the received bio signal. In one embodiment, the electronic device may receive the user's bio information from the external device through the communication device. For example, upon detecting a variation in the state of the electronic device, the bio sensor may be operated. Activating the bio sensor may be applying an electrical signal to the bio sensor to operate the bio sensor, varying the period at which the bio sensor is operated, or transferring a control signal (a software or hardware command instructing to start to collect sensor values) to the bio sensor. In one embodiment, the bio sensor may be provided in the external device, and the electronic device may be connected with the external device through the communication device, and the bio sensor of the external device may be driven in response to the control signal from the electronic device.

In operation 830, the bio information value may be compared with a preset value or previous bio information. For example, the electronic device may compare the bio information value with a threshold range or threshold value. For example, the electronic device may compare the bio information with the preset value or previous bio information to produce their difference (i.e., a variation) and may compare the difference with the threshold range or threshold value. In case the bio information value is within the threshold range or less than the threshold value, the electronic device may determine that the bio information is not substantially varied to perform operation 840, and in case the bio information value exceeds the threshold range or threshold value, the electronic device may determine that the bio information is substantially varied to perform operation 850. The preset value or previous bio information may be stored in the memory (e.g., the memory 130 or 230) of the electronic device or the external device (e.g., the server 106 or electronic device 104). The preset value may be bio information measured by one or more other users, a representative value or mean value of a user group (e.g., per-age mean value or per-gender mean value) or an experimental value measured by an organization (e.g., a research organization or academic community).

In operation 840, the period of obtaining the bio signal/information may be varied depending on the difference between the bio information value and the preset value or previous bio information. In case the bio information value is within the threshold range or less than the threshold value, the electronic device may determine that there is no substantial variation in the bio information and may increase the period of obtaining the bio signal/information (or interval of obtaining) or may stop obtaining the bio signal/information.

In operation 850, additional information (e.g., user association information) may be obtained depending on the difference between the bio information value and preset value or previous bio information. In case the bio information value exceeds the threshold range or threshold value, the electronic device may determine that there is a substantial variation in the bio information and may obtain the additional information associated with the bio information. The user association information may include at least one of information on the user, information on the electronic device, and information on the ambient environment of the electronic device. Additionally or alternatively, the electronic device may reduce the period of obtaining the bio signal/information (or obtaining interval).

In operation 860, at least one of a plurality of services associated with the user association information or bio information supported by the electronic device may be determined. In one embodiment, the electronic device may determine at least one service corresponding to the user association information and bio information among the plurality of services supported by the electronic device. In one embodiment, the electronic device may select at least one service corresponding to the user association information and the bio information among the plurality of services supported by the electronic device using a pre-stored first database. The first database may be stored in the memory of the electronic device or external device.

In one embodiment, the first database may have a form as shown in Table 1.

TABLE 1

| bio information | user association information | Service information |
|---|---|---|
| A11 | B11 | C11 |
| A11 | B12 | C12 |

TABLE 1-continued

| bio information | user association information | Service information |
|---|---|---|
| A12 | B11 | C13 |
| A12 | B12 | C14 |
| ... | ... | ... |

In Table 1, the bio information (e.g., A11, A12, ... ) may represent the type/content (e.g., blood pressure, heart rate, or blood sugar) of the bio information, a value range (e.g., blood pressure range, heart rate range, or blood sugar range) of a particular type of bio information, a value range of difference values (e.g., differences between the bio information and preset values) of particular types of bio information, or a value or level of a particular type of bio information. The user association information (e.g., B11, B12, ... ) may represent the type/content (e.g., disease information (e.g., high blood pressure, low blood pressure, or diabetes), body information, authentication information, impediment information, previous bio information, current exercise/activity information, current emotion/stress information, or event) of the user association information, a value, level, or value range (e.g., high blood pressure, low blood pressure, diabetes, time zone/day/weather, or geographical area) of a particular type of user association information. The service information (e.g., C11, C12, ... ) may represent the service type/content, such as a command, action, function, execution application, or application execution parameter.

In operation 870, the determined service may be provided. The service may include at least one of a variation in the user interface, user authentication, exercise coaching, information recommendation, information provision, information storage, information transmission, provision of function or service, preset content, restriction or blocking access to a function or service, variation in the settings of the electronic device, or control of an external device. The electronic device may display, to the user, at least a portion of the user association information and/or at least a portion of the bio information together or separately from the provision of the determined service.

Figure 59:
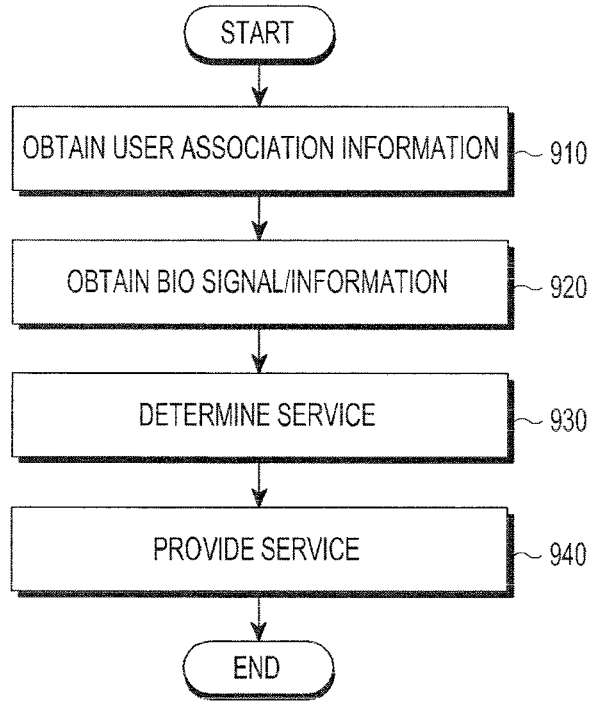
FIG. 59 is a flowchart illustrating a service providing method according to an embodiment.

FIG. 59 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 910 to 940.

In operation 910, the user association information may be obtained. The electronic device may obtain the user association information through at least one of a communication device (e.g., the communication interface 160, the communication module 220, the input/output interface 140, or the interface 270), an input device (e.g., the input/output interface 140, the input device 250, or the display 150), a sensor module (e.g., the sensor module 240), and a memory (e.g., the memory 130).

In operation 920, a bio signal and/or bio information may be obtained. The electronic device may measure the bio signal from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may produce bio information indicating the user's mental state or body state from the measured bio signal.

In operation 930, at least one service corresponding to the user association information and the bio information among a plurality of services supported by the electronic device may be determined. In one embodiment, the electronic device may select at least one service corresponding to the user association information and the bio information among the plurality of services supported by the electronic device using a pre-stored second database. The second database may be stored in the memory of the electronic device or external device.

In one embodiment, the second database may have a form as shown in Table 2.

TABLE 2

| user association information | bio information | Service information |
|---|---|---|
| B21 | A21 | C21 |
| B21 | A22 | C22 |
| B22 | A21 | C23 |
| B22 | A22 | C24 |
| ... | ... | ... |

In Table 2, the user association information (e.g., B21, B22, . . . ) may represent the type/content (e.g., disease information (e.g., high blood pressure, low blood pressure, or diabetes), body information, authentication information, impediment information, previous bio information, current exercise/activity information, current emotion/stress information, or event) of the user association information, a value, level, or value range (e.g., high blood pressure, low blood pressure, diabetes, time zone/day/weather, or geographical area) of a particular type of user association information. The bio information (e.g., A21, A22, . . . ) may represent the type/content (e.g., blood pressure, heart rate, or blood sugar) of the bio information, a value range (e.g., blood pressure range, heart rate range, or blood sugar range) of a particular type of bio information, a value range of difference values (e.g., differences between the bio information and preset values) of particular types of bio information, or a value or level of a particular type of bio information. The service information (e.g., C21, C22, . . . ) may represent the service type/content, such as a command, action, function, execution application, or application execution parameter.

In operation 940, the determined service may be provided. The service may include at least one of a variation in the user interface, user authentication, exercise coaching, information recommendation, information provision, information storage, information transmission, provision of function or service, preset content, restriction or blocking access to a function or service, variation in the settings of the electronic device, or control of an external device. The electronic device may display, to the user, at least a portion of the user association information and/or at least a portion of the bio information together or separately from the provision of the determined service.

In one embodiment, the electronic device may detect the user's sentimental state or emotional state from the measured bio signal and may provide various services depending on the detected state. The electronic device may select a service determined to be necessary to the user of the current state using the user association information, such as the user's personal information (user profile) or user's context information (context). For example, the electronic device may receive the user's bio signal, such as a pulse wave, through the HRV sensor mounted in the wrist watch device or the user's smartphone and may analyze the same to obtain physical stress, mental stress, or emotional information. The electronic device may provide a service appropriate for the user based on such stress/emotional information, and to that end, the electronic device may provide, recommend, or ban other services using the user's context or personal information even when it is a different type of stress.

In one embodiment, the personal information (or user information) may be information indicating the user's biological characteristic, and the personal information may be referenced by the operation of receiving or reading out the information stored in one or more of a local device, remote device, server, or cloud environment. The personal information may include one or more of the user's age, gender, height, weight, race, health treatment information, disease information, or impediment information. The health treatment information may include one or more of age, height, weight, waist measurement, body mass index, vision, hearing, blood pressure, total cholesterol, high-density lipoprotein (HDL) cholesterol, low-density lipoprotein (LDL) cholesterol, triglycerides, AST (SGOT), ALT (SGPT), gamma (r)-GPT, fasting blood sugar level, urinary protein, serum creatinine, hemoglobin, chest radiography information, oral examination information, maximum oxygen saturation, and maximum heart rate. The disease information may include one or more of diabetes, high blood pressure, low blood pressure, muscular skeletal disease, and osteoporosis. The personal information may include information obtained by gathering and storing bio signals by a device (i.e., the sensor device) having a bio sensor, and the sensor device may store a plurality of bio signals over time. For management and use of the personal information, the sensor device may analyze the bio signals to obtain the bio information and may then store the bio information. Since the body signal varies depending on the user's exercise history or health condition, the sensor device may support more useful services by storing and managing recent bio signal information or bio information. The personal information may include personal information for authentication for user authentication purposes. The impediment information may be information related to the user's physical exercise capacity or detection capacity, such as the user's physical disability information or injury. Since different services and UXs/UIs may be provided depending on the impediment information, the electronic device may consider such impediment information in determining a service. For example, in case the user has difficulty in running due to leg injury, the electronic device may recommend exercise, such as swimming, to the user by referencing such impediment information.

The user authentication operation may include bio authentication information to differentiate users, e.g., iris, fingerprint, voice pattern, face, sole pattern, palm pattern, hand veins, or walking pattern information. The personal information for authentication may include relevant information for recognizing iris, fingerprint, voice pattern, face, sole pattern, palm pattern, or hand veins (e.g., an image, characteristic information or pattern of the iris, fingerprint, voice pattern, face, sole pattern, palm pattern, or hand veins) For example, in case the user's personal data and registered user bio authentication information are stored in the database in association with each other, and the registered user succeeds in bio authentication, the user's personal data may be obtained.

The personal information may include indirect information associated with the user as well as the information on the user. For example, the indirect information may include information related to the user's activities that are stored in the user's electronic device, server, or cloud computing device, such as an address book related to the user, call history, SNS friends, favored applications, application running history, user preference information (e.g., preferred exercise information, preferred place-related information, preferred music and genre, or hobby). The personal information may be stored by the user's input or automatically using the user's activity-related information.

In one embodiment, the user's personal information may include one or more of body information and lifestyle information and may be used as basic data for providing a different service to each user. For example, the electronic device may obtain a physical characteristic and disease or major characteristics from a healthcare perspective and may manage healthcare and fitness guide or stress based on the same. The body information may include basic information, such as birth date (age), gender, height, weight, waist measurement, chest measurement, or race, may further include a disease history as disease information, and may include exercise restriction information as the impediment information. The exercise restriction information may correspond to physical information that may put a restriction during exercise or activity. The body information may include a disabled part, degree of disability, injured part, degree of injury, obesity, orthostatic hypotension, dizziness, ataxia, hyperlipidemia, diabetes, degenerative osteoarthritis, coronary artery disease, asthma, or atopy or may also include mental state information, such as depression, manic-depressive illness, or intelligence quotient. The body information may include administration information for preventing or treating disease for healthcare and may also include biological information, such as blood pressure, blood flow, heart rate (HRM, HRV), body temperature, breath, oxygen saturation, heart-lung sound detection, blood sugar, waist measurement, height, weight, calorie consumption, voice, skin resistance, EMG, ECG, step, ultrasonic wave image, or body mass index (BMI). The lifestyle information may include job, eating pattern, sleep information (e.g., sleep time, snoring or not, teeth grinding or not, or fatigue after sleep), or exercise habit.

Such personal information may be shared by one or more devices and may be stored in the electronic device, a server, or a second electronic device. The user's body information and lifestyle information may be updated, and latest information may be used to renew old information of other devices. For such purpose, when the devices are connected together, a particular user input occurs, or an update event arises, the information stored in the devices may be mutually updated.

The personal information containing the body information may be recorded in the memory of a local or remote device in the form of a database or electromagnetic waves. The recorded information may be encrypted together with the user's authentication information. The body information may be recorded in a preset format for a particular application or database or may follow the international or commercial standards for health services. If the electronic device downloads a health checkup report or information mapped in a bio information-related standardized format from the server, the electronic device may parse and map the information according to a format processable by the application embedded in the electronic device. For example, the HL7 CDA-based healthcare server platform technique is a server platform gathering various personal health records according to the HL7 CDA international standard format and stores and manages the same in the database. The HL7 CDA-based healthcare server platform technique, when requested for the personal health record of a particular patient from an external healthcare service, allows the record to be searched and provided.

Input of the personal information by the user interface may include one or more of the touchscreen of the electronic device, stylus pen, virtual keyboard, menu selection, writing recognition, and voice input. The electronic device may perform medical examination by interview or health questionnaire, may record life pattern information through entry of the user's answers, and may permit input, search, and use to only a particular user through the user authentication means. The electronic device may drive an application to enable the user to enter basic material and may inquire the user during exercise or activity for reevaluation and entry.

In one embodiment, one or more of text recognition or image code or electronic tag recognition may be used for entry and storage of the personal information. For example, a document, such as health checkup report or treatment record, may be provided to the user in the form of an electronic document or printed document. The electronic device may recognize one or more of the text, numeral, symbol, table, diagram, pattern, bar code, two-dimensional image code, or watermark recording the body information in the electronic document, such as an email, SNS, MMS, document file, or image file, may obtain the body information from the same, and may record the same in a preset format. For a physically printed document, the electronic device may receive the body information portion through, e.g., text recognition, image code recognition, or watermark recognition using an optical input device, such as a camera module or scanner, and may record the same in a preset format.

The electronic device may recognize the bar code or QR code in the drug wrapping paper, ingredient label or prescription of the medication for managing the administration information or the text such as the trademark or ingredient label of the medication to estimate and record the disease information. The electronic device may receive the information displayed on the medical and body information measuring device through text recognition or bar code recognition. The bar code may include a one-dimensional bar code (e.g., UPC or EAN) or two-dimensional bar code (e.g., data matrix, quick response code, PDF417, max code, or color based code), and the electronic device may recognize the watermark in the image. In case the recognized value is ID information, the electronic device may gather the product information through the database in the remote server or local device and may obtain detailed information on the product by doing search on the bar code of the product.

In case full text information is contained in the bar code, such as QR code, the electronic device may directly gather detailed information from the QR code. The electronic device may gather the product information through the database in the remote server or local device using the ID or text information included in the electronic tag, such as near field code (NFC), RFID, or electronic product code (EPC). In case the electronic tag contains the full text information, the electronic device may directly gather the detailed information from the electronic tag. The electronic device may receive the RFID tag through the RFID reader and may receive the image code information through the camera module or scanner. The electronic device may use an information search service using Internet of things (IoT) or machine-to-machine (M2M) technology.

The user's personal information may be input to the medical and bio information measuring device. The weight may be measured through a peripheral device of a console game player, such as Wii Fit Plus, or body composition analyzer (providing the function of computing the amount of each of parts distinguished as water, muscles, water, fat, and bones), body water meter, BMI meter, or weight scale. A meter using the bioelectrical impedance analysis (BIA) is a technique for measuring body water using an electrical method. Since a weak alternating current (AC) signal is transmitted to the human body, it flows along the body water, and this may be represented as a measurement value called impedance. Cardiovascular endurance may be measured by the composition analyzer (providing the amount of each part differentiated as water, muscles, water, fat, and bones) or aerobike or grasping power may be measured by a handgrip, and the measured information may be input to the electronic device.

The thickness of the body skin may be measured using calipers though a skin wrinkle thickness measuring method or this may be based to calculate the BMI. A measuring device using computed tomography (CT) or radioactive isotope may also come in use. The electronic device may receive personal information through communication with such medical/bio information measuring device. For example, the electronic device may perform discovery to obtain the identification information (e.g., device name, unique ID, MAC address, SIM card ID, phone number, or serial number) of the measuring device (e.g., BIA meter) or search for the user's electronic device (e.g., portable phone or wrist watch device), and after the two devices are connected together through wireless communication (e.g., Wi-Fi, Bluetooth, BLE, IrDA, IEEE 802 protocol, 2G, 3G, Piconet, LAN, BAN, or WAN), the electronic device may receive the body information measured by the measuring device. The discovery may also be conducted through the RFID sensor and reader.

For example, the RFID containing the identification information on the network of the measuring device may be recognized by the reader of the electronic device, or in the contrast, the address of the electronic device to which the measuring device is to gain access may be recognized using the RFID information of the electronic device. By inputting the user identification information (e.g., email address or phone number to the measuring device, the bio information may be directly transmitted to the user's electronic device or to the server or other remote device, and the transmitted information may be transferred back to the electronic device. As material to provide exact exercise coaching services, the material of the measuring devices may be transferred upon exercise load test. Here, the reference to terminate the exercise load test may be severe fatigue/dyspnea, ataxia, III/IV-degree chest pain, 3.0 mm or more ischemic ST segment depression, 1.0 mm or more ischemic ST segment elevation in non-Q wave induction, ventricular arrhythmia, supraventricular tachycardia, gradual reduction or abnormal increase in systolic blood pressure, heart rate reduction, or arrival at target heart rate.

Figure 60:
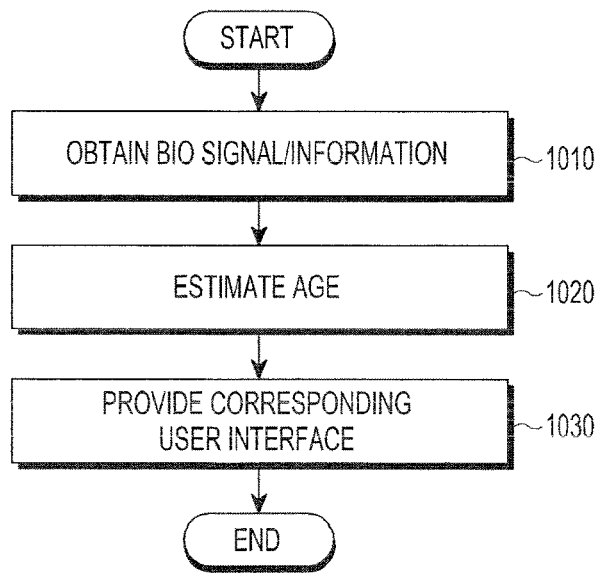
FIG. 60 is a flowchart illustrating a service providing method according to an embodiment.

FIG. 60 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1010 to 1030.

In operation 1010, a bio signal and/or bio information may be obtained. The electronic device may measure the bio signal for estimating age from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for estimating age from the measured bio signal. The bio signal for estimating age may include a pulse wave signal, ECG signal, blood pressure, HRV, HRM, RMR, and oxygen saturation, and the bio information for estimating age may include the blood vessel aging degree.

In operation 1020, the user's age may be estimated. In one embodiment, the electronic device may measure the vessel elasticity through pulse wave analysis and may determine the aging degree of vessel through the same.

In operation 1030, the user interface or service corresponding to the estimated user's age may be provided. The electronic device may display, to the user, at least a portion of the bio information and/or at least a portion of the estimated user's age together or separately from the provision of the user interface or service. In one embodiment, the electronic device may change the user interface currently displayed on the display into the user interface according to the user's age. The user interface or service may include at least one of changing guidance voices of the electronic device, changing voice volume, restriction access to a preset content or service, providing an alert feedback, or recommending information. The user interface may include a visual interface, such as graphic user interface (GUI), an auditory interface, such as guidance voice, and a tactile interface such as a haptic feedback. In one embodiment, the electronic device may select at least one service corresponding to the user association information and/or the bio information among the plurality of services supported by the electronic device using a pre-stored third database. The third database may be stored in the memory of the electronic device or external device.

In one embodiment, the third database may have a form as shown in Table 3.

TABLE 3

| bio information | user association information | service information |
|---|---|---|
| A31 | B31 | C31 |
| A31 | B32 | C32 |
| A32 | B31 | C33 |
| A32 | B32 | C34 |
| ... | ... | ... |

In Table 3, the bio information (e.g., A31, A32, . . . ) may represent, e.g., the type/content (e.g., blood vessel elasticity or blood vessel aging degree) of the age-associated information, value range (e.g., value range of blood vessel, value range of RMR, or value range of blood vessel aging degree) of the age-associated information, or value or level (e.g., the level or type of blood vessel aging degree). The user association information (e.g., B31, B32, . . . ) may represent the type/content (e.g., disease information (e.g., high blood pressure, low blood pressure, or diabetes), body information, authentication information, impediment information, previous bio information, current exercise/activity information, current emotion/stress information, or event) of the user association information, a value, level, or value range (e.g., high blood pressure, low blood pressure, diabetes, time zone/day/weather, or geographical area) of a particular type of user association information. The service information (e.g., C21, C22, . . . ) may represent the type of user interface, the service type/content, such as a command, action, function, execution application, or application execution parameter.

For example, the electronic device may automatically perform conversion so that the size of letters is increased in case the user is an elderly person or represent, e.g., the icon, as an animal character in case the user is a kid. The electronic device may analyze the bio signal/information to estimate the user's age and may provide a service corresponding thereto properly. The bio signal available to estimate the user's age may include blood pressure, HRV, HRM, oxygen saturation, pulse wave, or ECG signal. The RMR tends to be reduced by about 2% every ten years, and this may be estimated by the oxygen saturation or per-minute heart rate. The electronic device may estimate the user's age group by measuring the blood vessel aging degree using the HRV signal. The electronic device may determine a service by determining the user's age group through such age group estimation or may also determine whether the user is a valid user of the device or which one of users he is.

For example, the electronic device may measure the user's blood vessel aging degree through the HRV sensor and may provide the function of recommending one or more user interfaces or varying the user interface, banning the use, or hiding depending on the aging degree. Such user interface may include one or more of a letter, image, size, wall paper, sound characteristic, widget, icon, color, alarm, ringtone, volume, voice attribute, variation in word or sentence, speech-to-text (STT), or text-to-speech (TTS). For example, as aging, vision deterioration starts to occur in his forties, and he happens to prefer large letters to small ones. Also, if hearing deteriorates as aging, low-frequency voice, such as men's voice, is more audible than low-frequency voice, such as women's voice.

Accordingly, the electronic device may provide an interface or user mode appropriate for each user by enlarging the GUI, such as letters or images or providing a widget mode putting together apps proper for the silver generation. In the case of providing the UI through voice, the electronic device may do frequency conversion from female voice to male voice and provide the converted voice or may provide a separate male voice to allow the elderly to more easily hear it. Besides, the electronic device may increase the volume as compared with the volume for normal users. The blood vessel aging degree is associated with the elasticity of blood vessel or risk degree of heart disease, and thus, in case the blood vessel aging degree, elasticity of blood vessel, or risk degree of heart disease is not less than a preset reference, the type of content may be analyzed, so as to ban the playback of contents causing excessive excitement or fear. To that end, the electronic device may further include the task of determining the genre or age group recorded as metadata in the content itself.

In case the estimated age group is not more than a preset reference, the restriction on the visual or audible UX/UI is relatively small, and thus, the electronic device may decrease the volume of the sound attribute or relatively reduce the size of the GUI to increase the amount of information displayed. Further, in case the user is estimated to be younger than a preset reference, the electronic device may ban the contents improper for the age group or pay services or request an additional authentication operation. The authentication operation may include one or more of password, phone authentication, one-time password (OTP), or bio authentication information (e.g., iris, fingerprint, voice pattern, face, sole pattern, palm pattern, and/or hand vein information).

Such age estimation-based service may help to alert or prevent risk. For example, for the elderly whose blood vessel aging degree is high as not less than a preset reference, heavy exercise or exercise overburdening the cardiovascular system should not be recommended. Accordingly, the electronic device may directly detect the user's context information (e.g., weather, temperature, frozen area, wind gust, or environmental contamination information) based on the location of the electronic device, receive the same from other device wiredly or wirelessly connected to the electronic device, and if detecting the risk degree not less than a preset reference based on the context information, it may alert the user through a visual, audible, or haptic feedback or provide the type or method of proper exercise.

Such provision of the user interface may occur at a particular time or under the situation, such as the user's particular activity, and it may also occur when the user detects a bio signal by wearing the sensor-embedded electronic device or may also be caused by the event information (e.g., disaster information, alert SNS, text message at a particular number, or weather notification information) received from a remote device connected wiredly or wirelessly, such as the other electronic device. For example, the provision of the user interface may also occur when the temperature or heart rate is varied by a preset threshold or more by the temperature sensor.

The bio signal may differ depending on the user's activity states or may differ per user depending on the health condition or exercise history. For example, when an athlete relaxes, the average heart rate may be smaller than the average heart rate of average people when they are relaxing. The electronic device may determine a service to be provided considering one of health checkup information, disease information, or disability information among the user's personal information. In case the personal information includes one of diabetes, high blood pressure, low blood pressure, musculoskeletal disease, or osteoporosis, the electronic device may adjust the exercise strength to refrain from exercise, such as jogging, while recommending relatively light exercise, such as stretching or walking.

Figure 61:
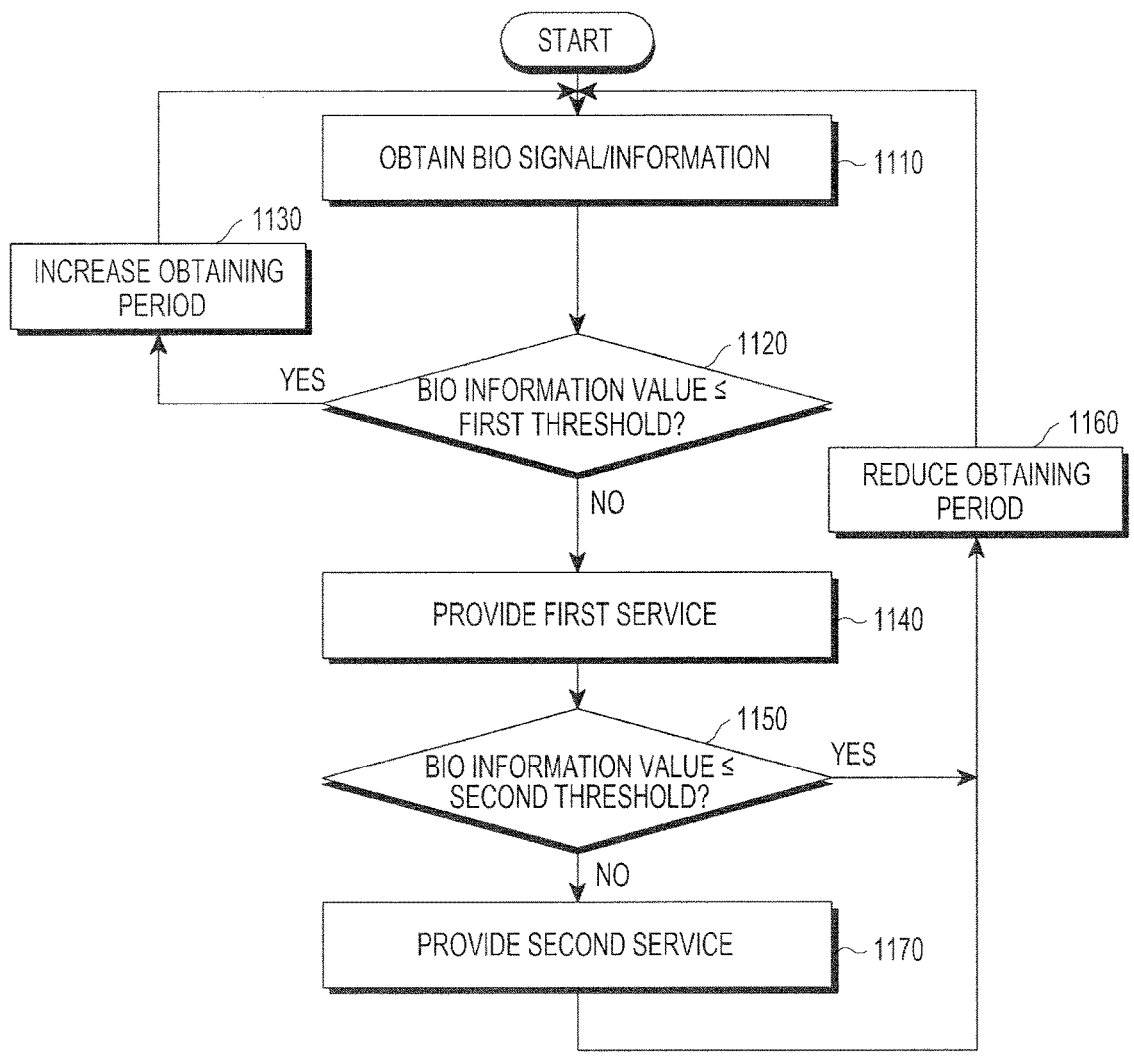
FIG. 61 is a flowchart illustrating a service providing method according to an embodiment.

FIG. 61 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1110 to 1170.

In operation 1110, a bio signal and/or bio information may be obtained. The electronic device may measure the bio signal from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for estimating age from the measured bio signal. The bio signal to estimate age may include at least one of blood pressure, ECG, HRM, HRV, PPG, oxygen saturation, or blood sugar, and the bio information may include at least one of blood pressure, elasticity of blood vessel, or blood sugar.

In operation 1120, the bio information value may be compared with a preset first value or previous bio information value. For example, the electronic device may compare the bio information value with a first threshold range or first threshold value. For example, the electronic device may compare the bio information value with the preset first value or previous bio information value to obtain the difference and may compare the difference with the first threshold range or first threshold. In case the bio information value is within the first threshold range or less than the first threshold value, the electronic device may determine that the risk degree is low to perform operation 1130, and in case the bio information value exceeds the first threshold range or first threshold value, the electronic device may determine that the risk degree is not less than a middle value to perform operation 1140. The preset value first value, first threshold range, or previous bio information value may be stored in the memory (e.g., the memory 130 or 230) of the electronic device or the external device (e.g., the server 106 or electronic device 104). The preset first value may be bio information measured by one or more other users, a representative value or mean value of a user group (e.g., per-age mean value or per-gender mean value) or an experimental value measured by an organization (e.g., a research organization or academic community).

In operation 1130, the period of obtaining the bio signal/information may be varied depending on the difference between the bio information value and the preset first value or previous bio information value. In case the bio information value is within the first threshold range or less than the first threshold value, the electronic device may determine that the risk degree is low and may increase or initialize the period of obtaining the bio signal/information (or interval of obtaining) or may stop obtaining the bio signal/information.

In operation 1140, a first service may be provided depending on the difference between the bio information value and the preset first value or previous bio information value. The electronic device may display, to the user, at least a portion of the bio information together or separately from the provision of the first service. In case the bio information exceeds the first threshold range or first threshold, the electronic device may determine that the risk degree is not less than a middle value to provide a preset first service. In one embodiment, the first service may include the operation of outputting at least one alarm signal (e.g., administration alert), and the at least one alarm signal may include at least one of a visual signal, an audible signal, and a tactile signal.

In operation 1150, the bio information value may be compared with a preset second threshold. The electronic device may compare the bio information value with the preset second value to obtain the difference and may compare the difference with the second threshold range or second threshold. In case the bio information value is within the second threshold range or less than the second threshold value, the electronic device may determine that the risk degree is a middle value to perform operation 1160, and in case the bio information value exceeds the second threshold range or second threshold value, the electronic device may determine that the risk degree is high a middle value to perform operation 1170. The preset second value, second threshold range, or the second threshold may be stored in the memory (e.g., the memory 130 or 230) of the electronic device or the external device (e.g., the server 106 or electronic device 104). The preset second threshold may be set to be larger than the first threshold.

In operation 1160, the period of obtaining the bio signal/information may be varied depending on the difference between the bio information value and the preset second value or previous bio information value. For example, the electronic device may determine the case of being less than the bio information value, second threshold range, or second threshold as the risk degree being a middle value to reduce the period of obtaining (or interval of obtaining) the bio signal/information or set the same as the minimum period.

In operation 1170, the second service may be provided depending on the difference between the bio information value and the preset second threshold. The electronic device may display, to the user, at least a portion of the bio information together or separately from the provision of the second service. For example, in case the bio information exceeds the second threshold range or second threshold, the electronic device may determine that the risk degree is high to provide a preset second service. In one embodiment, the second service may include the operation of increasing the number of times of outputting at least one alarm signal, type of at least one alarm signal, or strength of at least one alarm signal or transmitting an emergency distress signal at a preset contact.

In one embodiment, the electronic device may gather bio signals by the context information that is the flow of time for administration management. The electronic device may gather at least one signal/information among blood pressure, heart rate, HRM, HRV, PPG, oxygen saturation, and blood sugar using one or more sensors. The electronic device may derive one or more bio information among blood pressure, elasticity of blood vessel, and blood sugar by analyzing the bio signal. The electronic device may determine the variation in the bio information using one or more context information among a predetermined period, particular time, and elapse of a particular time, and if the bio information and its variation complies with a preset reference, it may perform a preset function. For example, a high blood pressure patient tends to show a deterioration of elasticity of blood vessel in case he does not take medication. In case the blood pressure variation is not less than a preset value, shows a large difference from the blood pressure variation before the time zone, or in case the blood pressure departs from a preset reference, the electronic device may provide a relevant user interface to allow a high blood pressure medication to be administered. The user interface may use one or more of a visual displaying method through a GUI, an audible displaying method through a preset audio or music, or a tactile displaying method through a haptic or vibration.

The detection of the risk degree may enhance its accuracy by using the personal information. The electronic device may determine the variation in the bio information by reflecting the user association information (e.g., context information or personal information) to provide the service. For example, if, for the high blood pressure patient, the information indicating that the user has high blood pressure may be referenced, the more exact context may be predicted for the corresponding context.

In case the risk degree increases over time, the electronic device may increase the frequency of measuring the bio signal/information. For example, even after performing the first function/service, the electronic device may perform the second function/service or vary the frequency of measuring according to a variation trend of the bio information. The electronic device may vary the attribute of the haptic feedback or attribute of content, sound, or voice displayed considering one or more of the variation trend of the bio information and the time elapsing after the initial function/service is performed. If the risk degree increases, the electronic device may increase the frequency of performing the function/service and the frequency of measuring the bio signal/information, and if the risk degree decreases, it may reduce the frequencies. As the risk degree increases, the electronic device may vary it for the user to recognize more easily by varying the color or size of the GUI elements, size of sound, brightness, frequency of blinking, or vibration size. For such references for determining the risk determination, e.g., in case a preset time or more is maintained in the high blood pressure state, in case the blood pressure gradually rises up, or in case an exercise activity with a preset strength or higher, such as running, is detected through the acceleration sensor while the blood pressure is a preset reference or more, it may be the case where the risk degree is high. In case the blood pressure is in a normal category or in case the speed at which the blood pressure drops is a preset speed or less and approaches a normal category, it may be determined as the case where the risk degree is low.

In case the bio information exceeds a preset risk degree, the electronic device may further perform another function/service to protect the user. For example, the electronic device may further perform one or more of the operation of transferring one or more of the user's context information, personal information, and bio information to one or more preset devices wiredly and/or wirelessly, the operation of outputting one or more of the information through a voice output or display output of a local device or remote device, or the operation of outputting audio. For example, for a heart attack, if bio signals are gathered through the HRV sensor, the range of variation in HRV being very narrowed before sudden heart attack occurs may be sensed. The electronic device may recognize the user with a heart disease through personal information and analyze the trend of the HRV which is bio information, allowing a risk to be known to the user. For example, if a likelihood of heart attack is detected or an activity such as the user's fall is detected through the acceleration sensor, the electronic device may transfer an emergency rescue request signal to the emergency center or disaster center via wireless communication and may include the location information and/or personal information stored in the electronic device in the emergency rescue request signal. For the people around the user to sense the emergency and notice its cause, the electronic device may output one or more of the bio signal/information, personal information, and first aid method related to the context on the display or through an audio, allowing them to help the user.

Figure 62:
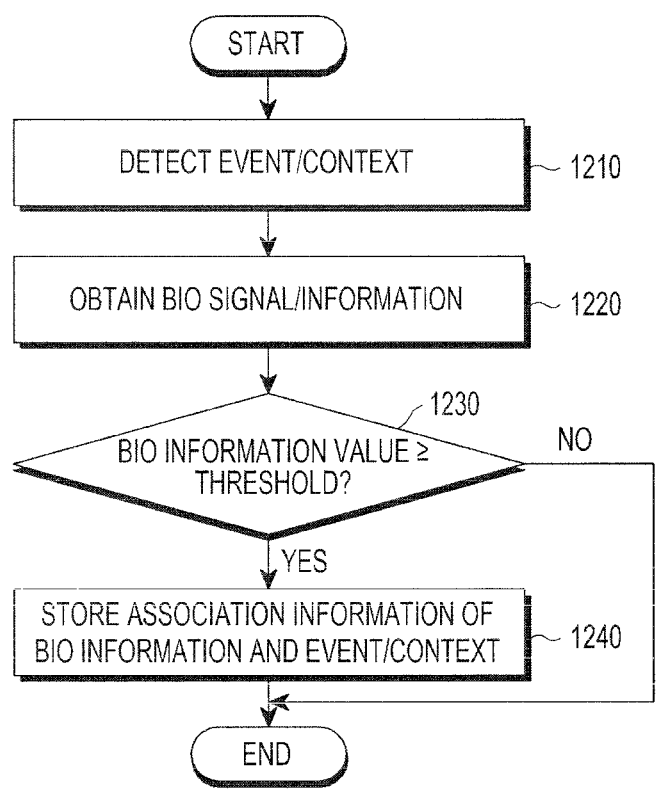
FIG. 62 is a flowchart illustrating a service providing method according to an embodiment.

FIG. 62 is a flowchart illustrating a service providing method according to an embodiment; The method may be performed by the electronic device (e.g., the electronic device 101 or 201), the processor (e.g., the processor 120 or 210) in the electronic device, or the service providing module (e.g., the service providing module 701). The method may include all or some of the operations 1210 to 1240.

In operation 1210, occurrence of an event/context in the electronic device may be detected. The event/context may include reception of a call, email, or message, arrival of a preset time/date/day, an increase in temperature/humidity, access to a preset content/service/application/website/geographical area, and detection of a preset activity/context. The electronic device may detect the occurrence of the event/context through a sensor module (e.g., the sensor module 240 or bio sensor 240I), a communication device (e.g., the communication interface 160, communication module 220, input/output interface 140, or interface 270), or an input/output device (e.g., the input/output interface 140 or input device 250).

In operation 1220, a bio signal and/or bio information may be obtained as the event/context occurs. The electronic device may measure the bio signal from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may produce bio information indicating the user's stress/emotional information from the measured bio signal. In one embodiment, the stress/emotional information may include the type of the stress/emotion and/or level or value of the stress/emotion. For example, the type of the stress/emotion may include one or more of brady cardia, tachycardia, physical fatigue, mental stress, anger, hate, grief, joy, reverence, happiness (platonic love, peace, or sense of tie), or romantic love, excitement, or lust obtained by determining one or more of the average heart rate, heart rate distribution, SDNN, RMSSD, and pNN50 obtained through the HRV. As another example, the type of stress may include one or more of the blood pressure variation, respiratory variation, and autonomic nerve balance obtained from one or more of the LF, HF, and LF/HF calculated from the PSD obtained through the HRV.

In operation 1230, the bio information value may be compared with a preset value or previous bio information value. For example, the electronic device may compare the bio information value with a threshold range or threshold value. For example, the electronic device may compare the bio information value with the preset value or previous bio information value to obtain the difference and may compare the difference with the threshold range or threshold. In case the bio information value is less than the preset threshold range or threshold, the electronic device may determine that there is no noticeable stress or emotional variation and terminate the method, and in case the difference is not less than the threshold range or threshold, the electronic device may determine that there is a noticeable stress or emotional variation and perform operation 1240. The preset value or previous bio information may be stored in the memory (e.g., the memory 130 or 230) of the electronic device or the external device (e.g., the server 106 or electronic device 104). The preset value may be bio information measured by one or more other users, a representative value or mean value of a user group (e.g., per-age mean value or per-gender mean value) or an experimental value measured by an organization (e.g., a research organization or academic community).

In operation 1240, the association information of the bio information and the event/context may be stored. In one embodiment, the electronic device may store the association information of the bio information and the event in a fourth database. The fourth database may be stored in the memory of the electronic device or external device.

In one embodiment, the fourth database may have a form as shown in Table 4.

TABLE 4

| event/context information | bio information | stress/emotional information |
|---|---|---|
| D41 | A41 | E41 |
| D42 | A42 | E42 |
| D43 | A43 | E43 |
| D44 | A44 | E44 |
| . . . | . . . | . . . |

In Table 4, the event/context information (e.g., D41, D42, . . . ) may represent the type/content of the event/ context, time/date/day of event/context, location of event, and identification information (e.g., storage location, identifier, or file name) of the content or file associated with the event/context. The bio information (e.g., A41, A42, . . . ) may represent the type/content (e.g., mean heart rate, or heart rate distribution) of the bio information, a value range (e.g., value range of mean heart rate or heart rate distribution) of a particular type of bio information, a value range of difference values (e.g., differences between the bio information and preset values) of particular types of bio information, or a value or level of particular bio information. The stress/emotional information (e.g., E41, E42, . . . ) may represent whether there is a stress/emotional variation, the type/content of stress/emotion, or level or value (e.g., frequency or mean value) of stress/emotion.

Figure 63:
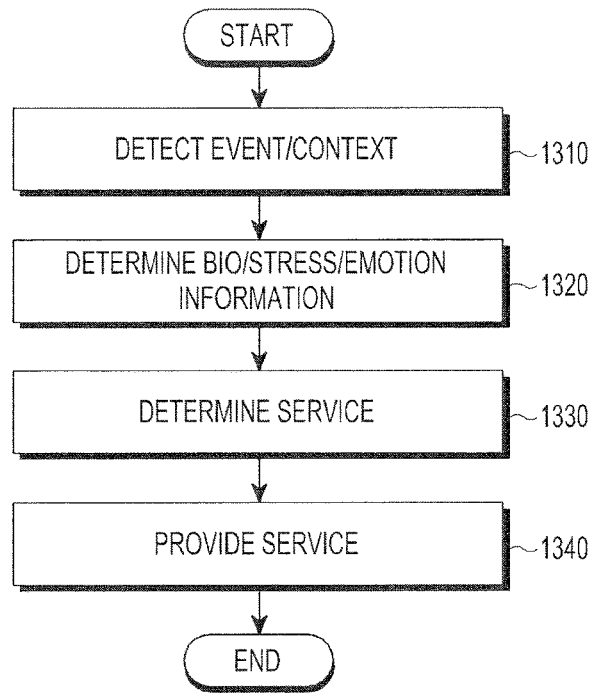
FIG. 63 is a flowchart illustrating a service providing method according to an embodiment.

FIG. 63 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1310 to 1340.

In operation 1310, occurrence of an event/context in the electronic device may be detected. For example, the event/context may include the case where the device turns on, the case where the device wakes up from the sleep state to state computation, the case where the user starts to detect bio signals through the sensor module, the case where the user detects wearing the electronic device or sensor-embedded wearable device, the case where an input by the user occurs, the case where a picture is taken, the case where a particular application is driven, the case where user authentication is performed and the user is recognized as valid, the case of detecting the user's movement that is more than a preset reference, the case where a bio signal/information departs from a preset range, the case where the bio signal/information causes a variation more than a preset reference, the case of wired or wireless connection with other external device, arrival at a particular place, time, day, season, or time period, elapse of time, or detecting a particular weather. For example, the event or context information may be provided by recognizing the travel or movement of the electronic device by the user through the acceleration sensor, positioning sensor, or GPS sensor. For example, the event or context information may be determined by the electronic device or provided by the user input, event, or information transferred from an external device or server, or cloud computing environment wiredly or wirelessly connected with the user device.

In operation 1320, as the event/context occurs, bio/stress/emotional information may be determined corresponding to the event/context. In one embodiment, the electronic device may search the fifth database stored in the electronic device or external device for the event/context information corresponding to the detected event/context. The electronic device may determine that the bio/stress/emotional information stored in the fifth database corresponding to the searched event/context information is the bio/stress/emotional information corresponding to the detected event. Such determination of the bio/stress/emotional information may include determining whether the fifth database has bio/stress/emotional information corresponding to the searched event/context and determining whether the event/context information corresponding to the detected event/context is searched from the database storing the event/context and bio/stress/emotional information-associated information.

In one embodiment, the fifth database may have a form as shown in Table 5.

TABLE 5

| event/context information | bio/stress/emotional information | service information |
| --- | --- | --- |
| D51 | F51 | G51 |
| D52 | F52 | G52 |
| D53 | F53 | G53 |
| D54 | F54 | G54 |
| . . . | . . . | . . . |

In Table 5, the event/context information (e.g., D51, D52, . . . ) may represent the type/content of the event/context, time/date/day of event/context, location of event/context, and identification information (e.g., storage location, identifier, or file name) of the content or file associated with the event/context. The bio/stress/emotional information (e.g., F51, F52, . . . ) may represent the type/content (e.g., mean heart rate or heart rate distribution) of the bio information, value range (e.g., value range of mean heart rate or heart rate distribution) of a particular type of bio information, a difference value (e.g., difference between the bio information value and a preset value) of a particular type of bio information, value or level of particular bio information, whether stress/emotion varies or not, type of stress/emotion, or level or value (e.g., frequency or mean value) of stress/emotion. The service information (e.g., G51, G52, . . . ) may represent the service type/content, such as a command, action, function, execution application, or application execution parameter.

In one embodiment, the electronic device may search the fifth database for the event/context information corresponding to the detected event/context, identify the type of bio/stress/emotional information stored in the fifth database corresponding to the searched event/context information, and obtain the identified type of bio/stress/emotional information from the user.

In operation 1330, the service corresponding to the event/context and/or bio/stress/emotional information may be determined. In one embodiment, the electronic device may search and determine the service stored corresponding to the event/context and/or bio/stress/emotional information from the fifth database stored in the electronic device or external device.

In operation 1340, the determined service may be provided. The determined service may include at least one of a variation in the user interface, user authentication, exercise coaching, information recommendation, information provision, information storage, information transmission, provision of function or service, preset content, restriction or blocking access to a function or service, variation in the settings of the electronic device, or control of an external device. The electronic device may display, to the user, at least a portion of the event/context information and/or at least a portion of the determined bio/stress/emotional information together or separately from the provision of the determined service.

The stress information, one type of bio information, may be obtained by analyzing one or more bio signals, such as HRV, ECG, heart rate, breath frequency, or skin resistance detected using one or more bio sensors. Such stress information may be associated with one or more of context information or personal information. The electronic device may perform a preset function/service according to the stress information corresponding to one or more of the context information or personal information.

In one embodiment, to detect the stress information, the electronic device may inquire the user through the input/output device (e.g., the input/output interface 140) according to a sharp variation in bio signal/information more than a preset level and analyze the result of the user's response to determine the presence or absence or level of stress.

In one embodiment, the electronic device may measure the stress information within a preset time upon or after an event occurrence context to measure the association with the event, evaluate the association between the event and the stress information, store each of the event and the stress information and/or the association in the database or accrue its occurrence count in the database or update the database with each representative value, latest value, mean value, or frequency. In case the event occurs and/or the association between the event and stress information is not less than a preset reference, the electronic device may automatically perform a preset function/service.

In one embodiment, in case there are a plurality of events associated with particular stress, the electronic device may extract one or more main factors of the events associated with the stress information and manage the extracted factors. The electronic device may extract a preset number of most critical, main factors from among several factors causing stress, and to that end, it may use the representative stress value or level per event or main factor analysis, independence verification, or correlation analysis.

In one embodiment, the electronic device may provide a service of varying the UI considering stress upon reception of a call or message. The electronic device may perform a preset function/service a preset time before the time when the event occurs or is estimated to occur. For example, in the case of such an event that a call is received from a particular other user or the user's email, message, or SNS is displayed on the display, the case where the user's stress level repeatedly occurs or a stress context of a preset level or more may occur one time or more. Through this, it may be known that the user is highly likely to be stressed out from communication with other user. The information of the other user may correspond to personal information, and the communication may correspond to the event or context information. In case the other user's communication attempt occurs, the electronic device may attempt to low the user's stress by performing other preset function/service prior to performing the communication (e.g., displaying the user interface according to the communication). For example, in the case of an incoming call, the electronic device may change the ringtone to rhythmical, tender, or preferred music or also to a humorous sound or GUI. The electronic device may provide a UI to send a comment such as "I can't take the phone. Please call back later" together with a general call reception UI according to the stress level. The user may immediately take the call or instead select to send a message.

In many cases, junk calls or messages have fixed phone numbers or phone numbers with a fixed area code. In case the phone number of the caller of the received call raises the user's stress level or the stress variation is a preset value or higher, the electronic device may provide a UI allowing the user to select the phone numbers to be handled as junk calls (e.g., block reception or delete records) or immediately delete the message.

In one embodiment, the electronic device may provide a stress management service based on time information. The context information may include information related to day, month, moon, time, season, weather, or temperature. For example, in case the user's stress level is relatively high on Monday than the other days, the electronic device may vary or display one or more of the wall paper, widget, icon, image, or theme on Monday to reduce stress. In case the wakeup alarm sound is analyzed to give more stress on Monday than the other days, the electronic device may vary the attribute of the audio or change the content to preferred music to eliminate stress. The attribute of the audio may include one or more of gender, volume, tone, character's voice, preferred content, music genre, or music atmosphere.

In one embodiment, the electronic device may provide a content recommending and banning service. The electronic device may recommend a proper content or vary the priority of content recommendation in case the user is under stress to mitigate the user's stress. In one embodiment, the electronic device may receive content information searched under the context or the user or other user's stress information stored in the remote device, cloud computing environment, or server. The contents may include one or more of an electronic book, image, webpage, SNS, multimedia, or game content, and the electronic device may first recommend the content most searched by the users who are at the stress level. When the user searches for content through an external device (e.g., a TV or computer), the electronic device may provide a content recommending and banning service. For example, upon detecting stress through the wrist watch-type HRV device, the stress information may be wiredly or wirelessly transferred directly to the TV using the wrist watch device or via the remote server or smartphone to the TV or a TV content managing server. The transferred stress information may be evaluated by the TV or TV content managing server, and one or more contents corresponding to the stress information may be provided to the user through the TV in the form of a list with priorities. Such content recommendation priority may vary depending on the user's emotion. For example, if the user's stress state is horror or fear, horror contents are excluded from recommended contents, and comedy contents may be provided. By contrast, if the user is under excitement, a documentary regarding beautiful nature may be recommended instead of violent contents. The event or context information may be related to location. For example, if a preset level or more of stress context occurs within a particular area including a certain place, the application or content information may be recommended which has been used at a preset frequency or probability or more by the user or other users in the area. The contents may include one or more of an electronic book, image, webpage, SNS, multimedia, or game content, and the electronic device may first recommend the content searched most frequently or latest by the users who are at the stress level.

In one embodiment, the electronic device may provide an application (e.g., breath adjusting application, exercise coaching application, or aroma spaying application) to release stress. The breath adjusting application provides a user interface that may release stress by guiding about the tempo and way to breath to release stress. The exercise coaching application may provide a user interface that, when the user has worked a preset time or more, may identify the user's physical or mental stress and allows the user to do stretching to have body tension or mental relaxation. The aroma spaying application, if it is equipped with the functionality that may spray or emit an aroma through air pressure, may automatically perform the function based on the user's bio information.

In one embodiment, the electronic device may restrict the contents depending on stress information. For example, in case the stress level is high, especially if the user is excited, he would highly likely make a wrong decision. Thus, such activity as required to be very careful or make a decision on a critical issue need be restricted. For example, in case either the stress level is 80% or higher or the discomfort index is 90% or higher, online payment or access to a shopping mall may be taken as examples of banned activities. Further, in order to avoid wrong communication, one or more function of calling, messaging, or SNS transmission at a preset phone number, email, address group, or other users may be banned. The banned operations may add the operation of releasing the ban in case one or more occurs of elapse of a preset time or going down to a preset stress level or less. The stress information corresponds to one or more of a state excited at a preset level or higher, depression, drowsiness, or physical fatigue.

The high frequency (HF) related to the parasympathetic nerve is related to the respiratory variation whose peak reduces while nervous and increases while relaxed and this is related with the mental or psychological fatigue or aging chronic stress. For example, the HF is shown low dung rage, concern, or fear and this may also be related to the hypofunction of digestive system. In case there is determined to be digestive hypofunction as the result of HF analysis through the HRV signal, the electronic device may recommend more digestible food or ban less digestible food. For example, in case the food recommendation application runs, and indigestion is worried about due to stress through the bio signal/information analysis, the electronic device may recommend one or more foods using the user's preferred foods (personal information) that digest well among nearby restaurants based on the location information (context information). For the user's preferred foods, among the personal information, the preferred food information entered by the user and eating history information entered for calculating calorie may be used. The electronic device may gather, e.g., the information on the stores the user frequently visits using the positioning technique or gather store information on the Internet, and in case the user enters food information in a particular area, the electronic device may gather, store, and use the information such as the frequency and association between such location information and the food information.

In one embodiment, the electronic device may provide a car control service. For example, the electronic device may perform a car control function, such as banning self-driving. In case the user is at a state (i.e., stress information) excited at a preset level or higher, depression, drowsiness, or physical fatigue, the user's recognition capability is lowered. The electronic device may ban self-driving under the context of detecting such stress information, run a public transportation-related application, or may restrict a particular function.

The electronic device may recognize entry of the user into his car through the camera mounted in the car by wiredly or wirelessly accessing the car control system or camera device in the car. The electronic device may detect the user's bio signal/information through the sensor module or wiredly/wirelessly connected wearable device and may transfer the control signal corresponding to the bio signal/information to the car control system. The electronic device may transfer the bio signal/information to the car control system and may determine and control functions permitted or banned by the car control system.

In one embodiment, the electronic device may detect a contact through the steering wheel or a sensor mounted on the steering wheel and may analyze the bio signal/information through one or more of the electronic device, wearable device, or car control system to perform a banning function if the stress level is a preset value or higher. For example, if the stress level measured through the ECG or GSR sensor mounted on the steering wheel is a preset value or higher, one or more functions may be performed among controlling the increase in RPM upon attempting quick acceleration to restrict such quick acceleration, increasing the brightness of the dashboard for more visibility, limiting the maximum speed, alerting if the speed is over a preset value, limiting the sports mode among car driving modes, turning on the headlight for more visibility while driving, or choosing a particular genre for emotional stability and user's favored music.

The car control technique may be performed through the infortainment system, and telematics and commercialized standard techniques may come in use. Various methods may be used for wired or wireless connection between the electronic device and the car control system. The wireless connection may use one or more of BT, Wi-Fi, BLE, IrDA, or IEEE 802 for mutual direct connection. The electronic device and the car control system may also be connected together through a cell network or satellite network, and the electronic device and the car control system may also be connected with each other via a control server or center for controlling the car. For example, the electronic device may generate a control signal of the car according to the bio signal/information. The control signal may be transmitted to the control server. The control server may verify the car control authority and transfer the control signal to the car control system. For example, the car control authority may be the car owner's phone number, ID or password, iris or other bio authentication information or the electronic device's ID or authentication information by the bio signal/information. The car control authority/information may be added during the course of transmitting or receiving the control signal. The control server may send a request for the car control authority/information when transmitting or receiving the control signal.

In one embodiment, the electronic device may provide a service of varying contents. In case the stress level is a preset value or higher, the electronic device may vary the contents. For example, in case the bio information is a preset stress level or higher, and a context information is sensed of receiving one or more of an email, SMS message, SNS, chatting message, or MIMS, the electronic device may analyze the content of the message before displaying or text-to-speech (TTS) outputting the message to the user in order to identify one or more words, sentences, images, or music with a preset risk level. The electronic device may convert high risk-level words or sentences into other text, voice, images, or music and output the same.

For example, the high risk level message contents may be one or more of slangs, cursed words, criticisms, or impolite way to talk, typos, threats, and unsorted sentence format. The electronic device may assess the risk level for each content and reflect and process the assessed result together with the stress level. For example, a heavy curse may have a higher risk level, and a light curse may have a lower risk level. The electronic device may display to the user a message content with a low risk level at a low stress level without varying the same and may output a message content with a low risk level at a high stress level, with the message content varied or hidden. The electronic device may evaluate the grade for each of the stress level and the risk level, collectively evaluate them through such an operation as adding, multiplying, or averaging the two grades, and may show, as it is, or vary the message content depending on the collectively evaluated result.

For example, the electronic device may evaluate the stress level in three groups (3—high, 2—slightly high, and 1—moderate) and also evaluate the risk level of the message content in three groups, and if the average of the stress level and the risk level of the message content is 2 or higher, the electronic device may then vary the message content or hid the corresponding portion. The electronic device may convert the determined word, phrase, or sentence in the message content by replacing the same with other symbols or refining the same or both. The electronic device may convert the message content into a voice signal using text-to-speech (TTS) and output the voice signal. In case the stress level, which is bio information from the bio signal measured while the voice is output or the message content is displayed, is varied by a preset reference or more, the electronic device may convert the message content. The electronic device may vary the information displayed while message analysis proceeds or display other UI. In the case of a voice, if the conversion is ended after pause, the electronic device may resume to output the voice or output the converted message again from the beginning.

In case the context information represents the operation of creating one or more messages of an email, SMS message, SNS, chatting message, or MIMS, the electronic device may determine the contents to be varied among the message contents depending on the stress information during or after the creation. In case the user is too excited or depressed and thus too emotional, he would likely create a message that may raise an issue in the future. In such case, the electronic device may perform the operation of representing the determined word, phrase, or sentence of the message content by one or more of deleting, replacing with other symbols, or refining the same depending on the risk level evaluation and stress level. In case a message is input as text (STT) using voice input, the electronic device may analyze and vary the inputted text result.

Figure 64:
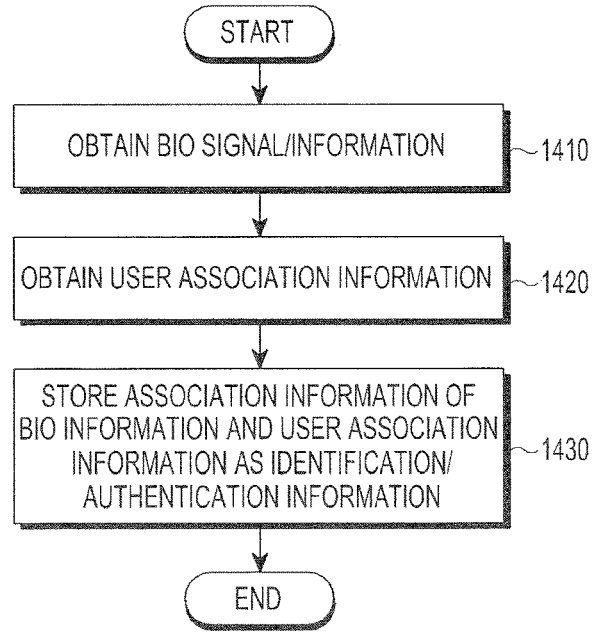
FIG. 64 is a flowchart illustrating a service providing method according to an embodiment.

FIG. 64 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1410 to 1430.

In operation 1410, a bio signal and/or bio information may be obtained. The electronic device may measure the bio signal for user authentication from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for user authentication from the measured bio signal. For example, the bio information for user authentication may include an HRV pattern, ECG pattern, iris image, voice, or hand vein image.

In operation 1420, the user association information may be obtained as the bio signal/information is obtained. The electronic device may obtain user association information, such as the time of measuring or obtaining the bio signal/information and/or the user's movement before/after the same, location, current time, the user's exercise strength, and type of the user's activity. The electronic device may obtain the time of measuring or obtaining the bio signal/information and/or the user association information before/after the same through at least one of a communication device (e.g., the communication interface 160, the communication module 220, the input/output interface 140, or the interface 270), an input device (e.g., the input/output interface 140, the input device 250, or the display 150), a sensor module (e.g., the sensor module 240 or bio sensor 240I), a camera module (e.g., the camera module 291), and a memory (e.g., the memory 130 or 230).

In operation 1430, the association information of the bio information and the user association information may be stored. In one embodiment, the electronic device may store the association information of the bio information and the user association information in a sixth database as user identification/authentication information. The sixth database may be stored in the memory of the electronic device or external device.

In one embodiment, the sixth database may have a form as shown in Table 6.

TABLE 6

| user information | bio information | user association information |
|---|---|---|
| H61 | A61 | B61 |
| H61 | A61 | B62 |
| H61 | A62 | B61 |
| H61 | A62 | B62 |
| H62 | A63 | B63 |
| ... | ... | ... |

In Table 6, the user information (e.g., H61, H62, . . . ) may represent information for identifying the user (e.g., ID or name). The bio information (e.g., A61, A62, . . . ) may represent the type/content (e.g., mean heart rate, heart rate distribution, HRV pattern, ECG pattern, iris image, voice, or hand vein image) of the bio information, a value range (e.g., value range of mean heart rate or heart rate distribution) of particular bio information, characteristic points (e.g., peak, edge, or pattern) of particular bio information, and their characteristic values, location where particular bio information is stored, value of particular bio information, identifier, and file name. The user association information (e.g., B61, B62, . . . ) may represent the type/content (e.g., movement, location, time/date/day, user's exercise strength, user's activity type, user's disease/disability/health information, current emotional/stress information, or event), or a value, level, or value range (e.g., movement level, exercise strength, time zone/day/weather, geographical area, disability degree, or disease/injury degree) of a particular type of user association information.

Figure 65:
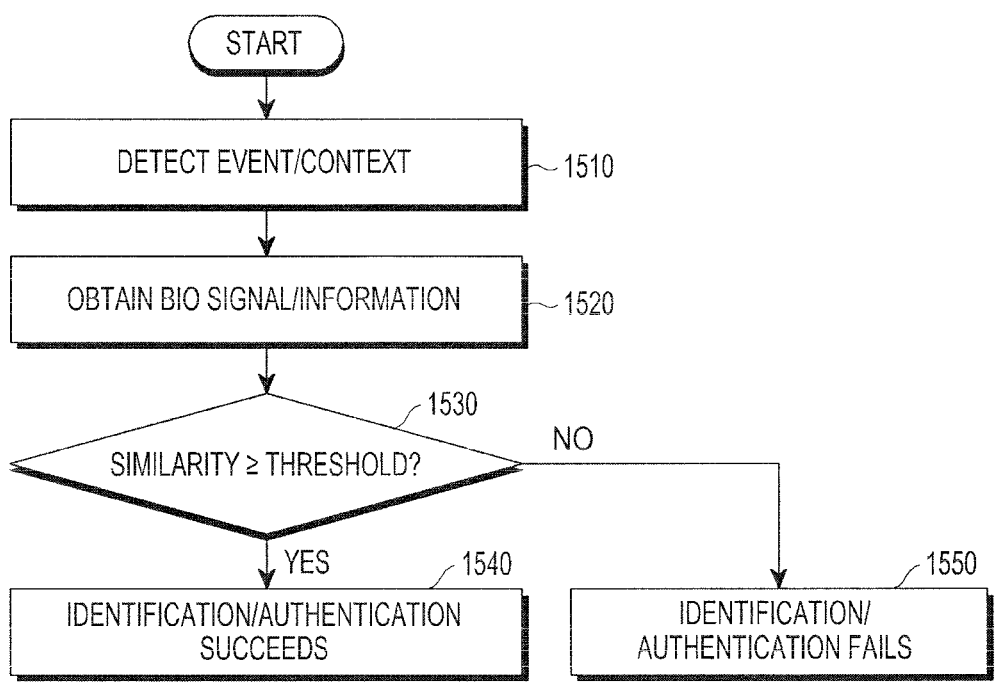
FIG. 65 is a flowchart illustrating a service providing method according to an embodiment.

FIG. 65 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1510 to 1550.

In operation 1510, occurrence of an event/context in the electronic device may be detected, which requires user authentication. For example, the event/context requiring user authentication may be the case where the device turns on or wakes up from the sleep state to start computation, the case where the personal information is transmitted/received from an external device, the case where the user starts to sense bio signals through the sensor module, the case where the user sense wearing the electronic device or sensor-embedded wearable device, the case where an input by the user occurs, or the case where a particular application runs.

In operation 1520, a bio signal and/or bio information may be obtained as the event/context occurs. The electronic device may measure the bio signal for user authentication from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for user authentication from the measured bio signal.

In operation 1530, the similarity between the obtained bio information and pre-stored (or registered) bio information may be determined, and the similarity may be compared with a preset threshold. In one embodiment, the electronic device may search the sixth database stored in the electronic device or external device for the user association information (or context information) corresponding to the context at the time of measuring or obtaining the bio signal/information and/or before/after the same (e.g., movement, location, time/date/day, user's exercise strength, user's activity type, or event). The electronic device may determine that the bio information corresponding to the searched user association information is the pre-stored (or registered) bio information to be compared with. For example, the electronic device may compare the pattern (or characteristic points defining the pattern) or value (e.g., heart rate) of obtained bio information with the pattern (or characteristic points defining the pattern) or value of the pre-stored (or registered) bio information of the pre-registered user to determine the similarity (e.g., the number of characteristic points identical with one another or with a difference within a threshold, or the ratio of the number or value (e.g., ratio in number of similar characteristic points relative to all the characteristic points).

In one embodiment, the electronic device may derive the personal information (e.g., disease/disability/health information) form the obtained bio information and may search the sixth database for the user association information corresponding to the derived personal information. The electronic device may determine that the searched user association information is the pre-stored (or registered) bio information to be compared with.

In case the similarity is a preset threshold or higher, the electronic device may determine in operation 1540 that the user identification/authentication succeeds, and in case the similarity is less than the preset threshold, the electronic device may determine in operation 1550 that the user identification/authentication fails. For example, in case the similarity is the preset threshold or higher, the electronic device may determine that the user of the obtained bio information is the same as the pre-registered user.

Figure 66:
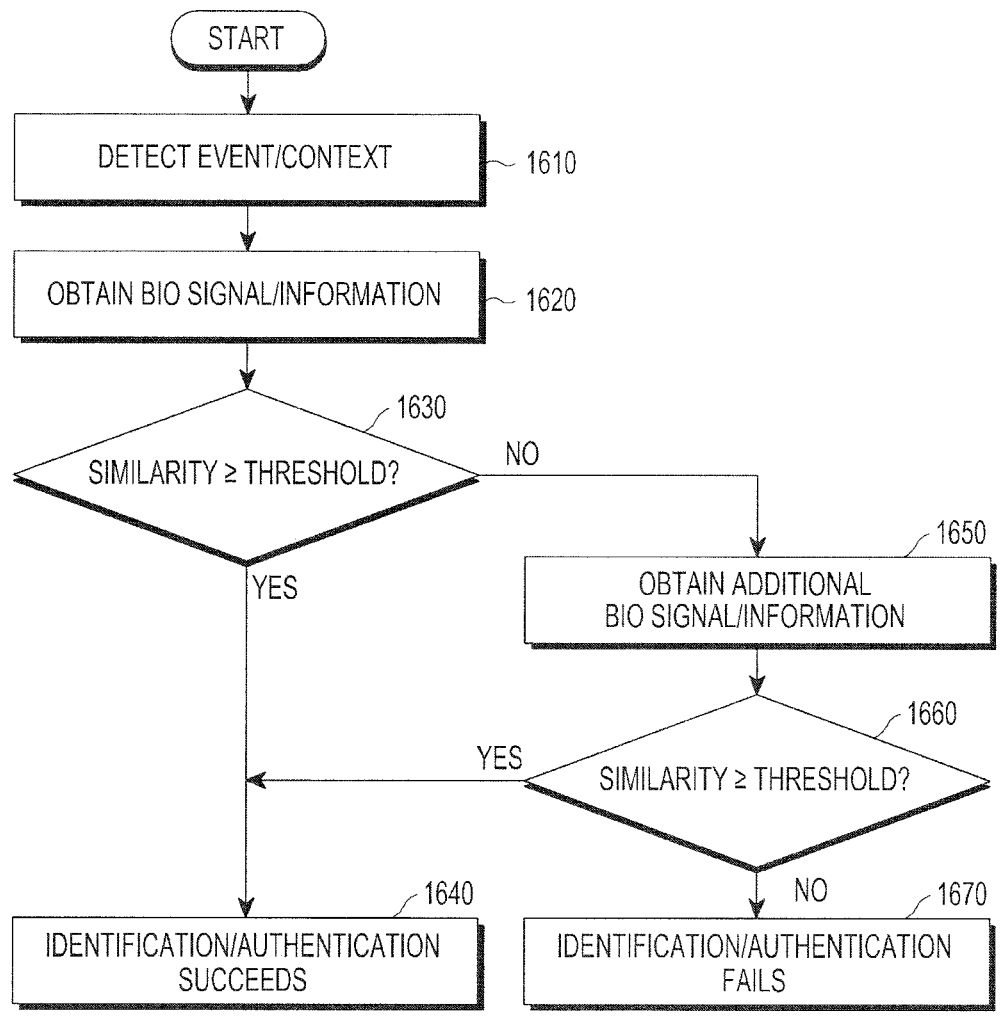
FIG. 66 is a flowchart illustrating a service providing method according to an embodiment.

FIG. 66 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1610 to 1670.

In operation 1610, occurrence of an event/context in the electronic device may be detected, which requires user authentication.

In operation 1620, a bio signal and/or bio information may be obtained as the event/context occurs. The electronic device may measure the bio signal for user authentication from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for user authentication from the measured bio signal.

In operation 1630, the similarity between the obtained bio information and pre-stored (or registered) bio information may be determined, and the similarity may be compared with a preset threshold. In one embodiment, the electronic device may search the sixth database stored in the electronic device or external device for the user association information (or context information) corresponding to the context at the time of measuring or obtaining the bio signal/information and/or before/after the same (e.g., movement, location, time/date/day, user's exercise strength, user's activity type, or event). The electronic device may determine that the bio information corresponding to the searched user association information is the pre-stored (or registered) bio information to be compared with. In one embodiment, the electronic device may derive the personal information (e.g., disease/disability/health information) form the obtained bio information and may search the sixth database for the user association information corresponding to the derived personal information. The electronic device may determine that the searched user association information is the pre-stored (or registered) bio information to be compared with.

In operation 1640, in case the similarity is a preset threshold or higher, the electronic device may determine that the user authentication succeeds, and in case the similarity is less than the preset threshold, the electronic device may perform operation 1650.

In operation 1650, an additional bio signal and/or bio information may be obtained. The electronic device may measure the additional bio signal for user authentication from the user through, e.g., a camera module (e.g., the camera module 291), an input device (e.g., the input/output interface 140, the input device 250, or the display 150), or a sensor module (e.g., the sensor module 240 or bio sensor 240I) and may derive additional bio information for user authentication from the measured bio signal. The type of the bio signal/information obtained in operation 1620 is different from the additional bio signal/information obtained in operation 1650. For example, the electronic device may obtain the bio signal (e.g., blood pressure, HRV, HRM, oxygen saturation, pulse wave, or ECG signal) through the sensor module in operation 1620 and may obtain an image (e.g., iris image, voice, or hand vein image) through the camera module in operation 1650.

In operation 1660, the similarity between the obtained additional bio information and pre-stored (or registered) bio information may be determined, and the similarity may be compared with a preset threshold. For example, the electronic device may compare the pattern (or characteristic points defining the pattern) or value (e.g., heart rate) of obtained bio information with the pattern (or characteristic points defining the pattern) or value of the pre-stored (or registered) bio information of the pre-registered user to determine the similarity (e.g., the number of characteristic points identical with one another or with a difference within a threshold, or the ratio of the number or value (e.g., ratio in number of similar characteristic points relative to all the characteristic points). In case the similarity is a preset threshold or higher, the electronic device may determine in operation 1640 that the user authentication succeeds, and in case the similarity is less than the preset threshold, the electronic device may determine in operation 1670 that the user authentication fails. For example, in case the similarity is the preset threshold or higher, the electronic device may determine that the user of the obtained bio information is the same as the pre-registered user.

Additionally or alternatively, the electronic device may perform operations 1650 and 1660 in case the similarity is the preset threshold or higher in operation 1630.

Since the electronic device may use the stored or received personal information, the electronic device may perform authentication on the user to protect the personal information. For example, if such an operation occurs as to receive a request for user authentication through the user's UI or by a particular function, the electronic device may receive one or more bio signals from the user and analyze the user's bio signals to extract one or more bio information. The electronic device may calculate the similarity between the extracted bio information and the bio information pre-stored in the database and may extract one or more user candidates for which the similarity is the preset reference or higher.

The particular function for user identification may include one or more of the user operating the electronic device, wearing the electronic device, sending particular information to other external device, or receiving the information. The electronic device may compute the matching rate of characteristic information through the authentication process, and if the matching rate is not more than a preset reference, may determine that the user is not the valid user of the electronic device. The database may be disposed in one or more of the electronic device, external device, remote device, server, or cloud computing environment, and the electronic device may be wiredly or wirelessly connected with the external device where the database is disposed.

The user's bio information may differ depending on contexts even when it is for the same user. For example, in the case of HRV, the pattern shows different periods and heart rates for when the user is relaxing and when the user does exercise. Since the sensor may sway or fails to tightly contact the user's body due to the movement to cause noise, the electronic device may use the movement information to correct the bio signal. The electronic device may further include the user's context information in identifying the user based on the bio information and may perform computation.

The user's bio signal has characteristics depending on the user's health condition and age. As an example, the ECG signal gathered through the ECG sensor or pulse wave signal gathered through the heart rate sensor shows the characteristics of heart activity per user. The electronic device may analyze the characteristic pattern of such waveform signal and may compare the same with the user's characteristic pattern previously used to thereby identify or authenticate the user.

For example, the length and shape of a P wave in the ECG reflects the size of the user's atrium, and the temporal length of the QRS complex interval, which is a combination of the Q wave, R wave, and S wave, reflects the user's heart conductance rate. The amplitude, duration, and shape of a waveform differs person-to-person, and they reflect the health condition, such as a heart disease, and may thus be used for identifying an individual. Such waveform may be deformed depending on stress states or as it adds noise according to the user's activity state. Since the healthy generally or in many cases present such waveforms within a normal category, the electronic device may enhance the recognition rate by separately gathering and managing the characteristic bio information for each person.

The electronic device may gather bio signals/information per user in advance under several contexts for user identification. For example, the electronic device may authenticate the user and gather the user's bio signals through one or more schemes of pattern lock, password, iris recognition, fingerprint recognition, voice recognition, hand vein recognition, and face recognition. The electronic device may record together the movement information on the context through a motion sensor, such as an acceleration sensor or gyro sensor and operate together the motion sensor upon future user identification to gather the movement information by the motion sensor together with the bio information and may compare the same with pre-stored bio signal/information and movement information, thereby enhancing the user recognition rate.

The electronic device may obtain an accelerated photoplethysmograph through the HRV sensor using the PPG sensor to determine whether they are the same user using one or more bio information such as vessel elasticity that hardly varies.

In one embodiment, the electronic device may perform the user authentication using one or more time or place. The context information may include one or more of the location and time of the electronic device, and the electronic device may select one or more user candidates that have the bio information history corresponding to the location and time. In many cases, the user performs repeated operations at a particular location and time. In such case, the bio signal/information tends to be similar. For example, an office worker working at an office has substantially the same work time and does desk work. Thus, similar bio signal/information patterns may be expected for the office worker in similar times and places.

The electronic device may enhance the accuracy of authentication by using a plurality of pieces of bio information rather than a single one. That is, in case the characteristics of several bio signals/information pieces, such as waveform patterns measured through the ECG sensor or mean heart rate, blood pressure, or HRV measured through the heart rate sensor are consistent for a particular user, it provides higher accuracy than when one sensor is used. Place-related information may include one or more of indoor positioning information or GPS information gathered from the electronic device or other external device. The electronic device may also determine the location by recognizing a particular wireless access point (AP) signal. The electronic device, upon reception of AP signals from the office and home, respectively, may determine the user's location based on the context information on the places and may compare the user's bio signal/information with pre-stored information.

In one embodiment, the electronic device may perform user authentication based on the user's activity information or user's exercise strength. The user may sense user activity information including one or more of the user's exercise strength or user's activity type to authenticate or identify the user. The user's bio signal may show different forms during relaxation and exercise. For example, the heart rate and oxygen saturation may vary during relaxation as compared with during exercise, and the bio information, such as the amplitude or frequency of peaks, duration of the pulse wave, waveform, or stress information in the HRV or ECG signal pattern may be varied. Further, since the bio signal may fail to come in tight contact with the skin during exercise as compared with during relaxation, noise signals may be added to the bio signal. The electronic device may previously store bio information per activity type or exercise strength for some users, and when sensing the activity type or exercise strength, it may sense corresponding bio information, and may compare the sensed information with the previously stored information to determine whether it complies with the user's characteristics. If there are several users, the electronic device may store bio information for each of one or more activity information pieces among the users' activity types or exercise strength per user and compare the sensed context information and sensed bio information with the pre-stored information to extract one or more users as candidates.

For example, in the resting state during which there is little user movement, the exercise strength corresponds to 1MET, and the electronic device may gather the bio information on the corresponding context and gather the user's bio information under the same exercise strength context in the future, and it may then compare the same with the pre-stored bio information to determine whether they are the same user. For example, the ECG signal strength or peak frequency varies when the user wears casual or tuxedo during the resting state. The electronic device may figure out common characteristics influencing the bio signal/information or detect the characteristics only for the corresponding user. For example, in the above scenarios, although the two cases show different waveform amplitudes and periods in the ECG pattern, the respective waveforms of the two cases may be averaged to produce averaged waveforms, or power spectrum densities may be obtained for the two cases and may be compared with each other. The electronic device may store a plurality of bio information pieces also for the same exercise strength or activity type. This is why, despite the same exercise strength, there may be various differentiating situations, such as the state of the worn clothes or slope of the road at jogging, and the electronic device may also use a plurality of bio sensors.

The user's exercise strength is related to the user's activity type. For example, a user with an exercise strength corresponding to METs 7.0 may do a type of activity, e.g., jogging, and receive pulse waves through the PPG sensor embedded in the wrist watch worn on the user's wrist. In this case, the user does exercise while swinging his arms, and thus, more signal noise may be added by mechanical/physical characteristics such as vibration, as compared with at rest. Such signal noise detected along with the PPG signal may be removed for peak-to-peak interval (PPI) detection of the PPG signal. The bio signal measured by the PPG sensor is activated commonly in a 0.04 Hz to 0.4 Hz frequency band. Thus, high-frequency noise may be eliminated using a low pass filter, such as Butterworth, Chebyshev, or Elliptic method. The following paper introduces a method for eliminating noise generated by motion using an acceleration sensor or gyro sensor. Correction may be made by a selective combining method that selects the best signal using several similar-type sensors.

J. Lee, Y. J. Woo, Y. J. Jeon, Y. J. Lee, and J. Y. Kim "Moving artefacts detection system for a pulse diagnosis system," J. Inst. Electron. Eng. Korea (IEEK), vol. 45, no. 5, pp. 21-27, September 2008.

H. K. Lee, J. H. Lee, J. W. Park, J. Lee, and K. J. Lee, "Detection of heart rate in PPG signals mixed with various hand motion," in Proc. Conf. Inform. Control Syst. (CICS), pp. 233-234, Ansung, Korea, April 2012.

Minho Kim, Taewook Kim, Sunghwan Jang, Dahee Ban, Byungseok Min, Sungoh Kwon, Noise-Robust Algorithm for PPG Signal Measurement, J-KICS) '13-12 Vol. 38C No. 12, 1085-1094, 2013, http,//dx.doi.org/10.7840/kics.2013.38C.12.1085.

The electronic device may determine the exercise strength at which the user does activity through several methods. For example, if a particular activity is sensed through the acceleration sensor, the electronic device may inquire about the type of the activity through the user interface after the activity is done and may record together the characteristic information on the movement through the acceleration sensor. If sensing a similar movement characteristic through the acceleration sensor later, the electronic device may compare the user's bio information corresponding thereto with the user's bio information actually received to determine whether the user is the previous user.

In one embodiment, the electronic device may measure the user's movement speed through GPS and may analyze the pattern information of the acceleration sensor to measure the type of exercise and exercise strength. For example, even when the user moves the same distance at the same speed, the electronic device records different motion patterns for when using a bicycle, walking or running, and using a car. The electronic device may determine the exercise strength, the approximate activity type of the user or exercise type by referring to such material as METs per user activity. For example, upon sensing a movement at 8 km/h through the GPS sensor, the movement by a car, movement by a bicycle, and movement by running show different signal patterns as received by the acceleration sensor. For example, in case the acceleration sensor is equipped in the wrist watch device, the variation in the acceleration sensor signal when running shows signal patterns sensitive to the exercise of upper and lower parts of the body or the wrist's movement. By contrast, the movement by the bicycle may present patterns related to the movement of the bicycle handlebar rather than the upper-lower movement of the body, and the movement by the car may show patterns related to the movement of the steering wheel different than that of the bicycle or more various in-car movements. In light of exercise strength, the running shows the highest exercise strength even though the movement occurs at the same speed, and the biking shows a higher exercise strength than driving the car.

In one embodiment, the pattern information by the acceleration sensor may differ depending on wearing positions. For example, when it is worn on the waist, a different pattern is shown than the wrist movement. While running, the variation in acceleration forwards (roll) becomes highest when taking a step and pulling back the body and lowest before putting the other foot. The acceleration sensor signal in the vertical direction (yaw) becomes highest when the two legs are put together while running and lowest when the legs are stretched so that the body is at the lowest position. While running around a length or track, variations may occur along lateral directions (pitch, side direction). At this time, although the vertical variation in the acceleration signal is sensed as very large or high, signals in different directions show small amplitudes or variations. Biking does not present a large acceleration variation as contrasted with when running forwards, but instead, may show unique movements in the vertical and lateral patterns depending on the riding positions. Car driving shows different patterns in all directions than those by running or biking.

The electronic device may compare the position and type of one or more sensors and movement pattern information with pre-stored pattern types to determine the type of the user's activity. The user's activity types may come in a larger category and a smaller category. For example, walking may belong to the larger category and may be divided into smaller category depending on the speed, location, method, tool, or purpose of walking. Table 7, part of 2011 Compendium of Physical Activities, a second update of codes and MET values, shows examples of the smaller category user activities (specific activity or CODE) and exercise strengths (METs) in case the larger category (major heading) of the user's activities is walking.

TABLE 7

| CODE | METS | MAJOR HEADING | SPECIFIC ACTIVITIES |
|---|---|---|---|
| 17082 | 5.3 | walking | hiking or walking at a normal pace through fields and hillsides |
| 17085 | 2.5 | walking | bird watching, slow walk |
| 17088 | 4.5 | walking | marching, moderate speed, military, no pack |
| 17090 | 8 | walking | marching rapidly, military, no pack |
| 17100 | 4 | walking | pushing or pulling stroller with child or walking with children, 2.5 to 3.1 mph |
| 17105 | 3.8 | walking | pushing a wheelchair, non-occupational |
| 17110 | 6.5 | walking | race walking |
| 17130 | 8 | walking | stair climbing, using or climbing up ladder (Taylor Code 030) |
| 17133 | 4 | walking | stair climbing, slow pace |
| 17134 | 8.8 | walking | stair climbing, fast pace |
| 17140 | 5 | walking | using crutches |
| 17150 | 2 | walking | walking, household |
| 17151 | 2 | walking | walking, less than 2.0 mph, level, strolling, very slow |
| 17152 | 2.8 | walking | walking, 2.0 mph, level, slow pace, firm surface |
| 17160 | 3.5 | walking | walking for pleasure (Taylor Code 010) |
| 17161 | 2.5 | walking | walking from house to car or bus, from car or bus to go places, from car or bus to and from the worksite |
| 17162 | 2.5 | walking | walking to neighbor's house or family's house for social reasons |
| 17165 | 3 | walking | walking the dog |
| 17170 | 3 | walking | walking, 2.5 mph, level, firm surface |
| 17180 | 3.3 | walking | walking, 2.5 mph, downhill |
| 17190 | 3.5 | walking | walking, 2.8 to 3.2 mph, level, moderate pace, firm surface |
| 17200 | 4.3 | walking | walking, 3.5 mph, level, brisk, firm surface, walking for exercise |
| 17210 | 5.3 | walking | walking, 2.9 to 3.5 mph, uphill, 1 to 5% grade |
| 17211 | 8 | walking | walking, 2.9 to 3.5 mph, uphill, 6% to 15% grade |
| 17220 | 5 | walking | walking, 4.0 mph, level, firm surface, very brisk pace |
| 17230 | 7 | walking | walking, 4.5 mph, level, firm surface, very, very brisk |
| 17231 | 8.3 | walking | walking, 5.0 mph, level, firm surface |
| 17235 | 9.8 | walking | walking, 5.0 mph, uphill, 3% grade |
| 17250 | 3.5 | walking | walking, for pleasure, work break |
| 17260 | 4.8 | walking | walking, grass track |
| 17262 | 4.5 | walking | walking, normal pace, plowed field or sand |
| 17270 | 4 | walking | walking, to work or class (Taylor Code 015) |
| 17280 | 2.5 | walking | walking, to and from an outhouse |
| 17302 | 4.8 | walking | walking, for exercise, 3.5 to 4 mph, with ski poles, Nordic walking, level, moderate pace |
| 17305 | 9.5 | walking | walking, for exercise, 5.0 mph, with ski poles, Nordic walking, level, fast pace |
| 17310 | 6.8 | walking | walking, for exercise, with ski poles, Nordic walking, uphill |
| 17320 | 6 | walking | walking, backwards, 3.5 mph, level |
| 17325 | 8 | walking | walking, backwards, 3.5 mph, uphill, 5% grade |

The electronic device may gather context information, such as travel distance, speed, place (topography), time, schedule, or travel direction, and may consider together the gathered bio information to more precisely determine the activity, e.g., the user's activity within the smaller category. For example, if the user travels at 3 mph on a gentle hill, and it is determined by the motion sensor as walking, the electronic device may determine that such smaller category user activity is an activity corresponding to code 17210 and 5.3 METs. For example, if the user moves on a sand field at an average speed, the electronic device may determine that the activity corresponds to code 17262 and 4.5 METs. The electronic device may record the bio information together with such user activity or exercise strength and use them for more exact user authentication. Code 17320 represents walking back, and the electronic device may determine using the acceleration sensor or gyro compass that its moving direction differs from the direction of the body. That is, since walking back and walking forward present different patterns as detected by the acceleration sensor, they may be easily distinguished. For example, the headphone or HMD equipped with a gyro compass may sense the direction of a view, and the band or watch device may determine the direction of the body by recognizing the position of wearing, and the travel directions being not identical may be sensed by the GPS or acceleration sensor.

Since the electronic device may reflect the user's latest body condition by continuously updating the context information and bio information with the latest information, providing for enhanced accuracy of activity determination. For example, even when a person doing little exercise gets his muscular power or body shape changed by continuous exercise, such change may be reflected by the update. For example, a user who keeps running shows a reduced pace when he is tired, and such change may also be reflected.

The electronic device may measure energy consumption for walking or running by analyzing the pattern information by the acceleration sensor. For example, in case the user runs, the travel distance may be calculated by multiplying the pace by the number of steps, and since the pace is related with his height, it may be calculated using an average pace as per the height or a pace set by the user's entry. If the travel distance is calculated, the average travel speed may be known by dividing the travel distance by the time, and the approximate exercise strength of running may be determined by the average travel speed. Running may be considered as different user activities depending on its speeds, and accordingly, different exercise strengths or energy consumptions may be determined.

Since the heart rate or oxygen consumption is related to energy consumption, and this is related to exercise strength, such bio information may be used to predict the exercise strength. At this time, a more specific energy consumption may be estimated using personal information, such as age or weight. The electronic device may determine the type of user activity using the motion sensor along with the bio information to determine its corresponding exercise strength from the METs table information and to measure energy consumption.

The electronic device may determine the user's activity type and analyze the bio signal/information during or immediately after the context to measure the user's exercise strength while simultaneously storing together the bio information. The electronic device may store movement information constituted of one or more of the user's activity type, movement pattern information, or exercise strength and one or more of the bio signal pattern or bio information corresponding thereto, and if sensing the user's movement information, find out one or more bio signal patterns or one or more bio information showing a preset matching degree (consistence ratio) corresponding thereto and discover the user corresponding thereto.

The determination of the user's exercise strength may be based on the type of activity, and the electronic device may use one or more motion sensors of the accelerometer, gyro sensor, GPS, gyro compass, geomagnetic sensor to determine the type of activity, or the electronic device may obtain the exercise strength by gathering one or more of the heart rate, HRV, or oxygen consumption through the bio sensor. The electronic device may utilize the user's personal information, such as height or weight, to more precisely estimate the exercise strength and energy consumption. Typically, the user's exercise strength is about 0.8 METs during sleep, 1 METs during resting or relaxing, and shows particular METs values depending on user's activities of the smaller category.

In one embodiment, the electronic device may authenticate the user based on the user's personal information. For example, the electronic device may use one or more personal information of the user's age, weight, blood vessel aging degree, blood pressure, ECG pattern, HRV pattern, disease information, or disability information to recognize or authenticate the user. The electronic device, if determining the bio information through the bio signal, may compare the same with the user's pre-registered personal information to determine whether he is the corresponding user. For example, the electronic device may analyze the pulse wave to obtain the accelerated photoplethysmograph, and when obtaining the blood vessel aging degree from the accelerated photoplethysmograph, may obtain one or more user candidates matching the blood vessel aging degree. For example, in case the user has a heart disease, since the bio information may be extracted from one or more signals of HRV, ECG, pulse wave, or heart rate sound, the electronic device, upon sensing such bio information, may determine the user using the disease information. For example, also in case the user has a joint disease or uncomfortable arm or leg, upon sensing such characteristic through the motion sensor, the electronic device may determine the user using the personal information. In case a health checkup or exercise capacity measurement has been previously done, and its corresponding records are accessible, the electronic device may compare the sensed bio information with the records to discover the user with a higher matching rate. Since such bio information may steadily vary, it may be time-sequentially managed by steadily updating the personal information with the bio information sensed at constant intervals or latest.

In one embodiment, the electronic device may perform the user authentication through a first and second authentication process. In identifying the user based on the bio information, the electronic device may include one or more of the user's context information, personal information, or user's activity information in doing calculation. The user authentication operation may further include an operation of recognizing one or more of iris, fingerprint, voice pattern, face, sole pattern, palm pattern, and hand vein information through a second authentication means, such as an optical sensor, image sensor, or fingerprint sensor. For example, upon registering the user's bio information or user activity information or personal information, the electronic device may authenticate and then register the user by performing the recognition operation. This may be done so to maintain security in recording sensitive user information. For example, if the user is difficult to determine, doubtful as a non-permitted user, or a function requiring a higher security level is determined to be driven when recognizing the bio information and user activity information, the electronic device may further perform the additional authentication operation using the second authentication means.

Various functions may be driven depending on the user recognized by performing user authentication based on the bio information. For example, when the user wears the wrist watch device, the user's pulse wave may be sensed by the device to authenticate the user. For example, if the electronic device is used by several family members, the electronic device may provide different GUIs to the users and may activate, deactivate, or recommend particular functions. For example, the purpose, amount, or history information of exercise set by the family members may be maintained and managed per person, and the electronic device may automatically sense the bio information, e.g., in case the user accesses the place where he frequently comes by for exercise, and perform user authentication, and may then drive an exercise coaching function proper for the user or let him know his previous exercise history. If a fitness program is driven in case the user authentication is performed, the target amount or exercise history for the authenticated user may be displayed, and a coaching function considering the previous exercise history may be provided.

For example, in case the electronic device, after user authentication, enters into the car and wirelessly connects with the control device of the car, the electronic device may transfer the user's profile information to the control device of the car. As a result, the front-rear distance and height of the seat may be adjusted to fit the user's profile by the car control device. For example, the car control device may automatically change the position of each mirror or tune in his preferred radio channel per user. The electronic device, when the user is authenticated, may provide corresponding services using the user's profile information or preference information.

Figure 67:
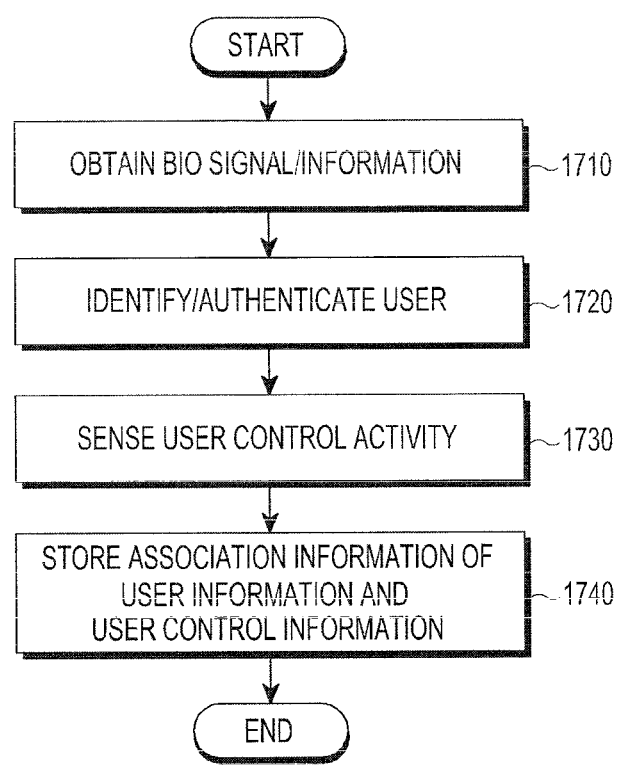
FIG. 67 is a flowchart illustrating a service providing method according to an embodiment.

FIG. 67 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1710 to 1740.

In operation 1710, a bio signal and/or bio information may be obtained. The electronic device may measure the bio signal for user authentication from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for user authentication from the measured bio signal. For example, the bio information for user authentication may include an HRV pattern, ECG pattern, iris image, voice, or hand vein image.

In operation 1720, the user may be identified/authenticated. The electronic device may determine the similarity between the obtained bio information and the user's pre-stored (or registered) bio information for each of at least one pre-registered user and may compare the similarity with a preset threshold. For example, the electronic device may compare the pattern (or characteristic points defining the pattern) or value (e.g., heart rate) of obtained bio information with the pattern (or characteristic points defining the pattern) or value of the pre-stored (or registered) bio information of the user to determine the similarity (e.g., the number of characteristic points identical with one another or with a difference within a threshold, or the ratio of the number or value (e.g., ratio in number of similar characteristic points relative to all the characteristic points). The electronic device may determine that the user of the obtained bio information is the registered user with a similarity not less than the preset threshold among the at least one pre-registered user (i.e., the two users are the same person).

In operation 1730, the control activity of the identified/authenticated user may be sensed. The electronic device may sense the device control activity, such as selection of content/channel, adjusting volume, or adjusting brightness by the identified/authenticated user. The electronic device may the control activity of the identified/authenticated user through at least one of a communication device (e.g., the communication interface 160, the communication module 220, the input/output interface 140, or the interface 270), an input device (e.g., the input/output interface 140, the input device 250, or the display 150), a sensor module (e.g., the sensor module 240 or bio sensor 240I), and a camera module (e.g., the camera module 291).

In operation 1740, the association information of the user information and the user control information may be stored. In one embodiment, the electronic device may store in the seventh database the association information of the user information (i.e., information on the identified/authenticated user) and the user control information (i.e., the information on the control activity of the identified/authenticated user). The seventh database may be stored in the memory of the electronic device or external device.

In one embodiment, the seventh database may have a form as shown in Table 8.

TABLE 8

| user information | context information | control information |
| --- | --- | --- |
| H71 | I71 | J71 |
| H71 | I72 | J72 |
| H71 | I73 | J73 |
| H72 | I74 | J74 |
| ... | ... | ... |

In Table 8, the user information (e.g., H71, H72, . . . ) may represent information for identifying the user (e.g., ID or name). The context information (e.g., I71, I72, . . . ) may represent the type/content (e.g., content playback, viewing channel, viewing advertisement, or access to an external device) of the context information. The control information (e.g., J71, J72, . . . ) may represent the type/content (e.g., selecting content, selecting channel, adjusting volume, adjusting brightness, or varying the settings of a particular function) of the control information, value or level (e.g., value range of volume or brightness) of particular control information, or content (e.g., a particular content or file identification information) of particular control information.

Figure 68:
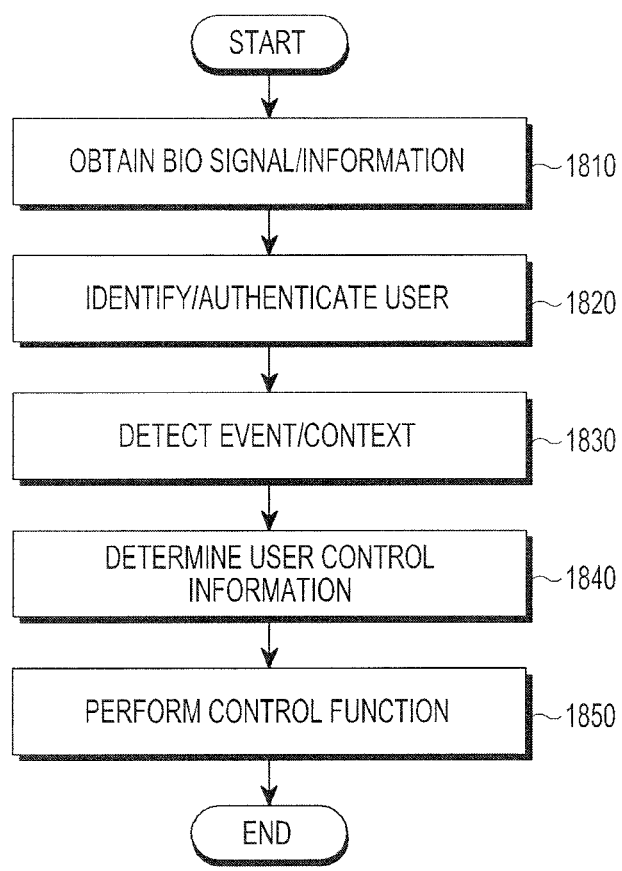
FIG. 68 is a flowchart illustrating a service providing method according to an embodiment.

FIG. 68 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1810 to 1850.

In operation 1810, a bio signal and/or bio information may be obtained. The electronic device may measure the bio signal for user authentication from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may derive bio information for user authentication from the measured bio signal.

In operation 1820, the user may be identified/authenticated. The electronic device may determine the similarity between the obtained bio information and the user's pre-stored (or registered) bio information for each of at least one pre-registered user and may compare the similarity with a preset threshold. For example, the electronic device may compare the pattern (or characteristic points defining the pattern) or value (e.g., heart rate) of obtained bio information with the pattern (or characteristic points defining the pattern) or value of the pre-stored (or registered) bio information of the user to determine the similarity (e.g., the number of characteristic points identical with one another or with a difference within a threshold, or the ratio of the number or value (e.g., ratio in number of similar characteristic points relative to all the characteristic points). The electronic device may determine that the user of the obtained bio information is the registered user with a similarity not less than the preset threshold among the at least one pre-registered user (i.e., the two users are the same person).

In operation 1830, occurrence of an event/context in the electronic device may be detected. For example, the event/context may include the case where a content/channel playback/view command is received from the user, the case where the playback of an advertisement is detected, the case where access of the external device is detected, and the case where running a particular application is detected. The electronic device may detect the occurrence of the event/context through a sensor module (e.g., the sensor module 240 or bio sensor 240I), a communication device (e.g., the communication interface 160, communication module 220, input/output interface 140, or interface 270), or an input/output device (e.g., the input/output interface 140 or input device 250).

In operation 1840, user control information corresponding to the identified/authenticated user and the event/context may be determined. In one embodiment, the electronic device may search a seventh database stored in the electronic device or external device for user information corresponding to the identified/authenticated user and event/context information corresponding to the detected event/context. The electronic device may determine that the control information stored in the seventh database corresponding to the searched user information and event/context information is the control information corresponding to the event/context and the identified/authenticated user.

In operation 1850, a control function according to the determined control information may be performed.

In one embodiment, upon identification/authentication of the user, the electronic device may record an activity pattern by which the user responds to a particular context or control pattern of the electronic device, along with the information on the context. In case the particular context occurs again, the electronic device may automatically reproduce the recorded activity pattern or control pattern of the electronic device.

In one embodiment, the electronic device may detect the particular context, gather/receive a control activity/function corresponding to the particular context from an external device that is a local device or connected via communication, and automatically run the gathered/received control activity/function.

The electronic device may obtain the bio signal/information, and in case the obtained bio information is identical to pre-registered bio information, may consider the user of the obtained bio information as a user who may use services of the electronic device. The electronic device may consider the particular user corresponding to the obtained bio information among several pre-registered users as a user who may use the services of the electronic device.

In one embodiment, the electronic device, when wiredly or wirelessly connected with other external device (e.g., a TV device or set top box), may transfer the user's name, phone number, or device identification number (e.g., SIM or MAC address) to the external device, and the external device may consider the same as identification information of the user.

In one embodiment, the electronic device may perform an identification/authentication operation using one user identification information of a preset ID input, password input, pattern lock input, fingerprint recognition, face recognition, voice recognition, sole pattern recognition, palm pattern recognition, and hand vein recognition.

In one embodiment, the electronic device may perform an authentication operation using the bio information and an authentication operation using the user identification information and may perform an operation for determining whether the pieces of user information authenticated by the two operations are identical or associated with each other. For example, the electronic device may obtain the pre-stored bio information of the user using the user's personal information obtained by performing the authentication operation using the user identification information and may perform an operation of identifying whether it is identical to the bio information gathered from other external device. In case the pieces of bio information are not identical to each other, the electronic device may restrict the user of the electronic device or external device or may perform the authentication operation again using the user identification information. In case the bio signal is not normally sensed, e.g., even when the user does not normally wear the wearable device for measuring bio signals, the electronic device may restrict the user of the electronic device or wearable device. This may prevent wrong users from using the wearable device, e.g., when the password is stolen.

In one embodiment, to control the TV functionality with a wrist watch device which is the wearable device, the user may wear the wrist watch device equipped with one or more wireless communication devices of IrDA or Bluetooth. When the user runs an app, selects or touches a button on the wrist watch device, or wears the wrist watch device to drive the function of controlling the TV through the wrist watch device, the bio sensor of the wrist watch device may be driven to authenticate the user. The smart wrist watch may perform the authentication operation through an operation requiring user identification information. Such authentication operation may be driven once, so that no separate authentication operation is required later. For example, the wrist watch device may periodically or intermittently identify whether the user's bio signals are sensed through the bio sensor, and when sensed, may determine that the user is not changed and abstain from performing the authentication operation. In case no bio signal is sensed, the wrist watch device may consider itself as away from the user's body and may perform the authentication operation again. The operation of sensing the bio signal may be performed in case a movement signal of the wrist watch device by the motion sensor is not less than a preset value, which may be done so to identify whether the wrist watch device is put on or taken off from the user. The wrist watch device may identify the bio signal in case the user manipulates the wrist watch device and may perform re-authentication if a preset time elapses after the initial authentication time.

The user identification or authentication may be performed by an external device rather than the wrist watch device. For example, one or more external device of a TV, set top box, or console game player may be connected with the wrist watch device through Bluetooth or Wi-Fi, and the external device may receive a wireless signal (e.g., RF or light signal) from the wrist watch device and may be thereby controlled. The external device may recognize the device sending the control signal to the external device by receiving one or more of the device identification number of the wrist watch device wirelessly connected, device name, user name, and phone number. When sending the control signal, the wrist watch device may send information for identifying/authenticating the user together, which is done so to support the context where several users control the external device through their respective devices. In one embodiment, the wrist watch device may perform user authentication and transmit the authenticated user information or device information to the external device.

The information on the operation performed through the electronic device by the user and relevant context information may be recorded in the electronic device and may be stored in the external device (e.g., one or more of a server, host terminal, smartphone, or wearable device) connected via communication. In one embodiment, the external device (e.g., the set top box, home network server, or TV) receiving the control signal from the electronic device may record the control signal information and relevant context information. The electronic device may be one of a mobile, portable, or wearable computing device with a TV remote controller function. For example, each user may view a particular TV channel at a particular time on a particular day or may prefer a particular program. The user may drive the electronic device, and if the corresponding day and time arrive or favored particular content is now in air, the user may drive the control function through the electronic device to view the favored channel or program.

For example, in case an intermediate advertisement is shown while viewing a movie, the user may run one or more control functions, such as adjust the volume, turn the channel, run the picture in picture (PIP) or picture by picture (PBP) function, manipulate other UIs, run an application, or press a button, by the user input. If the same or similar control function/operation is repeatedly performed under the same context, the electronic device may store information on the context and control function/operation to automatically run the control function/operation under the context later or may recommend the control function. For example, the operation of turning down the volume or muting while viewing an advertisement content may be similar operations. If sensing the context where the advertisement content is played, the electronic device may reduce the sound volume or mute or may perform the operation of recommending the user to select one of the two functions through one or more of the display and audio.

The electronic device may record the operation corresponding to such context information therein or in another external device. The context information, such as time, is relatively easy to store, but if the content should be determined, there may be required the operation of analyzing the content or receiving and analyzing the metadata of the content. The content metadata may be one or more metadata included in the image, video, or audio file or stream, description information separately added, or an electronic program guide (EPG) that is broadcast program information. The electronic device may receive and analyze such content metadata through the external device (e.g., server or other electronic device) connected via the network, or the second device (e.g., TV) controlled by the electronic device may receive and analyze the content metadata. Or, the result of analysis of the content metadata by the third electronic device, such as server or host terminal may be transferred to one of the electronic device, external device, and the second device.

For example, in case the user wears an earphone, the user may manipulate one or more functions of setting the user's preferred volume, setting the volume per genre, setting the equalizer, and setting or recommending the brightness of the display to play music, radio, DMB, video, or audio using the wearable device connected with the earphone or the earphone itself. In such case, when the context/event including one or more of occurrence of mutual switch between earphone or speaker modes, recognition/designation of an output sound device, playback of a particular type of content, running a player, UI manipulation, running an application, or reception of a call or message, as such context/event, the electronic device may perform one or more of the functions. The content type may include one or more of the advertisement, age group, information on preferred music (e.g., song title, genre, song writer, or singer), registered information on the searched video, and game that has been played before.

The function may include one or more of setting the user's preferred volume, setting the volume per genre, setting the equalizer, setting the display brightness or recommendation. The earphone may be a clip, earphone, or headphone-type wearable device and may be wiredly or wirelessly connected with other wearable device. In the case where the particular time zone or ambient noise degree is not more than a preset reference, in the case where the bright information by the optical sensor is not less than a preset reference, and in the case of approach to a preset place, a control operation as per each context/event may be performed.

When a particular control function runs, the electronic device may store the context/event information on the time when the function is performed and causing the function, and if the context/event occurs, it may automatically perform the function or recommend the function to the user. In one embodiment, in case the control function consists of several user inputs, if the context/event occurs, the electronic device may automatically generate minimum some of the input signals (or control signals) corresponding to the several user inputs. This may correspond to the auto-complete function that may complete by inputting only some letters or a sort of macro function used on the computer. For example, if some user input occurs under the occurrence of the context/event, the electronic device may determine whether the user input is related to a pre-stored control function and then it may automatically perform a previous function to eliminate the need for an additional user input.

For example, if there is a history that the user presses the volume-down key several times to shift to volume level 3 under the context where the advertisement content is played, the electronic device may put the volume down to volume level 3 even when the user presses the volume-down key once. Such auto-complete operation may proceed until it reaches a target state value, such as volume value or channel value, or one or more the order or count of pressing the key may be recorded, and if one of them is pressed, one or more of the order or count may be performed automatically. For example, if such history is stored that, when the advertisement is played, the volume-down key is pressed several times to reduce the volume, and then, after changing to a particular channel, the volume-up key is pressed several times to increase the volume, when the volume-down key is pressed once while the advertisement is broadcast, the electronic device may automatically perform the control of the stored key inputs, i.e., the operation of reducing the sound volume, and after changing channels, increasing the volume, without an additional key input.

Such function may also respond even when there are several operations under one context/event. For example, in case an advertisement broadcast comes in while cable TV 100 is viewed, such history might be stored that the user presses the volume-down key several times to reduce the volume in some cases and presses the channel up key to change to channel 105 in other cases. If the same context occurs, the electronic device may automatically turn back to the previous reduced volume level in case the user presses the volume-down key, and the electronic device may automatically turn to channel 105 in case the user presses key "1" or channel up key to turn the channel. For example, if under such context the user has turned the channel to channel 105 or channel 107, the electronic device may perform a recommendation function through one or more of the display or audio of the electronic device or the external device so that selection may be made together with relevant information on channels 105 and 107 when the user enters the key "1" or "10." In case the user presses or runs other key/function, e.g., PIP running key, which has nothing to do with the pre-stored function, the electronic device may record the corresponding operation and context.

If the user is determined through user authentication, the electronic device may record a plurality of activity patterns or device control patterns performed by the user under a particular context, together with the information on the context. Thereafter, in case such particular context occurs again, the electronic device may automatically reproduce the recorded activity pattern or device control pattern or recommend one or more functions.

Figure 69:
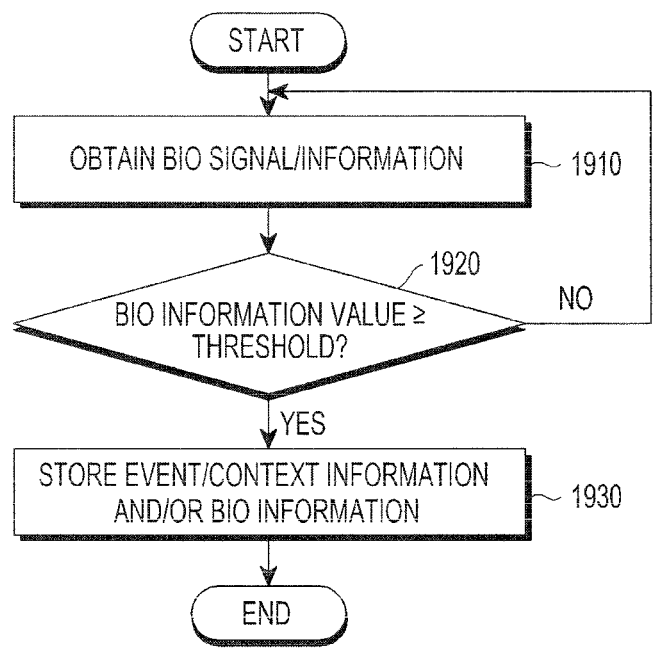
FIG. 69 is a flowchart illustrating a service providing method according to an embodiment.

FIG. 69 is a flowchart illustrating a service providing method according to an embodiment. The method may be performed by the electronic device (e.g., the electronic device 101 or 201), the processor (e.g., the processor 120 or 210) in the electronic device, or the service providing module (e.g., the service providing module 701). The method may include all or some of the operations 1910 to 1930.

In operation 1910, a bio signal and/or bio information may be obtained. The electronic device may measure the bio signal from the user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may produce bio information indicating the user's stress/emotional information from the measured bio signal. In one embodiment, the stress/emotional information may include the type of the stress/emotion and/or level or value of the stress/emotion. For example, the type of the stress/emotion may include one or more of brady cardia, tachycardia, physical fatigue, mental stress, anger, hate, grief, joy, reverence, happiness (platonic love, peace, or sense of tie), or romantic love, excitement, or lust obtained by determining one or more of the average heart rate, heart rate distribution, SDNN, RMSSD, and pNN50 obtained through the HRV. As another example, the type of stress may include one or more of the blood pressure variation, respiratory variation, and autonomic nerve balance obtained from one or more of the LF, HF, and LF/HF calculated from the PSD obtained through the HRV.

In operation 1920, the bio information value may be compared with a preset value or previous bio information value. For example, the electronic device may compare the bio information value with a threshold range or threshold value. For example, the electronic device may compare the bio information value with the preset value or previous bio information value to obtain the difference and may compare the difference with the threshold range or threshold. In case the bio information value is less than the preset threshold range or threshold, the electronic device may determine that there is no noticeable stress or emotional variation and repeatedly perform operation 1910, and in case the difference is not less than the threshold range or threshold, the electronic device may determine that there is a noticeable stress or emotional variation and perform operation 1930. The preset value or previous bio information may be stored in the memory (e.g., the memory 130 or 230) of the electronic device or the external device (e.g., the server 106 or electronic device 104). The preset value may be bio information measured by one or more other users, a representative value or mean value of a user group (e.g., per-age mean value or per-gender mean value) or an experimental value measured by an organization (e.g., a research organization or academic community).

In operation 1930, the time of measuring or obtaining the bio signal/information and/or event/context information and/or bio information before/after the same may be stored. The electronic device may identify that a noticeable stress or emotion variation occurs and may store in the memory (e.g., the memory 130 or 230) the information on the context or event causing such stress or emotion variation or associated therewith. In one embodiment, the electronic device may add the context/event information to the content file causing the stress or emotion variation and store the same. In an embodiment, the electronic device may store the event/context information and/or bio information at the time of measuring or obtaining the bio signal/information or before/after the same in an eighth database. The eighth database may be stored in the memory of the electronic device or external device.

In one embodiment, the eighth database may have a form as shown in Table 9.

TABLE 9

| event/context information | bio information | stress/emotional information | Category |
| --- | --- | --- | --- |
| D81 | A81 | E81 | K81 |
| D82 | A82 | E82 | K82 |
| D83 | A83 | E83 | K83 |
| D84 | A84 | E84 | K84 |
| ... | ... | ... | ... |

In Table 9, the event/context information (e.g., D81, D82, . . . ) may represent the type of the event/context, time/date/day of event/context, location of event, and identification information (e.g., storage location, identifier, or file name) of the content or file associated with the event/context. The bio information (e.g., A81, A82, . . . ) may represent the type (e.g., mean heart rate, or heart rate distribution) of the bio information, a value range (e.g., value range of mean heart rate or heart rate distribution) of a particular type of bio information, a value range of difference values (e.g., differences between the bio information and preset values) of particular types of bio information, or a value or level of particular bio information. The stress/emotional information (e.g., E81, E82, . . . ) may represent whether there is a stress/emotional variation, the type of stress/emotion, or level or value (e.g., frequency or mean value) of stress/emotion. The category (e.g., K81, K82, . . . ) may represent the information (e.g., arousal level or personal preference (e.g., good, moderate, or bad) classifying the stress/emotional information.

The electronic device, if sensing one or more of the variation in the bio information recognized through the sensor module or a particular user input, may perform the operation of gathering and recording the context information related thereto.

To recognize the variation in the user's emotion or sentiment, the electronic device may identify the stress state, e.g., through pulse wave analysis or ECG signal analysis. The acute stress may represent fear, anger, or concern. In one embodiment, the electronic device may determine various types of emotion using a plurality of different bio sensors. For example, MIT's Affective computing group has done several researches on the method for distinguishing several emotions, such as anger, hate, grief, joy, reverence, happiness (platonic love, peace, or sense of tie), or romantic love, excitement, or lust, by analyzing several bio signals, such as ECG or skin conductance. Further, there have been developed techniques for measuring the arousal level, such as aroused state or excited state, by analyzing the PPG signal amplitude, pulse to pulse interval (PPI) and pulse rate variability (PRV) through the PPG sensor. Further, the heart rate (RR), standard deviation of R-R interval (SD-RR), root mean square of SD (RMSSD), respiratory sinus arrhythmia (RSA), finger blood volume pulse amplitude (FBVPA), and finger pulse transit time (FPTT) were measured, and it was observed in the case of surprisal that the HR, SD-RR, and RMSSD were meaningfully increased after the surprisal stimulus has been applied as compared with before the surprisal stimulus had been applied, and the FBVPA was meaningfully reduced, and the FPTT was meaningfully shortened. Such measuring method and its results are disclosed in the following documents.

R. W. Picard et al, "Toward Machine Emotional Intelligence, Analysis of Affective Physiological State," IEEE Trans on pattern analysis and machine intelligence, vol 23, no. 10, 2001.

M. Pantic and L. Rothkrantz, "Toward an Affect-sensitive Multimodal Human-computer interaction," Proc. of the IEEE, vol. 91, no. 9, pp. 1370-1390, 2003.

C.-J. Kim, et al., A Study on Evaluation of Human Arousal Level using PPG Analysis, Journal of the Ergonomics Society of Korea, Vol. 29, Iss. 1, 2010, pp. 113-120.

Cardiovascular response to surprise stimulus, S. E. Jin, et al., Korean Journal of the Science of Emotion and Sensibility, vol. 14, Iss. 1, 2011, pp. 147-156.

For example, when one becomes nervous, his hands may sweat or when he is furious, his blood pressure may rise, or such biological variations may occur. Accordingly, the skin conductance sensor or blood pressure sensor may be used to determine such stress or emotional state. In order to measure the user's preference, the electronic device may determine the user's preference emotion based on one or more of the frequency or speed of eye blinks, increase/decrease in heart rate, increase/decrease in HRV, increase/decrease in blood pressure, breathing frequency, and increase/decrease in pupil size. The electronic device may determine an increase in the blinking frequency over a preset reference as being stressed out and may determine the pupil size being larger than a preset reference as the user's favor to the target he is viewing. In case of measuring the eye blinking or pupil size, the electronic device may use the wearable device, such as an image sensor-equipped HMD, which is capable of image-taking his eyes, or may use the camera device of the wrist watch device.

In case the user is wearing the wearable device, the wearable device may gather the context information of the user or device by analyzing the user's stress, arousal level, surprisal, or emotion.

In one embodiment, the electronic device may gather one or more bio signals of the user using one or more bio signal sensors and may analyze the bio signals to determine the bio information. If a variation in the bio information not less than a preset reference occurs, the electronic device may determine that a variation sensing event occurs, and it may gather and record the context/event information. The electronic device may further perform an operation of recording the bio information when recording the context/event information. The bio information may be one or more of a stress level, arousal level, surprisal, excitement degree, or emotion. The bio information may be obtained by determining one or more of the mean heart rate, heart rate distribution, SDNN/SDRR, RMSSD, pNN50, RSA, FBVPA, and FPTT or may be obtained by calculating one or more of LF, HF, and LF/HF from the PSD obtained by analyzing the HRV signal. The bio signal may be one or more relevant signals gathered from one or more sensors among blood pressure, ECG, respiration rate, heart rate, HRV, oxygen saturation, body temperature, EMG, or skin resistance.

The bio signal may be gathered at a preset period or by one or more of when a movement is sensed by one or more sensors of an acceleration sensor or tilt sensor, geo-magnetic sensor, or GPS, or when a function is driven by the user input.

In the daily life, variations in emotion/stress/sentiment occurs under various situations. The user may be surprised or excited when viewing a beautiful landscape while traveling or may feel happy seeing a pretty flower. The user may have the feeling of reverence looking at a magnificent building or release stress in a religious facility. The user may feel joyful meeting his acquaintance or may be shocked eye-witnessing a bad incident or when almost having an accident. The user may have a positive or negative feeling while website or SNS browsing through a computing device.

Such emotional variations indicate that very critical context information has occurred to the user, records on such context information may be used for various purposes. For example, if the user has an emotional change or surprise at a trip, the electronic device may record one or more of an image, video, and audio regarding the context/event as context/event information. In one embodiment, when gathering and recording the context/event information, the electronic device may determine one or more of the location or time of the electronic device, gather one or more of the time/place-based major information of one or more of the local information, travel information, weather information, and SNS/news information related to the recorded context/event information, and include the same in the context/event information. The context/event information may be stored in the form of text, url, thumbnail, keyword, document abstract information, or application identifier or in the form of one or more of a separate audio or video data. The electronic device may record one or more of the stress, arousal level, surprise, and emotion as he context/event information and may record variations in such information.

In one embodiment, the electronic device may provide a service of recording travel experience. For example, if the electronic device senses an emotional variation and drives the camera functionality or application to capture an image, the electronic device may include, in the metadata area of the image (in case of JPEG, exif field), one or more of one or more context/event information, e.g., location, weather, and local area-related information (e.g., the place of picture taking or names of nearby areas, historical events, tourist information, and main news about the area) and store the same. The electronic device may store the audio upon image capturing as the context/event information. The electronic device may store the context/event information separately from the image but in association with the image. The electronic device may display or output the associated metadata and audio when the captured image is searched later through an album or gallery application.

In one embodiment, the electronic device may perform one or more operations of transmitting the context/event information to other external device, running a particular application, recording/registering in the SNS, attaching to a message and sending, transmitting as an attached file, or producing an image album. For example, the electronic device may automatically register the captured image in the user's SNS blog, and at this time, it may make such setting as to enable only the user to search for the posted content as default. The electronic device may automatically transfer the context/event information gathered when there is an emotional variation as to one or more pre-designated contacts or a pre-designated group, e.g., those set as the family category in the address book. At this time, the context/event information may be transmitted through a pre-designated contact means (e.g., sns, mms, sms, or email).

For example, the electronic device may do one-time search on the images or videos stored in the memory using an electronic album application. For example, the electronic device may recognize the emotional variation within a preset place area or at a preset time to store the gathered relevant context/event information in one folder or store one or more of the time and place in the metadata area of a particular file. Such information may be searched sequentially one-by one or in a slide-show manner through the electronic album application or may be searched in bundle in the form of a magazine UX (tile-type layout) or in the form of an electronic book. The electronic device may display/output the context/event information when searching or playing the image or video using a multimedia player. The electronic device may record the place information as the context/event information and may provide an image on the map enabling the context/event to be searched. For example, the electronic device may display the thumbnail or icon of the image or video on a two-dimensional or three-dimensional map, so that the stored context/event information may be searched or played if the user selects or magnifies the same.

In one embodiment, the electronic device may temporarily store the context/event information. The electronic device may perform the operation of previously storing in real-time event information inputted from the GPS, acceleration sensor, audio sensor, or image sensor in the memory as temporary data and the operation of deleting the same after a preset time in order to record the context/event information at the time when the variation in the bio signal occurs. The electronic device may gather the time information through its embedded time information sensing device (e.g., the communication device wiredly receiving the time information from the watch device, GPS, or base station). The electronic device may gather the location information through its embedded location sensing device (e.g., the communication device, positioning device, or geo fence supporting device receiving signals from the GPS, Wi-Fi, BLE, RFID, or base station). The electronic device may gather in real-time movement-related information through the acceleration sensor or gyro sensor.

To record the context/event information, the electronic device may previously operate the image sensor or audio sensor (microphone) before sensing the bio signal. That is, in case a user input occurs for operating the bio sensor, the electronic device may gather the bio signal through the bio sensor after operating the image sensor or audio sensor. In case the bio sensor is operated at a preset period or by a time setting, the operation time may be identified. Thus, the electronic device may gather the context/event information during, before, or after gathering the bio information by previously operating the image sensor or audio sensor before a preset time.

The context/event information may include one or more of the information on the searched area, communication history, and contacts. The electronic device may record the contact of the acquaintance he called in the area or call history along with an image, video, or audio, and may identify the same later through a multimedia application or other context information searching function.

The electronic device may further perform the user authentication operation before using the electronic device or recording or transmitting the context information. The electronic device may perform the user authentication operation in case of being worn on the user or receiving a user input. The user authentication information includes previously recorded bio information, and the electronic device may determine whether the consistency between the user authentication information and the analyzed bio information is not less than a preset reference. The electronic device may receive the bio signal using the bio sensor and may analyze the same to analyze the consistency. The user authentication operation may include an operation of recognizing one or more of iris, fingerprint, voice pattern, face, sole pattern, palm pattern, and hand veins information.

Upon search on the stored context/event information, the electronic device may perform a classifying operation based on the recorded bio information. The electronic device may identify the bio information through sensing the variation and may then classify the same into one or more categories depending on the type of emotion, excitement, surprise, and stress. Each category may be classified into levels. For example, the arousal level may be classified into several levels, such as sleep, sleepy, awake, activity, and surprise, and the electronic device may operate different functions depending on the context.

In one embodiment, the electronic device may perform the operation of recommending content using the context/event information. For example, through sensing a variation in the user's sentiment state, the electronic device may use the context/event information to determine preference or recommend a function or content in case of searching the content. For example, the context/event information may be the operation of searching for one or more contents of SNS, webpage searching, searching electronic book, playing music, and playing video, and in case the sensed variation value is not less than a preset reference, the electronic device may perform various functions in relation to the context/event information. For example, the electronic device may record the preference variation along with the content information. In case the variation in the preference (emotion, stress, or arousal level) is not less than a preset value upon searching for some contents, the electronic device may record the preference variation. The variation in the preference may be a set of a previous value and subsequent value or trend information on the preference.

In one embodiment, the electronic device may record such preference variation and the content as the context/event information so that the context/event information may be used for the user's sentiment variation in some contexts. For example, if particular music shows a trend of mitigating stress, the electronic device may recommend or play the music in case the user is stressed out. For example, upon determining that the user has a sentiment of sadness, the electronic device may recommend or automatically perform the activities that the user had done before at such sentiment state, e.g., such function as playing his preferred game application, access to his preferred comedy website, or searching for family pictures. Such recommendation operation may be displayed as a GUI through the display or may be output as a voice interface through an audio.

For example, the electronic device may perform one or more of the functions of registering in the user's SNS, transmitting to other device/user, transmitting a message to the copyright owner, mailing, and recommending/disapproving, depending on the preference on the content while searching for the content. For example, if the user had many positive sentiments in a tourist site, the electronic device may assess that the site was good to visit or the travel had many joyful experiences in combination with the information on the tourist site or travel route or schedule information. The electronic device may assess a dangerous or unhappy travel for the tourist site or route with a plenty of negative sentiments. Such experience information per user may be shared through the SNS or computing environment, and in case some user enters the area or route with lots of negative experience or searches for information on such area or route, a service, such as an alert popup or recommendation of other places or other routes, may be provided. Further, in case that a travel had much positive experience, the electronic device may recommend a particular application or relevant contents (e.g., website or electronic book) by referencing the context/event information registered by other users.

The electronic device may provide services based on the sentiment on the content. The electronic device may receive information on the content being used, and the content may be the video being viewed, music file, text, image, or a combination thereof. The content information may be information that may be obtained by analyzing content signals, such as content title, whole time, or current playback time, and may be information received in addition to the content signal, metadata, or separate information (website, blog, SNS, or electronic program guide) received wiredly or wirelessly.

The electronic device may gather the user's bio information through the bio recognition sensor while using the content. The bio recognition sensor may be positioned inside or outside the electronic device and may be connected via wired or wireless communication to share information.

The electronic device may determine whether there is a variation relative to the existing one, such as variation in heart rate or sentiment, in order to detect or determine some variation in the user. In order to determine whether there is a variation, the electronic device may compare the measured bio information relative to the mean value of the user's bio information or compare variations within a preset period. The electronic device may compare the bio information value with others' values. The electronic device may identify whether there is a variation by determining whether such variation trend or variation is a preset size or more.

The electronic device may store at least one or more content information based on the determined result. The content information may include one or more of content play time, content scene information, content title, content type, and content file format. The electronic device may manage the content information and bio information in pair and may use the same later to analyze their association, and may store them through the server.

The electronic device may utilize services, such as advertisement, using the stored information. For example, the electronic device may gather reactions when users view a particular content and may provide various services, such as advertisement content usability assessment or user concentration-based application billing, based on the same.

Figure 70:
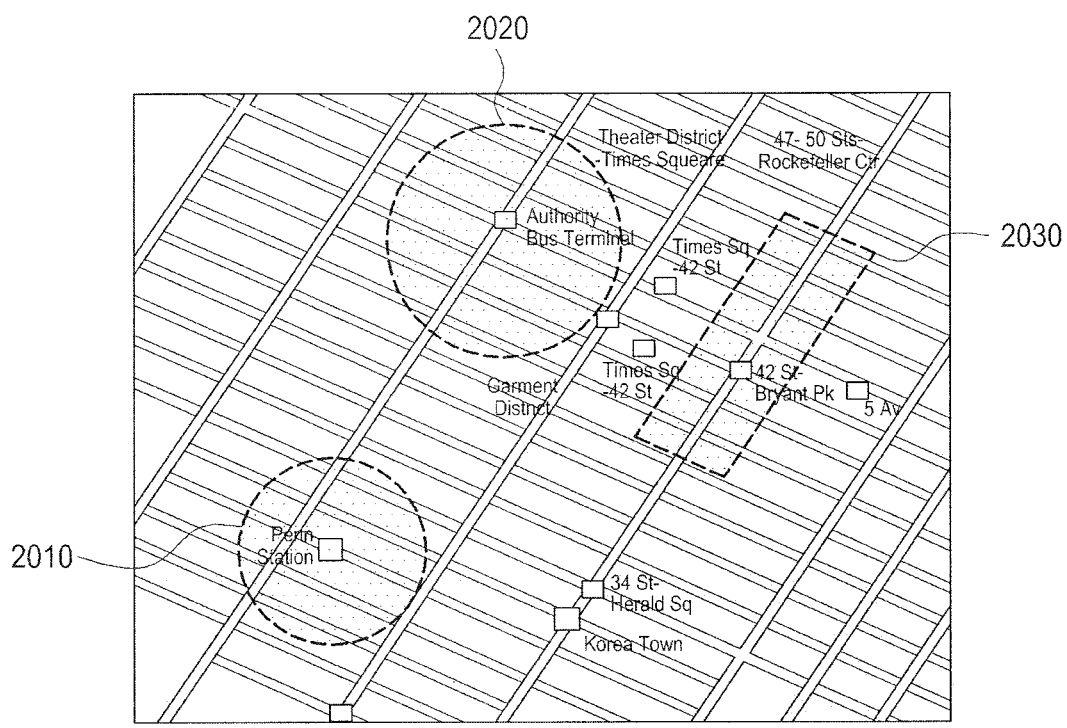
FIG. 70 is a view illustrating a service providing method according to an embodiment.

FIG. 70 is a view illustrating a service providing method according to an embodiment. The method may be performed by the electronic device (e.g., the electronic device 101 or 201), the processor (e.g., the processor 120 or 210) in the electronic device, or the service providing module (e.g., the service providing module 701).

The electronic device may detect the occurrence of such event/context that the electronic device approaches one of preset geo fences (including being positioned therein) through a sensor module (e.g., the sensor module 240 or bio sensor 240I), a communication device (e.g., the communication interface 160, communication module 220, input/output interface 140, or interface 270), or an input/output device (e.g., the input/output interface 140 or input device 250).

Referring to FIG. 70, a plurality of geographic areas, i.e., geo-fences, may be configured based on the bio information. For example, the first geo-fence 2010 may denote the area where there was lots of stressful experience, the second geo-fence 2020 the area where there was an intermediate level of stressful experience, and the third geo-fence 2030 the area where there were lots of joyful experience.

The electronic device may determine the bio/stress/emotional information corresponding to the context/event as the context/event associated with the geo-fence occurs. In one embodiment, the electronic device may search the database (e.g., fifth database) stored in the electronic device or external device for the event/context information corresponding to the detected event/context. The electronic device may determine that the bio/stress/emotional information stored in the database corresponding to the searched event/context information is the bio/stress/emotional information corresponding to the detected event.

The electronic device may determine the service corresponding to the context/event and/or bio/stress/emotional information and may provide the determined service to the user. The electronic device may display, to the user, at least a portion of the event/context information and/or at least a portion of the determined bio/stress/emotional information together or separately from the provision of the determined service. In one embodiment, the electronic device may search and determine the service stored corresponding to the event/context and/or bio/stress/emotional information from the database (e.g., the fifth database).

The electronic device may provide the service utilizing the bio information measured by the bio sensor and the location of measuring the bio information. The bio information and the location information may be measured by one or more sensors or devices, and the bio information and the location information may be measured by different devices, respectively, and the devices may mutually share at least one of the bio information and the location information through wireless connection. The location information may be measured from various sources by which location may be determined, such as Wi-Fi, BLE, NFC, beacon, or payment information, as well as GPS or may be inferred from the measurement data.

The electronic device, upon entrance into a high-stress area, may provide its relevant service utilizing the geo-fence. For example, the electronic device may run a particular function or recommend a function to the user based on the user's activities that have been done when the user was at a high stress level. For example, the electronic device may provide one of a preset content/service (e.g., application, webpage, content, exercise information, or travel information) to reduce stress. The electronic device may search for other users' SNS feeds or guides (e.g., way to handle, solution, healing content, or humor) related to the stress and provide the same to the user. The electronic device may generate an event or recommend a function to the user based on the user's activities that have mitigated stress or during which the stress was relatively low and may provide content related to the experience in the geo-fence where the stress is low. For example, the electronic device may provide information related to joyful experience such as pictures during travel.

If the user has been under extreme stress a lot or entered or expected to enter an area where its level is high, the electronic device may display a route or guide the user to an area where the stress level is low or where there was relatively less stressful experience through the navigation function.

In one embodiment, the electronic device may form a database as to the measured stress level or bio information mapped with the location information. The electronic device may provide a service by utilizing the bio information mapped with the location information of a plurality of users in the database. The plurality of users may be classified as per age, gender, hobby or job, and the electronic device may use the per-location stress level of other users with the most similar characteristics utilizing some user's personal information. For example, the electronic device may reference the stress level history of multiple unspecified users in the area when recommending the appointed place/tourist destination using the database. The electronic device may recommend several choices by referencing the stress level of the participating people in the area when recommending the appointed place/tourist destination. The electronic device may provide such sentiment-related options as "minimum stress/maximum joy or excitement" besides the shortest distance/minimum time when recommending the navigation route using the database.

In one embodiment, the electronic device may use other data or services than the geo-fence. For example, the electronic device may determine the bio information (e.g., heart rate, blood pressure, or body temperature) as per weather using a weather application and suggest or recommend the favorite place or location where the user has frequently visited. For example, since the body temperature might have been reduced or stress might have been high in an outdoor place on a windy or cold day, the electronic device may perform the recommendation function using additional information, such as the user experience-based bio information and weather, e.g., such as recommending the place (e.g., indoor, restaurant, coffee shop, or attraction site) where the stress level was low in the same location/area.

According to an embodiment, the method for providing a service by the electronic device may include the operation of obtaining the user's bio information, the operation of determining at least one service of a plurality of services related to the bio information, and the operation of providing the determined at least one service.

According to the embodiment, the user's bio information may include at least one of the user's identification information, body information, emotion information, health information, disease information, exercise information, stress information, and sleep information.

According to an embodiment, the method may further include the operation of detecting a variation in the state of the electronic device, and as the variation in the state of the electronic device is detected, the operation of obtaining the bio information may be initiated.

According to an embodiment, the method may further include whether a preset condition is met, and the operation of obtaining the bio information as the preset condition is met is initiated, wherein the preset condition may include at least one of a movement of the electronic device exceeding a threshold, a movement of the electronic device according to a preset gesture, a location movement of the electronic device to a preset area, a user input to the electronic device, occurrence of a preset in the electronic device, and switch between a sleep state of the electronic device and a wakeup state.

According to an embodiment, the electronic device may receive the bio information from an external device.

According to an embodiment, the method may further include the operation of comparing the bio information with a preset value or previous bio information and the operation of varying the period of obtaining the bio information according to the difference between the bio information and the preset value or the previous bio information.

According to an embodiment, the method may further include the operation of transmitting the bio information to the external device and the operation of receiving the information on the period of obtaining the bio information from the external device.

According to an embodiment, the method may further include the operation of obtaining the user association information, and the operation of obtaining the user's bio information may be initiated as the user association information is obtained, and at least one service corresponding to the user association information and the bio information among a plurality of services associated with the bio information supported by the electronic device may be determined.

According to an embodiment, the method may further include the operation of determining the user association information associated with the bio information of user association information pre-stored in the electronic device and may determine at least one service corresponding to the determined user association information and the bio information among a plurality of services associated with the bio information supported by the electronic device.

According to an embodiment, the method may further include the operation of determining the user association information associated with the bio information of user association information pre-stored in the electronic device, and at least one service corresponding to the determined user association information and the bio information among a plurality of services associated with the bio information supported by the electronic device may be determined, and the user association information may include at least one of the information on the user, information on the electronic device, and information on the ambient environment of the electronic device.

According to an embodiment, the determined at least one service may be at least one of a variation in the user interface, user authentication, exercise coaching, information recommendation, information provision, information storage, information transmission, provision of function or service, preset content, restriction or blocking access to a function or service, variation in the settings of the electronic device, or control of an external device.

According to an embodiment, the user's bio information may include the user's age, and the determined at least one service may change the user interface currently displayed into a user interface according to the user's age.

According to an embodiment, the user's bio information may include the user's age, and the determined at least one service may include at least one of changing guidance voices of the electronic device, changing voice volume, restriction access to a preset content or service, providing an alert feedback, or recommending information.

According to an embodiment, the method may further comprise the operation of comparing the bio information with a preset value, and the operation of providing the determined at least one service may include the operation of outputting at least one alarm signal according to the difference between the user's bio information and the preset value.

According to an embodiment, the method may further comprise the operation of comparing the bio information with a preset value, and the operation of providing the determined at least one service may include the operation of outputting at least one alarm signal according to the difference between the user's bio information and the preset value, and the at least one alarm signal may be at least one of a visual signal, an audible signal, and a tactile signal.

According to an embodiment, the method may further comprise the operation of comparing the bio information with a preset value, and the operation of providing the determined at least one service may include the operation of outputting at least one alarm signal according to the difference between the user's bio information and the preset value, and the at least one alarm signal may be at least one of a visual signal, an audible signal, and a tactile signal, and if the difference between the user's bio information and the preset value is larger than a threshold, the operation of increasing the period of obtaining the bio information or the count of outputting the at least one alarm signal, the type of the at least one alarm signal, or the strength of the at least one alarm signal may be included.

According to an embodiment, the method may further include the operation of obtaining the user's movement or location information, and the operation of providing the determined at least one service may include the operation of authenticating the user based on the user's bio information and the movement or location information.

According to an embodiment, the method may further include the operation of obtaining the current location or current time of the user, and the operation of providing the determined at least one service may include the operation of authenticating the user based on the current location or current time and the user's bio information.

According to an embodiment, the method may further include the operation of obtaining the user's exercise strength or activity type, and the operation of providing the determined at least one service may include the operation of authenticating the user based on the user's bio information and the exercise strength or activity type.

According to an embodiment, the operation of providing the determined at least one service may include the operation of comparing the user's bio information with a preset first value for user authentication, in case the difference between the user's bio information and the preset first value is not more than a threshold, the operation of obtaining additional bio information, and the operation of comparing the additional bio information with a preset second value for the user authentication.

According to an embodiment, the method may further include the operation of detecting an event, and the operation of providing the determined at least one service may include the operation of authenticating the user based on the user's bio information, the operation of searching a database stored in the electronic device or a first external device for an event matching the user and the event, and the operation of controlling the first external device or second external device or the electronic device based on the control information stored in the database.

According to an embodiment, the method may further include the operation of detecting an event, and the operation of providing the determined at least one service may include the operation of authenticating the user based on the user's bio information, the operation of searching a database stored in the electronic device or a first external device for an event matching the user and the event, and the operation of controlling the first external device or second external device or the electronic device based on the control information stored in the database, and the control operation may include at least one of adjusting volume of the first or second external device, changing the user interface, changing brightness, or changing channel.

According to an embodiment, the method may further include the operation of detecting the event, and the operation of providing the determined at least one service may include the operation of authenticating the user based on the user's bio information, the operation of detecting the control information of the electronic device associated with the event, and the operation of storing information on the event and the control information in the database of the electronic device or external device.

According to an embodiment, the operation of providing the determined at least one service may include the operation of comparing the user's bio information with a preset value, the operation of obtaining user association information according to the difference between the user's bio information and the preset value, and the operation of storing the bio information and the user association information in the database of the electronic device or external device.

According to an embodiment, the operation of providing the determined at least one service may include the operation of comparing the user's bio information with a preset value, the operation of obtaining user association information according to the difference between the user's bio information and the preset value, and the operation of storing the bio information and the user association information in the database of the electronic device or external device, and the user association information may include at least one of an image, a video, an audio, a location, a time, and weather.

According to an embodiment, the operation of providing the determined at least one service may include the operation of determining the category where the user's bio information belongs among a plurality of preset categories and the operation of storing the information on the content currently being played or the category in the database of the electronic device or the external device.

According to an embodiment, a storage medium readable by a machine recording a method for providing a service by the electronic device may include the operation of obtaining the user's bio information, the operation of determining at least one service of a plurality of services related to the bio information, and the operation of providing the determined at least one service.

According to an embodiment, the method for providing a service by the electronic device may include the operation of detecting an event, the operation of determining the bio information corresponding to the event, the operation of determining at least one service corresponding to the determined bio information among a plurality of services associated with the event supported by the electronic device, and the operation of providing the determined at least one service.

according to an embodiment, the operation of determining the bio information corresponding to the event may include may the operation of searching for an event identical to the event detected from the database stored in the electronic device or external device and the operation of determining that the bio information stored in the database corresponding to the searched event is the bio information corresponding to the detected event.

According to an embodiment, the operation of determining the bio information corresponding to the event may include may the operation of searching for an event identical to the event detected from the database stored in the electronic device or external device, the operation of identifying the type of the bio information stored in the database corresponding to the searched event, and the operation of obtaining the identified type of bio information from the user.

According to an embodiment, the method may further include the operation of obtaining the bio information and the operation of storing information on the event and the obtained bio information in the database of the electronic device or the external device.

According to an embodiment, the method may further include the operation of obtaining the user's bio information, the operation of comparing the obtained bio information with a preset value and the operation of storing information associated with the user's bio information and the event in the database of the electronic device or the external device according to the difference between the obtained bio information and the preset value.

According to an embodiment, the determined at least one service may be at least one of a variation in the user interface, user authentication, exercise coaching, information recommendation, information provision, information storage, information transmission, provision of function or service, preset content, restriction or blocking access to a function or service, variation in the settings of the electronic device, or control of an external device.

According to an embodiment, the operation of providing the determined at least one service may include the operation of transmitting the determined bio information to the external device, the operation of receiving the information associated with the bio information from the external device, and the operation of providing the received information.

According to an embodiment, the operation of providing the determined at least one service may include the operation of determining the control information of the external device corresponding to the determined bio information and the operation of transmitting the control information to the external device.

according to an embodiment, the operation of determining the bio information corresponding to the event may include may the operation of searching for the area where the electronic device is located from the database stored in the electronic device or external device and the operation of determining that the bio information stored in the database corresponding to the searched event is the bio information corresponding to the detected area.

According to an embodiment, in a storage medium readable by a machine recording a program for running a method for providing a service by the electronic device, the method may include the operation of detecting an event, the operation of determining the bio information corresponding to the event, the operation of determining at least one service corresponding to the determined bio information among a plurality of services associated with the event supported by the electronic device, and the operation of providing the determined at least one service.

Figure 71:
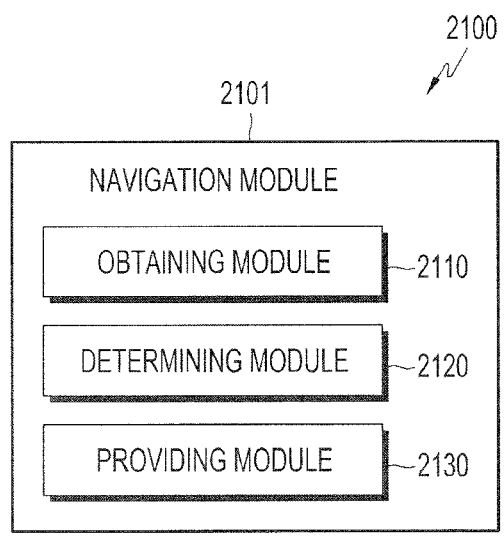
FIG. 71 is a block diagram illustrating a navigation module of an electronic device according to an embodiment.

FIG. 71 is a block diagram 2100 illustrating a navigation module 2101 (e.g., an additional functional module 170) of an electronic device (e.g., the electronic device 101 or 201) according to an embodiment. The navigation module 2101 may be the additional function module 170 shown in FIG. 51. Referring to FIG. 71, the navigation module 2101 may include an obtaining module 2110, a determining module 2120, and a providing module 2130. The navigation module 2101 may be provided separately from a processor (e.g., the processor 120 or 210) or may be fully or partially integrated with the processor.

According to an embodiment, the obtaining module 2110 may obtain information on a plurality of points.

According to an embodiment, the determining module 2120 may determine at least one reference point based on, at least, the obtained information.

In one embodiment, the determining module 2120 may set an initial route based on the plurality of points and may determine a reference candidate point included in a designated range from the initial route among reference candidate points as the reference point. The determining module 2120, in case the increase in the movement distance or time according to the virtual route including some reference candidate point is not more than a reference value, may determine the reference candidate point as the reference point. The determining module 2120 may determine the reference point according to designated priorities among the reference candidate points. The determining module 2120 may determine as the reference point automatically for some of the reference candidates and based on the user's input for others. The determining module 2120 may determine the point received from the external terminal as the reference point.

In one embodiment, the determining module 2120 may determine an initial route connecting the plurality of points based on the obtained information and may determine at least one reference point based on the initial route.

According to an embodiment, the providing module 2130 may provide a route direction including information on the reference point. The providing module 2130 may determine the route based on at least some of the plurality of points and the reference point or the plurality of points. The providing module 2130 may provide information on the ratio of the distance moving up to the reference point relative to the entire route. The providing module 2130 may provide a turn-by-turn direction in the route point included in the entire route along with the information on the reference point.

In one embodiment, the providing module 2130 may generate a final route based on some of the reference point and the initial route and may provide the information on the route point included in the final route and the information on the reference point. Other some of the reference points may not be included in the final route.

The navigation module 2101 may set a route based on obtained information and may provide the direction of the set route using the input/output interface (e.g., the input/output interface 140), the display (e.g., the display 150 or 260), and audio module (e.g., the audio module 280). According to an embodiment, the navigation module 2101 may be understood as a navigation engine. According to an embodiment, the navigation module 2101 may be understood as one control module along with the processor (e.g., the processor 120 or 210), and may be implemented in a single chipset (SoC). The navigation module 2101 may obtain data on the reference point stored in the memory (e.g., the memory 130 or 230) and extract, filter, or determine the reference point to be reflected for setting the route. According to an embodiment, the navigation module 2101 may process at least some of the information obtained from other components (e.g., the processor, memory, input/output interface, or communication device (e.g., communication interface 160 or communication module 220) and may provide the same to the communication device by various methods. For example, the navigation module 2101 may provide the information on the obtained or determined reference point to other electronic device (e.g., the electronic device 104 or server 106). Or, the navigation module 2101 may provide information on the generated initial or final route to other components or other electronic device.

According to an embodiment, the electronic device (e.g., the electronic device 101 or 201) may include an input/output interface for obtaining at least one destination information, the memory for storing the information on a plurality of reference points, and the processor determining some of the plurality of reference points as reference points to be provided as route direction based on at least destination information, and the processor may be configured to provide the route direction including the information on the determined reference point.

According to an embodiment, the electronic device may further include a positioning module determining the current location of the electronic device, and the processor may be configured to provide the route direction taking the current location as departure point information.

According to an embodiment, the memory may store at least one of the reference point designated by the service provider, the reference point set by the user, the reference point obtained through the application of the electronic device, or the reference point obtained by the user registration as the plurality of reference points.

According to an embodiment, the electronic device may further include the communication device for connection with the wearable device interworking with the electronic device, and the communication device may receive the location information on the occurrence of the designated marking operation in the wearable device, and the reference point obtained by the user registration may be configured to correspond to the location information on the occurrence of the marking operation.

According to an embodiment, the processor may be configured to parse the content transmitted or received through the application and to store some point obtained as the result of parsing as the reference point obtained by the application in the memory. According to an embodiment, the processor may be configured to reset the route including at least some of the determined reference points. According to an embodiment, at least some of the reference points may be configured to be not included in the route or to be located in the straight line section of the route.

The existing turn-by-turn route direction may provide a proper guide to the user at junctions or intersections. However, the user (or driver) turns directions by rote, while guided by the navigation (or the electronic device providing a route directing function) rather than based on the understanding of the overall route to arrive at the destination. In such case, the user might not remember the route well even though he has passed before.

Figure 72:
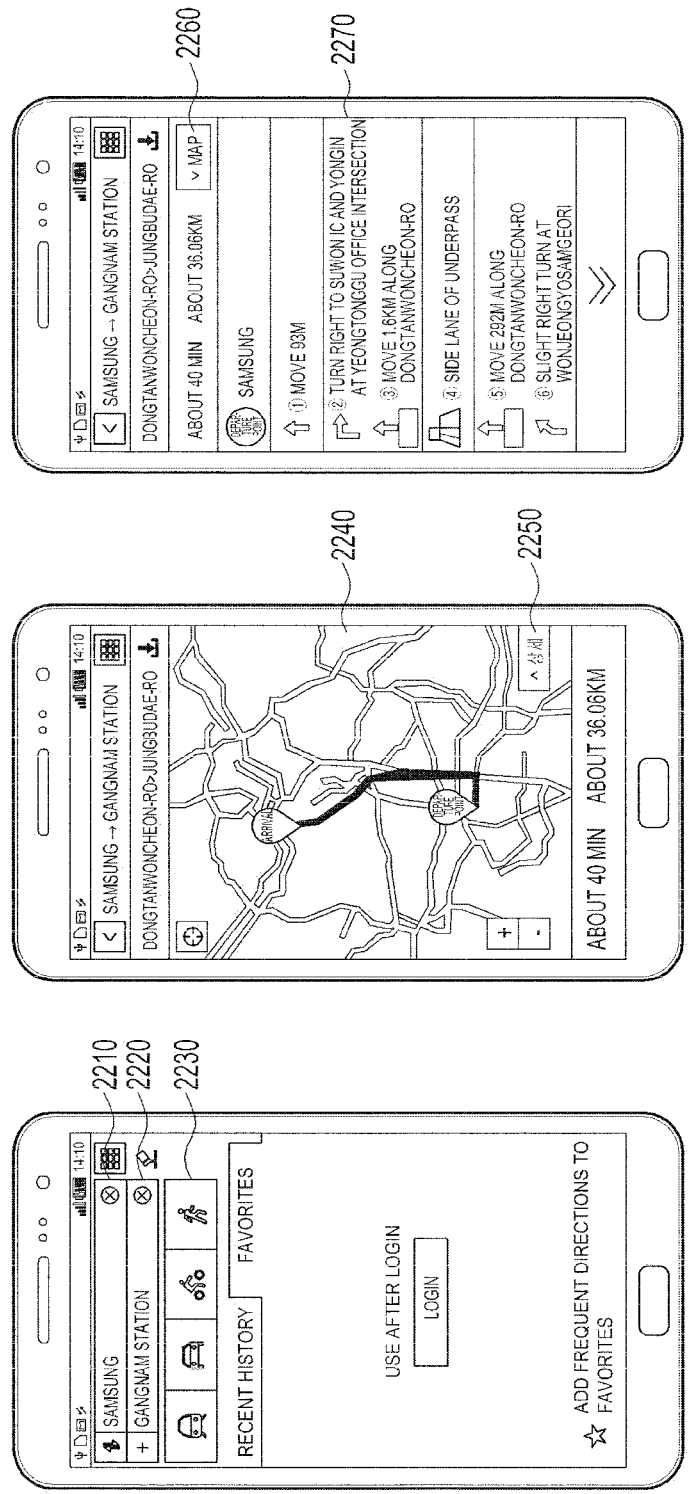
FIG. 72 illustrates an example of a route direction.

FIG. 72 illustrates an example of a route direction.

Referring to FIG. 72(a), the user may enter the departure point 2210 and destination 2220 and select the way to travel, and then, the electronic device may provide a route direction, such as the shortest or optimal route connecting the departure point 2210 and the destination 2220 as shown in FIG. 72(b). Since the map screen 2240 has a too large scale, the user may have difficulty in intuitively recognizing what route he has to use to travel. The user may generally identify the detailed route from the departure point to the destination by selecting the details button 2250.

However, referring to FIG. 72(c), the route from the departure point 2210 to the destination 2220 may be directed in a turn-by-turn manner. Since in the guide screen 2270 is very short relative to the entire route, such as 93 m or 292 m, the user has difficulty in grasping what routes he should select to travel from the departure point 2210 to the destination 2220. Further, even though there are some spots assisting in the user's appreciation, such as famous landmarks near the travel route, if he does not directly pass by the spots (e.g., buildings not directly connected with the highway but noticeable to the user when moving on the highway) or passes the spots without route change (e.g., simply driving straight), the guide as to the spots is not provided. Generally, the user may select the map button 2260 to display a map screen as shown in FIG. 72(b).

Various embodiments may provide the route direction including various reference points capable of the user's recognition in order to address such problems. Further, they may allow the process of selecting and determining various reference points to be based on the user's experience, and thus, a route direction familiar to the user may be provided.

According to an embodiment, a route divided based on reference points may be generated and made noticeable to the user, so as to provide the user with a better understanding on the entire route.

According to an embodiment, information on the place familiar to the user and easy to find based on the user's experience may be reflected to the route design, allowing the user to intuitively and quickly understand the route.

Figure 73:
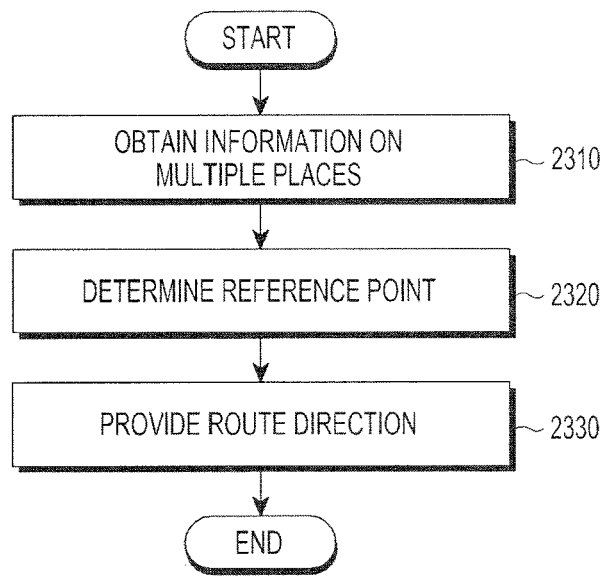
FIG. 73 illustrates a route direction providing process according to an embodiment.

FIG. 73 illustrates a route direction providing process according to an embodiment.

Referring to FIG. 73, in operation 2310, according to an embodiment, the electronic device may obtain information on a plurality of places. According to an embodiment, the electronic device may obtain the information on the plurality of places using various input devices, such as a touchscreen, voice recognition, and physical keyboard. For example, the electronic device, such as a smartphone, may receive inputs for the departure point and destination through a touch input on the virtual keyboard displayed on the screen.

According to an embodiment, the electronic device may receive only input for the destination. In such case, the electronic device may determine the current location of the electronic device using a GPS sensor, Wi-Fi, or GSM, or other mobile communication-based positioning module. The current location may correspond to the departure point of the route.

According to an embodiment, the electronic device may receive inputs for another destination or route points. For example, the electronic device may provide route directions for two or more destinations. For example, a route direction connecting the departure point-first destination (or route point)-second destination may be provided.

In operation 2320, the electronic device may determine at least one reference point at least based on the plurality of obtained places or points.

In this disclosure, the reference point is distinguished from route point or destination. Further, it is distinguished from the information on the point where a left turn, right turn, or U-turn should be made or intersection information provided by a turn-by-turn direction. The reference point is of concept including the place, building, or nature that may be considered as a reference when the user moves along the set route.

For example, in case the user moves via a particular intersection or makes a right turn at an intersection, the intersection corresponds to a place for the route direction (turn-by-turn direction) but a famous building located at a particular intersection may correspond to a reference point indicating that the building is present on the user's travel route or near the travel route. In case the building is included in the route points as per the existing method, the electronic device may generate a route passing by the building (e.g., directing to the front gate of the building or parking lot) and direct the user. However, according to an embodiment, in case the building is set as a reference point, the electronic device may direct the user by generating a route based on the departure point and destination information.

As another example, in case the driver moves along the route set based on the departure point and destination, he may pass by a place, such as a landmark (e.g., 63 building or Seoul Arts Center) in the straight section. In case the route direction is provided in the existing manner, although the landmark or so may remarkably enhance the user's understanding as to the route, no direction is provided if a left turn or right turn is not made at the place. However, according to an embodiment, although the user simply drives straight in the section, information (the name or image of the reference point or travel ratio relative to the entire route) on the point (reference point) may be provided.

Further, various methods for setting reference points are described below with reference to FIG. 78.

In operation 2330, the electronic device may provide a route direction including information on reference points. According to an embodiment, the route may be determined by the plurality of points (e.g., the departure point and destination, or route points as necessary). Further, according to an embodiment, the route may be determined including all or some of the plurality of points or reference points. A route direction including the information on the reference point is described with reference to FIGS. 74 and 75.

Figure 74:
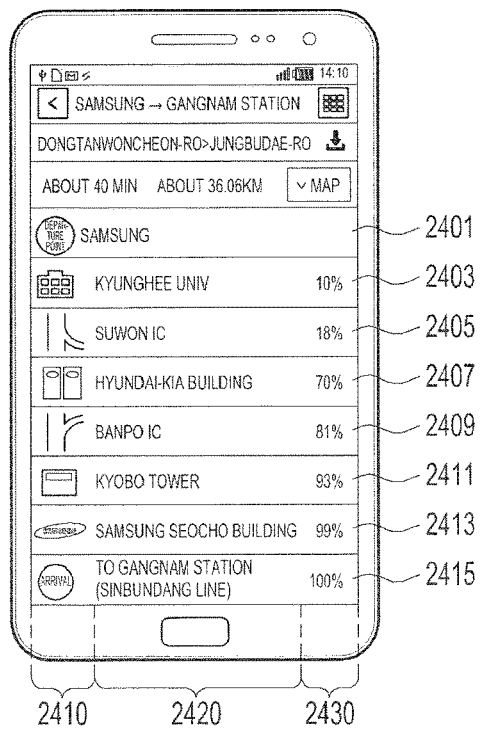
FIG. 74 illustrates an exemplary route direction screen using a reference spot according to an embodiment.

FIG. 74 illustrates an exemplary route direction screen using a reference spot according to an embodiment.

Referring to FIG. 74, the electronic device may obtain information on the departure point (e.g., Samsung building) and destination (e.g., Gangnam station) from the user. As described above, the departure point information may be obtained through the positioning module, and there may be two or more destinations. Hereinafter, for ease of description, Samsung building is the departure point, and Gangnam station is an only destination.

The electronic device may extract corresponding reference points between the set departure point and destination. The reference points may be stored in a storage space, such as the storage of the electronic device. According to an embodiment, the electronic device may transmit information on a route (e.g., the initial route or first route) generated based on the departure point and destination to the external device (e.g., server) and may receive information on reference points available on the route from the external device.

The electronic device may provide an entire route direction including the extracted reference points. The electronic device may let the user know what location each reference point corresponds to on the entire route through an equation, table, or image. In the example shown in FIG. 74, the entire route may include directions (items 2401, 2403, 2405, 2407, 2409, 2411, 2413, and 2415) having Kyunghee University, Suwon IC, Hyundai-Kia Building, Banpo IC, Kyobo tower, and Samsung Building as the reference points. Further, each item may include an area 2410 indicating the image or logo of its corresponding reference point, an area 2420 indicating the name of the reference point, and an area 2430 indicating the ratio corresponding to the distance up to the point on the entire route (or time taken to travel to the point). For example, referring to directional item 2407, it may provide an image representing Hyundai-Kia building and the information indicating that the distance to the reference point is about 70% (i.e., about 25 km from the departure point) of the entire route (about 36.06 km). Indeed, although Hyundai-Kia building is not located on the travel route (it is merely shown at the driver's right side when driving on Gyeongbu expressway), the user may recognize better the entire route through such reference points and may intuitively be aware how much he has driven to the destination while actually driving.

Figure 75:
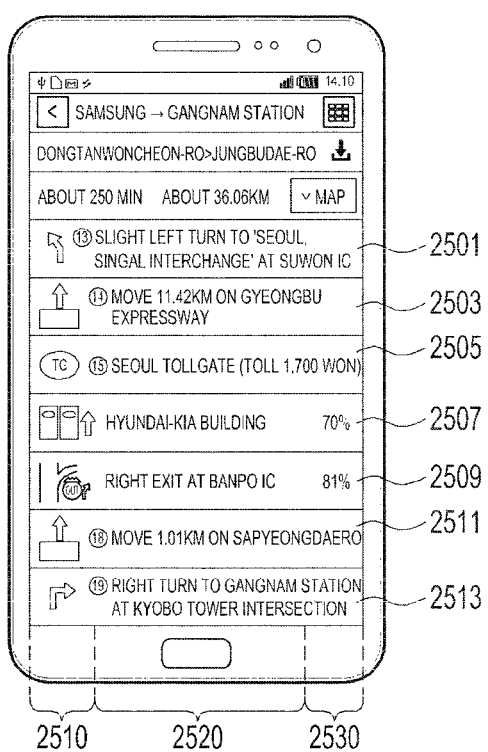
FIG. 75 illustrates an exemplary route direction screen obtained by combining a direction for a reference spot with a turn-by-turn direction according to an embodiment.

FIG. 75 illustrates an exemplary route direction screen obtained by combining a direction for a reference spot with a turn-by-turn direction according to an embodiment.

According to an embodiment, the overall route may be provided to the user as displayed only with the reference points, and the information on the reference points considering the complexity and the length of the overall route may be provided while the turn-by-turn information on each reference point may be provided. For example, among the provided directional items 2501, 2503, 2505, 2507, 2509, 2511, and 2513, the directional items 2501, 2503, 2505, 2511, and 2513 provide the turn-by-turn information, and the directional items 2507 and 2509 provide directional information on the reference points.

In FIG. 74, the area 2410 indicating the image or logo of its corresponding reference point may be replaced with the image area 2510 indicating the turn-by-turn direction in FIG. 75. In the case of the item providing the directional information on the reference point, the area 2420 indicating the name of the reference point in FIG. 74 may be replaced with the text area 2520 providing the turn-by-turn direction in FIG. 75. The area indicating the ratio (or time taken to travel up to the point) corresponding to the distance to the point on the overall route in FIG. 74 may be omitted or may be present only in the item (e.g., the directional items 2507 and 2509) providing the directional information on the reference point.

The direction in the form shown in FIG. 75 may be converted into the directional form shown in FIG. 74. For example, if the user selects the Hyundai-Kia building item (directional item 2407) on the screen shown in FIG. 74, a corresponding turn-by-turn directional information between Suwon IC (directional item 2405) and the Hyundai-Kia building item (directional item 2407) may be provided. Further, for example, if the user selects the Hyundai-Kia building item (directional item 2507) on the screen shown in FIG. 75, corresponding turn-by-turn information (e.g., directional items 2501, 2503, and 2505) between Suwon IC (not shown) and the Hyundai-Kia building item (directional item 2507) may be folded or disappear, and information on Suwon IC, which is a reference point, may be provided. As such, turn-by-turn route directions may be provided per section with respect to the reference point. If in the shown example the user selects directional item 2509 (a direction on the reference point, Banpo IC), turn-by-turn direction lists between directional item 2507 and directional item 2509 may be provided.

Figure 76:
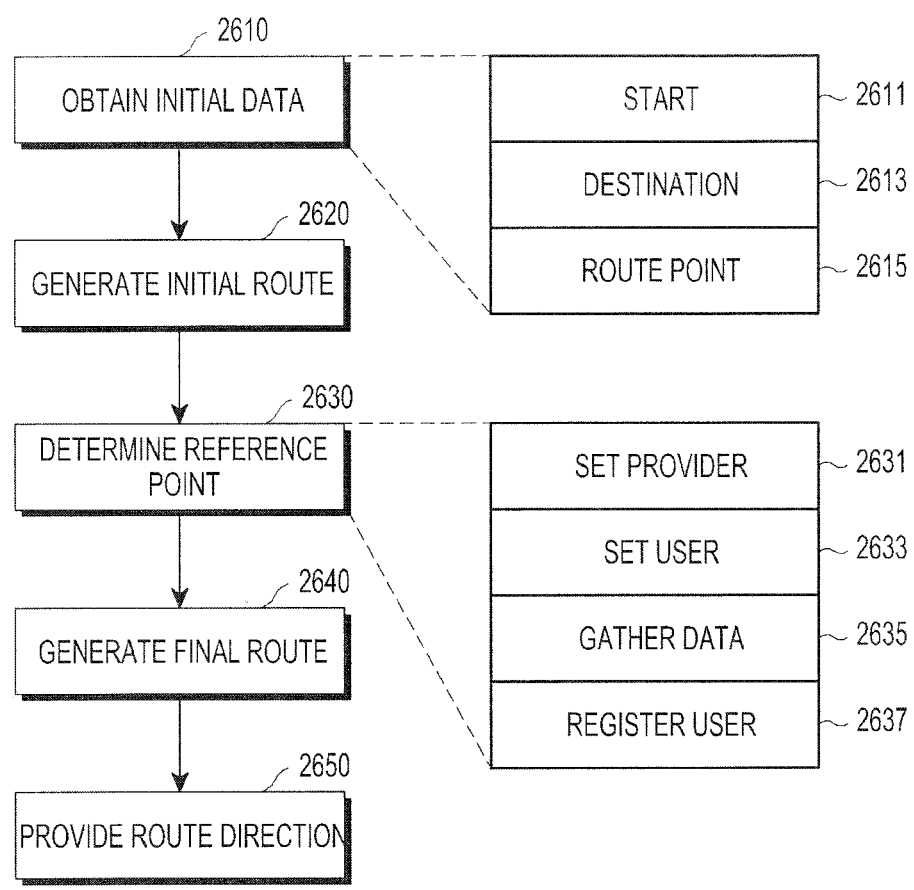
FIG. 76 illustrates a process for designing a route using a reference spot according to an embodiment.

FIG. 76 illustrates a process for designing a route using a reference spot according to an embodiment.

According to an embodiment, in operation 2610, the electronic device may obtain initial data. The initial data may be information on a plurality of points such as the departure point 2611, arrival (destination) 2613, and route point 2615. As described above, there may be a plurality of route points 2615 or destinations. Or, the departure point 2611 may be determined from the current location of the electronic device obtained using the positioning module.

According to an embodiment, in operation 2620, the electronic device may generate an initial route based on a plurality of points. The initial route may be determined by the initial data obtained in operation 2610. The initial route may be set as the optimal route reflecting real-time traffic context, the shortest distance route, the shortest time route, or various routes reflecting whether to use highway or the toll. According to an embodiment, in operation 2620, the electronic device may generate and provide two or more initial route candidates to the user and may finally generate the initial route based on the user's determination (choice). However, according to an embodiment, the electronic device may arbitrarily determine the initial route without the user's selection process.

In operation 2630, the electronic device may determine reference points. The electronic device may select some of a plurality of reference points stored in the electronic device or server and determine them as reference points to be provided for route direction. Various methods for determining the reference point are described below with reference to FIG. 78, and the plurality of stored reference points are described with reference to FIG. 76.

The plurality of reference points (e.g., reference point candidates) may be stored in the memory of the electronic device. The memory may store at least one of the reference point designated by the service provider, the reference point set by the user, the reference point obtained through the application of the electronic device, or the reference point obtained by the user registration as the plurality of reference points. In other words, the plurality of reference points may include a reference point 2631 determined by the (service/product) supplier, a reference point 2633 meeting a condition set by the user, a reference point 2635 inputted to the electronic device of the user or grasped from the content (message, email, or text) transmitted or received from the user's electronic device to other electronic device, and a reference point 2637 registered by the user using the electronic device or wearable device.

The reference point 2631 set by the supplier may be a reference point set by the service provider (e.g., the provider of a map application or navigation function or the manufacturer of the electronic device). For example, such facilities as landmarks, cultural properties, major road ICs, schools, or hospitals in each country or community may be set to be utilized as reference points in the step of providing the product or application. Such information on the reference point may be stored in the supplier server as well as the electronic device to be periodically updated.

The user set reference point 2633 may be a reference point set by the user. For example, the user may make a setting so that a gas station, airport, military camp, theater, or coffee shop is provided as the reference point. In such case, the corresponding items grasped from the map data may be classified as reference points. For example, in case the user makes a setting so that gas stations are set as reference points, if a gas station is located near the initial route, the electronic device may provide the gas station as a reference point. According to an embodiment, the user may be aware at what spot on the entire route the gas station is located. For example, the user may previously obtain the information indicating that there is no gas station between the 20% point of the entire route and the 80% point. This is much more efficient as compared with searching for nearby gas stations and detouring the route quickly after the fuel alert lights on.

The user may set a particular brand or franchise store as a reference point. For example, if the user sets a Starbucks store as a reference point, the electronic device may provide information on various Starbucks stores located near the initial route.

The reference point 2635 by gathering data may correspond to the place or building obtained through analysis of data exchanged through the electronic device. For example, a place (e.g., address of a company) mentioned in emails repeatedly exchanged with a client through an email application may be gathered as a reference point. Further, the place mentioned using a particular tag in the social networking service or place mentioned in the message or interactive application may be gathered as reference points. Further, the place searched by the user on a map application or navigation application or place, area name, or building input as a key word by the user on the Internet application may also be gathered as reference points.

The reference point 2635 by gathering data may be a reference point provided from other user (other user terminal). For example, when there is an appointment in the busy downtown, the user more familiar with the place may let the other know points worth referencing and may explain the route using the points. For example, in case there is a meeting at a Starbucks store in Gangnam station, if one user provides the other with a direction, like "keep going out of exit 2 of Gangnam station and turn right if you find a Citi bank, then keep going left at Dunkin donuts, and you see Starbucks at right hand," "City bank" or "Dunkin donuts" may correspond to reference points. In the case of the above route direction, the conventional navigation method gives such direction as "go straight A meters on Gangnamdaero, then turn right and go B meters, then turn left and go straight C meters, and you will arrive at the destination." Such method is not easy to find the way, is highly likely to let the driver pass intersections, and when revisiting the same place, requires again the assistance of the route directing application.

The reference point 2637 by the user registration may be a reference point registered using the menu or function of a particular application of the electronic device. This is described below with reference to FIG. 77.

In operation 2640, the electronic device may generate a final route by reflecting the determined reference points. According to an embodiment, the electronic device may provide the user with the existing route (e.g., initial route) and a final route reflecting the reference points and let the user choose one route. For example, in case the user chooses the route including a direction to the reference point, it may provide a route direction using the final route, and in case the user chooses the existing route (e.g., initial route), it may provide the route direction connecting the departure point and the destination as in the existing one. In such case, the initial route may be determined as the final route.

In operation 2650, the electronic device may provide a route direction. The electronic device may provide the route direction based on the methods described above in connection with FIGS. 73 to 75 or various combinations thereof.

Figure 77A:
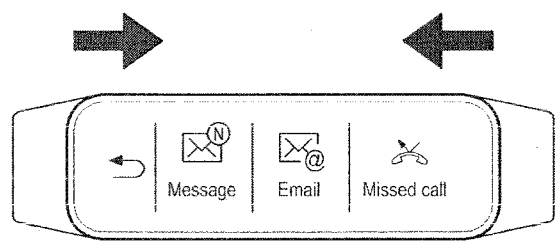
FIG. 77 illustrates an example of generating a reference spot by a user's registration according to an embodiment.
Figure 77B:
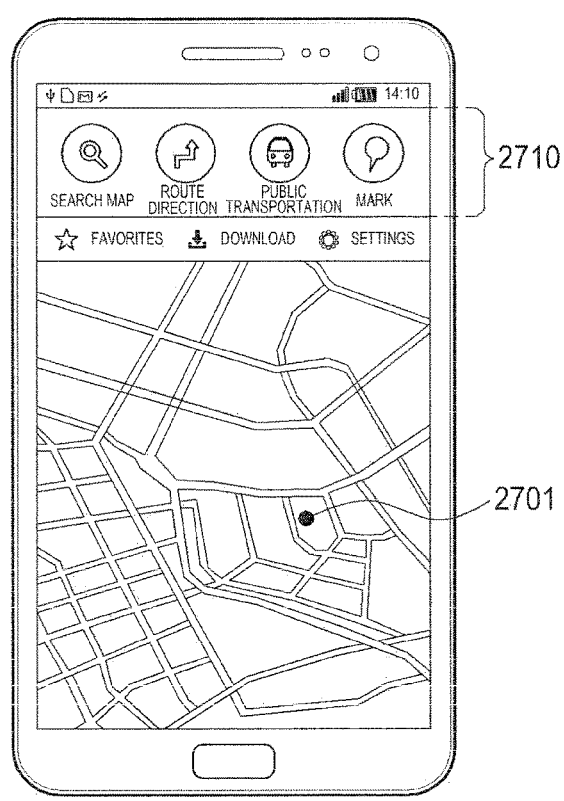

FIG. 77 illustrates an example of generating a reference spot by a user's registration according to an embodiment.

Referring to FIG. 77(a), the reference points may be generated using the wearable device. For example, the electronic device may connect with the wearable device via a short-range communication network (e.g., Bluetooth, near field communication (NFC), IrDA, Bluetooth low energy (BLE), Wi-Fi, or Wi-Fi direct). According to an embodiment, the electronic device may connect with the wearable device via a mobile communication network (e.g., 3G, LTE, or LTE-A).

The user may mark the corresponding place using a designated operation of the wearable device. For example, the wearable device may include a positioning module, such as a GPS module, to recognize the current location, and if a designated operation (e.g., such a touch input as if he pulls the display of the wearable device from its left or right side to its center) is conducted by the user, it may mark the current location and store it or transmit to the electronic device. The electronic device (e.g., the communication module of the electronic device) may receive the information on the location where the marking operation has occurred. Such received location information may be determined as the reference point 2637 by the user registration.

Referring to FIG. 77(*b*), the reference points may be generated using the electronic device. For example, the user may input a gesture for generating a toggle area 2710 of the electronic device (e.g., drag down from the top of the screen). At this time, among various menu items included in the generated area, the marking menu item may be selected to generate a marking on the current area or any point on the map 2701. The point marked through the marking menu item may be determined as the reference point 2637 by the user registration.

In the example shown in (a) or (b) of FIG. 77, the particular location of the electronic device or wearable device may be obtained as a GPS coordinate. Further, there may be several places corresponding to the point. For example, the coordinate corresponding to Gangnam station may be represented as a subway station, as an intersection, as a building name, or as the name of a particular franchise store (e.g., Starbucks). The electronic device or wearable device may provide various selection options for the marked point and may store the point as a representation selected by the user or may transmit it to the other electronic device.

Figure 78:
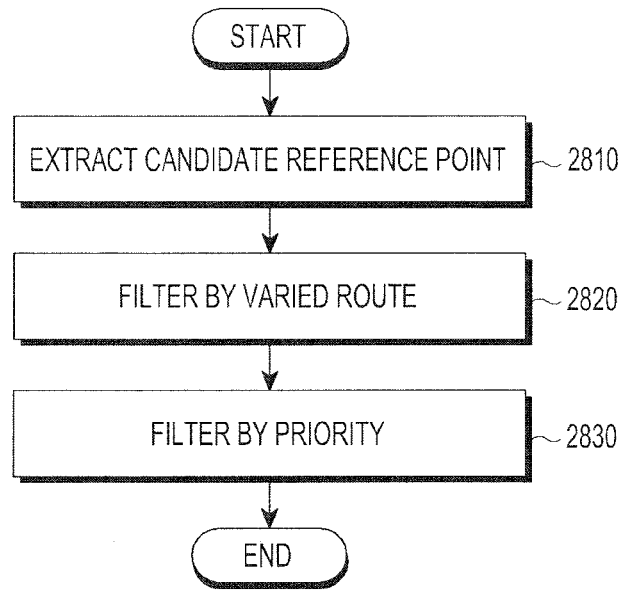
FIG. 78 illustrates a process for filtering a reference spot according to an embodiment.

FIG. 78 illustrates a process for filtering a reference spot according to an embodiment.

According to an embodiment, in operation 2810, the electronic device may extract a group of reference point candidates. For example, the electronic device may extract reference points meeting a designated condition among various reference points stored in the memory or present on the server as candidate reference points. For example, the electronic device may extract reference points distributed within a predetermined distance from the initial route as candidate reference points.

According to an embodiment, in operation 2820, the electronic device may filter some of reference points with respect to the varied route. For example, the electronic device may reset the route to be included in a first reference point route among the candidate reference points. For example, in case the initial route is a route connecting the departure point and destination via the shortest route, the route as reset may be a route connecting the departure point, first reference point, and destination by the shortest route. In case the reset route is longer by a designated distance or more than the initial route or in case the travel time by the reset route is longer than the travel time by the initial route, the electronic device may filter the first reference point. If the first reference point is filtered, the electronic device may perform the same operation on the second reference point. Unless the first reference point is filtered, the electronic device may include the first reference point as the reference points to be provided for route direction.

According to an embodiment, in operation 2830, the electronic device may filter the reference point with respect to priority. For example, the electronic device may first determine the reference point (e.g., the reference point 2637) by the user registration among the candidate reference points as the reference point. According to an embodiment, the electronic device may do such filtering in the order of the points determined as the reference points by multiple users among the candidate reference points. According to an embodiment, the electronic device may apply a weight to the use frequency of reference point, grade of reference point, or popularity of reference point provided by users through the SNS application to determine priorities and may perform the filtering based on the priorities.

According to an embodiment, operation 2820 and operation 2830 may be performed sequentially or selectively. For example, only operations 2810 and 2830 may be performed to determine reference points. Or, operation 2830 may be performed ahead of operation 2820. In such case, in case the reference point determined to have a higher priority is subject to a route variation of a threshold or more, the electronic device may request the user to confirm whether he desires to pass the reference point. As described above, according to an embodiment, since the overall route might not pass the reference point, the direction to the reference point may be provided without including the reference point in the travel route as long as it may be recognized by the user simply moving along the route.

According to an embodiment, a method for providing a route direction by an electronic device may include the operation of obtaining information on a plurality of points, the operation of determining at least one reference point based on the obtained information, and the operation of providing a route direction including the information on the reference point.

According to an embodiment, the route may be determined based on the plurality of points or at least some of the plurality of points and the reference point.

According to an embodiment, the operation of providing the route direction may provide information on a ratio of a travel distance to the reference point to the overall route. Further, the operation of providing the route direction may provide a turn-by-turn direction at a route point included in the overall route along with information on the reference point.

According to an embodiment, the operation of determining the reference point may include the operation of setting an initial route based on the plurality of points and the operation of determining a candidate reference point included in a designated range from the initial route among candidate reference points as the reference point.

According to an embodiment, the operation of determining the reference point may include, in case the increase in the movement distance or time according to the virtual route including some reference candidate point is not more than a reference value, the operation of determining the reference candidate point as the reference point.

According to an embodiment, the operation of determining the reference point may include the operation of determining the reference point according to a designated priority among the candidate reference points.

According to an embodiment, the operation of determining the reference point may include the operation of determining as the reference point automatically for some of the candidate reference points and based on a user input for some of the rest.

According to an embodiment, the operation of determining the reference point may include the operation of determining a point received from an external terminal as the reference point.

According to an embodiment, the operation of determining the reference point may include the operation of determining an initial route connecting the plurality of points based on the obtained information and the operation of determining at least one reference point based on the initial route.

According to an embodiment, the operation of providing the route direction may include the operation of generating a final route based on some of the initial route and the reference point and the operation of providing information on a route point included in the final route and information on the reference point based on the final route. Further, others of the reference points may not be included in the final route.

Figure 79:
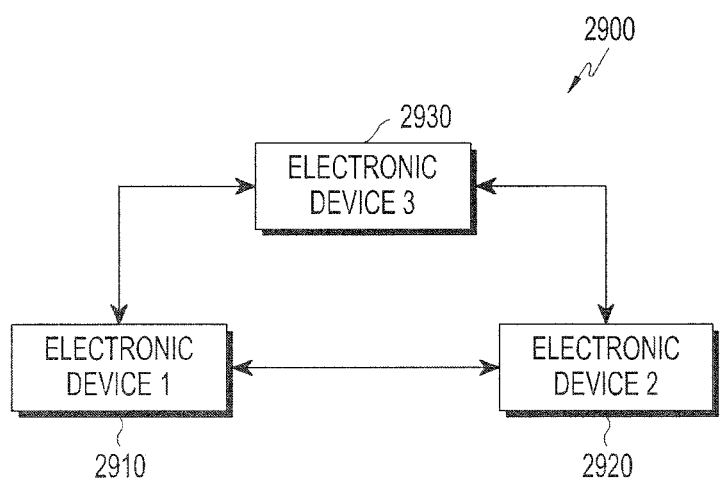
FIG. 79 is a view illustrating a communication control system according to an embodiment.

FIG. 79 is a view illustrating a communication control system according to an embodiment. The communication control system 2900 may include a first electronic device 2910, a second electronic device 2920, and a first electronic device 2930. Each of the first to third electronic devices 2910 to 2930 may have the same or similar configuration to the whole or part of the configuration of the electronic device 201 shown in FIG. 52 or the electronic device 101 shown in FIG. 51, for example.

The first electronic device 2910 and the second electronic device 2920 may automatically establish a communication connection without the user's involvement. The first electronic device 2910 or the third electronic device 2930 may perform a function of controlling the communication connection, i.e., a server function, and the first electronic device 2910 or third electronic device 2930 performing the server function may be referred to as a server device.

The first electronic device 2910 and the second electronic device 2920 each may include a sensor device (e.g., the sensor module 240) or bio sensor 240I), and the automated communication connection between the first electronic device 2910 and the second electronic device 2920 may be performed based on the first bio information obtained by the first electronic device 2910 and/or the second bio information obtained by the second electronic device 2920.

Figure 80:
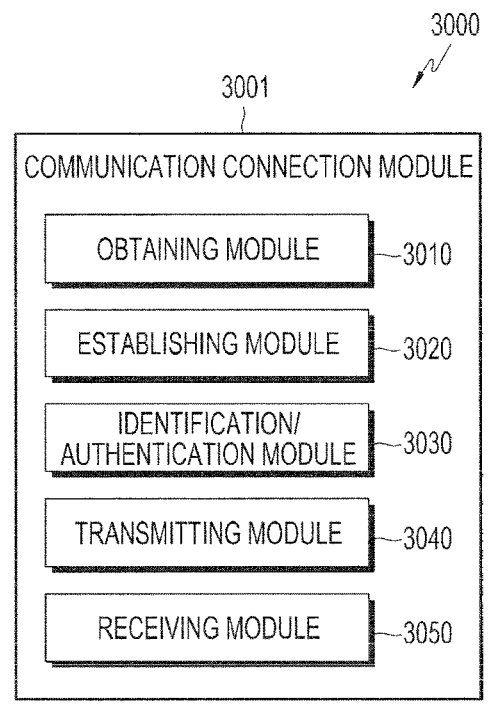
FIG. 80 is a block diagram illustrating a communication connection module of a first electronic device according to an embodiment.

FIG. 80 is a block diagram 3000 illustrating a communication connection module 3001 (e.g., an additional functional module 170) of a first electronic device (e.g., the electronic device 101 or 201) according to an embodiment. The communication connection module 3001 may be the additional function module 170 shown in FIG. 51. Referring to FIG. 80, the communication connection module 3001 may include an obtaining module 3010, an establishing module 3020, an identification/authentication module 3030, a transmitting module 3040, and a receiving module 3050. The communication connection module 3001 may be provided separately from a processor (e.g., the processor 120 or 210) or may be fully or partially integrated with the processor.

According to an embodiment, the obtaining module 3010 may obtain the first bio information of the first user. The first bio information of the first user may include at least one of the first user's identification information, body information, emotion information, health information, disease information, exercise information, stress information, and sleep information. The first bio information may include at least one of iris information, finger print information, palm pattern information, sole pattern information, hand vein information, voice information, blood pressure, HRV, HRM, oxygen saturation, ECG, EMG, brainwave, or skin resistance. In one embodiment, the obtaining module 3010 may measure a bio signal from the first user through a sensor module (e.g., the sensor module 240) and may produce first bio information indicating the first user's mental state or body state from the measured bio signal. In one embodiment, the obtaining module 3010 may receive the first user's bio signal through a communication device (e.g., the communication interface 160, the communication module 220, the input/output interface 140, and the interface 270) and may produce the first bio information of the first user from the received bio signal. In one embodiment, the obtaining module 3010 may receive the first user's first bio information through the communication device.

The obtaining module 3010 may obtain pairing information for connecting communication with the second electronic device based on the first bio information. The pairing information may include at least one of the ID of the second electronic device, phone number, SIM number, network address, IP address, MAC address, BT address, AP information, and password.

According to an embodiment, the identification/authentication module 3030 may identify/authenticate the first user of the first electronic device based on the first bio information. For example, the first electronic device may compare the pattern (or characteristic points defining the pattern) or value (e.g., heart rate) of the first bio information (e.g., heart rate signal) with the pattern (or characteristic points defining the pattern) or value of the pre-stored (or registered) bio information of the pre-registered user to determine the similarity (e.g., the number of characteristic points identical with one another or with a difference within a threshold, or the ratio of the number or value (e.g., ratio in number of similar characteristic points relative to all the characteristic points). In case the similarity is a preset threshold or higher, the first electronic device may determine that the user identification/authentication succeeds, and in case the similarity is less than the preset threshold, the electronic device may determine that the user identification/authentication fails. For example, in case the similarity is the preset threshold or higher, the electronic device may determine that the user of the obtained bio information is the same as the pre-registered user.

According to an embodiment, the transmitting module 3040 may transmit the first user association information on the first user or the first bio information to the third electronic device or second electronic device.

According to an embodiment, the receiving module 2050 may receive the paring information from the third electronic device or second electronic device. According to an embodiment, the receiving module 3050 may receive the second bio information from the second electronic device or third electronic device.

In one embodiment, the obtaining module 3010 may identify the first user of the first electronic device based on the first bio information through the identification/authentication module 3030, transmit the first user association information on the first user to the third electronic device through the transmitting module 3040, and receive the paring information from the third electronic device through the receiving module 3050. The first user association information may include at least one of information on the first user, information on the first electronic device, and information on the ambient environment of the first electronic device. The first user association information may include at least one of the identification information of the first user/first electronic device, body information, emotion information, health information, disease information, exercise information, activity information, stress information, and sleep information. The first user association information may include at least one of movement information of the first user and/or first electronic device, location information of the first user and/or first electronic device, current time/date/day/weather information, user input information, information on the occurrence of a preset event, an image, a video, and an audio. The first user association information may include at least one of account, ID, name, address, email address, phone number, and personal information.

In one embodiment, the obtaining module 3010 may include the operation of identifying the first user of the first electronic device based on the first bio information through the identification/authentication module 3030, transmitting the first user association information on the first user to the third electronic device through the transmitting module 3040, and receiving the paring information from the third electronic device through the receiving module 3050.

In one embodiment, the obtaining module 3010 may transmit the first bio information to the third electronic device through the transmitting module 3040, and receive the paring information from the third electronic device through the receiving module 3050.

In one embodiment, the establishing module 3020 may search for at least one peripheral device and establish a communication connection with the second electronic device identified by the pairing information among at least one searched peripheral device.

In one embodiment, the establishing module 3020 may determine whether the state or environment of the first electronic device meets a condition specified by the pairing information, if the state or environment of the first electronic device is determined to meet the condition specified by the pairing information, may establish a communication connection with the second electronic device identified by the pairing information. For example, the establishing module 3020 may measure the state or environment (e.g., location or time) of the first electronic device through the sensor module (e.g., the sensor module 240).

In one embodiment, the establishing module 3020 may obtain the location information of the first electronic device, determine whether the first electronic device is located in an area specified by the pairing information, if the first electronic device is determined to be located in the area specified by the pairing information, establish a communication connection with the second electronic device identified by the pairing information.

In one embodiment, the establishing module 3020 may obtain current time information, determine whether the current time is identical to a time specified by the pairing information, and if the first electronic device determines that the current time is identical to the time specified by the pairing information, establish a communication connection with the second electronic device identified by the pairing information.

In one embodiment, the obtaining module 3010 may transmit the first bio information to the second electronic device through the transmitting module 3040 and receive the pairing information from the second electronic device through the receiving module 3050.

In one embodiment, the obtaining module 3010 may transmit the first bio information to the second electronic device through the transmitting module 3040, receive the second bio information from the second electronic device through the receiving module 3050, and obtain the pairing information from the memory (e.g., the memory 130 or 230) in the first electronic device, the second electronic device, or the third electronic device.

In one embodiment, the obtaining module 3010 may receive the second bio information from the second electronic device through the receiving module 3050, and obtain the pairing information from the memory (e.g., the memory 130 or 230) in the first electronic device, the second electronic device, or the third electronic device. The establishing module 3020 may initiate to establish a communication connection in case the first bio information and the second bio information are associated with the same user.

Figure 81:
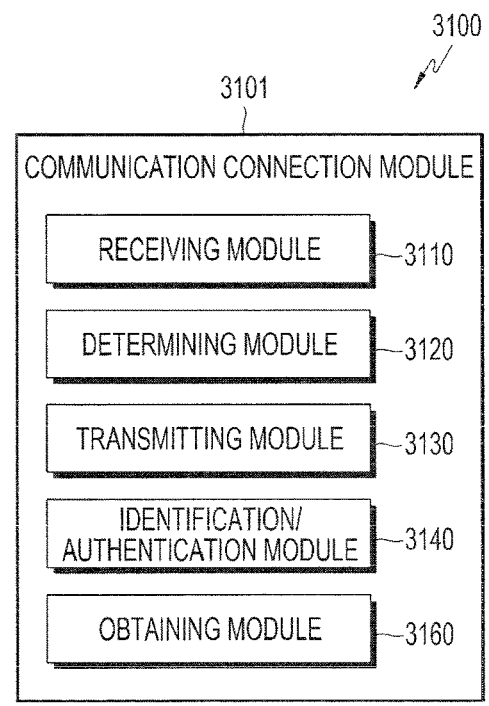
FIG. 81 is a block diagram illustrating a communication connection module of a third electronic device according to an embodiment.

FIG. 81 is a block diagram 3100 illustrating a communication connection module 3101 (e.g., an additional functional module 170) of a third electronic device (e.g., the electronic device 101 or 201) according to an embodiment. The third electronic device may also be referred to as a server device. The communication connection module 3101 may be the additional function module 170 shown in FIG. 51. Referring to FIG. 81, the communication connection module 3101 may include a receiving module 3110, a determining module 3120, a transmitting module 3130, an identification/authentication module 3140, and an obtaining module 3160. The communication connection module 3101 may be provided separately from a processor (e.g., the processor 120 or 210) or may be fully or partially integrated with the processor.

According to an embodiment, the receiving module 3110 may receive the first bio information of the first user from the first electronic device. The receiving module 3110 may receive the second bio information of the second user from the second electronic device. The first and second users may be the same or different, the first and second bio information may be the same or different, and the first and second information may be information measured from the same user or different users, respectively. In one embodiment, the receiving module 3110 may receive the first bio information and the second bio information from the first electronic device. In one embodiment, the receiving module 3110 may receive the first bio information and the second bio information from the second electronic device.

According to an embodiment, the determining module 3120 may determine a communication connection of the first electronic device and second electronic device based on the first bio information and/or second bio information.

According to an embodiment, the transmitting module 3130 may transmit the pairing information for connecting communication of the first electronic device and second electronic device to at least one of the first electronic device and the second electronic device. In one embodiment, the transmitting module 3130 may transmit second pairing information on the second electronic device to the first electronic device. In one embodiment, the transmitting module 3130 may transmit the first pairing information on the first electronic device to the second electronic device. In one embodiment, the transmitting module 3130 may transmit the second pairing information on the second electronic device to the first electronic device and may transmit the first pairing information on the first electronic device to the second electronic device.

According to an embodiment, the identification/authentication module 3140 may identify or authenticate the first user of the first electronic device based on the first bio information. The identification/authentication module 3140 may authenticate or identify the second user of the second electronic device based on the second bio information. In one embodiment, the identification/authentication module 3140 may search the database stored in the memory (e.g., the memory 130 or 230) from bio information identical to the first bio information and determine the user registered in the database corresponding to the searched bio information as the first user of the first bio information or the first electronic device. In one embodiment, the identification/authentication module 3140 may search the database stored in the memory (e.g., the memory 130 or 230) from bio information identical to the second bio information and determine the user registered in the database corresponding to the searched bio information as the first user of the second bio information or the second electronic device. In one embodiment, the identification/authentication module 3140 may compare the first bio information with the second bio information, and in case the first bio information is the same as the second bio information, determine that the first bio information and the second bio information are information from the same user.

According to an embodiment, the obtaining module 3160 may obtain the location/time information of the first electronic device. The obtaining module 3160 may obtain the location/time information of the second electronic device. Each location information may indicate the information on the current location of the electronic device. Each time information may indicate the information on the time of measurement, transmission, and reception of the bio information.

In one embodiment, the determining module 3160 may identify the first user of the first electronic device based on the first bio information through the identification/authentication module 3140 and determine that one of at least one electronic device associated with the first user is the second electronic device.

In one embodiment, the determining module 3160 may identify the first user of the first electronic device based on the first bio information through the identification/authentication module 3140 and determine that one of at least one electronic device associated with the first user is the second electronic device.

In one embodiment, the determining module 3120 may receive the second bio information from the second electronic device through the receiving module 3110 and determine the second electronic device based on the first bio information and the second bio information.

In one embodiment, the determining module 3120 may identify the first user of the first electronic device based on the first bio information through the identification/authentication module 3140, receive the second bio information from the second electronic device through the receiving module 3110, identify the second user of the second electronic device based on the second bio information through the identification/authentication module 3140, and determine one of at least one electronic device associated with the first user and the second user as the second electronic device.

In one embodiment, the determining module 3120 may receive the second bio information from the second electronic device through the receiving module 3110, compare the first bio information with the second bio information through the identification/authentication module 3140, identify the same user of the first electronic device and the second electronic device based on a result of the comparison, and determine one of at least one electronic device associated with the user as the second electronic device.

In one embodiment, the determining module 3120 may identify the first user of the first electronic device based on the first bio information through the identification/authentication module 3140, obtain the location information of the first electronic device through the obtaining module 3160, and determine the second electronic device having location information associated with the location information of the first electronic device according to a preset reference among at least one electronic device associated with the first user.

In one embodiment, the determining module 3120 may identify the first user of the first electronic device based on the first bio information through the identification/authentication module 3140, obtain the time information of the first electronic device through the obtaining module 3160, and determine the second electronic device having time information associated with the time information of the first electronic device according to a preset reference among at least one electronic device associated with the first user.

Figure 82:
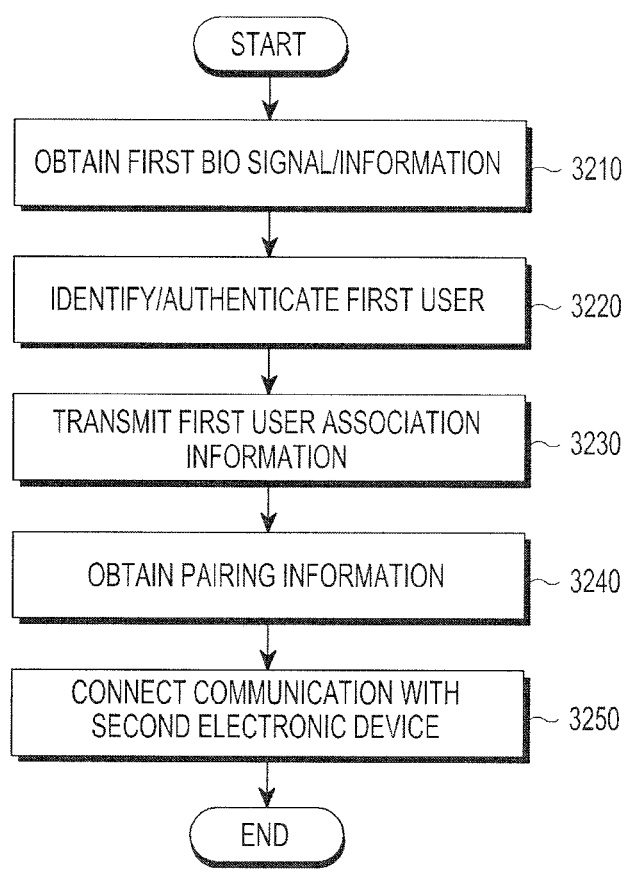
FIG. 82 is a flowchart illustrating a communication connection method of a first electronic device according to an embodiment.

FIG. 82 is a flowchart illustrating a communication connection method of a first electronic device according to an embodiment. The method may be performed by the first electronic device (e.g., the electronic device 101 or 201), the processor (e.g., the processor 120 or 210) in the first electronic device, or the communication connection module (e.g., the communication connection module 3001 or additional function module 170). The method may include all or some of the operations 3210 to 3250.

In operation 3210, the first bio information of the first user may be obtained. The first electronic device may measure the bio signal from the first user through, e.g., a camera module (e.g., the camera module 291), an input device (e.g., the input/output interface 140, the input device 250, or the display 150), a communication device (e.g., the communication interface 160, the communication module 220, or the interface 270), or a sensor module (e.g., the sensor module 240 or bio sensor 240I) and may produce first bio information indicating the user's mental state or body state from the measured bio signal. The bio signal may represent an electrical signal (e.g., an ECG signal or pulse wave signal) output from the bio sensor, and the first bio information may include at least one of the user's identification information, body information, emotion information, health information, disease information, exercise information, activity information, stress information, or sleep information. In one embodiment, the first electronic device may receive the user's bio signal from the external device through a communication device (e.g., the communication interface 160, the communication module 220, the input/output interface 140, or the interface 270) and may produce the first user's first bio information from the received bio signal.

In operation 3220, the first user may be identified/authenticated. The first electronic device may determine the similarity between the obtained first bio information and the user's pre-stored (or registered) bio information for each of at least one pre-registered user and may compare the similarity with a preset threshold. For example, the first electronic device may compare the pattern (or characteristic points defining the pattern) or value (e.g., heart rate) of obtained first bio information with the pattern (or characteristic points defining the pattern) or value of the pre-stored (or registered) bio information of the user to determine the similarity (e.g., the number of characteristic points identical with one another or with a difference within a threshold, or the ratio of the number or value (e.g., ratio in number of similar characteristic points relative to all the characteristic points). The first electronic device may determine that the first user of the obtained first bio information is the registered user with a similarity not less than the preset threshold among the at least one pre-registered user (i.e., the two users are the same person).

In one embodiment, operation 3220 may be omitted, and the first electronic device may transmit the first bio information to the third electronic device, and the third electronic device may identify/authenticate the first user based on the first bio information.

In operation 3230, as the first bio information is obtained or the first user is identified/authenticated, the first user association information may be transmitted to the third electronic device. In one embodiment, the first electronic device may transmit the first user association information to the third electronic device through the second electronic device. In one embodiment, the first electronic device may transmit the first user association information to the second electronic device. The first user association information may include at least one of the first bio information, the first user's identification information, identification information of the first electronic device, and first pairing information on the first electronic device. The first user association information may include at least one of account, ID, name, address, email address, phone number, and personal information. The pairing information may include at least one of the ID of the second electronic device, phone number, SIM number, network address, IP address, MAC address, BT address, and AP information. The first electronic device may obtain user association information, such as the time of measuring or obtaining the bio signal/information and/or the user's movement before/after the same, location, and current time. The electronic device may obtain the time of measuring or obtaining the bio signal/information and/or the user association information before/after the same through at least one of a communication device (e.g., the communication interface 160, the communication module 220, the input/output interface 140, or the interface 270), an input device (e.g., the input/output interface 140, the input device 250, or the display 150), a sensor module (e.g., the sensor module 240 or bio sensor 240I), a camera module (e.g., the camera module 291), and a memory (e.g., the memory 130 or 230).

In operation 3420, the pairing information for connecting connection of the first and second electronic devices may be obtained by the first electronic device. In one embodiment, the first electronic device may receive second pairing information on the second electronic device from the third electronic device. In one embodiment, the first electronic device may receive second pairing information on the second electronic device from the third electronic device through the second electronic device. In one embodiment, the first electronic device may receive the second pairing information from the second electronic device.

In operation 3250, the communication connection may be established between the first and second electronic devices based on the pairing information. In one embodiment, the first electronic device may automatically establish the communication connection with the second electronic device specified by the pairing information in the list of peripheral devices obtained through a discovery operation. In one embodiment, the first electronic device may search for at least one peripheral device and establish a communication connection with the second electronic device identified by the pairing information among at least one searched peripheral device. In one embodiment, the electronic device may determine whether the state or environment of the first electronic device meets a condition specified by the pairing information, if the state or environment of the first electronic device is determined to meet the condition specified by the pairing information, may establish a communication connection with the second electronic device identified by the pairing information. For example, the electronic device may measure the state or environment (e.g., location or time) of the first electronic device through the sensor module (e.g., the sensor module 240). In one embodiment, the electronic device may obtain the location information of the first electronic device, determine whether the first electronic device is located in an area specified by the pairing information, if the first electronic device is determined to be located in the area specified by the pairing information, establish a communication connection with the second electronic device identified by the pairing information.

In one embodiment, the electronic device may obtain current time information, determine whether the current time is identical to a time specified by the pairing information, and if the first electronic device determines that the current time is identical to the time specified by the pairing information, establish a communication connection with the second electronic device identified by the pairing information.

Figure 83:
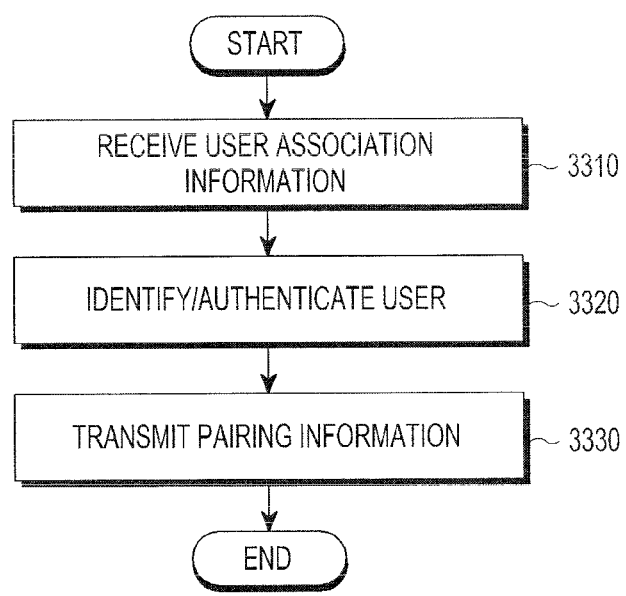
FIG. 83 is a flowchart illustrating a communication connection method of a third electronic device according to an embodiment.

FIG. 83 is a flowchart illustrating a communication connection method of a third electronic device according to an embodiment. The method may be performed by the third electronic device (e.g., the electronic device 101 or 201), the processor (e.g., the processor 120 or 210) in the third electronic device, or the communication connection module (e.g., the communication connection module 3101 or additional function module 170). The method may include all or some of the operations 3310 to 3330.

In operation 3310, the user association information may be received. The third electronic device may receive user association information from the first electronic device and/or second electronic device through the communication device (e.g., the communication interface 160, communication module 220, or interface 270). In one embodiment, the third electronic device may receive first user association information from the first electronic device and second user association information from the second electronic device. In one embodiment, the third electronic device may receive the first user's first bio information from the first electronic device and the second user's second bio information from the second electronic device. The first and second users may be the same or different, the first and second bio information may be the same or different, and the first and second information may be information measured from the same user or different users, respectively.

In operation 3320, the user corresponding to the received user association information may be identified/authenticated. The third electronic device may authenticate or identify the first user of the first electronic device based on the first user association information. The third electronic device may authenticate or identify the second user of the second electronic device based on the second user association information.

In operation 3330, the pairing information may be transmitted. The third electronic device may transmit the pairing information for connecting communication of the first electronic device and second electronic device to at least one of the first electronic device and the second electronic device. In one embodiment, the third electronic device may transmit the second pairing information on the second electronic device to the first electronic device and may transmit the first pairing information on the first electronic device to the second electronic device. In one embodiment, the third electronic device may perform transmission of the pairing information based on a ninth database representing the correlation of the user information, device information, and communication connection information. The ninth database may be stored in the memory of the third electronic device or external device.

In one embodiment, the ninth database may have a form as shown in Table 10.

TABLE 10

| user information | device information | communication connection information |
|---|---|---|
| H101 | L101 | M101 |
| H101 | L102 | M102 |
| H102 | L103 | M103 |
| H102 | L104 | M104 |
| ... | ... | ... |

In Table 10, the user information (e.g., H101, H102, . . . ) may represent the information (e.g., account, ID, name, address, email address, phone number, personal information, or bio information) for identifying the user. The device information (e.g., L101, L102, . . . ) may represent the information (e.g., ID, phone number, SIM number, network address, IP address, MAC address, or BT address) for identifying the electronic device and pairing information (e.g., ID, address, AP information, or password). The communication connection information (e.g., M101, M102, . . . ) may represent the information (e.g., ID of other user/electronic device, address, or account) for identifying the other electronic device to be connected with the electronic device or the user of the other electronic device or the state or environmental condition of the electronic device and/or the other electronic device to initiate the communication connection between the electronic device and the other electronic device.

Figure 84:
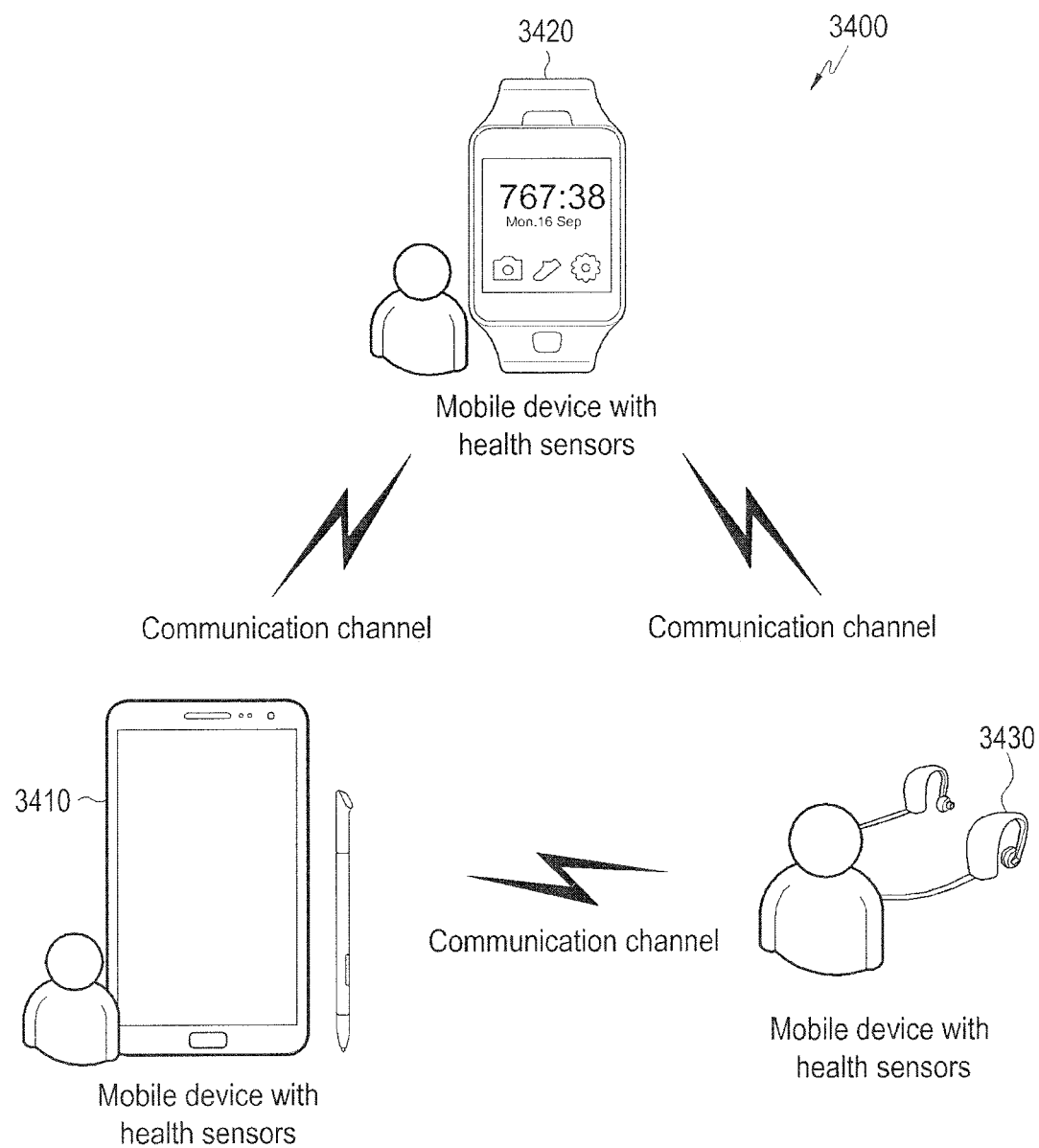
FIG. 84 illustrates a network environment between electronic devices according to an embodiment.

FIG. 84 illustrates a network environment 3400 among electronic devices 3410, 3420, and 3430 according to an embodiment. Each of the electronic devices 3410, 3420, and 3430 may have the same or similar configuration to the whole or part of the configuration of the electronic device 201 shown in FIG. 52 or the electronic device 101 shown in FIG. 51, for example. Referring to FIG. 84, according to an embodiment, the network environment 3400 may provide a wireless connection and data communication function between the electronic devices 3410, 3420, and 3430. The bio sensor-embedded electronic device may be operated in connection with other electronic devices. The bio sensor (e.g., PPG sensor)-embedded wrist watch device 3420 and the bio sensor (e.g., PPG sensor)-embedded earphone 3430 may be mutually connected through wireless communication, and in the case of playing multimedia, the earphone 3430 may output audio, and the wrist watch device 3420 may display a GUI. Further, a plurality of electronic devices, such as a bio sensor (e.g., PPG sensor)-embedded smartphone 3410, wrist watch device 3420, and earphone 3430, may be connected with one another, and the plurality of electronic devices may operate to utilize their mutual resources, such as separating and playing contents or communicating notifications.

For long-term information exchange, communication channels may be established for the electronic devices to communicate with one another. Each electronic device may search for peripheral devices through a discovery operation to establish a communication channel and may perform a pairing operation of establishing a communication channel by exchanging their addresses or IDs with a peripheral device. Typically, such communication connection may require the user to conduct several operations, e.g., the operation of requesting a discovery operation to search for peripheral devices, the operation of designating one of the searched peripheral devices, and the operation of inputting a password for communication connection. According to an embodiment, the electronic devices may automatically establish a communication connection through user identification/authentication.

The user identification/authentication may be performed by recognizing the bio information. The electronic device may analyze one or more bio signals/information of the user's blood pressure, blood flow, pulse wave, heart rate (HRM, HRV), body temperature, respiratory rate, oxygen saturation, heart-lung sound brain wave, skin resistance, EMG, ECG, and gait to determine whether the bio characteristic information has a preset reference or more of consistency with pre-stored user bio information. The electronic device may recognize one or more bio information of iris, finger print, voice pattern, face, sole pattern, palm pattern, hand vein, and gait pattern information and determine whether it has a predetermined reference or more of similarity with pre-stored user bio information to perform the user identification/authentication.

For example, to wirelessly connect a smart watch with a smartphone, the operation of recognizing the bio characteristic information by each device may be performed through a user input or running a health sensor. If the authentication using the bio characteristic information is performed and the user is authenticated as a valid user, the two devices each transmit user-related information to the server on the network. Such user related information may include one or more of account ID, name, address, email address, phone number, and personal information. The transmitted information transfers, to at least one device, access information for accessing the other device, so that they are associated or identical to each other, and the two devices may be connected together. The access information includes information related to short range communication of the device, e.g., one or more of the type of available communication, ID of the short range communication means, password for connection, SIM number, MAC address, BT address, and device identifier. The access information may be the same as the user related information or may be added when transmitting the user related information to the server. Or, in case the two user's information are associated or the same on the server, the server may additionally request. In the case of using the user related information, one device may recognize and use the bio characteristic information, and the other may recognize and use bio authentication information. Or, they may perform their own authentication using different types of health sensors and then connect.

In another embodiment, in case the two devices each transfer a bio signal or bio characteristic information to the server, and similarity between information received by the two devices is determined, at least similar bio signal or bio characteristic information should be able to be gathered. That is, in the case of connecting together a smartphone and a smartwatch, if the two devices both use a PPG, each pulse wave-related information may be transmitted to the server and may be analyzed to assess the similarity. Or, the two devices both may measure ECGs and transfer their waveforms to the server. Even when the same sensor is not used, at least, sensors with similarity should be used. For example, in case the smartphone uses an ECG, and the smartwatch uses a PPG, similar HRVs may be obtained from the ECG wave and pulse wave. This is why the R-R interval (RRI) and PPI values are similar except for the difference in time when each wave occurs.

If the devices use one or more of the time of occurrence of the mutual user authentication operation and the area where the authentication occurs, communication connection may be more easily made. That is, if the time of occurrence of the user authentication is within a predetermined time, and the two devices are recognized to be located within a short distance, the objects for which the user related information is to be compared are limited, and thus, the overall processing time for connection shortens.

Figure 85:
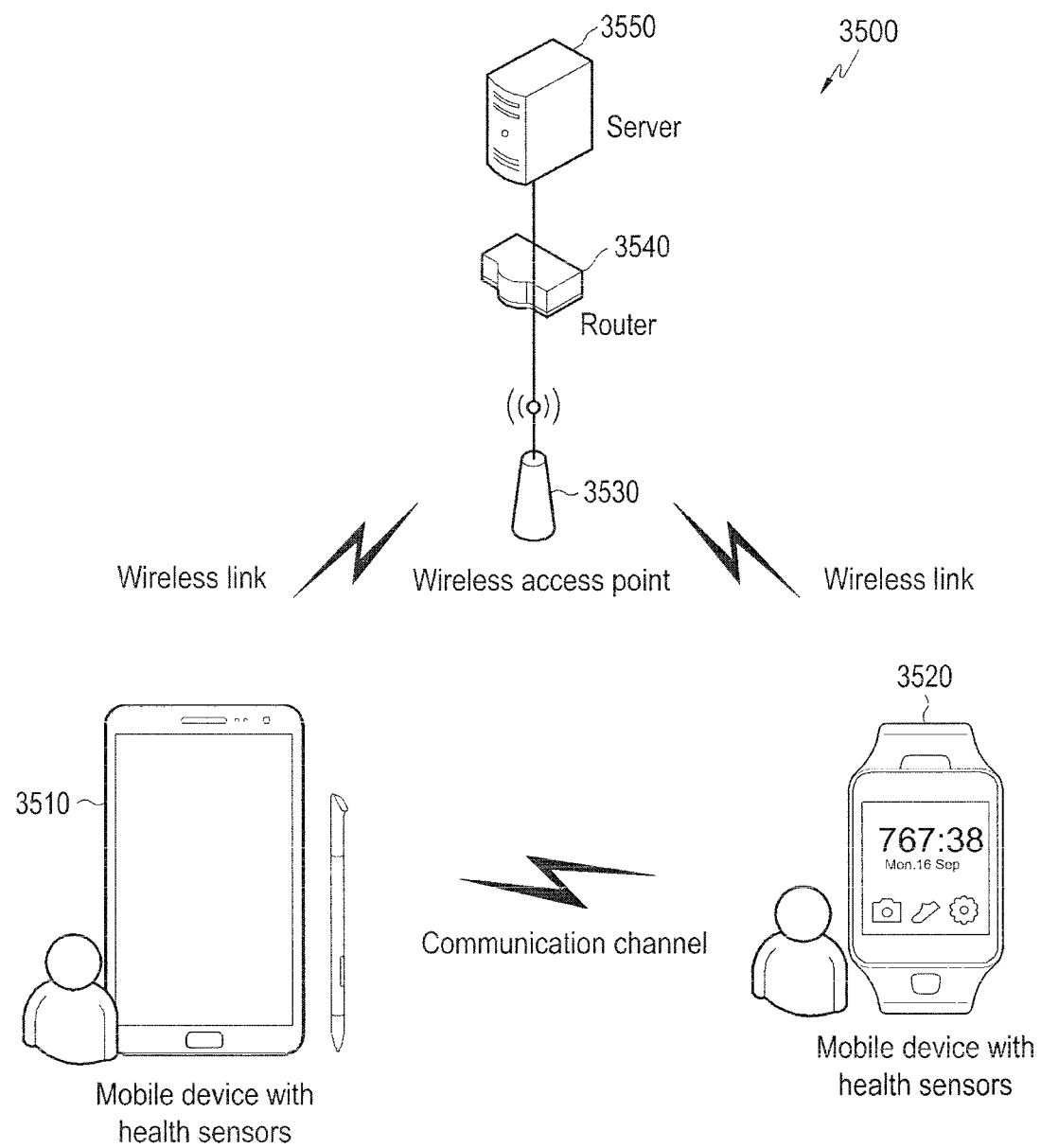
FIG. 85 illustrates a network environment between electronic devices according to an embodiment.

FIG. 85 illustrates a network environment 3500 (e.g., broadband network) between electronic devices according to an embodiment. Each of the electronic devices 3510, and 3520 may have the same or similar configuration to the whole or part of the configuration of the electronic device 201 shown in FIG. 52 or the electronic device 101 shown in FIG. 51, for example. Referring to FIG. 85, according to an embodiment, the process of connecting the two devices 3510 and 3520 may be performed by the server 3550. As an example, it may be assumed that the devices 3510 and 3520 having their respective health sensors, each, include a communication means allowing for connection with the other device and a communication means allowing for access to an IP network.

The devices 3510 and 3520 having a health sensor may be connected through their respective wireless modems to the server 3550 on the IP network. Further, the server 3550 on the IP network may manage each device. For example, the devices 3510 and 3520 having a health sensor, each, may communicate with the server 3550 through the wireless AP 3530 and the router 3540.

The server 3550 is not limited to the stereotypical servers. For example, one of the plurality of electronic devices may serve as a server or main electronic device to manage the devices with a health sensor. If the health sensor equipped device is activated, the device provides the server 3550 with the bio information and information indicating that it has been activated. At this time, the bio information may be overall raw data or may be information including a characteristic point that may prove that he is an individual among the data, i.e., data that has first undergone a computational process. Further, the data transmitted to the server 3550 may include information in addition to the bio information. For example, the data transmitted to the server may include information capable of proving the user (e.g., account, ID, name, unique number, or phone number) or the location information or time information of the device, or information related to the short range communication of the device (e.g., information indicating what type of short range communication means it has, the ID of the short range communication means, password for connection, or MAC address). The server 3550 may store and manage each device's information through the information, and although the information may be received whenever the bio information is activated, each device may perform the transmission only once at first, and it may then enable the server to manage the same or perform retransmission or periodical retransmission only when a variation occurs.

Figure 86:
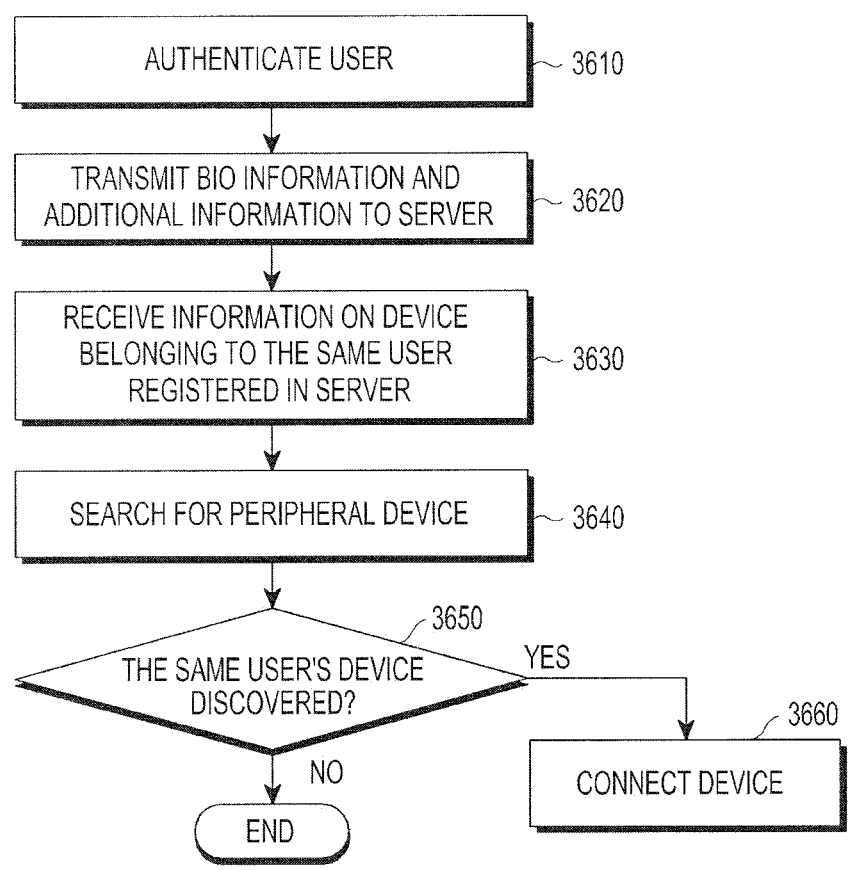
FIG. 86 is a flowchart illustrating an operational method of an electronic device according to an embodiment.

FIG. 86 is a flowchart illustrating an operational method of an electronic device according to an embodiment. The method may be performed by the electronic device (e.g., the electronic device 101 or 201), the processor (e.g., the processor 120 or 210) in the electronic device, or the communication connection module (e.g., the communication connection module 3001). The method may include all or some of the operations 3610 to 3660.

Referring to FIG. 86, the electronic device may manage inter-device connection of the user using the server. In operation 3610, if the user is authenticated through the health sensor, the electronic device transmits the user's bio information and person-related additional information to the serve in operation 3620. In operation 3630, the electronic device receives information on the counterpart device registered in the user from the server. The counterpart device may receive the electronic device's information from the server by performing the same operations as the electronic device. In operation 3640, the electronic device may search for peripheral devices, and if it is determined in operation 3650 as a result of the search based on the information received from the server that there is another electronic device registered in the same user, it may connect with the other device using the information received from the server.

The server may manage information necessary for device connection as well as the personal information. For example, the server has additional information as to what type of communication module each has. If the bio recognition proceeds, and one device is activated, the server identifies the communication means possessed by the activated device and identifies the communication resources of other devices. The communication resources include various communication means (e.g., Zigbee, Bluetooth, Wi-Fi direction, or BLE) capable of supporting device-to-device connection through the short range communication network. The server may request connection with the activated other device utilizing the communication means available to each device. In the above embodiment, each device may receive information for connection with the other device through each communication means and the server. For example, if the activated device and the registered device have a Bluetooth module, it may receive information necessary for pairing (e.g., a pin code or BT address) through the server to enable connection between the plurality of devices without the need for the user to input the information.

Figure 87:
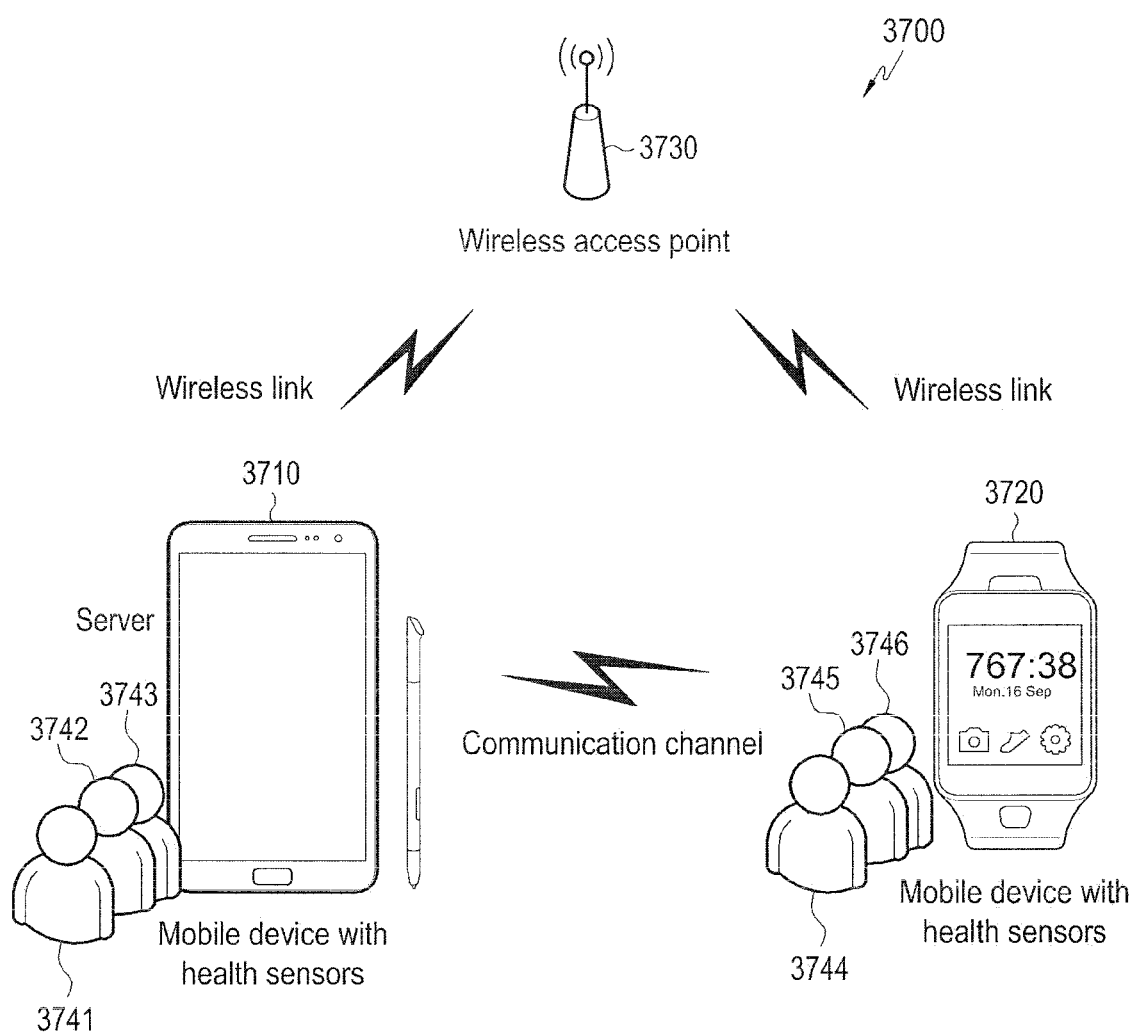
FIGS. 87 to 89 illustrate network environments between electronic devices according to embodiments of the present invention.
Figure 88:
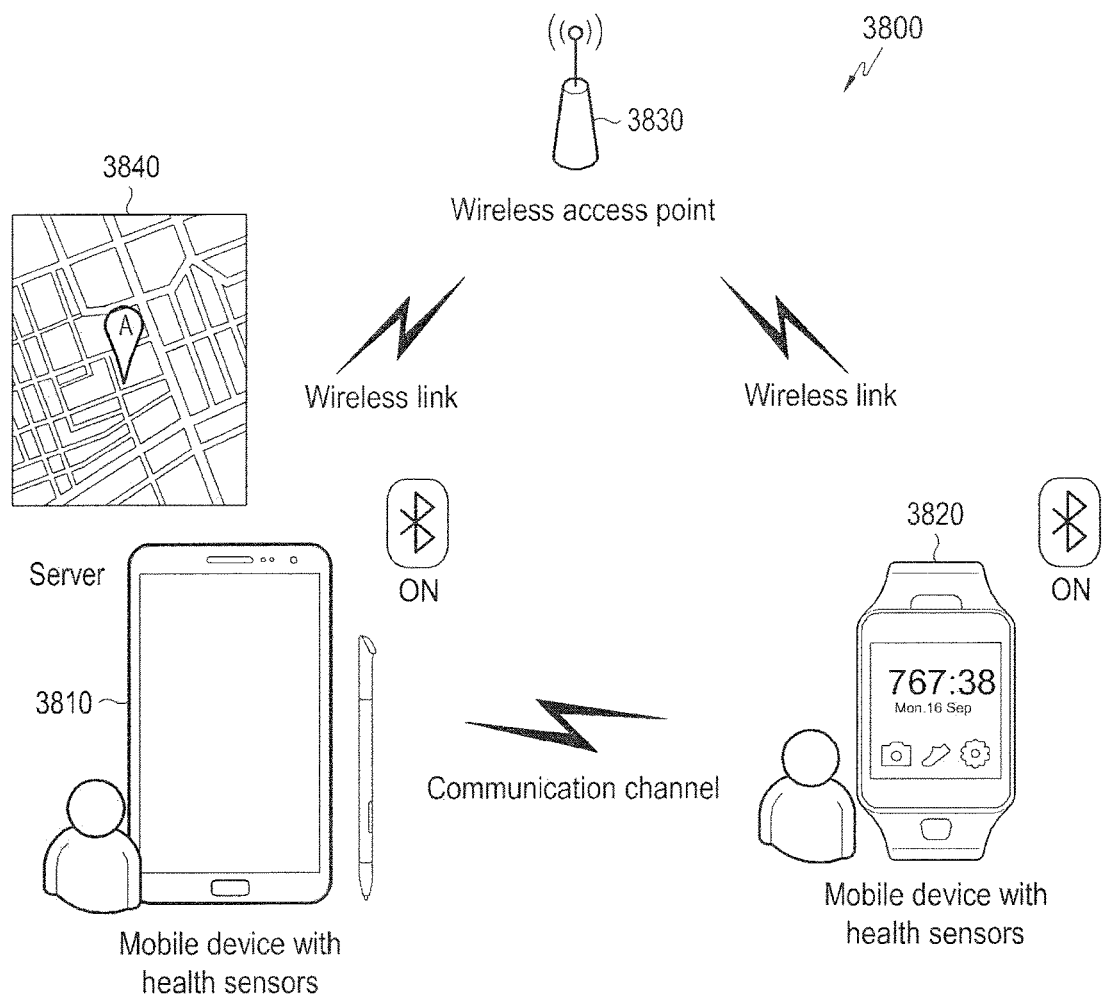
Figure 89:
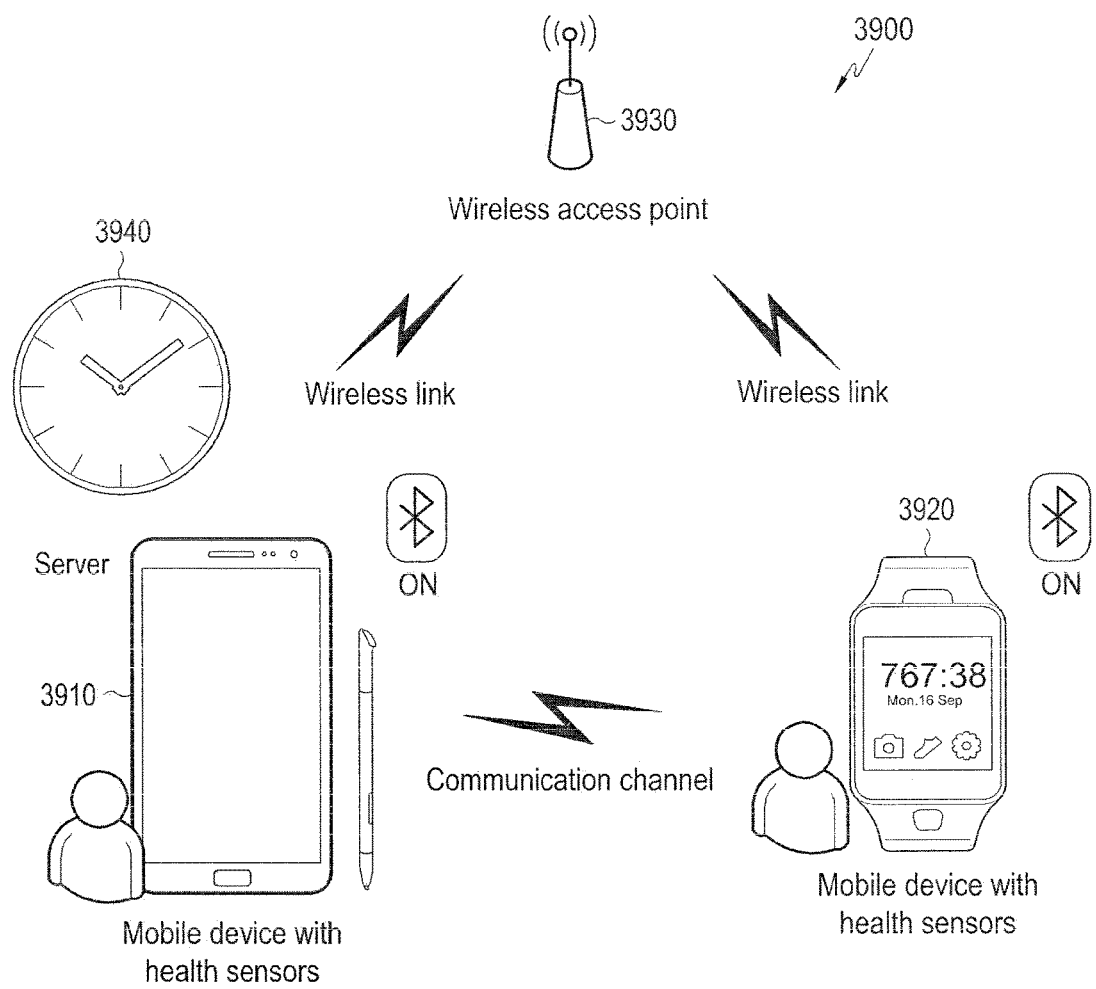

FIGS. 87 to 89 illustrate network environments between electronic devices according to embodiments of the present invention. Each electronic device may have the same or similar configuration to the whole or part of the configuration of the electronic device 201 shown in FIG. 52 or the electronic device 101 shown in FIG. 51, for example.

The network environment 3700 shown in FIG. 87 shows an example in which a plurality of electronic devices 3710 and 3720 with a health sensor each manage multiple users. For example, first to third users 3741, 3742, and 3743 may be registered in the first electronic device 3710 capable of functioning as a server for the second electronic device 3720, and fourth to sixth users 3744, 3745, and 3746 may be registered in the second electronic device 3720. The first electronic device 3710 and the second electronic device 3720 may directly communicate with each other. For example, the first electronic device 3710 may store information on the second electronic device 3720 or may receive the information through a wireless AP 3730 from a separate server.

According to an embodiment, device access management may be conducted to distinguish the multiple users. In the above embodiment, the term "user" may mean one person or this may also be constituted of a user group having the authority to use the same device. For example, such device as a tablet PC or smart TV shared by family members may be shared by multiple users.

In case of a user group, the authority of each user for the device may apply differentially per user. That is, the user group may receive an authority interchangeably for a device common to a plurality of permitted devices or a device permitted to an individual alone, and even with the same device, the authority to use may differ user by user. For example, even though a health sensor-equipped tablet PC individually used may be shared by all of the family members, if the health sensor-equipped watch type device used by the daddy is present in an accessible area in case the daughter uses the tablet PC, the connection between the two devices may be controlled and managed by the server.

The network environment 3800 shown in FIG. 88 shows an example of connecting two electronic devices using the location information 3840 of the first electronic device 3810 and/or second electronic device 3820. The first electronic device 3810 capable of functioning as a server for the second electronic device 3820 may directly communicate with the second electronic device 3820. For example, the first electronic device 3810 may store information on the second electronic device 3820 or may receive the information through a wireless AP 3730 from a separate server.

The network environment 3900 shown in FIG. 89 shows an example of connecting two electronic devices using the time information 3940 of the first electronic device 3910 and/or second electronic device 3920. The first electronic device 3910 capable of functioning as a server for the second electronic device 3920 may communicate with the second electronic device 3920 directly or via wireless AP 3930. For example, the first electronic device 3910 may store information on the second electronic device 3920 or may receive the information through a wireless AP 3930 from a separate server.

According to an embodiment, access using time or location information is also possible. As an example, as the additional information, one or more of the location information or time information may be included, and inter-device connection using the same may also be possible. When one device is activated through the location information of each device, such operation that only devices positioned in a connectable location, rather than all registered devices attempting to connect, may attempt connection, may be taken into account. Or, such configuration may be made where the characteristics of the devices remaining stationary at particular positions may be determined, and in case activation is done in a particular area, the devices within the area may establish connection.

The server manages the information on the location where the device is used or the time when the devices are connected or activated. Each device updates its location information periodically or when a designated event occurs, and the server manages the information.

Accordingly, the device may attempt inter-device connection automatically when it enters a particular area or upon determining that the two devices enter the same area, allowing for automated connection. Further, the above method may interwork with the power control method of the module itself in interoperation with a power control scheme. That is, unless the device meets the above condition, the inter-device communication means may enter a power save mode or maintain a sleep state or fully power off, and if the device meets the condition, it may activate the inter-device communication means to proceed with the connection. By contrast, the power control scheme may apply to both when the device enters the condition and when it exits the condition. As an example, such operation may be considered where upon entering a corresponding area, the Bluetooth module may turn on to perform a pairing operation, such as scanning, and if departing from the area, the Bluetooth module may turn off for power saving.

The time information may be utilized based on the current use time or average use time of the device. For example, since devices being used ever in a particular time are highly likely to be used simultaneously, such setting may be made as to allow connection to be attempted in a particular time zone, and a turned-on device may be determined using the information of turning on/off the device so that connection may be attempted. The server manages the information on the time when each device is connected or activated or the time when the device is used. Each device updates the information on the time when the device is used periodically or when a designated event occurs, and the server manages the information. Accordingly, the device enables automated connection by automatically attempting inter-device connection during a particular time interval or entering a particular time. Further, the above method may interwork with the power control method of the module itself in interoperation with a power control scheme. That is, unless the device meets the above condition, the inter-device communication means may enter a power save mode or keep the power in a sleep state or fully power off, and if the device meets the condition, it may activate the inter-device communication means to proceed with the connection. By contrast, the power control scheme may apply to both when the device enters the condition and when it exits the condition. As an example, such operation may be considered where upon arrival at a particular time, the Bluetooth module may turn on to perform a pairing operation, such as scanning, and if the particular time zone passes, the Bluetooth module may turn off for power saving.

Figure 90:
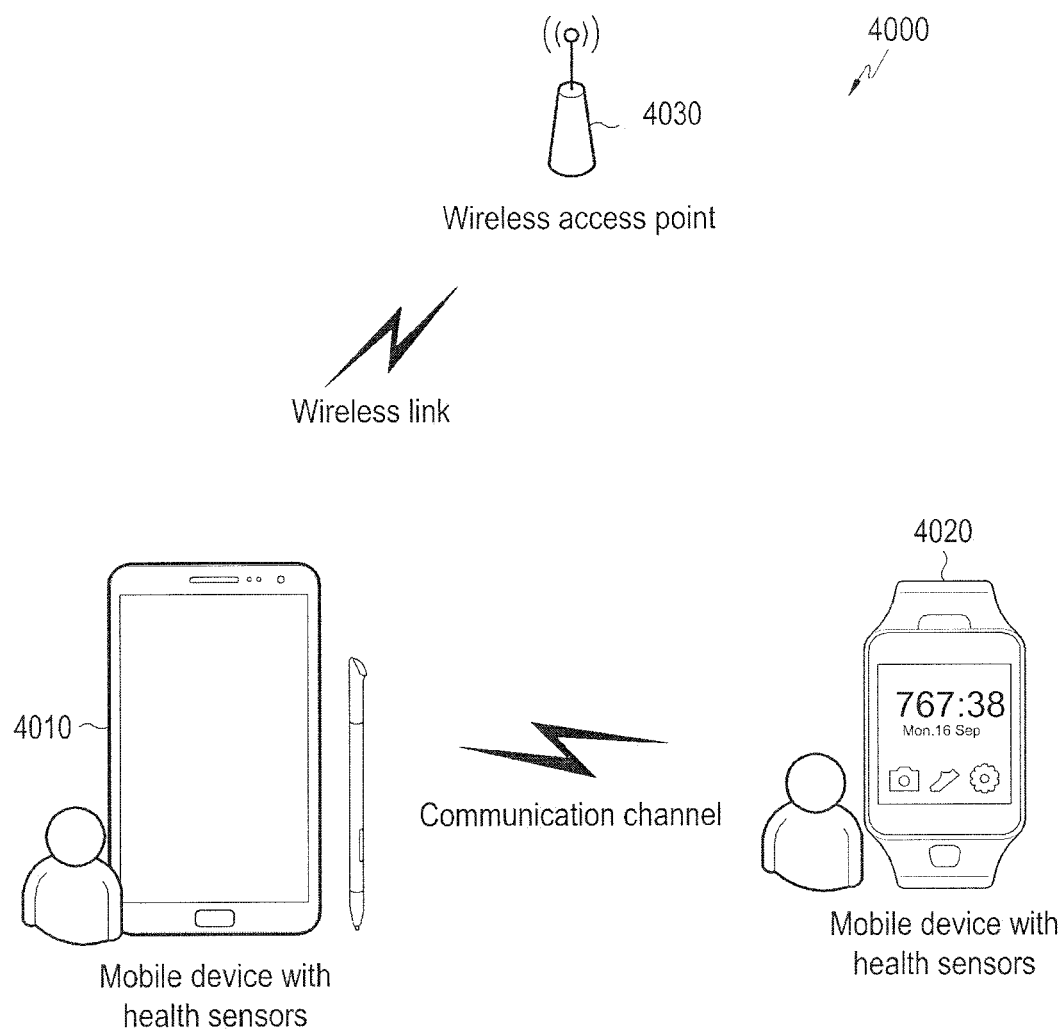
FIG. 90 illustrates a network environment between electronic devices according to an embodiment.

FIG. 90 illustrates a network environment 4000 between electronic devices according to an embodiment. For example, the health sensor-equipped electronic devices each may have only a first communication means allowing for inter-device connection or may have a second communication means that enables access to the IP network through the first communication means and the wireless AP 4030. For example, the first electronic device 4010 may have both the first and second communication means, and the second electronic device 4020 may have only the first communication means.

This example may apply where first and second electronic devices 4010 and 4020 each include both the first and second communication means.

In one embodiment, each device may attempt wireless connection from the time when the user(s) wears the two devices. At this time, each device may sense the bio signal, extract the bio information, and compare the bio information of the two devices attempting the wireless connection and in case the bio information are similar, it may complete the wireless connection. The operation of comparing the bio information may send bio information or its related information from the first electronic device to the second electronic device and compare, by the second electronic device, the information with the information extracted by the second electronic device. Or, the second electronic device may send the bio information or its related information extracted by the first and second electronic devices to the third electronic device, and the third electronic device may determine the similarity of the information.

Figure 91:
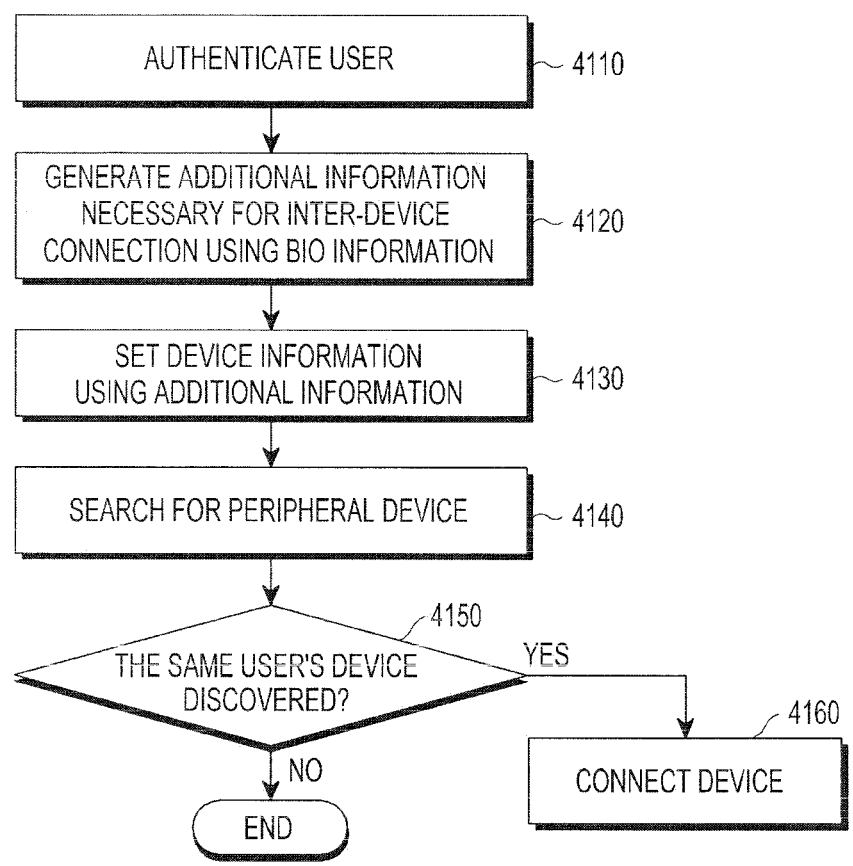
FIG. 91 is a flowchart illustrating an operation of an electronic device according to an embodiment.

FIG. 91 is a flowchart illustrating an operation of an electronic device according to an embodiment. The method may be performed by the electronic device (e.g., the electronic device 101 or 201), the processor (e.g., the processor 120 or 210) in the electronic device, or the communication connection module (e.g., the communication connection module 3001 or additional function module 170). The method may include all or some of the operations 4110 to 4160.

According to an embodiment, the electronic device may generate inter-device connection information of the user based on the information from the health sensor to manage the device connection.

In operation 4110, if the user is authenticated through the health sensor, the electronic device may generate additional information necessary for inter-device connection using the bio information in operation 4120. For example, it may gather the bio signal from the time when one user wears the two devices or the time when the operation of measuring the bio signal is performed, or the time when the user input (e.g., menu selection or button input) for each wireless connection is performed and may obtain one or more of the bio information or authentication information (e.g., user ID, name, unique number or other identification information) through the same.

In operation 4130, the electronic device may set device information using additional information. In operation 4140, the electronic device may search for peripheral devices. For example, the electronic device may broadcast the device information set using the bio information to the peripheral devices and may discover peripheral devices having the device information set using the bio information. If it is determined as a result of the search based on the bio information in operation 4150 that there is other device owned by the same user, the electronic device may connect with the other device in operation 4160.

Figure 92:
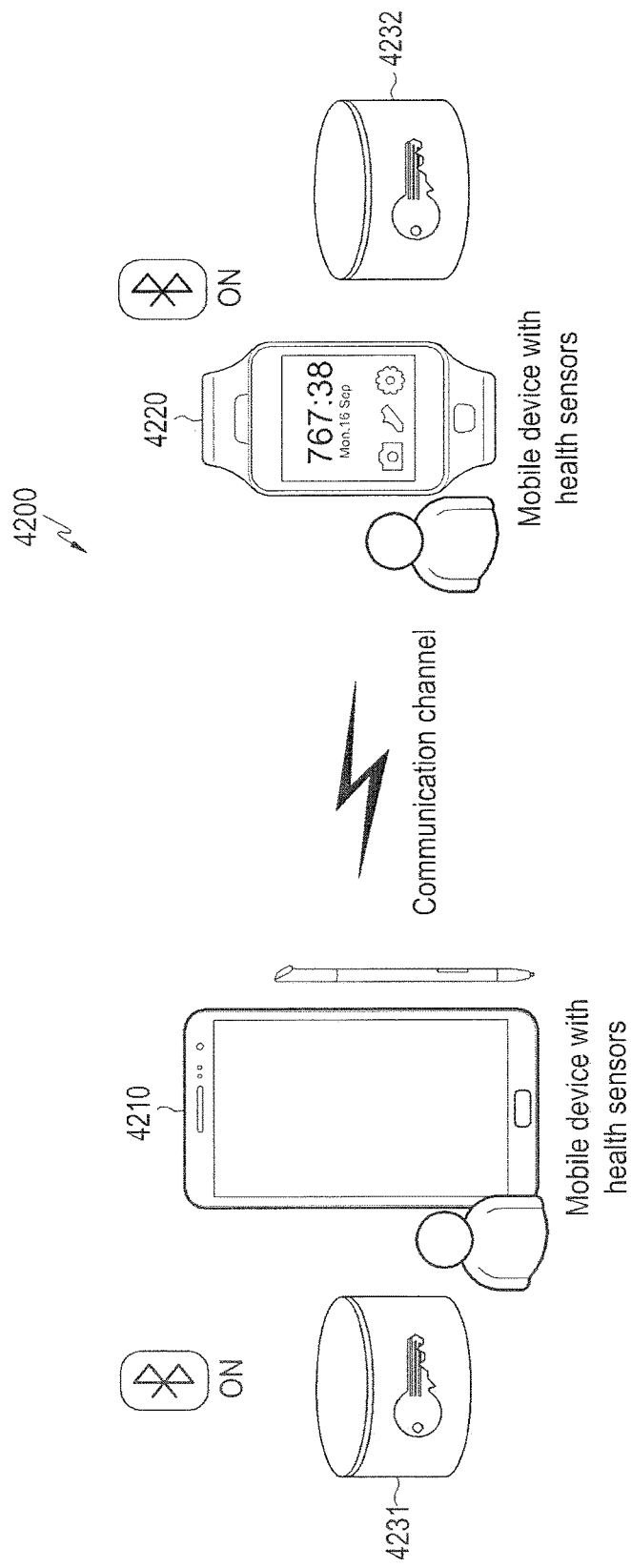
FIGS. 92 and 93 illustrate network environments between electronic devices according to embodiments of the present invention.
Figure 93:
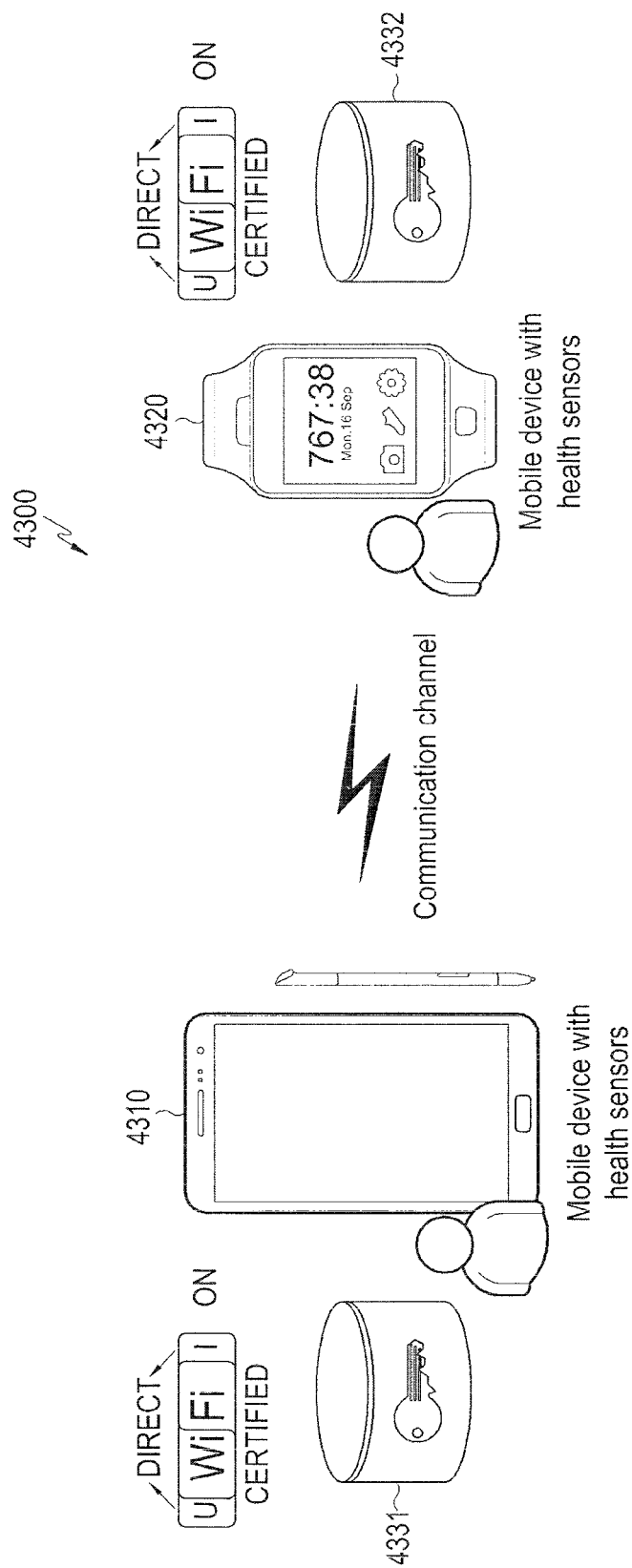

FIGS. 92 and 93 illustrate network environments between electronic devices according to embodiments of the present invention. Each electronic device may have the same or similar configuration to the whole or part of the configuration of the electronic device 201 shown in FIG. 52 or the electronic device 101 shown in FIG. 51, for example.

The network environment 4200 shown in FIG. 92 shows an example in which connection between the electronic devices 4210 and 4220 is performed through Bluetooth (BT) based on the bio information.

The network environment 4300 shown in FIG. 93 shows an example in which connection between the electronic devices 4310 and 4320 is performed through Wi-Fi direct based on the bio information.

In another embodiment, each device may attempt wireless connection from the time when the user wears the two devices. At this time, each device may sense the bio signal, extract the bio information, and use the same for authentication of the existing communication means. That is, the electronic device may automatically generate an inter-device connection password and the device name necessary for connection through the information obtained through the health sensor. Since the bio information has a different characteristic per individual, it may be configured to generate unique values 4231 and 4232 based on the bio characteristics. The thusly generated values 4231 and 4232 may be used to configure the ID value of each device in the inter-device communication. For example, the ID itself may be generated as a value, e.g., a particular stream of letters, using the value generated through the bio information, or the corresponding data may be added to a particular portion of the data constituting the ID. Further, it may also be considered to generate separate data capable of representing the value and additionally utilizing the value for the existing inter-device communication.

A more specific example is given below referring to current commonplace inter-device communication techniques. When a Bluetooth-based communication means is used, the Bluetooth-based connection is performed through the device name and pin code. In the above embodiment, if one device senses a bio signal, the Bluetooth device name and pin code may be generated based on the bio signal. The device name may be information extracted from the bio information alone or may also be generated in interoperation with the personal information of the device, such as account information. If the other device is activated by the same user, the device performs scanning as to whether there is a device name generated with the same bio information around using Bluetooth, and if there is a device name generated with the same bio information as a result of the scanning, it attempts to connect with the device. Further, since the security pin code required for connection with the device may also be generated based on the bio information, the two devices may connect together even without entering additional user information. This is not restricted to the two devices, and may also be used for connection between a plurality of devices, and even when several users share the device, the use by the user may be recognized, and thus, the information may be updated in real-time, allowing the same to apply fitting each user.

A similar example to the above embodiment may also be used for existing communication devices, such as Wi-Fi direct. FIG. 93 is a view illustrating an example of configuring inter-device connection using a Wi-Fi direct scheme. Since Wi-Fi direct performs inter-device connection in a similar way, it has the same basic operation. If one device is activated by the bio information, the device searches for peripheral devices using Wi-Fi direct. An access attempt is made to the device whose user is predicted to be the same among the searched devices using Wi-Fi direct, and at this time, the authentication scheme necessary for access may also use the values 4331 and 4332 generated based on the bio information. That is, if the user uses the device, the devices may mutually recognize that the device is used by the same user, and attempt to connect accordingly. Because, after the connection attempt, the authentication for connection may also be replaced with the authentication information generated based on the bio information, the devices may recognize that the devices are being used by the same user even without the user's additional input, and a security authentication procedure may also be performed based on the bio information without additional input.

In one embodiment, the inter-device connection based on the bio information may be made possible only for a particular time after the bio recognition is done. That is, if the device is activated using the bio information, a search is done as to whether there are other peripheral devices activated using the bio information, and the peripheral devices may be searched by stopping the search or making the period of search different from the initial one.

According to an embodiment, a method for connecting communication by a first electronic device may include the operation of obtaining first bio information, the operation of obtaining pairing information for communication connection with a second electronic device, and the operation of establishing the communication connection with the second electronic device using the pairing information.

According to an embodiment, the operation of obtaining the pairing information may include the operation of identifying a first user of the first electronic device based on the first bio information, the operation of transmitting first user association information on the first user to a third electronic device, and the operation of receiving the pairing information from the third electronic device.

According to an embodiment, the operation of obtaining the pairing information may include the operation of identifying a first user of the first electronic device based on the first bio information, the operation of transmitting first user association information on the first user to a third electronic device, and the operation of receiving the pairing information from the third electronic device, and the first user association information may include at least one of an account, an ID, a name, an address, an email address, a phone number, and personal information.

According to an embodiment, the operation of obtaining the pairing information may include the operation of transmitting the first bio information to the third electronic device and the operation of receiving the pairing information from the third electronic device.

According to an embodiment, the pairing information may include at least one of the ID of the second electronic device, phone number, SIM number, network address, IP address, MAC address, BT address, and AP information.

According to an embodiment, the first bio information may include at least one of iris information, finger print information, palm pattern information, sole pattern information, hand vein information, voice information, blood pressure, HRV, HRM, oxygen saturation, ECG, EMG, brainwave, or skin resistance.

According to an embodiment, the operation of establishing the communication connection may include the operation of searching for at least one peripheral device and the operation of establishing the communication connection with the second electronic device identified by the pairing information among the at least searched peripheral device.

According to an embodiment, the operation of establishing the communication connection may include the operation of determining whether the state or environment of the first electronic device meets a condition specified by the pairing information, if the state or environment of the first electronic device is determined to meet the condition specified by the pairing information, and the operation of establishing a communication connection with the second electronic device identified by the pairing information.

According to an embodiment, the operation of establishing the communication connection may include the operation of obtaining the location information of the first electronic device, the operation of determining whether the first electronic device is located in an area specified by the pairing information, and if the first electronic device is determined to be located in the area specified by the pairing information, the operation of establishing a communication connection with the second electronic device identified by the pairing information.

According to an embodiment, the operation of establishing the communication connection may include the operation of obtaining current time information, the operation of determining whether the current time is identical to a time specified by the pairing information, and if the current time is determined to be identical to the time specified by the pairing information by the first electronic device, and the operation of establishing a communication connection with the second electronic device identified by the pairing information.

According to an embodiment, the operation of obtaining the pairing information may include the operation of transmitting the first bio information to the second electronic device and the operation of receiving the pairing information from the second electronic device.

According to an embodiment, the operation of obtaining the pairing information may include the operation of transmitting the first bio information to the second electronic device, the operation of receiving the second bio information from the second electronic device, and the operation of obtaining the pairing information.

According to an embodiment, the operation of obtaining the pairing information may include the operation of receiving the second bio information from the second electronic device and the operation of obtaining the pairing information, and the operation of establishing the communication connection may be initiated in case the first bio information and the second bio information are associated with the same user.

According to an embodiment, in a storage medium readable by a machine recording a program for running a method for connecting communication by an electronic device, the method may include the operation of obtaining first bio information, the operation of obtaining pairing information for communication connection with a second electronic device, and the operation of establishing the communication connection with the second electronic device using the pairing information.

According to an embodiment, a method for connecting communication by a server device may include the operation of receiving first bio information from a first electronic device, the operation of determining a second electronic device to be connected via communication with the first electronic device based on the first bio information, and the operation of transmitting pairing information for communication connection of the first electronic device and the second electronic device to at least one of the first electronic device and the second electronic device.

According to an embodiment, the operation of determining the second electronic device may include the operation of identifying a first user of the first electronic device based on the first bio information and the operation of determining one of at least one electronic device associated with the first user as the second electronic device.

According to an embodiment, the operation of determining the second electronic device may include the operation of receiving the second bio information from the second electronic device and the operation of determining the second electronic device based on the first bio information and the second bio information.

According to an embodiment, the operation of determining the second electronic device may include the operation of identifying a first user of the first electronic device based on the first bio information, the operation of receiving the second bio information from the second electronic device, the operation of identifying the second user of the second electronic device based on the second bio information, and the operation of determining one of at least one electronic device associated with the first user and the second user as the second electronic device.

According to an embodiment, the operation of determining the second electronic device may include the operation of receiving the second bio information from the second electronic device, the operation of comparing the first bio information with the second bio information, the operation of identifying the same user of the first electronic device and the second electronic device based on a result of the comparison, and the operation of determining one of at least one electronic device associated with the user as the second electronic device.

According to an embodiment, the pairing information may include a condition on a state or environment of a corresponding electronic device of the first electronic device and the second electronic device to initiate the communication connection of the first electronic device and the second electronic device.

According to an embodiment, the pairing information may include a condition on a location of a corresponding electronic device of the first electronic device and the second electronic device to initiate the communication connection of the first electronic device and the second electronic device.

According to an embodiment, the operation of determining the second electronic device may include the operation of identifying a first user of the first electronic device based on the first bio information, the operation of obtaining location information of the first electronic device, and the operation of determining the second electronic device having location information associated with the location information of the first electronic device according to a preset reference among at least one electronic device associated with the first user.

According to an embodiment, the pairing information may include information on a time to initiate the communication connection of the first electronic device and the second electronic device.

According to an embodiment, the operation of determining the second electronic device may include the operation of identifying a first user of the first electronic device based on the first bio information, the operation of obtaining time information on the first electronic device, and the operation of determining the second electronic device having time information associated with the time information of the first electronic device according to a preset reference among at least one electronic device associated with the first user.

According to an embodiment, a storage medium readable by a machine recording a program to run a method for connecting communication by a server device may include the operation of receiving first bio information from a first electronic device, the operation of determining a second electronic device to be connected via communication with the first electronic device based on the first bio information, and the operation of transmitting pairing information for communication connection of the first electronic device and the second electronic device to at least one of the first electronic device and the second electronic device.

Figure 94:
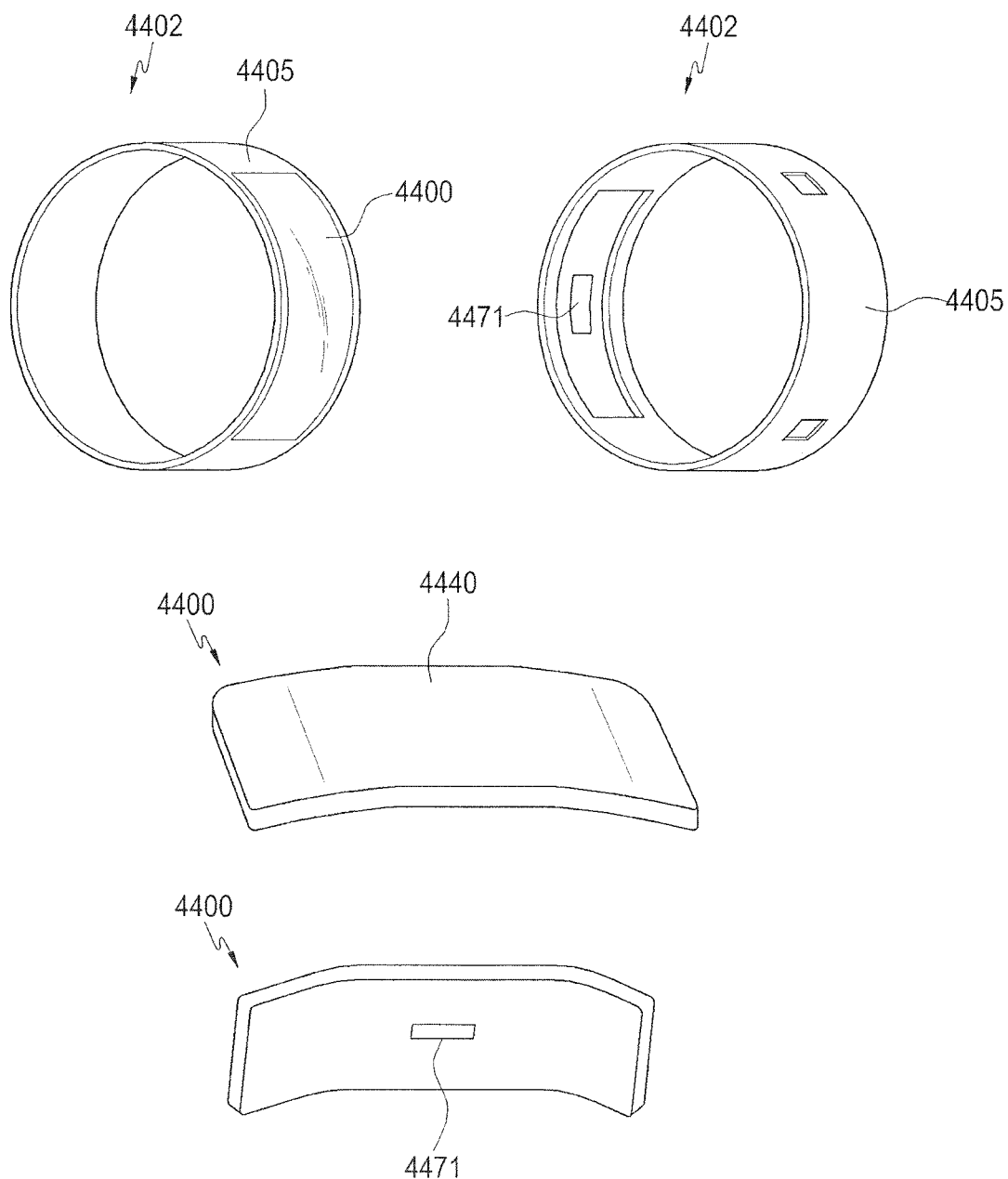
FIG. 94 illustrates an outer appearance of an electronic device module according to an embodiment.

FIG. 94 illustrates an outer appearance of an electronic device module according to an embodiment.

Referring to FIG. 94, the electronic module 4402 may be provided in the form of being wearable at various positions, such as a wrist, finger, ankle, or neck. The size or shape of the electronic module 4402 may be at least partially changed depending on where the electronic device is worn. The electronic module 4402 may include a ring-shape wearing body 4405 and an electronic device 4400 (e.g., the electronic device 101 or 201) disposed at a side of the wearing body 4405 as shown.

The wearing body 4405 has a predetermined width and thickness and may be provided to be shaped as a ring. An adjusting device may be disposed at, at least, a side of the wearing body 4405 to increase the radius when worn and to reduce the radius to be fixed to a predetermined portion after worn. The adjusting device may include at least one of a banding unit, a ring coupling unit, and a folding unit. The size of the wearing body 4405 may be varied depending on the characteristic of the wearing portion. A mounting portion where the electronic device 4400 is mounted may be provided at a side of the wearing body 4405. The mounting portion may be provided in a hole structure by which the electronic device 4400, after mounted, may be supported. For example, the mounting portion may be provided in a structure surrounding the electronic device 4400 to expose the front and rear surface of the electronic device 4400.

The electronic device 4400 may be mounted on the wearing body 4405. Further, the electronic device 4400 may escape from the mounting portion of the wearing body 4405. At least a portion of the rear surface of the electronic device 4400 may be internally exposed, while the electronic device 4400 is mounted on the wearing body 4405. A hear rate monitor (HRM) sensor 4471 (e.g., the bio sensor 240I) included in a sensor module (e.g., the sensor module 240) may be disposed in an area exposed while the electronic device 4400 is mounted on the wearing body 4405. For example, the HRM sensor 4471 may be disposed at the center on the rear surface of the electronic device 4400. The electronic device 4400 may analyze sensor signals gathered by the HRM sensor 4471 to determine the wearing state or wearing portion. A display module 4440 may be disposed on the front surface of the electronic device 4400. According to an embodiment, the display module 4440 of the electronic device 4400 may output in different display directions depending on the wearing state of the electronic device 4400. According to an embodiment, the electronic device 4400 may run different function depending on wearing portions. According to an embodiment, the electronic device 4400 may provide different information outputs for the same function depending on wearing portions.

Figure 95:
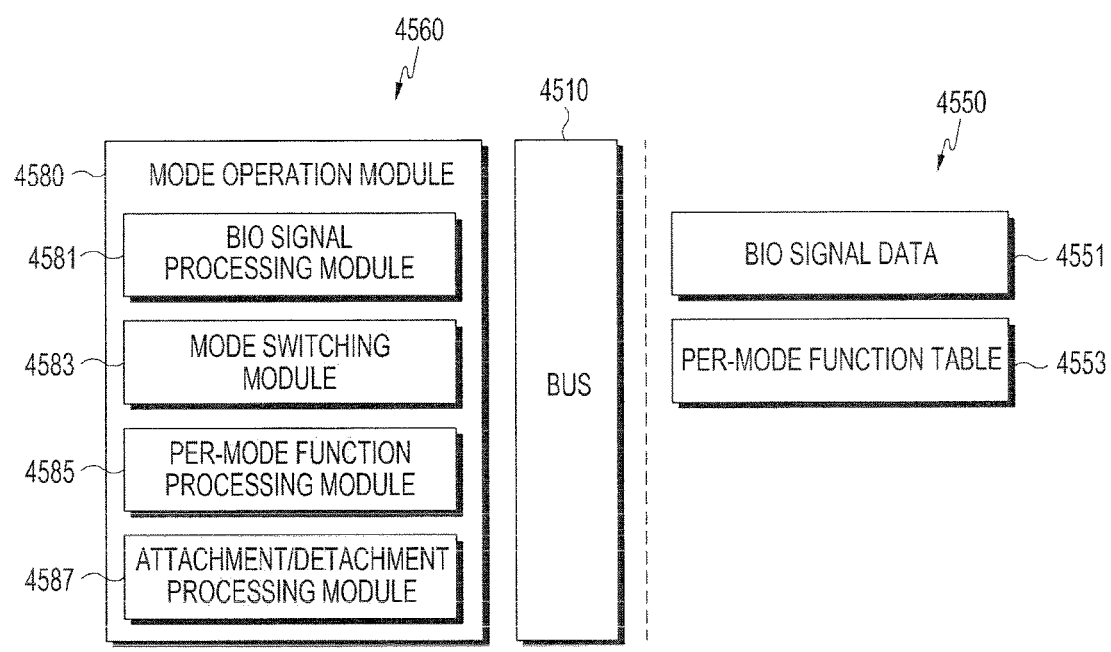
FIG. 95 illustrates a configuration of a mode operation module and a storage module according to an embodiment.

FIG. 95 illustrates a configuration of a mode operation module and a storage module according to an embodiment.

Referring to FIG. 95, the storage module (e.g., the memory 130) may include bio signal data 4551 and a per-mode function table 4553.

The bio signal data 4551 may include reference information. The reference information may be used as a reference to compare bio signals as described supra. According to an embodiment, the reference information may include a reference bio signal when worn on an outer side of a wrist (e.g., in case the PPG sensor contacts the outer side of the wrist) and a reference bio signal when worn on an inner side of the wrist (e.g., when the PPG sensor contacts the inner side of the wrist). Further, the reference information may include a reference bio signal related to an ankle, finger, or neck. According to an embodiment, the reference information may include a predetermined range value or reference value. For example, the reference information may include a range value or reference value determinable by wearing on the outer side of the wrist or a range value or reference value determinable by wearing on the inner side of the wrist. The bio signal data 4551 may include bio signals currently gathered by the sensor module. The bio signal may include a pulse wave detection signal.

The per-mode function table 4553 may be a table including at least one function list to be performed depending on the wearing state of the electronic device 4400. For example, the per-mode function table 4553 may include a wearing mode function table, a wearing release mode function table, and a loss mode function table. The wearing mode function table may include a per-wearing portion function table. According to an embodiment, a particular function item included in the wearing mode function table may have different definitions for the type of running for each wearing portion.

The mode operation module 4580 included or controlled by the control module 4560 (e.g., the processor 120) may be the additional function module 170 shown in FIG. 51.

The mode operation module 4580 may determine proximity information gathered by the HRM sensor 4471 and perform control to transmit wearing information or non-wearing information (or attaching/detaching information) of the electronic device 4400 to the electronic device 4400 or an external electronic device (e.g., the electronic device 104). According to an embodiment, the mode operation module 4580 may perform control to activate at least one sensor of an acceleration sensor and a gyro sensor in order to automatically determine the sleep state. The mode operation module 4580 may determine a sleep in mode state or sleep out mode state (sleep in/out) based on the analysis of the signals gathered by the HRM sensor 4471 and the gathered acceleration information and gyro sensor information. The mode operation module 4580 may perform control to perform a particular operation of the electronic device 4400 or a pre-defined particular function corresponding to the sleep in state or sleep out state. According to an embodiment, the mode operation module 4580 may gather, using a sensor, e.g., the HRM sensor 4471, bio information such as blood flow, blood pressure, or oxygen saturation varied by a physical variation at the portion adjacent to the electronic device, such as a finger movement, finger tapping, finger closing or opening, or wrist movement. The mode operation module 4580 may perform control to sense the signal of the gathered bio information to perform a particular operation based on first information (e.g., bio signal such as heart rate) and second information (e.g., user input, such as one tap, two tap, N tap, or long tap).

The above-described mode operation module 4580 may include a bio signal processing module 4581, a mode switching module 4583, a per-mode function processing module 4585, and an attaching/detaching processing module 4587.

The bio signal processing module 4581 may perform control to activate the sensor module corresponding to a particular signal such as an input signal generated from the input/output module or schedule information as set. The bio signal processing module 4581 may analyze the sensor signal transferred from the sensor module. The bio signal processing module 4581, if the sensor module transfers the sensor signal, may identify the reference information stored in the storage module 4550 to analyze whether it is worn or the wearing portion. The bio signal processing module 4581 may transfer the wearing state information and wearing portion information to the mode switching module 4583 and the per-mode function processing module 4585.

According to an embodiment, the bio signal processing module 4581 may vary the sensor period of the sensor module. For example, the bio signal processing module 4581 may make a subsequent sensor period of the sensor module determined by wearing longer than earlier. The bio signal processing module 4581 may perform control to make the subsequent sensor period of the sensor module determined by taking off longer than earlier or to deactivate the sensor module.

The bio signal processing module 4581 may support a training mode. For example, the bio signal processing module 4581 may perform control to output a guide message as to the portion where the electronic device 4400 is to be worn through the display module 4440 or input/output module (e.g., the input/output interface 140). The bio signal processing module 4581 may perform control to store the bio signal gathered by activating the sensor module after the guide message is output as reference information corresponding to the wearing portion. The bio signal processing module 4581 may gather the reference information on wearing on the inside of the wrist and the reference information on wearing on the outside of the wrist by performing the above operation. Further, the bio signal processing module 4581 may also gather reference information on wearing on the neck, ankle, finger, lower arm or upper arm.

The mode switching module 4583 may receive the wearing state information or wearing portion information from the bio signal processing module 4581. The mode switching module 4583, upon reception of the wearing information, may identify the wearing portion information. The mode switching module 4583, in case the wearing portion is a first portion (e.g., the inside of the wrist), may switch the UI of the display module 4440 into a first UI mode (horizontal mode or horizontal writing mode). The mode switching module 4583, in case the wearing portion is a second portion (e.g., the outside of the wrist), may switch the UI of the display module 4440 into a second UI mode (a vertical mode of the horizontal writing mode or vertical writing mode).

According to an embodiment, the mode switching module 4583, if in the wearing released state, may perform control to switch the display module 4440 to the sleep mode.

The per-mode function processing module 4585 may process a defined function according to the wearing state and wearing portion information transferred from the bio signal processing module 4581. For example, the per-mode function processing module 4585 may control the respective set functions of wearing or not, the wearing portion, and normal wearing release.

According to an embodiment, the per-mode processing module 4585 may control the cutoff of the power supply to the sensor module or cutoff of the power supply to the display module 4440 included in the electronic device 4400 when the electronic device 4400 is stored. Or, the per-mode function processing module 4585 may automatically turn the electronic device 4400 into a turn-off state when the electronic device 4400 is stored. During this course, the per-mode function processing module 4585 may control the HRM sensor 4471 to detect the sensor signal after the electronic device 4400 is normally released from the wrist, and if the sensor signal has a preset signal form (which is in the state with no pulse wave detection signal and where a noise signal corresponding to a predetermined illuminance is detected), it may determine that the electronic device 4400 is stored.

According to an embodiment, the per-mode function processing module 4585, if the electronic device 4400 is being charged, may perform control to deactivate the other components than the communication interface (e.g., the communication interface 160). If the electronic device 4400 is completely charged, the per-mode function processing module 4585 may perform control to switch the electronic device 4400 into a sleep mode or into a turn-off state. The per-mode function processing module 4585, if the charging state is released, may perform control to automatically activate the sensor module to detect whether it is worn or not.

According to an embodiment, the per-mode function processing module 4585, if the electronic device 4400 is worn on the first portion or second portion (e.g., the inside or outside of the wrist), it may perform function processing in a public mode. For example, the per-mode function processing module 4585 may perform control to output at least a portion of the message received when performing the public mode on the display module 4440. Further, the per-mode function processing module 4585 may perform control to output a message reception alarm. The per-mode function processing module 4585, if the electronic device 4400 is worn on the second or first portion (e.g., the outside or inside of the wrist), may perform function processing in a privacy mode. For example, the per-mode function processing module 4585, upon performing the privacy mode, may perform only display alarming or vibration alarming on the received message. The per-mode function processing module 4585 may control other function processes on emails or communication messages according to wearing types.

The attaching/detaching processing module 4587 may process identification of loss or not and prevention of loss by utilizing the HRM sensor 4471 as at least one of an illumination sensor or proximity sensor. For example, the attaching/detaching processing module 4587, if the detection of the bio signal (e.g., pulse wave detection signal) detected by the HRM sensor 4471 is terminated, may activate the acceleration sensor or gyro sensor or may analyze the acceleration sensor or gyro sensor already activated. The attaching/detaching processing module 4587 may determine the state where the electronic device 4400 escapes from the wearing portion based on the analyzed sensor signal. For example, the attaching/detaching processing module 4587 may determine the case where the electronic device 4400 escapes from the wearing portion while accelerating a predetermined distance or more as loss release. In case the acceleration or speed is irregularly changed as the electronic device 4400 escapes from the wearing portion within a predetermined distance, the attaching/detaching processing module 4587 may determine it as loss release.

According to an embodiment, if the electronic device 4400 is released from the wearing portion (e.g. if the detection of the pulse wave detection signal by the HRM sensor 4471 is terminated), the attaching/detaching processing module 4587 may process the sensor signal gathered by the HRM sensor 4471 in at least one of an illumination sensor processing scheme and a proximity sensor processing scheme. The attaching/detaching processing module 4587 may determine at least one of a proximity variation and an illuminance variation through a variation in the sensor signal gathered by, e.g., the HRM sensor 4471. In case at least one of the proximity variation and the illuminance variation shows a variation corresponding to predetermined loss release, the attaching/detaching processing module 4587 may determine it as loss release.

The attaching/detaching processing module 4587, if the electronic device 4400 is determined as loss release, may control the transmission of a predetermined message to the external electronic device. If the electronic device 4400 is determined as loss release, the attaching/detaching processing module 4587 may control at least one of the vibration module, display module 4440, and input/output module of the electronic device 4400 to output preset data. According to an embodiment, the electronic device 4400 may include a sensor module gathering signals, a module generating bio information based on some of the gathered signals, a module generating proximity information, at least, based on some of the gathered signals, a module generating illuminance information, at least, based on some of the gathered signals, and a module determining the state of the electronic device, at least, based on the bio information, the proximity information, or the illuminance information.

According to an embodiment, the bio information may be a heart rate.

According to an embodiment, the state of the electronic device may include the wearing state of the electronic device.

According to an embodiment, the electronic device may further include a control module controlling the electronic device using at least one of the bio information, the proximity information, or the illuminance information.

According to an embodiment, the control module may determine the wearing portion of the electronic device based on at least one of a frequency domain characteristic of the bio signal and a time domain characteristic thereof.

According to an embodiment, the control module may determine whether the electronic device is worn based on analysis of the proximity information, and if worn, may determine the wearing portion of the electronic device based on the bio signal analysis information.

According to an embodiment, the electronic device may further include a storage module storing the bio signal per particular portion of the wearer while the electronic device is worn on the wearer's particular potion as reference information.

According to an embodiment, the control module may perform comparison in similarity between the reference information and the gathered information to determine the wearing state and the wearing portion.

According to an embodiment, the control module may make the form of outputting the information from the electronic device different corresponding to the wearing state.

According to an embodiment, the control module may control at least one of a horizontal arrangement horizontal writing scheme on the information corresponding to the wearing state, a horizontal arrangement vertical writing scheme on the information corresponding to the wearing state, a vertical arrangement horizontal writing scheme on the information corresponding to the wearing state, a vertical arrangement vertical writing scheme on the information corresponding to the wearing state, a horizontally reversed scheme on the information corresponding to the wearing state, varying the position of the output of the soft button related to running a particular function corresponding to the wearing state, and varying the type of function of running the soft button output on the display module corresponding to the wearing state.

According to an embodiment, the control module may differently apply the function processing of the electronic device corresponding to the wearing state.

According to an embodiment, the control module may produce an alarm for the occurrence of event of the electronic device corresponding to the wearing state or output at least a portion of content of the occurring event of the electronic device.

According to an embodiment, the control module may perform authentication verification when the electronic device is not worn.

According to an embodiment, the electronic device 4400 may include a sensor module capable of gathering bio signals and a control module determining the wearing state based on at least one of bio signal of bio signal analysis information of the sensor signal gathered by the sensor module, proximity analyzed based on the sensor signal, and illuminance information analyzed based on the sensor signal.

According to an embodiment, the control module may determine the proximity information and perform control to output the wearing/not wearing (attachment/detachment) information through the electronic device or external electronic device.

According to an embodiment, the control module may automatically determine whether to enter the sleep state based on the bio information, acceleration information, and gyro information.

According to an embodiment, the control module may sense bio information through the electronic device and perform control to perform at least one particular operation of the electronic device or external electronic device. According to an embodiment, the control module may sense at least one varied bio information of the blood flow, blood pressure, and oxygen saturation varying depending on the bodily variation at the wearing portion of the electronic device and perform control to perform a particular operation of the electronic device based on the body operation inferred according to the bio information and the bodily variation.

Figure 96:
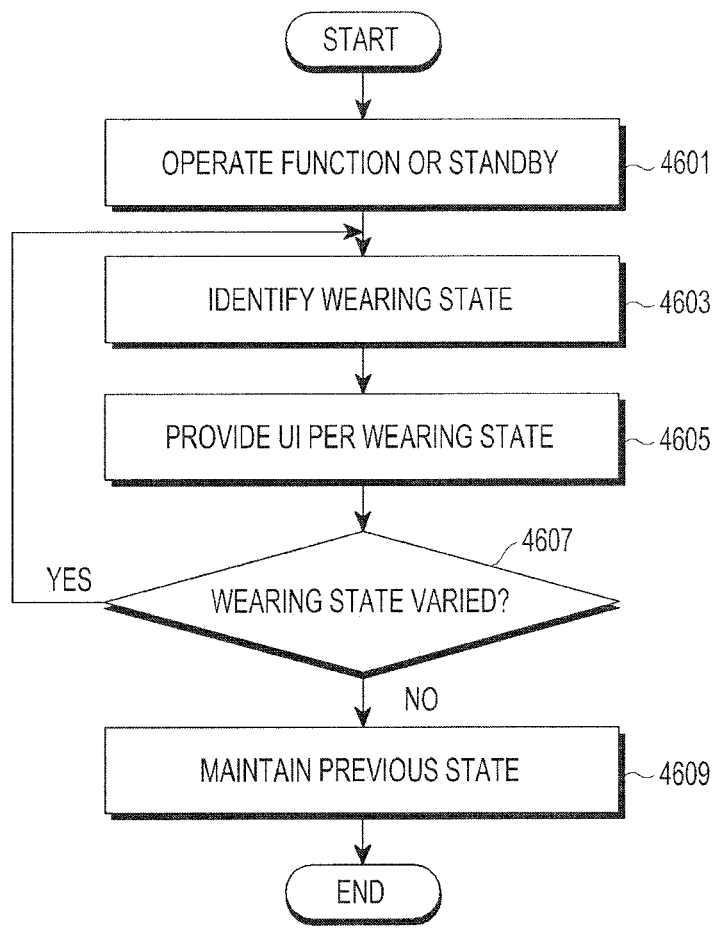
FIG. 96 illustrates a UI operation method of an electronic device per wearing state according to an embodiment.

FIG. 96 illustrates a UI operation method of an electronic device per wearing state according to an embodiment.

Referring to FIG. 96, the method of operating electronic device UIs per wearing state may control the function operation or standby in operation 4601. For example, the control module 4560 may perform control to operate the electronic device 4400 in a low power mode or sleep mode.

Here, the low power mode or sleep mode may be a mode in which the power supply to the display module 4400 is cut off, and power supply to a particular device component only is maintained. For example, the control module 4560 may perform control to supply power to the HRM sensor 4471 while cutting off power to other device components (e.g., the display module or communication interface). According to an embodiment, the control module 4560 may control the power supply to the electronic device 4400 corresponding to the occurrence of an input signal for turning on the electronic device 4400 and perform an initialization process in operation 4601. According to an embodiment, the control module 4560 may perform control to output audio data corresponding to a particular function, e.g., a sound playing function, of the electronic device 4400 in operation 4601.

In operation 4603, the control module 4560 may identify the wearing state of the electronic device 4400. For example, the control module 4560 may identify whether the sensor signal gathered by the HRM sensor 4471 contains a bio signal. If the control module 4560 receives a sensor signal not including a bio signal, it may determine that the electronic device 4400 is not worn. If the sensor signal is determined to include a bio signal, the control module 4560 may determine that the electronic device 4400 is worn on a predetermined portion of the user. According to an embodiment, the control module 4560 may determine the wearing portion of the electronic device 4400 according to characteristic of the gathered bio signal. For example, the control module 4560, in case the gathered bio signal corresponds to predetermined first reference information, may determine that the electronic device 4400 is worn on the inside of a wrist. The control module 4560, in case the gathered bio signal corresponds to predetermined second reference information, may determine that the electronic device 4400 is worn on the outside of a wrist. According to an embodiment, the control module 4560 may also determine the wearing state of a particular portion, e.g., a finger, ankle, neck, upper arm or lower arm, through comparison between pre-defined reference information and currently gathered sensor signal. In this connection, the control module 4560 may perform control to obtain the reference information per portion through a training mode.

In operation 4605, the control module 4560 may provide a UI per wearing state. For example, the control module 4560 may provide a UI according to the non-wearing state of the electronic device 4400 and a UI according to the wearing state of the electronic device 4400. The UI according to the non-wearing state of the electronic device 4400 may include, e.g., a UI, such as the turned-off state or lock screen state of the display module 4440. The UI according to the wearing state may differ per wearing portion. For example, the UI according to the wearing state may include a horizontal mode UI provided upon wearing on the inside of the wrist and a vertical mode UI provided upon wearing on the outside of the wrist.

In operation 4607, the control module 4560 may identify whether the wearing state is varied. The control module 4560 may activate the HRM sensor 4471 at predetermined periods in relation with identifying the variation in the wearing state to determine the wearing state variation. Or, the control module 4560 may identify the variation in the wearing state by operating the HRM sensor 4471 in real-time. In operation 4607, unless there is no variation in the wearing state, the control module 4560 may go to operation 4609 to perform control to maintain the previous state. The control module 4560 may re-perform operation 4607 of identifying whether the wearing state of the electronic device 4400 is varied while maintaining the previous state. Further, in case an event related to the termination of function of the electronic device 4400 occurs while maintaining the previous state, the control module 4560 may control the termination of function. The control module 4560, if a variation in the wearing state occurs in operation 4607, may go to operation 4603 to re-perform its subsequent operations.

Figure 97:
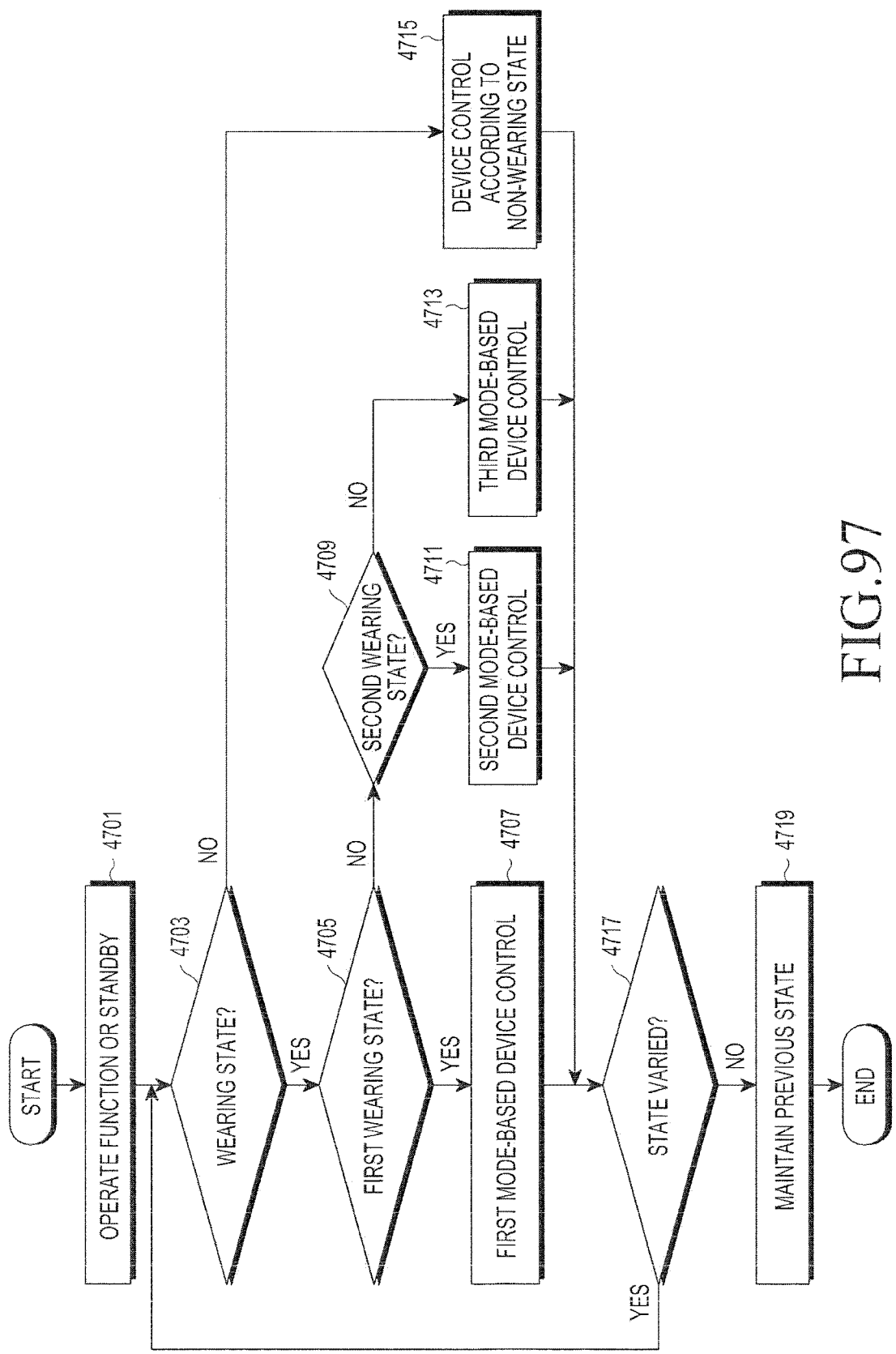
FIG. 97 illustrates an operation method of an electronic device per wearing state according to an embodiment.

FIG. 97 illustrates an operation method of an electronic device per wearing state according to an embodiment.

Referring to FIG. 97, the method of operating the electronic device per wearing state may control the function operation or standby in operation 4701. The control module 4560 may perform a particular function according to determined schedule information, e.g., a standby screen output function, a menu screen output function, or lock screen function. Or, the control module 4560 may perform control to maintain the sleep mode state in which the power supply to the HRM sensor 4471 is maintained, but power supply to the other device components is cut off.

In operation 4703, the control module 4560 may identify whether it is worn. The control module 4560 may identify the wearing state based on a sensor signal transferred from the HRM sensor 4471. In operation 4703, if the electronic device 4400 is determined to be worn, the control module 4560 may identify whether it is in a first wearing state (e.g., the state of being worn on the inside of a wrist) in operation 4705. If the electronic device 4400 is in the first wearing state in operation 4705, the control module 4560 may perform first mode based device control in operation 4707. According to an embodiment, the control module 4560 may perform control to output the whole or part of information related to performing a particular function. For example, the control module 4560, when a message is received, may perform control to output the whole or part of the content of the received message. According to an embodiment, if in the first wearing state, the control module 4560 may control a non-security mode operation. For example, the control module 4560 may support entry into the menu or displaying information without performing a separate authentication process upon operating the electronic device 4400.

Unless in the wearing state in operation 4705, the control module 4560 may identify in operation 4709 whether it is in a second wearing state (e.g., the state of being worn on the outside of the wrist). If determined in operation 4709 to be in the second wearing state, the control module 4560 may perform second mode based device control in operation 4711. According to an embodiment, the control module 4560 may perform control to output a notification for information to be outputted in relation with performing a particular function. For example, upon receiving a message, the control module 4560 may perform control to output a message reception notification. According to an embodiment, if in the first wearing state, the control module 4560 may control a security mode operation. For example, the control module 4560 may support entry into the menu or displaying information by performing an authentication process upon operating the electronic device 4400. In this connection, the control module 4560 may perform the operation of outputting an input window for entry of authentication information and the operation of identifying the inputted authentication information.

Unless in the second wearing state in operation 4709, the control module 4650 may perform third mode based device control in operation 4713. For example, in case the electronic device 4400 is worn on the upper arm, the control module 4560 may perform control to convert the information related to performing function via text to speech (TTS) and output the same. For example, upon receiving a message, the control module 4560 may perform control to convert the message content via TTS and output the same.

Unless in the wearing state in operation 4703, the control module 4560 may perform device control according to the non-wearing state in operation 4715. For example, the control module 4560 may power off the display module 4440 and perform a particular function, e.g., sound playing function. In this process, the control module 4560 may adjust the sensing period of the HRM sensor 4471 to be longer as compared with that in the wearing state, to thereby save power.

The control module 4560 may identify whether there is a variation in the wearing state in operation 4717. The control module 4560, if the wearing state is varied in operation 4717, may go to operation 4703 to re-perform its subsequent operations. The control module 4560, unless there is a variation in the wearing state in operation 4717, may maintain the previous state in operation 4719. While maintaining the previous state, the control module 4560 may re-perform operation 4717, and when the state is varied, may control the variation in function accordingly.

Figure 98:
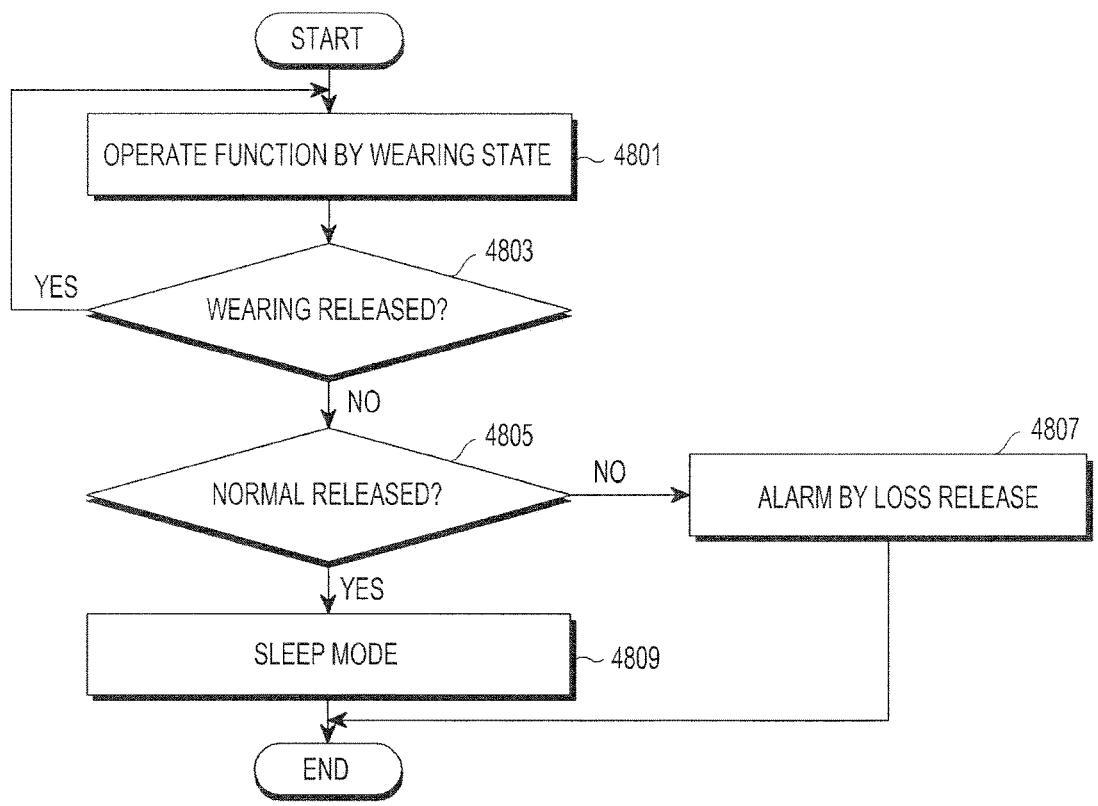
FIG. 98 illustrates an operation method of an electronic device related to preventing loss according to an embodiment.

FIG. 98 illustrates an operation method of an electronic device related to preventing loss according to an embodiment.

Referring to FIG. 98, the method of operating the electronic device in relation to preventing loss, the control module 4660 may perform a function operation according to the wearing state in operation 4801. For example, the control module 4560 may perform a health condition checkup of the wearer by analyzing bio signals provided from the HRM sensor 4471. Or, the control module 4560 may maintain the state of supporting the relay function or communication standby function such as notifying the reception of a communication message. Or, the control module 4560 may support a step counter function or clock display function corresponding to scheduled information.

In operation 4803, the control module 4560 may identify whether the wearing is released. In this relation, the control module 4560 may identify whether the sensor signal from the HRM sensor 4471 is varied. The control module 4560, if there is a variation in the sensor signal from the HRM sensor 4471, may determine it as occurrence of an event related to the wearing release. Unless the sensor signal from the HRM sensor 4471 is varied, the control module 4560 may go to a prior operation of operation 4801 to re-perform its subsequent operations.

If such a sensor signal variation as the electronic device 4400 is released from wearing in operation 4803, the control module 4560 may identify whether it is normal release in operation 605. In this relation, the control module 4560 may store and operate at least one of a variation value of the sensor signal related to the normal release and a variation value of the sensor signal related to abnormal release. The storage module 4550 may store the reference information related to normal release and the reference information related to abnormal release. The storage module 4550 may provide the reference information corresponding to a request from the control module 4560. The control module 4560 may gather the normal release-related reference information and abnormal release-related reference information through a training mode or gather them through a use history of the electronic device 4400.

If it is determined to be the normal release in operation 4805, the control module 4560 may perform a notification according to loss release in operation 4807. The control module 4560 may perform control to output a predetermined beef sound or particular audio data through the input/output module. The control module 4560 may perform control to vary the turn-on or turn-off state of the display module 4440 into the loss release state. The control module 4560 may perform control to vary the electronic device 4400 into a security mode and first perform an authentication process upon control request. According to an embodiment, upon loss release, the control module 4560 may control the communication interface to transmit a loss alarm message to a predetermined external electronic device.

According to an embodiment, in case the variation in the sensor signal provided from the HRM sensor 4471 corresponds to the abnormal release-related reference information, the control module 4560 may determine it as the loss release. In this process, if there is a variation in the sensor signal from the HRM sensor 4471, the control module 4560 may convert the sensor signal gathered by the HRM sensor 4471 into at least one of an illuminance sensor signal and proximity sensor signal and may determine at least one of the illuminance variation and proximity distance variation accordingly. If at least one of the illuminance variation and the proximity distance variation is similar to pre-defined abnormal release-related reference information, the control module 4560 may determine it as the abnormal release. Further, if at least one of the illuminance variation and the proximity distance variation is similar to pre-defined normal release-related reference information, the control module 4560 may determine it as the normal release. According to an embodiment, the control module 4560 may use only the normal release-related reference information or only abnormal release-related reference information. For example, the control module 4560, in case the sensor signal is not consistent with the normal release-related reference information, may determine it as the abnormal release. Or, the control module 4560, in case the sensor signal is not consistent with the abnormal release-related reference information, may determine it as the normal release.

If it is determined as the normal release in operation 4805, the control module 4560 may perform control to perform a function according to the normal release in operation, e.g., entry into the sleep mode, in operation 4809. The sleep mode may be a mode at which the power supply to the display module 4440 is cut off. The sleep mode may be a mode at which the operation period of the sensor module is prolonged.

Figure 99:
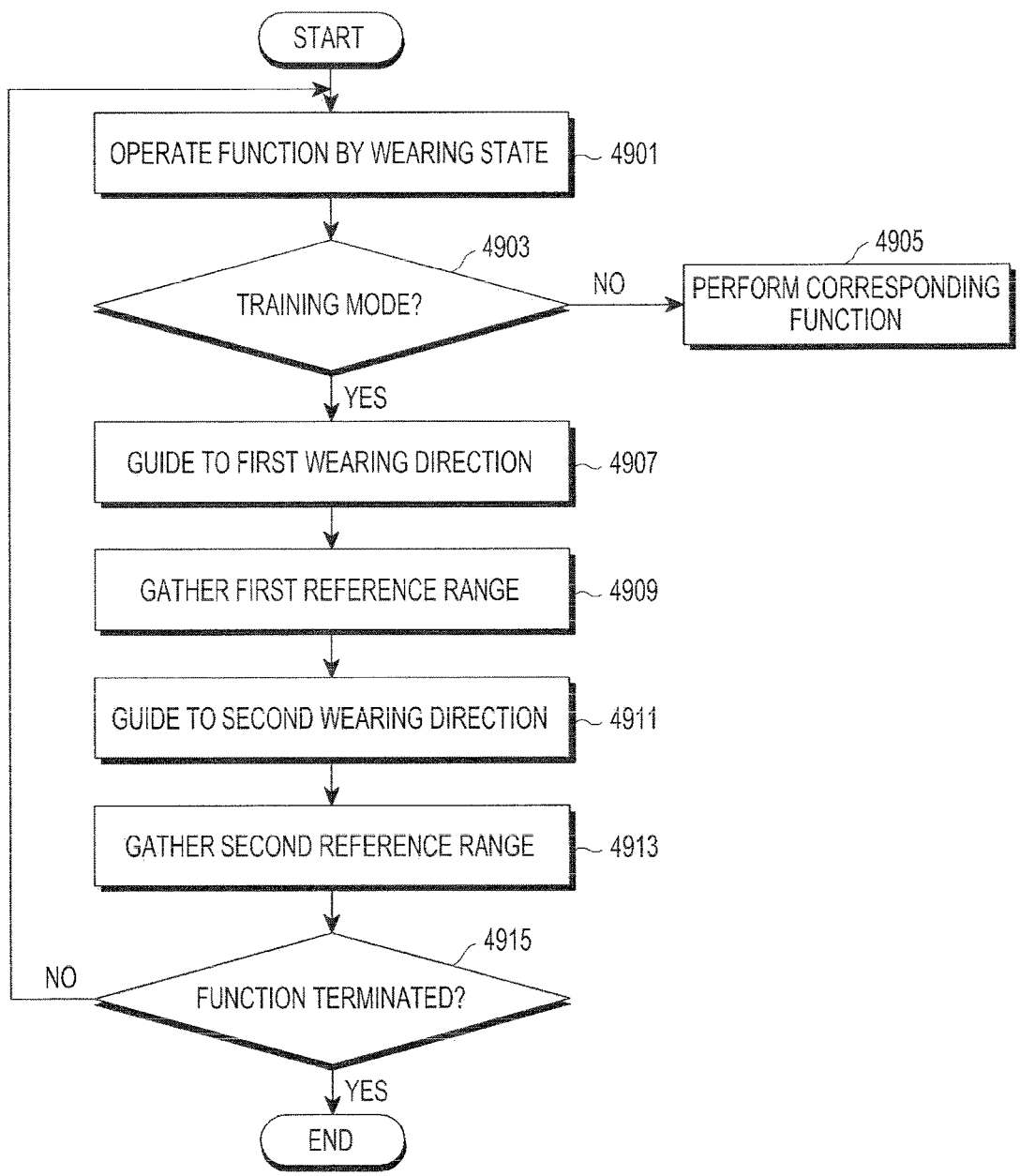
FIG. 99 illustrates an operation method of an electronic device related to a training mode according to an embodiment.

FIG. 99 illustrates an operation method of an electronic device related to a training mode according to an embodiment.

Referring to FIG. 99, in the training mode-related electronic device operation method, the control module 4560 may perform a function operation or standby in operation 4901. According to an embodiment, the control module 4560 may perform control to output an object or icon, or item or menu item related to running at least one function or app supported by the electronic device 4400. For example, the control module 4560 may perform control to output an object related to running a training function (function of gathering reference information per wearing state by the electronic device 4400).

In operation 4903, the control module 4560 may identify the occurrence of an event related to running the training mode. For example, the control module may identify whether an event of selecting the training mode function-related object occurs. Or, the control module 4560 may identify a scheduling event at which the electronic device 4400, if initially supplied with power, automatically activates the training mode. Or, the control module 4560 may identify whether a message related to entry into the training mode is received from other electronic device (e.g., the electronic device 101 or 102).

Unless an event related to running the training mode occurs in operation 4903, the control module 4560 may perform control to perform the function corresponding to the type of the event in operation 4905. For example, the control module 4560 may perform a sound play function corresponding to the type of the occurring event, a health coaching function (e.g., step counter function or cardiovascular state information providing function), or control of the function of shifting to the sleep mode (turned-off state of the display module).

If an event related to running the training mode occurs in operation 4903, the control module 4560 may perform a first wearing direction guidance in operation 4907. For example, the control module 4560 may output guide information (e.g., arrow information) guiding to the direction inserting to the wearing portion, with the electronic device 4400 worn on at least one of the left wrist, left ankle, left finger, left upper arm, left lower arm, and neck. The control module 4560 may gather a first reference range in operation 4909.

For example, the control module 4560 may gather bio signal information (e.g., at least one time of pulse wave signal or blood floor information in a blood vessel) while the electronic device is worn on a particular portion of the user's left body. The control module 4560 may generate reference information corresponding to the first reference range in the state of being worn on the particular portion with respect to the gathered bio signal information. The control module 4560, if the first reference range of bio signal information available as reference information is gathered, may guide to a first wearing direction guidance and first reference range gathering process complete.

The control module 4560 may perform a second wearing direction guidance in operation 4911. The control module 4560 may output guide information (e.g., arrow information) guiding to the direction inserting to the wearing portion, with the electronic device 4400 worn on at least one of the right wrist, right ankle, right finger, right upper arm, and right lower arm. The control module 4560 may gather a second reference range in operation 4913. The control module 4560 may generate reference information on the wearing direction and particular wearing portion based on the second reference range.

The control module 4560 may identify whether there is occurrence of an event related to the function termination in operation 4915. If there is no occurrence of the event related to the function termination in operation 4915, the control module 4560 may go to operation 4903 to re-perform the subsequent operations. The control module 4560, if the function termination-related event occurs in operation 4915, may perform control to stop the training mode function.

According to an embodiment, the control module 4560 may gather and store the reference information on the clip mode state and reference information on the non-wearing state in the training mode process. For example, the control module 4560 may gather sensor signals using the HRM sensor 4471 for a predetermined time after outputting guidance information on the non-wearing state in the training mode process. In this process, in case there is no bio signal by the HRM sensor 4471 and there is not approaching object by the analysis of sensor signals by the HRM sensor 4471, the control module 4560 may gather the corresponding information as reference information of the non-wearing state. The control module 4560 may gather, as the reference information on the clip mode state, the sensor signal in case there is no bio signal by the HRM sensor 4471 and there is an approaching object by the analysis of the sensor signal by the HRM sensor.

According to an embodiment, the method of operating the electronic device may include the operation of gathering sensor module-based signals and the operation of determining the state of the electronic device using at least one of bio information at least based on some of the gathered signals, proximity information at least based on some of the gathered signals, and illuminance information at least based on some of the gathered signals.

According to an embodiment, the bio information may be a heart rate.

According to an embodiment, the state of the electronic device may include the wearing state of the electronic device.

According to an embodiment, the method may include the operation of controlling the electronic device using at least one of the bio information, the proximity information, or the illuminance information.

According to an embodiment, the determining operation may include the operation of determining the wearing portion of the electronic device based on at least one of a frequency domain characteristic and time domain characteristic of the bio signal.

According to an embodiment, the determining operation may include the operation of determining whether the electronic device is worn based on the analysis of the proximity information and the operation of determining the wearing portion of the electronic device based on the bio signal analysis information.

According to an embodiment, the method may further include the operation of gathering bio signals while the electronic device is worn on a particular portion of the wearer and the operation of storing the bio signals per particular portion as reference information.

According to an embodiment, the determining process may include the operation of making comparison in similarity between the reference information and the gathered information to determine the wearing state and the wearing portion.

According to an embodiment, the method may further include the operation of making the type of outputting information by the electronic device different corresponding to the wearing state.

According to an embodiment, the outputting operation may include at least one of the operation of outputting the information in a horizontal arrangement horizontal writing scheme corresponding to the wearing portion, the operation of outputting the information in a horizontal arrangement vertical writing scheme corresponding to the wearing state, the operation of outputting the information in a vertical arrangement horizontal writing scheme corresponding to the wearing state, the operation of outputting the information in a vertical arrangement vertical writing scheme corresponding to the wearing state, the operation of outputting the information in a vertically reversed scheme corresponding to the wearing state, the operation of making different or varying the position of the output of the soft button related to running a particular function corresponding to the wearing state, and the operation of making different or varying the type of the function run by the soft button output on the display module corresponding to the wearing state.

According to an embodiment, the method may further include the operation of applying differently the function processing of the electronic device corresponding to the wearing state.

According to an embodiment, the applying operation may include at least one of the operation of alarming for the occurrence of the event of the electronic device corresponding to the wearing state and the operation of outputting at least a part of the content information on the occurring event of the electronic device.

According to an embodiment, the applying process may include the operation of performing authentication verification when the electronic device is not worn.

According to an embodiment, the method of operating the electronic device may include the operation of gathering a sensor signal of a particular sensor and the operation of determining the wearing state of the electronic device including the sensor based on at least one of bio signal analysis information of the gathered sensor signal, proximity information analyzed based on the sensor signal, and illuminance information analyzed based on the sensor signal.

According to an embodiment, the controlling operation may include at least one of the operation of determining the proximity information and performing control to output wearing/non-wearing state information through the electronic device or external electronic device, the operation of automatically determining whether to enter into a sleep state based on the bio information, acceleration information, and gyro information, and the operation of sensing the body information through the electronic device to perform at least one particular operation of the electronic device or the external electronic device.

According to an embodiment, the controlling operation may include the operation of sensing at least one varied body information of a blood flow, blood pressure, and oxygen saturation varying corresponding to a bodily variation in the portion where the electronic device is worn and performing control to perform a particular operation of the electronic device based on the bio information and body operation inferred according to the bodily variation.

Figure 100:
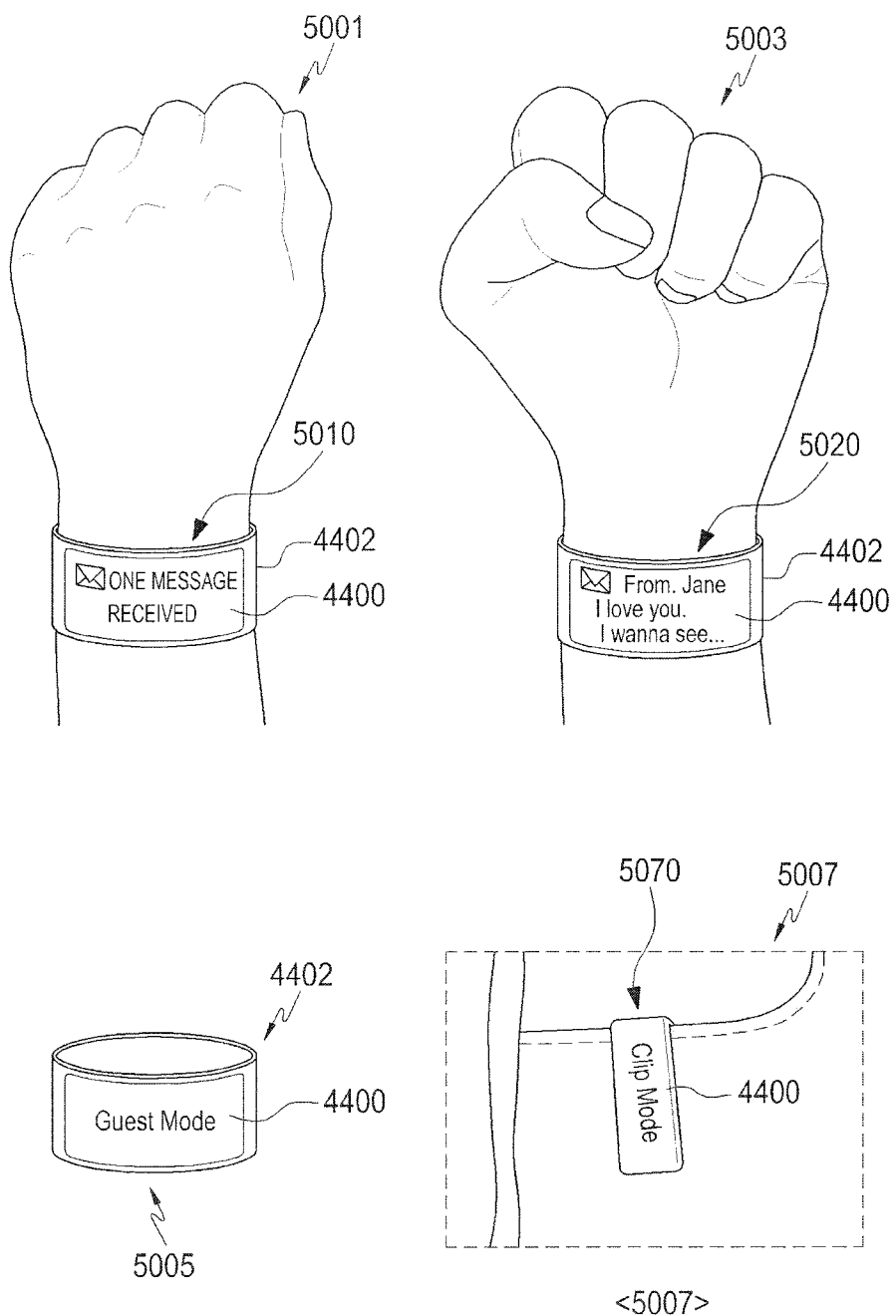
FIG. 100 illustrates mode control according to a wearing state of an electronic device according to an embodiment.

FIG. 100 illustrates mode control according to a wearing state of an electronic device according to an embodiment.

Referring to FIG. 100, the electronic module 4002 may be mounted so that the electronic device 4400 is disposed on the outside 5010 of the user's left wrist as in state 5001. The HRM sensor 4471 disposed in the electronic device 4400 may be disposed on the outside 5010 of the user's left wrist to detect sensor signals. The control module 4560 of the electronic device 4400 may analyze a sensor signal transferred from the HRM sensor 4471 to determine the type of the bio signal. For example, the control module 4560 may determine based on pre-stored reference information related to the outside 5010 of the left wrist that the electronic device 4400 is disposed on the outside 5010 of the left wrist. The bio signal measurement signal on the outside 5010 of the left wrist may differ from the bio signal measuring information on the inside 5020 of the left wrist. Further, the bio signal measurement information may differ between the right hand and the left hand. The reference information may include information on the characteristic points extracted from the bio signal measurement information showing different characteristics per portion.

Upon determining that the electronic device 4400 is disposed on the outside 5010 of the left wrist, the control module 4560 may perform control so that the information is outputted in a privacy mode (e.g., a function or mode of outputting an alarm or guidance information on the type information on the occurring event). For example, upon reception of a communication message, the control module 4560 may perform processing so that only message reception notification is output to the display module 4440.

The electronic module 4002 may be mounted so that the electronic device 4400 is disposed on the inside 5020 of the left wrist as in state 5003. The HRM sensor 4471 disposed in the electronic device 4400 may be disposed on the inside 5020 of the left wrist to detect sensor signals. The control module 4560 may identify that the electronic device 4400 is disposed on the inside 5020 of the left wrist using the reference information stored in the storage module 4550. If the electronic device 4400 is determined to be disposed on the inside 5020 of the left wrist, the control module 4560 may perform control to output information in a public mode (e.g., a function or mode of outputting at least a portion of the event content). For example, upon reception of a communication message, the control module 4560 may perform control to output at least a portion to the display module 4440.

Power on may be run while the electronic module 4402 is not worn on the user's body portion as in state 5005. Or, the electronic module 4402 may have state 5005 according to a mounting released state while mounted on the user's body portion. The control module 4560 may analyze the sensor signal gathered by the HRM sensor 4471 to identify whether the sensor signal includes a bio signal. The control module 4560 may identify the sensor signal not including a bio signal in case of state 5005. The control module 4560 may apply a security mode (guest mode) (e.g., a function or mode of abstaining from outputting an alarm or guidance information on event occurrence) to the electronic device 4400 that is in state 5005. For example, the control module 4560 may perform control to perform an authentication information verification process if there is occurrence of an input event on the display module 4440 from the input/output module, or reception of a communication message or arrival of schedule information, or occurrence of an event by running a particular app. In this relation, the control module 4560 may output an authentication information verification screen to the display module 4440. The control module 4560, if the authentication information verification is complete, may perform control to output the occurring event-related content through at least one of the display module 4440 and the input/output module (e.g., the input/output interface 140). According to an embodiment, the control module 4560, if the bio recognition by the HRM sensor 4471 fails or bio authentication fails, may output a predetermined simple message or restrict the output of the notification screen. The control module 4560 may perform control to perform bio recognition, bio authentication, or password authentication, and then to operate in any one of the public mode or privacy mode.

As in state 5007, the electronic device 4400, after escaping from the electronic module 4402, may be cradled at a particular position. For example, the electronic device 4400 may be disposed or mounted in the user's pocket or at a particular position 5070 (e.g., a position not directly contacting the user's body). The control module 4560 may analyze the sensor signal gathered from the HRM sensor 4471, and in case there is no bio signal, may perform proximity analysis on the received sensor signal. For example, in case the proximity is not more than a predetermined value, the control module 4560 may perform control to allow the electronic device 4400 to operate in the clip mode (e.g., a mode or function of performing a predetermined particular function, such as step counter or headset function.

Figure 101:
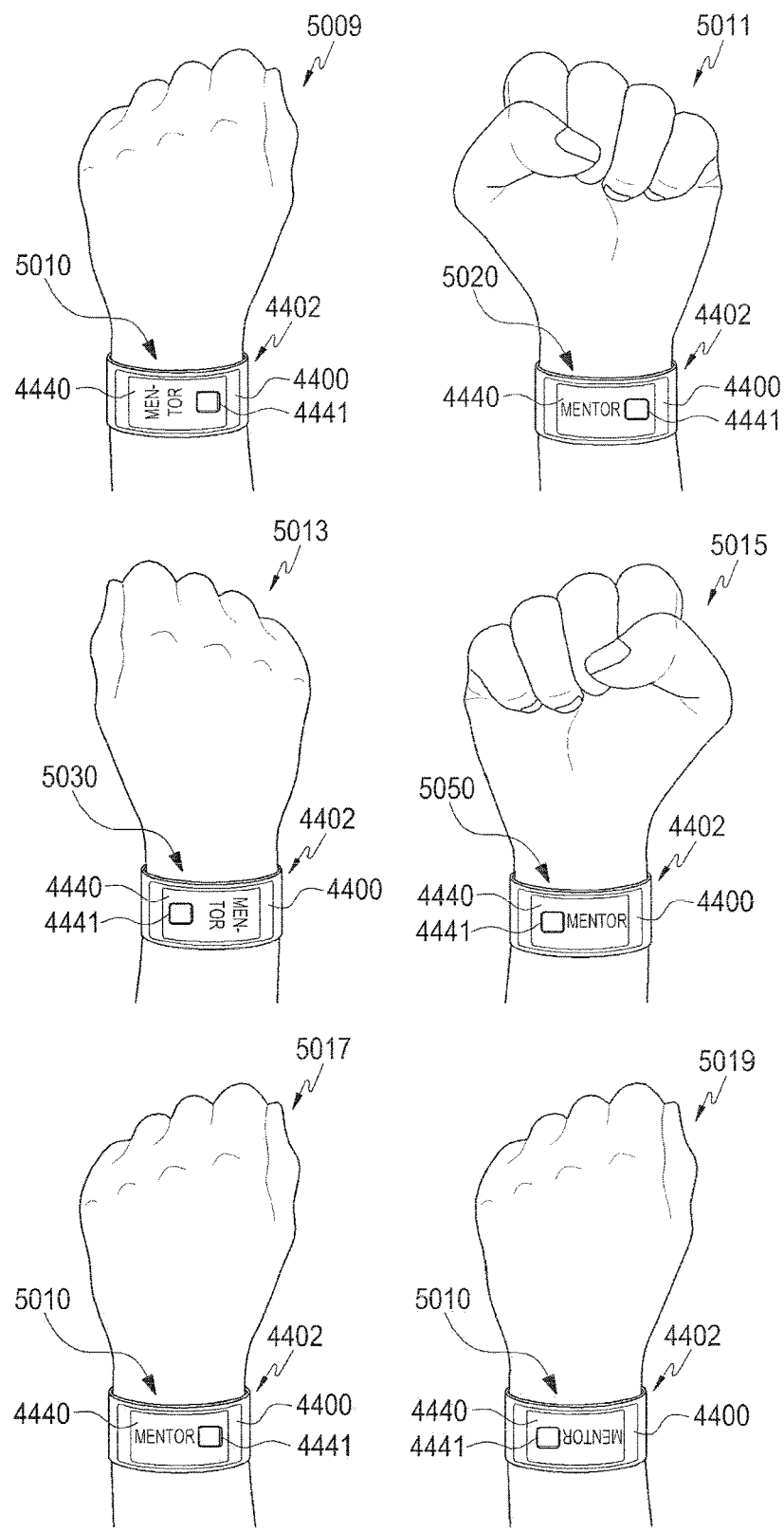
FIG. 101 illustrates UI control according to a wearing state of an electronic device according to an embodiment.

FIG. 101 illustrates UI control according to a wearing state of an electronic device according to an embodiment.

Referring to FIG. 101, the electronic module 4402 may be mounted on various portions of the user. For example, the electronic module 4402 may have the state of being mounted on the outside 5010 of the user's left wrist as in state 5009, the state of being mounted on the inside 5020 of the user's left wrist as in state 5011, the state of being mounted on the outside 5030 of the user's right wrist as in state 5013, and the state of being mounted on the inside 5050 of the user's right wrist as in state 5015. Further, while mounted on the left or right hand, the electronic module 4402 may be mounted in an upper direction where a side of the user's display module 4440 is disposed toward a finger as in state 5017 or a lower direction where a side of the user's display module 4440 is disposed towards the inside of the arm as in state 5019.

According to an embodiment, the control module 4560 of the electronic device 4400 may provide various UIs corresponding to the position where it is mounted. For example, the control module 4560, if it is in the state of being mounted on the outside 5010 of the user's left wrist as in state 5009, may support vertical writing-type information output by which the information of the display module 4440 is displayed left to right. According to an embodiment, the control module 4560, if it is in the state of being mounted on the inside 5020 of the user's left wrist as in state 5011, may support horizontal writing-type information output by which the information of the display module 4440 is displayed left to right. According to an embodiment, the control module 4560, if it is in the state of being mounted on the outside 5030 of the user's right wrist as in state 5013, may support vertical writing-type information output by which the information of the display module 4440 is displayed right to left. According to an embodiment, the control module 4560, if it is in the state of being mounted on the inside 5050 of the user's right wrist as in state 5015, may support horizontal writing-type information output by which the information of the display module 4440 is displayed left to right. According to an embodiment, the control module 4560, if it is in the state of being mounted on the outside 5010 of the user's left wrist and a side of the display module 4440 is disposed at an upper side as in state 5017, may support horizontal writing-type information output by which the information of the display module 4440 is displayed left to right. According to an embodiment, the control module 4560, if it is in the state of being mounted on the outside 5010 of the user's left wrist and a side of the display module 4440 is disposed at a lower side as in state 5019, may perform control to so that the information is outputted vertically reversed and in the horizontal writing-type by which the information of the display module 4440 is displayed left to right.

Meanwhile, according to an embodiment, the UI mode of the electronic device 4400 may be set corresponding to the user's input in the training mode or the setting may be varied. For example, the control module 4560 may gather information on the UI output direction during the course of gathering the reference information on the wearing state in the training mode. In this connection, the control member 4560 may provide a screen interface related to the UI output direction upon provision of the screen interface related to the training mode and may provide such support as to be able to set the UI output state or UI output direction according to a particular wearing state or non-wearing state or wearing portion.

According to an embodiment, the control member 4560 of the electronic device 4400 may identify the sleep state using sensor signals gathered by the HRM sensor 4471. For example, the control member 4560 may check whether to wear at predetermined time intervals (e.g., for one second every five minutes) for a time other than when charged. In this process, the control member 4560 may check only the proximity based on the collected sensor signal and then perform bio signal analysis according to whether it is proximate or not to check whether it is worn or not and where he sleeps or not. The control member 4560 may store and manage the bio signal on the sleep state as the reference information.

According to an embodiment, the control member 4560 may determine whether it is in the sleep state or not through proximity check and acceleration sensor signal check. In this process, the control member 4560 may transmit the sensor signal gathered by the HRM sensor 4471 based on the remote sensor framework (RSF) to the external electronic device as a proximity sensor signal to determine whether it is worn or not. The control member 4560, in case the wearer is in the sleep mode, may apply its corresponding UI mode (e.g., the sleep mode where the display module 4440 is turned off).

According to an embodiment, the control member 4560 may automatically determine the sleep mode by analyzing the signals gathered by the gyro sensor and acceleration sensor and HRM sensor. The control member 4560, if the sleep state is determined, may perform control to perform a particular function of the electronic device 4400, e.g., one of the sleep entry mode and sleep release mode. The sleep entry mode may be a mode allowing, e.g., the display module 4440 to turn off or enter into the deep sleep mode of the electronic device 4400. The sleep release mode may be a mode for performing a predefined particular function, e.g., a mode including at least one of the function of automatically outputting a clock function, the function of automatically gathering and outputting weather information, and the function of automatically running a set sound source.

According to an embodiment, the display module 4440 of the electronic device may provide a soft button 4441. The soft button 4441 may provide a shortcut function (healthcare function) for immediate entry into a particular function of the electronic device 4400 or a particular menu. Or, depending on settings, the soft button 4441 may provide the function of searching for particular data stored in the storage module 4550 or received and stored messages. Or, the soft button 4441 may support the function of automatically syncing with an external device (e.g., Bluetooth auto-pairing function). The above-described soft button 4441 may be relocated depending on the above-described wearing state. According to an embodiment, the soft button 4441 may be disposed inclined to the left side of the display module 4440 or to the right side depending on whether it is worn on the left hand or right hand. According to an embodiment, the position of the soft button 4441 on the display module 4440 may be varied depending on whether it is worn on the outside or inside of a wrist.

According to an embodiment, the control member 4560 may change functions run by the soft button 4441 depending on the wearing state. For example, if the soft button 4441 is selected while it is worn on the outside of the left wrist, the control member 4560 may perform control to basically run a first function (e.g., a clock display function). Further, if the soft button 4441 is selected while it is worn on the inside of the left wrist, the control member 4560 may perform control to basically run a second function (e.g., a message search function). Further, if the soft button 4441 is selected while it is worn on the inside of the right wrist, the control member 4560 may perform control to basically run a third function (e.g., a menu output function). If the soft button 4441 is additionally selected while the first function or second function runs, the control member 4560 may control the switch of menu functions.

According to an embodiment, the soft button 4441 may be set to have different running functions depending on different positions. For example, in case the soft button 4441 is disposed at a first position of the display module 4440 (e.g., when it is positioned within a predetermined distance from the leftmost edge while the display module 4440 is placed in the horizontal direction), the control member 4560 may run the first function (e.g., the menu output function) according to the selection of the soft button 4441. Or, in case the soft button 4441 is disposed at a second position of the display module 4440 (e.g., when it is positioned at the center or within a predetermined distance from the rightmost edge while the display module 4440 is placed in the horizontal direction), the control member 4560 may run the second function (e.g., the healthcare function, message search function, or clock function) according to the selection of the soft button 4441.

Figure 102:
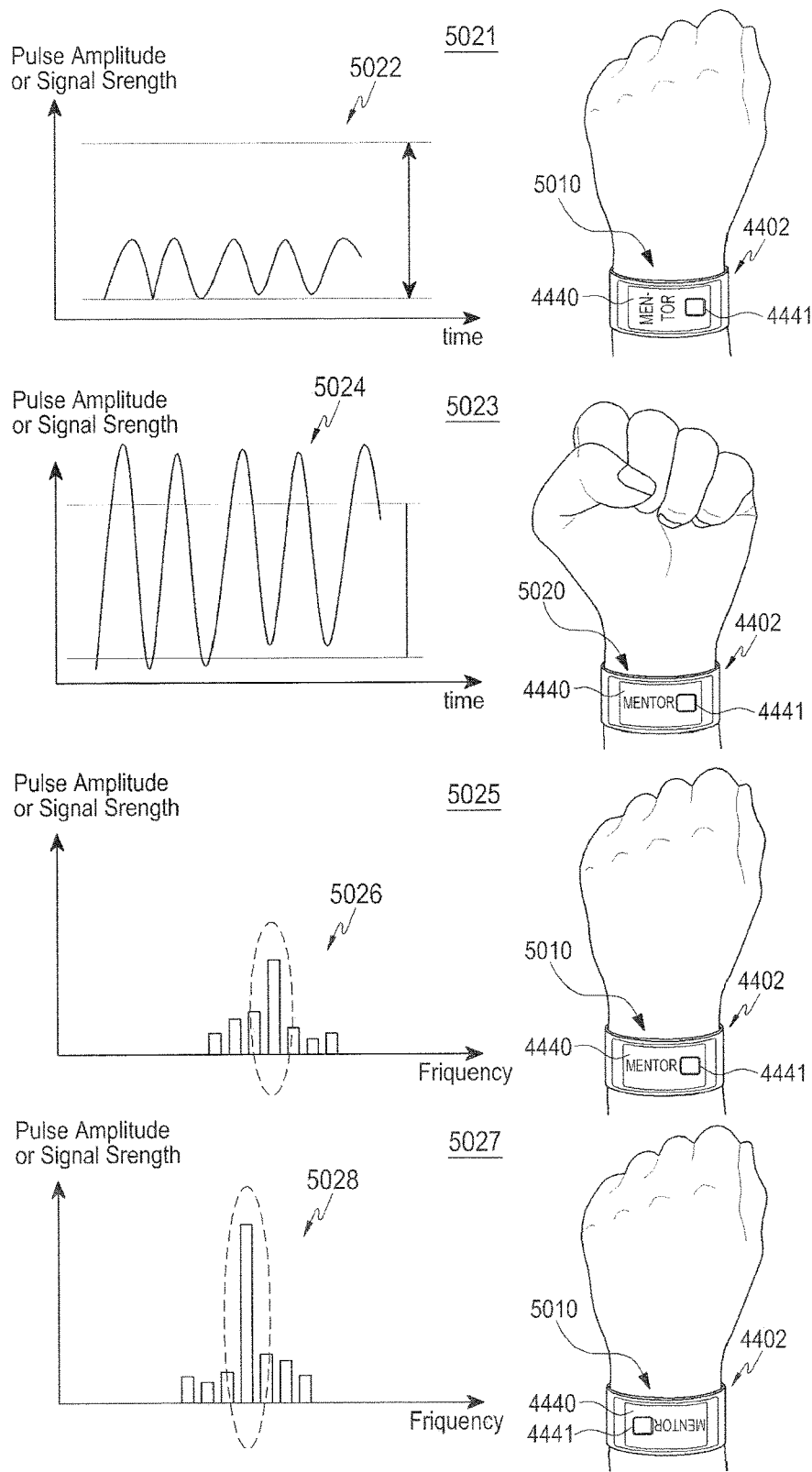
FIG. 102 illustrates mode control according to a wearing state of an electronic device according to an embodiment.

FIG. 102 illustrates mode control according to a wearing state of an electronic device according to an embodiment.

Referring to FIG. 102, the control member 4560 may perform time-series analysis on the sensor signal gathered by the HRM sensor 4471. For example, the control member 4560 may analyze the peak, amplitude, and inter-peak distance (RRI) of the signal in the time domain to determine whether it is worn or the wearing portion. The control member 4560 may analyze the main component frequency and main component frequency amplitude (power spectrum density), the amplitude of side components, and mutual ratio to determine the wearing state and wearing portion according to the gathered signal. In this process, the control member 4560 may perform inter-signal distinction according to the amplitude of the main component or side component of the frequency and the mutual ratio or may perform signal distinction through comparison in similarity with the stored reference information. According to an embodiment, the control member 4560 may identify pulse signal differences according to the wearing position (e.g., the left hand, right hand, inside or outside of the wrist, lower or upper side of the wrist) based on the blood vessel distribution differences. Further, the control member 4560 may perform signal analysis using the noise (SNR, the percentage at which the main component occupies) by the degree of contact when the electronic module 4402 is attached.

According to an embodiment, the electronic module 4402 may be mounted on the outside 5010 of the user's left wrist as in state 5021. Corresponding to the scheduling information or user input, the control member 4560 may activate the HRM sensor 4471 and perform control to gather sensor signals. The sensor signal provided from the HRM sensor 4471 may be shown in graph 5022. For example, the sensor signal gathered by the HRM sensor 4471 may be a wave signal within a particular range. If the HRM sensor 4471 gathers the sensor signal shown in graph 5022, the control member 4560 may determine that the sensor signal is the left wrist bio signal based on the form of the wave signal (e.g., the pattern of the wave signal) and may determine the state in which it is mounted on the outside 5010 of the left wrist based on the amplitude.

According to an embodiment, the electronic module 4402 may be mounted on the inside 5020 of the user's left wrist as in state 5023. The sensor signal provided from the HRM sensor 4471 activated under the control of the control member 4560 may be shown in graph 5024. For example, the sensor signal gathered by the HRM sensor 4471 may be a wave signal whose amplitude is over a particular range. If the HRM sensor 4471 gathers the sensor signal shown in graph 5024, the control member 4560 may determine that the sensor signal includes the left wrist bio signal by the analysis of the characteristic of the wave signal and may determine the state in which it is mounted on the inside 5020 of the left wrist based on the amplitude.

According to an embodiment, the electronic module 4402 may be mounted on the outside 5010 of the user's left wrist as in state 5025. The data obtained by performing frequency analysis on the sensor signal provided from the HRM sensor 4471 activated under the control of the control member 4560 may be shown in graph 5026. For example, the sensor signal gathered by the HRM sensor 4471 may be a signal having a particular frequency of a first amplitude. If the HRM sensor 4471 gathers the sensor signal analyzed in graph 5026, the control member 4560 may determine based on a particular frequency of the first amplitude that the electronic module 4402 is disposed in an upper direction on the outside 5010 of the user's left wrist.

According to an embodiment, the electronic module 4402 may be mounted on the outside 5010 of the user's left wrist as in state 5027. The data obtained by performing frequency analysis on the sensor signal provided from the HRM sensor 4471 activated under the control of the control member 4560 may be shown in graph 5028. For example, the sensor signal gathered by the HRM sensor 4471 may be a signal having a particular frequency of a second amplitude. If the HRM sensor 4471 gathers the sensor signal analyzed in graph 5028, the control member 4560 may determine based on a particular frequency of the second amplitude that the electronic module 4402 is disposed in a lower direction on the outside 5010 of the user's left wrist. The control member 4560 may apply different function running modes or different UI modes according to the shape in which the electronic module 4402 is disposed.

FIG. 103 illustrates a graph related to function running control of an electronic device according to an embodiment.

Referring to FIG. 103, in case the user's particular portion (e.g., a finger) is moved while the electronic device 4400 is worn on a particular portion (e.g., a wrist), the bio signal may be varied. For example, if the electronic device 4400 is worn on the wrist, a sensor signal of the HRM sensor 4471 as in state 5301 may be detected. According to an embodiment, the HRM sensor 4471 may detect the sensor signal having the shape shown when the body variation is in a particular moving state (e.g., a state with no body variation or state of opening the fingers) while it is worn on the wrist as in state 5301. For example, the HRM sensor 4471 may detect the sensor signal for the state with no separate body variation.

Here, if a movement of the finger occurs while the HRM sensor 4471 monitors, the control member 4560 may detect the sensor signal as in state 5303. For example, if a body variation occurs corresponding to the operation of tapping using the thumb and index finger with the fingers opened, the control member 4560 may receive its corresponding sensor signal variation from the HRM sensor 4471. For example, the HRM sensor 4471 may detect the sensor signal with a variation at the time when the body variation occurs (e.g., tapping using the thumb and index finger) as shown. According to an embodiment, the control member 4560 may detect a particular sensor variation value at the time when a movement of the hand or finger occurs. According to an embodiment, the control member 4560 may process particular function control corresponding to the finger movement. According to an embodiment, if it is in the state with no body variation or state where the body variation occurs within a preset range, the control member 4560 may perform control to perform the first function (e.g., the clock display function). If the body variation as in state 5303 occurs so that it is determined as a particular operation state (e.g., tapping using the thumb and index finger), the control member 4560 may perform control to perform the second function (e.g., weather display function). Here, the control member 4560 may perform control to run various functions (e.g., entry into privacy mode, entry into public mode, or entry into security mode) per operation state according to the body variation.

According to an embodiment, the control member 4560 may distinguish various forms of finger operation based on the movement of the hand, type of finger, or movement type of finger. The control member 4560 may map execution of a particular function to each distinguished form. If a particular operation occurs, the control member 4560 may process the execution of the mapped particular function. The control member 4560 provides support allowing the function control of the electronic device 4400 to be done according to the operation at the portion where the electronic device 4400 is worn even without direct control of the electronic device 4400.

According to an embodiment, the control member 4560 may perform control so that the sensor may sense and gather the varied bio information, such as the blood flow, blood pressure, or oxygen saturation, by the body variation at the portion adjacent to the electronic device 4400, such as the finger movement, finger tapping, opening/closing fingers, or wrist movement. The control member 4560 may perform control to extract second information (e.g., one tap, two tap, N tap, or long tap) as well as first information (e.g., heart rate) based on the gathered sensor signal and perform the above-described various particular operations based on the same.

According to an embodiment, the control member 4560 may classify the operations depending on the occurrence of tapping by the thumb or number of times of the operations. For example, the control member 4560 may distinguish and classify the operation of colliding fingers to each other or the operation of tapping, e.g., a table once with a particular finger, the operation of repeated tapping which does tapping several times at predetermined intervals (e.g., 100 ms<Evnet<200 ms), and the long tap operation where the body variation signal by tapping lasts a predetermined time (e.g., 100 ms or more).

The control member 4560 may apply the classified operations to running a particular app of the electronic device 4400 to perform various types of processing. According to an embodiment, when the repeated tap operation occurs while a call is received (e.g., reception of a call message, alarm message, or VoIP connection request), the control member 4560 may determine it as the occurrence of an input event corresponding to the call connection or acknowledgement (e.g., OK). If the long tap operation is generated while the call is received, the control member 4560 may determine it as occurrence of an input event, such as reject the call connection or cancel establishing channel.

According to an embodiment, if the repeated tap operation occurs while a notification, such as a message or email, is received, the control member 4560 may process the function of checking the content of the received message or email. For example, the control member 4560 may perform control to output a screen including the content of the received message or email on the display module 4440.

According to an embodiment, if the repeated tap operation occurs while the media control function is performed, the control member 4560 may perform control to shift to the next content of the currently played content in the content list. Further, if the long tap operation occurs while the media control function is performed, the control member 4560 may perform control to play a previous content in the content list.

According to an embodiment, upon detecting the sensor signal corresponding to a particular operation while a particular screen is output on the display module 4440 or a standby screen, menu screen, or a particular function running screen is output, the control member 4560 may control a screen switch. For example, when the tap operation occurs, the control member 4560 may perform control to remove the current screen from the display module 4440 while displaying another screen from the right side of the edge of the display module 4440 to the left or from the left side of the edge to the right. When the repeated tap operation occurs, the control member 4560 may perform control to remove the current screen from the display module 4440 while displaying another screen from the left side of the edge of the display module 4440 to the right or from the right side of the edge to the left. When the long tap operation occurs, the control member 4560 may perform control to terminate the screen search function and enter the screen indicated by the long tap operation (e.g., output the indicated screen on the entire screen of the display module 4440). The above-described control member 4560, in connection with preventing malfunctioning input of the electronic device 4400, may perform input event processing on a particular operation (e.g., tap operation) occurring within a predetermined time from the time when a predefined particular event occurs.

Figure 104:
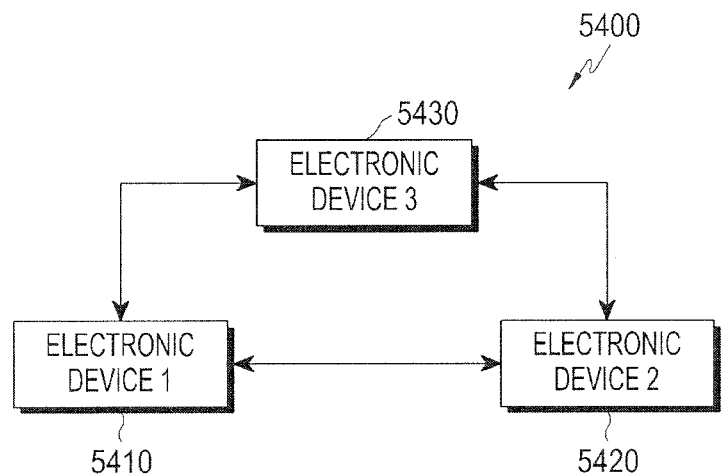
FIG. 104 is a view illustrating a network environment according to an embodiment.

FIG. 104 is a view illustrating a network environment 5400 according to an embodiment. The network environment 5400 may include a first electronic device 5410, a second electronic device 5420, and a third electronic device 5430. Each of the first to third electronic devices 5410 to 5430 may have the same or similar configuration to the whole or part of the configuration of the electronic device 201 shown in FIG. 52 or the electronic device 101 shown in FIG. 51, for example. The first electronic device 5410 and the second electronic device 5420 may correspond to the user's device, and the third electronic device 5430 may correspond to a server device.

The first electronic device 5410 and the second electronic device 5420 respectively may include sensor devices (e.g., the sensor module 240 or bio sensor 240I).

According to an embodiment, the first electronic device 5410 may include a memory (e.g., the memory 130 or 230), a processor (e.g., the processor 120 or 210), and a communication module (e.g., the communication interface 160 or communication module 220).

The processor may be configured to obtain a plurality of bio information on a user, store the plurality of obtained bio information in the memory, determine update periods or targets respectively for the plurality of stored bio information, and transmit the plurality of obtained bio information to the second electronic device 5420 and the third electronic device 5430, respectively, at different times through the communication module according to the determined update periods or targets.

The processor may be configured to transmit the plurality of obtained bio information to at least one external device, respectively, at different times.

According to an embodiment, the processor may be configured to classify the plurality of obtained bio information according to preset significances and assign update periods incrementing according to the priority of the significances to the plurality of classified bio information.

According to an embodiment, the processor may be configured to classify the plurality of obtained bio information according to preset significances based on the user's health information and assign update periods incrementing according to the priority of the significances to the plurality of classified bio information.

According to an embodiment, the processor may be configured to classify the plurality of obtained bio information according to preset first and second significances, transmit, through the communication module, bio information with the first significance of the plurality of bio information to the user's second electronic device 5420 and transmit, through the communication module, bio information with the second significance of the plurality of classified bio information to the third electronic device 5430, which corresponds to a public device.

According to an embodiment, the processor may be configured to determine priorities respectively for a plurality of bio information stored in the memory and sequentially delete the plurality of bio information according to the determined priorities.

According to an embodiment, the processor may be configured to determine priorities of the plurality of bio information stored in the memory based on the obtaining time, obtaining period or type of information and sequentially delete the plurality of bio information according to the determined priorities.

According to an embodiment, the processor may be configured to transmit through the communication module the plurality of obtained bio information to the second electronic device 5420 and the third electronic device 5430, respectively, at different periods.

According to an embodiment, the processor may be configured to determine whether the user is a user pre-registered in the first electronic device 5410 based on the plurality of obtained bio information and transmit the plurality of obtained bio information to the second electronic device 5420 corresponding to another electronic device of the pre-registered user.

Figure 105:
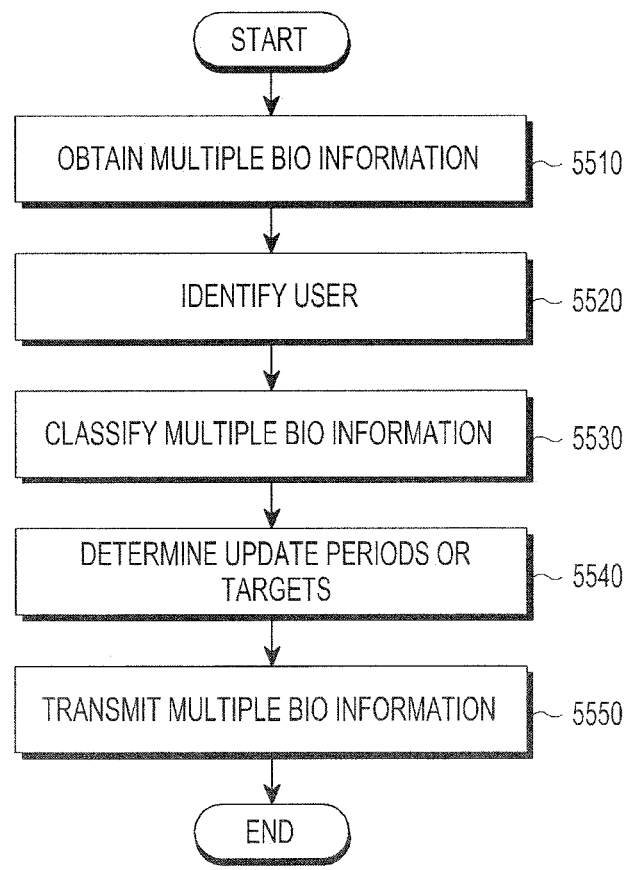
FIG. 105 is a flowchart illustrating a syncing method of a first electronic device according to an embodiment.

FIG. 105 is a flowchart illustrating a syncing method of a first electronic device according to an embodiment. The method may be performed by the first electronic device (e.g., the electronic device 101 or 201) or processor (e.g., the processor 120 or 210) of the first electronic device. The method may include all or some of the operations 5510 to 5550.

In operation 5510, the first electronic device may obtain a plurality of bio information on the user. For example, the first electronic device may include a sensor device, bio sensor, or health sensor (e.g., the storage unit 240 or bio sensor 240I), and the first electronic device may obtain the bio information through the sensor device or may receive bio information from the first electronic device.

In operation 5520, the first electronic device may determine whether the user is a user pre-registered in the electronic device based on the plurality of obtained bio information. The sync of the bio information may be performed on the electronic device of the pre-registered user.

In operation 5530, the first electronic device may classify the plurality of obtained bio information according to preset significances.

In one embodiment, the first electronic device may classify the plurality of obtained bio information according to the preset significances based on the user's health information.

In one embodiment, the first electronic device may classify the plurality of obtained bio information according to preset first and second significances.

In operation 5540, the first electronic device may determine the respective update periods or targets of the plurality of obtained bio information.

In one embodiment, the first electronic device may assign update periods incrementing according to the significances to the plurality of classified bio information.

In operation 5550, the first electronic device may transmit the plurality of obtained bio information to at least one external device at different times according to the determined update periods or targets.

In one embodiment, the first electronic device may transmit bio information with a first significance of the plurality of classified bio information to another electronic device of the user and bio information with a second significance of the plurality of classified bio information to a public device (e.g., server).

In one embodiment, the first electronic device may determine the respective priorities of the plurality of bio information stored in the electronic device and may sequentially delete the plurality of bio information according to the determined priorities.

In one embodiment, the first electronic device may determine the priorities for the respective bio information stored in the first electronic device based on obtaining time, obtaining period, or type of information and may sequentially delete the plurality of bio information according to the determined priorities.

In one embodiment, the first electronic device may transmit the plurality of obtained bio information to a plurality of external devices at different periods.

In one embodiment, there may be a machine readable storage medium recording a program for running a bio information sync method by the first electronic device, and the method may include the operation of obtaining a plurality of bio information on the user, the operation of determining update periods or targets on the plurality of obtained bio information, and the operation of transmitting the plurality of obtained bio information to at least one external device at different times according to the determined update periods or targets.

The user's bio information/sentiment information may be personal information, and the bio signal sensed by the sensor may be stored, converted, or transferred to another device from the moment that is sensed, and may be stored (logged) in a storage medium, or the stored information may be protected upon utilizing later.

The exercise information and bio information gathered through the sensor device in the wearable device or mobile device may be synced with information stored in a server or another device connected via communication means or may be mutually update to date or synced mutually. For example, the exercise history information including the user's step count and travel distance, and consumed energy (consumed calorie) may be manually updated to other device or server through the user's input or may be automatically updated (e.g., at predetermined periods or times).

Figure 106:
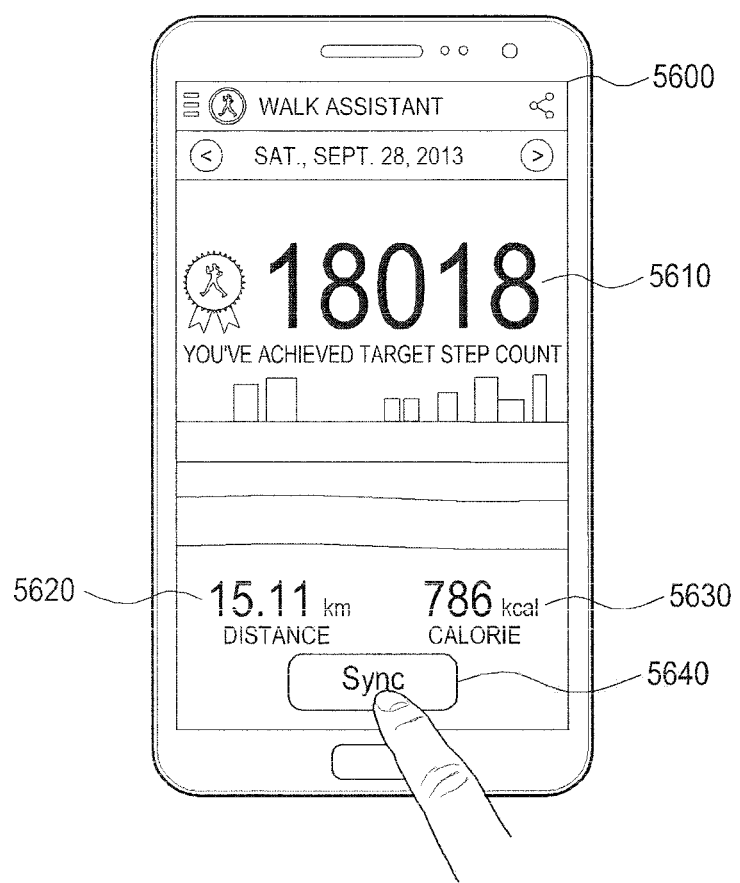
FIG. 106 illustrates an application screen of an electronic device according to an embodiment.

FIG. 106 illustrates an application screen of an electronic device (e.g., the electronic device 101 or 201) according to an embodiment. For example, FIG. 106 shows an example in which the application is manually updated by the user's selection. For example, the application screen 5600 may include the user's step count 5610, travel distance 5620, consumed energy 5630 (consumed calorie), and a button 5640 for sync. For example, in case the user selects the button 5640, the electronic device may transmit the exercise history information including the user's step count, travel distance, and consumed energy to other device or server.

The bio information gathered by the health sensor or user's exercise history, diet activity, or information on eaten food may be accrued for its data over time. Accordingly, since the raw data itself increases in capacity as the monitoring period prolongs, update to the server (cloud device) or web and other connected device needs to be done at predetermined units and periods. Further, the update and sync task may be performed so that the wearable device's health or bio information may be identified through other device or Internet. However, the wearable device suffers from the battery consumption issue and is not always connected with the other device via communication means. Accordingly, according to an embodiment, unnecessary exercise information sync may be eliminated, and sync may be done at a proper moment in preparation for when it is required by the user.

Information for sync or update may include information sensible by the sensor, such as information for user authentication (iris (retina) or fingerprint), bio signal information (ECG, EMG, EEG, EOG, or EGG (passive measurement), PPG, oxygen saturation (SpO2), blood sugar, cholesterol, or blood flow), bio impedance signal (e.g., GSR, body fat, skin hydration value, respiration (active measurement), biodynamical signal (e.g., breath, pulse wave, heart sound, calorie consumption, or ADL (activities of daily living), biochemical signal (e.g., blood analysis, or urine analysis).

Figure 107:
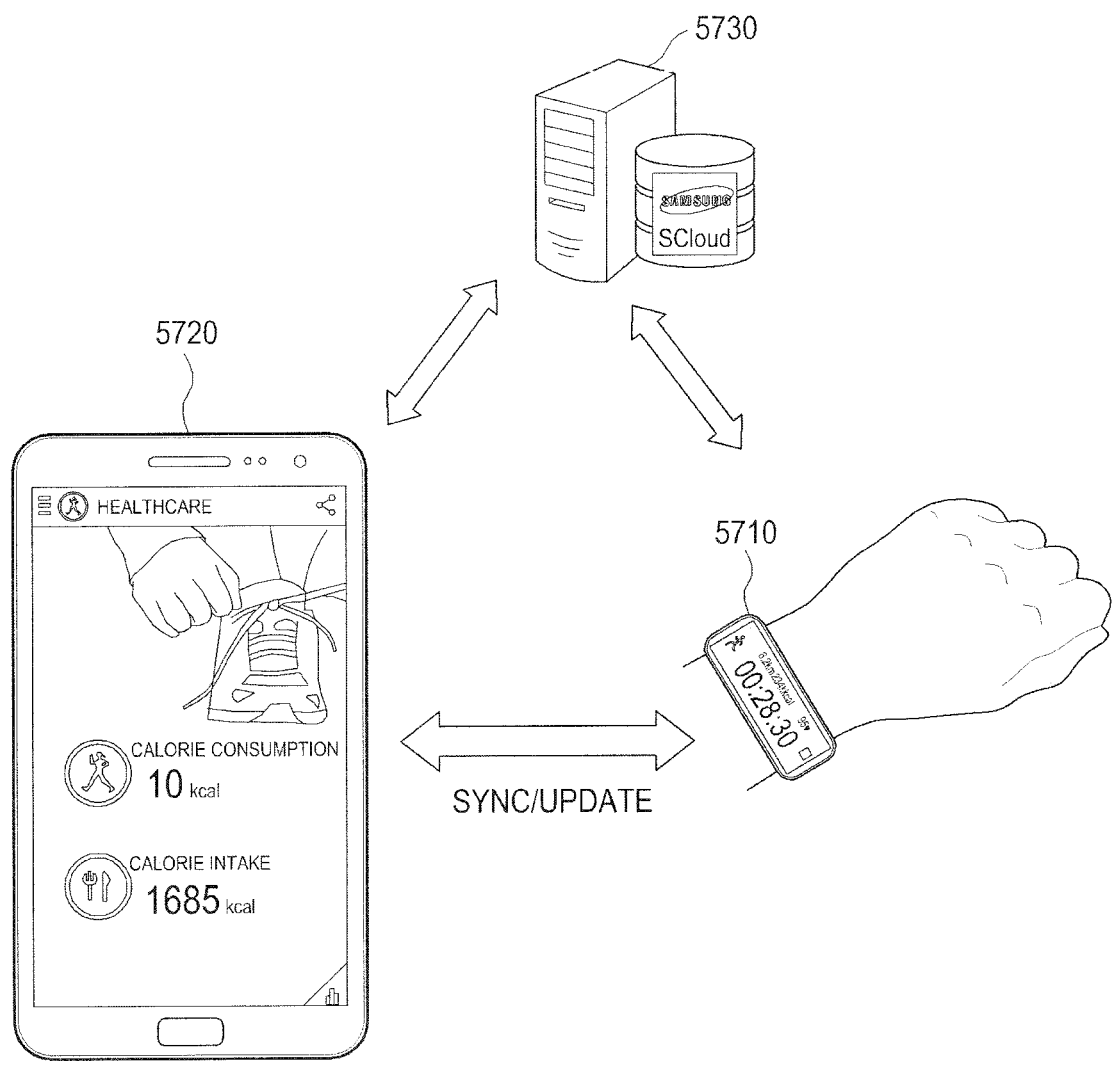
FIG. 107 illustrates a control environment of an application of an electronic device according to an embodiment.

FIG. 107 illustrates a control environment of an application of an electronic device according to an embodiment. For example, the electronic device may control the electronic device using one or more of the user's activity history and exercise history information. The wearable device 5710 (e.g., smartwatch) and the mobile device 5720 (e.g., smartphone) may include a bio signal sensor, such as HR, EMG, ECG, HRV, or PPG sensor, and an exercise information measuring sensor, such as a pedo meter, acceleration, gyro, geomagnetic, temperature, or humidity sensor. The data monitored by the sensor may be connected using a wired or wireless communication means, and sync may be established between the wearable device 5710 and the mobile device 5720 and the server 5730.

In one embodiment, in case the first electronic device equipped with a sensor (e.g., smartwatch or ear clip) accrues bio information and exercise information and updates to other device and server (cloud device), the significance of data may be first evaluated. For example, data with a high significance may be transmitted when information is transmitted to the second electronic device (its smartphone or wearable device), and data with a low significance may be transmitted to the third electronic device (e.g., server, cloud, or web service manager). For example, the HRV bio signal measured by the PPG sensor, since the user's health information (stress level or blood vessel elasticity) may be known by analyzing the same, is relatively high in risk when it is exposed to others. Accordingly, the HRV bio signal or health information is determined to be high in significance. As another example, if the heart rate for a day is measured by measuring the bio signals measured by the PPG sensor, this is relatively low in risk even when exposed to others. Further, there may be added the operation of encrypting and transmitting the information. Further, upon update and sync, the operation of first determining the final sync (update) time may be performed so that update is performed only when there is information corrected after the final sync time.

The wearable device may be restricted in memory capacity to a small size as compared with other devices. According to an embodiment, for efficient memory management, if a predetermined capacity or more of the available memory is being used or the available memory is down to a predetermined level or less, the information may be updated to the other device and server. The bio information and health information accrued in the memory may be automatically deleted depending on the priority (in order of time, particular period, or type of record). In the case of performing health-related sensing to measure daily exercise information, the health data occupies a significant large amount of the capacity of the wearable device and device, and thus, a memory management operation may be performed to secure available memory.

Figure 108A:
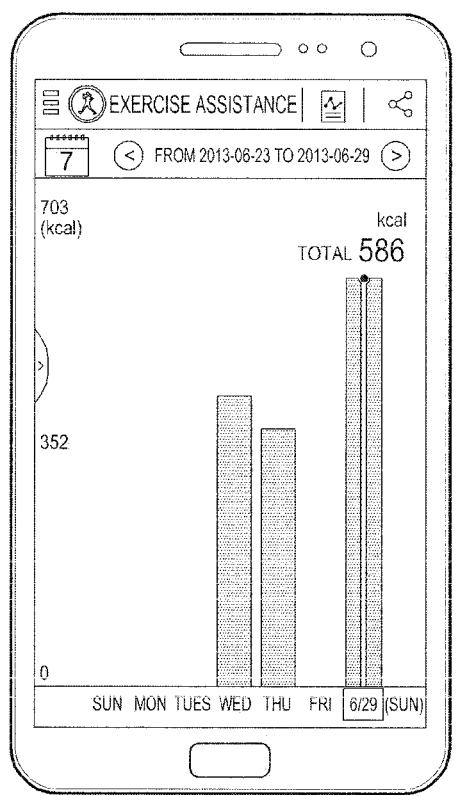
FIG. 108 illustrates an example of an application screen according to an embodiment.
Figure 108B:
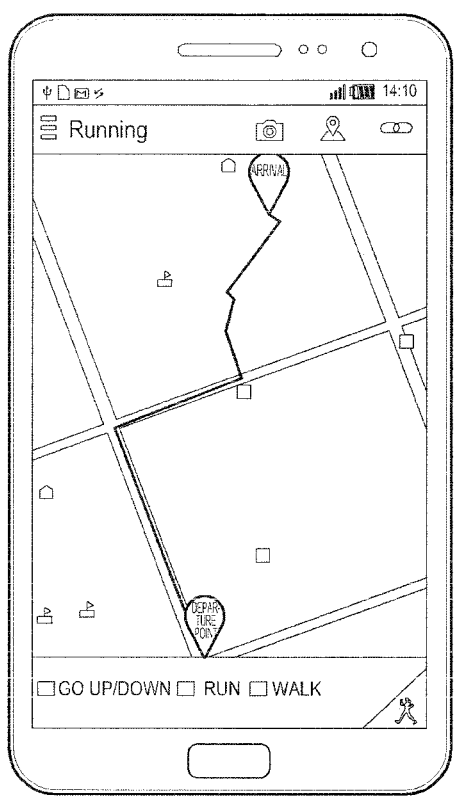

FIG. 108 illustrates an example of an application screen according to an embodiment. FIG. 108(a) shows the per-day calorie consumption in histogram, and FIG. 108(b) shows the path on the map.

For example, the exercise information may record all of a total walking distance, path of exercise, and record of location, calorie consumption, type of exercise, exercise load, and exercise duration in detailed units, such as by the time, day, or month. Such records all may be retained in the electronic device. However, such data may be sync and updated to web, server, or external device (app), and such records, user set data, and particular exercise type records that are not checked by the user any longer may be deleted to reduce the size of data occupying the storage space. If the user desires to check old data, the server and external device may temporarily load and show necessary data.

For example, in case update is done on 2013 Dec. 3, the daily exercise record from 2013 Oct. 1 to 2013 Oct. 1 may be deleted. Of course, the overall total distance, exercise duration, and total calorie consumption for the period may be updated, and the overall average values and sums may be retained in the electronic device.

The bio information may also be subjected to data update or deletion over time. However, the bio information may be stored by monitoring and sensing various signal data, and such information may be determined in different significances for a human being's health. For example, the blood pressure data is very critical for patients with high blood pressure, but it is not considered critical for healthy people with no blood pressure issue. Accordingly, although, upon sensing various bio signals, they all may be updated/synced simultaneously and old data may be deleted, sync may also be performed differently per bio signal.

For example, for patients with diabetes or users interested in blood sugar control, the blood sugar-related information may be set to be sensed or updated very frequently and to have a relatively long period of information storage. By contrast, other bio information may be set to be relatively less frequently sensed or updated.

Such data sync method and difference in period may be set by the user, and data measured by each sensor may be determined so that they may be automatically set by the device including the sensor and app (determining being off a predetermined range). For example, if the frequency or ratio at which the blood pressure is 160 or more is not less than a predetermined reference, the user may be determined as a patient with high blood pressure and the update method and period may be automatically varied. As another example, for the people with a not good condition of lung, the respiratory rate and respiratory rate-related respiration data may be updated/synced every hour, and data internally stored is not deleted, and the EGG data may be synced every week.

In one embodiment, in case the electronic device temporarily borrows and uses the electronic device like in a guest mode, even when paired with another device and connected with the server, it might not be synced. When the guest mode runs, it may interwork with an app of the other device, but it is highly likely to be used alone. In case the user temporarily wears the exercise/bio sensor device, this may be determined automatically/manually as other user and guest, and then, sync may not be done, or a separate DB may be newly created. According to an embodiment, if the values obtained by sensing various bio signals are determined to be different from the user's existing values, the user may be determined as other user.

According to an embodiment, the update and sync to the other device or server may be done manually as necessary, rather than automatically. For example, the sensor-equipped wearable device may be operated standalone, and the bio information and exercise information may be retained only in the wearable device.

Figure 109:
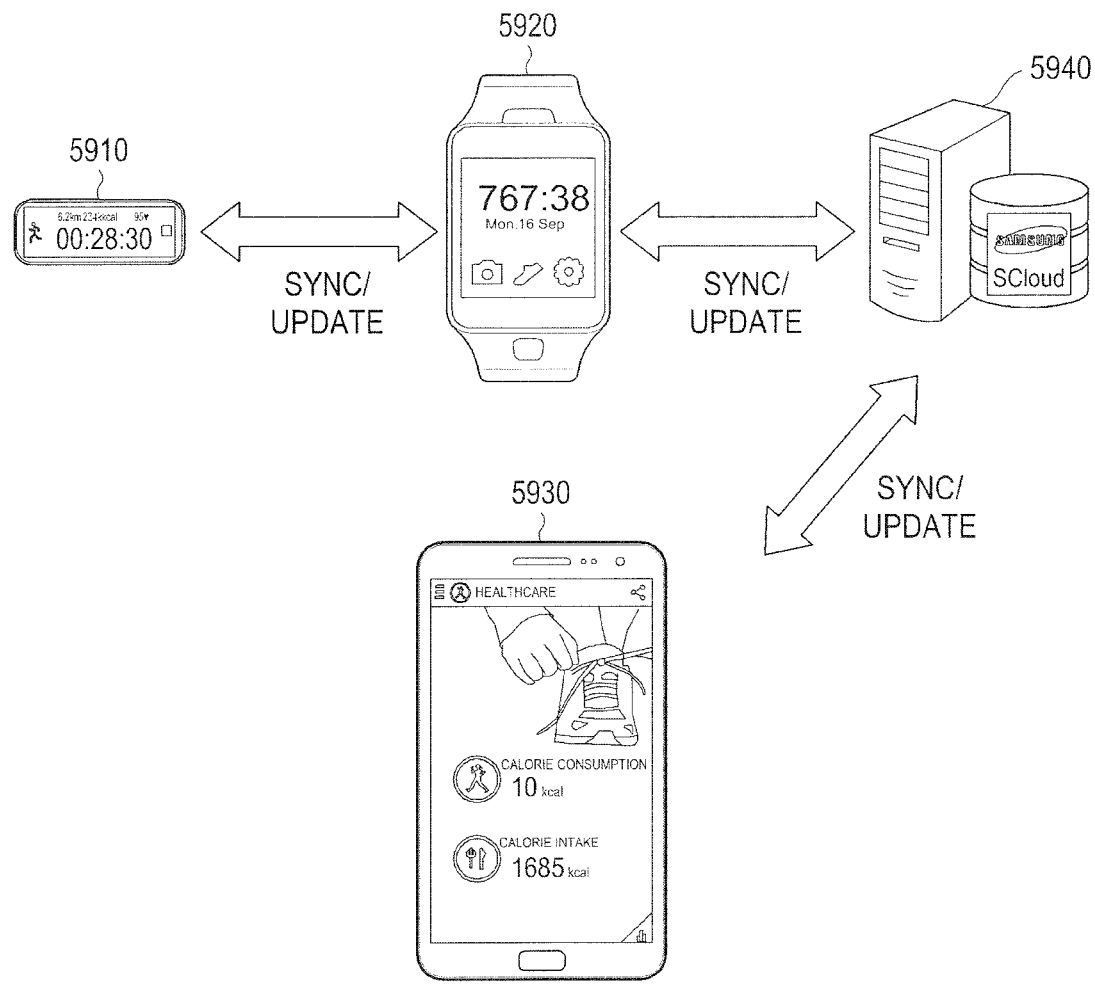
FIG. 109 illustrates a network environment for syncing between electronic devices according to an embodiment.

FIG. 109 illustrates a network environment for syncing between electronic devices according to an embodiment. According to an embodiment, in case several wearable devices capable of measuring exercise-related information and bio information are in connection, one device may function as a master to gather and mix the information and update the server therewith, and each device may separately do update. For example, if the first electronic device 5910 has only short-range communication functionality, such as Bluetooth or BLE, and it is thus difficult to sync with a remote external device, it may perform update and sync with the server 5940 via the second electronic device 5920. At this time, the second electronic device 5920 may forward data of the first electronic device 5910 and may mix the data of the first electronic device 5910 with the data of the second electronic device 5920 and may then proceed with the update and sync with the server 5940. The third electronic device 5930 may directly perform update and sync with the server 5940.

Figure 110:
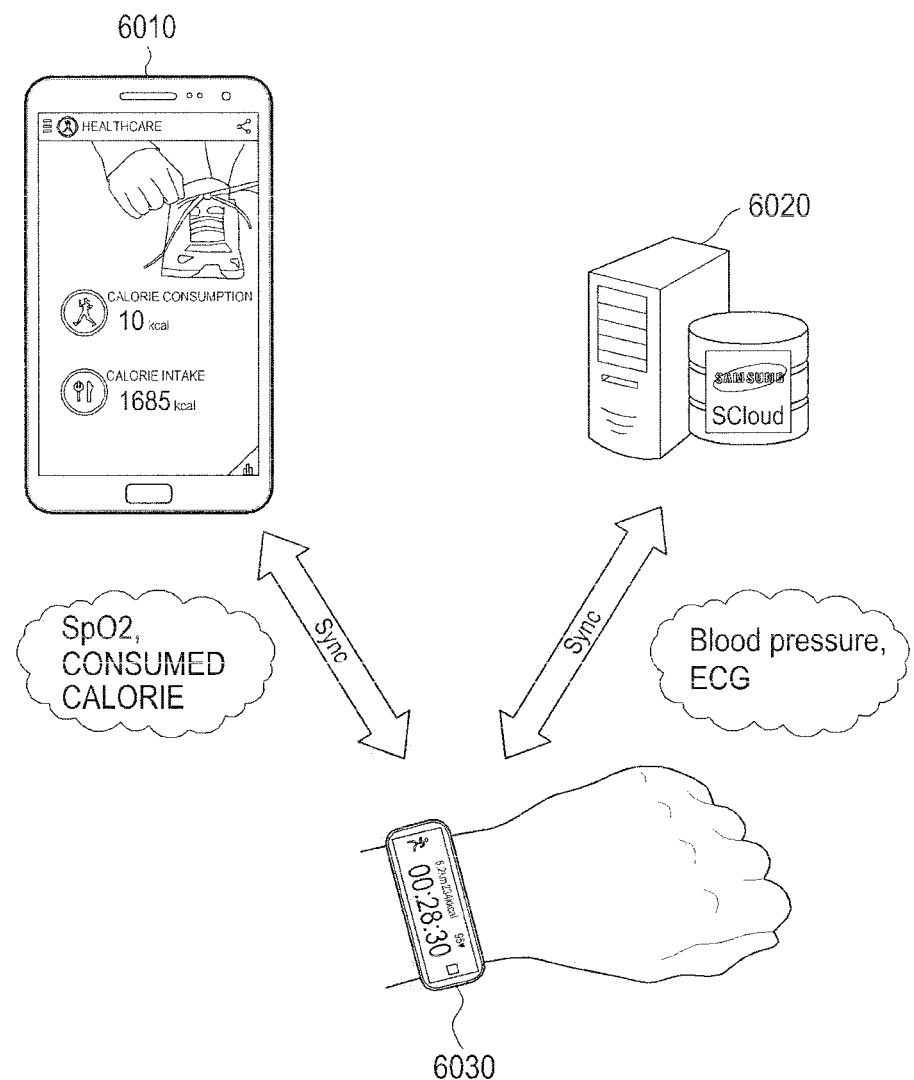
FIG. 110 illustrates a network environment for providing information between electronic devices according to an embodiment.

FIG. 110 illustrates a network environment for providing information between electronic devices according to an embodiment. According to another embodiment, in case one electronic device is connected with two or more external devices, it may classify different types of data updated on each external device and transmit the same. For example, the pedo meter data of the wearable device 6030 may be updated only on the server 6020 (e.g., cloud server), and HRM signals or EMG data may be updated on the mobile terminal 6010.

In one embodiment, in case the update or sync is automatically done even when the sensor-equipped wearable device 6030 does not manually sync the bio information and exercise information, such update and sync may be performed so that the count of information transmission is reduced to the minimum, and it may come in immediate use always when it is required by the user.

As an example, in case the exercise or bio sensor device is not used for a long term, or when the battery is replaced or charged, this may be sensed to perform update or sync. For such purpose, upon entering a low battery state or reaching a predetermined power level or lower, the electronic device may power off soon, and thus, update may be previously performed. Further, the unit of period of sync and range of data synced may be varied depending on the battery and power state of the electronic device. As an example, if the main electronic device and the wearable device capable of sensing bio information are paired together, and a function or application related to exercise or bio information runs on the main electronic device, this may be sensed and automatically updated. As another example, in case the battery level is a predetermined level or higher, sync/update may be more frequently done, and in case the battery level is down to the predetermined level or lower, the sync/update period may be increased. As another example, when the wearable device operating standalone is connected or paired with other electronic device later, update/sync may be performed to the paired device. In an embodiment, update may be performed after a set exercise goal is achieved. For example, if the user registers a goal of jogging 5 km in the health app, in case the goal is achieved, the update and sync may be performed between the two devices.

According to an embodiment, the update/sync may be performed at predetermined periods or time units (time, day, week, month, season, and year). Information for a predetermined period may be summarized and provided automatically at the end of a predetermined unit. As an example, the exercise load or diet-related information achieved per quarter (spring, summer, fall, and winter) may be shown.

Figure 111:
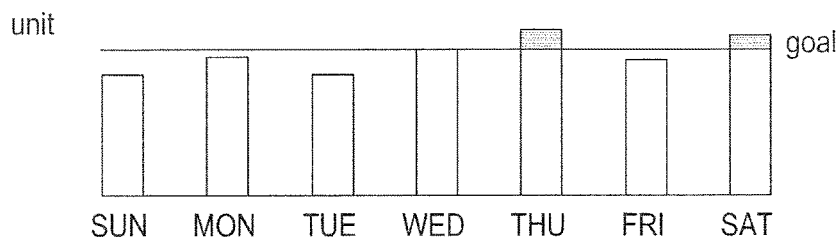
FIG. 111 illustrates an example of an application screen of an electronic device according to an embodiment.

FIG. 111 illustrates an example of an application screen of an electronic device according to an embodiment. For example, the application screen may display the exercise load done weekly. When the aimed exercise load is met or not met, the information may be updated or synced.

Figures 112A, 112B, 112C:
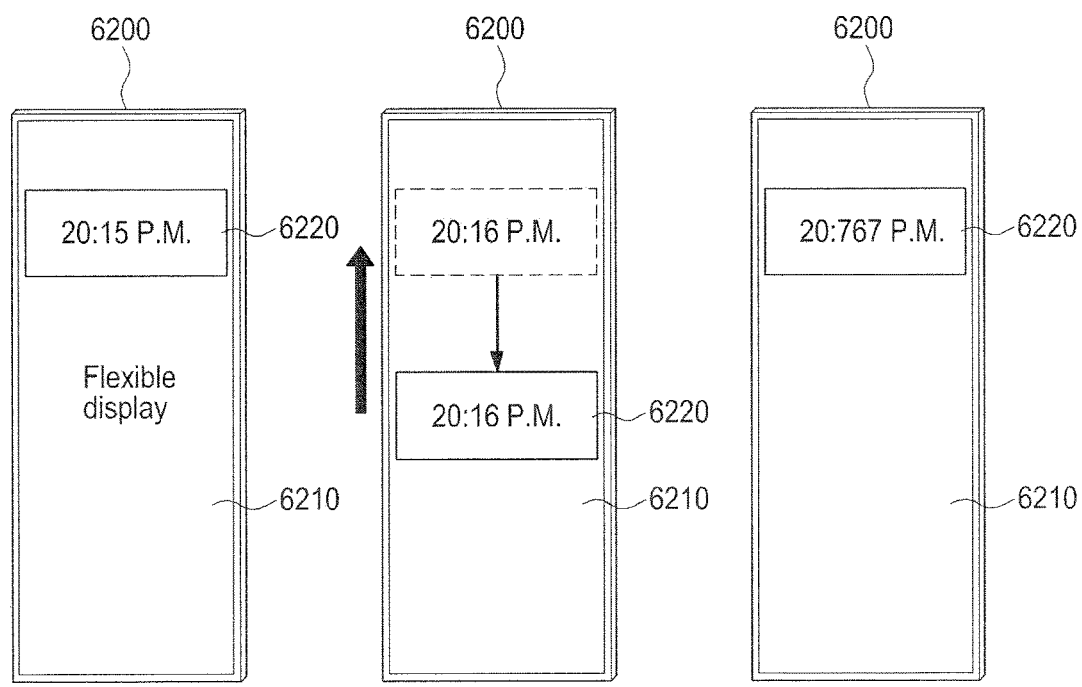
FIG. 112 illustrates a user interface of an electronic device according to an embodiment.

FIG. 112 illustrates a user interface of an electronic device according to an embodiment. According to an embodiment, the information display area or item may be displayed only on a portion of the entire screen of the display. The electronic device 6200 (e.g., wearable device) may have the same or similar configuration to the whole or part of the configuration of the electronic device 201 shown in FIG. 52 or the electronic device 101 shown in FIG. 51, for example.

The electronic device 6200 may include a flexible display 6210 (e.g., the display 150).

FIG. 112(*a*) shows the initial position of the information display item 6220 (e.g., time display item) displayed on a portion of the display 6210.

FIG. 112(*b*) shows that in case the electronic device 6200 is moved up by the user, the information display item 6220 is moved down. For example, in case the electronic device 6200 is erected vertically on the ground, and the user moves the electronic device 6200 in an upper direction perpendicular to the ground, with the top of the display 6210 oriented in the opposite direction of the gravity while the bottom of the display 6210 is oriented in the direction of the gravity, the electronic device 6200 senses its movement using the motion sensor or acceleration sensor (e.g., the acceleration sensor 240E), and the information display item 6220 is moved and displayed in the opposite direction of the moving direction.

Referring to FIG. 112(*c*), a predetermined time after the movement is sensed, the electronic device 6200 may display the information display item 6220 according to the initial position before the movement or variations in the movement.

Figure 113:
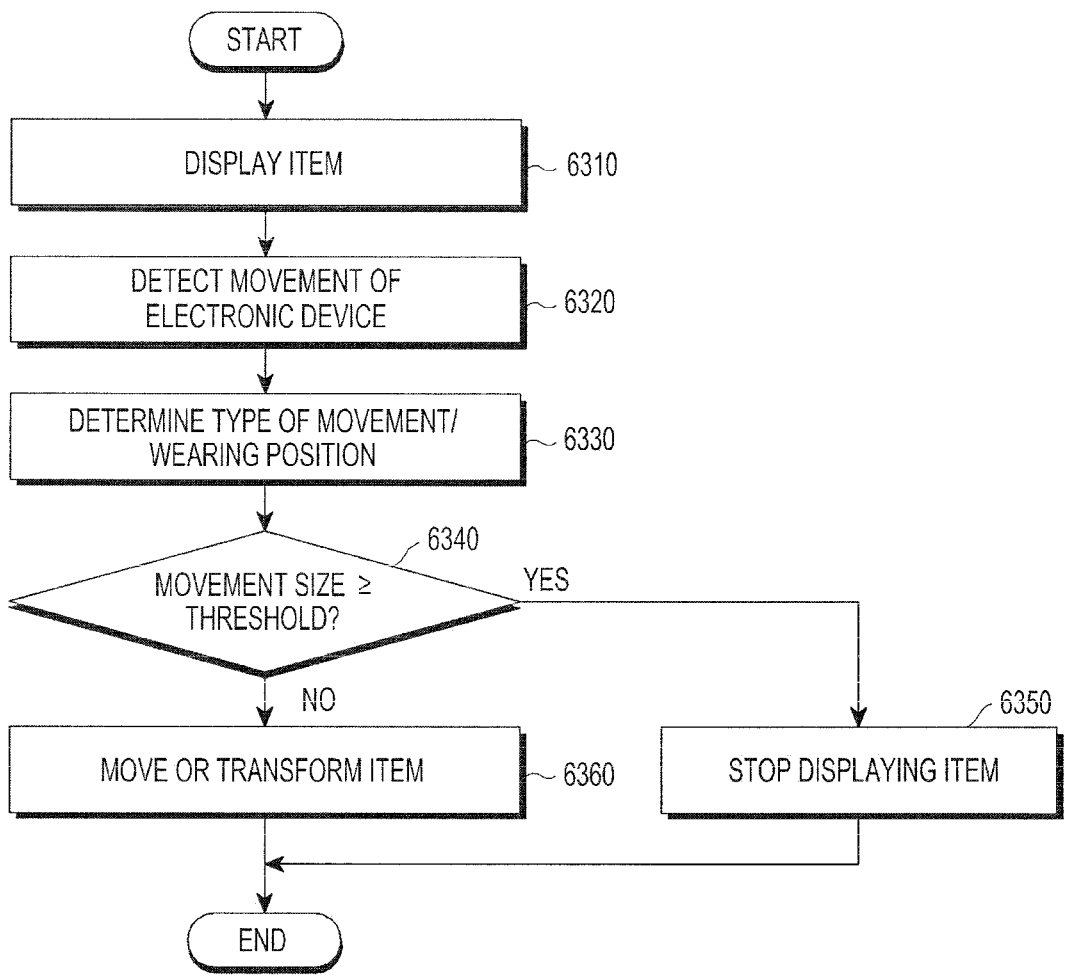
FIG. 113 is a flowchart illustrating a syncing method of an electronic device according to an embodiment.

FIG. 113 is a flowchart illustrating a syncing method of an electronic device according to an embodiment. The method may be performed by the electronic device (e.g., the electronic device 101 or 201) or processor (e.g., the processor 120 or 210) of the electronic device. The method may include all or some of the operations 6310 to 6360.

In operation 6310, the electronic device may display the item on at least a portion of the display (e.g., the display 150). For example, the item may include at least one of text, symbol, image, and icon.

In operation 6320, the electronic device may detect the movement of the electronic device using the sensor module (e.g., the sensor module 240). The electronic device may obtain information such as the type (e.g., rotation, tilting, or move) of the movement, size, or direction of the movement.

In operation 6330, the electronic device may determine the type of the movement and/or the location where the user wears the electronic device. For example, the electronic device may receive the information on the location of wearing from the user, information on the location of wearing from the settings information stored in the memory (e.g., the memory 130 or 230), or may obtain the information on the location of wearing based on the bio information through the sensor module.

In operation 6340, the electronic device may determine whether the size of the movement is not less than a preset threshold. In case the size of the movement is not less than the preset threshold, the electronic device may perform operation 6350, and in case the size of movement is less than the preset threshold, it may perform operation 6360. Operation 6340 may be selectively performed. By contrast, in case the size of movement is not less than the preset threshold, the electronic device may perform operation 6360, and in case the size of movement is less than the preset threshold, it may perform operation 6350.

In operation 6350, the electronic device may stop displaying the item or may abstain from the operation of moving or transforming the item. For example, the electronic device may cut off the power supply to the display (i.e., entry into the sleep mode).

In operation 6360, the electronic device may move or transform the item. In one embodiment, the electronic device may move or transform the item based on the size or direction of the movement and the type of movement of the electronic device.

In one embodiment, the electronic device may move or transform the item based on the location of wearing the electronic device, the size or direction of the movement of the electronic device, and the type of the movement of the electronic device.

In one embodiment, the operation of moving or transforming the item may include the operation of moving or expanding the item in the opposite direction of the movement of the electronic device.

In one embodiment, the movement of the electronic device may include rotation of the electronic device, and the operation of moving or transforming the item may include the operation of moving or expanding the item in the opposite direction of the rotational direction of the electronic device.

In one embodiment, in case a preset condition is met after the item is moved or transformed, the electronic device may restore the item to the original location or shape. For example, the condition may include expiration of a predetermined time and detection of the user's input.

In one embodiment, there may be provided a machine readable storage medium recording a program for running a method for displaying by an electronic device, and the method may include the operation of displaying an item on at least a portion of a display of the electronic device, the operation of detecting a movement of the electronic device, and the operation of moving or transforming the item based on the size or direction of the movement of the electronic device.

In one embodiment, the electronic device may include a display and a processor configured to display an item on at least a portion of the display, detect a movement through a sensor of the electronic device, and move or transform and display the item based on the size or direction of the movement of the electronic device.

In one embodiment, the processor may be configured to determine the type of the movement of the electronic device and move or transform and display the item on the display based on the size or direction of the movement of the electronic device and the type of the movement of the electronic device.

In one embodiment, the processor may be configured to determine the location of wearing the electronic device and the type of the movement of the electronic device and move or transform and display the item on the display based on the size or direction of the movement of the electronic device and the type of the movement of the electronic device and the location of wearing the electronic device.

In one embodiment, the item may include at least one of text, symbol, image, and icon.

In one embodiment, the processor may be configured to compare the size of the movement of the electronic device with a preset value, and in case the size of the movement of the electronic device is not less than the preset value, control the display to stop displaying the item.

In one embodiment, the processor may be configured to compare the size of the movement of the electronic device with a preset value, and in case the size of the movement of the electronic device is not less than the preset value, cut off the power supply to the display.

In one embodiment, the processor may be configured to move or expand and display the item on the display in the opposite direction of the movement of the electronic device.

In one embodiment, the movement of the electronic device may include rotation of the electronic device, and the processor may be configured to rotate or expand and display the item on the display in the opposite direction of the rotational direction of the electronic device.

In one embodiment, the processor may be configured to restore the item to the original location or shape and display the item on the display after the item is moved or transformed.

Figures 114A, 114B, 114C:
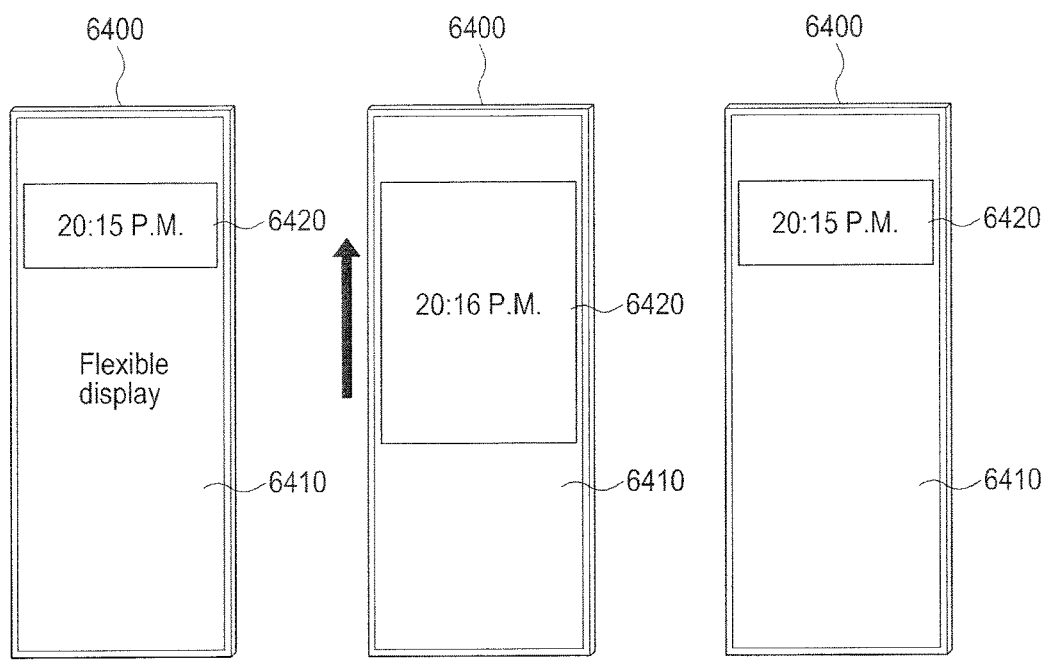
FIG. 114 illustrates a user interface of an electronic device according to an embodiment.

FIG. 114 illustrates a user interface of an electronic device according to an embodiment. The electronic device 6400 (e.g., wearable device) may have the same or similar configuration to the whole or part of the configuration of the electronic device 201 shown in FIG. 52 or the electronic device 101 shown in FIG. 51, for example. The electronic device 6400 may include a flexible display 6410 (e.g., the display 150).

FIG. 114(*a*) shows the initial shape of the information display item 6420 (e.g., time display item) displayed on a portion of the display 6410.

Referring to FIG. 114(*b*), the electronic device 6400 may detect the user's view using the camera module (e.g., the camera module 291), and in case the user's view is moved up, the electronic device 6400 may fix the upper position of the information display item 6420 and expand the information display item 6420 in the opposite direction of the user's view. For example, if the user's view moves within a display area of the information display item 6420 or predetermined distance, or after moving, maintains the view for a predetermined time or more, it may expand the display area of the information display item 6420.

Referring to FIG. 114(*c*), the electronic device 6400, if the user's view is fixed, may restore the information display item 6420 in the form before deformed/expanded.

Figure 115A:
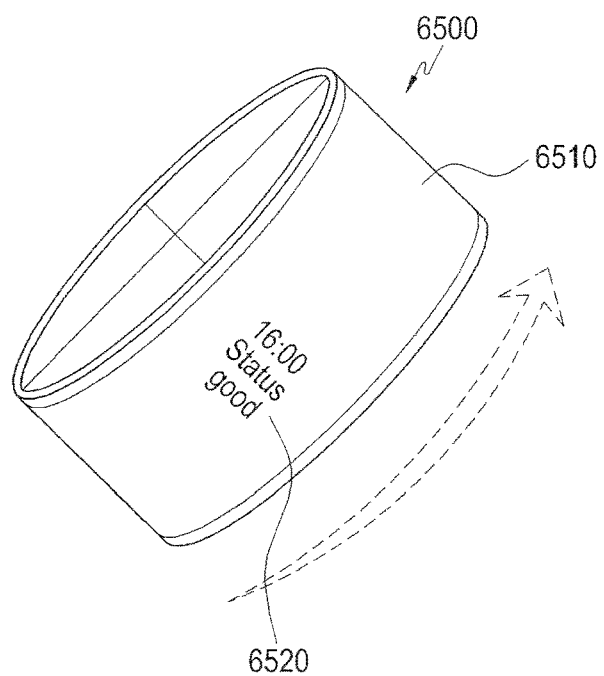
FIGS. 115*a* and 115*b* illustrate an example of a wearable electronic device according to an embodiment.
Figure 115B:
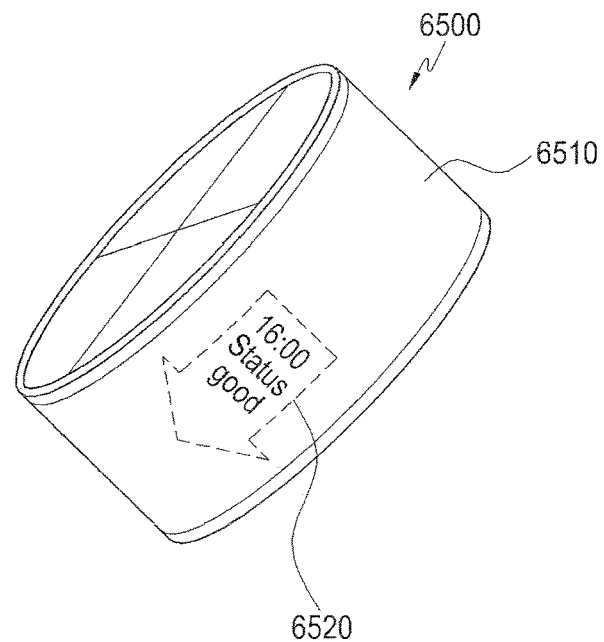

FIGS. 115*a* and 115*b* illustrate an example of a wearable electronic device according to an embodiment. The electronic device 6500 (e.g., wrist watch-type/bracelet-type wearable device) may have the same or similar configuration to the whole or part of the configuration of the electronic device 201 shown in FIG. 52 or the electronic device 101 shown in FIG. 51, for example.

For example, FIGS. 115*a* and 115*b* show an example of the information display by the movement of the electronic device 6500 in case the wearable electronic device 6500 including the flexible display 6510 is disposed in the form of a wrist watch or bracelet.

FIG. 115(*a*) shows the initial position of the information display item 6520 (e.g., time display item) displayed on a portion of the display 6510.

In FIG. 115*a*, when the user takes a motion (tilting or turning wrist) of turning his wrist counterclockwise, the information display item 6520 may be moved counterclockwise with respect to the existing central axis as shown in FIG. 115*b* so that information may be naturally provided to the user.

Figure 116:
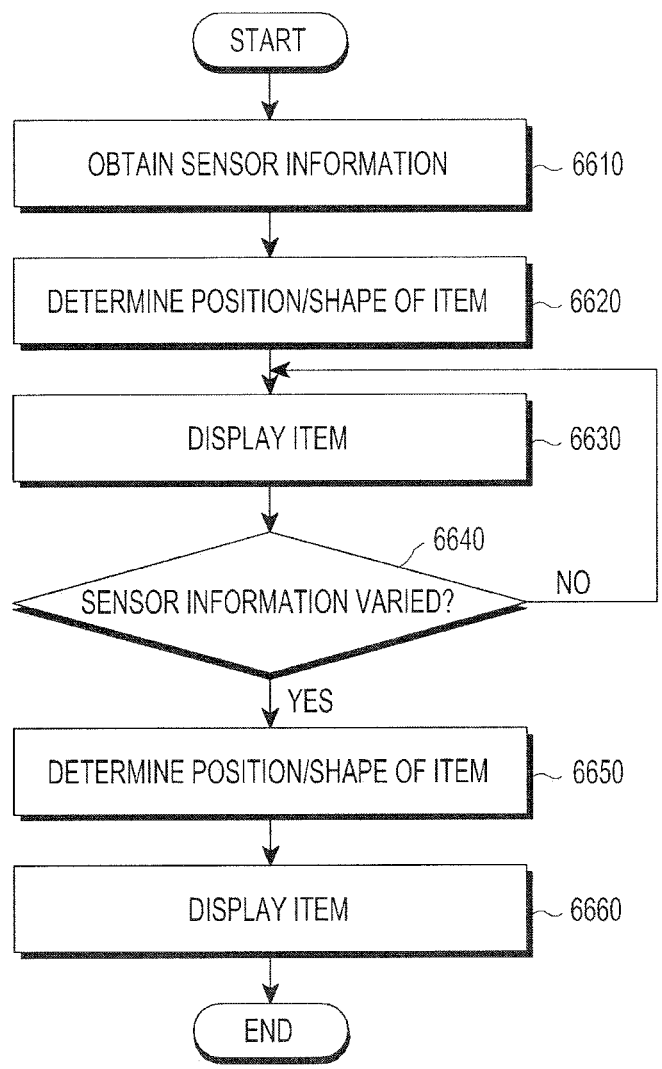
FIG. 116 is a flowchart illustrating an operation of an electronic device according to an embodiment.

FIG. 116 is a flowchart illustrating an operation of an electronic device according to an embodiment. For example, FIG. 116 is a flowchart illustrating determining a display area by the electronic device (e.g., the electronic device 101 or 201) including a flexible display (e.g., display 150) capable of partial display. The method may be performed by the electronic device or processor (e.g., the processor 120 or 210) of the electronic device. The method may include all or some of the operations 6610 to 6660.

In operation 6610, the electronic device may obtain sensor information from the sensor module (e.g., the sensor module 240) or the memory (e.g., the memory 130 or 230). The electronic device may obtain information such as the movement of the electronic device, the type (e.g., rotation, tilting, or move) of the movement, size, or direction of the movement, or the location of wearing the electronic device.

In operation 6620, the electronic device may determine the location where the item is to be displayed on the display and/or the shape of the item based on the sensor information.

In operation 6630, the electronic device may display the item on the display according to the determined location/shape.

In operation 6640, the electronic device may periodically monitor the sensor information and may determine whether the sensor information is varied. In case the sensor information is varied, the electronic device may perform operation 6650, and unless the sensor information is varied, it may maintain operation 6630.

In operation 6650, the electronic device may determine the location where the item is to be displayed on the display and/or the shape of the item based on the varied sensor information.

In operation 6660, the electronic device may display the item on the display according to the determined location/shape.

Figure 117:
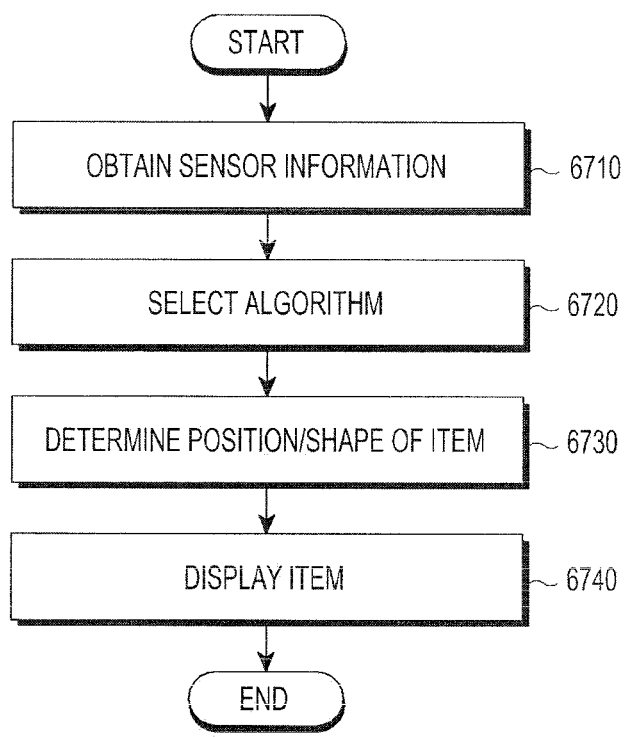
FIG. 117 is a flowchart illustrating an operation of an electronic device according to an embodiment.

FIG. 117 is a flowchart illustrating an operation of an electronic device according to an embodiment. For example, FIG. 117 shows a method of processing the information provided to the display according to the portion where the user wears it and displaying. The method may be performed by the electronic device (e.g., the electronic device 101 or 201) or processor (e.g., the processor 120 or 210) of the electronic device. The method may include all or some of the operations 6710 to 6740.

In operation 6710, the electronic device may obtain sensor information from the sensor module (e.g., the sensor module 240) or the memory (e.g., the memory 130). The electronic device may obtain information such as the movement of the electronic device, the type (e.g., rotation, tilting, or move) of the movement, size, or direction of the movement, or the location of wearing the electronic device.

In operation 6720, the electronic device may select an algorithm according to the wearing position of the electronic device.

In operation 6730, the electronic device may determine the position/shape of the item according to the selected algorithm.

In operation 6740, the electronic device may display the item on the display according to the determined location/shape.

For example, when the user wears the electronic device at a first position, a display method proper for the first position may be provided. For example, in case the user wears the electronic device on his right arm, the item may be displayed according to a preset first algorithm. For example, the electronic device may vary the user interface into vertical view or horizontal view using the sensor information, and since the wearable electronic device is worn on a portion where movements are frequent, a display method may be selected according to the algorithm proper for the wearing position in addition to the sensor information. For example, in case the wearing position of the electronic device is the left wrist and right wrist, when a tilt direction is sensed, the reference direction of the vertical UI and horizontal UI may be varied. For example, in case the electronic device is worn on the right wrist, upon sensing a movement within an angle or movement range where the joints of the right arm cannot be moved, the electronic device may determine it as noise and discard the variation in the sensor information.

Figure 118:
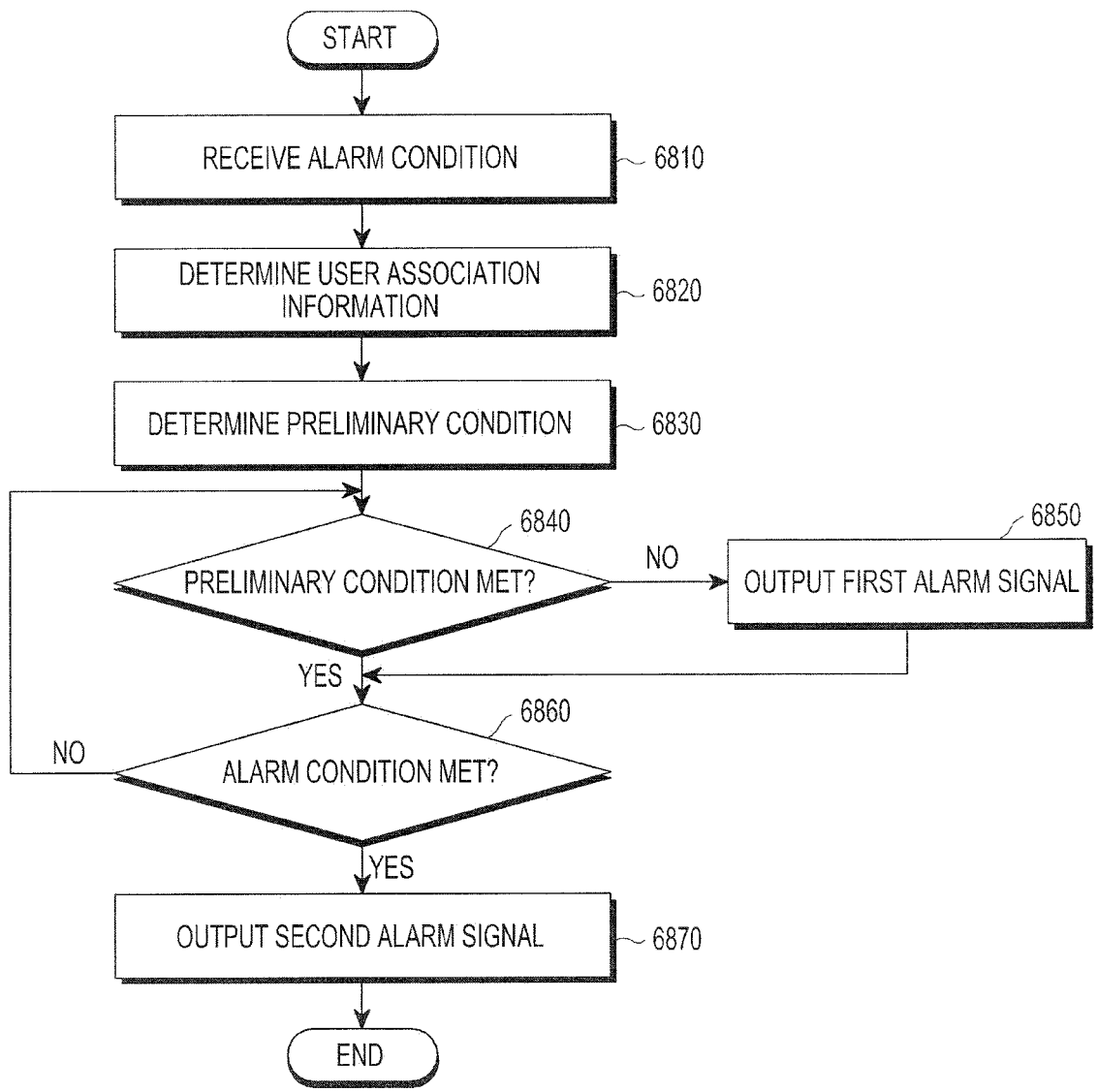
FIG. 118 is a flowchart illustrating an operation of an electronic device according to an embodiment.

FIG. 118 is a flowchart illustrating an operation of an electronic device according to an embodiment. The method may be performed by the electronic device (e.g., the electronic device 101 or 201) or processor (e.g., the processor 120 or 210) of the electronic device. The method may include all or some of the operations 6810 to 6870.

In operation 6810, the electronic device may receive an alarm condition. For example, the electronic device may receive the alarm condition from the user or external device. For example, the alarm condition may include at least one of the alarm date, alarm time, user's schedule, variation in the user's state, variation in the state of the electronic device, and variation in the state of the ambient environment of the electronic device.

In operation 6820, the electronic device may determine user association information associated with the alarm condition of user association information pre-stored in the memory (e.g., the memory 130). For example, the user association information may be sleep information.

In operation 6830, the electronic device may determine a preliminary condition based on the user association information. In one embodiment, the electronic device may transmit the user association information associated with the alarm condition of the user association information pre-stored in the memory to the external device through the communication device (e.g., the communication interface 160, the communication module 220, the input/output interface 140, or the interface 270) and receive the preliminary condition from the external device. For example, the preliminary condition may be the user's sleep time.

In operation 6840, the electronic device may determine whether to meet the preliminary condition. In case the preliminary condition is not met, the electronic device may perform operation 6850, and in case the preliminary condition is met, the electronic device may perform operation 6860.

In one embodiment, the electronic device may detect at least one of the user's state associated with the preliminary condition, the state of the electronic device, and the state of the ambient environment of the electronic device through the sensor module (e.g., the sensor module 240). The electronic device may determine whether the preliminary condition is met based on the detected state.

In one embodiment, the alarm condition may be the alarm time, and the preliminary condition may be the user's sleep time. The electronic device may detect the user's state through the sensor module at least the sleep time before the alarm time. In case the user's state is non-sleep state, the electronic device may determine that the preliminary condition is not met.

In operation 6850, the electronic device may output a first alarm signal in case the preliminary condition is not met. The first alarm signal may include a visual, audible, and/or tactile notification (e.g., an alarm sound, alarm message, or vibration).

In operation 6860, the electronic device may determine whether to meet the alarm condition. In case the alarm condition is not met, the electronic device may repeat operation 6840, and in case the alarm condition is met, it may perform operation 6870.

In operation 6870, the electronic device may output a second alarm signal in case the alarm condition is met. The second alarm signal may include a visual, audible, and/or tactile notification (e.g., an alarm sound, alarm message, or vibration).

According to an embodiment, there may be provided a machine readable storage medium recording a program for running an alarming method by an electronic device, and the method may include the operation of receiving an alarm condition, the operation of determining a preliminary condition corresponding to the alarm condition, the operation of determining whether the preliminary condition is met, and the operation of outputting a first alarm signal before the alarm condition is met according to whether the preliminary condition is met.

According to an embodiment, the electronic device may include a memory and a processor, and the processor may be configured to receive an alarm condition, store the received alarm condition in the memory, determine a printed layer corresponding to the alarm condition, store the determined preliminary condition in the memory, determine whether the preliminary condition is met, and output a first alarm signal before the alarm condition is met according to whether the preliminary condition is met.

According to an embodiment, the processor may receive the alarm condition from the user or an external device.

According to an embodiment, the processor may receive the preliminary condition from the user or an external device.

According to an embodiment, the processor may be configured to determine user association information associated with the alarm condition of user association information pre-stored in the memory and determine the preliminary condition based on the user association information.

According to an embodiment, the processor may be configured to transmit the user association information associated with the alarm condition of the user association information pre-stored in the memory to the external device through a communication module of the electronic device and receive the preliminary condition from the external device through the communication module.

According to an embodiment, the processor may be configured to detect at least one of the user's state, a state of the electronic device, and a state of an ambient environment of the electronic device through at least one sensor functionally connected with the electronic device and associated with the preliminary condition and determine whether the preliminary condition is met based on the detected state.

According to an embodiment, the processor may be configured to output a second alarm signal depending on whether the alarm condition is met.

According to an embodiment, in case the user stays up late although an alarm is set based on the analysis of the user's pattern and sensor information, the electronic device may induce the user to naturally go to bed by reminding the user of the setting of the wakeup alarm.

According to an embodiment, the electronic device may include an input/output interface receiving the user's desired sleep time and transferring the alarm and an alert for the user's non-sleep state (e.g., the input/output interface 140), a display (e.g., the display 150) displaying the sleep time and alarm time, a memory (e.g., the memory 130) storing the alarm time and minimum sleep time, a sensor module (e.g., the sensor module 240) identifying whether the user is asleep, and a processor (e.g., the processor 120) determining whether the user is in sleep using various information such as real-time information or sensor information and determining whether to sound the alarm.

In one embodiment, as the user sets a wakeup alarm, a sleep warning mode may be activated on the UI. For example, the settings menu has items for a sleep time thought to be proper by the user, and the alarm may be operated based on the proper sleep time. The sleep time may represent a desired sleep time that the user desires to sleep to the minimum before the alarm operates.

Figure 119:
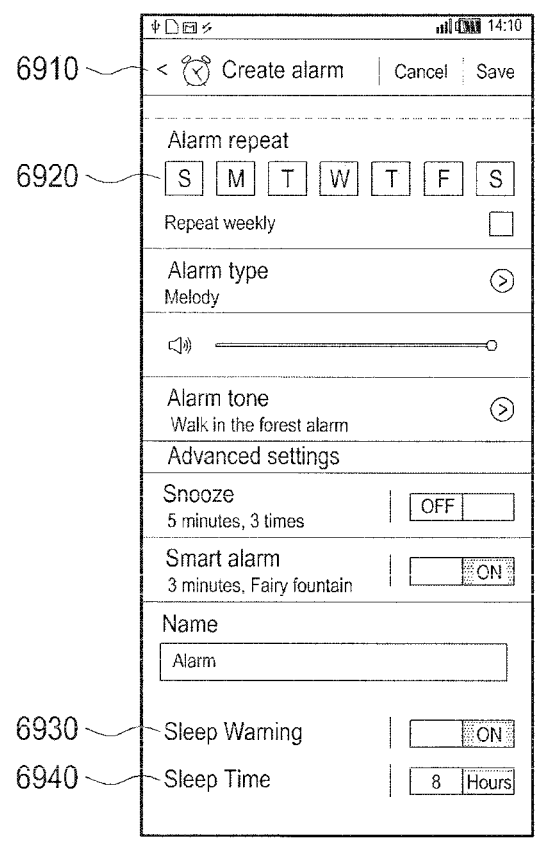
FIG. 119 illustrates a user interface of an electronic device according to an embodiment.

FIG. 119 illustrates a user interface of an electronic device according to an embodiment. Referring to FIG. 119, the sleep time 6940 designated by the user on the alarm setting UI 6910 of the electronic device (e.g., the electronic device 101 or 201) may be set manually by the user input or automatically using the user's activity history information. For example, if it is automatically set, the electronic device may gather the user's normal daily pattern, computes an average of the normal sleep times, and it may be shown as default value on the alarm setting UI 6910. The sleep time 6940 designated by the user on the alarm setting UI 6910 may not only interwork with each alarm but the function itself may apply to all of the alarms as well. For example, several alarms may be set through the alarm repetition menu 6920 on the alarm application, and the wakeup alarm time of Monday to Friday may be set to 6:00 AM, and the wakeup alarm time of Saturday and Sunday may be set to 9:00 AM. In such case, when the sleep time is set to 8 hours, it may apply to the settings of the two alarms, or different sleep times may be set for each desired alarm (Mon to Fri).

The sleep time 6940 designated by the user on the alarm setting UI 6910 may interwork with a scheduler, and rather than always fixed, may be intelligently varied or restricted in operation. For example, in case the sleep time itself is not guaranteed due to the schedule given the next schedule, varied operations, such as informing the user or abstaining from the notification operation, may be possible. The sleep time 6940 on the alarm setting UI 6910 may be selected from some proposed menus or may be set in the form directly inputted by the user.

If the user's desired sleep time 6940 is A time, and the alarm time is B A.M., with the sleep warning function 6940 turned on, the electronic device may check the ambient environment using the sensor module A hours before the notification occurs, and upon determining that the user stays awaken, it may show the user a notification message to induce the user to sleep considering that the user runs out of the proper sleep time.

Figure 120:
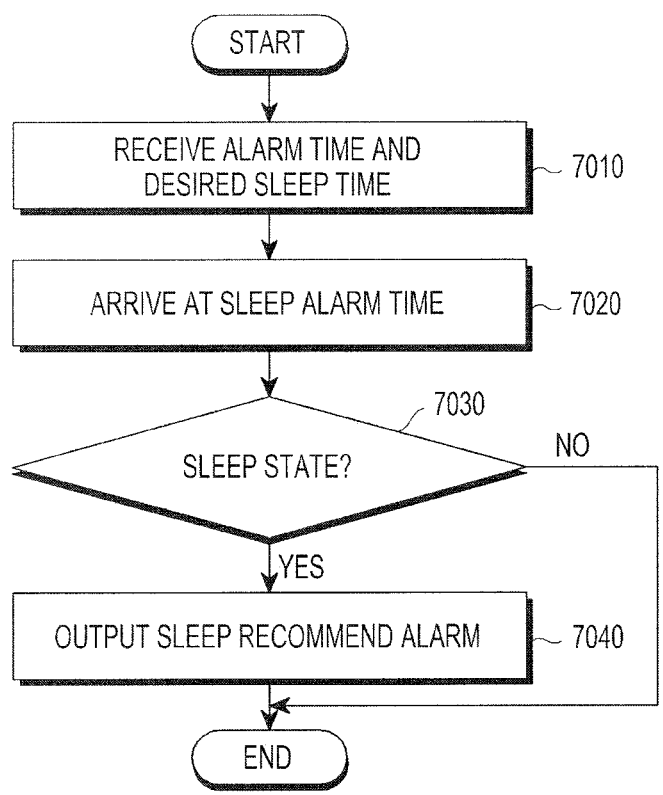
FIG. 120 is a flowchart illustrating an operation of an electronic device according to an embodiment.

FIG. 120 is a flowchart illustrating an operation of an electronic device according to an embodiment. The method may be performed by the electronic device (e.g., the electronic device 101 or 201) or processor (e.g., the processor 120 or 210) of the electronic device. The method may include all or some of the operations 7010 to 7040.

In operation 7010, the electronic device may receive an alarm time and desired sleep time from the user through the input/output interface (e.g., the input/output interface 140). The electronic device may receive the current time through the external network, and the electronic device may include a clock operating standalone.

In operation 7020, the electronic device may detect the arrival at the sleep alarm time. The sleep alarm time may be the time obtained by subtracting the desired sleep time from the alarm time.

In operation 7030, the electronic device may determine whether the user is in the sleep state. The electronic device may perform operation 7040 in case the user is in the sleep state and abstain from operation 7040 in case the user is not in the sleep state.

In operation 7040, in case the user is in the sleep state, the electronic device may output a sleep recommend alarm (e.g., a visual, audible, and/or tactile alarm) in case the user is in the sleep state.

The electronic device may determine whether the user stays up using sensor information. The electronic device may determine whether the user stays up using one or more of the backlight state of the electronic device, whether there is an application currently running, sensing a motion/movement by the sensor module, and a bio signal or bio information by the health sensor.

According to an embodiment, although the user does not use the electronic device, the input value to the illumination sensor, whether there is noise coming in the microphone, and sensing a movement using the camera module may be comprehensively considered in order to determine whether the user stays up. This is for grasping whether the user sleeps or not using the sensor of the electronic device even when the user does not use the electronic device or does not wear the electronic device.

In one embodiment, although the user is off the range of the sensor of the electronic device, the electronic device may interwork with the sensor information from other electronic device located in the home network, such as camera or motion sensor located at home to determine whether the user is in sleep.

In case several electronic devices are connected using wired or wireless communication, the electronic device determining whether the user is in sleep may differ from the electronic device driving the sensor and sensing. For example, the main electronic device (e.g., the smartphone or wearable device) may receive, via the communication module, the sensor information gathered or measured by the smart watch connected using the communication module and determine whether he is in sleep from the sensor information.

In one embodiment, the electronic device setting the user's sleep time may differ from the electronic device driving the sensor and sensing. That is, the smartphone may set the sleep time, and the sleep state of the user may be measured by the smart watch.

Figure 121:
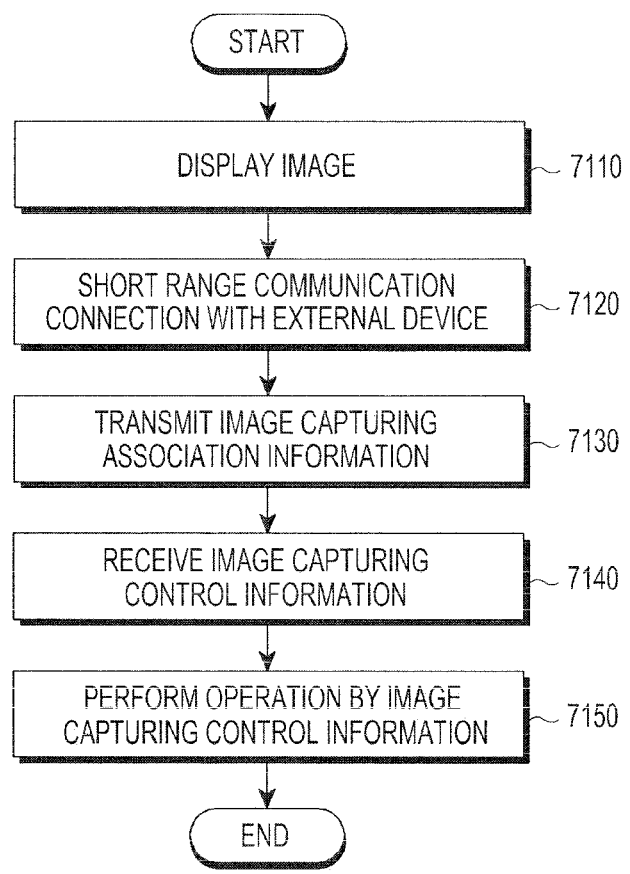
FIG. 121 is a flowchart illustrating an operation of a first electronic device according to an embodiment.

FIG. 121 is a flowchart illustrating an operation of a first electronic device according to an embodiment. The method may be performed by the first electronic device (e.g., the electronic device 101 or 201) or processor (e.g., the processor 120 or 210) of the first electronic device. The method may include all or some of the operations 7110 to 7150.

In operation 7110, the first electronic device may display the image (e.g., live preview image) captured using the camera module (e.g., the camera module 291) on the display (e.g., the display 150). The displayed image may be a still image or motion image, or live preview image.

In operation 7120, the first electronic device may perform short-range communication connection with the second electronic device through the communication module (e.g., the communication interface 160 or communication module 220). In one embodiment, operation 7120 may be performed before operation 7110.

In operation 7130, the first electronic device may transmit the image capturing-related information to the second electronic device through the communication module.

In one embodiment, the image capturing-related information may include at least one of information on the object in the displayed image, information on the quality of image capturing, information on the image capturing mode, image capturing settings, and information on the image capturing menu.

In one embodiment, the image capturing-related information may include information on the object in the displayed image or composition information on the object in the displayed image.

In one embodiment, the image capturing-related information may include information on the object in the displayed image or composition information on the object in the displayed image and at least one of brightness, exposure, focal length, image capturing mode, effect, resolution, white balance, and ISO sensitivity.

In operation 7140, the first electronic device may receive the image capturing control information from the second electronic device through the communication module.

In one embodiment, the image capturing control information may include control information on the image capturing of the object in the displayed object or composition variation information on the object in the displayed image.

In one embodiment, the image capturing control information may include at least one of information on the control of the image capturing quality, information on the control of the image capturing mode, information on the variation in the image capturing setting, and information on the selection of the image capturing menu and control information on the image capturing of the object in the displayed image or the composition variation information on the object in the displayed image.

In operation 7150, the first electronic device may perform an operation according to the image capturing control information. The first electronic device may output the result of processing the image capturing control information. For example, the first electronic device may perform, according to the image capturing control information, varying the image capturing quality, varying the image capturing mode, varying the image capturing setting, selecting the image capturing menu, transmitting/processing the control information on the image capturing of the object in the displayed image, transmitting/processing the composition variation information on the object in the display image, and transmitting image.

In one embodiment, the control information may include selection information on the object in the image, and the first electronic device may transmit the image capturing-related information to the third electronic device corresponding to the selected object.

In one embodiment, the control information may include selection information on the object in the image, and the first electronic device may transmit the captured image to the third electronic device corresponding to the selected object.

According to an embodiment, there may be provided a machine readable storage medium recording a program for running an image capturing method by an electronic device, and the method may include the operation of displaying an image, the operation of transmitting image capturing-related information to an external device, the operation of receiving control information associated with the image capturing from the external device, and the operation of processing the control information.

According to an embodiment, the electronic device may include a communication module, a display playing an image, and a processor, and the processor may be configured to transmit information associated with the image capturing through the communication module to the external device, receive the image capturing-related control information from the external device through the communication module, and output the result of processing the control information.

According to an embodiment, the processor may be configured to perform short-range communication connection with the external device through the communication module.

According to an embodiment, the processor may be configured to transmit the image capturing-related information to a device corresponding to the selected object through the communication module.

According to an embodiment, the processor may be configured to transmit the captured image to a device corresponding to the selected object through the communication module.

Upon image capturing, the first electronic device may receive information on the image capturing from a second electronic device paired remotely. For example, an image capturing command may be generated by the second electronic device connected with the first electronic device, but not by the first electronic device where the camera runs. The second electronic device connected via wired or wireless communication may provide a smaller display as compared with the first electronic device functioning as a host device (e.g., one or more of the camera, smartphone, and camcorder) and may provide limited functions. The second electronic device may play a role as a remote controller for image capturing and may provide commands, such as simple image capturing or varying mode.

In one embodiment, the second electronic device including a limited input device or output device may identify the information captured by the first electronic device, and the second electronic device may provide a user UX/UI to provide a function allowing remote image capturing to be done easily.

Figure 122:
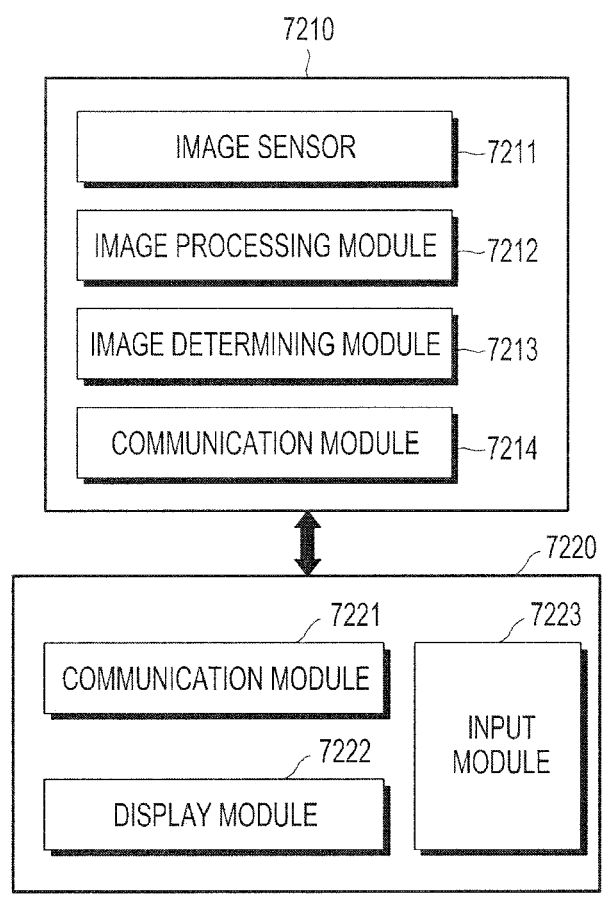
FIG. 122 illustrates block diagrams of electronic devices according to an embodiment.

FIG. 122 illustrates block diagrams of electronic devices according to an embodiment. For example, FIG. 122 shows the schematic configuration of the first electronic device 7210 having a camera and the second electronic device 7220 including a display and an input module. The first electronic device 7210 and the second electronic device 7220 each may have the same or similar configuration to the whole or part of the configuration of the electronic device 201 shown in FIG. 52 or the electronic device 101 shown in FIG. 51, for example.

If image capturing is started on the first electronic device 7210, the image of the object may be inputted through the image sensor 7211 in the camera module, and the image processing module 7212 may process the inputted image. The image determining module 7213 may process the information on the image extractable from the currently inputted image into the form/format supportable by the second electronic device 7220 and transfer to the first communication module 7214. The first communication module 7214 may receive the processed information and transmit the same to the second electronic device 7220. The image processing module 7212 and the image determining module 7213 may be integrated with the first processor (e.g., the processor 120 or 210).

The image determining module 7213 may analyze at least one or more characteristics based on the image inputted from the image sensor 7211. The image determining module 7213 may analyze the image provided as a preview from the first electronic device 7210 and may analyze all processable parameters and process the result of analysis in order to provide the information fitting the form/format supported by the second electronic device 7220. The image determining module 7213 may analyze the composition of the objects in the image. In order to remote do image capturing with the first electronic device 7210 mounted, the user may receive information on the preview image of the first electronic device 7210 through the second electronic device 7220. The first electronic device 7210 may analyze the composition of the object and provide the information on the current composition to the second electronic device 7220 in the form of text, sound, or symbol. The second electronic device 7220 may transmit the feedback on the information received from the first electronic device 7210 to the first electronic device 7210.

The second communication module 7221 of the second electronic device 7220 may transfer the received processed information to the second processor (e.g., the processor 120 or 210) in the second electronic device 7220, and the second processor may display the whole/part of the processed information on the display module 7222 (e.g., the display 150). The second electronic device 7220 may receive the image capturing control information through the input module 7223 (e.g., the input/output interface 140) and may transmit the image capturing control information to the first electronic device 7210 through the second communication module 7221. The second electronic device 7220 may be a wearable electronic device mounted on at least a portion of the user's body, and for convenience, main modules only are shown, and thus, additional modules may be added.

Figure 123:
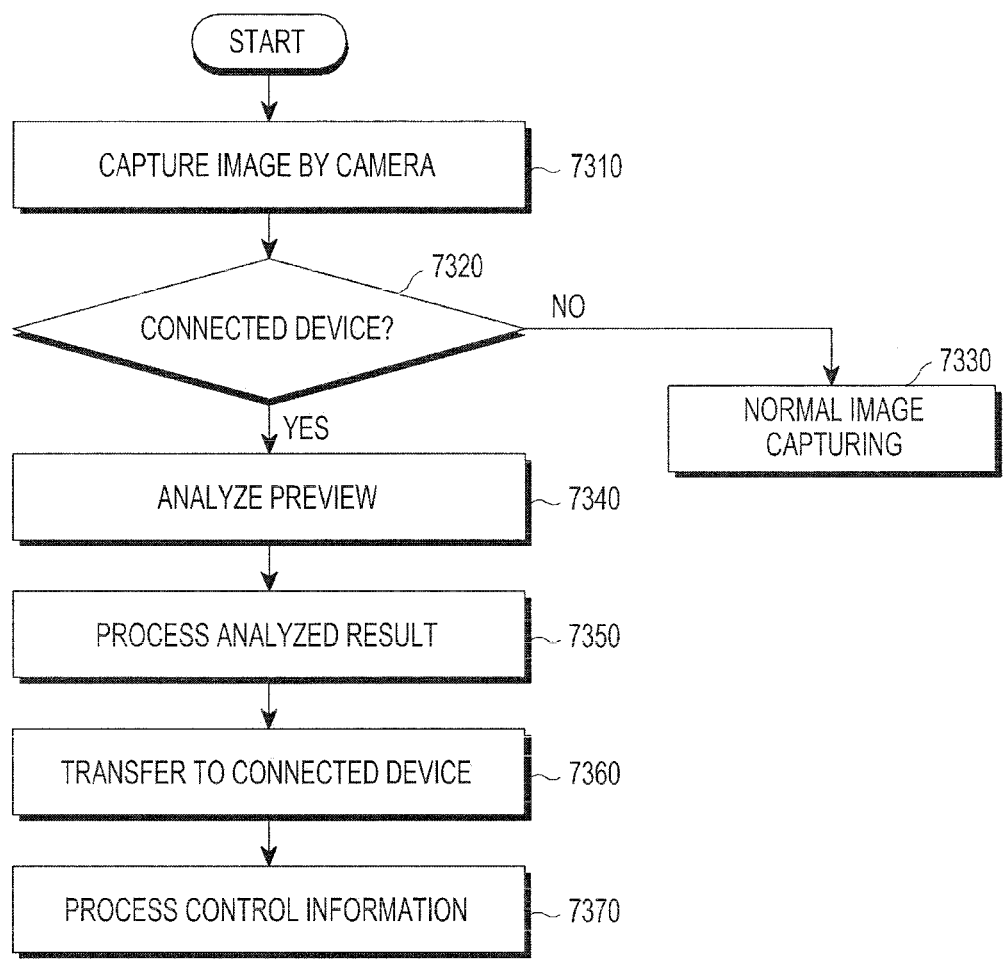

FIG. 123 is a flowchart illustrating an operation of a first electronic device according to an embodiment. For example, FIG. 123 is a flowchart illustrating the flow of image capturing according to connection to the second electronic device or no. The method may be performed by the first electronic device (e.g., the electronic device 101 or 201) or processor (e.g., the processor 120 or 210) of the first electronic device. The method may include all or some of the operations 7310 to 7370.

In operation 7310, the first electronic device may run the camera module (e.g., the camera module 291) to run the image capturing application, thereby initiating the camera image capturing.

In operation 7320, the first electronic device may determine whether there is the second electronic device connected with the first electronic device. The first electronic device, unless there is the second electronic device, may perform operation 7330, and if there is the second electronic device, may perform operation 7340 for remote control.

In operation 7330, the first electronic device may perform an operation according to the conventional general image capturing process.

In one embodiment, a menu for selecting the remote control by the second electronic device may be provided on the image event/context application.

In operation 7340, the first electronic device may analyze the preview image currently inputted.

In operation 7350, the first electronic device may gather information obtained from the preview image and may process the result of application to fit the type of the connected second electronic device.

In operation 7360, the first electronic device may transmit the analysis result to the second electronic device. The first electronic device may also transfer the analysis result whose form has been transformed according to the type of the second electronic device.

In operation 7370, the first electronic device may receive the control information from the second electronic device and process the received control information.

Figure 124:
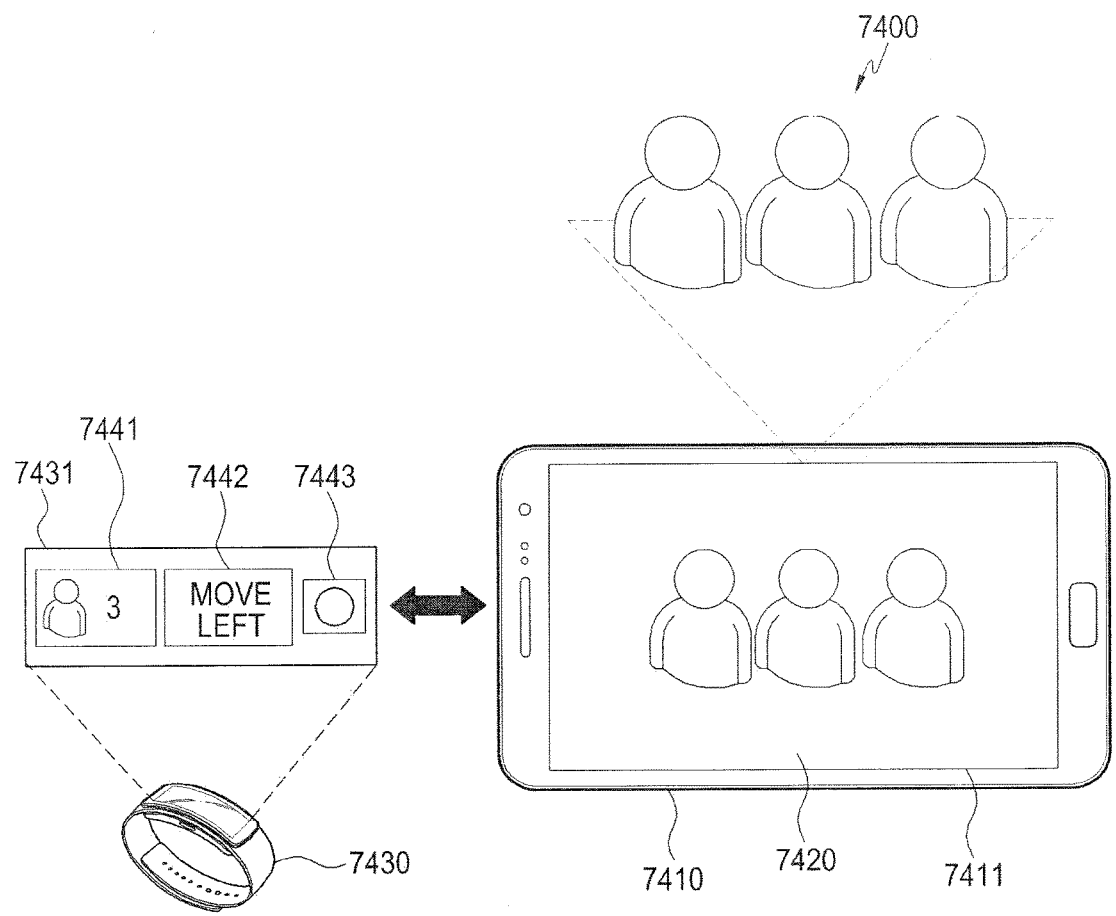

FIG. 124 illustrates an interworking environment between a plurality of electronic devices according to an embodiment. FIG. 124 shows one embodiment in which the information indicating that the first electronic device 7410 (e.g., the camera, camcorder, or smartphone) image-captures the object is displayed by the second electronic device 7430 (e.g., the smart watch or remote controller device). The first electronic device 7410 and the second electronic device 7430 each may have the same or similar configuration to the whole or part of the configuration of the electronic device 201 shown in FIG. 52 or the electronic device 101 shown in FIG. 51, for example.

For example, the first electronic device 7410 image-captures three people 7400. The first electronic device 7410 may display the preview image 7420 of the three people 7400 image-captured on the display 7411.

At this time, the first electronic device 7410 may determine that the current object is the three people through face recognition and quantifies the same and transfer to the second electronic device 7430. Further, the first electronic device 7410 may determine the composition of the object which is the master of the picture and determine which portion in the picture it is present and may provide the position to the user as a document or symbolically. Further, a button for picture taking may be provided. The second electronic device 7430 may display information 7441 on the number of people of the object, a button 7442 for inputting a composition adjusting command, and a button 7443 for initiating image capturing on the display 7431 based on the image capturing-related information received from the first electronic device 7410.

According to an embodiment, the first electronic device (e.g., the wearable electronic device) may determine the number of objects (e.g., people) and the suitability of the composition. Further, the first electronic device may modify the result when the object is moved according to the composition analysis feedback. The result of determining the preview of the first electronic device through the second electronic device may be related to at least one or more of all the elements that may affect the picture quality, such as composition, brightness, and focal length or may include its determination/evaluation/modification command.

Figure 125:
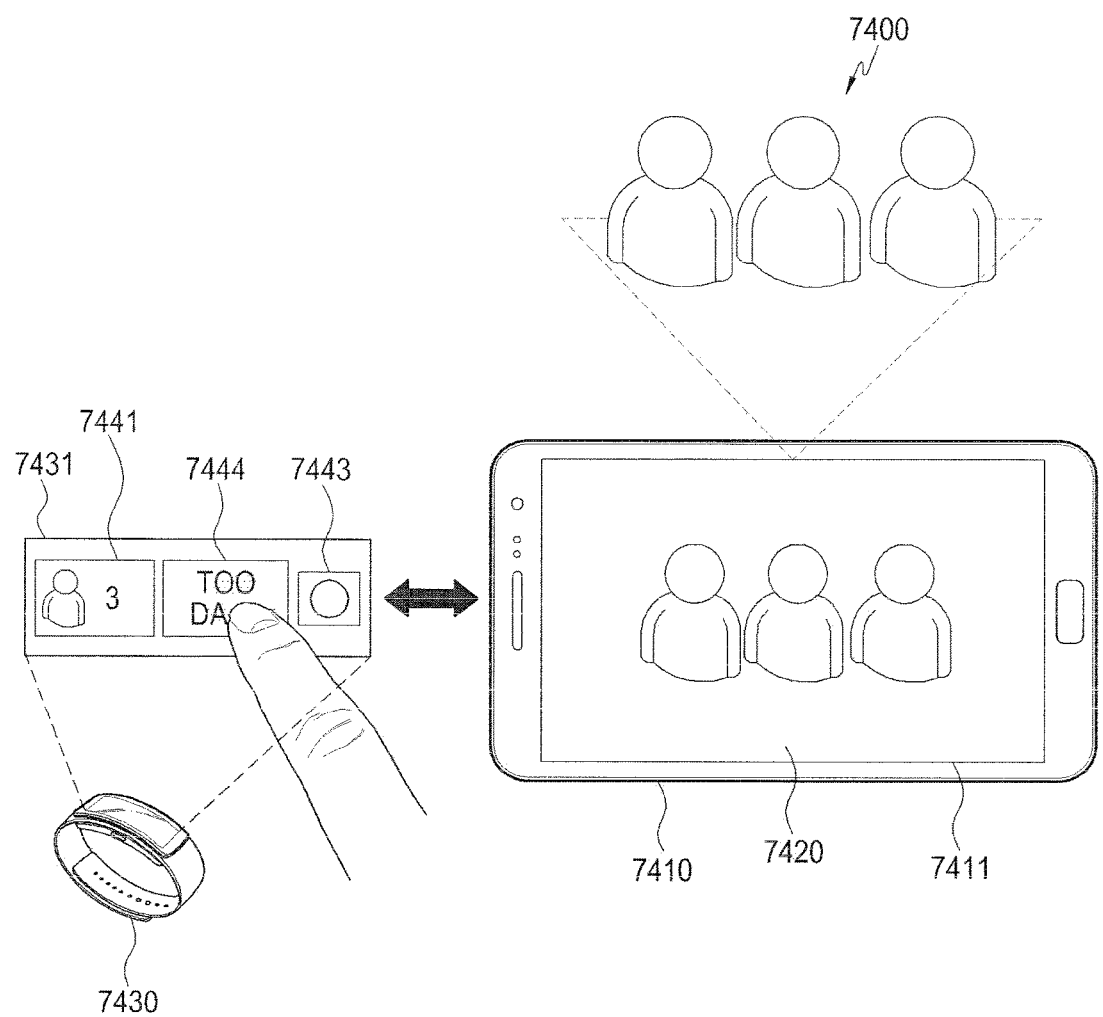

FIG. 125 illustrates an environment showing a control method of a wearable electronic device according to an embodiment. According to an embodiment, as a result of analyzing the image quality in the image determining module of the first electronic device 7410, when the image of the current preview is dark, the information 7444 may be provided through the second electronic device 7430. When receiving the type of information, the user may transfer the feedback for mode variation through the input device provided in the second electronic device 7430.

According to an embodiment, in case the picture to be captured is dark through the analysis of the image obtained through the camera, the first electronic device 7410 may send a request for the feedback for whether to vary mode to the user through the second electronic device 7430 for the mode variation information (e.g., various mode setting screens implemented by the user interface) capable of varying the image capturing mode on the object. At this time, upon entry to the second electronic device 7430 by the user, the second electronic device 7430 may transfer the mode variation command to the first electronic device 7410, and the first electronic device 7410 may perform the mode variation.

According to an embodiment, in case an object is recognized through the face recognition module of the first electronic device 7410, the second electronic device 7430 may provide the information (e.g., feedback corresponding to the selected information) selected by the user to the first electronic device 7410. The user may select information 7441 on the number of people of the information on the preview provided on the second electronic device 7430. At this time, the information counted and provided may be in the form of a number, or for the person whose identity has been grasped, such a command may be issued as to enable the result of image capturing to be transferred at the pre-stored contact through the first electronic device 7410.

According to an embodiment, it may also be set that the results of image capturing through the face information on the object provided to the second electronic device 7430 by the user may be all transferred through the first electronic device 7410.

According to an embodiment, the result of image capturing may be selectively transferred for each recognized person through the information on the people provided to the second electronic device 7430. Further, people to be shared for may be added from the people stored in the address book of the first electronic device 7410 in addition to the image-captured people.

According to an embodiment, upon image capturing, the second electronic device having limitations in display may be used to provide the information extracted from the preview displayed to the first electronic device so that some may be fed back, leading to increased usability.

Figure 126:
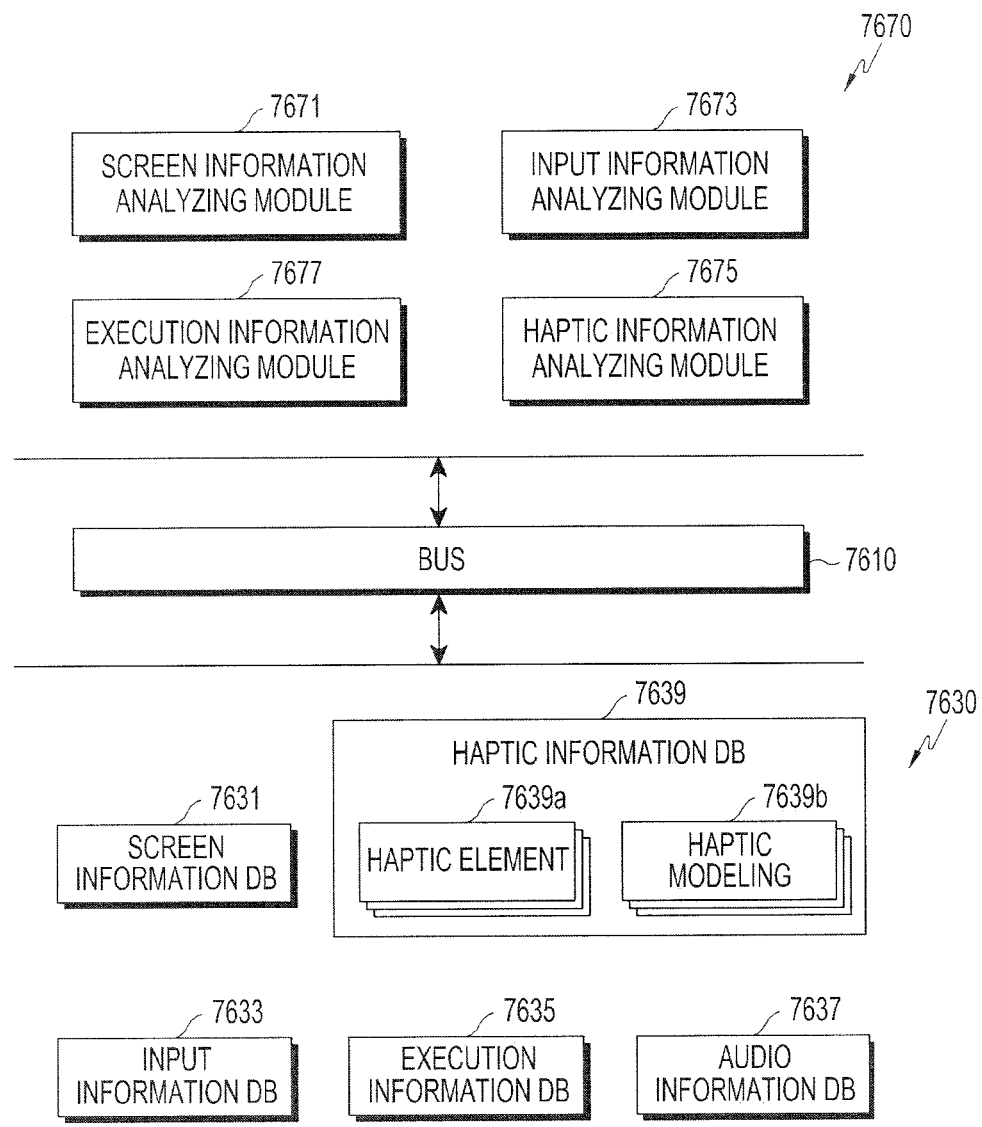

FIG. 126 is a block diagram illustrating a haptic support module 7670 of an electronic device (e.g., the electronic device 101 or 201) according to an embodiment. The haptic support module 7670 may be the additional function module 170 shown in FIG. 51.

Referring to FIG. 126, the memory 7630 may include at least one of a screen information database 7631, an input information database 7633, an execution information database 7635, an audio information database 7637, or a haptic information database 7639.

The screen information database 7631 may include screen information including at least one object included in the screen outputted or to be outputted on the display of the electronic device and at least one haptic information assigned to the screen information. The screen information may include at least designated object to be included in the display in relation with a particular application. According to an embodiment, the object may include, e.g., a background object, a thing object disposed on the background object, or a human object. Or, the object may include a virtual key button group including, e.g., at least one virtual key button or a plurality of virtual key buttons. Or, the screen information may include a panorama object, a 3D object, and an augmented reality object. Or, the object may include at least one of a dot, line, and surface. According to an embodiment, the object may include a surface (a two-dimensional surface or three-dimensional surface) formed as a closed loop. The closed loop may be used as a boundary area. The haptic area may be used as reference information by which the haptic information is differently assigned.

According to an embodiment, the screen information database 7631 may include the same or at least partially different haptic information assigned per particular object constituted of, e.g., at least one of dot, line, or surface. The screen information database 7631 may include haptic information assigned to the boundary area of a particular object constituted of at least one of the line or surface or the same or different haptic information assigned to the outside or inside of the particular object constituted of the surface. The screen information database 7631 may include the same or different haptic information assigned per outside position or per inside position of the particular object constituted of the surface.

The input information database 7633 may include reference input information corresponding to various input signals inputted through the input/output interface. For example, the input information database may include reference input information regarding distinguishing the type of the input object (e.g., an object, such as a finger, electronic pen, or general pen) generating an input signal, reference input information for distinguishing the type of input signal (e.g., a touch down input, touch drag input, touch release input, or touch holding input), and reference input information for distinguishing the input type through the state of the input signal (e.g., at least one of the position, speed, strength, area, duration, or time of the touch).

The input information database 7633 may include the same or different haptic information assigned to at least one reference input information described above. According to an embodiment, the input information database 7633 may include haptic information mapped differently per type of input object. Further, the input information database 7633 may include the haptic information mapped identically or differently to at least one the type of input signal generated according to the type of each input object or the state of the input state.

The execution information database 7635 may include execution information (e.g., information generated as the application is run on other electronic device) transmitted from the other electronic device (e.g., the electronic device 104 or server 106) or execution information gathered as the application runs. The execution information database 7635 may include execution information distinguished per time, application, or transmitting device.

The execution information database 7635 may include at least one haptic information mapped to at least one execution information. According to an embodiment, the execution information database 7635 may include haptic information assigned differently per time, application, or transmitting device. The execution information database 7635 may include at least one haptic information assigned per execution information. The execution information database 7635 may include information on the condition under which at least one haptic information assigned to the execution information is outputted. The condition information may include at least one of, e.g., the number of times at which the same type of execution information has been gathered, size of the execution information, or time when the execution information has been gathered.

The audio information database 7637 may include audio information mapped to at least one of screen information, input information, execution information, or haptic information. For example, the audio information database 7637 may include at least one audio information assigned for different haptic information. Or, the audio information database 7637 may include at least one audio information assigned for different haptic information, with particular screen information outputted on the display. Or, in case the haptic information mapped with particular execution information is outputted together, the audio information database 7637 may include at least one audio information set to be outputted together.

The haptic information database 7639 may include at least one of a haptic element 7639a or haptic modeling 7639b. The haptic element 7639a may include setting information related to at least one touch or texture provided based on the haptic module. For example, the haptic element 7639a may include haptic module control information related to implementation of at least one of a single form of the type of the touch or texture (e.g., at least one of smooth, rough, sticky, resistant, frictional, feeling skin pulled, or silky) or a combined form. According to an embodiment, in case the haptic module includes a frictional force haptic display, the haptic element 7639a may include haptic module control information related to the power control of the haptic module related to the implementation per direction or per size, such as a frictional feel, resistant feel, or repulsive force implemented through the frictional force haptic display.

The haptic modeling 7639b may include the haptic information related to the touch or texture modeled based on the haptic module control information. For example, the haptic modeling 7639b may include haptic information related to the control of at least one haptic module defining heavy smooth or light smooth. Or, the haptic modeling 7639b may include haptic information defined in implementing various degrees of roughness through the haptic module. According to an embodiment, the haptic modeling may include the haptic information applied to implement, through the haptic module, the haptic feedback (or touch or texture) set to be generated from at least one of a boundary area of a particular object, an outside area of the boundary area or inside area of the boundary area. The haptic information may include power control information driving the haptic module allowing a predetermined degree of roughness to be felt on, e.g., the boundary area of the object. The haptic information may include power control information of the haptic module related to the expression of texture set to be provided upon occurrence of a hovering or touch at a predetermined position outside the boundary area of the object. The haptic information may include power control information of the haptic module related to the duration, position, and degree of a particular tactile feel set to be provided corresponding to the touch or hovering speed.

The haptic support module 7670 may include at least one of a screen information analysis module 7671, an input information analysis module 7673, an execution information analysis module 7675, or a haptic information assigning module 7677.

The screen information analysis module 7671 may extract the screen information by analyzing the screen outputted or to be outputted on the display. The screen information analysis module 7671 may identify whether there is haptic information per screen information stored in the screen information database 7631. The screen information analysis module 7671, in case there is haptic information, may perform control to apply the haptic information to the screen information being outputted on the display. The screen information analysis module 7671, if such an event occurs where at least one object included in the screen information is touched or hovering occurs on the operation, may control the output of the haptic information by providing the assigned haptic information to the haptic module. In this operation, the screen information analysis module 7671 may perform control to assign the haptic information per operation included in the screen information for each object and output the haptic information corresponding to the event of selecting a particular object (e.g., at least one of an object touch event or hovering event indicating the object).

The screen information analysis module 7671, in case the extracted screen information is not present in the screen information database 7631, may provide the screen information to the haptic information assigning module 7677. According to an embodiment, the screen information analysis module 7671 may extract at least one object included in the particular screen information and transfer the extracted object to the haptic information assigning module 7677. In this operation, the screen information analysis module 7671 may transfer the screen-related information (e.g., information such as type of the screen-related application, identification information related to the screen, position of the object on the screen, and shape of the object) to the haptic information assigning module 7677. The screen information analysis module 7671, if receiving the haptic information per particular object from the haptic information assigning module 7677, may apply the haptic information to the screen information. The screen information analysis module 7671 may control the output of the haptic information assigned corresponding to the event currently generated from the display. According to an embodiment, the screen information analysis module 7671 may transfer the haptic update information including the newly generated screen information and the haptic information mapped thereto to the memory 7630 to control the update of the screen information database 7631.

The input information analysis module 7673, in case an input signal is generated through the input/output interface, may analyze the type of the input object. In this operation, the input information analysis module 7673 may identify the type of input object mapped to the form of the generated signal based on the stored signal form information per input object. For example, the input information analysis module 7673 may perform analysis as to whether the form of the generated signal is one by a finger, electronic pen, or general pen based on the stored signal form information per input object. The input information analysis module 7673, if the type of input object is identified, may identify the input information database 7633 in relation with whether there is haptic information mapped to the input object. The input information analysis module 7673 may control the output of the haptic information corresponding to the event occurring based on the haptic information identified by the input information database 7633.

The execution information analysis module 7675 may gather at least one of the execution information generated corresponding to running a particular application and the execution information to be transmitted from other electronic device (e.g., the electronic device 104 or server 106). The execution information analysis module 7675 may identify whether the haptic information mapped to the gathered execution information is present in the execution information database 7635. The execution information analysis module 7675, if there is the haptic information mapped to the execution information, may control the output of the haptic information corresponding to the gathering of the execution information. According to an embodiment, the execution information analysis module 7675 may identify a condition designated in relation to the execution information, and in case the execution information meets the designated condition, it may control the output of the related haptic information.

The haptic information assigning module 7677 may provide haptic information to at least one of screen information, input information, or execution information. For example, the haptic information assigning module 7677, if receiving information regarding at least one object included in the particular screen information, may identify whether there is the haptic information assigned to the object. The haptic information assigning module 7677, if the haptic information is present, may provide the same to the screen information analysis module 7671. Further, the haptic information assigning module 7677 may provide the haptic information corresponding to the input signal information provided from the input information analysis module 7673 to the input information analysis module 7673. Further, the haptic information assigning module 7677 may provide the haptic information mapped to the execution information provided from the execution information analysis module 7675 to the execution information analysis module 7675.

According to an embodiment, the haptic information assigning module 7677, in case there is no haptic information mapped to the screen information received from the screen information analysis module 7671, may assign the haptic information to the screen information corresponding to various conditions. For example, the haptic information assigning module 7677 may provide a screen allowing for selection of the haptic information to be provided for each of at least one object included in the screen information. The haptic information assigning module 7677 may perform haptic information mapping to at least one object corresponding to the user's selection and may perform control to store the result in the information database 7631. According to an embodiment, the haptic information assigning module 7677 may provide a screen related to the assignment of haptic information corresponding to at least one of the input information or execution information and may assign the haptic information selected by the user input. In this connection, the haptic information assigning module 7677 may control the output of the selection screen including an information output area regarding at least one of the screen information, input information, and execution information and an area from which at least one haptic information (e.g., smooth, rough, sticky, resistant, frictional, feeling skill pulled, or silky) may be selected.

According to an embodiment, the haptic information assigning module 7677 may detect the object mapped with the same or similar particular haptic information corresponding to the analysis of the particular object and perform control to automatically map the haptic information assigned to the object to the particular object. According to an embodiment, the haptic information assigning module 7677, in case an input signal is generated by a particular input object, may detect the input object mapped with the haptic information similar to the input signal and map the haptic information assigned to the input object to the particular input object. According to an embodiment, the haptic information assigning module 7677 may perform control to automatically map the haptic information assigned to the application related to the execution information to the particular execution information in relation to the particular execution information. In this operation, the haptic information assigning module 7677 may update at least one of the screen information database 7631, the input information database 7633, and the execution information database 7635.

The haptic information assigning module 7677 may control the update of the audio information database 7637 corresponding to the user control. In this connection, the haptic information assigning module 7677 may provide a screen including an area allowing for selection of at least one screen information, input information, execution information, or haptic information and an area allowing for selection of at least one audio information. The haptic information assigning module 7677 may perform control to map the particular haptic information or particular screen information, input information or execution information to the particular audio information according to the user's selection. The haptic information assigning module 7677 may perform control to store the mapped audio information in the audio information database 7637. The haptic information assigning module 7677, in case the particular haptic information is output on the particular screen or the particular haptic information is output in relation with the particular input information, or the particular haptic information is output corresponding to the occurrence of the execution information, may perform control to output together the mapped audio information.

According to an embodiment, the electronic device may include a haptic support module performing at least one of screen information analysis, input information analysis, or execution information analysis and assigning at least one haptic information according to the result of the analysis and a haptic module outputting a haptic feedback corresponding to the haptic information corresponding to the occurrence of an event.

According to an embodiment, the haptic support module may detect at least one object outputted or to be outputted on the screen and may set different haptic information per the object.

According to an embodiment, the haptic support module may set different haptic information for a boundary area of the object and an area other than the boundary area.

According to an embodiment, the haptic support module may set first haptic information for the boundary area of the object and second haptic information for the inside of the object and may set third haptic information for the outside of the object. Additionally or alternatively, no separate haptic information may be assigned to the outside of the object.

According to an embodiment, the haptic support module, if a particular one of the objects displayed on the display is selected, may change the haptic information assigned to the objects displayed on the display to other type of haptic information.

According to an embodiment, the haptic support module may set haptic information corresponding to at least one of the shape of the object outputted or to be outputted, the material related to the image where the object is displayed, and description information relating to the object.

According to an embodiment, the haptic support module may set different haptic information according to at least one of the type of the input object, the type of input signal generated by the input object, and the state of the input signal.

According to an embodiment, the haptic support module may set different haptic information per execution information gathered by running a particular function.

According to an embodiment, the haptic support module may receive execution information related to a healthcare function and may set different haptic information per type of the received execution information.

According to an embodiment, the haptic support module may identify the state where the electronic device is disposed when the event occurs and may set different points of output of the haptic feedback corresponding to the haptic information in the touch area related to the occurrence of the event according to the state of disposition of the electronic device.

According to an embodiment, the haptic support module may be configured to output different haptic events corresponding to at least one of the position of occurrence of the event in the object detected according to the result of the screen information analysis, the strength of the event signal (e.g., at least one of the strength of the touch pressure, the capacitance related to touch sensing or hovering sensing, the strength of the inputted sound or vibration, or the size of the area where a designated strength or more of signal is sensed when the event occurs), the proximity between the point where the event occurs and the object (e.g., one or more of the distance between the object and the point where the event occurs or the proximity between the object surface and the input object), or the duration of the event.

According to an embodiment, the haptic support module may be configured to output different haptic feedbacks for the area of the object and the boundary area of the object.

According to an embodiment, the haptic support module may be configured to suppress the output of a designated haptic feedback in case the strength of the signal applied to the object is a designated first strength (e.g., a signal having 40% or less of the sensible maximum signal strength or within a designated first range) or output the designated haptic feedback in case the pressure applied to the object is different from the designated first strength.

According to an embodiment, the haptic support module may be configured to run a function set in the object in case the pressure applied to the object has a designated second strength (e.g., a signal having 70% or more of the sensible maximum signal strength or within a designated second range (e.g., a range different from the first range). The first strength and the second strength or the first range and the second range may have various types and maximum values depending on the type of the sensor sensing signals.

According to an embodiment, if the first event is received from the area other than the area where the object detected as the result of the screen information analysis is disposed, the haptic support module may be configured to output the designated reference haptic feedback.

According to an embodiment, the haptic support module may be configured to output at least one of the haptic feedback having a designated strength or less or directional haptic feedback indicating the area where the object is disposed.

According to an embodiment, the haptic support module may be configured to output the haptic feedback corresponding to the object corresponding to at least one of the distance between the current location of the first event and the object or the travel speed in case the travel speed of the first event is not less than the designated speed.

According to an embodiment, if the first event is received from the area other than the area where the object is disposed, the haptic support module may be configured to suppress the output of the haptic feedback, and if the first event is received from the object, it may be configured to output the designated haptic feedback.

According to an embodiment, if the first event or second event different from the first event is received from the object, the haptic support module may be configured to run a function corresponding to the object.

According to an embodiment, if at least one object is displayed at a predetermined position of the display corresponding to at least one of the movement direction of the electronic device or the position where the electronic device is gripped, the haptic support module may be configured to output other haptic feedback corresponding to the position where the object is outputted.

According to an embodiment, the haptic support module may be configured to output different haptic feedbacks for a plurality of areas included in the object.

According to an embodiment, in case an event occurs from the area other than the object, the haptic support module may be configured to output the direction haptic feedback indicating the direction where the object is located at the position of the event.

According to an embodiment, the haptic support module may be configured to transmit information corresponding to the haptic feedback to other electronic device.

According to an embodiment, the haptic support module may be configured to switch the display into a turn-off state or maintain the turn-off state in relation to the output of the haptic feedback.

According to an embodiment, upon sensing the electronic device worn, the haptic support module may be configured to output the designated haptic feedback from at least a partial area (e.g., the overall electronic device) or the area where the wearing is sensed (e.g., a portion of the housing of the electronic device contacting the body), and upon sensing the entry of the electronic device into a designated location (an indoor or outdoor location area designated based on GPS or Wi-Fi signals), it may be configured to output the designated haptic feedback from at least a portion of the electronic device.

According to an embodiment, the haptic support module may be configured to terminate the output of the haptic feedback if the electronic device departs from the predetermined location or the electronic device is released from being worn.

According to an embodiment, the haptic support module may be configured to output at least one haptic feedback according to comparison between a set target value and information gathered based on a gathered sensor signal.

According to an embodiment, the haptic support module may be configured to output a haptic feedback from at least one of the display area of the electronic device or a bezel area.

According to an embodiment, the haptic support module may be configured to output a haptic feedback that differs in at least one of the shape or position corresponding to the size of the achievement ratio according to comparison with the target value.

According to an embodiment, the haptic support module may be configured to output a designated particular form of haptic feedback corresponding to the sensor signals accrued for a predetermined period or sensor signals currently gathered.

According to an embodiment, the haptic support module may be configured to output the haptic feedback guiding to adjust the speed detected based on the sensor signal.

According to an embodiment, the haptic support module may be configured to output a haptic feedback having at least one of the size or frequency of the haptic adjusted corresponding to the guidance to increase or reduce the speed.

According to an embodiment, the haptic support module may be configured to output at least one of the haptic feedback having at least one directionality related to the time information obtained corresponding to the result of the execution information analysis, the haptic feedback corresponding to the degree of sleep obtained corresponding to the result of the execution information analysis, and the haptic feedback corresponding to the size of the stress level obtained corresponding to the result of the execution information analysis.

According to an embodiment, the haptic support module may be configured to output the designated haptic feedback to the object corresponding to the inputted keyword or the result of the search for the keyword.

According to an embodiment, the haptic support module may be configured to output different haptic feedbacks per keyword corresponding to the frequency of inputting the keywords.

According to an embodiment, the haptic support module may be configured to run a function related to the object or a function related to the keyword corresponding to at least one of the object, the duration of the selected event, pressure strength, touch area, or electric charge.

According to an embodiment, the haptic support module may be configured to output different haptic feedbacks related to the keyword corresponding to at least one operation of entry of the keyword-related letter, handwriting recognition on the touchscreen or touchpad, and voice recognition.

According to an embodiment, in case there are a plurality of objects, the haptic support module may be configured to assign different haptic feedbacks to the objects corresponding to the similarity or reliability between the keyword and the objects.

According to an embodiment, the haptic support module may be configured to assign a directional haptic feedback indicating the target object disposed in the area not currently displayed on the display of the entire screen area.

According to an embodiment, the haptic support module may be configured to assign the directional haptic feedback to at least one object displayed on the display.

According to an embodiment, the haptic support module may be configured to assign different haptic feedbacks depending on the type of the target object corresponding to the result of the analysis.

According to an embodiment, the haptic support module may be configured to assign different haptic feedbacks corresponding to at least one of the case where the target object is hidden by other objects, the case where the target object is exposed, the size of the target object, and the position of the target object.

According to an embodiment, the haptic support module may be configured to output different haptic feedbacks corresponding to the distance between the position where the event occurs and the target object.

According to an embodiment, the haptic support module may be configured to display the screen area including the target object related to search of the entire screen area on the display as default.

According to an embodiment, the haptic support module may be configured to output different haptic feedbacks corresponding to the type of event related to varying the screen areas displayed on the display.

Figure 127:
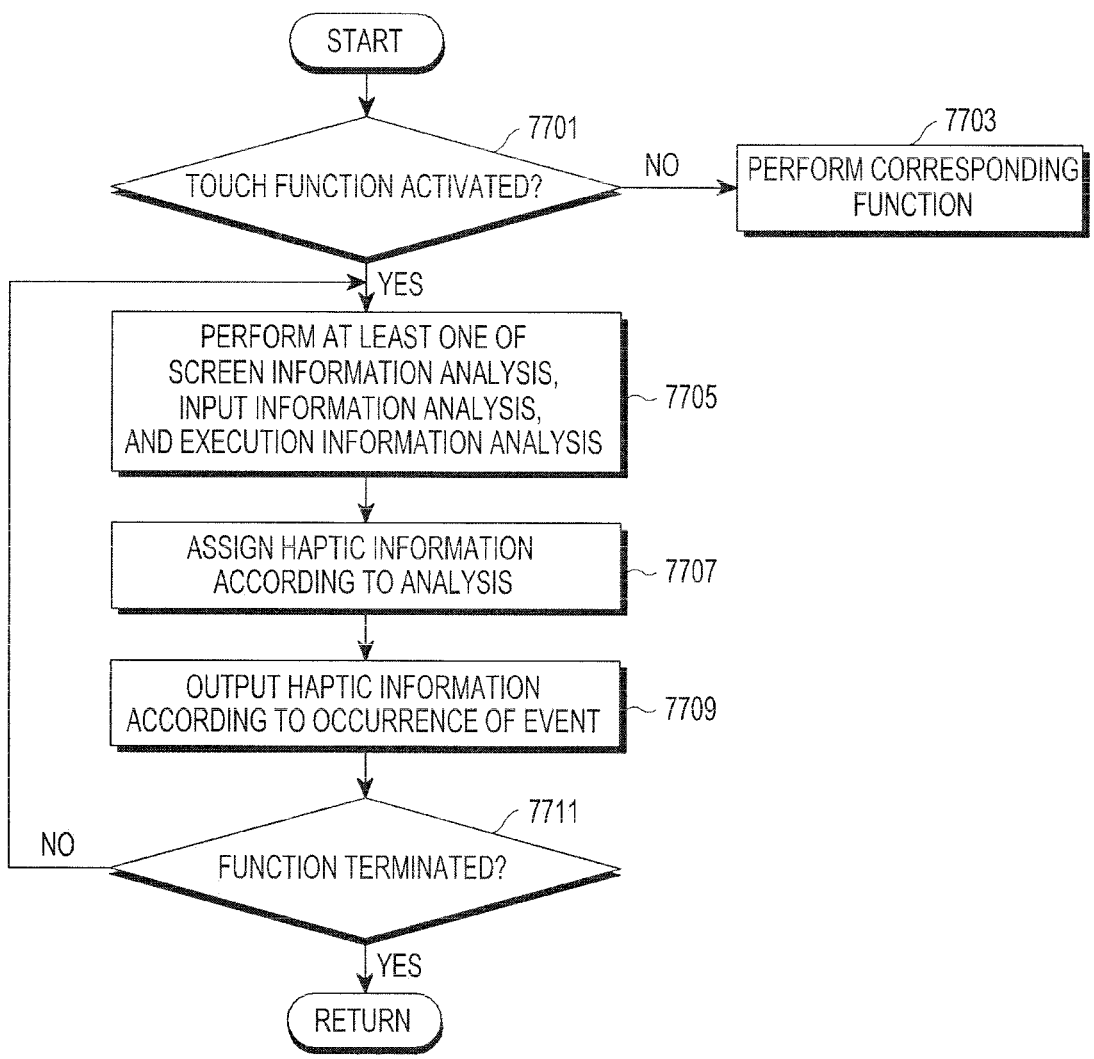

FIG. 127 illustrates a haptic information operation method according to an embodiment.

Referring to FIG. 127, in operation 7701, the haptic support module 7670 may identify whether the touch function is activated. For example, when a particular input event occurs, the haptic support module 7670 may identify whether the event is an input event related to releasing the sleep mode or an input event related to running a particular function (e.g., call function, schedule function, or alarm function). In case the particular event occurring in operation 7701 is not the event related to activating the touch function, the haptic support module 7670 may perform control to perform function corresponding to the event in operation 7703. For example, the haptic support module 7670 may adjust the volume corresponding to the type of input event. Or, the haptic support module 7670 may perform control to perform the voice search function corresponding to the type of the input event. Or, unless a separate event occurs, the haptic support module 7670 may perform control to maintain the previous state (sleep mode state or etc.) in operation 7703.

If an event related to activating the touch function occurs, the haptic support module 7670 may perform at least one of screen information analysis, input information analysis, or execution information analysis in operation 7705. For example, the haptic support module 7670 may perform control to activate the touch panel corresponding to the occurrence of the event. According to an embodiment, the haptic support module 7670 may gather screen information outputted on the display in relation to the occurrence of the event. The haptic support module 7670 may extract at least one object related to the haptic information mapping based on the gathered screen information analysis. According to an embodiment, the haptic support module 7670 may gather input information corresponding to the event related to activating the touch function. The haptic support module 7670 may perform analysis on the gathered input information to distinguish at least one of the type of the input object (e.g., finger, electronic pen, or general pen), the type of the input signal (e.g., touchdown input, touch drag input, touch release input, or touch holding input), the state of the input signal (e.g., at least one of the touched position and a variation, by a variation in the touched position, in the travel speed, touch strength, touch area, type of touch area, distribution of touch-related signals (e.g., capacitance or resistance) in the touch area, touch duration, or touch input signal over time). According to an embodiment, the haptic support module 7670 may gather the execution information of the function run corresponding to the occurrence of the event. The haptic support module 7670 may perform analysis on the type of the application related to the execution information or the time when the execution information occurs.

In operation 7707, the haptic support module 7670 may perform haptic information allocation (or setting) according to analysis. According to an embodiment, the haptic support module 7670 may identify the haptic information mapped to at least one object included in the screen information. According to an embodiment, the haptic support module 7670 may identify the haptic information mapped per type of the input object, the haptic information mapped per type of the input signal, and the haptic information mapped per state of the input signal. According to an embodiment, the haptic support module 7670 may identify the haptic information mapped per type of the execution information.

In operation 7709, the haptic support module 7670 may output the haptic information according to the occurrence of the event. According to an embodiment, upon occurrence of the event selecting a particular object included in the screen information (e.g., at least one of a touch event or hovering event) or event in the area where the particular object is outputted, the haptic support module 7670 may perform control to drive the haptic module based on the haptic information mapped to the object. According to an embodiment, when an input event is caused by the input object of the identified type, the haptic support module 7670 may perform control to drive the haptic module based on the haptic information mapped to the input object. According to an embodiment, the haptic support module 7670 may perform control to drive the haptic module based on the haptic information mapped to the execution information.

In operation 7711, the haptic support module 7670 may identify whether a function termination-related event occurs (e.g., an event including at least one of termination of the application, failing to sense the touch input signal, entry into the low power mode, setting haptic feedback non-supporting mode, failing to sense the user's bio signal, receiving a designated particular gesture event, and reception of a designated particular sensor signal (e.g., a sensor signal of the proximity sensor or sensor signal of the illumination sensor). The haptic support module 7670 may go to the previous operation to operation 7705 unless the function termination-related event occurs to re-perform the subsequent process. If the function termination-related event occurs, the haptic support module 7670 may go to operation 7703 to perform control to perform the function corresponding to the schedule information or a function according to the occurrence of the event. For example, the haptic support module 7670 may terminate the driving of the haptic module based on at least one of the screen information, input information, or execution information. If a particular event (an event requesting to output a fixed feedback) occurs, the haptic support module 7670 may perform control to output the haptic feedback according to the particular haptic information (the information configured to provide the same feedback regardless of the type of the received information) corresponding to the same. Or, the haptic support module 7670 may perform control to vary the screen display if the particular event occurs. Or, the haptic support module 7670 may perform control to stop driving the separate haptic module corresponding to the occurrence of the event.

Figure 128:
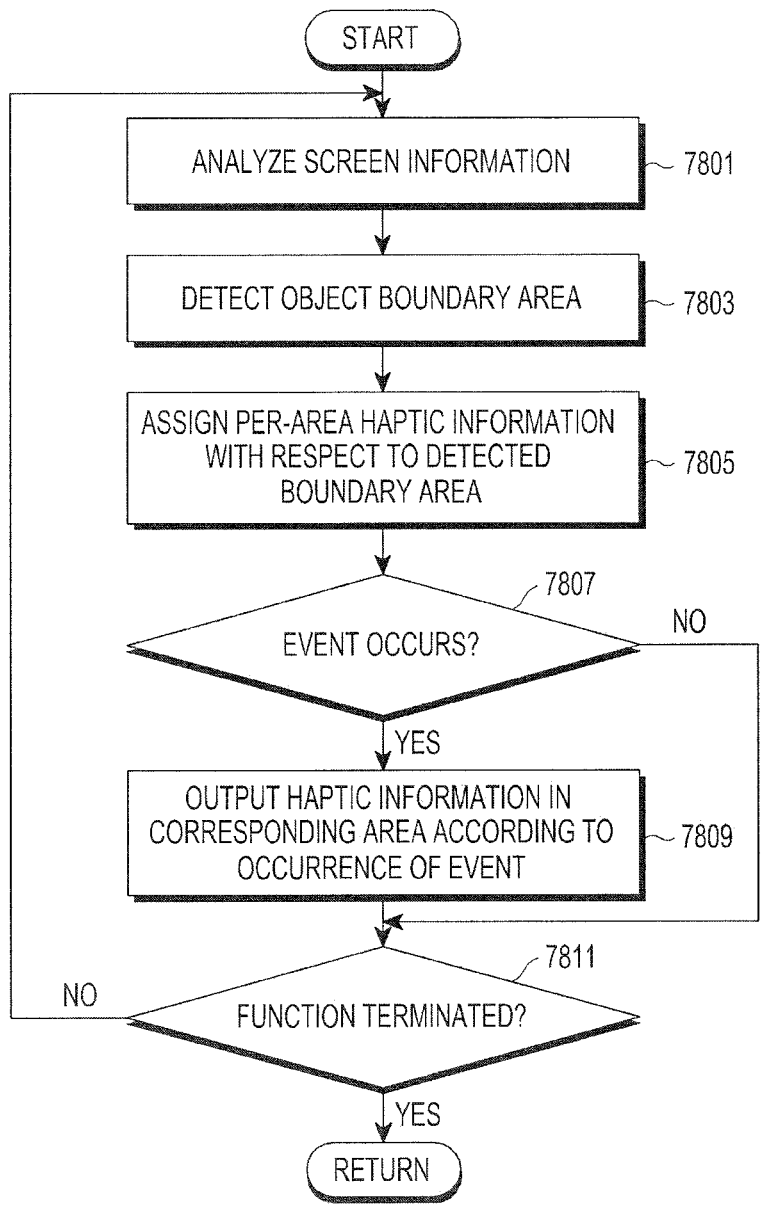

FIG. 128 illustrates an operation method of object-based haptic information among screen information according to an embodiment.

Referring to FIG. 128, in operation 7801, the haptic support module 7670 may perform screen information analysis. For example, the haptic support module 7670 may extract at least one object included in the screen currently outputted on the display or at least one object included in the screen to be outputted on the display.

In operation 7803, the haptic support module 7670 may detect, e.g., at least one object boundary area. For example, the haptic support module 7670 may detect the boundary area including a predetermined range with respect to the edge of the object or a predetermined area of the edge of the object having a predetermined surface or thickness. For example, the haptic support module 7670 may detect the predetermined range (e.g., a predetermined area adjacent to a line) including the line or line with a predetermined thickness or surface (e.g., a straight line, curved line, or free curved line) as the boundary area. The haptic support module 7670 may detect a partitioning line with a predetermined thickness or area to partition into a plurality of areas (or a predetermined area adjacent to the partitioning line) as the boundary area.

In operation 7805, the haptic support module 7670 may perform haptic information assignment per area with respect to the detected boundary area. For example, the haptic support module 7670 may assign the first haptic information to the boundary area, the second haptic information (e.g., information defined to be different from the tactile feel implemented by the first haptic information) to an area outside the boundary area, and the third haptic information (e.g., at least one of information defined to be different from the tactile feel implemented by the second haptic information or the information defined to be different from the tactile feel implemented by the first haptic information) to an area inside the boundary area. According to an embodiment, at least one of the first haptic information, the second haptic information, or the third haptic information may be haptic information providing different types of tactile feels.

According to an embodiment, the haptic support module 7670 may identify the haptic information assigned with respect to the boundary area from the screen information database 7631. The haptic support module 7670 may detect the first haptic information assigned to the boundary area, the second haptic information assigned to the area outside the boundary area, and the third haptic information assigned to the area inside the boundary area from the screen information database 7631.

In operation 7807, the haptic support module 7670 may identify whether an event occurs. For example, the haptic support module 7670 may identify whether an event (e.g., a touch event or hovering event) selecting or indicating at least one object outputted on the display occurs.

If the event occurs, in operation 7809, the haptic support module 7670 may perform control to output the haptic information mapped to the area (e.g., the object) according to the occurrence of the event. In this operation, the haptic support module 7670 may perform control to output the haptic information differentiated with respect to the boundary area of the object. According to an embodiment, the haptic support module 7670 may perform control to output the first haptic information corresponding to the event occurring outside the boundary area of the object. According to an embodiment, the haptic support module 7670 may perform control to output the second haptic information corresponding to the event occurring at the boundary area of the object. According to an embodiment, the haptic support module 7670 may perform control to output the third haptic information corresponding to the event occurring inside the boundary area of the object. According to an embodiment, there may be one or more areas where the event occurs. For example, in case a touch event is generated by a finger, the area contacted by the finger (e.g., the area where a touch signal is generated) may include at least one of the boundary area of the object, the area outside the boundary area, or the area inside the boundary area. In case the event occurs in a plurality of areas, the haptic support module 7670 may determine that the event occurs at the central point of the plurality of areas. According to an embodiment, the haptic support module 7670 may assign weights to the plurality of areas. The haptic support module 7670 may determine that the event occurs at an area with a larger weight among the plurality of areas. For example, in case the plurality of areas where the event occurs include a portion of the boundary area, the haptic support module 7670 may determine that the boundary area is selected. Or, the haptic support module 7670 may determine the point where the event occurs considering the weights assigned to the plurality of areas. For example, in case the event occurs in the plurality of areas including the boundary area and the area inside the boundary area, the haptic support module 7670 may determine the position where the event occurs considering the weight of the boundary area (e.g., the distance between the point where the event occurs and the boundary area or difference between the area of the occurrence in the boundary area of the area of the event (e.g., touch) and the area of the occurrence in the area other than the boundary area). According to an embodiment, the haptic support module 7670 may determine that a predetermined position or point is where the event occurs according to a predetermined reference of the area where the event occurs (e.g., some point or area of the area which is touched by a finger for finger touch, some area with respect to the central point or central point of the finger touched area, some point or area of the edge of the finger touched area, or some point or area of the edge in the direction of the drag after touched).

If no event occurs, the haptic support module 7670 may skip operation 7809.

In operation 7811, the haptic support module 7670 may identify whether a function termination-related event occurs. If the function termination-related event does not occur, the haptic support module 7670 may go to the previous operation to operation 7801 to re-perform its subsequent operations. If the function termination-related event occurs, the haptic support module 7670 may terminate the haptic information output function according to the screen information analysis. According to an embodiment, the haptic support module 7670 may control the output to the screen by running the application or perform control to shift to the sleep mode state (e.g., the state in which the display is turned off).

Figure 129:
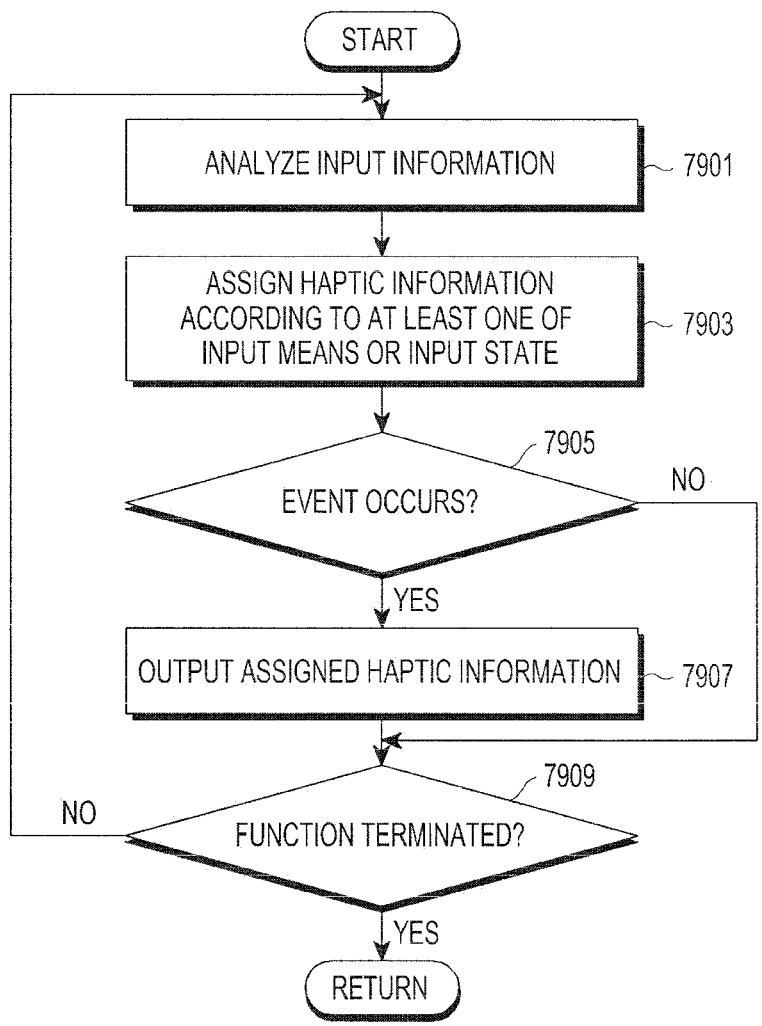

FIG. 129 illustrates a haptic information operation method based on the type of an input object according to an embodiment.

Referring to FIG. 129, in operation 7901, the haptic support module 7670 may perform input information analysis. According to an embodiment, the haptic support module 7670 may analyze the type of the input object. For example, the haptic support module 7670 may gather the touch event generated by the input object on the display supporting a touch function. The haptic support module 7670 may determine the type of the input object with respect to the size of the area where the touch event is caused by the touch event. In case the size of the area where the touch event occurs is not more than a designated size, the haptic support module 7670 may determine that a pen is the input object. In case the size of the area where the touch event occurs is not less than a designated size, the haptic support module 7670 may determine that a finger is the input object. According to an embodiment, the haptic support module 7670 may differentiate the electronic pen or finger based on a device related to the electronic pen recognition (e.g., a switch device capable of recognizing the electronic pen being mounted or unmounted or communication device related to electronic pen recognition). According to an embodiment, the haptic support module 7670 may differentiate the type of the electronic pen using various electronic elements arranged in the electronic pen. According to an embodiment, the haptic support module 7670 may differentiate the type of the input object based on the characteristics of the vibration signal or audio signal generated by a touch. For example, the haptic support module 7670 may determine the input object by recognizing the impact sound or vibration sensed by the microphone or motion sensor (e.g., the gyro sensor or acceleration sensor) if the touch is generated by the input object (e.g., a finger nail, finger joint, fingertip, or palm). According to an embodiment, the haptic support module 7670 may determine what input object has generated the signal by analyzing the particular pattern or characteristic (e.g., frequency or tone) of the impact sound or vibration signal generated differently depending on the type of the input object. For example, the haptic support module 7670 may differentiate the impact sound or vibration generated by at least one of the finger nail touch or finger pad touch. Further, the haptic support module 7670 may differentiate the impact sound or vibration of the touch by the pen tip of the pen or back portion of the pen. The haptic support module 7670 may differentiate the input object by distinguishing at least one of the impact sound or vibration signal and set the assignment and output of at least one input information accordingly. According to an embodiment, the haptic support module 7670 may determine the type of the input object based on at least one of the impact sound, the vibration, the location where the event occurs, the area of the occurrence, and the type of the surface of occurrence. For example, the haptic support module 7670 may differentiate the capacitive stylus pen or finger pad touched on the touchscreen based on at least one of the shape and form of the area where the event signal occurs.

According to an embodiment, the haptic support module 7670 may differentiate the type of the input event generated by the input means based on the state of the input signal. For example, the haptic support module 7670 may differentiate the touch down event, touch hold event, touch drag event, touch release event, or hovering event (e.g., the event sensed by the variation in capacitance generated in the contactless state or the event sensing the variation in capacitance or voltage having a different strength (not more or not less than the designated signal strength) than the signal strength defined to differentiate from the touch event). In the case of the touch hold event, the haptic support module 7670 may differentiate as different events depending on the time of the hold. In the case of the touch drag event, the haptic support module 7670 may differentiate the touch drag event into various event types based on at least one of the drag speed or distance.

In operation 7903, the haptic support module 7670 may perform haptic information assignment according to at least one of, e.g., the input means or input state. According to an embodiment, the haptic support module 7670 may assign the first haptic information corresponding to the input signal generated by the electronic pen. The haptic support module 7670 may perform assignment of different haptic information corresponding to the type of pen (e.g., assigning the first haptic information to the electronic pen with a first characteristic and the second haptic information to the electronic pen with a second characteristic). According to an embodiment, the haptic support module 7670 may assign the third haptic information corresponding to the input signal generated by the finger. The haptic support module 7670 may perform assignment of various haptic information according to the type of the finger (e.g., assigning the third haptic information to the thumb and the fourth haptic information (e.g., information defining a different tactile feel than that implemented by the third haptic information) to the index finger). In this operation, the differentiation between the thumb and the index finger may be performed based on the size of the touched area.

In operation 7905, the haptic support module 7670 may identify whether an event occurs. If an event occurs, the haptic support module 7670 may perform control to output the assigned haptic information according to the occurrence of the event in operation 7907. For example, the haptic support module 7670 may perform control to output the first haptic information corresponding to the occurrence of the event corresponding to the electronic pen input. The haptic support module 7670 may perform control to output the third haptic information corresponding to the occurrence of the event corresponding to the finger input.

Unless the event occurs, the haptic support module 7670 may skip operation 7907.

In operation 7909, the haptic support module 7670 may identify whether a function termination-related event occurs. If the function termination-related event does not occur, the haptic support module 7670 may go to the previous operation to operation 78301 to re-perform its subsequent operations. If the function termination-related event occurs, the haptic support module 7670 may terminate the haptic information output function according to the input information analysis. According to an embodiment, the haptic support module 7670 may control the output to the screen by running the application or perform control to shift to the sleep mode state (e.g., the state in which the display is turned off).

According to an embodiment, the type of the input signal may include at least one of the touch input, hovering sensing, proximity sensing, gesture input, force input, vibration input, and audio input. The state of the input signal may mean the characteristic of the signal inputted according to the type of the input signal. For example, the state of the input signal may include at least one of the position of signal, pattern of signal, signal frequency, duration of signal, amplitude of signal, strength of signal, distribution shape of signal, size of area where signal is inputted, shape of area where signal is inputted, distribution of detailed signal sets corresponding to the area, and variation over time in the signal or detailed signals. The type of input object may include an input object, such as the finger nail, finger joint, rubber, or wood, as well as the input means such as the stylus pen or finger. The type of the input device may include an input device adopting at least one of the capacitive scheme, resistant membrane scheme, optical scheme, electromagnetic induction scheme, ultrasound wave sensing, vibration sensing, and audio (sound wave) sensing, and it may include a keyboard, mouse, 3D mouse, joystick, data glove, HMD, or smart watch.

Figure 130:
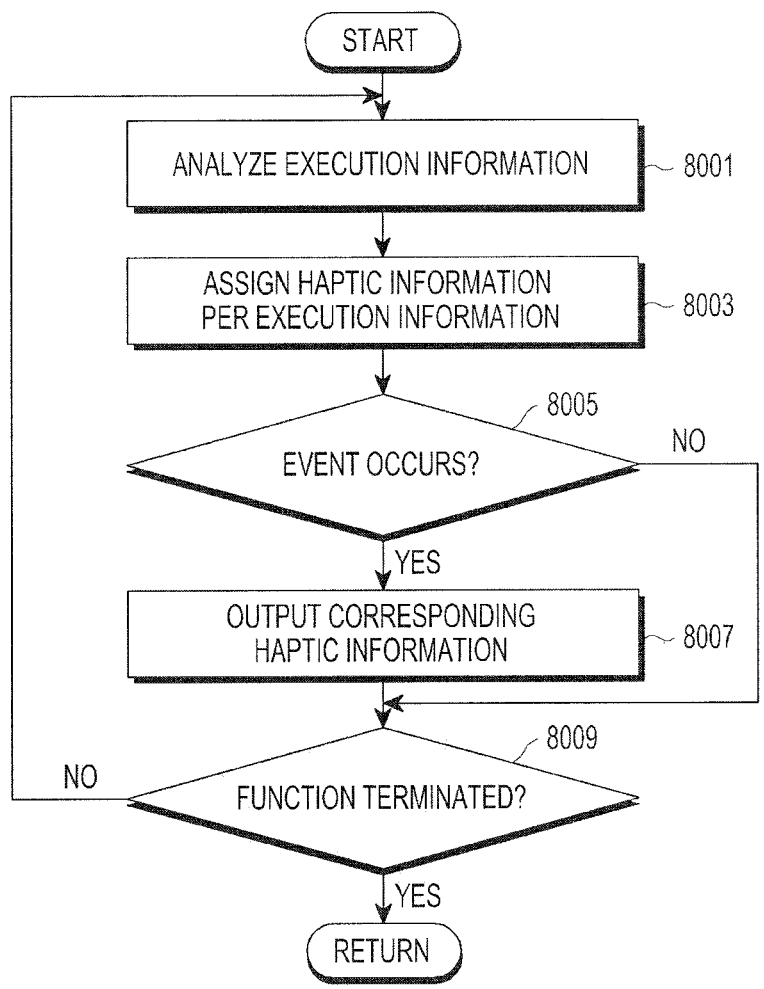

FIG. 130 illustrates an execution information condition-based haptic information operation method according to an embodiment.

Referring to FIG. 130, in operation 8001, the haptic support module 7670 may perform execution information analysis. According to an embodiment, if a particular application runs so that a particular function runs, the haptic support module 7670 may gather the execution information generated corresponding to the execution of the function. The haptic support module 7670 may identify the type of the gathered execution information and identify whether the identified execution information is information designated to output the particular haptic information. The haptic support module 7670 may identify the execution information database 7635 in this connection and may identify whether there is the haptic information mapped to the execution information.

In operation 8003, the haptic support module 7670 may assign haptic information per execution information, for example. If the gathered execution information is present in the execution information database 7635, the haptic support module 7670 may identify the mapped haptic information.

In operation 8005, the haptic support module 7670 may identify whether an event occurs. For example, the haptic support module 7670 may identify whether the event that the execution information meets a designated condition occurs. If the event occurs, in operation 8007, the haptic support module 7670 may perform control to output the assigned haptic information according to the occurrence of the event. For example, the haptic support module 7670 may perform control to drive the haptic module based on the haptic information mapped to the execution information corresponding to the execution information meeting the condition. According to an embodiment, the electronic device may run a healthcare function. The haptic support module 7670 may gather the heart rate information as the execution information as the health care function runs. In case the event that the gathered heart rate information is not less than a designated value or not more than the designated value occurs, the haptic support module 7670 may perform control to output the haptic information assigned to the execution information. According to an embodiment, the haptic support module 7670 may gather the count of exercise as the execution information corresponding to running the step counter function. In case the event that the count of exercise is not less than a designated value occurs, the haptic support module 7670 may perform control to output the assigned haptic information. According to an embodiment, the haptic support module 7670 may output directional haptic information indicating a predetermined area where the user intends to search on the particular screen information. If a particular event occurs on the search area, the haptic support module 7670 may perform control to output the designated haptic information.

Unless the event occurs, the haptic support module 7670 may skip operation 8007.

In operation 8009, the haptic support module 7670 may identify whether a function termination-related event occurs. If the function termination-related event does not occur, the haptic support module 7670 may go to the previous operation to operation 8001 to re-perform its subsequent operations. If the function termination-related event occurs, the haptic support module 7670 may terminate the haptic information output function according to the input information analysis. According to an embodiment, the haptic support module 7670 may perform control to output the screen according to the execution of the application or shift to the sleep mode state (e.g., the state of the display turning off, the state in which only sensor hub (or low power processing module) determining and managing whether the sensors are operated is operated or the low power mode state).

According to an embodiment, a method for operating haptic information according to an embodiment may set the operation of performing at least one of screen information analysis, input information analysis, or execution information analysis, the operation of assigning at least one haptic information according to the result of the analysis, and the operation of outputting the haptic feedback corresponding to the haptic information corresponding to the occurrence of the event.

According to an embodiment, the operation of analyzing the screen information may set the operation of detecting at least one object outputted on the screen or to be outputted on the screen and the operation of assigning different haptic information per object.

According to an embodiment, the operation of assigning may set the operation of detecting a boundary area of the object and the operation of assigning different haptic information to the boundary area and an area other than the boundary area.

According to an embodiment, the operation of assigning may set the operation of assigning first haptic information to the boundary area of the object, the operation of assigning second haptic information to an inside of the object, and the operation of assigning third haptic information to an outside of the object or abstaining from assigning haptic information.

According to an embodiment, the method may set the operation of varying the haptic information assigned to other objects corresponding to the selection of a particular object of the objects.

According to an embodiment, the operation of assigning may set at least one of the operation of assigning haptic information corresponding to the shape of at least one object outputted on the screen or to be outputted on the screen, the operation of assigning haptic information according to the material of the object by analyzing the content of at least one object outputted on the screen or to be outputted on the screen, and the operation of assigning haptic information corresponding to the setting information related to the object.

According to an embodiment, the operation of analyzing the input information may set at least one of the operation of analyzing the type of the input object, the operation of analyzing the type of the input signal generated by the input object, and the operation of analyzing the state of the input signal.

According to an embodiment, the operation of assigning may set at least one of the operation of assigning different haptic information per input object, the operation of assigning different haptic information according to the type of the input signal, and the operation of assigning different haptic information according to the state of the input signal.

According to an embodiment, the operation of analyzing the execution information may set the operation of identifying execution information gathered and the operation of assigning different haptic information per execution information.

According to an embodiment, the method may set the operation of identifying an arrangement state of the electronic device, upon occurrence of the event (e.g., the pose state of the electronic device in a three-dimensional space or motion variation state, angle at which the electronic device is tilted with respect to the ground (or horizontal line) or angle at which the electronic device is tilted or rotated with respect to the axis perpendicular to the ground) and the operation of setting different haptic feedback output points in the touch area related to the occurrence of the event according to the arrangement state of the electronic device. According to an embodiment, the operation of outputting may set the operation of outputting different haptic events corresponding to at least one of the position where the event occurs in the object detected as the result of screen information analysis, the signal strength of the event (e.g., at least one of the strength of the sensed pressure, strength of the voltage, capacitance by a touch or hovering, and size of input area (e.g., touched area)), proximity between the point where the event occurs and the object (at least one of the distance between the object and the point where the event occurs or the proximity between the object surface and the input object).

According to an embodiment, the operation of outputting may set the operation of outputting different haptic feedbacks outputted from the central portion of the object and the boundary area of the boundary area.

According to an embodiment, the operation of outputting may set the operation of suppressing the output of the haptic feedback in case the pressure applied to the object is different from a designated value (e.g., less than the designated value) and the operation of outputting a designated haptic feedback in case the strength of the signal applied to the object is different from a designated value (e.g., not less than the value).

According to an embodiment, in case the strength of the signal applied to the object is different from the designated value (e.g., not less than the value), the operation of running a function set in the object may be set.

According to an embodiment, the operation of outputting may set the operation of outputting a designated reference haptic feedback when a first event is received in an area other than the area where the object detected as a result of the screen information analysis is disposed.

According to an embodiment, the operation of outputting the reference haptic feedback may set at least one of the operation of outputting a directional haptic feedback indicating the area where the object is disposed and the operation of outputting a haptic feedback having a designated size or less.

According to an embodiment, the operation of outputting may set the operation of adjusting the time of output of the haptic feedback corresponding to the object corresponding to a travel speed of the first event and the distance between the current location of the first event and the object in case the travel speed of the first event is a designated speed or more.

According to an embodiment, the operation of outputting may set the operation of suppressing the output of the haptic feedback if the first event is received in the area other than the area where the object is disposed and the operation of outputting the designated haptic feedback when the first event is received on the object.

According to an embodiment, the method may set the operation of running a function corresponding to the object if the first event or a second event different from the first event is received on the object.

According to an embodiment, the operation of assigning may set the operation of performing assignment so that other haptic feedback is outputted corresponding to the position where the object is outputted if at least one object is displayed at a predetermined position of the display corresponding to at least one of the movement direction or position of grasping the electronic device.

According to an embodiment, the operation of assigning may set the operation of performing assignment so that different haptic feedbacks are outputted in a plurality of areas included in the object.

According to an embodiment, the operation of outputting may set the operation of, in case an event occurs in an area other than the object, outputting a directional haptic feedback indicating the direction where the object is located at the position of the event.

According to an embodiment, the operation of outputting may set the operation of transmitting information corresponding to the haptic feedback to another electronic device.

According to an embodiment, the method may set the operation of switching the display into a turn-off state or maintaining the turn-off state in relation with outputting the haptic feedback. According to an embodiment, the operation of outputting may set at least one of the operation of, upon sensing that the electronic device is worn, outputting a designated haptic feedback designated by the area where the wearing is sensed (e.g., a portion of the housing of the electronic device contacting the body, a portion of the area where the haptic module is disposed, or by the haptic module), the operation of outputting the designated haptic feedback in case the electronic device enters a designated position (a predetermined indoor or outdoor position designated based on GPS or Wi-Fi signal or a predetermined locational area range), and the operation of, upon sensing that the electronic device is worn, performing an output so that the designated haptic feedback is transferred to the overall worn electronic device (e.g., the overall haptic module disposed in the electronic device or at least some haptic module configured so that the entire electronic device may feel the haptic feedback).

According to an embodiment, the operation of outputting may set the operation of terminating the output of the haptic feedback if the electronic device departs from a designated position or the electronic device is released from being worn.

According to an embodiment, the operation of outputting may set the operation of outputting at least one haptic feedback according to comparison between a set target value and information gathered based on a sensor signal gathered.

According to an embodiment, the operation of outputting may set the operation of outputting the haptic feedback from at least one of the display area or bezel area of the electronic device.

According to an embodiment, the operation of outputting may set at least one of the operation of outputting different types of haptic feedbacks corresponding to the size of the achievement rate according to the comparison with the target value and the operation of varying the position of outputting the haptic feedback corresponding to the size of the achievement rate according to the comparison with the target value.

According to an embodiment, the operation of outputting may set the operation of outputting a designated particular type of haptic feedback corresponding to the sensor signal accrued for a predetermined period or sensor signal currently gathered.

According to an embodiment, the operation of outputting may set the operation of outputting the haptic feedback guiding to adjust the speed detected based on the sensor signal.

According to an embodiment, the operation of outputting may set the operation of outputting a haptic feedback having at least one of the strength of the haptic or frequency adjusted to increase the speed and the operation of outputting the haptic feedback having at least one of the strength of the haptic or frequency adjusted to reduce the speed.

According to an embodiment, the operation of outputting may set the operation of outputting the haptic feedback having at least one directionality related to time information obtained corresponding to the result of the execution information analysis, the operation of outputting the haptic feedback corresponding to the degree of sleep obtained corresponding to the result of the execution information analysis, and the operation of outputting the haptic feedback corresponding to the stress level obtained corresponding to the result of the execution information analysis.

According to an embodiment, the operation of assigning may set the operation of assigning the information configured to output the designated haptic feedback to the object corresponding to the result of keyword search or inputted keyword.

According to an embodiment, the operation of assigning may set the operation of assigning the information configured to output different haptic feedbacks for each keyword corresponding to the frequency of inputting the keyword.

According to an embodiment, there may be set the operation of running the function related to the object or the function related to the keyword corresponding to at least one of the duration of the event of selecting the object, strength of pressure, touched area, or electric charge.

According to an embodiment, the operation of assigning may set the operation of assigning different haptic feedbacks related to the keyword corresponding to at least one operation of input of the keyword-related letter, handwriting recognition on the touchscreen or touchpad, and voice recognition.

According to an embodiment, the operation of assigning may set the operation of assigning different haptic feedbacks to the object corresponding to the similarity or reliability between the object and the keyword in case there are a plurality of objects.

According to an embodiment, the operation of assigning may set the operation of assigning a directional haptic feedback indicating a target object disposed in the area not currently displayed of the entire screen area.

According to an embodiment, the operation of assigning may set the operation of assigning the directional haptic feedback to at least one object displayed on the display.

According to an embodiment, the operation of assigning may set the operation of assigning different haptic feedbacks depending on the type of the target object corresponding to the result of the analysis.

According to an embodiment, the operation of assigning may set the operation of assigning different haptic feedbacks corresponding to at least one of the case where the target object is hidden by other objects, the case where the target object is exposed, the size of the target object, and the location of the target object.

According to an embodiment, the operation of outputting may set different haptic feedbacks corresponding to the distance between the position where the event occurs and the target object.

According to an embodiment, the method may set the operation of displaying the screen area including the target object related to search of the entire screen area on the display as default.

According to an embodiment, the operation of outputting may set the operation of outputting different haptic feedbacks corresponding to the type of event related to varying the screen area displayed on the display.

Figure 131:
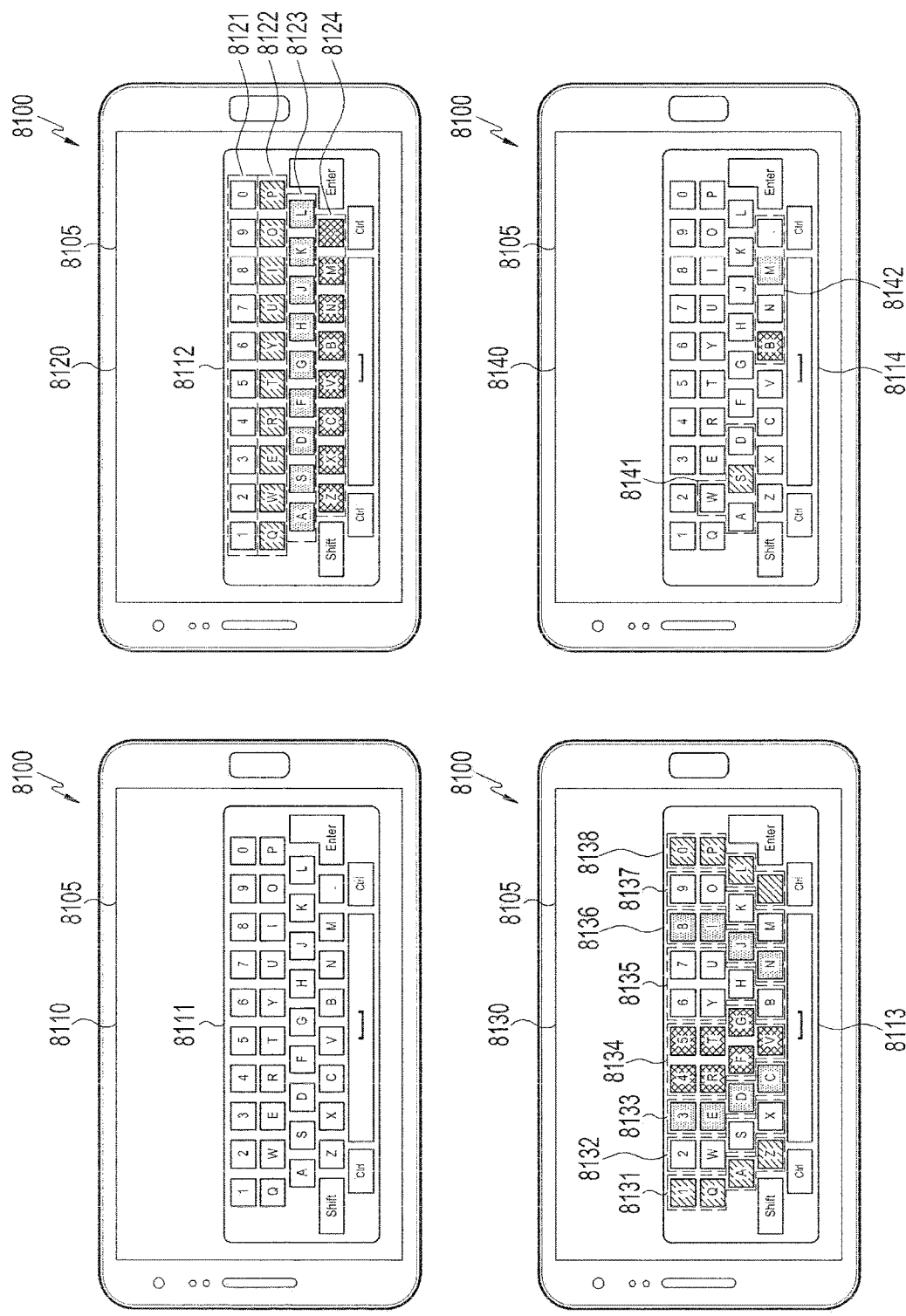

FIG. 131 is a view illustrating an example of a screen for describing a per-object haptic information operation according to an embodiment. The haptic information operation shown in FIG. 131 may be screen information analysis-based haptic information operation.

Referring to FIG. 131, according to an embodiment, the display 8105 of the electronic device 8100 may output a virtual input object 8111 as in state 8110. The virtual input object 8111 may include at least one object related to inputting a letter. For example, the virtual input object 8111 may include at least one virtual numeric key-related object, at least one virtual letter key-related object, and at least one virtual function key-related object. The haptic support module 7670 may assign the first haptic information to at least one object included in the virtual input object 8111. For example, the haptic support module 7670 may assign the same first haptic information to all the objects included in the virtual input object 8111. The haptic support module 7670 may perform first haptic information-based haptic module operation if such event occurs that selects a particular object included in the virtual input object 8111, e.g., at least one of the virtual numeric key-related object, and virtual function key-related object.

The above-described virtual input object 8111 shows an example of the virtual keyboard and may have such form that several keys are arranged by a software GUI layout. Upon sensing the input event by a touch or hovering in the area where the keys are arranged, the haptic support module 7670 may perform control to output the haptic feedback or audio indicating that the event-sensed key has the input. In case the input event occurs in an area other than the key area, the haptic support module 7670 may perform control to abstaining from generating the haptic feedback. The virtual keyboard may various modifications depending on the type of display or applications. Accordingly, the GUI layout and arrangement of the keys may be varied while an input is made through the virtual keyboard. For example, if the operation of turning the electronic device 8100 is sensed to switch into the vertical mode while entering letters using the QWERTY-type virtual keyboard in the horizontal mode on the electronic device 8100 capable of sensing the horizontal mode and the vertical mode through the motion sensor (e.g., the acceleration sensor, gyro sensor, tilt sensor, or gravity sensor), the position of the virtual keyboard is changed while the virtual keyboard itself may simultaneously be changed into the numeric key mapping type layout that has been used for T9 or a particular electronic device 8100. The haptic support module 7670 may provide different haptic feedbacks according to the relative distance or distance between the keys to differentiate the currently entered key and other keys. In this connection, the haptic support module 7670 may set a haptic layout for haptic feedbacks corresponding to the GUI layout (e.g., the arrangement of objects displayed on the display). Here, the GUI layout may differ from the haptic layout.

According to an embodiment, the display may output the virtual input object 8112 as in state 8120. The haptic support module 7670 may perform per-row haptic information assignment on the virtual input object 8112. For example, the haptic support module 7670 may assign different haptic information to each row for the virtual function key-related objects included in the virtual input object 8112. According to an embodiment, the haptic support module 7670 may assign first haptic information to first row objects 8121. The haptic support module 7670 may assign second haptic information to second row objects 8122. The haptic support module 7670 may assign third haptic information to third row objects 8123. The haptic support module 7670 may assign fourth haptic information to fourth row objects 8124. If the event selecting or indicating a particular object included in the first row objects 8121 occurs, the haptic support module 7670 may perform control to output the haptic module based on the first haptic information. If the event related to the particular object included in the second row objects 8122 occurs, the haptic support module 7670 may perform control to output the haptic module based on at least one of the second haptic information (e.g., information defined to differently implement at least one of the touch or texture set in the first haptic information or strength (or strength) of the vibration, or vibration pattern or vibration period).

According to an embodiment, the display may output the virtual input object 8113 as in state 8130. The haptic support module 7670 may perform per-column haptic information assignment on the virtual input object 8113. For example, the haptic support module 7670 may assign different haptic information to each column for the virtual function key-related objects included in the virtual input object 8113. According to an embodiment, the haptic support module 7670 may assign first haptic information to first column objects 8131. The haptic support module 7670 may assign second haptic information to second column objects 8132. The haptic support module 7670 may assign third haptic information to second row objects 8133. The haptic support module 7670 may assign fourth haptic information to fourth row objects 8134. The haptic support module 7670 may assign the fifth haptic information to the fifth row objects 8135, the sixth haptic information to the sixth row objects 8136, the seventh haptic information to the seventh row objects 8137, and the eighth haptic information to the eighth row objects 8138. The first to eighth haptic information may include information defined to express different touches or textures. According to an embodiment, the first to the eighth haptic information may have the same haptic information in rows that do not neighbor each other. For example, the third haptic information may be set to have the same information as the first haptic information or fifth haptic information.

As described above, the haptic support module 7670 may provide support to allow the user to grasp a relative position of the key the user currently enters by giving other strengths, patterns, directivity, or textures per row or column. For example, in the case of state 8130, the keys entered per finger may provide the same haptic feedback and may be used for practicing keyboard typing or correcting the way to type on the keyboard.

According to an embodiment, the display may output the virtual input object 8114 as in state 8140. The haptic support module 7670 may assign haptic information per predetermined virtual key group to the virtual input object 8114. For example, the haptic support module 7670 may assign different haptic information to each virtual key group for the virtual function key-related objects included in the virtual input object 8114. According to an embodiment, the haptic support module 7670 may assign first haptic information to first group objects 8141. The haptic support module 7670 may assign second haptic information to second group objects 8142. The first and second haptic information may include information defined to express different touches or textures.

According to an embodiment, the haptic support module 7670 may set at least one key included in the key group as a reference area and provide a reference haptic feedback. According to an embodiment, in state 8140, S included in the first group object 8141 may be set to correspond to the down arrow, and the middle finger of the left hand may be positioned. The other keys included in the first group object 8141 may function as their respective arrows of particular directions with respect to S. Here, the haptic support module 7670 may assign S with the haptic information that is different in characteristic than the other keys included in the first object 8141 e.g., at least one the haptic strength, degree of roughness, frequency, vibration period, and vibration duration) to define S as the reference area.

According to an embodiment, the reference haptic feedback may correspond to a search operation for determining the position of the corresponding key or key group. For example, in case a touch and drag occurs on the surface of the keyboard where the key is positioned or the surface of the touchscreen, or in case a motion is made in the hovering state, the haptic support module 7670 provides the reference haptic feedback allowing the position of the reference area to be known. If the touch or hovering-related signal is determined to be a search operation, the haptic support module 7670 may provide various haptic feedbacks according to the area where the input is sensed. For example, in case the search operation occurs in a designated particular key (e.g., the key assigned with running a particular function), e.g., the S key area, the haptic support module 7670 may temporarily provide a heavy vibration or haptic feedback of a particular pattern. O, upon sensing the search operation in an external area other than the S key area, e.g., an F key area adjacent to S, the haptic support module 7670 may perform control to generate a haptic pattern with the directivity to the S direction.

Or, if it is determined to be the search operation, the haptic support module 7670 may assign designated haptic information to only the reference area. Corresponding to this, the haptic support module 7670 perform control to abstain from outputting a separate haptic feedback in the input signal generated in the area other than the reference area. The haptic support module 7670 may provide a predetermined haptic feedback corresponding to the designated haptic information corresponding to the input signal generated in the reference area. The haptic support module 7670 may provide support to output the designated haptic feedback only in the reference area so that the user may concentrate on finding the reference area and may provide support so that the user may easily recognize the reference area or area desired to be selected by simply moving the finger without viewing the display. According to an embodiment, if the input signal generated from the reference area is generated for a predetermined time or more, the haptic support module 7670 may further include the operation of stopping providing the predetermined haptic feedback corresponding to the designated haptic information.

According to an embodiment, in case the input signal with a strength smaller than a designated value is input when the input is generated at the virtual key input object on the touchscreen, the haptic support module 7670 may generate the haptic feedback according to the designated first haptic information. For example, in case the contact area of the touch input is smaller than a designated reference, the force of the touch input is small, or the electric charge or inputted sound volume is low, the haptic support module 7670 may perform control to generate the haptic feedback according to the designated first haptic information on the touchscreen area where the contact occurs or generate a predetermined vibration. In this operation, the haptic support module 7670 may perform control to abstain from applying the input related to the first haptic information. If an input larger than a designated value (e.g., a pressure larger than a designated pressure or a touch longer than designated touch duration), the haptic support module 7670 may perform control to perform an actual function corresponding to the input. In this operation, the haptic support module 7670 may perform control to generate a haptic feedback according to the second haptic information.

The key group may be set to be differentiated depending on the position of the finger and have different haptic feedbacks. For example, the little finger of the left hand may be used to input 1, q, a, and z, and the ring finger of the left hand may be used to input 2, w, s, and x. Accordingly, the haptic support module 7670 may make such configuration as to divide the respective keys of the fingers into groups and provide a different haptic feedback to each group. The per-finger key area group may be dynamically varied.

According to an embodiment, in case the shift of the position where the input signal occurs on the display is faster than a predetermined reference, the haptic support module 7670 may provide only haptic feedback based on the designated haptic information corresponding to the input signal. The haptic support module 7670 may perform control to suppress the execution of a function related to the object selected or indicated by the input signal. Additionally, upon approaching within a predetermined distance before entering the area related to the particular object, the haptic support module 7670 may perform control to generate the haptic feedback based on the designated haptic information prior to the designated time. For example, if a predetermined speed of touch drag event or a hovering position shift event (e.g., the event that the position moves while hovering) occurs on the touchscreen, the haptic support module 7670 may perform control to predict the direction and speed of the touch drag event or hovering position shift event to output the haptic feedback based on the designated haptic information on a predetermined area. Or, the haptic support module 7670 may perform control to output a designated haptic information-based haptic feedback in a predetermined distance or area before the touch drag event or hovering position shift enters a predetermined area. Through the above-described operation, in case the travel speed of the touch drag or the travel speed of the hovering position is a predetermined speed or higher, the haptic support module 7670 may compensate for the context where the haptic feedback generated in the designated area is not normally provided to the user (e.g., the context where the haptic feedback is provided to the designated area after the touch object such as finger passes the designated area, so that the user fails to receive the haptic feedback).

Or, the haptic support module 7670 may perform control to output the designated haptic information-based haptic feedback within a predetermined time after the touch event or hovering event passes the predetermined area.

According to an embodiment, the haptic support module 7670 may provide the haptic feedback to feel the maximum frictional force after the touch event or hovering event passes the vertex related to the object outputted on the display. For example, the haptic support module 7670 may perform control to output the set first haptic information-based haptic feedback to provide a predetermined strength or more of frictional force or resistance after passing the vertex formed based on the virtual height information forming the boundary area of the object or the position where the angle difference is varied by a predetermined size or more and the object when the position of the user input (e.g., the position where the touch event is inputted, the position where the touch signal is sensed by the touch drag event or the position where the hovering event occurs) passes the boundary area of the particular object. According to an embodiment, the haptic support module 7670 may perform control to provide the second haptic information-based haptic feedback providing a smooth feel with a predetermined strength immediately before providing the first haptic information-based haptic feedback so as to feel a predetermined strength or more of frictional force or resistance. Additionally, in case the event shift by the user input is at a speed lower than a designated value, the haptic support module 7670 may perform control to provide the designated first haptic information-based haptic feedback.

According to an embodiment, if the touch event is continuously generated in a plurality of object areas where the particular haptic feedback is provided, the haptic support module 7670 may provide a particular haptic information-based haptic feedback to have the feel that the user input (e.g., touch event) exits the previous object area in the boundary area of the plurality of object areas and the feel of entering the subsequent object area. For example, when the user input moves from the center of the particular object to the boundary area of the object, the haptic support module 7670 may perform control to output the haptic information-based haptic feedback set to maintain the degree of roughness that is relatively soft or a relatively weak haptic strength until before reaching the designated boundary area. Or, the haptic support module 7670 may perform control to output the haptic information-based haptic feedback set to gradually increase the haptic strength or degree of roughness as the user input moves from inside the object to the boundary area. The haptic support module 7670 may perform control to output the haptic feedback according to the haptic information set to express relatively the largest haptic strength or roughness or a predetermined size or more in the boundary area.

According to an embodiment, the haptic support module 7670 may perform control to output the haptic feedback based on the haptic information having a relatively larger haptic strength or roughness degree as compared with the user input moving from inside the object to the outside corresponding to the user input entering the boundary area from the outside area of the particular object. In this operation, the haptic support module 7670 may operate at least one of the strength or roughness to correspond to the height of the virtual haptic modeling or the degree of depth.

Based on the above-described support, the haptic support module 7670 may provide the haptic feedback corresponding to the operation of rubbing the key object surface with the finger from inside of the key object to outside and the haptic feedback corresponding to the finger operation moving from outside the key object to the inside of the key object in order to simulate the tactile feel that may be provided by a physical keyboard on the virtual keyboard displayed on the display. For example, the haptic support module 7670 may provide the haptic feedback corresponding to the tight skin feel or frictional force on the physical key boundary area on the virtual key boundary area. According to an embodiment, the haptic support module 7670 may differently express various haptic feedbacks differentiated depending on the shape of the object and the direction of the finger's movement. For example, in case the finger touches and moves along the shape of the boundary area of the object, the haptic support module 7670 may perform control to output the haptic feedback based on the haptic information set to provide a smoother tactile feel as compared with when it moves perpendicular to the arrangement direction of the boundary area.

According to an embodiment, the haptic support module 7670 may configure a haptic layout to provide a haptic feedback by modeling the shape of the input object (e.g., finger, pen, finger nail, ball, or eraser). According to an embodiment, the haptic support module 7670 may configure a haptic layout providing a relatively weak or smooth feedback or providing no feedback for the boundary areas of the keys when the touch event is generated by the input object so that the input object having a touch area of a predetermined size or area corresponds to the context of touching the boundary area of the physical keyboard having a narrow gap between the key boundary areas.

The physical keyboard is depressed in the area between the keys, and thus, only small object, such as a pen or finger nail, may contact the area between the keys, and a large object, such as a finger, cannot contact the area. According to an embodiment, the haptic support module 7670 may simulate the context of the physical keyboard and input object on the virtual keyboard. For example, in case a touch signal, touch drag signal, or hovering signal generated on at least a portion of the intermediate area between objects (e.g., the area between the boundary areas of the objects) is sensed, and the area or length (the length of the signal by the touch trajectory or hovering trajectory) where the signal is sensed is not more than a predetermined size (e.g., narrower or shorter than the intermediate area), the haptic support module 7670 may set the haptic layout to output a predesignated haptic feedback corresponding to the intermediate area.

According to an embodiment, in case a touch signal, touch drag signal, or hovering signal including at least a portion of the intermediate area formed between the objects, e.g., the area between the boundary areas of the objects, is sensed, and the area or length where the signal is generated is larger than a predetermined size (e.g., the area or length of the intermediate area), the haptic support module 7670 may set the haptic layout to abstain from outputting the haptic feedback based on predesignated particular haptic information.

According to an embodiment, the haptic support module 7670 may recognize a sound wave or vibration pattern generated by the contact of the input object inputted through the input device to determine the type of the input object. The haptic support module 7670 may perform control to set whether the haptic feedback is on/off or the type of the haptic feedback between the boundary areas corresponding to the determined type of the input object. For example, when bringing the input object in contact with the display, the haptic support module 7670 may gather and recognize the sound wave or vibration generated by the input device (e.g., the microphone, ultrasonic wave sensor, acceleration sensor, or vibration sensor) to determine the type of the input object. According to an embodiment, the haptic support module 7670 may recognize at least one of the sound wave, vibration, the position where the event occurs, the area of occurrence, and the shape of the area of occurrence to determine the type of the input object. For example, the haptic support module 7670 may differentiate the capacitive stylus pen and finger pad touching the touchscreen based on the shape and form of the area where the event signal occurs. In this operation, the haptic support module 7670 may recognize the input object generating the event as the pen or finger based on at least one of, e.g., a relatively small event occurrence area or a shape relatively close to a particular shape (e.g., circle).

Figure 132:
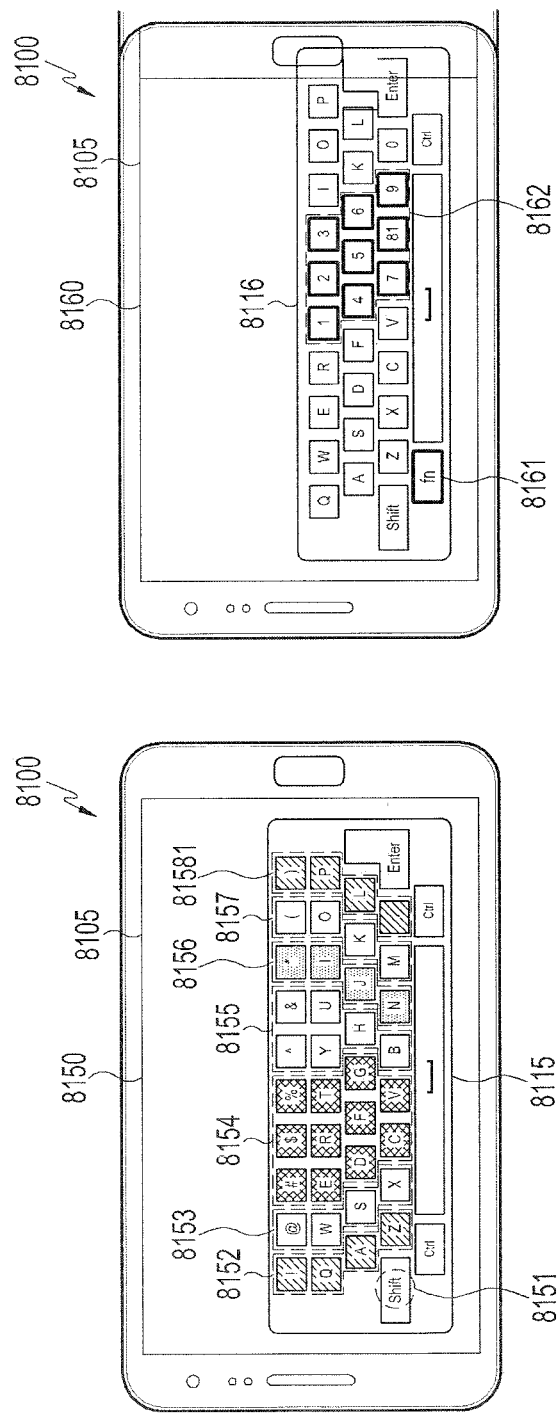

FIG. 132 is a view illustrating an example of a screen for describing a per-composite object haptic information operation according to an embodiment.

Referring to FIG. 132, according to an embodiment, the display may output an object 8113 (e.g., a virtual keyboard for entering small letters or numbers) as in state 8130 according to whether the virtual function key (e.g., shift key 8151) operates or may output a virtual input object 8115 (e.g., a virtual keyboard for capital letters or special letters) as in state 8150. Further, the toggled state of the virtual function key may be displayed on the display through one or more of the symbol, color, size, or shape variation. According to an embodiment, in the case of state 8130, the haptic support module 7670 may assign the first haptic feedback to be outputted corresponding to the selection of at least one of the virtual keys 8131 to 8138. Further, in the case of state 8150, the haptic support module 7670 may assign the second haptic feedback to be outputted corresponding to the selection of at least one of the virtual keys. The haptic support module 7670 may perform per-row haptic information assignment on the virtual input object 8115 and may perform haptic information assignment different from the prior one in relation with the selection of a particular virtual key. For example, in case the first function key object 8151 is selected among the virtual key-related objects included in the virtual input object 8115 (e.g., in the case where the touch event occurs and lasts or selection is maintained through the toggle function), the haptic support module 7670 may assign the first haptic information to the first row objects 8152. In the state where the function key object 8151 is selected, the haptic support module 7670 may assign second haptic information to second column objects 8153. In the state where the function key object 8151 is selected, the haptic support module 7670 may assign third haptic information to third column objects 8154. In the state where the function key object 8151 is selected, the haptic support module 7670 may assign fourth haptic information to fourth column objects 8155. In the state where the function key object 8151 is selected, the haptic support module 7670 may assign fifth haptic information to fifth column objects 8155, in the state where the function key object 8151 is selected, the haptic support module 7670 may assign sixth haptic information to sixth column objects 8155, and in the state where the function key object 8151 is selected, the haptic support module 7670 may assign seventh haptic information to seventh column objects 8155. The first to seventh haptic information may include information defined to express different touches or textures from the haptic information described above in connection with state 8130 of FIG. 131.

According to an embodiment, the above-described state 8150 may be an embodiment related to the virtual key input object in case a key is pressed with the shift key pressed. The haptic support module 7670 may assign different haptic information for the virtual key object selected together with the pressing of the shift key and for the virtual key object selected while the shift key is not pressed.

According to an embodiment, the display may output the virtual input object 8116 corresponding to the selection of the function key object 8161 as in state 8160. The haptic support module 7670 may assign particular haptic information to a group of some keys of the virtual input object 8116. For example, the haptic support module 7670 may assign first haptic information to the key group 8162 converted corresponding to the selection of the function key object 8161 of the virtual key-related objects included in the virtual input object 8116. The haptic support module 7670 may assign second haptic information to the remaining keys.

According to an embodiment, the above-described state 8160 may represent an embodiment in which some of the keys provide a numeric input key function when the function key object 8161 is pressed. The haptic support module 7670 may provide a different haptic feedback to each of the function key area, numeric key area, and letter key area. Corresponding to this, the user may be aware that the key inducing a particular service mode stays pressed and may easily determine in a tactile manner that the type of each inputted information differs according to the area.

The above-described service mode causing a feedback difference may include the selection of one or more keys of the ctrl key, alt key, shift key, function key (F1 to F12 or window start key), language setting changing key (e.g., one or more of the English-Korea mode change key, Chinese mode key, Japanese input key, and IME setting key), caps lock, pause, number lock, and scroll lock. The service mode may be achieved by running a particular application. For example, in case the game mode is set by running game as in state 8140 of FIG. 131, the haptic support module 7670 may make a setting so that different haptic feedbacks are outputted to the used key groups. Such haptic feedback function may allow the current state of the device to be known. For example, in order to be aware whether the caps lock area stays pressed in the virtual keyboard, if the user performs user entry on the key, it may be determined whether the inputted signal is an input corresponding to a discovery operation (e.g., one or more of a touch signal or touch drag signal weaker than a predetermined strength, or touch signal duration not more than a predetermined time, or hovering signal), the haptic support module 7670 may provide support to turn on/off the haptic feedback depending on the state or output two different haptic feedbacks to allow the state of the device to be recognized.

According to an embodiment, the area of each key in the above-described virtual keyboard may not be fixed. For example, the position of each key may be adjusted by the user's settings or habit, and the central position of the key area or the size of key may differ. For example, if the user's such habit is accrued and analyzed that presses the left-side boundary area of the "a" key with his little finger, in case a particular input event occurs a predetermined number of times or more, the electronic device 8100 may compute the distribution of the input positions to make a slight shift or increase the area of the key in a predetermined direction so that the position of the key corresponds to the point where the input event occurs. In this case, the haptic feedbacks may also be varied corresponding to the transformed key area. Further, the electronic device 8100 may determine the user currently making input by analyzing the distribution data of input positions. For example, the electronic device 8100 may recognize the user using at least one of the login information or face recognition information of the person using it and bio information (e.g., iris, fingerprint, heart rate pattern or hand vein pattern), and when an input event (e.g., an even by pressing a virtual key at a particular position or a touch at a particular position on the touch panel) occurs, store the input position information in association with the user information. Based on this, the electronic device 8100, if the input event occurs, may compare the input position information on the input event with stored input position information to determine the user currently using the electronic device 8100. In relation with correcting habit, the haptic support module 7670, in case an input is applied to the boundary area, may investigate its input area distribution and frequency to provide a haptic feedback giving a stronger or more rough feel that may be easily felt by the user.

According to an embodiment, the haptic support module 7670 may process the user input giving a haptic feedback under several differentiated contexts. For example, the haptic support module 7670 may provide a first input mode in which a signal by contact or hovering by an input tool or finger is generated on the input device surface, and the information or function of the corresponding key does not run, and at least one basic haptic feedback is provided. Such first input mode may apply to the case where the input signal value generated in a resistive membrane touch sensing device is not more than a predetermined value, the case where a hovering signal is generated in a capacitive sensor device, or upon touching, a signal not more than a predetermined value is generated, the case where a shear force not more than a predetermined value is generated in a force input scheme, the case the area where a contact or input occurs is not more than a predetermined area in a constant voltage or optical scheme, or the case where an input is generated by a predetermined first input means, such as a finger nail or finger joint. The haptic support module 7670 may provide a second input mode in which unlike the first input mode, information corresponding to an actual key is inputted. In case the first input mode is maintained for a predetermined time or more or less, in case an input signal value in the first input mode is not less than a predetermined value (voltage, capacitance, induced current, or shear force), in case a signal is generated in a predetermined area or more in the first input mode, or in case information is inputted through the second input means such as a finger or stylus pen, the haptic support module 7670 may provide the second input mode.

If at least one finger touches the virtual keyboard of the touchscreen so that a signal less than a predetermined strength (e.g., a pressure or electrical variation not more than a designated strength) is sensed, the haptic support module 7670 may evaluate that the keys placed on the fingers correspond to the first input mode state and may provide a predetermined haptic feedback (e.g., haptic feedback set as default or particular designated haptic feedback). In such state, if a variation event with a predetermined strength or more (e.g. in case the contact area with a pressure is larger than a designated size, the capacity is larger than a designated strength, the strength of a force is larger than a designated strength, or the key down speed or key up speed is larger than a designated value) occurs, the haptic support module 7670 may evaluate it as switch into the second input mode. Corresponding thereto, the haptic support module 7670 may perform control so that the character or text corresponding to the inputted key is inputted or control the functional operation corresponding to the inputted key. If the finger is moved while remaining touched in the first input mode, the haptic support module 7670 may support a predetermined haptic feedback only when the position where the touch signal is generated matches a predetermined reference area and may switch into the discovery mode where no input occurs. If the variation in the touch signal generated as the finger moves in the discovery mode is not more than a predetermined reference value (e.g., at least one of a designated travel speed or designated travel distance per unit time) or the travel position of the finger shows a variation within a predetermined area for a predetermined time or more, the haptic support module 7670 may switch into the first input mode. If an event corresponding to the condition of the second input mode in the discovery mode occurs, the haptic support module 7670 may release the discovery mode and switch into the second input mode.

According to an embodiment, if the input signal is sensed by a continuous movement, such as a drag, flick, or hovering, or a movement, such as a motion or gesture, the haptic support module 7670 may activate the discovery mode. For example, corresponding to the protrusion and depression of the F key or J key in the physical keyboard, the haptic support module 7670 may set the F key and K key area as a reference area corresponding to the basic location where the fingers are to be placed on the virtual keyboard, such as the F key and K key, and in case an input signal occurs in the reference area or an adjacent area within a predetermined distance, provide a particular haptic feedback. Accordingly, the user may easily identify the position of the corresponding keys through the haptic feedback generated in the F and K key when moving at least one finger or palm or pen through hovering or by contacting the touch sensing area.

According to an embodiment, for an area other than the reference area, another haptic feedback (e.g., another haptic feedback provided in case a user input is sensed from a boundary area surrounding the reference area) other than the haptic feedback for reference area may be additionally provided.

According to an embodiment, if a touch drag event occurs in a virtual object having virtual height information in the friction display, the haptic support module 7670 may give different frictional forces for the event occurrence positions and provide haptic feedbacks. For example, the haptic support module 7670 may provide a haptic feedback corresponding to the haptic information allowing a largest frictional force to be felt immediately after passing through a virtual vertex of the object (after a predetermined time or predetermined distance passes), so as to comply with the user's cognitive experience. Further, the haptic support module 7670 may output a haptic feedback based on the haptic information corresponding to a smooth texture immediately before a touch object, e.g., finger, arrives at a virtual vertex of the object (before the predetermined time or distance passes) and provides a haptic feedback based on the haptic information corresponding to a rough texture immediately after passing the vertex, thereby allowing the user to feel an increased difference in texture.

According to another embodiment, the haptic support module 7670 may set two groups depending on the travel speed of the touch drag event or hovering shifting event and provide a different haptic feedback characteristic for each group. For example, in case the travel speed of the touch object is not more than a designated speed, the haptic support module 7670 may provide a haptic feedback allowing the frictional force to be felt relatively more at the boundary area of the virtual object, and in case the speed is not less than a designated speed, provide a haptic feedback allowing the frictional force to be felt less. By contrast, in order to emphasize the texture at the boundary area, the haptic support module 7670 may provide a haptic feedback corresponding to a relatively more frictional force or more rough texture in case the travel speed is not less than a designated speed.

Figure 133:
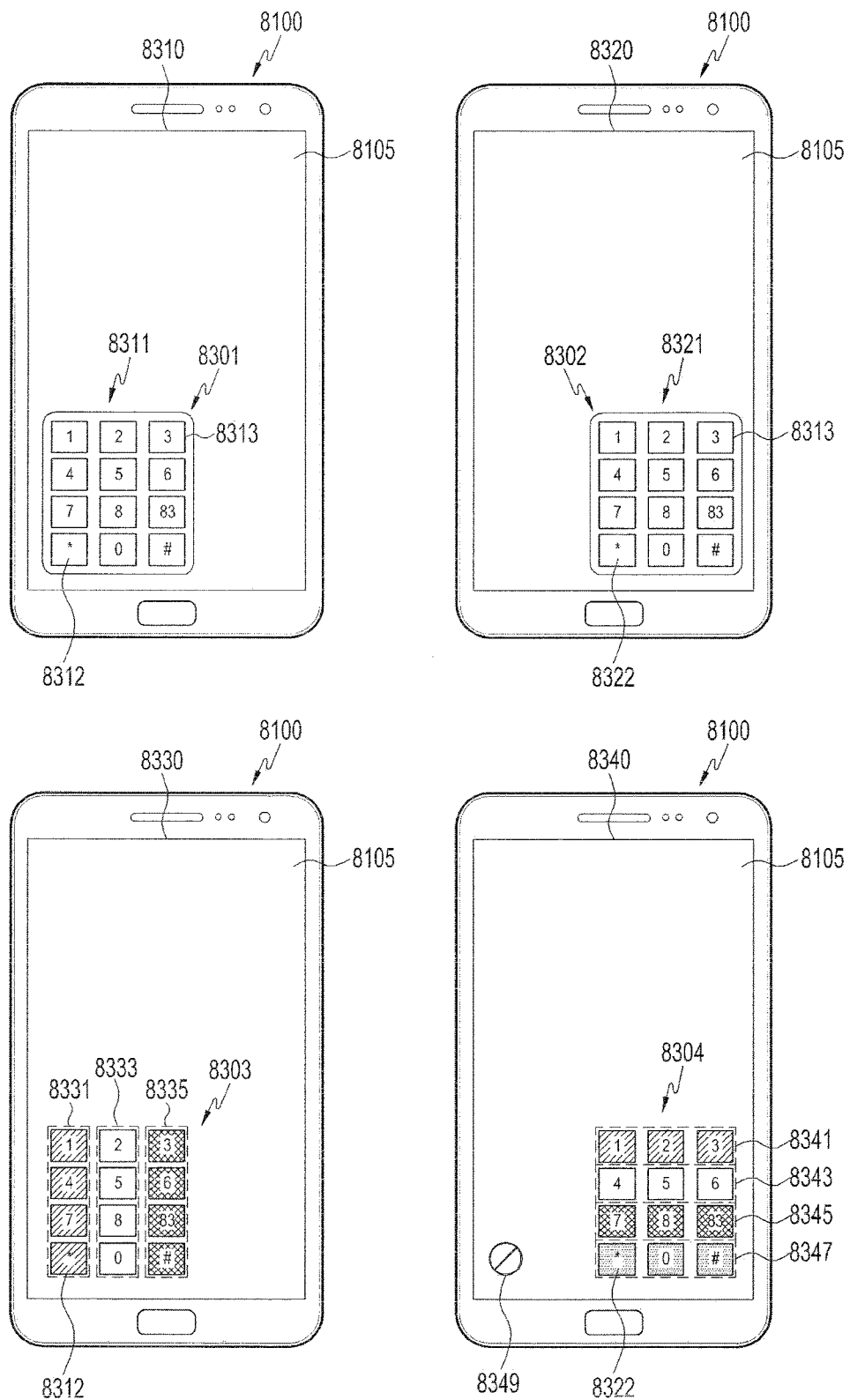

FIG. 133 illustrates a screen interface related to a one-hand input-related haptic information operation according to an embodiment.

Referring to FIG. 133, in the one-hand mode, the UI is not fixed to a particular area, and the position provided may be varied depending on one or more contexts of the movement of the electronic device 8100 and the position of the finger contacting the electronic device 8100. For example, the haptic support module 7670 may recognize the tilting, rotational state, or motion of the electronic device 8100 by the acceleration measuring sensor (accelerometer), gyro sensor, or geomagnetic sensor and may vary the position, size, or ratio of the UI corresponding to the horizontal UI mode or vertical UI mode set according thereto. As another example, the haptic support module 7670 may sense the position of the finger or palm sensed by the grip sensor, touch sensor, or pressure sensor to determine whether the device is held by the left hand or right hand. For example, in case the electronic device 8100 is held by the left hand, the haptic support module 7670 may perform control so that the virtual keyboard is positioned closer to the left area of the display (e.g., within a designated distance from the left edge of the display), and in case the electronic device 8100 is held by the right hand, the haptic support module 7670 may perform control so that the virtual keyboard is positioned closer to the right area of the display (within a designated distance from the right edge of the display). According to an embodiment, in case the upper or lower end of the electronic device 8100 is held, the virtual keyboard may be positioned closer to the upper or lower end close to the corresponding hand for easier entry with the thumb. For example, state 8310 of FIG. 133 may be the virtual keyboard displayed in case relatively the left hand holds at the position closer to the lower end of the terminal. The haptic support module 7670 may provide a particular haptic feedback corresponding to the position where the input occurs or the position, direction, or function of the UI. According to an embodiment, the haptic support module 7670, if a particular application runs, may perform control to output the first key group object 8301 on the display in state 8310. Here, the haptic support module 7670 may partition into the key area 8312, the boundary area 8313 surrounding the key area 8312, and the edge area 8311 corresponding to the outside of the boundary area 8313 in relation with the first key group object 8301. Further, the haptic support module 7670 may additionally or alternatively partition into the edge area 8311 and the outside area corresponding to the outside of the edge area 8311. The haptic support module 7670 may assign different haptic information to the key area 8312 and the boundary area 8313. The haptic support module 7670 may assign different haptic information from the haptic information assigned to the key area 8312 and the boundary area 8313 or abstain from assigning separate haptic information to at least one of the edge area 8311 or the outside area. According to another embodiment, it may assign haptic information different from the haptic information corresponding to the key area 8312 to the edge area 8311 surrounding the key areas. The edge area 8311 may be in the form of a boundary line with a predetermined thickness surrounding the first key group object 8301 or may be the remainder of each key area in the first key group object 8301.

According to an embodiment, in order to recognize the varied virtual keyboard area, the user may discover the keyboard area through a hovering or dragging or tap and hold input. In such discovery mode, if a user input occurs in an area adjacent to the area where the first key group object 8301 is disposed, the haptic support module 7670 may provide the user with a reference haptic feedback that may inform the user of the direction or distance of the position of the first key group object 8301 from the position of the user's input. The reference haptic feedback may provide a different touch or texture than the haptic feedback generated from the boundary area 8313 or edge area 8311 and the haptic feedback generated from the key area 8312.

Since the physical keyboard mostly has the key or input area constituted of keys projecting beyond the peripheral portion of the keyboard, the user may recognize the boundary area 8313 or edge area 8311 from the difference between the boundary area (edge) of the key or key input area or the other areas by touching or fumbling the keyboard with his hand tip. In order for the touchscreen or touchpad to provide the tactile feel of the boundary area 8313, the haptic support module 7670 may assign the first haptic information (e.g., information set to stimulate the Meissner corpuscle) to at least one of the boundary area 8313 or edge area 8311. For example, the first haptic information may be information set to output a stimulus with a range from about 3 Hz to about 100 Hz or from 25 Hz to 40 Hz through the haptic module. According to an embodiment, the haptic support module 7670 may assign haptic information related to the array pin included in the haptic module or piezo element control-related haptic information so that the user's finger may recognize the boundary area when it is positioned in a predetermined area of the display or passes the area. For example, in case the haptic module corresponding to a plurality of array pins or a layer of a plurality of piezo elements is placed under the elastic screen sheet or flexible touch panel (e.g., touchscreen panel TSP), the haptic support module 7670 may control the variation in shape of at least some of the piezo elements or the two-dimensional or three-dimensional movement of the array pins according to the haptic information. Accordingly, the electronic device may provide the haptic feedback corresponding to the touched object on the screen sheet or touch panel. According to another embodiment, a band-shaped haptic module constituted of piezo elements may be mounted on the touchscreen or touchpad to provide a particular haptic feedback to the display under the control of the haptic support module 7670. According to an embodiment, in the case of the touchscreen or touchpad capable of sensing touch input signals, the haptic support module 7670 may provide haptic feedbacks only to the area where the touch input signal is generated.

According to an embodiment, in case the user input occurs in the boundary area 8313 or edge area 8311 of the object, the haptic support module 7670 may perform control to output a designated strength of vibration from the area or output a haptic feedback with a frequency of 250 Hz to 300 Hz stimulating the Pacinian corpuscle from the area. According to an embodiment, the haptic support module 7670 may provide various haptic feedbacks by controlling the electric field between the electrode and finger.

According to an embodiment, the haptic support module 7670 may assign first haptic information to the key area 8312 and second haptic information to the boundary area 8313 or edge area 8311. For example, the haptic support module 7670 may assign the first haptic information or second haptic information related to a frequency haptic feedback with a predetermined strength to provide a feel as if the user touches a silky object. According to an embodiment, the haptic support module 7670 may set the haptic feedback with a frequency of 0.4 Hz to 3 Hz stimulating the Merkel's disk sensing a tiny pressure to the first haptic information or second haptic information. According to an embodiment, the haptic support module 7670 may assign a haptic feedback with a fast frequency to the first haptic information or second haptic information to provide a silky texture feel to the user. According to an embodiment, the haptic support module 7670 may assign the haptic information allowing the nerve terminal sensing the hot-cold variation to feel a predetermined temperature as the first haptic information or second haptic information.

According to another embodiment, the haptic support module 7670 may assign the first haptic information to the key area 8312, the second haptic information to the boundary area 8313, and the third haptic information to the edge area 8311.

According to an embodiment, in case the second key group object 8302 corresponding to the one-hand mode UI is outputted on the display that used to output the first key group object 8301 as in state 8320, the haptic support module 7670 may assign the third haptic information related to the haptic feedback indicating that it is not the normal input area to the area (e.g., the edge area 8313) other than the boundary area 8321 or key area 8322. The second key group object 8302 may include the key area 8322 and the boundary area 8321. For example, the third haptic information may be information providing a haptic feedback in the form of a slow and heavy vibration. Or, the third haptic information may be a light vibration with a predetermined strength or less (a tactile feel having a difference from the second haptic information). According to an embodiment, the haptic support module 7670 may generate and assign different haptic information based on air pressure or hot-cold change as well as vibration or frequency. The haptic support module 7670 may perform control to assign various forms (circle, ellipse, straight line, curved line, or wave shape) of haptic information by using different directions of movement per haptic feedback using, e.g., array pins, and additionally giving a time difference or variation in the movement direction.

According to an embodiment, the haptic support module 7670 may perform control to output the third key group object 8303 to the display as in state 8330. The third key group object 8303 does not have a boundary area but may include a first key column 8331, a second key column 8333, and a third key column 8335. The haptic support module 7670, if assigning the first haptic information to the first key column 8331 in the third key group object 8303 and the second haptic information to the second key column 8333, may perform control to assign the third haptic information to the third key column 8335.

According to an embodiment, the haptic support module 7670 may perform control to output the fourth key group object 8304 to the display as in state 8340. The fourth key group object 8304 does not have a boundary area but may include at least one of a first key row 8341, a second key row 8343, a third key row 8345, or a fourth key row 8347. The haptic support module 7670, if assigning the first haptic information to the first key row 8341 in the fourth key group object 8304 and the second haptic information to the second key row 8343, may perform control to assign the third haptic information to the third key row 8345 and the fourth haptic information to the fourth key row 8347. Additionally, in case an area 8349 other than the fourth key group object 8304 is touched, the haptic support module 7670 may perform control to output a fifth haptic information-based haptic feedback guiding to the fourth key group object 8304 corresponding to the same.

Figure 134:
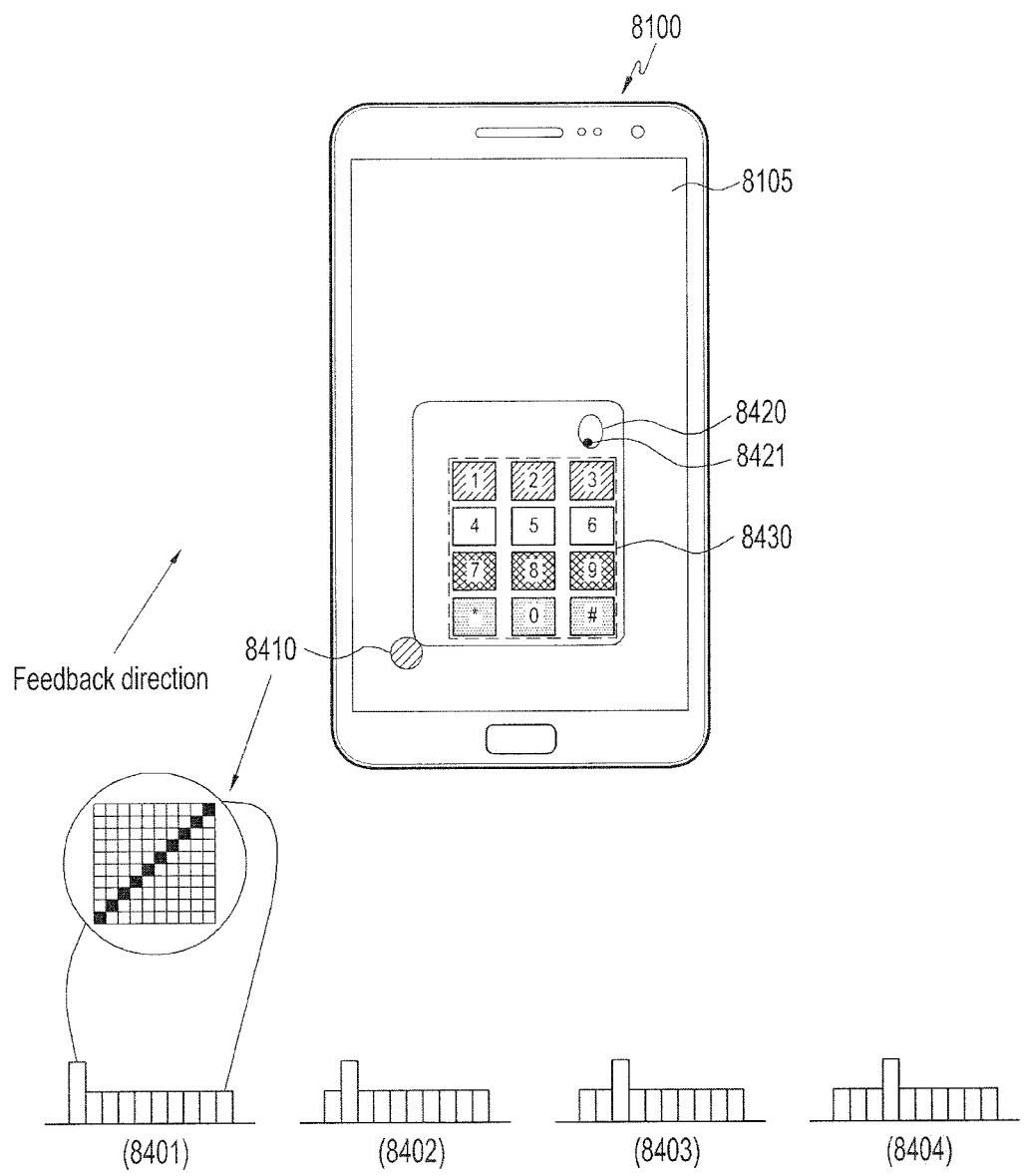

FIG. 134 illustrates a screen interface related to a direction-related haptic information operation according to an embodiment.

Referring to FIG. 134, the haptic support module 7670 may output a numeric key group object 8340. The numeric key group object 8340 may include a plurality of key objects. In case an input occurs in the outside area 8410 of the numeric key group object 8430, the haptic support module 7670 may provide a reference haptic feedback as shown. For example, the haptic support module 7670 may perform control to generate a directional haptic feedback to indicate that the numeric key group object 8430 is present in the upper and right direction in the touched outside area 8410. In this operation, the haptic support module 7670 may perform control to output haptic information having the physical shape deformed using the haptic module including the array pin, piezo element, or tiny vibration element. Or, the haptic support module 7670 may support a directional haptic feedback output in such a manner that, after several vibration elements are arranged at predetermined intervals or at predetermined positions, the vibrations in the necessary direction are left while the remaining vibrations are canceled off. Or, the haptic support module 7670 may provide the haptic feedback gradually varying the position where the positioned finger is stimulated in a capacitive manner, thereby providing a directional tactile fee. States 8401 to 8404 in FIG. 134 are for displaying the pattern of the virtual haptic feedback. As an example, in the case of the piezo element or array pin, the haptic support module 7670 may express the directivity or strength through the variation in physical height based on the position where the elements or pins are arranged. As another example, the capacitive scheme may make the expression through the position and strength of stimulus.

According to an embodiment, the haptic support module 7670 may provide a reference haptic feedback. For example, if the numeric key 5 is the reference area, the haptic support module 7670 may provide the reference haptic feedback upon sensing a hovering or touch input on the numeric key. In this case, the haptic support module 7670 may perform control to abstaining from providing other haptic feedbacks until a user input occurs in the reference area. For example, upon sensing a user input by a predetermined speed of drag or hovering, the haptic support module 7670 may not provide a separate haptic feedback, but when the user input is positioned on the corresponding key (e.g., numeric key 5), may provide a predetermined reference haptic feedback.

According to an embodiment, he haptic support module 7670 may provide support so that the reference area or key area may be discovered using the directional haptic feedback. For example, in case a touch occurs, the haptic support module 7670 may identify a predetermined size of touch area 8420 as shown. The haptic support module 7670 may allow the haptic feedback to be outputted in the reference area of the touch area 8420 or an adjacent partial area 8421 in the direction of the key area. In this relation, the haptic module may be provided to be able to output the haptic feedback in a matrix pattern to the overall display.

As described above, according to an embodiment, a method for operating haptic information and electronic device supporting the same may set the operation of setting a service mode, the operation of configuring a predetermined layout according to the service mode and arranging components according to the layout, the operation of dividing the components into two or more groups according to the service mode, and the operation of setting a haptic layout setting a different haptic feedback for each group.

According to an embodiment, the device and method may set the operation of sensing occurrence of an input event in an area of the components arranged by the layout and the operation of generating a predetermined haptic feedback corresponding to the haptic layout corresponding to the position where the input event occurs.

According to an embodiment, in the device and method, setting the service mode may be an operation achieved by at least one of inputting a particular key, running an application, or a particular event in the electronic device. The operation of setting the service mode may include the operation of setting at least one of a per-row position notification mode, a per-finger feedback support mode, a numeric key mode by a function key, an upper cap mode, a lower cap mode, a symbol input mode, a QWERTY mode, a T9 mode, a 3×4 key mode, a game mode, a one-hand UI mode, a language mode, a toggle mode, a page turning mode, a 3D interaction mode, a remote controller mode, a time notification mode, a weather notification mode, a bio information notification mode, and a data globe mode.

According to an embodiment, the device and method may further include the operation of determining information on at least one material of at least one component by the service mode and the operation of setting a haptic feedback corresponding to the material information.

According to an embodiment, the device and method may include the operation of differentiating the components according to the attribute or content of the components. The attribute of the components may include at least one of a virtual texture, hardness, material, temperature, or pattern.

According to an embodiment, the device and method may further include the operation of determining the content of the components and the operation of giving an attribute matching the determined content. According to an embodiment, the device and method may further include the operation of expressing in graphics the components arranged along the layout on the display and the operation of recognizing the motion of the electronic device and changing into its corresponding layout and haptic layout.

According to an embodiment, the device and method may include the operation of setting a boundary area in the haptic layout and the operation of generating another haptic feedback when an input event occurs in the boundary area.

According to an embodiment, the device and method, in case a movement, such as a movement on a plane of a hovering, a flick, or a drag, is steadily generated, may include the operation of providing different haptic feedbacks for the case of passing through the boundary area and the case of moving along the boundary area.

According to an embodiment, the device and method, in case it is generated by a movement, such as a movement on a plane of a hovering, a flick, or a drag and passes through the boundary area by the movement, may provide different haptic feedbacks separately for the operation in which it moves from inside the boundary area to the outside and the operation in which it moves from outside the boundary area to the inside.

According to an embodiment, the device and method, in case an operation and input event of setting a reference area occurs in the haptic layout, may include the operation of setting a directional haptic feedback guiding at least one of the direction or distance from the position where the input event occurs to the reference area.

According to an embodiment, at least one of the strength, pattern, frequency, speed, duration, and display of direction may be differently set depending on the direction or distance between the reference area and the position where the input event occurs in the directional haptic feedback.

According to an embodiment, the operation of configuring the layout may include the operation of gathering input information in the service mode and the operation of analyzing the gathered input information and at least one of the operation of modifying the layout according to the analyzed input information or the operation of varying the designated haptic feedback.

According to an embodiment, the components may include at least one of a key, button, line, menu, image, diagram, letter, character string, symbol, background, and foreground.

According to an embodiment, at least one of the frequency, vibration duration, vibration pattern, vibration strength, vibration directivity, vertical movement height, repulsive force, temperature variation, air pressure, and constant voltage strength of the haptic feedback may be defined differently.

According to an embodiment, in the device and method, the haptic feedback may include at least one of a vibration, frequency, electrostatic force, heat absorption, heat generation, suction force, jet force, vertical mechanical movement, horizontal mechanical movement, electromagnetic force, and piezo element deformation stimulating at least one of Meissner's corpuscle, Pacinian corpuscle, Merkel's disk, or Ruffini's Ending.

According to an embodiment, the operation of setting the haptic layout may include the operation of separating the components of the layout into haptic components and the operation of setting a different haptic feedback for each separated haptic component.

According to an embodiment, the device and method may further include the operation of resetting at least one of a predetermined reference or more of width, size, area, and volume in case at least one of the area, width, size, and volume of the haptic component is not more than a designated value.

According to an embodiment, the device and method may include the operation of sensing an input mode of the input event, the operation of generating a first haptic feedback in case the input event is a first input mode, and the operation of performing at least one of inputting the information corresponding to the corresponding component or running the corresponding function in case the input event is a second input mode.

According to an embodiment, the device and method may include the operation of outputting the second haptic feedback in case the input event is the second input mode. The first haptic feedback may differ from the second haptic feedback.

According to an embodiment, the device and method may set a particular input mode according to at least one of the condition where the input signal value of the input event is maintained for a predetermined time within a predetermined area (a partial area of the input device, such as a touch screen or touch pad), the condition where at least one of the shear force, pressure, air pressure, constant voltage, temperature difference, and induced current inputted based on the input device is not more than a designated value, the condition where the area corresponding to the input signal is not more than a predetermined area, the condition where the input means (e.g., one or more of finger, pen, fingertip, joint, palm, rubber, wood, or metal) is of a particular type (e.g., when determined using one or more of the pattern of sound signal or vibration signal by the input means and frequency), the condition where hovering or proximity event occurs, the condition where a predetermined number or more of multi-touch inputs occur, and the condition where the input signal continuously moves like a drag or flick.

According to an embodiment, the device and method may include the operation of identifying the reference area in the haptic layout in case the particular input mode is terminated and a predetermined input is sensed within a predetermined time, the operation of identifying the reference area in the haptic layout, the operation of identifying the position where the input signal is generated, the operation of generating a particular haptic feedback in case the input signal is generated in the reference area, and the operation of deactivating to prevent generation of a haptic feedback set in the haptic layout in case the position where the input signal is generated is not in the reference area.

According to an embodiment, the device and method may include the operation of releasing the reference mode if the input signal remains in the reference area for a predetermined time or more after the haptic feedback is generated in the reference area.

According to an embodiment, the device and method may include the operation of simultaneously providing at least one of a sound, audio, and voice feedback along with the haptic feedback.

According to an embodiment, in the device and method, the layout, component, and the haptic layout may be a two-dimensional or three-dimensional object.

According to an embodiment, the device and method may further include the operation of sensing the size of the area where the input signal is generated based on the layout and the haptic layout, the operation of determining the type of the input object based on the size, the operation of modeling the shape of the input object, the operation of determining whether the input object can come in virtual contact with the component of the layout in the virtual physical space based on the layout of the area where the input signal is generated, the operation of determining the area where the virtual contact occurs and other area, and the operation of setting a haptic layout for the area where the virtual contact occurs and the other areas by the result of the determination.

According to an embodiment, the operation of setting the haptic layout may further include the operation of abstaining from providing a haptic feedback for the area where the virtual contact does not occur or providing another haptic feedback.

According to an embodiment, the device and method may further include the operation of previously generating a predetermined haptic feedback according to the haptic layout corresponding to the component if the input signal is generated adjacent to the component on the route where entry is predicted within a predetermined distance in case a variation in the position of input by a flick, hovering, or drag is generated on the display by a predetermined speed or more.

According to an embodiment, the device and method may include the operation of maintaining the haptic feedback generated by the user input signal related to some component in case the input position variation is generated by a predetermined speed or more by a flick, hovering, or drag, and terminating the haptic feedback when the user input signal departs from the component area by a predetermined distance or more. The component has virtual depth or height information, and according to an embodiment, the device and method may further include the operation of adjusting the haptic feedback attribute of at least one of the strength of the haptic feedback, frictional force, and resistant feel based on the haptic layout configured by the depth or height.

According to an embodiment, the device and method may further include the operation of maximally or minimally adjusting the haptic feedback attribute after a predetermined time or distance passes from the virtual vertex or lowest point of the component in case the input position variation is generated by a predetermined speed or more by a flick, hovering, or drag.

According to an embodiment, the device and method may include the operation of applying the haptic feedback by applying the haptic feedback attribute reversely before performing the operation of maximally or minimally adjusting the haptic feedback.

FIG. 135 illustrates a screen interface related to a remote control-related haptic information operation according to an embodiment.

Referring to FIG. 135, the haptic support module 7670 of the electronic device 8100 may perform control to output the control object 8510 on the display 8105 corresponding to running a particular function as shown. The control object 8510 may include at least one object. According to an embodiment, the haptic support module 7670 may assign different haptic information to the outside area and inside area of the control object 8510. For example, the haptic support module 7670 may assign the first haptic information to the inside area 8511 of the control object 8510. The haptic support module 7670 may assign the second haptic information to the boundary area 8512 of the power source object included in the control object 8510. The haptic support module 7670 may assign the third haptic information to the inside area 8513 of the power source object. The third haptic information may be, e.g., non-directional haptic feedback.

According to an embodiment, the control object 8510 may include a direction object 8515. The haptic support module 7670, when the event selecting the direction object 8515 occurs, may perform control to output the haptic feedback pattern in the order of 8501, 8503, 8505, and 8507 in the direction object area for the direction object 8515 to indicate right directivity as shown. For example, when a selection event (e.g., one or more input signal of the touch signal, hovering signal, or touch drag signal) is sensed from the direction object 8515 area, the haptic feedback indicating the right directivity may be outputted to the area where the signal is generated (e.g., the contact area of the input object generating the touch signal and the direction object area). As an example, if an input signal is generated from the area (touch screen or touch pad) of the input device corresponding to other direction object, the haptic support module 7670 may perform control to output the directional haptic feedback corresponding to the indication of the direction of the object.

According to an embodiment, the control object 8510 shown in FIG. 135 may be an object corresponding to a TV remove controller. Accordingly, the haptic support module 7670 may support different haptic feedbacks for several buttons or key areas constituting the remote controller UI. For example, the haptic support module 7670 may assign the first haptic information to the area, such as the power or OK button. The haptic support module 7670 may assign the second haptic information or abstain from assigning separate haptic information to the area where no keys are arranged. The haptic support module 7670 may assign the haptic information having a directional haptic feedback to objects requiring the indication of the directivity, e.g., objects related to changing channel or volume.

According to an embodiment, if a finger touches the directional object 8515 area, the haptic support module 7670 may perform control to provide a haptic feedback according to running the first input mode and maintain the touch, and if a predetermined time elapses, change the channel or volume according to running the second input mode. Here, if a movement occurs in the first input mode or second input mode, the haptic support module 7670 may provide support to change into the discovery mode to determine the position of each key object through the haptic feedback.

According to another embodiment, upon sensing an input signal with a predetermined strength or less (e.g., a touch signal or hovering signal with a strength less than a designated strength) in the directional object 8515 area, the haptic support module 7670 may provide a haptic feedback according to running the first input mode, and upon sensing a signal with a predetermined input signal strength or more (e.g., an input signal having a strength not less than the designated strength), may perform control to change the channel or volume according to running the second input mode. Here, upon sensing the shift in position of the input signal (e.g., the touch drag signal or hovering movement signal moving while hovering) in the first input mode or second input mode, the haptic support module 7670 may provide support to change into the discovery mode to determine the position of each key object through the haptic feedback.

As described above, according to an embodiment, the device and method may perform the operation of communicating signals for remote control by being connected with the external device wirelessly or wiredly, and here, the electronic device may have a touchscreen-type display having the haptic module and display a graphic user interface for controlling multimedia on the touchscreen. The graphic user interface may have at least one graphic element indicating the directivity and may include the operation of setting first haptic information having a particular directivity on an area where the graphic element is displayed and the operation of outputting the haptic feedback corresponding to the first haptic information if sensing the first user input in the area where the graphic element is displayed.

According to an embodiment, the device and method may include the operation of transferring a control signal to the external device (e.g., one or more of the TV, smartphone, audio device, and AV device) wirelessly or wiredly (e.g., one or more of IrDA, Wi-Fi, Bluetooth, Li-Fi, LTE, 2G, or 3G) if the second user input is sensed in the area where the graphic element is displayed.

According to an embodiment, in the device and method, the function of controlling the multimedia may include at least one of channel up/down, volume up/down, and rewind/fast forward. For example, the control object 8520 shown in FIG. 135 may be an object for controlling a multimedia function. Accordingly, the haptic support module 7670 may support different haptic feedbacks for at least one button or key area constituting the multimedia control UI. For example, the haptic support module 7670 may assign the first haptic information to the play and pause icon area 8523. According to an embodiment, the haptic support module 7670 may assign the second haptic information to the boundary area 8522 of the play and pause icon area 8523. At this time, if necessary, the first haptic information and the second haptic information may be assigned to output different haptic feedbacks. As another example, the haptic support module 7670 may assign the third haptic information indicating left directivity to the Rewind icon area 8524 and the fourth haptic information indicating the right directivity to the Fast forward icon area 8525. According to an embodiment, the control object 8520 may assign the fifth haptic information to the background area 8521 other than each icon area. According to an embodiment, content display information (e.g., at least one of audio content information or video play screen or image lookup screen) may be displayed on the background area 8521.

According to an embodiment, the haptic support module 7670 may analyze the content displayed on the background area 8521 and assign the fifth haptic information related to the content. For example, the haptic support module 7670 may parse the song title "Under the sea" displayed on the background area 8521 and then may recognize the parsed words are words related to water through character recognition. The haptic support module 7670 may select water-related haptic information and assign as the fifth haptic information. For example, the fifth haptic information may be haptic information providing a sticky or moist texture.

The haptic support module 7670 may use at least one of character recognition, handwriting recognition, and image recognition schemes to analyze the content and may perform content analysis through analysis of the content-related metadata (e.g., one or more of ID3Tag of music content, EXIF of JPEG file, caption information of video, and subtitle information of music).

According to an embodiment, the content analysis may be processed by the haptic support module 7670. According to an embodiment, the haptic support module 7670 may transfer the content or keywords or sentences to the remote device (e.g., at least one of the server, smartphone, wearable device, laptop computer, or PC) wiredly or wirelessly and receive the result of the analysis by the remote device, thereby setting the haptic information according to the analysis of content. In this operation, the haptic support module 7670 may store the content analysis result and its corresponding haptic information in the memory in association with each other. If the new content analysis result is gathered, the haptic support module 7670 may set the assignment of haptic information according to the result of content analysis based on the associated haptic information stored in the memory.

According to an embodiment, the device and method may include the operation of outputting a haptic feedback corresponding to the second haptic information upon sensing a user input in the boundary area having a predetermined size and surrounding the area where the graphic element is displayed.

According to an embodiment, the device and method may include the operation of providing a haptic feedback different from the first haptic information upon sensing a user input in an area other than the area where the graphic element is displayed.

FIG. 136 is a view related to a virtual key button-related haptic information operation according to an embodiment.

Referring to FIG. 136, according to an embodiment, the electronic device may provide a surface texture of the physical keyboard in the operation of operating the virtual keyboard. For example, as shown in 8610 of FIG. 136, the traverse section of the physical keyboard may have a flat or concave surface where the finger contacts at the top of the key. Further, 8620 of FIG. 136 shows the shape of the longitudinal section of the physical keyboard. Such structure is for further reducing typing errors considering the movement direction and contact position of the fingers.

The electronic device may allow the virtual keyboard to simulate a similar texture to that of the physical keyboard, and as shown in 8630 of FIG. 136, may thus provide different haptic feedbacks to the key boundary area 8631 and the key inside area 8632, respectively, configuring the particular virtual keyboard 8634 of the virtual keyboard. According to an embodiment, upon sensing an input, such as placing a finger on the boundary area or hovering on the boundary area, the haptic support module 7670 may provide the first haptic feedback corresponding to the first haptic information, and otherwise, may provide the second haptic feedback corresponding to the second haptic information. For example, the haptic support module 7670 may provide a haptic feedback in relation to sensing the boundary line.

In one embodiment, if the area where the input is sensed includes the boundary area, it may provide the first haptic feedback. In another embodiment, in case the ratio in size of the key boundary area 8631 to the input-sensed area is a predetermined reference or more or less, or in case the distance between the center of the input-sensed area and the key boundary area 8631 is within a predetermined distance, it may determine that the boundary area is sensed. The haptic support module 7670 may simultaneously provide different haptic feedbacks respectively for both the key boundary area 8631 and the key inside area 8632 in the input-sensed area, and it may determine whether the key boundary area 8631 is sensed according to a predetermined reference and may accordingly provide only one feedback.

The first haptic feedback may differ from the second haptic feedback in at least one of the frequency, vibration duration, vibration pattern, vibration strength, vibration directivity, height, repulsive force, temperature, air pressure, and constant voltage strength. According to an embodiment, the haptic support module 7670 may provide the first haptic feedback allowing a predetermined strength or more strength or rough material to be felt in the key boundary area 8631 and may provide the second haptic feedback allowing a silky material or a predetermined strength or less to be felt in the key inside area 8632. As another example, the haptic support module 7670 may use a frequency stimulating Meissner's corpuscle or Pacinian corpuscle to implement the first haptic feedback and a frequency stimulating Merkel's disk to implement the second haptic feedback. In this case, the haptic support module 7670 may provide support so that the user feels as if he runs his finger on an edge with a tiny protrusion on its surface or the user may relatively easily fee a vibration based on the first haptic feedback. The haptic support module 7670 may provide support allowing the user to feel a tiny pressure distribution on the touched surface based on the second haptic feedback. According to an embodiment, the haptic support module 7670 may provide a frequency of 5 Hz to 400 Hz to Ruffini's ending so that he feels as if he rubs the surface or feels skin pulled in or out.

According to an embodiment, when an event occurs in the key boundary area 8631, the haptic support module 7670 may provide the first haptic feedback, and when an event occurs in the key inside area 8632, it may provide the second haptic feedback. When an event occurs in the key outside area 8633, it may provide the third haptic feedback. For example, the haptic support module 7670 may perform control so that the outside area 8633 outputs the third haptic feedback with a predetermined value or less of strength, the first haptic feedback has the predetermined value or more, and the second haptic feedback has an intermediate strength of value. According to an embodiment, the haptic support module 7670 may continuously vary the strength or frequency of haptic as well as providing a predetermined strength of haptic feedback per divided area. The haptic support module 7670 may perform control to output the haptic feedback according to continuously varying frequency or vibration strength in relation with the feel of a bend in the key inside area 8632.

The third haptic feedback for the outside area 8633 positioned at each edge may have different configurations in the area provided and the increase/decrease in the frequency or strength of the feedback. According to an embodiment, the haptic support module 7670 may set the key boundary area 8631 related to the haptic feedback to be broader than the displayed GUI area.

The layout for the virtual keyboard may include various components, such as keys, a keyboard background image, letters, virtual keyboard boundary line, boundary line of each key, letters, numbers, symbols, or diagrams on the keys. Its corresponding haptic layout may be the haptic component having the same area as the component of the layout or may differ. Here, the haptic support module 7670 may divide one key into the key inside area 8632, the key battery 8631, and the outside area 8633 and may divide them into different haptic components. According to an embodiment, for the area corresponding to the various components displayed together in the key inside area 8632, it may be designated as another haptic component.

According to an embodiment, the haptic support module 7670 may set the fourth haptic information in the area of particular keys, e.g., F and J keys, frequently used as the initial position of the finger. The fourth haptic information may be information allowing the shape of a protrusion or depression to be felt or corresponding to a haptic feedback represented using a particular vibration pattern, directivity of vibration, temperature difference, air pressure, or height or movement direction of array pin.

According to an embodiment, the haptic support module 7670 may assign various haptic information and output haptic feedbacks corresponding to the black keys of a piano. Further, the haptic support module 7670 may support the assignment of haptic information and provision of haptic feedbacks in relation to a method for expressing the position and vibration forms of the strings of a string instrument. For example, the haptic support module 7670 may make such a setting that the first haptic information corresponding to the sixth string of a guitar provides a stronger haptic feedback than the second haptic information assigned to the first string.

According to an embodiment, in case a haptic module capable of force feedback is provided (e.g., one or more of the scheme capable of varying the height and vibration feedback by a plurality of piezo elements, an electromagnet scheme, and an array pin scheme), the haptic support module 7670 may provide repulsive force-related haptic feedbacks. In this operation, the haptic support module 7670 may provide force feedbacks fitting the repulsive force coefficient of the physical keyboard, such as mechanical, membrane, or pentagraph type. Additionally or alternatively, the haptic support module 7670 may provide a silky, rough, or other tactile texture by adjusting the frequency or the number of vibrations to provide a form combined with the force feedback.

FIG. 137 is a view illustrating a page shifting-related haptic information operation according to an embodiment.

Referring to FIG. 137, according to an embodiment, the haptic support module 7670 may provide a UI effect, such as natural page turning, through the page turning effects (PTE). In this operation, the haptic support module 7670 may provide a particular haptic feedback corresponding to the shape of turning pages by the GUI. According to an embodiment, the display 8105 of the electronic device 8100 may output a layout object 8701 representing the shape of pages before turned as in state 8710. Further, the display of the electronic device may output a layout object 8702 representing the shape of pages that are turned as in state 8720.

In the case of turning pages of a physical paper book, page turning is done by pulling an edge of the page by a finger. At this, the piece of paper is bent inwards, and the finger contacts the back side of the piece of paper. In such operation, since the finger comes in contact with the edge of the piece of paper, the user has a rough feel, and if contacting the page when turning pages, the user has a smooth peel of the piece of paper. To respond to this, the haptic support module 7670 may perform control to output the first haptic feedback providing a relative rough or hard feel corresponding to the first event 8711 of contact through touching or touching and dragging the edge or corner of the book. As in states 8720 and 8730, corresponding to the page being rolled inwards so that the finger slides and contacts the backside of the piece of paper, the haptic support module 7670 may perform control to output the second haptic feedback having one or more of a vibration, frequency, electromagnetic movement, mechanical movement, and air pressure giving a relatively weak or smooth feed corresponding to the second event 8721. The haptic support module 7670 may abstain from providing a separate haptic feedback when the page is fully turned as in state 8740.

According to an embodiment, while the page is bent by the user's input (e.g., touch drag event) corresponding to the first event 8711, the haptic support module 7670 may differently output at least one of the strength or degree of roughness or output duration of the first haptic feedback (e.g., larger or smaller than the prior one) based on at least one the travel distance of the user input or position on the page or duration of the first event. Based on this, the haptic support module 7670 may express the physical phenomenon that paper has a repulsive elastic force (or repulsive force or elastic force) gradually increasing while being bent. For example, when the page is bent by the user's touch drag event, the haptic support module 7670 may make settings so that the strength or degree of roughness may be maximized immediately the first event 8711 changes into the second event 8721. The degree of increase may be set to increase first-order linearly or in a logarithm function or exponential function manner.

FIG. 138 is a view illustrating a page edge folding-related haptic information operation according to an embodiment.

Referring to FIG. 138, in case the first event (e.g., the event occurring in the edge area of the displayed page) generated by the user input moves on the touch panel (e.g., moves inwards of the page), the haptic support module 7670 may perform control to output at least a portion of the page (e.g., a right edge of the page) to be bent from state 8751 up to state 8758. In this operation, the haptic support module 7670 may perform control to output different haptic feedbacks corresponding to the degree of being bent from state 8751 to state 8758. For example, while at least a portion of the page is bent from state 8751 to state 8757, the haptic support module 7670 may perform control so that at least one of the strength or degree of roughness of the first haptic feedback increases and may determine state 8758 where the vertex and edge of the page are not included in the position of the user input as a variation in the input event to provide the second haptic feedback. Since state 8757 indicates that the vertex or edge is included in the area or position where the user input event occurs and is right before being off to state 8758, the haptic support module 7670 may perform control to output a haptic feedback that has a maximum value in at least one of the rough texture feel or strength.

Although in FIGS. 137 and 138, the example has been described in which the corner of the page is bent and turned so that the backside is shown, the corner of the page may be turned reversely so that the page is bent to form a convex shape, and the page is turned by the elastic force of the convex shape.

According to an embodiment, in FIG. 137, the haptic support module 7670 may provide a predetermined first haptic feedback when the first event 8711 occurs at the position of the edge of the page firstly turned, and in order to simulate the elasticity, the haptic support module 7670 may provide a haptic feedback that gradually increases the rough feel while the second 8721 of dragging with the tip of the page held, it may allow the rough feel to have a predetermined value or more when the page is finally flipped off (e.g., the time when the first event switches into the second event).

According to an embodiment, the operation of simultaneously turning several pages and the haptic feedback may also be supported. For example, the haptic support module 7670 may generate the first event 8711 by the first user input on the edge of one page of FIG. 137, increase the number of pages to be turned according to the duration of the first event 8711, and accordingly provide various haptic feedbacks. For example, when a touch hold event occurs on the edge of one page, the haptic support module 7670 may output the first haptic feedback, if the touch hold event is maintained within a predetermined distance from the point where the event first occurs, measure the touch duration (Td=Tn−T) of the time (Tn) of occurrence of the last touch hold event among one or more touch hold events generated after the touch hold event occurrence time (T), and if it is the same or larger than predetermined duration (e.g., a predetermined time Tm), output the second haptic feedback and initialize as T=Tn. If Td is smaller than Tm, it does not update T, and updates the occurrence time of a new touch hold event generated after Tn with Tn to thereby measure Td. At this time, the second haptic feedback may be the same as the first haptic feedback or may be one obtained by varying the attribute of the first haptic feedback (e.g., one or more of strength and vibration duration).

As another example, the second haptic feedback may be outputted whenever the touch signals are continuously generated within an area with a predetermined range including the edge of one page. Thereafter, when a page turning operation (e.g., touch drag or flick) occurs, the haptic support module 7670 may perform control to increase the number of pages turned, and corresponding to the increased number of pages, may output the third haptic feedback (e.g., an increase in the texture roughness or vibration strength according to the number of pages). According to the above example, whenever the touch hold is maintained on one edge of page, the user may detect the increase in the number of pages to be turned or increasing pages by the second haptic feedback, and upon performing the operation of simultaneously turning pages by a touch drag, the haptic support module 7670 may output the third haptic feedback different form when turning one page, allowing the user to experience various haptic feedbacks.

The determination of the area of the component where the user input (e.g., the first event 8711 or second event 8721) is sensed may be performed based on at least one of identifying a predetermined point on the input device (e.g., touch screen) area where the user input signal is sensed, identifying the component occupying in a largest ratio the area where the input signal is sensed, identifying the component close to a predetermined point on the input device area where the user input signal is sensed, identifying the component occupying in a largest ratio any area including a predetermined point on the input sensing device area where the user input signal is sensed, and the case where at least a portion of a particular component is present on the area where the input signal is sensed. Although the boundary area is simply one line, in case it is present in the area for sensing the input signal, with its portion covered by the finger, the haptic support module 7670 may generate a haptic feedback for the boundary area.

FIG. 139 is a view illustrating a page flipping-related haptic information operation according to an embodiment.

Referring to FIG. 139, as shown in state 8771 to state 8777, the haptic support module 7670 may display in such a manner that a page is slid on its subsequent page with its vertex or edge pressed, and in case the touch event 8711 by the finger departs from the vertex or edge of the turning page, the page is flicked over by the elastic force of the page being bent. In this operation, the haptic support module 7670 may provide the touch object generating the touch event 8711 with a haptic feedback corresponding to the texture corresponding to the surface of the subsequent page. Further, the haptic support module 7670 may adjust the strength of the resistant feel provided to the touch object generating the touch event 8711 corresponding to the variation in the degree of the turning page being bent. For example, the haptic support module 7670 may perform control to output the haptic information corresponding to the maximum resistant fee from the point of the touch event 8711 in state 1375 of the turning page. The haptic support module 7670 may remove the resistant feel-related haptic elements in state 8777.

According to another embodiment, if such touch event 8711 occurs as to move the right portion of the right page displayed on the display to the left page area while pressed by the touch object (e.g., touch drag event), the haptic support module 7670 may display the pages so that the right page is rolled convexly so that the right edge of the right page is positioned on the left page area. If such touch event 8711 occurs as to stop moving under such situation, take off the touch object or quickly move in a different direction (e.g., the right direction) than the previous movement direction at a speed larger than a predetermined speed, the haptic support module 7670 may display so that the rolled page turns over to the left.

In another embodiment, upon receiving such a touch event (or hovering event) 8711 that the touch object selects a page on the display to move and then stops moving, and under the situation, it moves slowly in a different direction from the prior movement direction at a speed less than the predetermined speed (a designated speed or less), the haptic support module 7670 may control the display so that the rolled page is restored to the right as it originally used to. According to an embodiment, upon receiving the touch event 8711 that, while turning pages by the user input, the movement stops and the hand is touched off or it moves in a different direction than the previous one, the haptic support module 7670 may display so that the page is turned over or comes back to the original state depending on the position of the touch event in the page area or travel distance according to the previous movement operation of the event. For example, if such touch event 8711 occurs where the right edge area of the right page is selected by the finger and is moved to the left, and the finger is then off when not exceeding ½ of the width of the right page, the haptic support module 7670 may display so that the page returns to the original state. According to an embodiment, if such touch event 8711 occurs where the finger is off after moving ½ or more to the left, the haptic support module 7670 may display so that the page is over to the left. Corresponding to the above-described display operation, the haptic support module 7670 may provide at least one haptic feedback or a haptic feedback with a gradually varying strength or strength to the point where the touch event 8711 or a predetermined range from the point. As described above, according to an embodiment, the device and method may include the operation of setting a first layout where visual components of a page are arranged, the operation of setting a first haptic layout setting at least one haptic feedback according to the area of the visual components constituting the first layout of the page, the operation of sensing a first user input, and the operation of outputting the predetermined first haptic feedback according to the area of components where the first user input is sensed.

According to an embodiment, the device and method may include the operation of sensing a second user input of moving a predetermined distance or more from the position where the first user input occurs and the operation of sensing a variation in position according to the same.

According to an embodiment, the device and method may include the operation of setting a second layout in which the first layout is transformed to represent the page shape according to the second user input, the operation of setting the second haptic layout according to the second layout, and the operation of outputting the predetermined second haptic feedback according to the area of the components where the second user input is sensed.

According to an embodiment, the device and method may include the operation of setting a boundary area including at least a portion of at least one area of upper, lower, left, right edge, or vertex area of the page in the first layout in the area as the haptic component of the first haptic layout.

According to an embodiment, the device and method may further include the operation of varying the attribute of the first haptic feedback or setting one or more of the second haptic feedback or third haptic feedback when the first user input is sensed in the area including at least a portion of the boundary area and predetermined duration elapses.

According to an embodiment, the device and method may further include the operation of making a setting to increase the number of pages turned by a page turning effect as the first user input is sensed in the area including at least a portion of the boundary area, and predetermined duration elapses.

According to an embodiment, the device and method may include the operation of setting a boundary area including at least a portion of at least one area of upper, lower, left, right edge, or vertex area of the page in the second layout in the area as the haptic component of the second haptic layout.

According to an embodiment, the device and method may include the operation of determining whether the second user input is sensed in the area including at least a portion of the boundary area and the operation of generating different second haptic feedbacks for the boundary area and not.

According to an embodiment, in the device and method, the second haptic feedback may further include the operation of making a setting to increase the number of pages turned by a page turning effect as the second user input is sensed in the area including at least a portion of the boundary area, and predetermined duration elapses.

According to an embodiment, the device and method may further include the operation of including and varying at least one of the frequency, vibration duration, vibration pattern, vibration strength, vibration directivity, vertical movement height, repulsive force, temperature variation, air pressure, and constant voltage strength of the second haptic feedback, according to the number of pages.

According to an embodiment, in the device and method, the electronic device may be a touchscreen-equipped electronic book reader.

FIG. 140 is a view related to a haptic information operation according to input information according to an embodiment.

Referring to FIG. 140, according to an embodiment, the first external device 9001 may be connected with the first electronic device via a local network, such as Bluetooth or Wi-Fi, and the first electronic device 9000 may be connected with the second electronic device 9004 via a wideband network 9062, such as GSM, CDMA, 4G, or 5G. In the above-described structure, the electronic devices and external devices may support touch input and haptic feedback output. According to another embodiment, the first external device 9001 may be connected with the first electronic device via the wideband network 9062. According to another embodiment, the first electronic device 9000 may be connected with the second electronic device 9004 via the wireless local network.

According to an embodiment, if a user input (e.g., one or more touch input, touch drag, hovering, and touch hold) event occurs in the first external device 9001, the first external device 9001 may recognize the input object, detect haptic information corresponding to the input object and input gesture, and transfer the same to the first electronic device 9000. The first electronic device 9000 may output the received haptic information. Or, the first electronic device 9000 may transfer the received haptic information to the second electronic device 9004. The second electronic device 9004 receiving the haptic information may output a haptic feedback corresponding to the haptic information. Or, the second electronic device 9004 may transfer the haptic information to the second external device 9002. The second external device 9002 may output a haptic feedback according to the received haptic information.

According to an embodiment, if a particular message is created by a finger while calling another person using the electronic device, the created message may be transmitted to the other electronic device and its corresponding haptic information transmission may be supported. At this time, if the input means is not the finger but a pen, haptic information may be transmitted that has a smaller strength of vibration pattern in a narrower area than the finger. For example, if the text "I love you" is inputted to the first electronic device or the first external device 9001 by the pen, the text may be written on at least one of the second electronic device 9004 or the second external device 9002 while a haptic feedback according to the haptic information corresponding to the input means may be outputted. In this operation, the text writing and the haptic feedback output may be synced with each other.

In one embodiment, at least one of the first electronic device 9000, the second electronic device 9004, or the external device 9001 or 9002 may set haptic information providing different haptic feedbacks depending on the gesture related to the input information inputted, input strength, input position, input speed, input area, and input means. For example, at least one of the first electronic device 9000 or the second electronic device 9004 may differently set the haptic information according to at least one of the haptic information corresponding to a knock using the finger joint, the position of rubbing or holding with the finger, and the strength of holding. For example, the first electronic device 9000 having a pressure sensor or touch sensor (e.g., capacity or resistive membrane sensor) in its bezel may determine the strength of the user holding the electronic device with the area, pressure, or capacitance of the touch. Based on this, upon sensing the input signal by the gesture input on the touchscreen, the first electronic device 9000 may transfer the strength of holding and gesture-related information to the second electronic device 9004. The second electronic device 9004 receiving at least one the strength information or gesture-related information may provide, as the haptic information, information related to at least one of the haptic feedback having the strength proportional to the holding strength information or a predetermined haptic feedback corresponding to the gesture information.

According to an embodiment, the transferred haptic feedback-related information may be played through the haptic module of the second electronic device 9004 or the second external device 9002. For example, the haptic feedback corresponding to the haptic information may be outputted through at least one haptic module disposed on the back surface of the second external device 9002. According to an embodiment, the haptic feedback corresponding to the haptic information may also be outputted through the haptic playing device integrated with the front-side display device.

FIG. 141 is a view related to a haptic information operation according to clock function execution information according to an embodiment.

Referring to FIG. 141, according to an embodiment, the haptic support module 7670 of the electronic device 9100 may perform control to output time information on a display 9105 area as in state 9110. If a touch event (e.g., one or more of touch down, touch up, touch drag event or touch hold event) or hovering event occurs on a predetermined area of the electronic device 9100, the haptic support module 7670 may output the haptic feedback information corresponding to the time. As in state 9110, the electronic device may display the time information using a minute hand and hour hand or numbers.

The haptic support module 7670, if a designated event occurs, may obtain current time information. The haptic support module 7670 may perform control to output the haptic feedback corresponding to the particular haptic information at the position corresponding to the current time information. For example, the haptic support module 7670 may perform control to output the first haptic feedback corresponding to the minute hand area 9122 and the second haptic feedback corresponding to the hour hand area 9121 as in state 9120. For example, upon sensing a touch or hovering on the hour hand area 9121, the haptic support module 7670 may provide the second haptic feedback, and upon sensing a touch on the minute hand area 9122, it may provide the first haptic feedback. Since the hour hand area 9121 is smaller in length and area than the minute hand area 9122, the hour hand area 9121 and the minute hand area 9122 may be easily differentiated by the discovery mode. In this operation, the haptic support module 7670 may output the haptic feedback having directivity to provide support for easily recognizing the time.

According to an embodiment, the haptic support module 7670 may perform control to output different first haptic feedback and second haptic feedback on the hour plate 9131 and minute plate 9132 of the dial area 9103 as in state 9130. In this operation, the haptic support module 7670 may provide the second haptic feedback at a larger strength or at a larger degree of roughness than the first haptic feedback, providing support allowing for more intuitive distinction. Or, the haptic support module 7670 may apply different sizes to the haptic feedback areas of the dial area 9103. For example, the haptic support module 7670 may set the hour plate 9131 to be relatively larger in area than the minute plate 9132 and provide a designated haptic feedback to the overall set area or only a portion of the area where the touch occurs.

According to an embodiment, the haptic support module 7670 may perform control to output a haptic feedback on the bezel 9104 area corresponding to the positions of the hour hand and minute hand as in state 9140. For example, the haptic support module 7670 may perform control to output the first haptic feedback to the hour hand indication bezel area 9141 of the bezel area 9104. The haptic support module 7670 may perform control to output the second haptic feedback to the minute hand indication bezel area 9142 indicated by the minute hand.

In the above-described examples, the haptic support module 7670 may sequentially provide the haptic feedbacks to the hour hand area and minute hand area or the dial area. Based on this, the haptic support module 7670 may support easier distinction when the hour hand overlaps the minute hand.

In the above-described embodiments, the haptic feedback is provided in the first input mode or discovery mode (e.g., a mode in which the haptic feedback is provided only in the hour and minute hand area upon movement by a touch and drag or hovering, or a directional haptic feedback is provided for the area other than the hour and minute hand area) and may perform the operation of varying the time in the second input mode. Further, in the first input mode or discovery mode, the display may remain in the power saving mode or screen lock mode where it does not turn on. To that end, in case the proximity of an approaching object is within a predetermined reference through the sensor hub supporting low power driving in the electronic device or an input occurs in the touch sensing device while the screen on key is not pressed in the screen off state, it may be automatically set to the first input mode or discovery mode. Further, another haptic feedback may also be provided to the boundary area of each area. According to an embodiment, corresponding to the occurrence of a designated particular event, the electronic device may provide the time information based on the haptic feedback while keeping the display in the turn-off state (e.g., maintaining the sleep mode or the state in which only the light emission part of the display is off). Accordingly, the user may identify the time information based on the haptic feedback without identifying the display. Examples of the particular event may include at least one event of occurrence of a touch hold event in the electronic device (e.g., the display area or touchable bezel area), sensing a motion signal by the movement of the electronic device (e.g., motion signal with a predetermined strength or more gathered by the acceleration sensor or gyro sensor embedded therein), and sensing the approach of the object by the proximity sensor (e.g., the state in which the distance between the particular object and the display of the electronic device is within a predetermined distance).

FIG. 142 is a view related to an external environment and per-healthcare function-related execution information haptic information operation.

Referring to FIG. 142, according to an embodiment, the electronic device 9200 may provide a haptic feedback related to identifying at least one of weather, moisture, temperature, and bio information. In this operation, the haptic support module 7670 may represent the service-related information in a slide bar or grid-type layout. Or, in case a touch (e.g., one or more of touch down, touch up, touch drag event, or touch hold event) or hovering event occurs on the bezel or screen, the haptic support module 7670 may provide a haptic feedback to a particular area (e.g., the touchscreen or area which contacts the user's body), providing support so that a relative ratio or degree of a particular item of the service information may be identified through the relative position. According to another embodiment, the haptic support module 7670 may transfer the relative ratio or degree of the particular item corresponding to the area where the event occurs through at least one of the strength, frequency, or directivity of the vibration on the entire electronic device rather than the particular area.

As in state 9210, the electronic device 9200 may output at least one of weather variation, moon variation, temperature variation, or moisture variation, together with the first haptic feedback on the bar-type area of the display 9205 that may output a predetermined haptic feedback (e.g., the first haptic feedback). In this operation, the haptic support module 7670 may output the first haptic feedback corresponding to the position or number of marks 9211 arranged in each information bar. Accordingly, the user may grasp the relative ratio of the particular service information through the position or number of the marks 9211. The haptic support module 7670 may perform control to output different haptic feedbacks between the bar areas where the marks 9211 are displayed.

According to an embodiment, as in state 9220, the electronic device may represent four images for the type of weather from clear to rainy to display the weather information and highlight the image corresponding to the current weather. According to an embodiment, the electronic device may provide support allowing the weather of several local areas to be shown simultaneously by providing the weather information-related images along with several local information. According to an embodiment, the electronic device may provide support to output a plurality of images corresponding to daily per-hour weather variations or weekly weather variations.

In order to obtain such location information-based weather information, the electronic device may gather location information and based on this may search and obtain the weather information through the network 9062. For example, the electronic device may recognize the location of a local area where the user is currently in through the GPS sensor or wireless signals from the bio signal and receive the weather information on the corresponding local area through a remote server or other electronic device connected via a wired or wireless network. The electronic device may display the weather information hourly on the day or per date.

In this operation, upon sensing a designated input on the weather area displayed on the touch-based display, the haptic support module 7670 may provide a particular haptic feedback to provide support so that the user may easily identify weather even without viewing the display. The haptic support module 7670 may provide support to provide different haptic feedbacks for the boundary areas of the image areas and to recognize the relative position at which the input-sensed area is located on the display.

In state 9220, some images show a ratio as per current clearness. The haptic support module 7670 may provide support to differentiate clearness areas based on the first haptic feedback. The haptic support module 7670 may provide support to provide the second haptic feedback to the bar area 9221 at the lowermost boundary area of the clearness area for easier identification of the clearness ratio. Further, the haptic support module 7670 may also provide another haptic feedback to the bar area 9221 at the lower side of the boundary area.

According to an embodiment, the haptic support module 7670 may provide different haptic feedbacks depending on the content information as in state 7670. For example, the haptic support module 7670 may provide haptic feedbacks with different tactile feels in the respective weather display areas 9222. By doing so, the haptic support module 7670 may provide support allowing today's or weekly weather forecast to be identified even without viewing the display. The haptic support module 7670 may provide a haptic feedback corresponding to the display area where the event occurs. If weekly weather or hourly weather of the day is shown, the haptic support module 7670 may not provide a haptic feedback for other dates or times but provide a haptic feedback only for the weather display area 9223 corresponding to the current time or date. Or, the haptic support module 7670 may provide a predetermined haptic feedback corresponding to today's weather or current time in the touchscreen area where the user input occurs regardless of the weather area. For example, if it is clear, the haptic support module 7670 may provide a haptic feedback of a smooth or silky texture when a particular event occurs on the display. If it is overcast or the probability of rainfall is a predetermined value or higher, the haptic support module 7670 may provide a haptic feedback of a sticky or rough feel while varying the strength, speed, or pattern. In this operation, the haptic support module 7670 may express more or less of clouds or high or low probability of rainfall by making the degree of tactile feel or texture different.

According to an embodiment, in case it is windy by a predetermined strength or higher, the haptic support module 7670 may provide its strength and direction through a directional haptic feedback (e.g., a haptic feedback having a direction, speed, and strength). According to an embodiment, the haptic support module 7670 may provide the directivity of the haptic feedback from the upper and left side to the lower and right side, corresponding to the direction of the wind. The haptic support module 7670 may provide haptic feedbacks corresponding to various shapes of winds corresponding to the speed and strength of the wind. According to an embodiment, the haptic support module 7670 may provide the haptic feedback with a particular tactile feel or texture only in case the user input occurs in a particular highlighted area or in an entire area other than the slide bar.

According to an embodiment, as in state 9230, the haptic support module 7670 may perform control to gather execution information related to the healthcare function and output this on the display or bezel while outputting particular haptic information. For example, the haptic support module 7670 may perform control to output designated haptic information related to the target value and current exercise load. In this operation, the haptic support module 7670 may output different haptic feedback information depending on the strength of the achievement. Further, the haptic support module 7670 may perform control to provide the haptic feedback through the haptic module disposed in the display or output through the haptic module disposed in the bezel. According to an embodiment, in case the achievement ratio by the exercise load is 50% of the target value, the haptic support module 7670 may perform control to output the haptic feedback corresponding to the achievement ratio 50% in the six o'clock area 9231 of the bezel. In case the achievement ratio by exercise is 50% of the designated target value, the haptic support module 7670 may output the haptic feedback (e.g., the same or different type of feedback from that for achievement ratio 50%) corresponding to achievement ratio 75% in the nine o'clock area 9233 of the bezel. When the user's body contacts a particular point in the bezel area (e.g., the bezel point corresponding to the achievement ratio), the haptic support module 7670 may perform control to give a feedback only for the corresponding area or output a corresponding haptic feedback to the entire electronic device.

FIG. 143 illustrates a per exercise speed-related execution information haptic information operation among health coaching functions according to an embodiment.

Referring to FIG. 143, the electronic device 9300 may be in the state of being able to be worn on the user, e.g., as in state 9310. The electronic device may set an exercise load corresponding to the user input control and represent its corresponding current achievement in a haptic feedback. According to an embodiment, the electronic device may output at least one type of haptic feedback at a particular position of the bezel according to the current achievement. Accordingly, the user may easily recognize the current achievement based on the type and occurrence position of the haptic feedback. In the case of running an application setting an exercise load and coaching, the electronic device may recognize the user's motion and accordingly provide a haptic feedback.

The electronic device shown in state 9310 may include a bio information sensor device (e.g., one or more of photoplethysmography (PPG) sensor, pulse wave sensor, electrocardiogram (ECG), sleep sensor, brain wave sensor, EMG sensor, blood sugar sensor, and cholesterol sensor) capable of recognizing bio information corresponding to one or more of the user's hear rate, blood pressure, heart rate variability (HRV), accelerated plethysmo (APG), blood vessel aging degree, oxygen saturation, blood sugar, heart-lung sound, skin resistance, EMG, ECG, gait, cholesterol, brain wave, or body temperature. Further, the electronic device may include a motion sensor device capable of recognizing the user's position, direction, or motion, such as acceleration sensor, GPS, gyro sensor, geo-magnetic sensor, or digital compass. The electronic device may provide a service, such as user healthcare, exercise coaching, sensing degree of sleep, or stress care, based on one or more of the bio or movement information sensed by the above-described sensor devices.

According to an embodiment, the electronic device may control the operation of sensing the body attached state or worn state based on the above-described sensor devices, and if determined to be in the body contacting state or body worn state, may control the operation of assigning haptic information. The operation of sensing the body contacting state or worn state may be determined by analyzing the characteristics of the bio signal when the electronic device is worn based on the bio sensor. For example, the electronic device may determine, as the normal wearing state, when including at least one of the state in which the DC component of the optical signal inputted through the PPG sensor is a predetermined signal strength or more (e.g., not less than a designated signal strength or designated ratio relative to the maximum strength), the state in which the AC component of the sensed PPG signal is a predetermined reference or more (e.g., not less than a designated AC amplitude or designated amplitude ratio relative to the maximum amplitude), the state in which the signal-to-noise ratio (SNR) for a designated period is larger than a designated value, and the state in which a result of comparing the signal pattern (e.g., frequency or period) of sensed bio signal with a designated (e.g., pre-defined or pre-stored) signal pattern is normal (e.g., the state of having the signal pattern designated as normal state).

According to an embodiment, the electronic device may provide various service functions (e.g., one or more of healthcare, exercise coaching, sensing degree of sleep, stress care, and emotion care) as in state 9230 to state 9360. For example, the haptic support module 7670 of the electronic device may perform control to output the screen including the exercise type-related object 9321 and exercise state-related object on the display as in state 9320. In one embodiment, the haptic support module 7670 may assign particular haptic information to the service type-related object 9321. In this operation, the haptic support module 7670 may perform at least one of the operation of assigning the first haptic information to the boundary area 9302 of the service type-related object 9321 or the operation of assigning the second haptic information to the inside area 9301 of the exercise type-related object 9321. According to an embodiment, the first haptic information may differ from the second haptic information.

According to another embodiment, the haptic support module 7670 of the electronic device may assign particular haptic information set to output a haptic feedback corresponding to the occurrence of event in the state where the display powers off or displays no object. For example, according to an embodiment, in case a particular event occurs (e.g., an event generated or received by the electronic device), the electronic device may perform control to output the haptic feedback corresponding to the occurrence of the event without turning on the display, and Accordingly, the user may identify the information corresponding to the occurrence of the event only with the haptic feedback without looking up the display. Examples of the particular event may include at least one of the event that a touch hold event occurs on the display or bezel of the electronic device, the event that a predetermined strength or more of motion signal (e.g., a signal corresponding to a predetermined speed or higher of walking or running) is sensed by one or more sensors of the acceleration sensor, gyro sensor, or GPS embedded therein by the movement of the electronic device, the event of determining whether some object is present within a predetermined distance from the display of the electronic device by the proximity sensor, and the event of identifying the state in which the display is disposed in the direction along which the user cannot view (e.g., at least one of the state in which the display of the watch device worn on the wrist is oriented in the direction of gravity and the state where the user's face or eyes are not recognized by the camera facing in the same direction as the display). Through such operation, the electronic device may support the function of protecting the user's personal information or power control.

According to an embodiment, the haptic support module 7670 of the electronic device may perform control to output the screen including the exercise coaching-related object 9331 as in state 9330. The haptic support module 7670 may assign different haptic information to the boundary area 9302 and inside area 9301 of the exercise coaching-related object 9331. The exercise coaching-related object 9331 may include information guiding to increasing speed. The haptic support module 7670 may make such settings that the haptic feedback corresponding to the exercise coaching-related object 9331 is larger in feedback strength or frequency of occurrence per unit time than haptic feedbacks related to other exercise coaching-related objects. According to an embodiment, the haptic support module 7670 may guide to increasing speed by repeating more patterns (speed-increasing pattern) in the pattern that is less frequent within the same time.

According to an embodiment, the haptic support module 7670 may perform control to output the haptic feedback when the input object, such as the user's finger or palm, covers the display area by a predetermined ratio (e.g., 60%) or more. According to an embodiment, when the event occurs corresponding to the input object contacting at least one area of the boundary area 9302 of the object 9331 and the inside area 9301, the haptic support module 7670 may perform control to output the haptic feedback only in the area where the touch event signal of the input object being contacted is generated. According to another embodiment, when the event occurs corresponding to the input object contacting at least one area of the boundary area 9302 and inside area 9301 of the object 9331, the haptic support module 7670 may perform control to generate the haptic feedback in the boundary area or object area where the contact with the input object occurs.

According to an embodiment, the haptic support module 7670 of the electronic device may perform control to output the screen including the exercise coaching-related object 9341 on the display as in state 9340. The exercise coaching-related object 9341 may provide the same information as the exercise coaching-related object 9331, which may be represented in a different manner. The haptic support module 7670 may assign different haptic information to the arrow inside area 9301 and the boundary area 9302 corresponding to the edge of the arrow of the exercise coaching-related object 9341. According to an embodiment, the haptic support module 7670 of the electronic device may perform control to output the screen including the exercise coaching-related object 9351 on the display as in state 9350. For example, the haptic support module 7670 may detect the travel speed of the electronic device based on the sensor signal provided from the sensor module. Based on the detected travel speed, the haptic support module 7670 may perform control to output the exercise coaching-related object 9351 including the information guiding to maintain the current speed. The haptic support module 7670 may perform control to assign different haptic information to the inside area 9301 and the boundary area 9302 of the exercise coaching-related object 9351. The haptic support module 7670 may abstain from providing the haptic feedback corresponding to the exercise coaching-related object 9351. Or, the haptic support module 7670 may perform control to provide the haptic feedback fitting the current pace (e.g., the exercise speed or walking speed) or generate haptic feedbacks at a predetermined interval.

According to an embodiment, the haptic support module 7670 may perform control to output the exercise coaching-related object 9361 corresponding to the information guiding to reducing speed corresponding to the travel speed of the electronic device on the display as in state 9360. The haptic support module 7670 may perform control to assign different haptic information to the inside area 9301 and the boundary area 9302 of the exercise coaching-related object 9361. The haptic support module 7670 may analyze the user's exercise pattern that is currently generated for outputting a haptic feedback related to instructing to reduce speed and provide a haptic feedback at a slower speed than that, so that the exercise pattern may be synced with the haptic feedback. In case the haptic feedback is disposed on the surface contacted by the user's body, e.g., in case it is positioned on the bottom of the watch device, the haptic support module 7670 may provide a particular haptic feedback using at least one of the haptic strength, pattern variation, directivity, and period.

According to an embodiment, in relation to the exercise coaching guide, the haptic support module 7670 may perform control to increase the frequency of occurrence of per-unit time haptic feedbacks to guide to increasing the exercise speed and decrease the frequency of occurrence of per-unit time haptic feedbacks to guide to reducing the exercise speed. The haptic support module 7670 may provide a predetermined beat feel through the haptic feedback generated at different frequencies depending on the exercise speed. Accordingly, the haptic support module 7670 may guide at least one of the user's exercise speed or form to be assisted by the haptic feedback. Additionally or alternatively, the haptic support module 7670 may provide an audio feedback corresponding to the haptic feedback (e.g., one or more of the user's preferred music or beatbox selected based on the designated music or play history).

According to an embodiment, the haptic support module 7670 may provide guide information or haptic feedback according to an exercise coaching service, such as running or pushup. The electronic device (e.g., the wrist watch-type device) may be equipped with an acceleration sensor, gyro sensor, or heart rate monitoring (HRM) sensor in relation to running pace coaching. The electronic device may sense at least one sensor signal corresponding to the pulse wave from the radial artery or ulnar artery or the user's body motion to obtain bio signal information such as the user's motion or heart rate and may compare it with a predetermined reference value to output information for coaching the user properly for the current context on the display or haptic module.

According to an embodiment, the electronic device may perform control to obtain the user's basic information, such as the user's weight, height, age, and gender according to the user input, and after setting an exercise target according to the user input, provide exercise coaching information according to running a relevant application. The electronic device may provide, as exercise target items, target calorie consumption, securing basal fitness, staying healthy, reinforcing fitness, and reinforcing cardio pulmonary function. If the exercise target items are set, the electronic device may automatically set the user's exercise coaching-related information, such as exercise type, exercise strength, and exercise pace information. According to an embodiment, the electronic device may provide, as the exercise coaching-related information, daily target step count, pace setting information per running time zone, pushup count, and per-fitness exercise type try count.

The electronic device may check the heart rate corresponding to the user's movement information and continuously store the same to form time-series data. The electronic device may analyze the exercise load context thus far based on the time-series data and provide proper information according to the exercise coaching information. The haptic support module 7670 may provide the instruction information for running pace as the designated haptic feedback information while controlling not to output separate exercise coaching exercise on the display. According to an embodiment, the electronic device may provide the haptic feedback corresponding to the motion of the hand wearing the electronic device while running (the action of putting the hand on the screen of the wrist watch device). Here, the electronic device may provide a haptic feedback through the surface of the device contacting the user's wrist.

According to an embodiment, in case the event that runs the exercise coach application before starting exercise occurs, in case the electronic device enters a preset area (detecting the entry into the designated area by analyzing GPS or Wi-Fi signals), or in case the time scheduled for exercise arrives, the electronic device may support the exercise coaching information providing function. In case the exercise coach app is terminated or the exercise load remains below a predetermined value for a predetermined time or longer, or in case the bio signal information with a predetermined value or more is not sensed for a predetermined time or more, if the motion event that the electronic device is separated from the user's body, or the strap release event or the event that detachable sensor device is separated from the connector is gathered, the electronic device may automatically terminate the haptic feedback service.

According to an embodiment, in case the heart rate or body motion pattern information departs from a predetermined area for a predetermined time or more, the electronic device may perform particular information output on the main coaching event on at least one of the display or haptic module. For example, in case the running speed or heart rate is higher or lower than the interval where a predetermined speed is set for a predetermined time or more, the electronic device may perform a particular event alarm. In order to indicate the occurrence of a main event during exercise, the haptic support module 7670 may generate a vibration strong (of a designated strength) enough to attract the user's attention, and if the user places his hand on the display, output the above-described various haptic feedbacks corresponding to the information.

In the case of the haptic feedback with directivity, the haptic support module 7670 may perform processing so that it may also be sensed on an area other than the boundary area 9302. While the directional haptic feedback is provided, other haptic feedbacks may be stopped from being outputted. According to an embodiment, the haptic support module 7670 may perform control to output various haptic feedbacks in a predetermined sequence, sequentially or corresponding to occurrence of an event. Accordingly, the haptic support module 7670 may allow for easier notice for the area where the haptic feedback is first provided and other areas where haptic feedbacks are generated. Further, the haptic support module 7670 may provide support allowing it to be recognized that the haptic feedback may be provided in a predetermined area of the electronic device, or after informing the user that there is information to look up on the entire area, provide relevant information in case the actual touch input is maintained.

As described above, according to an embodiment, the device and method may include the user profile creation operation of receiving at least one of the user's gender, age, height, weight, waist measure, and body condition, the operation of setting an exercise target to coach the user for his exercise, the operation of sensing at least one of the body motion, step count, travel distance, or bio signal information through at least one sensor mounted on the user's body, the operation of computing at least one exercise information of the user's exercise type, exercise load, exercise duration, calorie consumption, heart rate pattern, exercise pace, exercise speed, and exercise distance using at least one of the sensed body motion signal or bio signal, the operation of generating an exercise coaching guide to be provided to the user using the exercise target and exercise information based on the user profile, the operation of setting a haptic feedback based on the generated exercise coach guide, and the operation of outputting the set haptic feedback.

According to an embodiment, the device and method may further include the operation of displaying the generated exercise coach guide on the display.

According to an embodiment, in the device and method, the body condition may include at least one of whether injured or not, whether disabled or not, the portion of the injury or disability, degree of fatigue, work load, eating pattern, and sleep time-related information.

According to an embodiment, in the device and method, the bio signal information may include at least one of blood pressure, pulse wave, brain wave, EMG, heart rate, heart rate pattern, oxygen saturation, and blood sugar.

According to an embodiment, in the device and method, the sensor may include at least one of a gyro sensor, GPS, ECG, ECGs, HRM sensor, hear rate variability (HRV) sensor, two or more acceleration sensors, blood pressure sensor, oxygen saturation sensor, ppg, photoplethysmogram, radial artery sensor, and ulnar artery sensor, and the haptic feedback may correspond to at least one of directivity, pattern, strength, and texture for exercise coaching.

According to an embodiment, in the device and method, the haptic feedback may be outputted when the user input is sensed on the touchscreen. Different haptic feedbacks may be provided for two or more areas.

According to an embodiment, in the device and method, the different haptic feedbacks may include at least one of a haptic feedback corresponding to the boundary area, a haptic feedback corresponding to the coaching information, a directional haptic feedback indicating the coaching information, and a haptic feedback corresponding to the basis area of the progress bar or circular progress bar.

According to an embodiment, in the device and method, upon sensing the user input on the touchscreen, the haptic support module 7670 may enlarge or shrink the area where the haptic feedback is provided to fit the size of the sensed area.

FIG. 144 illustrates a per-stress-related execution information haptic information operation according to an embodiment.

Referring to FIG. 144, the electronic device shown in state 9410 may analyze the bio signal information as in states 9420, 9430, and 9440 to grasp at least one of the degree of sleep or stress and display the same. In the case of stress, the user's stress level may be displayed in a progress bar. In case a user input (e.g., a touch, touch drag or touch hold or hovering) occurs on the area including the progress bar, the haptic support module 7670 may perform control to output haptic feedback information according to the set haptic information. According to an embodiment, the haptic support module 7670 may provide a dot-type haptic feedback corresponding to the scheme of displaying the current level of the maximum level as shown in 9430 of state 9410 to correspond to the Likert-scale scheme. For example, in 9430, the haptic support module 7670 may provide the indication (e.g., up to five levels) that displayable stress level is represented in a predetermined number of levels together with the current stress level through the haptic feedback area.

If the stress level information is derived, the haptic support module 7670 may perform control to output the first fastening brackets based on a predetermined number of haptic feedback areas corresponding to the same. At this time, the remaining haptic feedback areas may maintain the second haptic feedback or may not output haptic feedbacks. The haptic support module 7670 may provide an animation-type representation as in 9440 in order to provide the pattern variation and directivity of the haptic feedback. For example, the haptic support module 7670 may provide a dot-type animation feedback that increase the haptic feedback area from level 0 up to the maximum level over time and then repeats the provision from level 0.

FIG. 145 illustrates a per-deep sleep degree-related execution information haptic information operation according to an embodiment.

Referring to FIG. 145, the electronic device shown in state 9510 may support the display of execution information and output of the haptic feedback according to the same as in state 9520 or 9530. For example, the electronic device may provide information related to the degree of sleep using a circular progress bar. When the circular progress bar is touched, the haptic support module 7670 may provide various haptic feedbacks according to the shape of the circular progress bar. For example, the haptic support module 7670 provides the haptic feedback corresponding to the area 9531 filled by the degree of sleep in the circular progress bar, so that a tactile feel may be provided along the shape by touching the entire corresponding area or progress bar. According to an embodiment, the haptic support module 7670 may perform control to display the degree of sleep corresponding to the percentage in the filled area 9531 in the circular progress bar and to output the first haptic feedback corresponding to the filled area 9531. The haptic support module 7670 may provide the second haptic feedback for the area 9532 for unfilled area in the circular progress bar. The second haptic feedback may differ from the first haptic feedback in texture, strength, pattern, and directivity. The haptic support module 7670 may assign the third haptic feedback to the boundary area 9533 of the circular progress bar. According to an embodiment, the haptic support module 7670 may control an animation-type output providing directivity or particular pattern to the haptic feedback. For example, the haptic support module 7670 may provide information while increasing the haptic feedback area from circular type to arc type in the animation type.

According to an embodiment, the haptic support module 7670 may assign particular haptic information to a relevant object displaying a sentimental state. In this regard, the electronic device may provide the sentimental state information including at least one of anger, hate, grief, joy, reverence, happiness (platonic love, peace, or sense of tie), and romantic love, or excitement or lust. According to an embodiment, the electronic device (e.g., wearable device) may provide arousal level-related information, such as arousal state or excitement state, by analyzing at least one of the PPG signal amplitude, pulse to pulse interval (PPI), and pulse rate variability (PRV) gathered through the equipped PPG sensor. The haptic support module 7670 may set various haptic feedback outputs corresponding to the sentimental level information on the sentimental state. For example, the haptic support module 7670 may provide a designated haptic feedback (or different haptic feedback per state or level) based on at least one of at least one sentimental state or sentimental level amplitude of each sentimental state. According to an embodiment, the haptic support module 7670 may measure the sentimental level for each of a plurality of emotional states and make a setting so that the designated haptic feedback is outputted in the sentimental state corresponding to the largest sentimental level (in this operation, the haptic feedback corresponding to the amplitude of the sentimental level may be outputted). In this operation, the haptic support module 7670 may provide at least one output of visual information or audio information on at least one of the sentimental state or sentimental level of the display of the electronic device. In this connection, the electronic device may provide support to store visual information or audio information corresponding to at least one of the sentimental state or sentimental level and output it corresponding to gathering the information.

In the above description, although the electronic device is the wrist watch-type device as an example, the electronic device may also be a smartphone or wearable computing device. According to an embodiment, the wrist watch-type electronic device may gather bio signal information or transfer processed coaching information to another electronic device via at least one of wired or wireless communication, and the actual information may be outputted through the haptic module and display mounted in the other electronic device. According to an embodiment, the electronic device may be mounted on a body portion, such as the chest, leg, or ear using a belt, strap, or clip, and the body motion or bio information may be obtained from the heart rate or the blood vessel of the leg, foot, or ear.

Although in the embodiments the methods are described in which the haptic feedbacks are generally provided from the same or nearby area of the GUI on the display, the haptic feedbacks may also be provided anywhere in the area where there is touch input regardless of the GUI. For example, in the case of the above-described animation haptic feedback, if the finger touches the touchscreen, the electronic device may perform control so that the haptic feedback may be provided in the display area inside the touched area. For example, the haptic support module 7670 may restrict the area where the circular animation haptic feedback or dot animation feedback to the inside of the touched area. According to an embodiment, upon sensing a sensor signal of covering the entire display with a hand, the haptic support module 7670 may perform control to output a particular haptic feedback also in the overall display area or bezel area. Accordingly, the area where the haptic feedback is provided need not be identical to the GUI (e.g., screen information), and its position and size may be adjusted to fit the sensed touched area.

As described above, the electronic device and method may include the operation of sensing at least one of a body motion or bio signal information through at least one sensor mounted in the user's body, the operation of computing at least one body or sentimental condition information of the user's stress level or degree of sleep using at least one of the sensed body motion signal or bio signal, and the operation of setting a haptic feedback based on the generated physical or sentimental condition information.

According to another embodiment, the electronic device and method may include the operation of determining whether information to be transferred to the user (execution information) has occurred, the operation of setting the type and output oxygen saturation of the first haptic feedback in relation to the information to be transferred to the user, the operation of determining whether it is the condition where the second haptic feedback occurs, the operation of, in case it meets the condition where the second haptic feedback occurs, outputting the second haptic feedback, the operation of sensing a user input at the set output position, and the operation of, if the user input sensed at the set output position meets the first haptic feedback condition, outputting the set first haptic feedback.

According to an embodiment, in the device and method, the condition where the second haptic feedback occurs may include at least one of the case where an input is sensed by the operation of sensing that the user input is generated at the output position of the first haptic feedback, the case where the significance of the information to be transferred to the user is not less than a predetermined value, the case where although a predetermined time or more elapses after the information to be transferred to the user occurs, the user does not look up, and the case where the movement of the electronic device is recognized by the user movement while the information to be transferred to the user is generated but is not looked up.

For example, if the wearable device measures the bio information of the user wearing the bio sensor-equipped wearable device on his wrist and performs an exercise coaching function for running, an over pace occurs, it may set the first haptic feedback to provide a guide instructing the user to slow down the pace. However, if the user does not look up the wearable device (e.g., in case there is no touch event for a predetermined time or the user input to turn on the display is not generated) or the over pace context steadily occurs and lasts for a predetermined time or more, it may output the second haptic feedback (e.g., one or more of haptic feedbacks giving a strong advance to the entire wearable device or accompanied with audio) to alert the user.

According to an embodiment, in the device and method, the condition where the first haptic feedback occurs may include at least one of the case where the user input is generated for a predetermined time or more at the set output position (e.g., one or more of a touch hold or touch drag or keeping hovering) or the case the user input is sensed at the output position after the second haptic feedback is generated.

FIG. 146 is a view related to a per-input object haptic information operation according to an embodiment.

Referring to FIG. 146, as described above in connection with the above embodiments, in the method of inputting information using the touch sensing device, the electronic device may recognize the object performing a touch input and support different haptic feedbacks depending on the type of the object. In relation to the method of recognizing the touch input tool, the electronic device may sense an impact sound or vibration of the surface upon touch, analyze the pattern of the inputted signal, analyze what object has the closest pattern from the previously stored database and analyze it as the object. According to an embodiment, the electronic device may detect patterns with different impact sounds or vibrations according to the nail, knuckle, fingertip, and finger pad area as in state 9610. Further, the electronic device may detect different impact sounds or vibrations for the case 9621 where the touch is made by the finger nail tip or fingertip, the case 9631 where the touch is made by the finger pad, or the case where the two touches are simultaneously made (e.g., touch is made by both the finger nail tip and fingertip (9622) as in state 9620 or 9630. Further, the electronic device may detect different impact sounds or vibrations for the case 9641 where it is touched by the pen tip and the case 9642 where it is touched by a back tip (e.g., wood or rubber material) of the pen as in state 9640.

According to an embodiment, in case the electronic device uses an electronic pen (e.g., stylus pen), the electronic device may assign a unique ID to each pen and may sense the same to determine the type of the input object. To that end, the electronic device may utilize a wireless device, such as rf-id, IrDA, or Bluetooth or saw sensor and may utilize unique serial numbers of unique devices connected wiredly. As described above, in case the electronic device provides haptic feedbacks with different characteristics, such as strength or frequency, depending on the input object, the user may recognize the input object by the haptic feedback.

Further, it may provide the same basic haptic feedback to various input objects so that the user may feel similar haptic feedbacks even though the input object differs. In this operation, the electronic device may provide the same haptic feedback by varying the frequency or vibration strength of the per-input object haptic feedback. Accordingly, according to an embodiment, the haptic information operation method may further include the operation of setting haptic feedback conversion information according to the input means.

As described above, according to an embodiment, the electronic device and method may set the operation of setting haptic feedback conversion information according to the input object, the operation of configuring a predetermined layout and arranging components according to the layout, the operation of sensing that an input event is generated in the area of the components arranged by the layout, the operation of sensing the input means, the operation of setting the haptic feedback conversion information according to the input means, and the operation of setting the haptic feedback converted using the feedback conversion information according to the haptic layout corresponding to the position where the input event occurs.

According to an embodiment, the input means may include the operation of determining at least one of a knuckle, fingertip, finger nail, pen tip, pen, and a blunt portion of the data glove.

According to an embodiment, the device and method may include the operation of buffering the impact sound or vibration generated when the input means contacts the input sensing device in the memory through the sound input device or vibration input device in order to sense the input means, the operation of analyzing the buffered impact sound or vibration to generate and store a unique identification pattern, and the operation of comparing the inputted identification pattern with a pre-stored identification pattern to determine that it is the object having the closest pattern.

According to an embodiment, the device and method may include the operation of assigning a unique ID to at least one wireless signal of rf-id, IrDA, or Bluetooth or saw sensor or the operation of assigning a unique identifier to a wiredly connected input means and determining the same in order to sense the input means.

According to an embodiment, the device and method may further include the operation of identifying an external device to transfer the converted haptic feedback information and the operation of transmitting the converted haptic feedback information to the external device using at least one wireless network of Wi-Fi, Bluetooth, Zigbee, ieee802, Li-Fi, and BLE.

According to an embodiment, the device and method may further include the operation of setting different haptic feedbacks depending on the gesture, input strength, input position, input speed, and input area inputted by the determined input means.

The electronic device may be at least one of a smartphone, tablet PC, laptop computer, PMP, wrist watch, necklace, belt, shoe, cap, glasses, or HMD.

FIG. 147 is a view related to a per-touch area haptic information operation according to an embodiment.

Referring to FIG. 147, states 9710 and 9730 show embodiments of feedback provision area for the finger contact surface. For example, when the virtual key is pressed on the touchscreen of the tablet PC or smartphone placed on the floor by a finger, the haptic support module 7670 may perform control to provide a haptic feedback to the same or substantially similar area to the finger contact area as in state 9710 and provide a haptic feedback only to a portion of the contact area as in state 9730.

State 9720 shows an example of the contact surface of the finger in the physical keyboard. The physical keyboard is shaped so that its top is high and its bottom is low, and the keys arranged therein are shaped to have the surface inclined according to keyboard angles. Accordingly, the finger surface contacting a key is positioned closer to the fingertip area rather than the finger pad as compared with state 9710 where the hand contacts the plane.

The haptic support module 7670 may provide a haptic feedback to a relatively upper end area in the area where the input object contacts the electronic device in order to provide the user with such a tactile feel as if the electronic device is inclined at a predetermined angle with respect to the ground even when it is disposed horizontally to the ground as in state 9730. Accordingly, the haptic support module 7670 may output a haptic feedback to the fingertip area rather than the actual contact surface to provide such feel as to use the physical keyboard. According to an embodiment, the haptic operation method by the haptic support module 7670 may set the operation of setting a virtual slope of the virtual keyboard, the operation of adjusting the shape and position of the contact area according to the slope, and the operation of setting a haptic feedback in the adjusted contact area. According to another embodiment, the haptic operation method may set the operation of previously designating and storing one or more of a predetermined relative area, position, ratio, and shape where the haptic feedback is to be set, the operation of determining the contact area, and the operation of designating the type of the haptic feedback and the area where the haptic feedback is to be set based on the determined contact area. According to an embodiment, the haptic operation method may perform processing so that in relation to determining the direction of the fingertip, among input event areas generated from the layout of the virtual keyboard, the high-slope direction (e.g., the direction with a high slope with respect to the ground in the electronic device having a predetermined slope or the area of the upper end portion of a particular virtual keyboard area included in the virtual keyboard) may match the fingertip direction.

According to an embodiment, the haptic support module 7670 may detect the inclined angle of the electronic device using the gyro sensor or acceleration sensor. The haptic support module 7670 may adjust the area where the haptic feedback is outputted in the touch area corresponding to the inclined angle. For example, the haptic support module 7670 may perform control to output the haptic feedback in a position leaning towards the edge of the touch area corresponding to the inclination of the electronic device.

FIG. 148 is a view related to detecting a touch area and a haptic information operation according to the same according to an embodiment.

Referring to FIG. 148, according to an embodiment, the electronic device may include at least one key object 9821, 9823, and 9825 arranged on the display panel outputting screen information on the display area, at least one or more touch elements respectively mapped or included in the key objects 9821, 9823, and 9825, and at least one optical sensor 2211 disposed between the touch elements. The touch elements may be arranged to be mapped to the key objects 9821, 9823, and 9825. At least one optical sensor 9811 may be disposed between the boundary areas of the touch elements arranged in a matrix or slip form. According to an embodiment, the optical sensor 9811 may be disposed in a matrix or slit form in the boundary areas of the touch elements arranged in the matrix or slit form. The drawing shows a portion of the optical sensor 9811. The electronic device may include an image processing module gathering image information obtained by the optical sensor 9811 and capable of processing the gathered image information. The image processing module may be disposed to be included in, e.g., the haptic support module 7670, an application processor (AP), or a call processor (CP). According to an embodiment, the image processing module may be included in the camera module.

According to an embodiment, the electronic device may include a capacitive touch sensor, analyze the distribution of capacitive values by a touch event 9812 inputted to each cell, and recognize that the key area with the broadest capacitive value distribution is selected. Or, the electronic device, when the touch event 9812 occurs, may detect an image of a proximate fingertip using a hovering or embedded optical sensor LCD along with the position of the point. According to an embodiment, the electronic device may recognize that the key object in which the image area corresponding to the touch event 9812 overlaps broadest is selected. In this operation, when recognizing the image of the fingertip using the embedded optical sensor LCD, the electronic device may recognize the image by making comparison as to the brightness (strength) of the image area of the fingertip proximate within a predetermined distance. Based on the area corresponding to the recognized image, the electronic device may support the output of the haptic feedback.

According to an embodiment, the electronic device may correct or process erroneous input using the optical sensor 9811. For example, in case the operation processing a particular touch event 9812 input as an erroneous input (e.g., determining it with the frequency of occurrence of the input of the backspace key after a particular key is inputted) steadily occurs, the electronic device may modify at least one of the layout of the key area and the haptic layout. According to an embodiment, if the touch event 9812 occurs between points 9821, 9823, and 9812, the electronic device may analyze the image captured by the optical sensor 9811 and determine that the point where the image is distributed broadest, e.g., point 9812, is selected. Corresponding to this, the haptic support module 7670 may perform control to output a particular haptic feedback based on the haptic information assigned to point 9812.

According to an embodiment, the haptic support module 7670 may provide a predetermined haptic feedback corresponding to the occurrence of an error without modifying the error. Or, the haptic support module 7670 may allow the area of C button corresponding to point 9812 from a GUI perspective momentarily to increase to include the touch point to indicate that C is inputted.

FIG. 149 is a view related to a haptic information operation in virtual reality according to an embodiment.

Referring to FIG. 149, according to an embodiment, the electronic device may include a head mounted display (HID) device 9900 and a data glove 9902. The HID device 9900 and the data glove 9902 may form a communication channel by at least one of wired or wireless communication. For example, the data glove 9902 may provide at least one of its location information or movement information to the HMD device 9900 based on at least one of the acceleration sensor, gyro sensor, and gravity sensor. The data glove 9902 may include a haptic module. The data glove 9902 may include the haptic module including various types of haptic sensors to represent being smooth, degree of roughness, or being silky for virtual objects 9911, 9913, and 9915. The haptic module may be disposed on the finger portion or joint of the data glove 9902 to output the haptic feedback corresponding to the haptic information. Further, the data glove 9902 may include a haptic support module 7670. Or, the data glove may receive haptic information related to driving the haptic module from the HMD device 9900 including the haptic support module 7670 and output at least one of the haptic feedback or force feedback corresponding to the haptic information.

The HMD device 9900 may include a camera and image display device and display the data glove 9902 on the image based on the information provided from the data glove 9902. In this operation, the HMD device 9900 may provide any one of augmented reality or virtual reality. According to an embodiment, the HMD device 9900 may also include a haptic module to output a predetermined haptic feedback.

According to an embodiment, the HMD device 9900 may support the control of the virtual space 9910 by the data glove 9902 in the environment where at least one virtual object 9911, 9913, and 9915 constituting virtual reality (VR) or augmented reality (AR) are arranged on the virtual space 9910. In this relation, the HMD device 9900 may assign at least one haptic information to the virtual objects 9911, 9913, and 9915 arranged in the virtual space 9910. The HMD device 9900 may provide glove virtual objects 9921 and 9923 corresponding to the data glove 9902 on the virtual space 9910. The HMD device 9900 may adjust the position or state of the data glove 9902 on the virtual space 9910 depending on the movement information or state information provided from the data glove 9902. In this operation, the HMD device 9900 may provide a particular haptic feedback output related to at least one of the position or state of the data glove 9902. A plurality of glove virtual objects 9921 and 9923 may be provided corresponding to the number of data gloves 9902. The glove virtual objects 9921 and 9923 may output particular haptic feedbacks independently or in interoperation with each other. For example, in case the glove virtual object 9921 of the glove virtual objects 9921 and 9923 contacts particular virtual objects 9911, 9913, and 9915, the HMD device 9900 may provide the corresponding haptic information to any one side of the data glove 9902 corresponding to the glove virtual object 9921. Or, the HMD device 9900 may also transmit haptic information to all the data gloves 9902.

According to an embodiment, in the environment where there are a plurality of glove virtual objects 9921 and 9923 corresponding to the data glove 9902, in case one glove virtual object 9921 is used to discover the virtual objects 9911, 9913, and 9915, the HMD device 9900 may support a first input mode or discovery mode. For example, the HMD device 9900 may perform control to abstain from running a separate function even when contacting the virtual objects 9911, 9913, and 9915 using the glove virtual object 9921 or even when the glove virtual object 9921 is disposed at the proximate position. In case the glove virtual object 9921 and the glove virtual object 9923 simultaneously overlap a particular virtual object, the HMD device 9900 may perform control to perform a second input mode or function running mode related to the corresponding virtual object. In the above-described operation, the HMD device 9900 may provide particular haptic information to only a side of the data glove 9902 corresponding to the glove virtual object 9921 in the discovery mode using the glove virtual object 9921. According to an embodiment, in relation to the glove virtual object 9923 contacting the virtual object, the HMD device 9900 may support the discovery mode (e.g., a position discovery environment for the virtual object contacted by the glove virtual object or positioned within a predetermined distance). Or, the HMD device 9900 may perform control to operate in the function running mode assigned to the corresponding virtual object in relation to the virtual object contact by the glove virtual object 9923.

The HMD device 9900 may provide a virtual space 9910 including a virtual plane of a (x,y) curved surface where the virtual objects 9911, 9913, and 9115 are arranged. Here, the HMD device 9900 may set the edge of the curved surface to the boundary area. In case the glove virtual objects 9921 and 9923 corresponding to the data glove 9902 departs off the boundary area of the curved surface, the HMD device 9900 may transfer first haptic information to the data glove 9902. In case the glove virtual objects 9921 and 9923 overlap any one of the virtual objects 9911, 9913, and 9915, the HMD device 9900 may transfer second haptic information to the data glove 9902. In this operation, the HMD device 9900 may arrange the plurality of objects 9911, 9913, and 9915 on the virtual space 9910 corresponding to the running function. The HMD device 9900 may assign different haptic information to the virtual objects 9911, 9913, and 9915, respectively. The HMD device 9900 may transfer the haptic information assigned to the virtual objects 9911, 9913, and 9915 overlapping the data glove 9902 to the data glove 9902. The data glove 9902 may output the haptic feedback corresponding to the haptic information assigned to each virtual object 9911, 9913, and 9915.

According to an embodiment, the HMD device 9900 may provide a plurality of virtual spaces 9910. For example, the HMD device 9900 may arrange a plurality of virtual spaces 9910 displayed in one plane to overlap in the z direction. At least one virtual object may be disposed in the plurality of virtual spaces 9910 arranged in the Z direction. Or, there may be a virtual space where no virtual object is present. The HMD device 9900 may control the data glove 9902 so that different haptic feedbacks are provided per virtual space contacted according to the movement of the glove virtual objects 9921 and 9923. The above-described virtual objects 9911, 9913, and 9915 may have a 2D or 3D shape. The virtual objects 9911, 9913, and 9915 arranged on the virtual space 9910 may be represented as any three-dimensional objects, e.g., in various shapes, such as rectangular parallelepiped, sphere, cone, or pyramid, and a portion of the surface of the 3D object may be displayed. The HMD device 9900 may assign the corresponding haptic information per predetermined portion of the virtual objects so that a rough or sharp texture, such as an edge, or the transforming portion may be felt for the virtual objects 9911, 9913, and 9915. For example, the HMD device 9900 may assign the same or different haptic information in units of at least some of vertex, edge, corner, and surface.

The discovery mode or first input mode for searching for the position of the virtual objects 9911, 9913, and 9915 may be executed when the corresponding glove virtual objects 9921 and 9923 move to the data glove 9902 or contact or approach the surface of the virtual objects 9911, 9913, and 9915. The second input mode supporting the execution of function or entry of information related to the virtual objects 9911, 9913, and 9915 may be driven when the contact or approach for the virtual objects 9911, 9913, and 9915 is maintained for a predetermined time or corresponding to a particular movement or state of the data glove 9902. The data glove 9902 may be configured as a wrist watch-type device, and the haptic support module 7670 may be included on the surface contacting the wrist on the bottom surface of the wrist watch or in the display module of the wrist watch.

FIG. 150 illustrates a haptic information operation method related to input error correction according to an embodiment.

Referring to FIG. 150, according to an embodiment, in the error correction-related haptic information operation method, in operation A01, the haptic support module 7670 may run a haptic function corresponding to the occurrence of an event or according to a setting (e.g., the function of assigning and outputting haptic information according to the result of screen information analysis, result of input information analysis, or result of execution information analysis or the function of outputting assigned haptic information).

In operation A03, the haptic support module 7670 may analyze the input information. In this relation, the haptic support module 7670 may analyze the input information inputted through the input/output interface. For example, the haptic support module 7670 may perform spell check on the inputted text information. In operation A05, the haptic support module 7670 may identify whether an error occurs on the input information analysis.

In case an error occurs, in operation A07, the haptic support module 7670 may perform control to output error-related haptic information. In case no error occurs, in operation A09, the haptic support module 7670 may perform control to output input information-related haptic information. In this operation, in case there is no haptic information related to the input information, the haptic support module 7670 may abstain from outputting haptic information.

In operation A11, the haptic support module 7670 may identify whether there is a function termination-related event. In case there is no function termination-related event, the haptic support module 7670 may go to operation A03 to re-perform its subsequent operations. If there is a function termination-related event, the haptic support module 7670 may perform control to terminate the haptic function. Additionally or alternatively, the haptic support module 7670 may perform control to support the execution of a function of the electronic device according to the designated schedule information after terminating the haptic function or shift into the sleep mode.

In relation to the above-described error correction, according to an embodiment, the haptic support module 7670 may perform control to output a particular melody corresponding to input of a key. Accordingly, if the key input speed varies, the haptic support module 7670 may vary the melody accordingly. For example, the haptic support module 7670 may map a piano keyboard for the key input. If a particular key input occurs, the haptic support module 7670 may perform control to output a sound corresponding to the corresponding piano key. The haptic support module 7670 may perform control to accelerate the corresponding melody output as the key input speed increases and decelerate the corresponding melody output as the key input speed decreases. The melody or piano key mapping may be adjusted corresponding to the variation in the user settings.

The haptic support module 7670 may perform control to detect a typing error occurring in the key input process, and if a typing error occurs, analyze the same to provide a sound or melody different from the set melody along with a particular haptic feedback output. The user who conducts key input while listening to at least one of the haptic feedback or audio feedback of a familiar melody may intuitively recognize the occurrence of the typing error through the audio feedback or haptic feedback varied when the typing error occurs. The haptic support module 7670 may support easier typing error recognition or correction by outputting a recommended word for the erroneously typed portion or differentiating the erroneously typed portion from the surrounding input information (e.g., by highlighting).

According to an embodiment, the haptic support module 7670 may perform control to provide at least one of an audio feedback or haptic feedback after the text is complete or after information input to a paragraph or page is complete. For example, if a typing error function runs, the haptic support module 7670 may provide at least one of highlighting, underlining, color changing, or resizing to the word or phrase with an error. In this operation, the haptic support module 7670 may assign particular haptic information to at least one of the erroneously typed sentence, word, or letter. If a touch event or hovering event selecting or indicating the area including the typing error occurs, the haptic support module 7670 may perform control to output a haptic feedback corresponding to the haptic information. In this operation, the haptic support module 7670 may provide a first input mode or discovery mode related to the search for the erroneously typed area (e.g. the paragraph, sentence, or letter with the typing error). The haptic support module 7670 may perform control to output a haptic feedback related to detection of the erroneously typed area in the first input mode or discovery mode. If a set event (e.g., an event maintaining a touch or hovering for a predetermined time or an event corresponding to a particular gesture input) occurs in the erroneously typed area, the haptic support module 7670 may control the switch into the second input mode. If switching into the second input mode, the haptic support module 7670 may perform control to output provide a list of recommended words or output a virtual input object in relation to typing error correction.

Based on the above-described operation, the haptic support module 7670 may easily discover typing errors based on a touch gesture, such as flick, drag, or hovering, on the screen including a number of words. In this connection, the haptic support module 7670 may perform control to provide different haptic feedbacks for the area with the typing error and a typing error-free area and set the circumferential edge of the area with the erroneously typed paragraph or word as the boundary area to output another haptic feedback. If an event (e.g., a touch or hovering event) occurs in a typing error-free area, the haptic support module 7670 may support a directional haptic feedback (e.g., the direction indicating the area where the typing error occurs at the point where the touch occurs) guiding to the position of the typing error.

As described above, according to an embodiment, the electronic device and method may include the operation of configuring a predetermined layout according to a service mode and arranging components according to the layout, the operation of differentiating the components into two or more groups according to the service mode, the operation of setting a haptic layout setting different haptic feedbacks for the groups, the operation of sensing that an input event occurs in the area of the components arranged by the layout, and the operation of generating a predetermined haptic feedback according to the haptic layout corresponding to the position where the corresponding input event occurs.

According to an embodiment, the input is input of letters, and the electronic device and method may set the operation of determining that a character string constituted of at least one character has a typing error or a word not previously set and the operation of adding the typing error or the word not previously set to the layout and haptic layout as a component.

According to an embodiment, the device and method may set the operation of deactivating the haptic feedback for a remaining area other than the area where the typing error or word not previously set is positioned in the haptic layout.

According to an embodiment, the device and method may include the operation of outputting at least one of an audio or variation according to a predetermined haptic feedback order or a predetermined melody order for each character input.

According to an embodiment, the device and method may include the operation of determining that a typing error or word not previously set is inputted in a character string constituted of at least one character in inputting the character and the operation of generating a haptic feedback with a dissonant melody or an inconsistent vibration duration, rhythm or frequency.

FIG. 151 illustrates a screen information-related haptic information operation according to an embodiment.

Referring to FIG. 151, the electronic device A100 may output screen information including at least one object on the display A105. For example, the electronic device A100 may output banner objects or advertisement objects on the layout constituting the screen. The object displayed on the display A105 may include information related to various textures or tactile feels. For example, the object may be in such an image form that information is printed on a sheet of paper or cloth or that information is engraved on a metal or wood plate. The haptic support module 7670 may analyze the above-described image form corresponding to the content information on the object and recognize the same as the material of the object. For example, the haptic support module 7670 may recognize paper material as an electronic book. Here, the haptic support module 7670 may recognize different smooth or rough feels corresponding to the position, area, or image analysis result, corresponding to the paper analysis of the electronic book. The haptic support module 7670 may assign the haptic information corresponding to the analysis result to the corresponding object.

According to an embodiment, in case the object displayed on the display is an advertisement image related to clothes, the haptic support module 7670 may perform recognition of the material of the corresponding object based on the material or description of the clothes. The haptic support module 7670 may assign the corresponding haptic information to the corresponding object based on the recognition of the material. In this operation, the haptic support module 7670 may perform letter parsing and letter analysis on the link information related to a particular object, e.g., the text information or advertisement description information in the form of XML or HTML extracted from the webpage and perform the material recognition on the corresponding object based on the same.

According to an embodiment, the haptic support module 7670 may estimate the touch or feel on the result of search based on the keyword inputted through a search function and information related to the corresponding keyword. For example, in case the name of a beach is searched by the search function, the haptic support module 7670 may assign the texture or tactile feel, such as water or sand related to the beach, to the corresponding search result. The haptic support module 7670 may set or vary the haptic layout on the object by grasping direct or indirect object-related information through an application, document parsing, or image analysis.

According to an embodiment, the haptic support module 7670 may provide at least one of a haptic feedback or visual information feedback corresponding to the keyword search in the document. If a touch event occurs in the touchscreen-type display, the haptic support module 7670 may perform control to output a particular haptic feedback corresponding to the distance between the touch event and the keyword corresponding to the search result based on the discovery mode support. The haptic support module 7670 may perform control to run a function related to the keyword searched corresponding to the occurrence of the event related to at least one of a predetermined strength or more of touch pressure, touch area, touch time, and touch gesture shape. For example, the haptic support module 7670 may automatically transfer the website link related to the selected keyword or corresponding keyword to the search engine.

The haptic support module 7670 may apply the above-described various embodiments to various keywords as shown. For example, in case the keywords are displayed by a word cloud function, the haptic support module 7670 may change haptic feedbacks depending on the significance for each keyword (at least one of the frequency of input of the keyword, time of input, and frequency of showing up). For example, the electronic device may analyze the keywords of at least one document, such as webpage, thesis, patent, speech, or news article to emphasize in color or size and display main keywords according to the use frequency or subject, depending on the designated appropriateness or significance. According to an embodiment, the haptic support module 7670 may assign the information configured to output the designated haptic feedback to the object corresponding to the result of keyword search or inputted keyword.

The haptic support module 7670 may assign particular haptic information to each area where the corresponding keyword is displayed depending on the significance of the detected keywords. For example, the haptic support module 7670 may assign first haptic information to the keyword A110 and second haptic information to the keyword A120. The strength or frequency of the first haptic information or second haptic information may differ corresponding to the significance of the corresponding keyword.

According to an embodiment, the haptic support module 7670 may output the keyword selected through an input, such as a touch input, on the displayed document, based on a text-to-speech (TTS) function. In this operation, the haptic support module 7670 may perform control to output different haptic feedbacks in the boundary areas of the keywords to provide distinctive recognition between the keywords.

According to an embodiment, if the selection of a particular keyword (or selection of an object corresponding to the keyword) occurs through an input signal with a designated time or more, a designated pressure or more, designated touch area or more, or designated electric charge or more, the haptic support module 7670 may perform control to run the function related to the keyword. According to an embodiment, when OK and cancel buttons are shown on the popup window, the haptic support module 7670 may assign different haptic information to the areas respectively corresponding to the buttons. The haptic support module 7670 may support to differentiate the buttons through different haptic information-based haptic feedbacks in the discovery mode. If an input signal related to the selection of a particular button occurs after the discovery mode, the haptic support module 7670 may perform control to run the function assigned to the corresponding button. According to an embodiment, in case the user keeps the electronic device in, e.g., a pocket, the user may differentiate a particular object using a haptic feedback in the discovery mode without pulling out the electronic device. The user may perform control to run a function according to the selection of the object.

According to an embodiment, the device and method may include an input operation for searching for information, and the operation of setting the haptic layout may include the operation of setting the haptic layout so that the haptic feedback occurs in the area of at least one component corresponding to the searched information.

According to an embodiment, the input operation may perform the operation of inputting text through the virtual keyboard or the operation of inputting one or more of a word, keyword, or sentence to be searched for through at least one operation of handwriting recognition on the touchscreen or touchpad or voice recognition.

According to an embodiment, the searched information may include at least one of a character, image, virtual button, menu, or list.

According to an embodiment, the searched information may include at least one of a human face (e.g., a facial image or human silhouette), an animal image, or plant image. As an example, if the name of a particular person is inputted through the input operation while looking up a group picture image including several people, when a touch input signal occurs in the facial area of the corresponding person, the haptic support module may make a setting to provide its corresponding haptic feedback. As another example, in case the person's facial area differs from the area where the touch signal occurs, the haptic support module may make a setting to provide a directional haptic feedback indicating the person's facial area in the area where the touch signal occurs or output haptic feedbacks with different intensities depending on the distance between the two areas. Accordingly, in case the two areas differ, the person's facial area may be easily discovered, and if an input occurs in the facial area, another haptic feedback may be provided.

According to an embodiment, the device and method may include the operation of computing the similarity or reliability with the inputted information upon searching for information and the operation of setting the strength, texture, and pattern of the haptic feedback depending on each similarity in case there are a plurality of searched information. Here, the similarity or reliability may be determined by a word matching ratio between the keyword and searched result. According to an embodiment, the similarity or reliability may be determined by the frequency at which the keyword appears in the search result (e.g., the object corresponding to the search result).

According to an embodiment, it may include the operation of determining the content of the components and assigning the texture appropriate for the area of the haptic layout depending on the content.

According to an embodiment, the layout may include at least one of a document, spread sheet, electronic book, word cloud, or image.

FIG. 152 is a view illustrating a configuration of a system according to an embodiment.

Referring to FIG. 152, the system may include a wearable electronic device A300 and a main electronic device A400. The wearable electronic device A300 means an electronic device (e.g., a smart watch or smart glasses) wearable on the user's body.

The wearable electronic device A300 and the main electronic device A400 may be connected together via a network. For example, the wearable electronic device A300 and the main electronic device A400 may be connected together via Bluetooth. According to an embodiment, the main electronic device A400 may be connected with at least one wearable electronic device A300 (e.g., a plurality of wearable electronic devices) via a network.

According to an embodiment, the setting values of the main electronic device A400 may be varied through the wearable electronic device A300. According to an embodiment, the setting values may include at least one of sound/variation/mute mode setting, notification setting, wireless network setting, screen brightness setting, font size setting, or language setting. For example, the setting values may include a sound/variation mode setting, sound type, sound strength, vibration pattern, whether to receive notification, condition for receiving notification, type of notification to be received, wireless fidelity (Wi-Fi) setting, Bluetooth setting, and global positioning system (GPS) setting.

According to an embodiment, the wearable electronic device A300 may receive user's manipulation to vary the setting values of the main electronic device A400. For example, the wearable electronic device A300 may receive touch manipulation of a designated pattern on the touchscreen. According to an embodiment, the wearable electronic device A300 may provide a UI to vary the setting values of the main electronic device A400. The wearable electronic device A300 may receive the user manipulation through the UI provided through the display. According to an embodiment, the wearable electronic device A300 may provide a UI per type of the setting value. According to an embodiment, the wearable electronic device A300 may provide a UI per electronic device connected via a network.

According to an embodiment, the wearable electronic device A300 may display, on the display screen, an object indicating that the setting values of the main electronic device A400 may be varied. For example, the wearable electronic device A300 may display a main electronic device icon for an item for which the setting value of the main electronic device may be varied on the UI screen (e.g., menu screen) for varying the setting values.

According to an embodiment, the wearable electronic device A300, upon receiving the user manipulation, may transmit a control signal for varying the setting value of the main electronic device A400 to the main electronic device A400.

The main electronic device A400 may vary the setting value according to the control signal received from the wearable electronic device A300. For example, the main electronic device A400 may change the setting value from the sound mode to the variation mode. As another example, the wearable electronic device A300 may vary the setting value to abstain from transmitting the notification information even when a designated event occurs. As another example, the wearable electronic device A300 may vary the setting value to transmit only a portion of the notification information if the designated event occurs.

In the above-described embodiment, although the embodiment has been described in which the setting value of the main electronic device A400 is varied by the user manipulation inputted to the wearable electronic device A300, the setting value of the wearable electronic device A300 may also be varied by the user manipulation inputted to the main electronic device A400.

According to an embodiment, the wearable electronic device A300 and the main electronic device A400 may share setting values. For example, the wearable electronic device A300 may transmit the setting value to the main electronic device A400, and the main electronic device A400 may transmit the setting value to the wearable electronic device A300. According to an embodiment, the wearable electronic device A300 or the main electronic device A400 may transmit the setting value to the main electronic device A400 or the wearable electronic device A300 at a predetermined period or when the setting value is varied.

According to an embodiment, the wearable electronic device A300 and the main electronic device A400 may sync setting values. For example, if the setting values differ, the external device or the main electronic device A400 may sync them with the setting value varied latest. As another example, if differing from the setting value of the main electronic device A400, the wearable electronic device A300 may sync it with the setting value of the main electronic device A400.

According to an embodiment, the main electronic device A400, if connected via the network with a new wearable electronic device, may share the setting value with the new electronic device. According to an embodiment, the electronic device newly connected with the network may sync its setting value with the setting value of the existing electronic device (e.g., the main electronic device A400).

According to an embodiment, if a designated event occurs, the main electronic device A400 may transmit notification information on the event to the wearable electronic device A300. For example, when receiving an SMS message, the main electronic device A400 may transmit notification information on the SMS message to the wearable electronic device A300.

According to an embodiment, the wearable electronic device A300 may sense the user's state and transmit relevant information to the main electronic device A400. For example, the wearable electronic device A300 may sense whether the user sleeps and information on whether he sleeps to the main electronic device A400. As another example, the wearable electronic device A300 may sense whether it is worn by a designated user or other user and transmit to the main electronic device A400.

According to an embodiment, the wearable electronic device A300 may determine the state of the wearable electronic device A300 and transmit to the main electronic device A400. For example, the wearable electronic device A300 may grasp whether to wear, battery state, whether it is being charged, or the current position to the main electronic device A400.

According to an embodiment, the main electronic device A400 may transmit the notification information according to the state of the wearable electronic device A300 or the user's state. For example, if the user sleeps, although a designated event occurs, it may abstain from transmitting the notification information to the wearable electronic device A300. As another example, in case the wearable electronic device A300 is not worn by the designated user, it may abstain from transmitting the notification information. As another example, if the wearable electronic device A300 is being charged, although the designated event occurs, it may abstain from transmitting the notification information to the wearable electronic device A300. As another example, if the current position of the wearable electronic device A300 or main electronic device A400 corresponds to a designated position (e.g., a conference room), it may abstain from transmitting the notification information.

According to an embodiment, the wearable electronic device A300 may display only a portion of the notification information received from the main electronic device A400. For example, in case of receiving the notification information including text and image from the main electronic device A400, the wearable electronic device A300 (e.g., a smart watch) may display only the text. In case the wearable electronic device A300 (e.g., smart glasses) is smart glasses, if receiving the notification information including text and image from the main electronic device A400, it may display only the image.

According to an embodiment, the wearable electronic device A300 may display the entire notification information by the user manipulation while display only a portion of the notification information received from the main electronic device A400. For example, the image and text both together may be displayed by the user manipulation with only the image displayed on the smart glasses.

According to an embodiment, the main electronic device A400 may transmit only a portion of the notification information according to the characteristic of the wearable electronic device A300. The main electronic device A400, if connected with the wearable electronic device A300 via the network (or in the connecting process), may receive device characteristic information (e.g., type of the wearable electronic device or size of display) from the wearable electronic device A300. The main electronic device A400 may transmit only a portion of the notification information according to the device characteristic information of the wearable electronic device A300. For example, the main electronic device A400, if the wearable electronic device A300 is smart glasses, may transmit only the image of the notification information including the text and image. As another example, the main electronic device A400, if the wearable electronic device A300 is smart watch, may transmit only the text of the notification information including the text and image.

The wearable electronic device A300 may display a portion of the notification information received from the main electronic device A400. According to an embodiment, the wearable electronic device A300 may send a request for the overall notification information to the main electronic device A400 according to the user manipulation. The main electronic device A400, when receiving the request for the overall notification information, may transmit the overall notification information to the wearable electronic device A300.

According to an embodiment, the main electronic device A400, in case of being connected with a plurality of wearable electronic devices via the network, may transmit the notification information (the whole or part) depending on priority. For example, the main electronic device A400, in case of being connected with a smart watch (first priority) and smart glasses (second priority), may transmit the notification information to the first priority device, i.e., the smart watch, if a designated event occurs. The main electronic device A400, unless the notification identification information is received from the smart watch for a designated time, may transmit the notification information to the second priority device, i.e., the smart glasses.

FIG. 153 is a view illustrating a method of controlling a system according to an embodiment.

Referring to FIG. 153, the wearable electronic device A300 may receive the user manipulation varying the setting value (A401). For example, the wearable electronic device A300 may receive touch manipulation of a designated pattern on the touchscreen. According to an embodiment, the wearable electronic device A300 may provide a UI to vary the setting values of the main electronic device A400. The wearable electronic device A300 may receive the user manipulation through the UI provided through the display. According to an embodiment, the wearable electronic device A300 may provide a UI per type of the setting value. According to an embodiment, the wearable electronic device A300 may provide a UI per electronic device connected via a network.

According to an embodiment, the wearable electronic device A300 may display, on the display screen, an object indicating that the setting values of the main electronic device A400 may be varied. For example, the wearable electronic device A300 may display a main electronic device icon for an item for which the setting value of the main electronic device may be varied on the UI screen (e.g., menu screen) for varying the setting values.

The wearable electronic device A300, if the user manipulation is received, may transmit control information to the main electronic device A400 (A403).

The main electronic device A400 may vary the setting value according to the control signal received from the wearable electronic device A300 (A405).

The wearable electronic device A300 and the main electronic device A400 may share setting values (A407). For example, the wearable electronic device A300 may transmit the setting value to the main electronic device A400, and the main electronic device A400 may transmit the setting value to the wearable electronic device A300. According to an embodiment, the wearable electronic device A300 or the main electronic device A400 may transmit the setting value to the main electronic device A400 or the wearable electronic device A300 at a predetermined period or when the setting value is varied.

According to an embodiment, the wearable electronic device A300 and the main electronic device A400 may sync setting values based on the shared setting value (A409). For example, if the setting values differ, the external device or the main electronic device A400 may sync them with the setting value varied latest. As another example, if differing from the setting value of the main electronic device A400, the wearable electronic device A300 may sync it with the setting value of the main electronic device A400.

According to an embodiment, the main electronic device A400, if connected via the network with a new wearable electronic device, may share the setting value with the new electronic device. According to an embodiment, the electronic device newly connected with the network may sync its setting value with the setting value of the existing electronic device (e.g., the main electronic device A400).

FIG. 154 is a view illustrating a method of controlling a system according to an embodiment.

Referring to FIG. 154, the wearable electronic device A300 and the main electronic device A400 may be connected via a network (A501). For example, the wearable electronic device A300 and the main electronic device A400 may be connected together via Bluetooth.

According to an embodiment, the wearable electronic device A300 may sense whether the user sleeps (A503). For example, the wearable electronic device A300 may sense whether the user sleeps using a gyro sensor or heart rate sensor. According to an embodiment, the wearable electronic device A300 may transmit the user's sleep state to the main electronic device A400 (A505).

According to an embodiment, if a designated event (e.g., reception of an SMS message) occurs (A507), the main electronic device A400 may determine whether the user is in sleep (A509). If the main electronic device A400 determines that the user is in sleep (Ad509—Yes), the main electronic device A400 may restrict the notification (A511). For example, the main electronic device A400 may abstain from transmitting the notification information to the wearable electronic device A300. If the main electronic device A400 determines that the user is not in sleep (A509—No), the main electronic device A400 may transmit the notification information on the occurring event (A513).

Although in the embodiment described in connection with FIG. 154, the notification information is transmitted depending on whether the user is in sleep, the notification information may also be transmitted based on whether the wearable electronic device A300 is worn, whether it is worn by the designated user, battery state, whether it is being charged, and current position.

FIG. 155 is a view illustrating a method of controlling a system according to an embodiment.

Referring to FIG. 155, the main electronic device A400 may be connected with a plurality of wearable electronic devices A300 via a network (A601). The main electronic device A400 may set priority to the plurality of wearable electronic devices A500 connected via the network. According to an embodiment, the main electronic device A400 may set priority depending on the user manipulation or the characteristics of the wearable electronic devices. If a designated event (e.g., reception of an SMS message) occurs, the main electronic device A400 may transmit notification information according to the priority. For example, the first wearable electronic device may be set with a first priority, and the second wearable electronic device may be set with a second priority. If a designated event occurs (A603), the main electronic device A400 may transmit the notification information to the first wearable electronic device with the first priority (A605).

The first wearable electronic device, if receiving the notification information from the main electronic device A400, may display the notification information on the display screen (A607). According to an embodiment, the first wearable electronic device may display a portion of the notification information received from the main electronic device A400. For example, in case of receiving the notification information including text and image from the main electronic device A400, only the image may be displayed.

According to an embodiment, the first wearable electronic device may display the entire notification information by the user manipulation while display only a portion of the notification information received from the main electronic device A400. For example, the image and text both together may be displayed by the user manipulation with only the image displayed on the smart glasses.

The first wearable electronic device may determine whether the user identifies the notification information (A609). If the user identifies the notification information (A609—Yes), the first wearable electronic device may transmit the notification identification information to the main electronic device A400 (A611).

If a designated time elapses after the notification information is transmitted, the main electronic device A400 may determine whether the notification identification information is received (A613). If the notification identification information is not received (A613—No), the main electronic device A400 may transmit the notification information to the second wearable electronic device with the second priority (A615).

The second wearable electronic device, if receiving the notification information from the main electronic device A400, may display the notification information (A617).

FIG. 156 is a view illustrating a method of controlling a system according to an embodiment.

Referring to FIG. 156, the main electronic device A400 may be connected with the wearable electronic device A300 via a network (A701).

The wearable electronic device A300, if connected with the main electronic device A400 via the network (or in the connecting process), may transmit device characteristic information (e.g., type of the wearable electronic device or size of display) to the main electronic device A400.

If a designated event occurs (A703), the main electronic device A400 may transmit a portion of the notification information to the wearable electronic device A300 (A707). The main electronic device A400, if the wearable electronic device A300 is smart watch, may transmit only the text of the notification information including the text and image. As another example, the main electronic device A400, if the wearable electronic device A300 is smart glasses, may transmit only the image of the notification information including the text and image.

The wearable electronic device A300 may display the notification information received from the main electronic device on the display screen (A709). According to an embodiment, the wearable electronic device A300 may send a request for the overall notification information to the main electronic device A400 according to the user manipulation (A711). The main electronic device A400, when receiving the request for the overall notification information, may transmit the overall notification information to the wearable electronic device A300 (A713). The wearable electronic device A300 may display the overall notification information received from the main electronic device A400 on the display screen (A715).

FIG. 157 is a block diagram illustrating a configuration of a wearable electronic device according to an embodiment. FIG. 158 is a view illustrating an example of receiving a touch input.

Referring to FIG. 157, the wearable electronic device A300 may include an input module A310, a communication module A320, a display A330, a memory A340, a sensor module A350, and a control module A360.

The input module A310 may receive user manipulation. The input module A310 may be implemented as at least one of a touchscreen or touchpad operated by the user's touch input, a key pad or key board with various function keys, number keys, special keys, and character keys, a motion recognition sensor recognizing the user's motion, and a voice recognition sensor recognizing the user's voice.

According to an embodiment, the input module A310 may receive the user manipulation to vary the setting value of the main electronic device A400. For example, the wearable electronic device A300 may receive touch manipulation of a designated pattern on the touchscreen. For example, referring to FIG. 158, the input module A310 may receive touch manipulation in a diagonal direction of the touchscreen. According to an embodiment, the input module A310 may receive the user manipulation through a UI provided through the display A330.

According to an embodiment, the input module A310, if only a portion of the notification information received from the main electronic device A400 is displayed on the display A330, may receive the user manipulation to display the overall notification information.

According to an embodiment, the input module A310, in case only a portion of the notification information is received from the main electronic device A400, may receive the user manipulation to send a request for the overall notification information to the main electronic device A400.

The communication module A320 may be connected via a network with the main electronic device A400 to communicate various information or control signals. According to an embodiment, the communication module A320 may transmit a control signal varying the setting value of the main electronic device A400 to the main electronic device A400 according to the user manipulation inputted to the input module A310. For example, the communication module A320, if the user manipulation shown in FIG. 158 is inputted, may transmit a signal for controlling entry into an anti-disturbance mode (e.g., the mode in which the main electronic device A400 does not transmit the notification information) to the main electronic device A400.

According to an embodiment, the communication module A320 may transmit the setting value to the main electronic device A400 to share the setting value with the main electronic device A400 and may receive the setting value from the main electronic device A400. According to an embodiment, the communication module A320 may transmit the setting value to the main electronic device A400 or the wearable electronic device A300 at a predetermined period or when the setting value is varied.

According to an embodiment, the communication module A320 may transmit the user's state to the main electronic device A400. For example, the communication module A320 may transmit whether the user is in sleep to the main electronic device A400. As another example, the communication module A320 may transmit whether a designated user wears it to the main electronic device A400. According to an embodiment, the communication module A320 may transmit the state of the wearable electronic device A300 (e.g., whether the wearable electronic device is worn, battery state, whether it is being charged, and current position) to the main electronic device A400.

According to an embodiment, the communication module A320 may receive notification information on the event occurring in the main electronic device A400. For example, if the main electronic device A400 receives an SMS message, it may receive the SMS message from the main electronic device A400.

According to an embodiment, the communication module A320, in case only a portion of the notification information is received from the main electronic device A400, may send a request for the overall notification information to the main electronic device A400 according to user manipulation to receive the overall notification information.

According to an embodiment, the communication module A320, if the user identifies the notification information displayed on the display A330, may transmit the notification identification information to the main electronic device A400.

The display A330 may provide a UI for varying the setting value of the main electronic device A400. According to an embodiment, the input module A310 may receive the user manipulation through a UI provided through the display. According to an embodiment, the display A330 may provide a UI per type of the setting value. According to an embodiment, the display A330 may provide a UI per electronic device connected via the network.

According to an embodiment, the display A330 may display, on the display screen, an object indicating that the setting values of the main electronic device A400 may be varied. For example, the display A330 may display a main electronic device icon for an item for which the setting value of the main electronic device may be varied on the UI screen (e.g., menu screen) for varying the setting values.

The display A330 may display the notification information received from the main electronic device A400. According to an embodiment, the display A330 may display only a portion of the notification information received from the main electronic device A400. For example, in case of receiving the notification information including text and image from the main electronic device A400, the display may display only the text. According to an embodiment, the display A330 may display the overall notification information according to the user manipulation.

According to an embodiment, if the wearable electronic device A300 is in the anti-disturbance mode, the display A330 may display, in gray, the information displayed on the display screen. Accordingly, the user may intuitively recognize whether the wearable electronic device A300 is in the anti-disturbance mode.

The memory A340 may store the setting value of the wearable electronic device A300. According to an embodiment, the memory A340 may store the setting value of the main electronic device A400 received from the main electronic device A400.

The sensor module A350 may include various sensors. For example, the sensor module A350 may include a gyro sensor, acceleration sensor, grip sensor, proximity sensor, illumination sensor, and heart rate sensor. The sensor module A350 may be operated under the control of the control module A360 to obtain various sensing values.

The control module A360 may control the overall operation of the wearable electronic device A300. According to an embodiment, the control module A360 may determine the state of the user or the wearable electronic device A300. For example, the control module A360 may determine whether the user is in sleep using the sensing value measured by the heart rate sensor, bio sensor, or gyro sensor. As another example, the control module A360 may determine whether it is worn by a designated user or other user using the sensing value measured by the heart rate sensor or bio sensor. Besides, the control module A360 may determine whether the wearable electronic device A300 is worn, battery state, and whether it is being charged.

According to an embodiment, the control module A360 may sync the setting value with the main electronic device A400. For example, the control module A360, if the setting value of the wearable electronic device A300 differs from the setting value of the main electronic device A400, may sync the setting value of the wearable electronic device A300 with the setting value varied latest. As another example, the control module A360, if the setting value of the wearable electronic device A300 differs from the setting value of the main electronic device A400, may sync the setting value of the wearable electronic device A300 with the setting value of the main electronic device A400.

FIG. 159 is a view illustrating a UI displayed on a wearable electronic device according to an embodiment.

According to an embodiment, the display A330 may display an object (or a UI) indicating that the setting values of the main electronic device A400 may be varied. For example, as shown in FIG. 159(a), the display A330 may display an object B10 indicating that the setting value of the main electronic device A400 may be varied on the menu screen for the setting value. For example, referring to FIG. 159(a), an icon object B10 shaped as the main electronic device A400 may be displayed.

According to an embodiment, the display A330 may provide a UI to vary the setting values of the main electronic device A400. For example, referring to FIG. 159(b), the display A330 may display icons B20 and B30 indicating the wearable electronic device and the main electronic device on the menu screen for the setting value. If the wearable electronic device icon B20 is selected on the menu screen as shown in FIG. 159(b), a menu screen for varying the setting value of the wearable electronic device B20 may be provided. If the main electronic device icon B30 is selected, a menu screen for varying the setting value of the main electronic device shown in FIG. 159(c) may be provided. Referring to FIG. 159(c), the display A330 may display an icon B40 indicating that it is the menu for varying the setting value of the main electronic device.

FIG. 160 is a block diagram illustrating a configuration of a main electronic device according to an embodiment.

Referring to FIG. 160, the main electronic device A400 may include an input module A410, a communication module A420, a display A430, a memory A440, and a control module A450.

The input module A410 may receive user manipulation. The input module A410 may be implemented as at least one of a touchscreen or touchpad operated by the user's touch input, a key pad or key board with various function keys, number keys, special keys, and character keys, a motion recognition sensor recognizing the user's motion, and a voice recognition sensor recognizing the user's voice.

According to an embodiment, the input module A410 may receive the user manipulation to vary the setting value of the wearable electronic device A300. According to an embodiment, the input module A410 may receive the user manipulation through a UI provided through the display A430.

The communication module A420 may be connected via a network with at least one wearable electronic device A300 to communicate various information or control signals. According to an embodiment, the communication module A420 may transmit a control signal varying the setting value of the wearable electronic device A300 to the wearable electronic device A300 according to the user manipulation inputted to the input module A410.

According to an embodiment, the communication module A420 may receive the control signal varying the setting value from the wearable electronic device A300.

According to an embodiment, the communication module A420 may transmit the setting value to the wearable electronic device A300 to share the setting value with the wearable electronic device A300 and may receive the setting value from the main electronic device A400. According to an embodiment, the communication module A320 may transmit the setting value to the main electronic device A400 or the wearable electronic device A300 at a predetermined period or when the setting value is varied.

According to an embodiment, the communication module A420 may receive the user's state from the wearable electronic device A300. For example, the communication module A420 may receive whether the user is in sleep from the wearable electronic device A300. As another example, the communication module A420 may receive whether it is worn by a designated user from the wearable electronic device A300. According to an embodiment, the communication module A420 may receive the state of the wearable electronic device A300 (e.g., whether the wearable electronic device is worn, battery state, whether it is being charged, and current position) from the wearable electronic device A300.

According to an embodiment, if a designated event occurs, the communication module A420 may transmit notification information on the event to the wearable electronic device A300. For example, when receiving an SMS message, the communication module A420 may transmit notification information on the SMS message to the wearable electronic device A300.

According to an embodiment, the communication module A420, if connected with the wearable electronic device A300 via the network (or in the connecting process), may receive device characteristic information (e.g., type of the wearable electronic device or size of display) from the wearable electronic device A300.

The display A430 may provide a UI for varying the setting value of the wearable electronic device A300. According to an embodiment, the input module A410 may receive the user manipulation through a UI provided through the display. According to an embodiment, the display A430 may provide a UI per type of the setting value. According to an embodiment, the display A430 may provide a UI per electronic device connected via the network.

According to an embodiment, the display A430 may display, on the display screen, an object indicating that the setting values of the main electronic device A400 may be varied. For example, the display A430 may display a main electronic device icon for an item for which the setting value of the main electronic device may be varied on the UI screen (e.g., menu screen) for varying the setting values.

The memory A440 may store the setting value of the main electronic device A400. According to an embodiment, the memory A440 may store the setting value of the wearable electronic device A300 received from the wearable electronic device A300. According to an embodiment, the memory A440 may store the user's state or state of the wearable electronic device A300 received from the wearable electronic device A300. According to an embodiment, the memory A440 may store the device characteristic information received from the wearable electronic device A300.

The control module A450 may perform the overall operation of the main electronic device A400. According to an embodiment, the control module A450 may vary the setting value according to the control signal received from the wearable electronic device A300.

According to an embodiment, the control module A450 may sync the setting value with the wearable electronic device A300. For example, the control module A450, if the setting value of the wearable electronic device A300 differs from the setting value of the main electronic device A400, may sync the setting value of the main electronic device A400 with the setting value varied latest.

According to an embodiment, the control module A450 may perform control to transmit the notification information according to the state of the wearable electronic device A300 or the user's state. For example, if the user sleeps, although a designated event occurs, the control module A450 may abstain from transmitting the notification information to the wearable electronic device A300. As another example, in case the wearable electronic device A300 is not worn by the designated user, the control module A450 may perform control to abstain from transmitting the notification information. As another example, if the wearable electronic device A300 is being charged, although the designated event occurs, the control module A450 may perform control to abstain from transmitting the notification information to the wearable electronic device A300. As another example, if the current position of the wearable electronic device A300 corresponds to a designated position (e.g., a conference room), the communication module A420 may perform control to abstain from transmitting the notification information.

According to an embodiment, the control module A450 may perform control to transmit only a portion of the notification information according to the device characteristic information of the wearable electronic device A300. For example, if the wearable electronic device A300 is smart glasses, the control module A450 may perform control to transmit only an image of the notification information including the image and text. As another example, if the wearable electronic device A300 is a smart watch, the control module A450 may perform control to transmit only the text of the notification information including the image and text.

According to an embodiment, the control module A450, in case of being connected with a plurality of wearable electronic devices via the network, may perform control to transmit the notification information (the whole or part) depending on priority. For example, the control module A450, in case of being connected with a smart watch (first priority) and smart glasses (second priority), may perform control to transmit the notification information to the first priority device, i.e., the smart watch, if a designated event occurs. The control module A450, unless the notification identification information is received from the smart watch for a designated time, may perform control to transmit the notification information to the second priority device, i.e., the smart glasses.

FIG. 161 is a view illustrating a UI displayed on a main electronic device according to an embodiment.

Figures 161A, 161B, 161C:
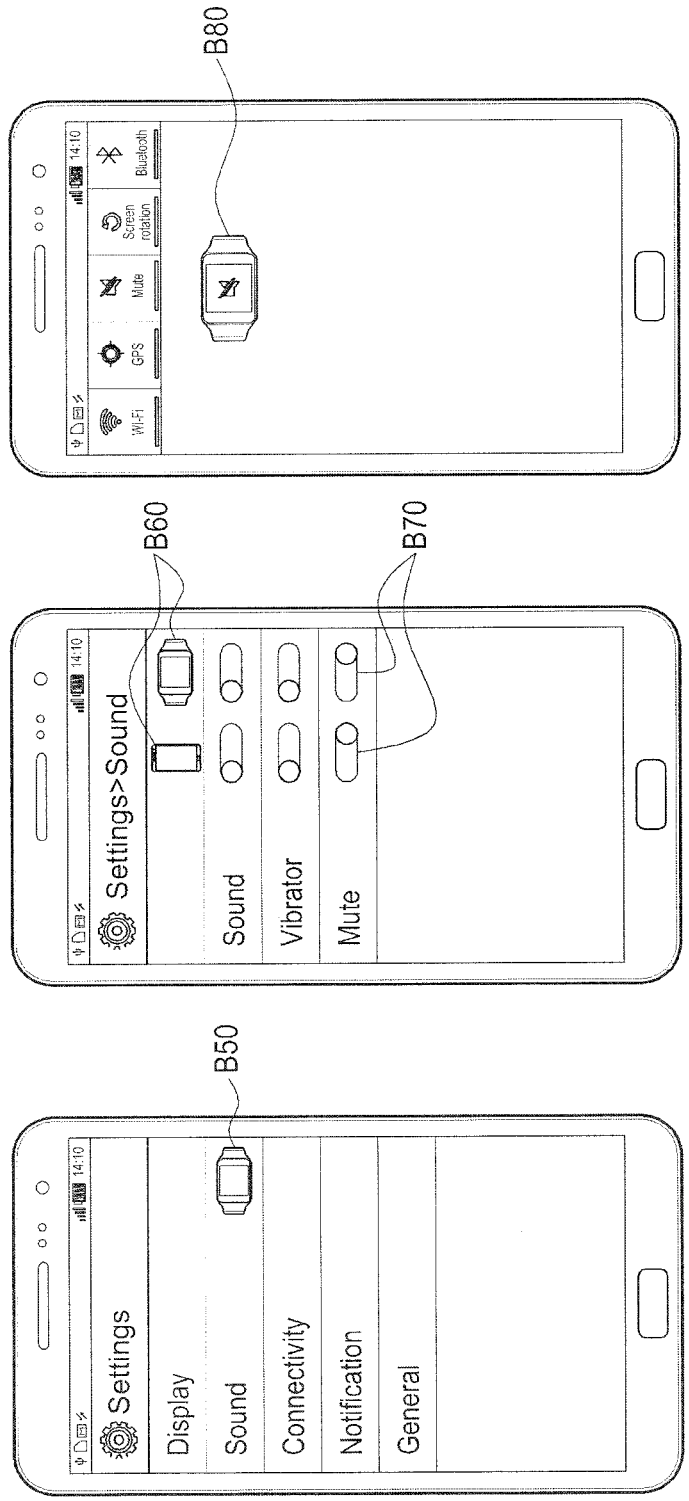

According to an embodiment, the display A430 may display an object (or a UI) indicating that the setting values of the wearable electronic device A400 may be varied. For example, as shown in FIG. 161(a), the display A430 may display an object B50 indicating that the setting value of the wearable electronic device A300 may be varied on the menu screen for the setting value. For example, referring to FIG. 161(a), an icon object B50 shaped as the wearable electronic device A300 may be displayed. The shape of the object B50 may be determined based on the device characteristic information received from the wearable electronic device A300.

According to an embodiment, the display A430 may provide a UI to vary the setting values of the wearable electronic device A400. For example, referring to FIG. 161(b), the display A430 may provide a UI for varying the respective setting values of the wearable electronic device and main electronic device on the menu screen for settings. Referring to FIG. 161(b), if the wearable electronic device icon B20 is selected on the menu screen as shown in FIG. 159(b), a menu screen for varying the setting value of the wearable electronic device B20 may be provided. According to an embodiment, an object B60 for differentiating the wearable electronic device A300 and the main electronic device A400 may be displayed on the menu screen. According to an embodiment, a UI B70 may be provided for varying the setting value for each of the wearable electronic device A300 and the main electronic device A400. According to an embodiment, a UI may be provided to vary the setting value of the wearable electronic device A300 on the menu screen for varying the setting value of the main electronic device A400. For example, referring to FIG. 161(c), a UI B80 may be provided for varying the sound setting of the wearable electronic device on the menu screen for varying the setting value of the main electronic device A400.

FIG. 162 is a flowchart illustrating a method of controlling a wearable electronic device according to an embodiment.

Referring to FIG. 162, the wearable electronic device A300 may receive the user manipulation varying the setting value of the main electronic device A400 (B310). For example, the wearable electronic device A300 may receive touch manipulation of a designated pattern on the touchscreen. For example, as described referring to FIG. 158, the wearable electronic device A300 may receive touch manipulation in a diagonal direction of the touchscreen. According to an embodiment, the wearable electronic device A300 may receive user manipulation through a UI provided on the display screen.

The wearable electronic device A300, upon receiving the user manipulation, may transmit a control signal for varying the setting value of the main electronic device A400 to the main electronic device A400 (B320).

According to an embodiment, the wearable electronic device A300 may transmit the setting value to the main electronic device A400 to share the setting value with the main electronic device A400. The wearable electronic device A300 may receive the setting value of the main electronic device A400 from the main electronic device A400.

According to an embodiment, the wearable electronic device A300 may sync the setting values with the main electronic device A400. For example, the wearable electronic device A300, if its setting value differs from the setting value of the main electronic device A400, may sync it with the setting value varied latest. As another example, if differing from the setting value of the main electronic device A400, the wearable electronic device A300 may sync it with the setting value of the main electronic device A400.

FIG. 163 is a flowchart illustrating a method of controlling a main electronic device according to an embodiment.

Referring to FIG. 163, the main electronic device A400 may receive whether the user is in sleep from the wearable electronic device A300 (B410). If a designated event (e.g., reception of an SMS message) occurs (B420), the main electronic device A400 may determine whether the user is in sleep (B430).

If the user is in sleep (B430—Yes), the main electronic device A400 may restrict the transmission of notification to the wearable electronic device A300 (B440). If the user is not in sleep (B430—No), the main electronic device A400 may transmit the notification information related to the event to the wearable electronic device A300 (B450).

According to an embodiment, the main electronic device A400 may receive whether the wearable electronic device A300 is worn, whether it is worn by a designated user, battery state, whether it is being charged, and current position from the wearable electronic device A300 in operation B410. The main electronic device A400 may determine in operation B430 whether the electronic device A300 is worn, whether it is worn by the designated user, whether it is being charged, and whether the current position is a designated position. The main electronic device A400 may restrict the notification or transmit the notification information to the wearable electronic device depending on the result of determination.

FIG. 164 is a flowchart illustrating a method of controlling a main electronic device according to an embodiment.

Referring to FIG. 164, the main electronic device A400 may receive the device characteristic information from the wearable electronic device A300. If a designated event occurs (B520), the main electronic device A400 may transmit a portion of the notification information to the wearable electronic device A300 (B530). The main electronic device A400, if the wearable electronic device A300 is smart watch, may transmit only the text of the notification information including the text and image. As another example, the main electronic device A400, if the wearable electronic device A300 is smart glasses, may transmit only the image of the notification information including the text and image.

According to an embodiment, the main electronic device A400, when receiving the request for the overall notification information from the wearable electronic device A300, may transmit the overall notification information to the wearable electronic device A300.

FIG. 165 is a flowchart illustrating a method of controlling a main electronic device according to an embodiment.

Referring to FIG. 165, if a designated event (e.g., reception of an SMS message) occurs (B610), the main electronic device A400 may transmit notification information according to the priority. The main electronic device A400 may set priority to the plurality of wearable electronic devices connected via the network. According to an embodiment, the main electronic device A400 may set priority depending on the user manipulation or the characteristics of the wearable electronic devices. For example, the first wearable electronic device A500 may be set with a first priority, and the second wearable electronic device may be set with a second priority. If a designated event occurs (B610), the main electronic device A400 may transmit the notification information to the first-priority wearable electronic device A500 (B620).

If a designated time elapses after the notification information is transmitted, the main electronic device A400 may determine whether the notification identification information is received (B630. The main electronic device A400 may terminate if the notification identification information is received (B630—Yes). If the notification identification information is not received (B630—No), the main electronic device A400 may transmit the notification information to the second wearable electronic device with the second priority (B640).

FIG. 166 is a block diagram B700 illustrating a device management module B701 of an electronic device (e.g., the electronic device 101) according to an embodiment. The device management module B701 may be the additional function module 170 shown in FIG. 51.

Referring to FIG. 166, the device management module B701 may include a receiving module B710, an identifying module B720, and an input/output control module B730. The receiving module B710 may obtain at least one of, e.g., various information associated with the electronic device (e.g., movement information, brightness information on the surroundings of the electronic device or state information on the electronic device) or bio signal of the user for the electronic device.

According to an embodiment, the receiving module B710 may receive the user's bio signal for the electronic device. For example, the receiving module B710 may directly obtain (e.g., sense) the bio signal generated from the user for the electronic device. Or, the receiving module B710 may indirectly obtain, from an external device, the user's bio signal obtained through the external device (e.g., the electronic device 104 or server 106) for the electronic device.

The bio signal may include a signal corresponding to at least one of, e.g., ECG, heart rate, heart rate variation, fingerprint, iris, body fat, oxygen saturation, pulse, body temperature, skin hydration value, skin moisture index, blood vessel information, face, voice, eyeball, palm lines, vein, EMG, or brain wave. To receive the above-enumerated various bio signals, the receiving module B710 or the external device may include, e.g., an ECG sensor (e.g., electrocardiogram (ECG) sensor or electrocardiography (EKG) sensor), heart rate sensor (e.g., photoplethysmography (PPG), heart rate monitor (HRM) sensor, or heart rate variability (HRV) sensor), fingerprint sensor, iris sensor, body fat measuring sensor, oxygen saturation sensor, temperature sensor, skin hydration measuring sensor, skin moisture measuring sensor, face recognition sensor, palm line recognition sensor, vein recognition sensor, EMG sensor, or brain wave measuring sensor. According to an embodiment, the various sensors to sense the user's bio signals are not limited to the above-enumerated ones.

According to an embodiment, the receiving module B710 may obtain the user's blood flow through a photoplethysmography (PPG) sensor. Further, the receiving module B710 may measure a variation in blood flow for a designated time (e.g., about one minute) through the PPG sensor. The PPG sensor may obtain bio information, such as, e.g., heart rate, heart rate variation or ECG, based on the variation in the blood floor. According to an embodiment, the receiving module B710 may obtain the user's electroencephalogram (EEG) signal as the bio information through the brain wave measuring sensor. According to an embodiment, the receiving module B710 may obtain the user's heart rate signal as at least a portion of the bio information through the ECG measuring sensor.

According to an embodiment, the receiving module B710 may obtain at least one information of the movement information of the electronic device, event, state information of the electronic device, external environment information, or distance information between the electronic device and the external device communicating with the electronic device. For example, the receiving module B710 may directly obtain the at least one information. Or, the receiving module B710 may indirectly obtain the at least one information obtained through the electronic device (e.g., the electronic device 101) or external device (e.g., the electronic device 104 or server 106) from the external device.

According to an embodiment, the receiving module B710 may obtain the movement information (e.g., travel distance, travel direction or rotational angle) of the electronic device through a motion sensor (e.g., acceleration sensor, gyro sensor, geo-magnetic sensor or global positioning system (GPS) module) functionally connected with the electronic device or external device. Further, the receiving module B710 may obtain the event occurring in the electronic device or external device. For example, the event may include a call receiving event, a message receiving event, an alarm event, a schedule information notification event, or social network service (SNS) event.

According to an embodiment, the receiving module B710 may obtain the state information of the electronic device. The state information of the electronic device may include, e.g., power state information (e.g., remaining battery information) or processing load information of the processor included in the electronic device. According to an embodiment, the receiving module B710 may obtain external environment information on the electronic device (e.g., the electronic device 101). The external environment information may include, e.g., information on the brightness of the surroundings of the electronic device, sound information generated from the surroundings of the electronic device (e.g., amplitude, frequency, or wavelength of sound), olfactory information or location information.

According to an embodiment, the receiving module B710 may obtain the distance information between the electronic device (e.g., the electronic device 101) and the external device (e.g., the electronic device 104 or server 106) communicating with the electronic device. For example, the receiving module B710 may obtain the distance information between the electronic device and the external device based on the strength of communication signal transmitted from the external device to communicate with the electronic device. For example, in case the strength of the communication signal corresponds to a first designated range (e.g., in case it is stronger than a designated strength), the receiving module B710 may determine that the distance between the electronic device and the external device is a first designated distance (e.g., a distance shorter than a reference distance at which they may communicate with each other). By contrast, in case the strength of the communication signal corresponds to a second designated range (e.g., in case it is weaker than a designated strength), the receiving module B710 may determine that the distance between the electronic device and the external device is a second designated range (e.g., a distance longer than a reference distance at which they may communicate with each other).

The identifying module B720 may identify the attachment/detachment state of the electronic device for the user based on, e.g., at least bio signal (e.g., whether to sense bio signal or attribute information of the bio signal (e.g., strength of bio signal or pattern of bio signal). The attachment/detachment state may include, e.g., a detached state (or unworn state) or attached state (or worn state) or incompletely attached state (or incompletely worn state). The detached state may include a state in which the electronic device is separated from the user's body. The attached state may include a state in which the electronic device is normally attached to the user's body. The incompletely attached state may include a state in which the electronic device is abnormally attached to the user's body. According to an embodiment, the described attachment/detachment of the electronic device (e.g., attached, detached, or incompletely attached) is an example, and various definitions or settings as to the attachment/detachment state may be made depending on the user's settings or designer of the electronic device.

According to an embodiment, the electronic device may determine the attachment/detachment state of the electronic device based on whether the bio signal is sensed. For example, the electronic device may be a smart watch. In case the smart watch is not worn on the user's wrist (e.g., in case the smart watch is in a pocket of the user's clothes, slung over the user, or placed in the bag, or in case the smart watch is positioned on an object (e.g., desk) other than the user's body), the bio signal for the user is not sensed, and the identifying module B720 may identify the attachment/detachment state of the smart watch as the detached state.

By contrast, in case the smart watch is normally (e.g., completely) worn on the user's wrist, the user's bio signal is sensed normally (e.g., in a predetermined signal pattern or in a strength enough to identify what type of signal the corresponding signal is), and the identifying module B720 may identify the attachment/detachment state of the smart watch as the attached state. In case the smart watch is abnormally (e.g., loosely) worn on the user's wrist, the user's bio signal is sensed incompletely (e.g., in case the strength or pattern of the sensed bio signal is not constant), and the identifying module B720 may identify the attachment/detachment state of the smart watch as the incompletely attached state. As another example, upon failing to sense the user's fingerprint through the receiving module B710 (e.g., the fingerprint recognition sensor), the identifying module B720 may identify the attachment/detachment state of the electronic device as the detached state. Further, in case the receiving module B710 senses the user's fingerprint, the identifying module B720 may sense the attachment/detachment state of the electronic device as the attached state.

According to an embodiment, the identifying module B720 may identify the attachment/detachment state of the electronic device using the strength of bio signal. In case the strength of the bio signal corresponds to the first designated range (e.g., in case it is larger than a first strength), the identifying module B720 may identify the attachment/detachment state of the electronic device as the attached state. In case the strength of the bio signal corresponds to the second designated range (e.g., in case it is smaller than a second strength), the identifying module B720 may identify the attachment/detachment state of the electronic device as the detached state. In case the strength of the bio signal corresponds to the third designated range (e.g., in case it is larger than the second strength and smaller than the first strength), the identifying module B720 may identify the attachment/detachment state of the electronic device as the incompletely attached state.

For example, the pulse signal obtained through the receiving module B710 (e.g., heart rate sensor) may include the first to third designated ranges according to the attachment/detachment state of the electronic device. The pulse wave signal received by the PPG sensor may include one or more of AC (alternating component) or DC (direct current component). The AC is a component caused by the heart's contraction and dilation, and the DC is a component caused by the degree of absorption or reflection by the body. In case the DC level value corresponding to the optical signal ranges from minimum 0 level to maximum 200,000 level, the received pulse wave signal may be display device as e.g., not more than about 60,000 level (e.g., the first designated range, detached state), e.g., not less than about 80,000 level (e.g., the second designated range, attached state), or outside the range, e.g., more than 60,000 level and less than 80,000 level (e.g., the third designated range, incompletely attached state). Such DC signal level value is determined through the process of amplifying the received signal, and thus, the range may differ depending on amplification range settings. Further, since the DC level value may be increased by ambient light also in the detached state, the value obtained by performing the operation of removing the received ambient light components may be used. As another example, the identifying module B720 may determine that the electronic device has one state (e.g., the detached state) of the detached state, attached state, or incompletely attached state based on the range (e.g., the incompletely attached state) corresponding to the strength (e.g., the range in which the measured DC level is about 30% to about 50% of the maximum value measurable by the receiving module B710) of the pulse wave signal currently obtained through the receiving module B710. To that end, one or more of the mean value, maximum value or minimum value of the DC level sensed for a designated period may be used.

According to an embodiment, the identifying module B720 may determine the attachment/detachment state of the electronic device according to the amplitude of the AC component of the bio signal. The amplitude of the AC component may use one or more of the amplitude of R wave measured by the heart rate sensor, the amplitude of the peak of the AC component measured by the PPG sensor, or the amplitude of an accelerated plethysmo. As an example, in case the amplitude of the AC signal corresponding to the bio signal received through the receiving module B710 meets a designated condition (e.g., in case it is about 20% to about 60% of the designated maximum amplitude), it indicates that the increase-decrease difference in light by the light receiver according to the dilation of the blood vessels when the heart contracts (increase in the amount of blood) and the increase in the blood vessels when the heart dilates (decrease in the amount of blood) is small, and thus, the electronic device may be determined to be in the incompletely attached state. For example, as the amplitude of AC signal is less than about 20% of the designated maximum amplitude, and particularly, approaches 0%, this means that there is little dilation and contraction of blood vessels, and it may be determined to be in the state (e.g., the detached state) of being covered by an object other than the body or being influenced a lot by ambient light. Accordingly, if the amplitude of the AC signal is in the range exceeding 60% of the designated maximum amplitude, it may be determined to be in the attached state. As another example, in case the pulse wave signal received by some PPG sensor is configured to include AC signal and DC signal, if the DC signal is close to the maximum level value, and the AC signal is very weak and not more than a predetermined value, it may be determined that only the DC component is strong, and the AC signal is weak. Accordingly, for such case, it is determined that although the amount of light received by the PPG sensor is large but the reflecting light or transmissive light of the blood vessel is not actually measured, and thus, it may be determined to be in the detached state.

According to an embodiment, the identifying module B720 may determine the signal-to-noise ratio (SNR) of the bio signal and determine the attachment/detachment state of the electronic device. For the received pulse wave signal, e.g., in case the SNR corresponding to the optical signal received is in excess of a threshold (e.g., about −8 dB) for a designated time (e.g., about five seconds), it may be determined to be in the normal attached state, and otherwise, in the incompletely attached state or detached state.

According to an embodiment, the identifying module B720 may determine the attachment/detachment state of the electronic device according to the signal pattern (e.g., frequency or period) of the bio signal. The identifying module B720 may compare the signal pattern of the bio signal received through the receiving module B710 with a designated (e.g., predefined or pre-stored) signal pattern. The designated signal pattern may be a pattern determined based on, e.g., the attribute (e.g., the type of bio signal indicating fingerprint, brain wave, pulse wave, or heart rate) of the bio signal. Further, the designated signal pattern, in case the electronic device is normally attached to the user, may include patterns of sensible signals.

In case the degree of similarity or identicality (e.g., degree of similarity) between the signal pattern of the bio signal and the designated signal pattern corresponds to a first designated range (e.g., lower than the first similarity), the identifying module B720 may identify the attachment/detachment state of the electronic device as the detached state. In case the similarity between the signal pattern of the bio signal and the detached state signal pattern corresponds to a second designated range (e.g., higher than the second similarity), the identifying module B720 may identify the attachment/detachment state of the electronic device as the attached state. In case the similarity between the signal pattern of the bio signal and the designated signal pattern corresponds to a third designated degree (e.g., higher than the first similarity and lower than the second similarity), the identifying module B720 may identify the attachment/detachment state of the electronic device as the incompletely attached state.

For example, the identifying module B720 may compare the signal pattern of an ECG signal obtained through the receiving module B710 (e.g., heart rate sensor) with a designated signal pattern (e.g., P, Q, R, S, or T wave). In this case, the designated signal pattern may include, e.g., in the case of ECG signal, a signal pattern (e.g., P, Q, R, S, or T wave) corresponding to the active current of the heart, and in the case of brainwave signal, a signal pattern corresponding to an electrical signal generated from the brain nerve (e.g., delta wave (about 0.2 Hz to about 4 Hz), theta wave (about 4 Hz to about 8 Hz), alpha wave (about 8 Hz to about 13 Hz), beta wave (about 13 Hz to about 30 Hz), or gamma wave (about 30 Hz to about 50 Hz).

In case the signal pattern of the obtained ECG signal and the designated signal pattern are identical (or similar) at a degree higher than, e.g., the first similarity (e.g., about 70%), the identifying module B720 may identify the attachment/detachment state of the electronic device as the attached state. In case the signal pattern of the obtained ECG signal and the designated signal pattern are identical at a degree lower than, e.g., the second similarity (e.g., about 30%), the identifying module B720 may identify the attachment/detachment state of the electronic device as the detached state. In case the signal pattern of the obtained ECG signal and the designated signal pattern are identical at a degree lower than, e.g., the first similarity (e.g., about 70%) and higher than, e.g., the second similarity (e.g., about 30%), the identifying module B720 may identify the attachment/detachment state of the electronic device as the incompletely attached state.

According to an embodiment, the identifying module B720 may identify detailed information (e.g., whether the user carries the electronic device or not) on the attachment/detachment state of the electronic device further based on the movement of the electronic device. For example, the identifying module B720 may further identify whether in the detached state of the electronic device the user carries the electronic device (e.g., whether the electronic device is placed in the bag (or clothes pocket) the user carries (carry) or the electronic device is positioned in other object (e.g., desk) off the user (not carry).

The state of carrying may include, e.g., the state in which the electronic device is not attached (or worn) on a portion of the user corresponding to the electronic device, and the electronic device is positioned in another portion of the user (e.g., in the case of smart watch, it is on the palm, but not on the wrist). The user's body portion corresponding to the electronic device may be the user's wrist, e.g., in case the electronic device is a smart watch, and the user's head, e.g., in case the electronic device is an HMD. Further, the state of carrying may include the state in which the electronic device is placed in the pocket of the user's clothes or the bag the user carries or slings, for example. For example, the non-carrying state may include the state in which the electronic device is left in a place (e.g., table) not influenced by the user's motion.

According to an embodiment, the identifying module B720 may identify whether the electronic device is carried based on the strength of the movement of the electronic device. For example, in case the strength of movement corresponds to a first designated range (e.g., larger than a designated strength), the identifying module B720 may identify the electronic device as carried by the user (or the state where the electronic device is positioned in a transportation means). In case the strength of movement corresponds to a second designated range (e.g., smaller than a designated strength), the identifying module B720 may identify the electronic device as not carried by the user.

According to an embodiment, the identifying module B720 may identify whether the electronic device is carried further based on the signal pattern for the movement of the electronic device. For example, the identifying module B720 may identify whether the user carries the electronic device based on the similarity between the signal pattern corresponding to the movement and patterns designated according to user's various motions. The designated patterns may include, e.g., data patterns (e.g., speed, acceleration, or degree of shake) respectively corresponding to the user's walking motion and running motion. Further, the designated pattern may include data information (e.g., speed, acceleration, or degree of shake) corresponding to various transportation means.

According to an embodiment, the identifying module B720 may authenticate (or identify) the user based on at least one of bio signal or movement of the electronic device. For example, in case the bio signal is used for user authentication, e.g., a memory (e.g., the memory 130) functionally connected with the electronic device may store a first bio signal corresponding to a first user and a second bio signal corresponding to a second user. In case the bio signal received through the receiving module B710 corresponds to the first bio signal, the identifying module B720 may determine that the user for the electronic device (e.g., the user using the electronic device) is the first user. Further, in case the bio signal received through the receiving module B710 corresponds to the second bio signal, the identifying module B720 may determine that the user for the electronic device is the second user.

As another example, in case the bio signal is iris information, the identifying module B720 may compare the iris information obtained through the receiving module B710 with iris information designated per user. In case there is designated iris information corresponding to the obtained iris information, the identifying module B720 may determine that the user corresponding to the designated iris information is the user for the electronic device.

According to an embodiment, in case the movement is used for user authentication, e.g., a memory (e.g., the memory 130) functionally connected with the electronic device may store first movement information corresponding to the first user and second movement information corresponding to the second user. In case the movement information received through the receiving module B710 corresponds to the first movement information, the identifying module B720 may determine that the user using the electronic device is the first user. Further, in case the movement information received through the receiving module B710 corresponds to the second movement information, the identifying module B720 may determine that the user using the electronic device is the second user.

For example, in case the movement is a walk (e.g., in case the user walks), the identifying module B720 may compare the walking information obtained through the receiving module B710 with walking information designated per user. In case there is designated walking information corresponding to the obtained walking information, the identifying module B720 may determine that the user corresponding to the designated walking information is the user for the electronic device.

According to an embodiment, the identifying module B720 may identify the significance of the event obtained through the receiving module B710. The identifying module B720 may designate the degree of significance for the event. The degree of significance may be designated based on, e.g., the type of event for the user (or degree of emergency). For example, a first degree of significance (e.g., a high significance) may be designated for a call reception event, a second degree of significance (e.g., a significance lower than the first degree of significance) may be designated for a message reception event, and a third degree of significance (e.g., a significance lower than the second degree of significance) may be designated for an alarm event. Or, the degree of significance may be determined based on, e.g., the emergency of the content indicated by the event. As an example, in case an event occurs from an important person associated with the user, or in case the event includes an emergent content (e.g., content associated with an emergency, such as car accident or fire), the degree of significance may be designated to be high.

The input/output control module B730 may independently control each of a plurality of input/output devices functionally connected with the electronic device, e.g., based on, at least, the attachment/detachment state of the electronic device (e.g., the electronic device 101). For example, the input/output control module B730 may independently (e.g., individually) control (e.g., adjust) at least one of turn-on/turn-off for each of the plurality of input/output devices (e.g., microphone, display, speaker, or haptic device) or the strength of an input signal or output signal through the plurality of input/output devices according to the attachment/detachment state (e.g., detached state, attached state, or incompletely attached state) determined based on the bio signal or movement information.

According to an embodiment, the input/output control module B730 may turn off at least one of the plurality of input/output devices in case the electronic device is in the state of being attached to the user (e.g., in case no bio signal is sensed or in case the smart watch is determined to be positioned in a pocket of the user's clothes or object (e.g., desk) other than the body). For example, the electronic device (e.g., the electronic device 101) may be a wearable electronic device that may be worn by the user to play content, such as a headphone-type electronic device or earphone-type electronic device. For example, in case the electronic device is in the state of being detached from the user, the input/output control module B730 may turn off the display to stop playing video so that at least a portion of the content is not played or turn off the speaker to stop playing sound or turn off the haptic device to stop playing variation.

According to an embodiment, the input/output control module B730 may turn on at least one of a plurality of input/output devices in case the electronic device is in the state of being attached to the user (e.g., in case the bio signal is normally sensed or in case the smart watch is determined to be properly (e.g., completely) worn on the user's wrist). For example, the input/output control module B730 may turn on the display to play video, turn on the speaker to play sound, or turn on the haptic device to play variation.

According to an embodiment, the input/output control module B730 may independently control at least one of the plurality of input/output devices to provide the feedback (e.g., notification) for the incompletely attached state to the user in case the electronic device is in the state of being incompletely attached to the user (e.g., in case the bio signal is abnormally sensed or in case the smart watch is determined to be improperly (e.g., loosely) worn on the user's wrist). For example, in case the smart watch is incompletely attached to the user so that the bio signal is not normally sensed, the input/output control module B730 may provide visual information through the display to the user as a feedback, provide sound information through the speaker, provide vibration information through the haptic device, or provide olfactory information through the olfactory output device. The case where the bio signal is not normally sensed may be, e.g., when sensing one or more of the case the bio signal received through the receiving module B710 shows an inconsistent pattern, the case it has a weak signal strength at which it is difficult to identify the type of signal, or the case where the SNR is not more than a threshold. According to an embodiment, the input/output control module B730 may output a message instructing to further loosen or tighten the straps of the smart watch as at least a portion of the visual information.

According to an embodiment, in case the electronic device is in the state of being detached from the user (e.g., in case no bio signal is sensed or in case the smart watch is not attached to the user or the sensor is exposed externally), the input/output control module B730 may independently control at least one of the plurality of input/output devices to provide a feedback (e.g., notification) for the detached state to the user.

According to an embodiment, in case an output signal (or input signal) is outputted (or inputted) through al one of the plurality of input/output devices based on the attachment/detachment state of the electronic device, the input/output control module B730 may independently control the signal strength of each of at least one device. For example, in case a smart watch, as an example of the electronic device, is in the attached state, the input/output control module B730 may control the screen brightness of the display to be "high," the sound output strength of the speaker to be "low" or the vibration strength of the haptic device to be "medium." By contrast, in case the smart watch is in the detached state, the input/output control module B730 may control the screen brightness of the display to be "low (or turn-off)," the sound output strength of the speaker to be "high" or the vibration strength of the haptic device to be "low."

The input/output control module B730 may independently control each of the plurality of input/output devices further based on, e.g., the movement of the electronic device. For example, the input/output control module B730 may control each of the plurality of input/output devices so that a stronger output signal may be provided in case the strength of the movement for the electronic device is "high" (e.g., in case the user carrying (or wearing) the electronic device walks or runs fast) than in case the strength of movement for the electronic device is "low" (e.g., in case the user carrying the electronic device walks slow or makes a tiny motion at rest). For example, the input/output control module B730 may determine the vibration strength of the haptic device as "high" in case the strength of movement is "high," as "medium" in case the strength of movement is "medium," and as "low" in case the strength of movement is "low."

According to an embodiment, the input/output control module B730 may control each of the plurality of input/output devices to provide notification information corresponding to an event based on the movement of the electronic device. For example, in case the strength of the movement of the electronic device is "high," it is difficult to identify the information provided through the display, and thus, a notification for reception of a social networking service (SNS) message may be provided to the user through a sound of the speaker or vibration of the haptic device. By contrast, in case the strength of movement of the electronic device is "low," the input/output control module B730 may provide a notification for reception of the message through, e.g., the display.

According to an embodiment, the input/output control module B730 may differently control each of the plurality of input/output devices depending on the significance of the event generated by the electronic device. For example, even when the strength of movement for the electronic device is "strong," in case the significance of the attribute of the message received by the electronic device is high (e.g., in case the content of the message is important, urgent, or the sender of the message is an important person), the input/output control module B730 may turn on the display and may increase the strength of the variation of the haptic device or the strength of sound of the speaker. By contrast, although the strength of movement for the electronic device is "low," in case the significance of the message is low (e.g., in case the content of the message contains blocked characters, junk message, or there is no information on the sender), the input/output control module B730 may turn off the display and decrease the sound volume of the speaker or vibration strength of the haptic device.

According to an embodiment, the input/output control module B730 may differently control each of the plurality of input/output devices according to time information in case the event includes the time information. For example, for an alarm event, the input/output control module B730 may gradually increase the signal strength for the plurality of input/output devices as it comes close to the time designated for the notification event. Further, for example, for a schedule event, the input/output control module B730 may turn on only the haptic device to provide only vibration a first time (e.g., about one hour) before the time designated in the schedule event. The input/output control module B730 may turn on the haptic device and speaker device to provide both vibration and sound a second time (e.g., about 30 minutes) before the time designated in the schedule event.

According to an embodiment, the input/output control module B730 may control the plurality of electronic devices further based on an application running on the electronic device. For example, in case the application running on the electronic device is an application using the user's bio signal (e.g., a stress measuring application), the input/output control module B730 may control the plurality of input/output devices so that other applications are not run or notification information corresponding to other applications is not provided.

According to another embodiment, although the application using bio signals is running on the electronic device, in case the significance of the message received by the electronic device is high, the input/output control module B730 may provide a notification for the message to the user using at least one of the plurality of input/output devices. For example, the input/output control module B730 may provide a notification for the message by turning on the display, decreasing the sound volume of the speaker, or decreasing the vibration strength of the haptic device.

According to an embodiment, the input/output control module B730 may independently control each of the plurality of input/output devices based on the distance between the electronic device (e.g., the electronic device 101) and external device (e.g., the electronic device 104 or server 106). For example, in case the distance between the electronic device and the external device is determined to be relatively short (e.g., in case the distance between the electronic device, a smart watch, and the external device, a mobile phone, is determined to be about 1 m or more or less), the input/output control module B730 may turn off at least one input/output device or decrease the signal strength for each of the plurality of input/output devices. By contrast, in case the distance between the electronic device and the external device is determined to be relatively long (e.g., in case the distance between the electronic device, a smart watch, and the external device, a mobile phone, is determined to be 5 m or more or less), the input/output control module B730 may increase the signal strength for the plurality of input/output devices.

According to an embodiment, as the distance between the electronic device and the external device varies, the identifying module B720 may adjust (e.g., set) the signal strength for the plurality of input/output devices to gradually increase. Further, in case an application for discovering the external device (e.g., a device discovery application) runs on the electronic device, the input/output control module B730 may support the user to discover the external device by adjusting (e.g., setting) the signal strength for each of the plurality of input/output devices included in the external device to increase.

According to an embodiment, the input/output control module B730 may control each of the plurality of input/output devices further based on the state information of the electronic device. For example, in case the remaining battery of the electronic device is high (e.g., 60% or more), the input/output control module B730 may turn on the display consuming much battery power or adjust the vibration strength of the haptic device or sound of speaker to increase. By contrast, in case the remaining battery of the electronic device is low (e.g., about 30% or less), the input/output control module B730 may turn off the display and adjust the vibration strength of the haptic device or speaker sound to decrease.

According to an embodiment, the input/output control module B730 may control each of the plurality of input/output devices further based on the user's authentication information on the electronic device. For example, in case the user of the electronic device is determined to be an adult, the input/output control module B730 may turn on each of the plurality of input/output devices and may adjust the signal strengths corresponding to the plurality of input/output devices according to the degree at which the user controls the plurality of input/output devices. By contrast, in case the user of the electronic device is determined to be a minor, the input/output control module B730 may turn off at least one of the plurality of input/output devices and may control the plurality of input/output devices to restrict the user's control on the electronic device. Meanwhile, the input/output control module B730 may also control the plurality of input/output devices further based on the type of content provided through the electronic device (e.g., adult content or kid content) as well as the user's authentication information.

According to an embodiment, the input/output control module B730 may control each of the plurality of input/output devices further based on external environment information on the electronic device (e.g., brightness information of the surroundings of the electronic device, sound information, olfactory information, or location information). For example, in case the strength of sound generated around the electronic device is "weak," the user may sense even a weak sound form the speaker. Thus, the input/output control module B730 may perform control so that the sound volume of the speaker decreases. By contrast, in case the strength of sound generated from the surroundings of the electronic device is "strong," the input/output control module B730 may perform control so that the sound volume of the speaker increases (e.g., so as to be stronger than "strong," which is the strength of the sound generated form the surroundings of the electronic device). Further, in case the strength of sound generated from the surroundings of the electronic device is "strong," the user might not sense even a strong sound from the speaker. Thus, the input/output control module B730 may turn on the haptic device to provide a vibration to the user.

Further, in case the strength of a smell generated from the surroundings of the electronic device is "weak," the user may sense even a weak smell. Thus, the input/output control module B730 may control the olfactory output device to output a weak smell. By contrast, in case the strength of a smell generated from around the electronic device is "strong," the input/output control module B730 may control the olfactory output device to output a strong smell (e.g., a smell stronger than "strong," which is the strength of the smell generated from around the electronic device).

According to an embodiment, the input/output control module B730 may determine setting information for each of a plurality of input/output devices based on an attachment/detachment state in order to independently control the plurality of input/output devices according the attachment/detachment state of the electronic device. The setting information may include a method for running each of the plurality of input/output devices functionally connected with the electronic device, for example. For example, the execution information may include turn-on/turn-off information for each of the plurality of input/output devices, strength of input signal inputted through the plurality of input/output devices, or strength of output signal outputted through the plurality of input/output devices. The input/output control module B730, e.g., in case the electronic device is in the detached state, may determine the setting information so that the display "turns off, the sound volume of the speaker is "high," or the vibration strength of the haptic device is "weak."

According to an embodiment, the input/output control module B730 may control the plurality of input/output devices further based on the setting information set by the user for the plurality of input/output devices. For example, in case the electronic device is in the detached state, although the display is supposed to turn off according to the detached state, if the user sets it to remain turning on, the input/output control module B730 may turn on the display.

According to an embodiment, although the display, speaker, haptic device, or olfactory output device is provided as examples of the plurality of input/output devices, embodiments of the present invention are not limited thereto. Further, although in the embodiments of the present invention, ranges designated for various information (e.g., movement information or state information of the electronic device) are provided as examples to determine the attachment/detachment state for the electronic device, embodiments of the present invention are not limited the designated ranges and may be implemented to various designated ranges by the user's setting information or the designer of the electronic device. According to an embodiment, the plurality of input/output devices functionally connected as described in the embodiments of the present invention may include, e.g., input/output devices included in the electronic device itself (e.g., the electronic device 101) or input/output devices included in an external device (e.g., the electronic device 104 or server 106) communicating with the electronic device.

According to an embodiment, an electronic device (e.g., the electronic device 101) controlling a plurality of input/output devices may include a receiving module (e.g., the receiving module B710) for receiving a user's bio signal (e.g., pulse wave signal) in the electronic device, an identifying module (e.g., the identifying module B720) for identifying an attachment/detachment state of the electronic device for the user at least based on the bio signal (e.g., signal strength or pattern of the pulse wave signal or amplitude of AC wave), and an input/output control module (e.g., the input/output control module B730) for independently controlling (e.g., control the sound output strength of a speaker to be high or turn off a haptic device) each of the plurality of input/output devices (e.g., a speaker or haptic device) functionally connected with the electronic device at least based on the attachment/detachment state.

According to an embodiment, the receiving module may obtain, as the bio signal, at least one of, e.g., ECG, heart rate, heart rate variation, fingerprint, iris, body fat, oxygen saturation, pulse, body temperature, skin hydration value, skin moisture index, blood vessel information, face, voice, eyeball, palm lines, vein, EMG, or brain wave.

According to an embodiment, the identifying module may obtain attribute information (e.g., signal strength or signal pattern of the bio signal) of the bio signal and may determine the attachment/detachment state as an attached state in case the attribute information corresponds to a first designated range, the attachment/detachment state as a detached state in case the attribute information corresponds to a second designated range, and the attachment/detachment state as an incompletely attached state in case the attribute information corresponds to a third designated range.

According to an embodiment, the identifying module may authenticate the user using at least one of the bio signal or movement information of the electronic device. For example, in case the bio signal is fingerprint information, the identifying module may determine that the user is a first user in case the fingerprint information is first fingerprint information and that the user is a second user in case the fingerprint information is second fingerprint information.

According to an embodiment, the identifying module may obtain a signal strength of the bio signal and may determine that the attachment/detachment state is the attached state in case the signal strength corresponds to a first designated range and that the attachment/detachment state is the detached state in case the signal strength is a second designated range.

According to an embodiment, the identifying module may determine that the attachment/detachment state is the incompletely attached state in case the signal strength corresponds to a third designated range.

According to an embodiment, the input/output control module may be configured to provide a feedback (e.g., a notification) for the incompletely attached state or detached state to the user through at least one of the plurality of input/output devices in case the electronic device is in the incompletely attached state or detached state.

According to an embodiment, the identifying module may identify an application (e.g., a stress measuring application) running on the electronic device.

According to an embodiment, the input/output control module may control each of the plurality of input/output devices (e.g., such control as to not run other applications or not provide notification information corresponding to other applications) further based on the application.

According to an embodiment, the input/output control module may determine setting information corresponding to each of the plurality of input/output devices at least based on the attachment/detachment state and control a corresponding device (e.g., the haptic device) among the plurality of input/output devices (e.g., the speaker or haptic device) based on the setting information.

According to an embodiment, the setting information may include at least one of turn-on/turn-off information for each of the plurality of input/output devices and strength information for an input signal or output signal through the plurality of input/output devices.

According to an embodiment, the input/output control module may control the turn-on or turn-off of each of the plurality of input/output devices.

According to an embodiment, the plurality of input/output devices may include at least one of a speaker, a haptic device, an olfactory output device, or a display, and the input/output control module may control at least one of a sound volume of the speaker, a vibration strength of the haptic device, a smell strength of the olfactory output device, or a brightness of the display.

According to an embodiment, the input/output control module may control the signal strength for at least one of the plurality of input/output devices based on the signal strength corresponding to external environment information (e.g., brightness information of the surroundings of the electronic device or sound information or olfactory information generated from around the electronic device).

According to an embodiment, the input/output control module may control the plurality of input/output devices further based on at least one of state information of the electronic device, movement information of the electronic device, authentication information on the user, and information on the distance between an external device communicating with the electronic device and the electronic device.

According to an embodiment, the input/output control module may control the plurality of input/output devices further based on the significance of an event obtained from the electronic device (e.g., significance of the content of a message, degree of emergency, or significance of the sender of the message).

According to an embodiment, the input/output control module may provide notification information on the event using at least one (e.g., speaker) of the plurality of input/output devices (e.g., the speaker or haptic device) based on the significance of the event.

FIG. 167 is a flowchart B800 illustrating a method of controlling a plurality of input/output devices by an electronic device (e.g., the electronic device 101) according to an embodiment. In operation B810, the electronic device (e.g., the receiving module B710) may receive the user's bio signal (e.g., pulse wave signal). According to an embodiment, the electronic device (e.g., the receiving module B710) may obtain at least one information (hereinafter, "context information for electronic device" for ease of description) of the movement information of the electronic device, event, state information of the electronic device, external environment information, or distance information between the electronic device and the external device communicating with the electronic device.

In operation B820, the electronic device (e.g., the identifying module B720) may identify the attachment/detachment state of the electronic device for the user at least based on the bio signal (e.g., the signal strength of the pulse wave signal). According to an embodiment, the electronic device may identify detailed information (e.g., whether the user carries the electronic device or not) on the attachment/detachment state of the electronic device further based on the context information on the electronic device.

In operation B830, the electronic device (e.g., the input/output control module B730) may independently control each of a plurality of input/output devices (e.g., speaker, display, haptic device, or olfactory output device) functionally connected with the electronic device at least based on the attachment/detachment state. For example, the electronic device may determine at least one of the turn-on/turn-off of each of a plurality of input/output devices, the strength of sound outputted through the speaker, brightness information of the display, the strength of vibration of the haptic device, or the strength of smell from the olfactory output device depending on at least the attachment/detachment state.

FIG. 168 is a flowchart B900 illustrating a method of controlling a plurality of input/output devices by an electronic device (e.g., the electronic device 101) according to an embodiment. The description of the same or similar parts to those shown in FIG. 167 among the operations of FIG. 168 is omitted. In operation B910, the electronic device (e.g., the receiving module B710) may receive the user's bio signal (e.g., brain wave signal). In operation B930, the electronic device (e.g., the identifying module B720) may identify the attachment/detachment state of the electronic device for the user at least based on the bio signal (e.g., the signal strength of the brain wave signal).

In operation B950, the electronic device (e.g., the input/output control module B730) may determine the setting information corresponding to each of the plurality of input/output devices functionally connected with the electronic device at least based on the attachment/detachment state. For example, the setting information may include information on at least one of whether the turn-on/turn-off information for each of the plurality of input/output devices is set, the strength of input signal inputted through the plurality of input/output devices, or strength of output signal outputted through the plurality of input/output devices.

In operation B970, the electronic device (e.g., the input/output control module B730) may independently control a corresponding device among the plurality of input/output devices based on the setting information. For example, in case the setting information on the display is "turn off," the setting information on the speaker is "high," and the setting information on the haptic device is "low," the electronic device may turn off the display, set the sound volume of the speaker to "high" and output sound, and reduce the variation strength of the haptic device and output vibration.

FIG. 169 is a flowchart C01 illustrating a method of controlling a plurality of input/output devices (e.g., the display, haptic device, or speaker) by an electronic device (e.g., the electronic device 101) according to an embodiment. According to an embodiment, the electronic device may control each of a plurality of heterogeneous input/output devices functionally connected with the electronic device according to various context information (e.g., the user's bio signal or movement for the electronic device) associated with the electronic device.

For example, in operation C10, the electronic device (e.g., the receiving module B710) may sense a movement as one context information for the electronic device and the user's bio signal for the electronic device. In operation C20, the electronic device (e.g., the identifying module B720) may compare, e.g., the bio signal for the user with a designated value (e.g., a preset reference associated with the bio signal) (e.g., determine which one of a plurality of preset ranges the strength of bio signal corresponds to). In operation C21, the electronic device (e.g., the identifying module B720), in case the bio signal is larger than the designated value, may determine that the electronic device is attached to the user. By contrast, in operation C23, the electronic device, in case the bio signal is not more than the designated value, may determine that the electronic device is detached from the user.

According to an embodiment, the electronic device (e.g., the identifying module B720) may identify, e.g., a more detailed state (e.g., the movement or location for the electronic device) for the electronic device based on the movement of the electronic device along with the attachment or detachment of the electronic device. For example, in operations C30 and C40, the electronic device may compare the strength of movement for the electronic device with a designated value (e.g., a preset reference associated with the movement) (e.g., determine which one of a plurality of preset ranges it corresponds to in association with the strength of the movement).

According to an embodiment, in case the electronic device is attached to the user, in operation C31, if the strength of movement is larger than a designated value, the electronic device may determine that the electronic device is on the move (e.g., in case the user wears the electronic device and does strenuous exercise or walking). Or, in operation C33, in case the strength of movement is not more than a designated value, the electronic device may determine that the electronic device is stationary (e.g., when the user wearing the electronic device uses a stress measuring application).

According to an embodiment, in case the electronic device is detached from the user, in operation C41, if the strength of movement is larger than a designated value, the electronic device may determine that the user carries the electronic device. For example, the electronic device may determine that the electronic device is carried by the user in a place other than where it is supposed to be positioned (e.g., for a smart watch, on the palm or pocket of the clothes the user wears). In operation C43, in case the movement strength is not more than a designated value, the electronic device may determine that the user does not carry the electronic device (e.g., the electronic device is placed on the desk where it is not affected by the user's movement).

According to an embodiment, the electronic device (e.g., the input/output control module B730) may control each of the display, haptic device, and speaker in various manners depending on the state (e.g., move, carry, or non-carry) for the electronic device determined by the attachment/detachment state and movement. For example, in operation C50, in case the electronic device is on the move while remaining attached to the user, the electronic device may "turn off" the display, set the vibration strength of the haptic device to "high," and set the sound volume of the speaker to "high." In operation C60, in case the electronic device is stationary while remaining attached to the user, the electronic device may turn on the display, set the vibration strength of the haptic device to low, and turn off the speaker.

In operation C70, in case the electronic device is detached from the user but is carried by the user, the electronic device may "turn off" the display, "turn off" the haptic device, and set the sound volume of the speaker to "high." In operation C80, in case the electronic device is completely separated from the user in the detached state, the electronic device may "turn off" the display, "turn off" the haptic device, and "turn off" the speaker.

According to an embodiment, a method for controlling a plurality of input/output devices may include the operation of receiving a user's bio signal (e.g., brain wave signal) in the electronic device, the operation of identifying an attachment/detachment state of the electronic device for the user at least based on the bio signal (e.g., the signal pattern of the brain wave signal), and the operation of independently controlling each of the plurality of input/output devices (e.g., a display or microphone) functionally connected with the electronic device at least based on the attachment/detachment state.

According to an embodiment, the receiving operation may include the operation of obtaining, as the bio signal, at least one of, e.g., ECG, heart rate, heart rate variation, fingerprint, iris, body fat, oxygen saturation, pulse, body temperature, skin hydration value, skin moisture index, blood vessel information, face, voice, eyeball, palm lines, vein, EMG, or brain wave.

According to an embodiment, the identifying operation may include the operation of obtaining attribute information (e.g., signal strength or signal pattern of the bio signal) of the bio signal and may determine the attachment/detachment state as an attached state in case the attribute information corresponds to a first designated range, the attachment/detachment state as a detached state in case the attribute information corresponds to a second designated range, and the attachment/detachment state as an incompletely attached state in case the attribute information corresponds to a third designated range.

According to an embodiment, the identifying operation may include the operation of authenticating the user using the bio signal or movement information of the electronic device. For example, the authenticating operation may include the operation of determining that the user is a first user in case the movement information corresponds to first movement information, and the user is a second user in case the movement information corresponds to second movement information.

According to an embodiment, the identifying operation may include the operation of obtaining a signal strength of the bio signal and may determine that the attachment/detachment state is the attached state in case the signal strength corresponds to a first designated range and that the attachment/detachment state is the detached state in case the signal strength is a second designated range.

According to an embodiment, the identifying operation may include the operation of determining that the attachment/detachment state is the incompletely attached state in case the signal strength corresponds to a third designated range.

According to an embodiment, the independently controlling operation may include the operation of providing a feedback (e.g., a notification) for the incompletely attached state or detached state to the user through at least one of the plurality of input/output devices in case the electronic device is in the incompletely attached state or detached state.

According to an embodiment, the identifying operation may include the operation of identifying an application (e.g., a stress measuring application) running on the electronic device.

According to an embodiment, the independently controlling operation may include the operation of controlling each of the plurality of input/output devices (e.g., such control as to not run other applications or not provide notification information corresponding to other applications) further based on the application.

According to an embodiment, the independently controlling operation may include the operation of determining setting information corresponding to each of the plurality of input/output devices at least based on the attachment/detachment state and controlling a corresponding device (e.g., the display) among the plurality of input/output devices (e.g., the display and microphone) based on the setting information.

According to an embodiment, the setting information may include at least one of turn-on/turn-off information for each of the plurality of input/output devices and strength information for an input signal or output signal through the plurality of input/output devices.

According to an embodiment, the independently controlling operation may control the turn-on or turn-off of each of the plurality of input/output devices.

According to an embodiment, the plurality of input/output devices may include at least one of a speaker, a haptic device, an olfactory output device, or a display, and the independently controlling operation may include the operation of controlling at least one of a sound volume of the speaker, a vibration strength of the haptic device, a smell strength of the olfactory output device, or a brightness of the display.

According to an embodiment, the independently controlling operation may include the operation of controlling the signal strength for at least one of the plurality of input/output devices based on the signal strength corresponding to external environment information (e.g., brightness information of the surroundings of the electronic device or sound information or olfactory information generated from around the electronic device).

According to an embodiment, the independently controlling operation may include the operation of controlling the plurality of input/output devices further based on at least one of state information of the electronic device, movement information of the electronic device, authentication information on the user, and information on the distance between an external device communicating with the electronic device and the electronic device.

According to an embodiment, the independently controlling operation may include the operation of controlling the plurality of input/output devices further based on the significance of an event obtained from the electronic device (e.g., significance of the content of a message, degree of emergency, or significance of the sender of the message).

According to an embodiment, the independently controlling operation may include the operation of providing notification information on the event using at least one (e.g., haptic device) of the plurality of input/output devices (e.g., the speaker or haptic device) based on the significance of the event.

FIG. 170 illustrates a communication protocol C100 between a plurality of electronic devices (e.g., the electronic device C110 and the electronic device C130) according to an embodiment. Referring to FIG. 170, the communication protocols C100 may include, e.g., a device discovery protocol C151, a capability exchange protocol C153, a network protocol C155, and an application protocol C157.

According to an embodiment, the device discovery protocol C151 may be a protocol for each electronic device (e.g., the electronic device C110 or the electronic device C130) to detect an external electronic device that the electronic device may communicate with or to link itself to the detected external electronic device. For example, the electronic device C110 (e.g., the electronic device 101) may detect the electronic device C130 (e.g., the electronic device 104) as its communicable device through a communication scheme (e.g., Wi-Fi, BT, or USB) available in the electronic device C110 using the device discovery protocol C151. The electronic device C110 may obtain and store identification information about the detected electronic device C130 using the device discovery protocol C151 in order to establish a communication link with the electronic device C130. The electronic device C110 may establish such communication link with the electronic device C130 based on, e.g., at least the identification information.

According to an embodiment, the device discovery protocol C151 may be a protocol for mutual authentication between the plurality of electronic devices. For example, the electronic device C110 may perform authentication between the electronic device C110 and the electronic device C130, at least, based on communication information for linkage with the electronic device C130 (e.g., media access control (MAC) address, universally unique identifier (UUID), subsystem identification (SSID), or information provider (IP) address).

According to an embodiment, the capability exchange protocol C153 may be a protocol for exchanging information relating to capabilities of services supportable by the electronic device C110 or the electronic device C130. For example, the electronic device C110 and the electronic device C130 may swap the information regarding the capabilities of the services that they are currently providing through the capability exchange protocol C153. The exchangeable information may include identification information indicating particular services supportable by the electronic device C110 and the electronic device C130. For example, the electronic device C110 may receive identification information of the particular service provided by the electronic device C130 from the electronic device C130 through the capability exchange protocol C153. In this case, the first electronic device C110 may determine whether the electronic device C110 may support the particular service based on the received identification information.

According to an embodiment, the network protocol C155 may be a protocol for controlling the flow of data that is communicated between electronic devices (e.g., the electronic device C110 and the electronic device C130) communicably connected with each other, e.g., so that the electronic devices may provide services while interworking with each other. For example, at least one of the electronic device C110 or the electronic device C130 may conduct error control or data quality control using the network protocol C155. Additionally or alternatively, the network protocol C155 may determine the transmission format of data communicated between the electronic device C110 and the electronic device C130. Further, at least one of the electronic device C110 or the electronic device C130 may manage, at least, a session (e.g., session connection or session termination) for data exchange between the electronic devices C110 and C130 using the network protocol C155.

According to an embodiment, the application protocol C157 may be a protocol for providing a procedure or information for exchanging data related to services offered to an external electronic device. For example, the electronic device C110 (e.g., the electronic device 101) may provide a service to the electronic device C130 (e.g., the electronic device 104 or the server 106) through the application protocol C157.

According to an embodiment, the communication protocols C100 may be standard communication protocols, protocols designated by an individual or an organization (e.g., a communication device/system manufacturer or network provider) or combinations thereof.

FIG. 171 is a block diagram illustrating a device control module of an electronic device (e.g., the electronic device 101) according to an embodiment. The control module C260 may be the additional function module 170 shown in FIG. 51.

Referring to FIG. 171, a memory C250 (e.g., the memory 130) may include a state control table C251 and a function processing table C253.

The state control table C251 may include a state control information table, a device state table, and a UI control table. The state control information table may be a table related to the state control information among the control information. According to an embodiment, the state control information table may include state control information including commands or a command set to be performed corresponding to at least one context information. For example, the state control information table may include state information having a function (e.g., communication connection release alarm or pause or stop running the function interworking with the external device) to be performed when the communication connection with the external device (e.g., the electronic device 104) is released and power control information (e.g., cut off power supply to communication module or cut off power supply to GPS module) of the device element.

According to an embodiment, the state control information table may include state control information to be run on the electronic device and the state control information to be transmitted to the external device. For example, the state control information table may include state control information having the function (e.g., remaining battery alarm, request charge alarm, and stop running function interworking with external device when not charged) to be performed according to the remaining battery state of the electronic device and power control information (e.g., cut off power supply to the GPS module and cut off power supply to sensor module 240 related to supporting function) of the device element. Further, the state control information table may include state control information having the function (e.g., remaining battery alarm of external device, request charge external device alarm, and transfer of function performable on the electronic device among functions running on the electronic device) to be performed according to the remaining battery state of the external device and power control information (e.g., cut off power supply to communication module related to communication connection with external device, cut off power supply to sensor module (e.g., the sensor module 240) related to interworking with the external device, control the communication module power of the external device, and control the sensor module power of the external device) of the device element.

The device state table may include an operation state table of at least one device element included in the electronic device, e.g., the GPS module or sensor module. The device state table may separately store the device element run by the external device in the process of interworkng with the external device and the device element run in the process of running the function of the electronic device. Accordingly, the table information in the device state table may be updated according to at least one of running or terminating the function interworking with the external device, the communication connection state with the external device, or power on/off the external device. Further, the table information related to the device element in the device state table may be updated corresponding to running or terminating a particular function. According to an embodiment, the device state table may have state information related to the GPS module. In case the GPS module is requested to be activated from the external device, the device state table may store the GPS module as the state of being turned on or activated by the external device. In case the communication connection with the external device is released, the GPS module-related function of the external device is terminated, or the external device is turned off or deactivated, the GPS module in the device state table may be turned into the turn-off state. The function processing module C290 may control the on/off state of the device elements corresponding to the device state table.

The UI control table may store UI control information to be transmitted to the external device corresponding to request information (e.g., context information). According to an embodiment, the UI control table may include various UI control information to be transmitted to the external device corresponding to schedule information. The UI control table may include each UI control information to be transmitted to the external device according to at least one of weather information, location information, sunrise/sunset information, season information, event information, official celebration day information, personal celebration day information, and advertisement information.

According to an embodiment, the UI control table may include basic UI control information. The basic UI control information may include at least one item (e.g., A, B, C, and D). According to an embodiment, in case the weather information includes rain-related information, the basic UI control information may be changed into the form including some items (e.g., A, B, and C) corresponding to the weather information, or at least one of the size, position, or color of at least one of the existing items is varied or the item may be exchanged (e.g., A, B, C, and E). According to an embodiment, the basic UI control information may be prepared for each of at least one context information. The basic UI control information for each context information may be provided so that at least one item is varied as the type or attribute of each context information is varied.

The function processing table C253 may include a list of function processes to be performed on the electronic device corresponding to at least one item included in the UI control information. According to an embodiment, in case the UI control information contains walking, running, biking, or mountain climbing items in relation with a health coaching function, the function processing table C253 may include a list of functions processed on the electronic device per item. For example, the function processing table C253 may include a sound playing app as a list to be run in relation with the selection of the mount climbing item. The function processing table C253 may include a navigation function app as a list to be run in relation with the selection of the bicycle item.

The state control module C281 of the control module C260 may include a context information gathering module C283, a state-related information extracting module C285, and a state processing module C287.

The context information gathering module C283 may gather at least one context information. The context information gathering module C283 may identify the schedule information stored in the memory C250 to identify whether there is schedule information to be notified at the present time. The context information gathering module C283 may gather weather information corresponding to occurrence of a particular event or at a preset period. According to an embodiment, the context information gathering module C283 may access a server device providing weather information upon forming a communication channel with the external device and receive the weather information from the server device. According to an embodiment, the context information gathering module C283, upon receiving the feedback on running the particular function (e.g., the health coaching function) from the external device, may control the access to the server device and reception of weather information. According to an embodiment, the context information gathering module C283, if a communication channel with the external device is formed or a particular function is run on the external device, may gather the location information. The context information gathering module C283 may monitor the remaining battery, and if the remaining battery is not more than a predetermined value, it may gather this as the context information. The context information gathering module C283 may perform monitoring on a particular communication module (e.g., the communication module forming a communication channel with the external device) of the communication interface (e.g., the communication interface 160), and if the signal strength of the communication channel is not more than a predetermined value or the communication channel is released, it may gather it as the context information. The context information gathering module C283 may transfer the gathered context information to the state-related information extracting module C285.

The state-related information extracting module C285 may extract the state control information using the state control table 151 and the context information provided from the context information gathering module C283. For example, the state-related information extracting module may detect the state control information corresponding to the received context information from the state control information table. The state-related information extracting module C285 may transfer the extracted state control information to the state processing module C287.

The state processing module C287 may transmit the state control information to the external device. The state processing module C287 may transmit per-context information UI control information corresponding to the state control information or particular context information to the external device. According to an embodiment, in case at least a portion of the state control information is information applied to the electronic device, the state processing module C287 may transfer the information to the function processing module C290.

The function processing module C290 may perform the function or output the alarm corresponding to the state control information provided from the state processing module C287. Further, the function processing module C290 may identify the function processing list corresponding to the selection information received from the external device by referring to the function processing table C253. The function processing module C290 may perform control to run the function registered in the function processing list. For example, the function processing module C290 may automatically activate the sound playing app corresponding to the selection information received from the external device and output the played audio data. In this process, the function processing module C290 may perform control to transfer audio data to the accessory device (e.g., headset, earphone, wireless headset, or wireless speaker) connected to the electronic device. The function processing module C290 may perform control to play at least one sound source among the sound sources stored in the memory C250 and play the sound source based on a pre-defined sound source list.

According to an embodiment, the function processing module C290 may maintain the state of the display (e.g., the display 150) as the previous state during the course of processing the particular function. For example, the function processing module C290 may perform control to play the sound source or output the played sound source while maintaining the display in the turn-off state. Or, the function processing module C290 may set the display to a particular screen state (e.g., standby screen, home screen, or particular menu screen) and control the playback of the sound source and the output of the played sound source through background processing.

FIG. 172 illustrates a device state table according to an embodiment.

Referring to FIG. 172, the device state table may include state information per device operation for the particular device element (e.g., the GPS module GPS, the acceleration sensor ACC, or the gyro sensor GYRO) included in, e.g., the electronic device. For example, the GPS module item in the device state table may indicate the state turned on by the external device C400. The GPS module item may indicate the state turned off by the electronic device. In this relation, the GPS module of the electronic device may be activated while currently having the turn-on state.

According to an embodiment, the control module C260 may switch the GPS module into the turn-off state in case the communication channel between the external device C400 and the electronic device is released or the external device C400 turns into the turn-off state. In this case, the GPS module related to the external device C400 in the device state table may turn from the turn-on state to the turn-off state.

According to an embodiment, in case the GPS module is in the turn-on state corresponding to running the particular function (e.g., navigation function) of the electronic device, even though the communication connection with the external device C400 is released or the external device C400 turns into the turn-off state, the control module C260 may maintain the GPS module in the turn-on state.

As described above, the device state table may store information as to whether it has the turn-on state or turn-off state in relation to performing the function of the external device C400 for the device elements included in the electronic device. Further, the device state table may store information as to whether it has the turn-on state or turn-off state in relation to performing the function of the electronic device for the device elements included in the electronic device. The control module C260 may restore the device element of the electronic device having the turn-on state or turn-off state into the original state by the external device C400 corresponding to at least one of the release of the communication connection with the external device C400, the remaining battery state of the external device C400, the turn-off state of the external device C400, and the termination of the particular function of the external device C400. During this course, the control module C260 may perform control to identify the device state table information related to the electronic device for the device elements (e.g., the GPS module, sensor module, and server device access-related communication interface) and so that the device elements have the state corresponding to the information put in the device state table.

According to an embodiment, the device state table may indicate the operation state of the particular device elements (e.g., the GPS module or sensor module) corresponding to the communication connection state between the electronic device and the external device C400, the release state, or remaining battery state. For example, the device state table may include at least one sensor state information included in the sensor module of the electronic device activated by a request from the electronic device upon failure to forming a communication channel between the electronic device and the external device C400 under the control of the control module C260. The device state table may include at least one sensor state information of the activated sensor module corresponding to a request from the electronic device and a request from the external device C400 and the GPS module state information activated according to the request from the external device C400 upon communication connection between the electronic device and the external device C400 under the control of the control module C260.

According to an embodiment, the device state table may include the state information that the operation of the GPS module activated by the external device C400 is temporarily stopped and the state information that the activated sensor turns deactivated according to a request from the external device C400, upon releasing the communication connection between the electronic device and the external device C400 under the control of the control module C260. Accordingly, the electronic device may pause the operation of the GPS module activated in relation with the support of the external device C400 for a predetermined time. The device state table may include the state information of the GPS module deactivated in the battery low state of the electronic device under the control of the control module C260 and the state information that the activated sensor turns deactivated by the request from the electronic device and external device C400. In this state, the electronic device may transmit an alert message on the battery low state of the electronic device to the external device C400 and deactivate the sensor module that is requested by the external device C400 or is not used for operating the particular function of the electronic device. The device state table may include the state information maintaining the GPS module in the activated state in the battery low state of the external device C400 under the control of the control module C260 and the state maintaining the sensor activated by the request from the electronic device and the request from the external device C400 in the activated state. In this state, the electronic device may transmit an alert message for the battery low state of the external device C400 to the external device C400.

In the above description, although examples of the device elements of the device state table are the GPS module, acceleration sensor, and gyro sensor, various embodiments are not limited thereto. For example, the device state table may further include device state information of various elements, such as the illumination sensor, the microphone related to running the voice recognition function, the headset or ear set related to audio output, and the communication module related to audio output.

According to an embodiment, the electronic device may include a control module C260 extracting the state-related information corresponding to the context information related to the communicable external device C400 and controlling at least one of the electronic device and the external device C400 based on the state-related information and at least one device element activated or deactivated in relation to the operation of the external device C400 corresponding to the control of the control module C260.

According to an embodiment, the electronic device may include at least one of a communication interface receiving at least one of weather information, location information, time information, weather information, information on the event of a predetermined local area, advertisement information, remaining battery information on the external device C400, and channel state information with the external device C400 and a memory C250 storing at least one of official celebration day information, personal celebration day information, personal schedule information, and remaining battery information on the electronic device.

According to an embodiment, the control module C260 may generate state control information controlling the activation or deactivation of at least one device element of the electronic device and at least one device element of the external device C400 based on the state-related information.

According to an embodiment, the control module C260 may activate the device element of the electronic device related to the support of a function run on the external device C400 upon communication connection between the electronic device and the external device C400.

According to an embodiment, in case the communication connection between the electronic device and the external device C400 connected via communication is released, the control module C260 may temporarily pause or deactivate the operation of the device element of the electronic device related to the support of the function run on the external device C400.

According to an embodiment, in case the electronic device enters the low battery state while the electronic device and the external device C400 are connected via communication, the control module C260 may deactivate at least one device element running on the electronic device and the device element of the electronic device related to the support of the function running on the external device C400.

According to an embodiment, the in case the external device C400 enters the low battery state while the electronic device and the external device C400 are connected via communication, the control module C260 may deactivate the device element of the activated electronic device related to the external device C400.

According to an embodiment, the control module C260 may maintain the device element operating on the electronic device among the activated device elements related to the external device in the activated state.

According to an embodiment, the control module C260 may generate screen interface control information related to the control of the screen interface of the external device C400 based on the state-related information and transmit the screen interface control information to the external device C400.

According to an embodiment, the control module C260 may receive the selection information corresponding to selection of at least one item included in the screen interface and activate the device element of the electronic device corresponding to the received selection information or activate a particular app of the electronic device.

According to an embodiment, the electronic device may include a control module performing control to activate the sensor corresponding to the request information, upon receiving the request information requesting to activate the sensor in relation to running the function of the external device and the communication interface forming the communication channel with the external device.

According to an embodiment, the control module may transmit at least one of at least a portion of the sensor signal gathered by the activated sensor and the signal processed based on the sensor signal to the external device.

According to an embodiment, the control module may perform control to deactivate the activated sensor according to at least one of the event related to the termination of the running function of the electronic device, the event related to the release of the communication connection with the external device, and the event related to a variation in the remaining battery of the electronic device or the external device.

According to an embodiment, the control module may restore the state of the sensor into the previous state to the connection with the external device corresponding to the occurrence of the event.

According to an embodiment, the control module may generate the screen interface control information outputted on the external device based on the gathered context information and transmit to the external device.

According to an embodiment, the control module may perform control to output at least one function selection object executable on the external device based on the gathered context information to the sub display module of the external device.

According to an embodiment, the control module, if receiving the particular function selection information from the external device, may output at least one app related to the received function selection information and automatically activate the same.

According to an embodiment, the control module may perform control to gather, based on the communication interface, the context information including at least one of weather information, location information, time information, weather information, information on the event of a predetermined local area, advertisement information, remaining battery information on the external device, and communication channel state information with the external device and at least one of official celebration day information, personal celebration day information, personal schedule information, and remaining battery information on the electronic device.

According to an embodiment, the control module may generate and store the state information table on at least one of the sensor activated or deactivated by the request from the external device and the sensor activated or deactivated by the request from the electronic device.

According to an embodiment, the control module may update the state information table when the activation or deactivation of the sensor is varied by releasing the communication connection with the external device or request from the external device.

FIG. 173 illustrates an external device according to an embodiment.

Referring to FIG. 173, the external device C400 may include a sub bus C410, a sub input module C420, a sub communication module C430, a sub display module C440, a sub storage module C450, a sub sensor module C470, and a sub control module C460. The external device C400 may further include an audio module supporting the output or gathering of the audio data.

The sub bus C410 may support the signal transfer between the sub input module C420, the sub communication module C430, the sub display module C440, the sub storage module C450, the sub sensor module C470, and the sub control module C460. According to an embodiment, the sub bus C410 may transfer the state control information received by the sub communication module C430 to the sub control module C460. The sub bus C410 may transfer the UI control information received by the sub communication module C430 to the sub display module C440 corresponding to the control of the sub control module C460. The sub bus C410 may transfer the event generated from the sub display module C440 or sub input module C420 to the sub control module C460 and transfer to the sub communication module C430 corresponding to the control of the sub control module C460.

The sub input module C420 may generate the input signal related to the operation of the external device C400. The sub input module C420 may include a physical key such as the home key. In case the sub display module C440 includes a touch function, the sub display module C440 may operate as the sub input module C420. The sub input module C420 may generate the event selecting a particular item form the UI including at least one item outputted on the sub display module C440. The generated event may be transferred to the sub control module C460.

The sub communication module C430 may form a communication channel with the electronic device (e.g., the electronic device 101 or 201). The sub communication module C430 may be, e.g., a communication module (e.g., a Bluetooth module or Wi-Fi direct communication module) forming a direct communication channel. The sub communication module C430 may receive at least one of the state control information and UI control information from the electronic device. The sub communication module C430 may transmit selection information selecting a particular icon or menu item from the menu screen or icon screen of the external device C400 to the electronic device. The sub communication module C430 may transmit the event information that the particular item is selected from the UI outputted on the sub display module C440 to the electronic device. According to an embodiment, the sub communication module C430 may transmit context information (e.g., the remaining battery information of the external device C400 or particular function termination information of the external device C400) related to the external device C400 to the electronic device.

The sub display module C440 may output the screen related to the operation of the external device C400. For example, the sub display module C440 may output a standby screen or menu screen of the external device C400. According to an embodiment, the sub display module C440 may output a clock information screen, a health coaching app icon output screen, and a schedule information screen. According to an embodiment, the sub display module C440 may output a screen corresponding to the basic UI control information received from the electronic device. Further, the sub display module C440 may output the screen corresponding to the varied UI control information varied by the context information gathered by the electronic device. The sub display module C440 may output a screen by selecting at least one item included in the screen corresponding to the UI control information and the information output screen related to the execution of the item.

The sub storage module C450 may store the app and data necessary for the operation of the external device C400. For example, the sub storage module C450 may store the content related to the screen corresponding to the UI control information received from the electronic device. Here, the content may include at least one item image and text information. The sub storage module C450 may store the UI control information provided from the electronic device.

The sub sensor module C470 may include at least one sensor operated on the electronic device C400. For example, the sub sensor module C470 may include a gyro sensor. The sub sensor module C470 may include an image sensor. In case the external device C400 interworks with the electronic device to perform a particular function, the sensor overlapping in function the sensor module operated on the electronic device may be deactivated. Of the sub sensor module C470, the sensor that was activated but then deactivated by the sensor operation of the electronic device may be automatically activated in case the communication channel with the electronic device is released or the electronic device is turned off.

The sub control module C460 may perform the processing and transfer of data of the external device C400 and the processing and transfer of control signals. According to an embodiment, the sub control module C460 may perform control to form a communication channel with the electronic device corresponding to the event occurring on the sub input module C420 or the communication connection request from the electronic device. Upon receiving at least one of the state control information and UI control information from the electronic device, the sub control module C460 may process the received information. For example, the sub control module C460 may control the activation or deactivation of at least one sensor of the sub sensor module C470 corresponding to the state control information. The sub control module C460 may control, e.g., at least one remaining battery alarm of at least one of the electronic device and the external device C400, an alarm requesting to charge the external device C400, and processing the transfer of a function performable on the electronic device among functions performed on the external device C400, corresponding to the state control information. According to an embodiment, the sub control module C460 may perform control to output the screen including at least one item on the sub display module C440 corresponding to the received UI control information. When a particular item is selected, the sub control module C460 may perform control to transmit the selection information to the electronic device.

FIG. 174 illustrates an electronic device operation method according to an embodiment.

Referring to FIG. 174, the control module C260 may perform the function operation or standby in operation C501. For example, the control module C260 may output a standby screen or particular menu screen. Or, the control module C260 may output a screen according to performing a particular function, have a sleep state, or may output a lock screen. According to an embodiment, the control module C260 may output a screen including a particular functional icon or particular menu that may instruct to interwork with the external device C400. Or, the control module C260 may control the communication interface (e.g., the communication interface 160) to have a communication standby state capable of reacting to the scan operation of the external device C400.

The control module C260 may identify whether an event related to the interworking function occurs in operation C503. According to an embodiment, the control module C260 may identify whether an event according to the selection of the icon or menu instructing to interwork with the external device C400 occurs. According to an embodiment, the control module C260 may identify whether a schedule event related to the interoperation with the external device C400 occurs. According to an embodiment, the control module C260 may identify whether an event corresponding to the reception of a communication connection request message from the external device C400 occurs. Or, the control module C260 may identify whether an event requesting to activate the app necessary to interwork with the external device C400 occurs. If no event related to the interworking function occurs, the control module C260 may perform control to perform the function in operation C505. For example, the control module C260 may perform control to run a particular function (e.g., sound source playing function, broadcast receiving function, or call function) corresponding to the type of the generated event or apply the event function to the function previously running. Or, the control module C260 may perform control to shift the electronic device into the sleep mode or turn-off state according to the type of the event.

If the interworking function-related event occurs in operation C503, the control module C260 may form a communication channel with the external device C400. For example, the control module C260 may control the communication interface (e.g., the communication interface 160) to form a communication channel with the external device C400, such as Bluetooth communication or Wi-Fi direct communication scheme. The control module C260 may perform control to gather the context information in operation C507. According to an embodiment, the control module C260 may generate the context information, and if the determined context information is gathered, may form a communication channel with the external device C400.

The control module C260 may identify the gathered context information and may identify whether there is context information related to the variation in the external device state in operation C509. The control module C260, if there is context information related to the variation in the state of the external device C400, may generate its corresponding control information. The control information may include, as mentioned above, at least one of the state control information controlling the activation or deactivation of at least one of the device elements of the external device C400 and the UI control information related to the UI control of the external device C400. The control module C260 may transmit the control information to the external device C400 in operation C511.

The control module C260 may identify whether selection information is received from the external device C400 in operation C513. Here, the selection information may be information corresponding to selection of any one item of at least one item included in the UI of the external device C400.

If the selection information is received in operation C513, the control module C260 may process the function according to the selection information in operation C515. For example, upon receiving the selection information corresponding to the selection of the item related to running a particular function from the external device C400, the control module C260 may perform control to activate the device element of the electronic device related to performing the function or activate the app related to performing the function.

The control module C260 may identify whether an event related to the termination of the function occurs in operation C517. If no event related to the termination of the function occurs in operation C517, the control module C260 may go to operation C507 to re-perform its subsequent operations. According to an embodiment, if no event related to the termination of the function occurs in operation C517, the control module C260 may go to the operation before operation C515 to maintain the function processing according to the selection information. If the event related to the termination of the function occurs in operation C517, the control module C260 may perform control to terminate the interworking function with the external device C400 and may go to operation before operation C501 to re-perform its subsequent operations. During this course, the control module C260 may perform control to deactivate the activated communication interface, GPS module, and sensor module including at least one sensor in relation to the support of the interworking function with the external device C400.

If the context information related to the variation in the state of the external device is not gathered in operation C509, the control module C260 may go to operation C517 skipping operations C511 to C515. Further, in case there is no reception of the selection information within a predetermined time of operation C513 from the external device C400, the control module C260 may skip operation C515 and go to operation C517.

FIG. 175 illustrates an external device operation method according to an embodiment.

Referring to FIG. 175, the sub control module C460 of the external device C400 may perform the function operation or standby in operation C601. For example, the external device C400 may perform a clock function, schedule information output function, or communication standby function in operation C601. Or, the external device may output a functional icon or menu related to the interworking function with the electronic device (e.g., the electronic device 101). Or, the external device C400 may perform assignment of a particular key button related to the interworking function with the electronic device. Or, the external device C400 may have a communication standby state for corresponding to the scan operation from the electronic device.

The sub control module C460 may identify whether an event related to the interworking function occurs in operation C603. For example, the sub control module C460 may identify whether an event corresponding to the selection of menu or key button or a functional icon related to running the interworking function occurs in operation C603. Or, the sub control module C460 may identify whether there is an event corresponding to the reception of communication connection request message from the electronic device. According to an embodiment, the sub control module C460 may identify whether there is an event requesting to activate a particular app (e.g., health coaching app or disease care function app) requiring the interworking with the electronic device.

The sub control module C460, if no interference related to the interworking function occurs, the control module C260 may perform control to perform a particular function in operation C605. For example, the sub control module C460 may perform control to perform a particular function (e.g., clock display function, weather display function, step counter function, and pulse wave detection function) of the external device (e.g., the external device C400). Or, the sub control module C460 may shift the external device into the sleep mode state (e.g., the turn-off state or low power operation mode of the sub display module C440). Or, the sub control module C460 may shift the external device into the turn-off state if the event related to the turn-off of the external device occurs.

If the event related to the interworking function occurs, the sub control module C460 may form a communication channel with the electronic device. The sub control module C460 may identify whether there is reception of control information in operation C607. Upon reception of the control information, the sub control module C460 may perform function control according to the control information in operation C609.

According to an embodiment, the sub control module C460, if receiving the state control information from the electronic device, may control the activation or deactivation of at least one sensor included in the sub sensor module C470 corresponding to the same. According to an embodiment, the sub control module C460 may shift the sub communication module C430 into the deactivation state corresponding to the state control information. According to an embodiment, the sub control module C460 may output the alert message transmitted from the electronic device upon reception of the state control information (e.g., the alarm message of the communication state with the electronic device being in the weak electric field state, the alarm message of the electronic device being in the low battery state, and the alarm message of the external device being in the low battery state).

According to an embodiment, the sub control module C460 may receive UI control information from the electronic device. The sub control module C460 may perform control to output the UI corresponding to the UI control information to the sub display module C440. Here, the UI control information may include UI-related information (e.g., background screen information, item image and text information, and item location information) to be displayed on the sub display module C440 of the external device. Or, the UI control information may include instruction information instructing to output at least one particular item of the UI-related information stored in the sub storage module C450 of the external device to have a particular shape and location.

The sub control module C460, upon receiving the UI control information in operation C609, may identify whether the selection event selecting a particular item (e.g., a particular function icon or menu item) included in the screen of the sub display module C440 is received in operation C611. The sub control module C460, upon reception of the selection event in operation C611, may transmit the selection information corresponding to the selection event to the electronic device in operation C613. According to an embodiment, when receiving the state control information, the sub control module C460 may skip operations C611 and C613 after operation C609 to go to operation C615. In case there is no reception of the control information in operation C607, the sub control module C460 may skip operations C609 to C613 to go to operation C615. Further, if there is no occurrence of the selection event within a predetermined time in operation C611, the sub control module C460 may skip operation C613 to go to operation C615.

The sub control module C460 may identify whether the event related to the termination of the function occurs in operation C615. If the function termination-related event does not occur, the sub control module C460 may go to operation C617 to perform control to maintain the interworking state with the external device C400. The sub control module C460 may re-perform the operations after operation C607. If the function termination-related event occurs, the sub control module C460 may go to the operation before operation C601 to re-perform its subsequent operations.

FIG. 176 is a signal flowchart of a request information operation system according to an embodiment.

Referring to FIG. 176, the electronic device C200 and the external device C400 may have a connection state in operation C701. In this relation, the electronic device C200 may attempt to form a communication channel by scanning the external device C400 as default when power is supplied. Or, the electronic device C200 may attempt to form a communication channel with the external device C400 at a predetermined period or when a particular app is activated or there is an interworking request. According to an embodiment, the external device C400 may attempt to form a communication channel with the electronic device C200 by scanning the electronic device C200 as default when power is supplied. Or, as described above, if such an event occurs where the particular app is requested to be activated or interworking with the electronic device C200 is requested, it may attempt to form a communication channel with the electronic device C200.

The electronic device C200 may gather first context information in operation C703. Here, the first context information may include message information, advertisement information, schedule information, location information, weather information, time information, season information, event information, communication connection state information with the external device C400, and communication connection information between the electronic device C200 and other electronic device, which are gathered through the communication interface (e.g., the communication interface 160). Further, the first context information may include the schedule information stored in the memory C250 of the electronic device C200 and the battery state information of the electronic device C200. The electronic device C200 may detect the control information according to the first context information in operation C705. The electronic device C200 may transmit the detected control information to the external device C400 in operation C707.

The external electronic device C400, upon reception of the control information from the electronic device C200, may perform state control or UI control according to the control information in operation C709. For example, the external electronic device C400 may control the activation or deactivation of at least one of the sub sensor module C470 and the sub communication module C430. The external electronic device C400 may output the particular UI by the UI control to the sub display module C440.

According to an embodiment, the external electronic device C400 may gather second context information in operation C711. For example, the external electronic device C400 may gather, as the second context information, the battery state information of the external electronic device C400, communication connection state information with the electronic device C200, particular function running information, and information on the time elapsing after the particular function runs. The external electronic device C400 may transmit the gathered second context information to the electronic device C200 in operation C713.

The electronic device C200, upon reception of the second context information from the external electronic device C400, may perform the state control corresponding to the second context information in operation C715. For example, the electronic device C200 may activate or deactivate at least one sensor included in the sensor module (e.g., the sensor module 240) of the electronic device C200 corresponding to the second context information. The electronic device C200 may control the activation or deactivation or temporary operation termination of the communication interface (e.g., GPS module or communication module supporting direct communication scheme) of the electronic device C200 corresponding to the second context information. The electronic device C200 may transmit a determined alert message or alarm message corresponding to the second context information to the external electronic device C400.

According to an embodiment, the method for operating a device may include the operation of gathering context information by the electronic device C200, the operation of extracting state-related information related to control of an external electronic device C400 communicable with the electronic device C200, and the operation of controlling at least one of the external electronic device C400 and the electronic device C200 based on the state-related information.

According to an embodiment, the gathering operation may include the operation of gathering at least one of weather information, location information, time information, weather information, information on the event of a predetermined local area, advertisement information, remaining battery information on the external device C400, and channel state information with the external device C400 using the communication interface (e.g., the communication interface 160) and the operation of gathering at least one of official celebration day information, personal celebration day information, personal schedule information, and remaining battery information on the electronic device C200 based on information stored in the memory C250.

According to an embodiment, the controlling operation may include the operation of generating state control information controlling the activation or deactivation of at least one device element of the electronic device C200 and at least one device element of the external device C400 based on the state-related information.

According to an embodiment, the controlling operation may further include the operation of activating the device element of the electronic device C200 related to the support of a function run on the external device C400 upon communication connection between the electronic device C200 and the external device C400.

According to an embodiment, in case the communication connection between the electronic device C200 and the external device C400 connected via communication is released, the controlling operation may further include the operation of temporarily pausing or deactivating the operation of the device element of the electronic device C200 related to the support of the function run on the external device C400.

According to an embodiment, in case the electronic device C200 enters the low battery state while the electronic device C200 and the external device C400 are connected via communication, the controlling operation may further include the operation of deactivating at least one device element running on the electronic device C200 and the device element of the electronic device C200 related to the support of the function running on the external device C400.

According to an embodiment, the in case the external device C400 enters the low battery state while the electronic device C200 and the external device C400 are connected via communication, the controlling operation may the operation of deactivating the device element of the activated electronic device C200 related to the external device C400.

According to an embodiment, the controlling may further include the operation of maintaining the device element operating on the electronic device C200 among the activated device elements related to the external device C400 in the activated state.

According to an embodiment, the controlling operation may include the operation of generating screen interface control information related to the control of the screen interface of the external device C400 based on the state-related information and transmitting the screen interface control information to the external device C400.

According to an embodiment, the controlling operation may include the operation of receiving the selection information corresponding to selection of at least one item included in the screen interface from the external device C400 and activating the device element of the electronic device C200 corresponding to the received selection information or activating a particular app of the electronic device C200.

According to an embodiment, the method for operating the device according to request information may include the operation of forming a communication channel with the external device, the operation of receiving request information requesting to activate the sensor in relation with running the function of the external device, and the operation of controlling to activate the sensor corresponding to the request information.

According to an embodiment, the method may the operation of transmitting at least one of at least a portion of the sensor signal gathered by the activated sensor and the signal processed based on the sensor signal to the external device.

According to an embodiment, the method may further include the operation of receiving at least one of the event related to the termination of the running function of the electronic device, the event related to the release of the communication connection with the external device, and the event related to a variation in the remaining battery of the electronic device or the external device and the operation of deactivating the activated sensor according to the reception of the event.

According to an embodiment, the method may further include the operation of restoring the state of the sensor into the previous state to the connection with the external device corresponding to the occurrence of the event.

According to an embodiment, the method may further include the operation of receiving context information, the operation of generating screen interface control information outputted on the external device based on the gathered context information, and the operation of transmitting the screen interface control information to the external device.

According to an embodiment, the method may further include the operation of performing control to output at least one function selection object executable on the external device based on the gathered context information to the sub display module of the external device.

According to an embodiment, the method may further include the operation of receiving the particular function selection information from the external device and the operation of outputting at least one app related to the received function selection information and automatically activating the same.

According to an embodiment, the operation of gathering the context information may include the operation of gathering, based on the communication interface, the context information including at least one of weather information, location information, time information, weather information, information on the event of a predetermined local area, advertisement information, remaining battery information on the external device, and communication channel state information with the external device and the operation of gathering at least one of official celebration day information, personal celebration day information, personal schedule information, and remaining battery information on the electronic device.

According to an embodiment, the method may further include the operation of generating the state information table on at least one of the sensor activated or deactivated by the request from the external device and the sensor activated or deactivated by the request from the electronic device and the operation of storing the state information table.

According to an embodiment, the method may further include the operation of updating the state information table when the activation or deactivation of the sensor is varied by releasing the communication connection with the external device or request from the external device.

According to an embodiment, the method for operating the device according to request information may include the operation of receiving request information to be activated from the external device connected via communication, the operation of activating the sensor based on the received request information, the operation of transmitting data generated based on the activated sensor to the external device, and the operation of deactivating the activated sensor in case the communication connection with the external device is released or the battery runs out.

FIG. 177 illustrates function mode-related control according to an embodiment.

Referring to FIG. 177, the electronic device C200 may maintain the GPS module in the turn-off state, the acceleration sensor in the turn-off state, and the gyro sensor in the turn-off state as in state C801. Here, although in the state screen C801, the GPS module item C811, the acceleration sensor item C813, and the gyro sensor item C815 are shown in the form of being displayed on the display module C240 (e.g., the display 150), various embodiments are not limited thereto. The state screen C801 shows the GPS module item C811, the acceleration sensor item C813, and the gyro sensor item C815 for understanding the state of the GPS module, acceleration sensor, and the gyro sensor, and the GPS module item C811, the acceleration sensor item C813, and the gyro sensor item C815 may be omitted according to varying the UI.

The electronic device C200, if the event related to the function interworking with the external device C400 is generated, may transmit defined UI control information to the external device C400. Here, as described above, the interworking function-related event may include various events (e.g., the event forming a communication channel with the external device C400, the event requesting to run a particular app, and the event of notifying of running a particular app in the external device C400). If the interworking function-related event occurs, the electronic device C200 may gather context information and generate UI control information corresponding thereto.

If receiving the UI control information from the electronic device C200, the external device C400 may output a first UI screen C830 to the sub display module C440 as in state C803. The first UI screen C830 may include function items C831, C833, C835, and C837 related to health coaching, e.g., the walking item C831, running item C833, biking item C835, and mountain climbing item C837. Accordingly, the external device C400 may provide an environment where it may immediately enter the first UI screen C830 upon interworking with the electronic device C200 or upon powering on. If any item, e.g., the mountain climbing item C831 of the function items C831, C833, C835, and C837 is selected, the external device C400 may generate selection information. The external device C400 may transmit the selection information to the external device C200.

If receiving the selection information on the mountain climbing item C831 from the external device C400, the electronic device C200 may perform control to activate or deactivate a particular device element accordingly. For example, the electronic device C200 may activate the GPS module as in state C805. Accordingly, the GPS module item C8111 may display the turn-on state. The electronic device C200 may maintain the acceleration sensor and gyro sensor in the deactivated state. Accordingly, the acceleration sensor item C813 and the gyro sensor item C815 may display the turn-off state. Although the state screen C805 also displays the GPS module item C8111, the acceleration sensor item C813, and gyro sensor item C815, the items may be omitted from display depending on UI settings.

FIG. 178 illustrates an operation as per a surrounding environment of an electronic device according to an embodiment.

Referring to FIG. 178, the electronic device C200 may gather sensor signals of the illumination sensor as context information as in state C901 and output to the display module C240. The control module C260 may analyze the illumination sensor signal to identify whether the ambient context is night time. In this process, the control module C260 may gather the current profile server and the sunrise/sunset time information at the current position. The control module C260 may analyze the sunrise/sunset time information and illumination sensor information at the current position to extract the current state-related information (e.g., night time). The control module C260 may generate control information (e.g., UI control information corresponding to the nighttime environment) based on the state-related information. The control module C260 may transmit the control information to the external device C400.

The external device C400, upon receiving the control information related to the nighttime environment from the electronic device C200, may output its corresponding screen on the sub display module C440 as in state C903. In one embodiment, the external device C400 may output the screen including the nighttime mode item C931 on the sub display module C440 as in state C903a. In one embodiment, the external device C400 may output the screen in which the nighttime walking item C931 is larger than other function items C933, C935, and C937 on the sub display module C440 as in state C903b. The external device C400 may output the screen in which the walking item C938 has a different color than the other function items C933, C934, and C936 on the sub display module C440 as in state C903c.

According to an embodiment, the external device C400 may output the items not fitting the nighttime context in a disapproving form. For example, the external device C400 may output mountain climbing (dangerous) item C937 and biking (dangerous) item C935 as in state C903b. The external device C400 may output the mountain climbing (dangerous) item C937 and the biking (dangerous) item C935 in a different color or background from the other function items C932 and C933. According to an embodiment, the external device C400 may output the running item C933 and walking item C938 in a different color and size from the other items C934 and C936 as in state C903c. For example, the external device C400 may output the running item C933 and walking item C938 in a larger size than the other items C934 and C936. According to an embodiment, the external device C400 may change the order of the items corresponding to the control information and output the same.

According to an embodiment, the electronic device C200 may gather weather information as the context information and output on the display module C240 as in state C905. In this relation, the electronic device C200 may access the server device at predetermined periods (e.g., every hour, every 12 hours, or every day) to gather the weather information at the current location or particular location. The electronic device C200 may analyze the weather information and generate control information corresponding to a particular context (e.g., storm or heavy rain). For example, the electronic device C200 may generate the same control information as that at the nighttime in case the storm or heavy rain information is included in the weather information. The external device C400 receiving the control information may output any one of the screens as in state C903.

FIG. 179 illustrates a schedule-related operation according to an embodiment.

Referring to FIG. 179, the electronic device C200 may output the time-designated schedule information corresponding to the context information corresponding to arrival of the time. The display module C240 may output the schedule information as in state D01 corresponding to the control of the control module C260. The control module C260 may generate control information according to the gathering the context information including the schedule information and transmit the same to the external device C400. In this relation, the control module C260 may extract state-related information (e.g., mountain climbing) from the schedule information. The control module C260 may generate control information corresponding to the extracted state-related information. The control module C260 may form a communication channel with the external device C400 and transmit the control information to the external device C400. Here, the control information may include the UI control information corresponding to the state-related information extracted from the schedule information.

If receiving the UI control information from the electronic device C200, the external device C400 may output its corresponding screen as in state D03. In one embodiment, the external device C400 may output the screen including the mountain climbing item D31 on the sub display module C440 as in state D03a. In one embodiment, the external device C400 may output the screen in which the mountain climbing item D31 is disposed in a different size from the other function items D33, D35, and D37 on the sub display module C440 as in state D03b. In one embodiment, the external device C400 may output the screen in which the mountain climbing item D31 has a different color from the other function items D33, D35, and D37 on the sub display module C440 as in state D03c. If the event selecting the mountain climbing item D31 occurs, the external device C400 may transmit the selection information corresponding to the occurring event to the electronic device C200.

According to an embodiment, the electronic device C200 may gather the current location information using the GPS module. In case the current location information indicates a predetermined area, e.g., Chunggye mountain, the electronic device C200 may output the current location information on the display module C240 in step D05. Here, the electronic device C200 may output the current location information with coordinate information or with the place name such as Chunggye mountain.

The electronic device C200 may gather the current location information as the context information. The electronic device C200, in case the current location is included in a particular determined location, e.g., a mountain area, may generate its corresponding control information. The electronic device C200 may transmit the generated control information to the external device C400. Accordingly, the external device C400 may output the screen of state D03 as mentioned at the location on the sub display module C440.

According to an embodiment, if particular schedule information is outputted at the corresponding time as in state D01, the electronic device C200 may identify the information put in the schedule information. For example, the electronic device C200 may extract "mountain climbing" information from the schedule information. If the "mountain climbing" information is extracted, the electronic device C200 may activate the GPS module to gather the current location information. In case the current location is included in the mountain area at the determined particular location, the electronic device C200 may generate the above-described control information and transmit to the external device C400. According to an embodiment, in case the current location information is included in an area other than the mountain, the electronic device C200 may omit the generation and transmission of the control information. The electronic device C200 may perform control to output the message requesting to identify the schedule information.

According to an embodiment, the electronic device C200 may gather the current location information as in state D05, and in case the current location information is included in the mountain area, it may identify the schedule information as in state D01. In case the schedule information includes "mountain"-related information, it may generate control information and transmit to the external device C400.

The electronic device C200, upon receiving the selection information from the external device C400, may perform its corresponding particular function. For example, the electronic device C200 may perform a sound source playing function and Internet access function related to the mountain climbing item D31 as in state D07. In this process, the electronic device C200 may perform the sound source playing function and Internet access function through the background processing with the screen lock set. The electronic device C200 may play a mountain climbing-related sound source in relation to performing the sound source playing function or may play the sound source searched through the Internet search. Further, the electronic device C200 may gather information regarding a pre-defined particular keyword, e.g., weather information, local area information, and information on famous restaurants, through the Internet search function. The electronic device C200 may output the gathered search information and sound source playing information on the display module C240. According to an embodiment, the electronic device C200 may output the information on the sound source playing function and Internet access function on the display module C240, while in the home screen state as in state D09. States D07 and D09 show examples of the search information related to Cheonggye mountain and playing music related to mountain climbing.

FIG. 180 illustrates a state control table operation related to forming a communication channel according to an embodiment.

Referring to FIG. 180, the electronic device C200 may manage the state control table related to the state of the device element during the course of interworking with the external device C400. In this course, the electronic device C200 may assign flags and manage in relation with varying the state of the device element. According to an embodiment, the electronic device C200 may have the state where the GPS module turns off, the state where the accessory module turns off, and the state where the gyro sensor turns on as in state D101 before forming a communication channel with the external device C400. Such state information may be outputted on the display module C240 or may be omitted from being outputted.

The electronic device C200 may have the state control table D110 corresponding to the state of the device elements in state D101. The state control table D110 may represent the use state of the external device C400 and the electronic device C200 for the GPS module, acceleration sensor, and gyro sensors. For example, the state control table D110 may have the information on the state in which the GPS module, acceleration sensor, and gyro sensors have not been requested to be activated from the external device C400 (the state information where no request to use is made). The state control table D110 may have the information on the state in which the GPS module, and acceleration sensors have not been requested to be activated by the electronic device C200. The state control table D110 may have the information on the state in which the gyro sensor has been requested to be activated by the control module C260 of the electronic device C200.

According to an embodiment, as in state D103, the external device C400 and the electronic device C200 may for a communication channel, and the electronic device C200 may generate UI control information corresponding to the gathering of the context information and transmit to the external device C400. The external device C400 may output the screen corresponding to the UI control information to the sub display module C440. The external device C400 may transmit selection information corresponding to the event occurring from at least one of the sub display module C440 or sub input module C420 to the electronic device C200. In this process, at least one of the external device C400 and the electronic device C200, e.g., the external device C400, may request to activate the GPS module of the electronic device C200. As in state D103, in relation with interworking with the external device C400, the electronic device C200 may have the state where GPS module is turned on, the state where the acceleration sensor is turned off, and the state where the gyro sensor is turned on. The electronic device C200 may output the state information of the sensors on the display module C240. Or, the state information may be omitted from being displayed.

The state control table D130 may have the state information that the GPS module of the electronic device C200 has been requested to be activated by the external device C400. The state control table D130 may have the state information that the acceleration sensor and the gyro sensor of the electronic device C200 have been not requested to be activated by the external device C400. The state control table D130 may have the state information that the GPS module and acceleration sensor of the electronic device C200 have been not requested to be activated by the control module C260 of the external device C400. The state control table D130 may have the state information that the gyro sensor of the electronic device C200 has been requested to be activated by the electronic device C200.

FIG. 181 illustrates a state control table operation related to disconnection according to an embodiment.

Referring to FIG. 181, the electronic device C200 may manage the state control table related to the state of the device element during the course of releasing the communication connection with the external device C400. For example, the electronic device C200 may have the state where the GPS module turns on, the state where the accessory module turns off, and the state where the gyro sensor turns on as in state D201 while forming a communication channel with the external device C400. Such state information may be outputted on the display module C240. Or, the state information may be omitted from being displayed. The electronic device C200 may have the state control table D210 corresponding to the state of the device elements. The external device C400 may output the UI screen including at least one item corresponding to the state of being communication connected with the electronic device C200 on the sub display module C440.

The state control table D210 may have the state information that the PGS module has been requested to be activated by the external device C400 and the state information that the acceleration sensor and gyro sensors have not been requested to be activated by the external device C400. The state control table D210 may have the state information that the GPS module and acceleration sensor have not been requested to be activated by the electronic device C200. The state control table D210 may have the information on the state in which the gyro sensor has been requested to be activated by the control module C260 of the electronic device C200.

If the communication connection between the electronic device C200 and the external device C400 is released as in state D203, the electronic device C200 may shift the GPS module from the turn-on state to the turn-off state. In this process, the electronic device C200 may deactivate the communication module used for communication connection with the external device C400. The electronic device C200 may output the information on the turn-on state or turn-off state of the device elements on the display module C240. The external device C400 may output the information related to the release of the communication connection with the electronic device C200 on the sub display module C440 in state D203.

In relation with the release of the communication connection, the state control table D230 may have the state information that the GPS module of the electronic device C200 has been requested to be paused by the external device C400. The state control table D230 may have the state information that the acceleration sensor and the gyro sensor of the electronic device C200 have been not requested to be activated by the external device C400. The state control table D230 may have the state information that the GPS module and acceleration sensor of the electronic device C200 have been not requested to be activated by the external device C400. The state control table D130 may have the state information that the gyro sensor of the electronic device C200 operated independently from the operation of the external device C400 is in the state of having not been requested to be activated by the external device C400 but has been requested to be activated by the electronic device C200. According to an embodiment, if the communication connection released state is maintained even after a predetermined time elapses, the electronic device C200 may change the state information that the GPS module has been paused into the state information that activation has not been requested in the state control table D230.

FIG. 182 illustrates a state control table operation related to a low battery status of an electronic device according to an embodiment.

Referring to FIG. 182, as the power is consumed by operating the device, the electronic device C200 may have the power state that power is not more than a predetermined value, e.g., the low battery state. In this case, the electronic device C200 may release the communication connection with the external device C400.

According to an embodiment, before entering the low battery state, the electronic device C200 may have the state where GPS module is turned on, the state where the acceleration sensor is turned off, and the state where the gyro sensor is turned on as in state D301. The state information of each device element may be outputted on the display module C240. Or, the state information may be omitted from being displayed. Before the electronic device C200 enters the low battery state, the external device C400 may output the UI screen including at least one item related to interworking with the electronic device C200 on the sub display module C440.

The electronic device C200 may have the state control table D310 in state D301 before entering the low battery state. The state control table D310 may have the state information that the PGS module has been requested to be activated by the external device C400 and the state information that the acceleration sensor and gyro sensors have not been requested to be activated by the external device C400. The state control table D310 may have the state information that the GPS module and acceleration sensor have not been requested to be activated by the electronic device C200. The state control table D310 may have the information on the state in which the gyro sensor has been requested to be activated by the control module C260 of the electronic device C200.

As the electronic device C200 enters the low battery state, the electronic device C200 may release the communication connection with the external device C400 as in state D303. The electronic device C200 may transmit the information on the low battery state of the electronic device C200 before releasing the communication connection to the external device C400. The electronic device C200 may shift the GPS module from the turn-on state to the turn-off state as in state D303 corresponding to entry into the low battery state. Further, the electronic device C200 may shift the gyro sensor from the turn-on state to the turn-off state in relation to the low battery state. In this process, the electronic device C200 may deactivate the communication module used for communication connection with the external device C400. The external device C400 may receive the information on entry into the low battery state of the electronic device C200 from the electronic device C200 before releasing the communication connection. The electronic device C400 may output the information regarding the low battery state of the electronic device C200 to the sub display module C440 as in state D303.

The electronic device C200 may have the state control table D300 in relation to entry into the low battery state. The state control table D330 may have the state information that the GPS module, the acceleration sensor and the gyro sensor of the electronic device C200 have been not requested to be activated by the external device C400. Further, the state control table D330 may have the state information that the GPS module, the acceleration sensor and the gyro sensor of the electronic device C200 have been not requested to be activated by the electronic device C200. The electronic device C200 may minimize power consumption by deactivating the sensor module and GPS module in relation to entry into the low battery state. In this state, the electronic device C200 may perform control to maintain the mobile communication, such as 3G/4G, in the standby state.

FIG. 183 illustrates a state control table operation related to a low battery status of an external device according to an embodiment.

Referring to FIG. 183, the external device C400 may support to perform a particular function in interoperation with the electronic device C200 as in state D401. For example, the external device C400 may output a screen including at least one item related to health coaching to the sub display module C440 by running the health coaching function interworking with the electronic device C200. In relation with supporting services based on the external device C400, the electronic device C200 may have the state where GPS module is turned on, the state where the acceleration sensor is turned off, and the state where the gyro sensor is turned on. The state information of each device element may be outputted on the display module C240. Or, the state information may be omitted from being displayed. The electronic device C200 may have the state control table D410 corresponding to the communication connection state.

The state control table D410 may have the state information that the PGS module has been requested to be activated by the external device C400 and the state information that the acceleration sensor and gyro sensor have not been requested to be activated by the external device C400. The state control table D410 may have the state information that the GPS module has been requested to be activated by the electronic device C200, the state information that the acceleration sensor has not been requested to be activated by the electronic device C200, and the gyro sensor has been requested to be activated by the electronic device C200.

As the power is consumed by operating the device, the external device C400 may have the power state that power is not more than a predetermined value, e.g., the low battery state. The external device C400, upon entry into the low battery state, may output the information on the low battery entry state to the sub display module C440 as in state D403. The external device C400, upon entry into the low battery state, may transfer its information to the electronic device C200. The electronic device C200 may release the communication connection with the external device C400 in relation with entry into the low battery state of the external device C400.

As the electronic device C400 enters the low battery state, the electronic device C200 may release the communication connection with the external device C400. In relation with entry into the low battery state of the external device C400, the electronic device C200 may have the state where GPS module is turned on, the state where the acceleration sensor is turned off, and the state where the gyro sensor is turned on as in state D403. In this process, the electronic device C200 may deactivate the communication module used for communication connection with the external device C400.

The state control table D430 may have the state information that the GPS module, the acceleration sensor and the gyro sensor of the electronic device C200 have been not requested to be activated by the external device C400. The state control table D430 may have the state information that the GPS module has been requested to be activated by the electronic device C200, the state information that the acceleration sensor has not been requested to be activated by the electronic device C200, and the gyro sensor has been requested to be activated by the electronic device C200. If the communication connection is released as the external device C400 enters the low battery state, the electronic device C200 may perform control to maintain the activated device elements in the turn-on state in relation to the operation of the electronic device C200.

FIG. 184 illustrates a device operation method according to an embodiment.

Referring to FIG. 184, in the device operation method, the electronic device C200 may identify whether an event related to a request for communication connection with the external device C400 occurs in operation D501. For example, the electronic device C200 may identify whether a message related to a request for communication connection is received from the external device C400. Or, the electronic device C200 may identify whether there is an input event or schedule information requesting for communication connection with the external device C400.

If the event related to the request for communication connection with the external device C400 occurs in operation D501, the electronic device C200 may process a communication connection according to the event. For example, the electronic device C200 may directly form a communication channel with the external device C400 using at least one communication module included in the communication interface 130.

The electronic device C200 may receive the sensor information to be activated from the external device C400 in operation D503. In this connection, if a request related to running a particular function occurs with the communication channel with the electronic device C200 formed, the external device C400 may identify whether the sensor supporting to run the function is included in the external device C400. In case the sensor related to running the particular function is not in the external device C400, the external device C400 may transfer the sensor information requested to run in relation to running the function to the electronic device C200.

In operation D505, if receiving the sensor information including the information on the sensors requested to run from the external device C400, the electronic device C200 may perform control to activate each sensor based on the information. For example, the electronic device C200 may receive sensor information corresponding to the GPS module activation request from the external device C400. The electronic device C200 may activate the GPS module corresponding to the activation request from the external device C400.

The electronic device C200 may transmit data generated based on the sensor through the communication interface (e.g., the communication interface 160) in operation D507. For example, the electronic device C200 may transfer the sensor signal gathered by the GPS module requested to be activated by the external device C400 to the external device C400. In this process, the electronic device may transfer the sensor signal gathered by a particular sensor signal as it is or may process and transfer the sensor signal corresponding to running a function of the external device C400. According to an embodiment, in case the function run by the external device C400 is mountain climbing, the electronic device C200 may transmit map information within a predetermined range from around the current location and the sensor signal gathered by the GPS module, along with the map information, to the external device C400. According to an embodiment, the electronic device C200 may analyze the travel speed of the external device C400 and may adjust the period of transmission of the sensor signal gathered by the GPS module in real-time to be varied. According to an embodiment, the electronic device C200 may transmit only a portion of the information gathered by the GPS module according to the attribute of the function run by the external device C400. For example, the electronic device C200 may compute the location information corresponding to the accuracy of the function run on the external device C400 from the information gathered by the GPS module and transmit the location information corresponding to the accuracy to the external device C400.

The electronic device C200 may identify whether disconnection of communication with the external device C400 or battery shortage (e.g., at least one of the battery shortage of the electronic device C200 and the battery shortage of the external device C400) occurs in operation D509. The electronic device C200 may control the performing of operation D507 in case communication disconnection or battery shortage does not occur in operation D509.

If the disconnection of communication with the external device C400 or battery shortage occurs in operation D509, the electronic device C200 may go to operation D511 to control the deactivation of the sensor. In this process, the electronic device C200 may deactivate the sensors requested to be deactivated by the external device C400. The electronic device C200, in case the sensors activated by the external device C400 are requested to be activated by the control module C260, may perform control to remain activated under the control of the electronic device C200. The electronic device C200 may update the state information table if the activated sensor turns deactivated corresponding to the termination of the function interworking with the external device C400.

Additionally or alternatively, the electronic device C200, if receiving an event related to the termination of the currently running function from the external device C400, may go to operation D511. Additionally or alternatively, the electronic device C200 may terminate the function interworking with the external device C400 and go to operation D511 if an event occurs which is related to the release of the function interworking with the external device C400 or termination of the function from the input/output interface (e.g., the input/output interface 140).

As described above, according to an embodiment, the device operation method and device supporting the same may provide support so that the electronic device C200 grasps the context information (e.g., schedule or location of user) and adaptively (or actively) vary the screen elements (e.g., objects or items, background, or arrangement of objects outputted on the screen) of the sub display module C440 of the external device C400 based on the information so that the user may easily select a function in the external device C400.

Further, according to an embodiment, in case the electronic device C200 includes a sensor related to the support of a function selected by the sub display module C440 of the external device C400 (e.g., a function according to the selection of a particular object or item displayed in relation to the execution of function on the menu screen), the device operation method and device supporting the same may request the electronic device C200 to activate the sensor and receive a sensor signal from the electronic device C200 to support the execution of the function. Here, in case the sensor related to the execution of the particular function is included in both the external device C400 and the electronic device C200, such process may be performed so that the sensor of the electronic device C200 may be utilized as default. Additionally or alternatively, according to an embodiment, the device and method may operate the sensor disposed in the external device C400 according to the remaining battery state in at least one state of the case where the remaining battery of the electronic device C200 is not more than a predetermined level or the remaining battery of the external device C400 is not less than a predetermined level.

Further, according to an embodiment, the device operation method and device supporting the same may restore the state of the electronic device C200 into a state before interworking with the external device C400 corresponding to at least one context of when a particular function of the external device C400 is terminated, when communication connection with the external device C400 is released, or when the remaining battery of at least one of the electronic device C200 or the external device C400 is not more than a predetermined level. For example, if the communication connection with the external device C400 is released, the electronic device C200 may restore the sensor activated by the request from the external device C400 into the state according to the setting of the electronic device C200.

According to an embodiment, the device operation method and device supporting the same may recommend at least one function (app) to be run on the electronic device C200 in relation with the function selected by the external device C400. For example, if a mountain climbing function is selected by the external device C400, the electronic device C200 may perform control to automatically run a sound source playing app and web access function in relation with the mountain climbing function, or if receiving function selection information of the external device C400 for easier execution and selection, output to the display module D240 corresponding thereto.

FIG. 185 is a block diagram E200 illustrating a control module E201 of an electronic device (e.g., the electronic device 101) according to an embodiment.

Referring to FIG. 185, the control module E201 may include a state determining module E210, a direction determining module E220, and a content control module E230. The control module E201 may be the additional function module 170 shown in FIG. 51.

The state determining module E210 may determine the current state of the user (hereinafter, "user state") who uses the electronic device based on sensing data gathered from one or more sensors (e.g., the acceleration sensor, gyro sensor, or HRV sensor) included in the sensor module (e.g., the sensor module 240). For example, if the user's heart rate measured by the HRV sensor is 85 to 130, the state determining module E210 may determine that the user is doing exercise.

The user state determined by the state determining module may include the type of exercise being done by the user, the progress state of the exercise, the strength of the exercise, and the user's health condition. According to an embodiment, the electronic device may previously receive body information, such as the user's age, height, or weight, from the user in order to more exactly grasp the user state.

According to an embodiment, the state determining module may determine a stress level for the user. For example, it is assumed that when the user's heart rate is 70 to 90, it is normal. The state determining module may determine that the stress level for the user is low if the user's heart rate is 91 to 100, that the stress level for the user is medium if the heart rate is 101 to 115, and that the stress level for the user is high if the heart rate is 116 or more. Further, in case the stress level departs from a preset value range, the state determining module may control the display (e.g., the display 150) to display a stop exercise alarm so that the user may stop the exercise he is now doing. For example, also in case the stress level for the user corresponds to medium or high among high, medium, and low, the control module E210 may control the display to display the stop exercise alarm so that the user may stop the exercise he is now doing.

The direction determining module E220 may determine the direction of the display, particularly, the screen displaying contents, by analyzing signals, i.e., sensing signals, gathered from one or more sensors (e.g., acceleration sensor or gyro sensor) included in the sensor module.

The direction determining module E220 may compute the rotational direction of the screen. For example, if the electronic device is of wrist watch type, the screen displaying one or more contents may be in the state of having turned 30 degrees with respect to the center of the user's left wrist.

The content control module E230 may determine the display direction of the contents displayed on the screen based on the screen direction determined by the direction determining module E220. For example, if the content displayed on the screen is text, the content control module E230 may determine that the text is displayed horizontally or vertically depending on the direction of the screen. That is, the content control module E230 may control the display so that the text is outputted from left to right or from top to bottom.

According to an embodiment, the content control module E230 may control the display so that two or more contents displayed on one screen are outputted in different directions. For example, it is assumed that first text, second text, and an image are displayed on the screen. The content control module E230 may determine that the first text and image are displayed from left to right on the screen and that the second text is displayed from top to bottom on the screen.

The content control module E230 may determine the manner of displaying the outputted contents based on the user state determined by the state determining module. For example, in case the user's movement is strenuous (e.g., in case the user does high-movement strength exercise), the state determining module may restrict the number of contents displayed through the display or the size of each content. Further, the state determining module may allow the user to easily identify the contents by increasing the size of the content. For example, in case the user's movement is not strenuous, such as when the user abstains from doing exercise or take a light walk, the state determining module may not restrict the number of contents displayed through the display. Further, the state determining module may control the display to reduce the size of the content and display a plurality of contents on the same screen or may control the display so that the screens including a plurality of contents may be sequentially displayed.

According to an embodiment, an electronic device may include a display including a screen displaying a content and a control module controlling the display to obtain sensing data, determine a user's current state based on the sensing data, determine a content to be displayed on the screen based on the current state, and display the content.

According to an embodiment, the sensing data may include one or more of the user's blood pressure, blood flow, heart rate, body temperature, respiratory rate, oxygen saturation, heart-lung sound, or blood sugar.

According to an embodiment, the control module may determine one or more of the type of exercise the user is doing, the strength of the exercise, the progress state of the exercise, the travel direction of the user, and the travel speed.

In one embodiment, the control module may adjust the number of contents to be displayed on the screen depending on the strength of exercise.

In one embodiment, the control module may reduce the number of contents to be displayed on the screen as the exercise strength increases and increase the number of the contents to be displayed on the screen as the exercise strength decreases.

In one embodiment, the control module may adjust the number of contents to be displayed on the screen depending on the travel speed.

In one embodiment, the control module may reduce the number of contents to be displayed on the screen as the travel speed increases and increase the number of the contents to be displayed on the screen as the travel speed decreases.

In one embodiment, the control module may determine the user's stress level, determine whether the stress level is not less than a preset threshold, and in case the stress level is not less than the threshold, control the display to display a stop exercise alarm on the screen.

In one embodiment, the control module, in case the stress level is less than the threshold, may control the display to display a content allowing the user to continue the exercise.

In one embodiment, the control module may determine the direction of the screen based on the sensing data, determine the display direction of the content based on the direction of the screen, and control the display to display the content depending on the display direction.

In one embodiment, the control module, in case the horizontal length of the screen is larger than its vertical length, may control the display to display the content in a horizontal direction.

In one embodiment, the control module, in case the vertical length of the screen is larger than its horizontal length, may control the display to display the content in a vertical direction.

In one embodiment, the control module may control the display to display the content on a portion of the screen in the horizontal direction and control the display to display on a remaining portion of the screen in the vertical direction.

In one embodiment, the control module may determine a rotational angle of the screen based on a slope of the electronic device included in the sensing data and may control the display to display the content in a leaning position to a direction of the screen based on the rotational angle.

In one embodiment, the control module, in case the angle between the direction of the screen and the opposite direction of the user's view is less than a preset reference value, may control the display to display the content in the horizontal direction.

In one embodiment, the control module, in case the angle between the direction of the screen and the opposite direction of the user's view is not less than the preset reference value, may control the display to abstain from displaying the content on the screen.

In one embodiment, the control module may determine the degree of the user's movement as the user's state determined based on the sensing data, and if the degree of the user's movement is not less than a preset reference value, may restrict the number of contents displayed on the screen.

In one embodiment, the control module may not restrict the number of contents displayed on the screen if the degree of the user's movement is less than the preset reference value.

FIG. 186 is a flowchart illustrating an example of a method of displaying content by an electronic device according to an embodiment.

Referring to FIG. 186, the sensor module may gather sensing data under the control of the control module E201 (E302). The sensing data may include various sensor values measured by the sensor module (e.g., the user's blood pressure, heart rate, body temperature, respiratory rate, oxygen saturation, heart-lung sound, or blood sugar).

The control module E201 of the electronic device E201 may determine the user's current state based on the sensing data (E304). The user's current state may be whether the user does exercise, and if so, the type of the exercise, the progress state of the exercise, the strength of the exercise, and the user's health condition.

If the user's current state is determined in step E304, the content control module E230 may determine a content to be displayed on the screen based on the user's current state (E306). For example, if the user's exercise strength is high, the content control module E230 may determine the current time and calorie consumption as the content to be displayed on the screen. By contrast, if the exercise strength is low, the content control module E230 may determine the current time, exercise duration, calorie consumption, heart rate, and blood pressure as the content to be displayed on the screen and may determine to display more contents than when the exercise strength is medium.

The display may display the content determined by the content control module E230 in step E306 on the screen (E308).

FIG. 187 is a flowchart illustrating an example of a method of displaying content by an electronic device according to an embodiment.

Referring to FIG. 187, the sensor module may gather sensing data under the control of the control module E201 (E402). The sensing data may include various sensor values measured by the sensor module (e.g., the speed, acceleration, slope, or GPS coordinates of the electronic device).

The control module E201 of the electronic device may determine the direction of the screen of the display based on the sensing data (E404). Here, the direction of the screen may be the direction in which light is emitted from a LCD when the screen is assumed to be implemented as the LCD. For example, under the assumption that the electronic device is implemented in a circular wrist watch type, the direction determining module E220 may determine a variation in the orientated direction varied by the movement (e.g., a tilt of the electronic device worn on the wrist) and the oriented direction of the screen using sensing data (e.g., the travel speed, travel acceleration, travel direction, or slope of the electronic device) measured by the acceleration sensor or gyro sensor of the electronic device in step E404.

If the direction of the screen is determined in step E404, the content control module E230 may determine the display direction of the content based on the direction of the screen (E406). For example, the content control module E230 may determine that the text displayed on the screen is displayed in the horizontal or vertical direction.

The display may display one or more contents on the screen according to the display direction of the screen determined in step E406 (E408).

Although it is described in connection with FIG. 187 that the direction of the screen indicates the direction in which the screen faces, the direction in which the screen may be a direction (orientation) in which the contents displayed on the screen are sorted. For example, it is assumed that the screen is implemented as a rectangular LCD. The direction of the screen may be a sorted direction of the contents displayed on the rectangular LCD (e.g., from left to right or from top to bottom). According to an embodiment, the content control module E230 may determine the direction of the user's view or user's arm movement and determine the angle at which the screen turns with respect to the view direction based on the user's arm movement or user's view direction. For example, the content control module E230 may determine which one of the landscape mode and portrait mode the electronic device is positioned closer to.

FIG. 188 is a flowchart illustrating another example of a method of displaying content by an electronic device according to an embodiment.

Referring to FIG. 188, the sensor module may obtain or gather sensing data under the control of the control module E201 (E502). Here, the sensing data generated by the sensor module may include one or more of the travel speed, travel acceleration, travel direction, or slope of the electronic device, and the sensing data may also include one or more of the user's blood pressure, heart rate, respiratory rate, oxygen saturation, calorie consumption, ECG, and EMG.

The control module E201 of the electronic device may determine the direction of the screen of the display or the user's current state based on the sensing data (E504). Here, the direction of the screen may be the direction in which light is emitted from a LCD when the screen is assumed to be implemented as the LCD. For example, if it is assumed that the electronic device is implemented in a circular wrist watch-type, the direction determining module E220 may determine that the direction of the screen is in the state of having turned 30 degrees clockwise with respect to the center of the user's left wrist in step E504. The user's current state determined by the control module E201 in step E504 may be, e.g., the state in which the user wearing the electronic device implemented as a wearable device is doing exercise (e.g., walking, jogging, or swimming).

If the user's current state or direction of screen is determined in step E504, the content control module E230 may determine the content to be displayed on the screen and the display direction of the content based on the user's current state and the direction of the screen (E506). For example, it is assumed that the content to be displayed on the screen is text saying "Message from Jim," and the font size of the characters in the text is the same. The content control module E230 may control the display to display the text in the horizontal or vertical direction according to the direction of the screen. Further, if the user's state is determined to be in the state of doing exercise, the content control module E230 may perform control so that "Message from" and "Jim" in the text are different in output size from each other. According to an embodiment, the control module E201 may process the text "Message from Jim" having the same font size to reduce the font size of "Message from" while increasing the font size "Jim." At this time, the font color of "Jim" may be different from the color of the other text for distinction.

The display may display the content on the screen according to the display direction determined in step E506 (E508).

According to an embodiment, a method for operating an electronic device may include the operation of determining movement information of the electronic device through an acceleration sensor or gyro sensor, the operation of determining bio information for a user by analyzing one or more bio signals, and the operation of controlling the operation of the electronic device according to the movement information and the bio information.

According to an embodiment, the method for operating the electronic device may include the operation of determining whether a communication module communicating with an external device is connected with the external device and the operation of controlling the operation of the electronic device according to a state of connection with the external device.

According to an embodiment, the method for operating the electronic device may include the operation of pairing with one or more external devices, the operation of determining movement information of the electronic device using a motion sensor, the operation of determining the bio information for the user by analyzing one or more bio signals, the operation of determining a service that may be provided to the user from the electronic device based on the movement information or the bio information, and the operation of providing the service to the user.

According to an embodiment, a method for displaying a content by an electronic device may include the operation of obtaining sensing data, the operation of determining a current state of a user based on the sensing data, the operation of determining the content to be displayed on a screen based on the current state, and the operation of displaying the content on the screen.

According to an embodiment, the method for displaying the content by the electronic device may include the operation of obtaining sensing data for determining a direction of the screen, the operation of determining the direction of the screen based on the sensing data, the operation of determining a display direction of the content according to the direction of the screen, and the operation of displaying the content according to the display direction.

FIG. 189 is a flowchart illustrating another example of a method of displaying content by an electronic device according to an embodiment. In FIG. 189, the user is assumed to do exercise.

Referring to FIG. 189, the sensor module may obtain sensing data under the control of the control module E201 (E602). Here, the sensing data obtained by the sensor module may include one or more of the travel speed, travel acceleration, travel direction, or slope of the electronic device, and the sensing data may also include one or more of the user's blood pressure, heart rate, respiratory rate, oxygen saturation, calorie consumption, ECG, and EMG.

The control module E201 of the electronic device may determine the user's current state based on the sensing data (E604). The user's current state determined by the control module E201 in step E604 may include the type, strength, or progress state of the exercise being done by the user wearing the electronic device implemented as a wearable device. If the user is doing exercise, the user's current state may include the user's stress level. According to an embodiment, the control module E201 may determine the user's stress level in step E604. The stress level may be determined based on the exercise being done by the user, the strength of the exercise, the progress state of the exercise, the time required for the exercise, or the body temperature, blood pressure, or heart rate of the user.

If the user's current state is determined in step E604, the control module E201 may determine whether the user's stress level is not less than a threshold (E606). The threshold may be a reference value for determining whether the user may continue to do exercise. For example, if the user's heart rate is 100 or more, the control module E201 may determine that the stress level is the threshold or more. Further, if the user's systolic blood pressure is 160 mmHg or more, the control module E201 may determine that the stress level is the threshold or more. As described above, if the stress level is the threshold level or higher, the control module E201 may request the user to stop exercise.

In case it is determined in step E606 that the stress level is the threshold or higher (E606, yes), the control module E201 may control the display to display a stop exercise alarm requesting the user to stop exercise on the screen (E608). By displaying the stop exercise alarm as above, the electronic device may prevent a threat to the user's health.

If it is determined in step E606 that the stress level is less than the threshold (E606, no), the control module E201 may determine an operation according to the user's current state (E612). The control module E201 may control the electronic device to run the operation determined in step E614. If the stress level is less than the threshold, the control module E201 may control the display to display, e.g., an exercise course, on the screen so that the user may continue the exercise.

According to an embodiment, a method for operating an electronic device may include the operation of determining movement information of the electronic device based on sensor data measured by a sensor module, the operation of determining bio information on a user by analyzing one or more bio signals, and the operation of controlling an operation of the electronic device according to the movement information and the bio information.

According to an embodiment, the method for operating the electronic device may include the operation of determining whether a communication module communicating with an external device is connected with the external device and the operation of controlling the operation of the electronic device according to a state of connection with the external device.

According to an embodiment, the method for operating the electronic device may include the operation of pairing with one or more external devices, the operation of determining movement information of the electronic device using an acceleration sensor or gyro sensor, the operation of determining the bio information for the user by analyzing one or more bio signals, the operation of determining a service that may be provided to the user from the electronic device based on the movement information or the bio information, and the operation of providing the service to the user.

According to an embodiment, a method for displaying a content by an electronic device may include the operation of obtaining sensing data, the operation of determining a current state of a user based on the sensing data, the operation of determining the content to be displayed on a screen based on the current state, and the operation of displaying the content on the screen.

According to an embodiment, the method for displaying the content by the electronic device may include the operation of obtaining sensing data for determining a direction of the screen, the operation of determining the direction of the screen based on the sensing data, the operation of determining a display direction of the content according to the direction of the screen, and the operation of displaying the content according to the display direction.

Figure 190A:

FIG. 190 is a view illustrating an example of a method of displaying content by an electronic device according to an embodiment. In FIGS. 190(a) and (b), it is assumed that the user wears the electronic device on a portion of his body. Various contents displayed on the screen by the display may be displayed in image form, and the image displayed over the entire screen is referred to as a "screen image."

FIG. 190(a) shows a basic screen image (E701) of the electronic device, and the screen include the current time, date, and day. For example, in case the user is not doing exercise, the control module E201 may control the display to display the basic screen image E701.

Figure 190B:

FIG. 190(b) shows an example of content displayed on the screen through the display by the electronic device in case the user does exercise. In FIG. 190(b), it is assumed that the user does jogging. Referring to FIG. 190(b), the control module E201 of the electronic device may control the display to display one or more exercise mode screen images E711, E712, E713, and E714. The exercise mode screens may display contents, such as the type of exercise, exercise duration, remaining time, travel distance, calorie consumption, user's heart rate, stress level due to exercise, or progress rate of exercise. The exercise mode screen images E711 to E714 of FIG. 190(b), respectively, are the screen image E711 showing the exercise index, the screen image E712 showing the exercise duration, the screen image showing the user's stress level, and the screen image E714 showing the progress rate of exercise. According to an embodiment, the exercise mode screen images E711, E712, E713, and E714, respectively, may be switched into other screen images by the user's input entered through the screen of the display, such as a scroll input. For example, if a scroll input that moves from above to down or from right to left is entered while the exercise mode screen image E711 is displayed on the screen E150, the display may switch the exercise mode screen information E711 into the exercise mode screen image E712 and displays. Although only user input through the screen is described in connection with FIG. 190, the user input may be a voice input or gesture input according to other embodiments. Further, the electronic device may trace the user's view and may recognize the user's traced view as the user input. The control module E201 may control the electronic device according to various user inputs, such as the voice input, gesture input, or user's view, e.g., switching screen images displayed on the screen or controlling the scroll.

In case the electronic device runs the exercise mode, the user does exercise, and thus, although the electronic device displays the exercise mode screen images (e.g., the exercise mode screen images E711, E712, E713, and E714) along with a vibration, the user might not identify it. In case the user fails to identify the exercise mode screen image as described above, the electronic device may automatically set the exercise mode screen image that the user has failed to identify as an initial screen image or default screen image. For example, in case a particular exercise mode screen image along with a vibration is displayed, but is determined to have not been identified by the user, the control module E201 may set the particular exercise mode screen image as the home screen image until the user identifies it. Accordingly, the user need not enter a separate input to the electronic device in order to identify the particular exercise mode screen image. Further, since the particular exercise mode screen image may be set as the initial screen image, the number of screen images that are unnecessary for the user to identify may be reduced, thus leading to power savings in the electronic device.

Figure 191A:
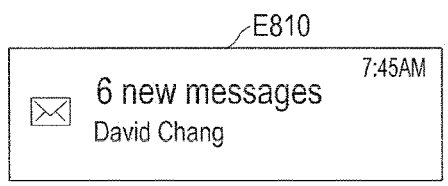

FIG. 191 is a view illustrating an example of a method of displaying content by an electronic device according to an embodiment. In FIGS. 191(a) and (b), it is assumed that the user wears the electronic device on a portion of his body, and the user is doing exercise.

FIG. 191(a) shows a message notification screen image E810 to inform the user of the number of messages received by the electronic device or that a new message has arrived. The display may display the number of new messages unread by the user, the sender of message, and the current time through the notification screen image E810. In FIG. 191(a), the number of new messages unread by the user is six.

The electronic device may receive a user input for displaying the content of new message while displaying the message notification screen image E810. For example, while the message notification screen image E810 is displayed on the screen, the electronic device may receive a user input by which the user taps the screen surface with his fingertip or stylus pen to display the content of message. If the user input to display the content of message is inputted to the electronic device, the control module E201 may control the display to switch the screen image from the notification screen image E810 to the message display screen image E820.

Figure 191B:
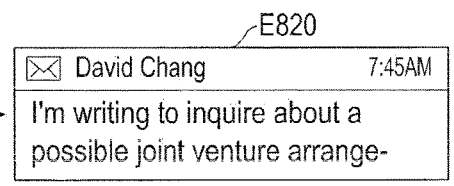

FIG. 191(b) shows the message display screen image E820 displaying the content of one of the new messages. The display may display, e.g., the sender, content of message, current time, or reception time through the message screen image E820.

In one embodiment, the electronic device may switch the screen image from the message display screen image E820 to the message notification screen image. While the message display screen image E820 is being displayed through the display as shown in FIG. 191(b), the electronic device may receive a user input to display the content of the message. For example, while the message notification screen image E810 is displayed through the display, the electronic device may receive a user input by which the user taps the screen surface with his fingertip or stylus pen to display the content of message. If the user input to display the content of message is inputted to the electronic device, the control module E201 may control the display to switch the screen image from the notification screen image E810 to the message display screen image E820.

Figure 192A:
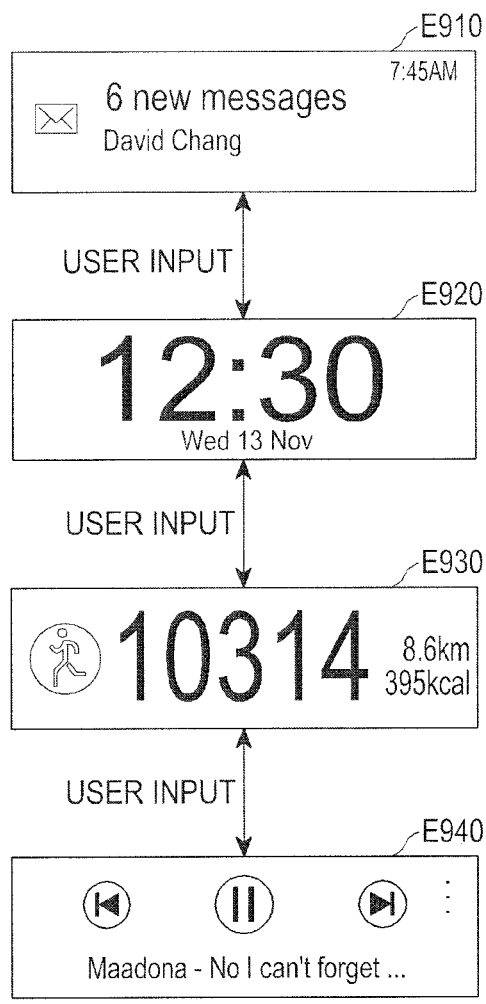

FIG. 192 is a view illustrating an example of a method of displaying content by an electronic device according to an embodiment. In FIGS. 192(a) and (b), it is assumed that the user wears the electronic device on a portion of his body.

Figure 192B:
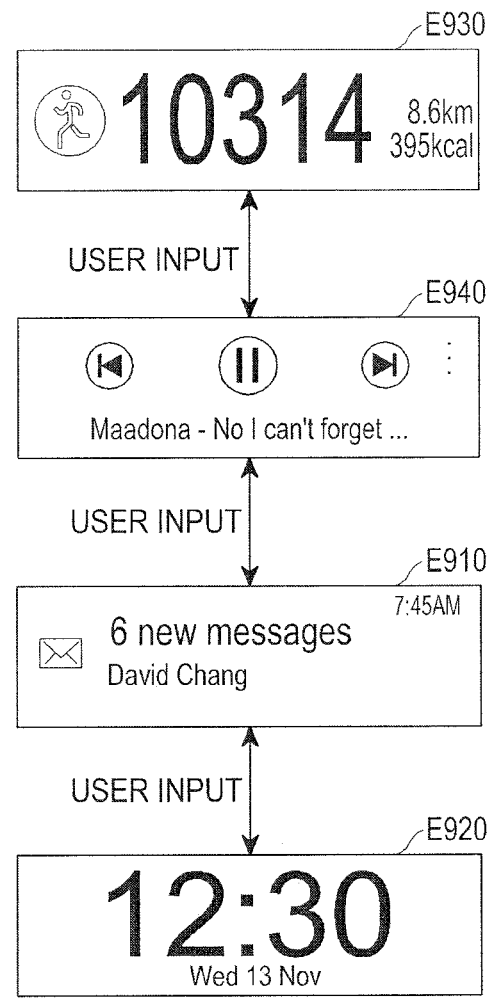

FIGS. 192(a) and (b) shows, in order, screen images displayed on the display of the electronic device. FIG. 192(a) shows screen images in case the user is not doing exercise, and FIG. 192(b) shows screen images in case the user is doing exercise.

According to an embodiment, in case the electronic device is implemented as a wearable device, the screen may be configured of a card-type UI considering the limited size of the screen. For example, each screen image displayed on the screen may be configured in the form of a page, and the user may look up other pages by sequentially flipping the pages through a touch or flick input. In this case, the order of pages may be previously determined, and FIGS. 192(a) and (b) shows a card-type UI, e.g., an example in which such configuration is made that one page is displayed on one screen and is displayed on the screen. Here, the order of pages may be varied by the user input or arbitrarily by the electronic device.

For example, in case the electronic device is connected with another electronic device (e.g., the electronic device 104) through a communication means (e.g., the communication interface 160), the electronic device may first display GUIs related to a connection event with the other electronic device, i.e., pages, on the screen.

An example is described with reference to FIG. 192 under the assumption that the initial screen image of the electronic device is the current time screen image E920 displaying the current time. The control module E201 of the electronic device may set the current time screen image E920 as the initial screen image and may control the display to display the current time screen image E920 ahead of the other screen images E910, E930, and E940.

According to an embodiment, the electronic device may receive a message from the other electronic device (e.g., the electronic device 104). The reception of the message from the other electronic device by the electronic device is referred to as a "message reception event." In case the message reception event occurs, the control module E201 of the electronic device may reset the initial screen image to the message alarm screen image E910 related to the message. Since the message alarm screen image E910 is reset as the initial screen image, the display may display the message alarm screen image E910 ahead of the other screen images E920, E930, and E940. Further, the screen images may be switched in the order of "message alarm screen image E910→current time screen image E920→exercise mode screen image E930→music play screen image E940" according to a user input.

According to another embodiment, if a preset time elapses after the message reception event occurs, the control module E201 may control the electronic device so that the current time screen image E920 is reset as the initial screen image.

As described above, the electronic device may vary the priority of the screen images displayed through the display. According to an embodiment, the electronic device may change order of display of each screen image so that screen images related to an event (e.g., a message reception event, user state alarm event, or exercise mode alarm event) generated by the other electronic device may be first displayed but not in the order of latest screen images being currently looked up by the user. Thus, the user may easily recognize the latest event or information generated in the electronic device. According to an embodiment, a preset time after the event occurs, the electronic device may change the order of display of the screen images back to the order of screen images before the event occurs even without receiving a separate user input. Thus, the user may easily identify in order the screen images displayed on the electronic device.

Referring to FIG. 192(a), the electronic device displays the message alarm screen image E910 as the initial screen image. As shown in FIG. 192(a), the electronic device may display contents in the order of "message alarm screen image E910→current time screen image E920→exercise mode screen image E930→music play screen image E940." According to an embodiment, the message alarm screen image E910, which is the initial screen image, may be an initial screen image designated by the user, an initial screen image designated as default of the electronic device, or a termination screen image for when the user has used the electronic device before. The electronic device may switch the screen images according to a user input. Upon sensing a user input (swipe input) pushing the surface of the screen, e.g., from above to left, while the message alarm screen image E910 is in display, the electronic device may display the current time screen image E920. By contrast, upon receiving the user input pushing the surface of the screen E150 from left to right, the electronic device may display the music play screen image E940. Likewise, upon receiving the user input pushing the screen surface from left to right while the current time screen image E920 is in display or the user input pushing the screen surface from left to right, the message alarm screen image E910 or exercise mode screen image E930 may be displayed.

Upon receiving the user input pushing the screen surface from left to right while the exercise mode screen image E930 is in display or the user input pushing the screen surface from left to right, the current time screen image E920 or music play screen image E940 may be displayed. Upon receiving the user input pushing the screen surface from left to right while the music play screen image E940 is in display or the user input pushing the screen surface from left to right, the exercise mode screen image E930 or message alarm screen image E910 may be displayed.

According to another embodiment, it is assumed that the electronic device is the host device, and the other electronic device is a companion device implemented as a wearable device, and that the host device and the companion device are connected together through their respective communication means. It is also assumed that the data displayed on the companion device by the host device (e.g., the electronic device) may be displayed on the host device, and the data displayed on the host device by the companion device may be displayed on the companion device.

The host device may assign priorities to events generated in the companion device (e.g., the wearable device) equipped with one or more sensors. The host device (e.g., the electronic device) may display the event related to the companion device ahead of the event generated in the host device.

For example, it is assumed that the companion device is a PPG sensor-equipped smart watch. The companion device may measure the bio information (e.g., heart rate) of the user wearing the companion device using the PPG sensor and display on its screen. Further, the companion device may transmit the bio information measured through the PPG sensor to the host device. The host device may first display the bio information received from the smart watch on its screen, allowing the user to identify the same. That is, the host device may assign priority to the bio information and may receive the bio information from the companion device while simultaneously displaying the bio information on its screen in real-time.

Generally, the sync between the host device and the companion device, which is the wearable device, may be done at preset periods rather than in real-time. Further, the connection between the host device and the companion device may be broken, so that the sync between the two devices may fail. Accordingly, the user may have difficulty in identifying health-related notifications such as the bio information through the host device.

In order to allow the notifications to be easily identified, according to an embodiment, the host device (e.g., the electronic device) may provide priority to bio information-related events transferred from the wearable device (e.g., the electronic device 104).

FIG. 192(b) shows an example in which in case the user starts to do exercise or is doing exercise, the electronic device implemented as a wearable device displays the exercise mode screen image (E930) including the user's exercise load (e.g., travel distance or calorie consumption) as the initial screen image.

The control module E201 of the electronic device may analyze the sensing signal measured by the acceleration sensor or bio sensor, and if the user's exercise load is not less than a preset exercise load or a preset heart rate, determine that the user's current state is the state of doing state. If the user is determined to be doing exercise, the control module E201 may automatically set the exercise mode screen image E930 as the initial screen image and display on the screen even without receiving a separate user input. Accordingly, as shown in FIG. 192(b), the electronic device may display contents in the order of "exercise mode screen image E930→music play screen image E940→message alarm screen image E910→current time screen image E920." In a similar manner to FIG. 192(a), the screen images E910 to E940 may be switched according to a user input also in FIG. 192(b).

Figure 193A:
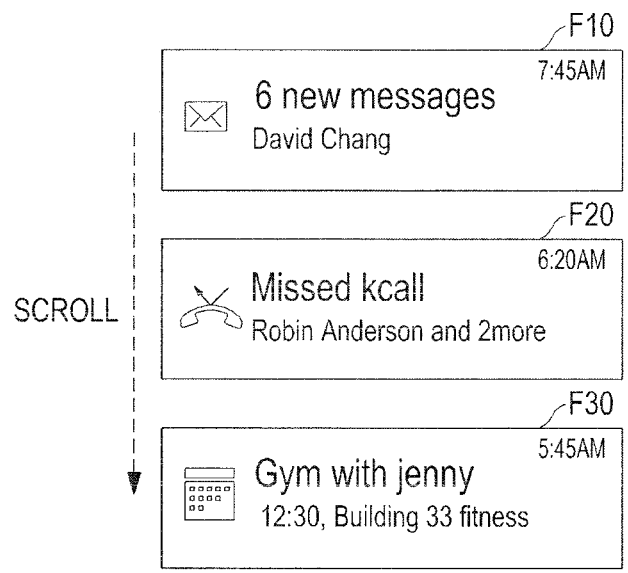

FIG. 193 is a view illustrating an example of a method of displaying content by an electronic device according to an embodiment. In FIGS. 193(a) and (b), it is assumed that the user wears the electronic device on a portion of his body.

Figure 193B:
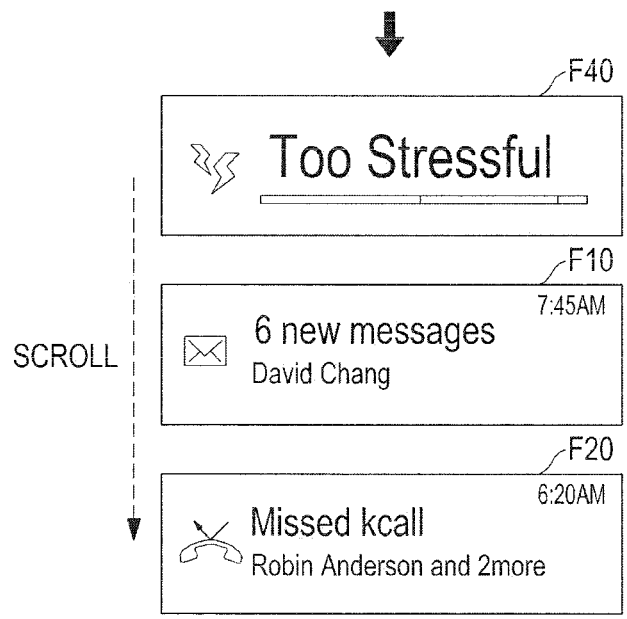

FIG. 193(a) shows screen images displayed on the screen of the display in case the user is not doing exercise, and FIG. 193(b) shows screen images in case the user does exercise.

Referring to FIG. 193(a), in case the user is not doing exercise, the display of the electronic device displays the message alarm screen image F10 as the initial screen image. Further, if an input to switch screen images, e.g., an operation of pushing the screen surface from above to down with, e.g., the user's finger or stylus pen, is entered to the electronic device, the control module E201 may control the display to display other screen image. In FIG. 193(a), a missed call notification screen image F20 and an exercise schedule notification screen image F30 are displayed subsequent to the message alarm screen image F10.

In case the user is doing exercise, the control module E201 may control the display to display the user's stress level by the exercise as the initial screen image. FIG. 193(b) shows a stress level screen image F40 indicating the user's stress level. If the user starts to do exercise, the control module E201, even when not receiving a separate input from the user, may automatically set the stress level screen image F40 as the initial screen image. By setting the stress level screen F40 as the initial screen image, the electronic device may allow the user doing exercise to identify his stress level in real-time.

According to an embodiment, in case the user's exercise load is not more than a preset exercise load, such as when the user strolls, or the user's stress level measured by the HRV sensor is not more than a preset value, the message alarm screen image F10 may be set as the initial screen image as shown in FIG. 193(a). Further, if the user's stress level is determined to be as high as a preset threshold or higher due to excessive exercise, the stress level screen image F40 may be set as the initial screen image as shown in FIG. 193(b) or the user's stress level or user's current state may be separately displayed on an upper end of the screen.

Figures 194A, 194B:
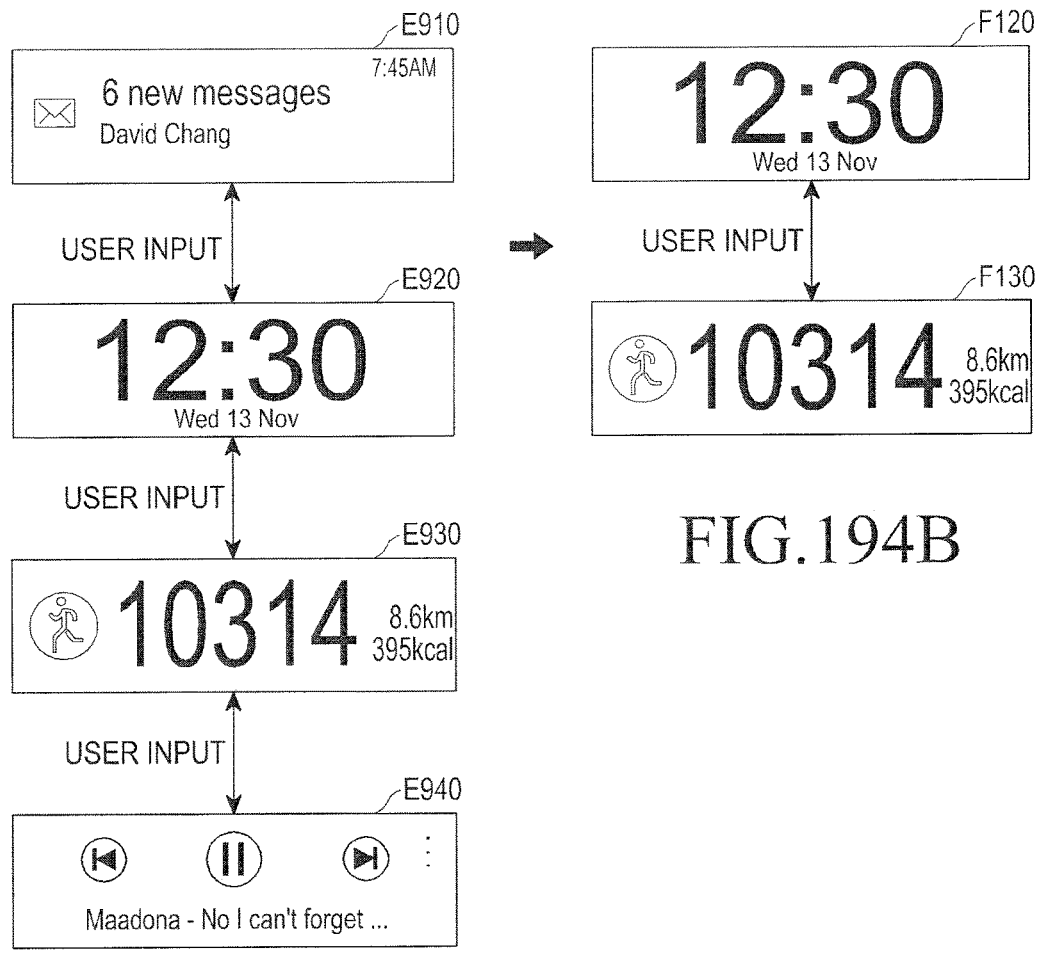

FIG. 194 is a view illustrating an example of a method of displaying content by an electronic device according to an embodiment. In FIGS. 194(a) and (b), it is assumed that the user wears the electronic device on a portion of his body. It is also assumed that the electronic device in FIG. 194 is a companion device and interworks with another electronic device.

FIG. 194(a) shows the content displayed on the screen through the display in case the electronic device interworks with the electronic device which is the host device. Referring to FIG. 194(a), the electronic device displays the message alarm screen image E910 as the initial screen image. As shown in FIG. 194(a), the electronic device may display contents in the order of "message alarm screen image E910→current time screen image E920→exercise mode screen image E930→media play screen image E940."

The electronic device may switch the screen images displayed on the screen according to a user input. Upon receiving the user input pushing the screen surface from right to left while the message alarm screen image E910 is in display or the user input pushing the screen surface from left to right, the electronic device may display the current time screen image F120 or media play screen image E940 on the screen. Likewise, upon receiving the user input pushing the surface of the screen E150 from left to right while the current time screen image F120 is in display or the user input pushing the screen surface from left to right, the message alarm screen image E910 or exercise mode screen image F130 may be displayed.

Further, the electronic device may provide the user with functions provided from the host device or content stored in the host device through interworking with the external electronic device. Assuming that in FIG. 194(a) the messaging function and music playing function are provided form the external electronic device which is the host device, the message alarm screen image E910 and the media play screen image E940 may be displayed on the screen through the display only in case the electronic device interworks with the external electronic device which is the host device.

FIG. 194(b) shows screen images displayed on the screen through the display in case the electronic device does not interwork with the external electronic device which is the host device, i.e., in case the electronic device operates in a standalone mode. If the interworking with the external electronic device which is the host device is terminated, the functions provided from the external electronic device may not be provided to the user by the electronic device. The control module E201 may control the display to provide only screen images according to functions providable to the user regardless of whether it connects with the external electronic device, i.e., unique functions of the external electronic device.

Since the functions according to the message alarm screen image E910 and the media play screen image E940 among the screen images E910 to E940 shown in FIG. 194(a) are functions provided by the external electronic device, they cannot be provided to the user in case the electronic device does not interwork with the external electronic device. Accordingly, in FIG. 194(b), only the current time screen image F120 and the exercise mode screen image F130 may be displayed on the screen through the display.

According to an embodiment, in case the electronic device implemented as a wearable device operates standalone, e.g., upon failing to receive a message transmitted from the host device (e.g., the electronic device 104) or when the connection with the external electronic device is terminated, the control module E201 may remove the screen image associated with the mode in which communication with the external electronic device is required. That is, in case the electronic device operates standalone, the control module E201 may display only the mode screen images displayable when the electronic device operates standalone through the display. Accordingly, only in case the multimedia content stored in the electronic device implemented as the wearable device is controllable, the control module E201 may display the media play screen image E940 through the display.

According to another embodiment, the control module E201 may record the use history of the application frequently used by the user at a particular time or particular location in the memory (e.g., the memory 130). If one or more events of such event that the current time arrives at a particular time or such event that the electronic device enters the particular location occur, the control module E201 may automatically display the initial entry screen image of the application frequently used by the user at the particular time or particular location on the screen through the display. According to an embodiment, the control module E201, when arriving at the particular time or particular location, may change the screen image allowing the user to easily select the frequently used application.

The control module E201 may compute the respective preferences of applications based on one or more of the use frequency or total use time of each application. The control module E201 may arbitrarily arrange the menu or execution icons for selecting the respective applications depending on the respective preferences of the applications. For example, the control module E201 may arrange them so that they are easily noticeable to the user by displaying the execution icon corresponding to the higher-preference application to be larger than other execution icons or displaying it at the center of the screen through the display. According to an embodiment, the control module E201 may evaluate the preference corresponding to each application according to the location information of the electronic device. In case the electronic device enters the place with a higher preference per application or while the user is active in the area including the location (e.g., a geofence-set area or an area where the signal strength of the access point (AP) is not less than a preset reference value), the control module E201 may control the display to vary the attribute of at least one of the menu for running the application or the position, size, and color of the execution icon and display them.

FIGS. 195a and 195b are views illustrating another example of a method of displaying content by an electronic device according to an embodiment.

FIG. 195a is a view illustrating a user input F251 for rejecting to receive a call in case the user F201 is not doing exercise, and FIG. 195b is a view illustrating a user input F252 for rejecting to receive a call in case the user F201 is doing exercise. In FIGS. 195(a) and (b), it is assumed that an incoming call is received from the sender "Peter Smith" to the electronic device.

Referring to FIG. 195a and FIG. 195b, the user F201 may drag to the left at a point F230 on the screen F210 as the user inputs F251 and F252 to reject call reception. The user input entered to the electronic device by dragging from a point to another as described above is referred to as a "drag input."

Although the drag input F251 of FIG. 195a and the drag input F252 of FIG. 195b both are for rejecting the reception of calls incoming to the electronic device, the drag inputs F251 and F252 have different drag lengths d1 and d2. The drag length d2 of the drag input F252 shown in FIG. 195b is larger than the drag length d1 of the drag input F251 shown in FIG. 195a. In case the user F201 is not doing exercise, the electronic device may reject call reception if the length of the drag input F251 is not less than d1. Further, in case the user F201 is doing exercise, the electronic device may reject call reception only if the length of the drag input F252 is not less than d2.

Although FIGS. 195a and 195b both show the drag inputs F251 and F252 for rejecting call reception, the reference values for determining whether the drag inputs F251 and F252 are valid may differ depending on whether the current state of the user F201, i.e., whether the user F201 is doing exercise. In case the user is doing exercise, the user F201 moves more than in case he is not doing exercise, and thus, it is highly likely to enter a wrong user input to the electronic device. Accordingly, as shown in FIGS. 195a and 195b, the reference value when the user F201 is doing exercise may be larger than the reference value when he is not.

As shown in FIGS. 195a and 195b, despite the same user input F251 and F252, different reference values for determining whether the user input is valid may be applied, preventing a malfunction of the electronic device due to a wrong user input by the user.

According to an embodiment, the user input F230 may be at least one of a swipe, tap, long press, and hovering. When receiving the user input F230, the control module E201 may apply different reference values for identifying the user input F230 depending on the current state of the user or electronic device. For example, in case the user moves fast or does strenuous exercise, the user may have difficulty in identifying the screen of the electronic device due to a quick movement in the portion where the electronic device is mounted. Further, in case the user is doing strenuous exercise, the user may have difficulty in distracting his attention or may not have a room to look up the screen for a long time due to the strenuous exercise. In the above-described case, the user input (e.g., a touch or flick) entered through the electronic device may have a larger error or inaccuracy in the input value by the user input (e.g., position, pattern, or strength of input) than when the user does not exercise or move.

Accordingly, the control module E201 may determine whether each function of the electronic device operates according to the strength of gesture, duration of the touch input, or speed of gesture input entered through the camera module (not shown), touched area, distance of flick or drag, or touch strength of the user input.

FIG. 196 is a view illustrating an example of a method of displaying content by an electronic device according to an embodiment. In FIG. 196, the electronic device displays a vertical UI through the display. The vertical UI is a UI providing a screen longer vertically, and the horizontal UI is a UI providing a screen longer horizontally.

Referring to FIG. 196, first to third screen images F311, F312, and F313 may be displayed on the screen of the display. The first screen image F311 may include alarm-related contents, the second screen image F312 healthcare-related contents, and the third screen image F313 message-related contents. In FIG. 196, the electronic device, upon receiving the first to fourth inputs F321, F322, F323, and F324, may switch screen images displayed on the screen. It is assumed in FIG. 196 that the first to fourth inputs F321 to F324 for switching screen images are entered while the second screen image F312 is being displayed on the display.

Referring to FIG. 196, the first input F321 is to push the second screen image F312 from down to above while the user selects a point on the screen using his finger or stylus pen. If the first input F321 is entered, the control module E201 may control the display to switch the screen image from the second screen image F312 to the third screen image F313.

The second input F322 is to push the second screen F312 from above to down while the user selects a point on the screen using his finger or stylus pen. If the second input F322 is entered, the control module E201 may control the display to switch the screen image from the second screen image F312 to the first screen image F311.

The third input F323 is to push the second screen image F312 from left to right while the user selects a point on the screen using his finger or stylus pen. If the third input F323 is entered, the control module E201 may control the display to switch the screen image from the second screen image F312 to the first screen image F311.

The fourth input F324 is to push the second screen F312 from right to left while the user selects a point on the screen using his finger or stylus pen. If the fourth input F324 is entered, the control module E201 may control the display to switch the screen image from the second screen image F312 to the third screen image F313.

That is, whether the user input (e.g., a swipe input) is entered vertically or horizontally, the screen image or menu GUI displayed through the display of the electronic device may be moved or varied horizontally or vertically. Thus, the user using the electronic device may be avoided from confusion due to the automated switch of screen images on the electronic device using the horizontal/vertical screens. Further, a switch of screen images is done in the manner shown in FIG. 196, allowing the user to enter a user input to the electronic device in a consistent, simplified manner.

According to another embodiment, although the electronic device is in the form longer vertically rather than the electronic device formed to be longer horizontally as shown in FIG. 196, the user input as shown in FIG. 196, e.g., the swipe/flick signals inputted through the user interface, may be received. Further, in the screen image switching manner as described in connection with FIG. 196, the screen images of the electronic device may be automatically switched.

FIG. 197 is a view illustrating an example of a method of displaying content by an electronic device according to an embodiment.

Referring to FIG. 197, the electronic device E101 may be implemented as a host device and may interwork with an external electronic device E104 which is a companion device. As shown in FIG. 197, the external electronic device E104 which is the companion device may be implemented as a wearable device (e.g., a circular wrist watch-type wearable device) and may be worn on a portion of the user's body. Further, the electronic device E101 which is the host device may be located at a position where it may communicate with the external electronic device E104 to control the external electronic device E104. The external electronic device E104 shown in FIG. 197 is in the state of running the exercise mode under the control of the electronic device E101 and plays an audio file under the control of the electronic device E101. The external electronic device E104 may display the screen F450 including information (e.g., song title or play time) on the playing audio file and a menu (e.g., volume control, pause, or stop) for control related with playing the audio file.

According to an embodiment, the external electronic device may determine the degree of the movement of the user wearing the external electronic device (e.g., sprint or walking) and differentially apply the output level of audio and voice depending on the degree of the movement. Accordingly, the external electronic device may provide a sound output level and input level (e.g., microphone) optimized for the user's hearing sense.

For example, in case the user happens to call while exercising hard, the external electronic device may increase or reduce the output of the speaker or microphone as compared with when the user does not exercise. The external electronic device may control the input/output level, e.g., by adjusting the volume, sensitivity, or noise filtering of the speaker, microphone, Bluetooth headset, or headphone in order to vary the call voice level. Thus, the user may easily hear sound from the external electronic device or input sound to the external electronic device even during exercise.

FIG. 198 is a view illustrating an example of a method of displaying content by an electronic device according to an embodiment. The external electronic device E104 shown in FIG. 198 may be a circular wrist watch-type wearable device as shown in FIG. 197 and may be in the state of interworking with the host device E101.

FIG. 198 shows the case where, when the user's movement is a preset reference value or more, that is, when the user does strenuous exercise, the external electronic device outputs sound at the maximum level. The external electronic device E104 of FIG. 198 is playing the song file "Let it Be", and the song file may be outputted through the speaker at the maximum volume. The external electronic device may display the screen F550 including information (e.g., song title or play time) on the playing audio file and a menu (e.g., volume control, pause, or stop) for control related with playing the audio file.

According to an embodiment, in case the degree of the user's movement is a preset reference value or more, for example, in case the strength of the exercise the user is doing is high, the external electronic device worn on the user may temporarily stop the operation of displaying the notification to the user through the display.

The external electronic device may stop displaying the notification (Notification interrupt) and store the notification in the memory of the external electronic device. Thereafter, if the degree of the user's movement sensed through the sensor module is determined to be less than the preset reference value, an alarm stored in the memory may be displayed and provided to the user. Accordingly, the external electronic device may reduce power consumption and allows the user to identify the alarm in a comfortable manner.

According to an embodiment, the external electronic device may receive, from the user, various user inputs, such as swipe, tap, long press, or hovering. According to an embodiment, the external electronic device implemented as a wearable device may reduce input errors by blocking some user inputs when the user is doing exercise or the user's movement is as large as a preset reference value or more. For example, if the user is doing pushup or immediately after he has done pushup, the hovering input may not be precisely entered to the external electronic device. Accordingly, the control module E201 may abstain from receiving the hovering input, or although it is entered, disregard the hovering input within a predetermined time (e.g., while the user does pushup).

According to an embodiment, if a particular application (e.g., an application related to one or more of healthcare, SNS, phone, alarm, image viewer, or media play) runs on the electronic device, the external electronic device implemented as a wearable device may display a counter application. The counter application may be an application associated with the particular application running on the electronic device or including at least some functions of the particular application. For example, in case the host device (e.g., the electronic device) is running the user's healthcare application (e.g., an application related to the heart rate sensor, food calorie management, calorie consumption check, or exercise coaching), the external electronic device which is the companion device may also display a health coaching screen related to the healthcare application.

As another example, if the host device (e.g., the electronic device) displays pictures through a gallery application, the electronic device which is the companion device may also run the gallery application or provide a user interface (UI) for entry into the gallery application to the user. Accordingly, the user may easily approach the gallery application through the electronic device. As another example, in case the user runs a video play application through the host device (e.g., the electronic device 103), the electronic device which is the companion device may also run the video play application. At this time, the host device may play video, and the companion device may display information on the video (e.g., TV channel information, movie title, or cast information) or play list on the screen. Of course, the two devices, i.e., the host device and the companion device, may simultaneously display the same content on their screens.

As another example, it is assumed that the user runs a document editing application (e.g., note or word processor) through the host device (e.g., the electronic device 104). In the above case, the control module E201 of the electronic device which is the companion device implemented as wearable device may pop up the document editing application on the screen through the display. Further, the control module E201 may control the electronic device so that the document editing application is run corresponding to a one-time user input by the user. For example, the control module E201 of the electronic device which is the companion device may display, as a popup, contents including a minimum portion of the document content or icon related to the document editing application on the screen through the display. Further, if the user selects or adjusts the popup, the control module E201 may run the document editing application or control the display to display a document editing window rather than the popup.

FIG. 199 is a view illustrating an example of a method of displaying content by an electronic device according to an embodiment.

It is assumed in FIG. 199 that the electronic device and the external electronic device interwork with each other. According to an embodiment, the electronic device may be the host device, and the external electronic device may be the companion device.

Since the electronic devices 101 and 104 interwork with each other, the application running on the electronic device which is the host device may also be run on the external electronic device which is the companion device.

Referring to FIG. 199, a note-related application is run on the electronic device E101 and is displayed on the screen through the display. Accordingly, the note-related application may also be run on the external electronic device E104 which is the companion device and may be displayed on the screen F650.

According to an embodiment, in case the electronic devices E101 and E104 interworking with each other run and display the same application, the operation by the user input entered to the electronic device E101 or external electronic device E104 may be simultaneously run and displayed on the electronic device E101 and the external electronic device E104. For example, if the user generates a new note through the external electronic device E104, the electronic device E101 which is the host device, as well as the external electronic device E104, may generate a new note and display it on the screen through the display.

FIG. 200 is a view illustrating an example of a method of displaying content by an electronic device according to an embodiment. In FIG. 200, the electronic device displays a horizontal UI providing a horizontally longer screen on the screen through the display. Further, it is assumed in FIG. 200 that the user is doing exercise.

FIG. 200(*a*) shows contents, e.g., screen images F711 and F712, which may be displayed through the display for each case where the strength of the user's exercise is high or low.

At this time, the control module E201 may determine the exercise strength based on, e.g., variation in the user's movement, movement speed, movement duration, and calorie consumed per unit time.

Figure 200A:
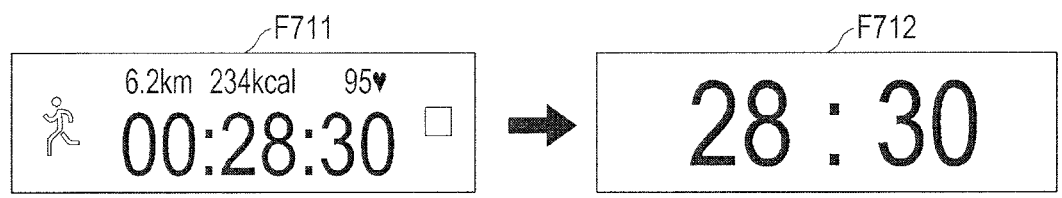

Referring to FIG. 200(a), in case the strength of the user's exercise is low, the information on the exercise the user is doing exercise, e.g., the type of exercise (e.g., running), travel distance (e.g., 6.2 km), calorie consumed by the exercise (e.g., 234 cal), the user's heart rate (e.g., 95), and exercise duration (e.g., 00:28:30), is displayed on the screen. In case the strength of exercise is low, the user may easily check the screen of the electronic device while exercising. Since the strength of the user's exercise belongs to a weak category, the user may continue the exercise while receiving, from the electronic device, while the display of the electronic device receives, from the electronic device, the contents, e.g., the first screen image F711 including the type of exercise, travel distance, calorie consumption, heart rate, or time required for exercise. Although the first screen image F711 includes five contents, five or more contents may be displayed through the display according to another embodiment. According to another embodiment, multiple contents may be displayed on the screen through the display while the screen image switches.

If the strength of the user's exercise increases, the second screen image F712 including only the exercise duration of the user may be provided to the user by the display. In case the strength of exercise is high, it may be difficult for the user to check the screen of the electronic device while simultaneously doing exercise. Accordingly, the control module E201 may control the display to provide a limited number of information among information on the exercise the user is doing to the user. In case the contents provided to the user through the display are limited, the control module E201 may control the display to first display the highest-priority content depending on the respective priorities of the contents. It is assumed in FIG. 200(a) that among the type of exercise, travel distance, calorie consumption, heart rate, and exercise duration, the exercise duration has a higher priority than the others.

Figure 200B:
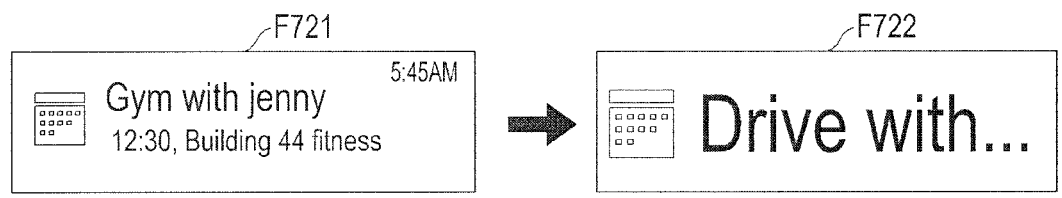

FIG. 200(b) shows contents, e.g., screen images F721 and F722, which may be displayed through the display for each case where the strength of the user's exercise is high or low, like FIG. 200(a) does.

Referring to FIG. 200(b), in case the strength of the user's exercise is low, the user's schedule may be displayed on the screen as in the third screen image F721. The third screen image F721 includes current time, schedule content, date, and location. Since various contents displayed on the screen of the display may be more easily identified in case the strength of exercise is low than when the strength of exercise is high, the control module E201 may control the electronic device so that various contents all are included and displayed in one screen image, e.g., the third screen image F721.

By contrast, in case the strength of the user's exercise is high, the user's schedule may be displayed on the screen as in the fourth screen image F722. The fourth screen image F722 includes only schedule content. Since the user has more difficulty in identifying various contents displayed on the screen of the display in case the strength of exercise is high than when the strength of exercise is low, the control module E201 may control the electronic device so that one content is included and displayed in one screen, e.g., the fourth screen image F722. At this time, the control module E201 may determine the content to be displayed on the screen of the display according to priority. In FIG. 200(b), the highest-priority content may be the schedule content. Accordingly, the control module E201 may control the display to display only the schedule content on the screen.

Although as shown in FIG. 200 the electronic device may display only input information of various information (e.g., the second screen image F712 and the fourth screen image F722), according to another embodiment, the control module E201 of the electronic device may sequentially display several information every preset time (e.g., 10 sec) while switching screens. In case the information is displayed while the screen images are sequentially switched, the control module E201 may various adjust the size or shape of image, letter, number, symbol, animation, video, icon, or GUI for displaying information through the display, depending on the user's exercise level or strength.

FIG. 201 is a view illustrating an example of a method of displaying content by an electronic device according to an embodiment. In FIG. 201, the electronic device displays a horizontal UI providing a horizontally longer screen through the display. Further, it is assumed in FIG. 201 that the user is doing jogging.

FIG. 201(a) to (c) shows an example in which the contents, e.g., screen images, displayed on the display are varied depending on the strength of exercise the user is doing. For example, the control module E201 may vary the amount of information or GUI size included in the screen image displayed on the screen depending on the strength of exercise.

Assuming that the strength of exercise comes in high, medium, and low, FIG. 201(a) shows a content displayed on the screen when the strength of exercise is low, (b) a content displayed on the screen when the strength of exercise is medium, and (c) a content displayed on the screen when the strength of exercise is high.

Referring to FIG. 201(a), in case the strength of exercise is "low," the control module E201 may control the display to display on the screen a first screen image F810 including the type (jogging) of the exercise, time required for exercise (00:28:30), exercise distance (6.2 km), calorie consumption (234 kcal), and heart rate (95). Further, the display may display a menu button F811. If receiving a user input selecting the menu button F811 from the user, the electronic device may display other contents than the contents (type of exercise, time required for exercise, exercise distance, calorie consumption, and heart rate) displayed in the first screen image F810.

Further, the control module E201 may display an exercise route as the second screen image F818 along with the first screen image F810. Since the strength of exercise is low, the control module E201 may control the display so that the second screen image F815 includes the map, the user's current location, the user's travel distance, the user's travel speed, time required for exercise, calorie consumption, heart rate, current time, and travel direction (left turn after move 120 m). Further, the display may display a menu button F811.

Referring to FIG. 201(b), in case the strength of exercise is "medium," the control module E201 may control the display to display on the screen a first screen image F820 including the type (jogging) of the exercise, time required for exercise (00:28:30), and exercise distance (6.2 km). Further, the display may display a menu button F821 on the screen. If receiving a user input selecting the menu button F821 from the user, the electronic device may display other contents than the contents (type of exercise, time required for exercise, and exercise distance) included in the first screen image F820.

Further, the control module E201 may display an exercise route as the second screen image F825 along with the second screen image F820. Since the strength of exercise is medium, the control module E201 may control the display so that the second screen image F825 includes the map, the user's current location, the user's travel distance, the user's travel speed, time required for exercise, calorie consumption, heart rate, and travel direction (left turn after move 120 m). Further, the display may display the menu button F811, and the map included in the second screen image F825 in FIG. 201(*b*) may be one represented more briefly than the map included in the second screen image F818 in FIG. 201(*a*).

Referring to FIG. 201(*c*), in case the strength of exercise is "high," the control module E201 may control the display to display on the screen a first screen image F830 including exercise distance (6.2 km). Further, the display may display a menu button F831. If receiving a user input selecting the menu button F831 from the user, the electronic device may display other contents than the contents (exercise distance) included in the first screen image F830.

Further, the control module E201 may display a travel direction as the second screen image F835 along with the first screen image F830. Since the strength of exercise is high, the control module E201 may control the display so that the second screen image F835 includes the remaining distance (3 km), predicted time required (00:15:20), and travel direction (left turn after move 120 m). Further, the display may display a menu button F831, and the second screen image F835 in FIG. 201(*c*) may be displayed more briefly than the second screen images F818 and F825 in FIGS. 201(*a*) and (*b*), and among the contents, the map may also be omitted.

According to an embodiment, the electronic device may adjust the amount of various contents displayed through the display. The control module E201 of the electronic device may adjust per level the amount of content displayed through the display. Hereinafter, representing the amount of content displayed through the display at a level is referred to as "display-degree level." The control module E201 of the electronic device may summarize per step the information corresponding to the content by reducing the amount of content displayed through the display according to the display-degree level.

For example, it is assumed that the schedule table includes detailed information, such as time, place, purpose, and attendee of meeting schedule, current time, and icon corresponding to the meeting schedule. If the display-degree level is 3, the control module E201 may display the detailed information on the screen so that the whole detailed information is included in one screen image. If the display-degree level is 2, the control module E201 may control the display so that only the time, place, and purpose of the meeting schedule are included in one screen image. If the display-degree level is 1, the control module E201 may control the display so that only the remaining time and place of the meeting schedule may be displayed in one screen.

As another example, it is assumed that the electronic device displays a call message screen image. If the display-degree level is 3, the control module E201 may control the display so that the caller's name, face picture, and phone number are included in one screen image. If the display-degree level is 2, the control module E201 may control the display so that the caller's name and phone number are included in one screen image. If the display-degree level is 1, the control module E201 may control the display so that only the caller's name is displayed on one screen image.

As another example, it is assumed that the electronic device displays a news article or message (SMS or MMS) on the screen.

If the display-degree level is 3, the control module E201 may control the display so that the detailed content of the news article or message may be included and displayed on one screen image. If the display-degree level is 2, the control module E201 may control the display so that the headline or summary of the news article or summary of the message may be included and displayed on one screen image. If the display-degree level is 1, the control module E201 may control the display so that only the headline of the news article or a head portion of the message may be included and displayed on one screen image. Further, a natural language processing or statistical scheme-based document summarizing engine for such data processing may be previously installed on the electronic device. According to another embodiment, the document summarizing engine may be included in the external device or server, and the electronic device may receive the news article or message summarized by the document summarizing engine through the communication interface (e.g., the communication interface 160) and display it.

As another example, the control module E201 of the electronic device may determine the significance of each content displayed through the display in level units depending on the user's current state or current context. Further, the control module E201 may determine content to be displayed through the display depending on the significance. For example, right after the user starts to run as shown in FIG. 201(*a*), the control module E201 may control the display to display contents with a significance level of 1. The significance level 1 contents may be a detailed map including the user's running route, the user's calorie consumption, and the exercise load, and the control module E201 may control the display so that the calorie consumption and the exercise load may be alternately displayed on the detailed map. Sometime after the user starts to run as shown in FIG. 201(*b*), the control module E201 may control the display to display the significance level 2 contents. The significance level 2 contents may be a map briefly showing the user's running route, the user's running speed, and calorie consumption as shown in FIG. 201(*b*). The control module E201 may control the display to display the user's running speed and calorie consumption on the brief map together with the map. A significant time after the user starts to run as shown in FIG. 201(*c*), the control module E201 may control the display to display the significance level 3 contents. The significance level 3 contents may be the travel direction of the running user, and the control module E201 may control the display to briefly display the travel direction in an arrow or text. FIG. 202 is a view illustrating an example of a method of displaying content by an electronic device according to an embodiment. FIG. 202 shows an example in which six screen images F910, F920, F930, F940, F950, and F960 through the display. In FIG. 202, the user is currently running, and accordingly, the control module E201 may control the display so that each screen image F910 to F960 includes only one content and menu button F905.

Referring to FIG. 202, the first screen image F910 may include the calorie consumption (234 kcal) and the menu button F905, the second screen image F920 may include the travel distance (6.2 km) and the menu button F905, the third screen image F930 may include the heart rate and the menu button F905, the fourth screen image F940 may include the travel speed (12.2 km/h) and the menu button F905, the fifth screen image F950 may include the exercise type (running)

and the menu button F905, and the sixth screen image F960 may include the time required for exercise (00:28:30) and the menu button F905.

According to an embodiment, upon receiving the user input pushing the screen from right to left with any one point on the screen selected, the electronic device may switch the screen images from the first screen image F910 to the second screen image F920, from the second screen image F920 to the third screen image F930, from the third screen image F930 to the fourth screen image F940, from the fourth screen image F940 to the fifth screen image F950, from the fifth screen image F950 to the sixth screen image F960, or from the sixth screen image F960 to the first screen image F910.

According to an embodiment, the electronic device may display screen images for representing their respective contents displayed through the display in order at preset times. For example, the electronic device may switch the screen images from the first screen image F910 to the second screen image F920, from the second screen image F920 to the third screen image F930, from the third screen image F930 to the fourth screen image F940, from the fourth screen image F940 to the fifth screen image F950, from the fifth screen image F950 to the sixth screen image F960, and from the sixth screen image F960 to the first screen image F910 every ten seconds and may repeat such switching operation. Further, the electronic device may receive a touch, tap, flick, swipe, voice input, and pressing a button previously provided in the electronic device, as the user input, from the user. The electronic device may run the user's desired mode, display the user's desired screen image, or switch the screen image according to the user input.

According to an embodiment, upon receiving the user input pushing the screen from left to right with any one point on the screen selected, the electronic device may switch the screen images from the first screen image F910 to the sixth screen image F960, from the second screen image F920 to the first screen image F910, from the third screen image F930 to the second screen image F920, from the fourth screen image F940 to the third screen image F930, from the fifth screen image F950 to the fourth screen image F940, or from the sixth screen image F960 to the fifth screen image F650.

FIGS. 203*a* to 203*c* are views illustrating another example of a method of displaying content by an electronic device according to an embodiment; It is assumed in FIGS. 203*a* to 203*c* that the electronic device is implemented as a wrist watch-type wearable device. Further, FIGS. 203*a* to 203*c* are views illustrating examples of identifying content outputted from the wearable device worn on the user's wrist when the electronic device implemented as the wrist watch-type wearable device is worn on the user.

FIG. 203*a*(*a*) shows an example in which the user wears the electronic device E101 on his right hand G01, and FIG. 203*a*(*c*) shows an example in which the user wears the electronic device E101 on his left hand G02. Further, FIG. 203*a*(*b*) shows the view direction G11 incident onto the screen of the electronic device E101 and the coordinate system G51 in case the user wears the electronic device E101 on his right hand G01.

Referring to FIG. 203*a*, the electronic device E101 may be worn on the user's right hand G01 or left hand G02. In case the electronic device E101 is worn on the user's right hand G01 or left hand G02, the direction w facing the user's eyes (the opposite direction of the direction G11 in which the user views the screen, i.e., the opposite direction of the view), when referring to the coordinate system G51, is identical or similar to the direction z of the screen, i.e., the direction in which the screen faces.

If the direction z of the screen is identical to the opposite direction w of the view or the angle between the direction z of screen and the opposite direction w of the view is not more than a reference angle (e.g., 30°) and the direction z of the screen is similar to the opposite direction w of the view, the control module E201 may control the display so that the content is outputted in a horizontal direction (left to right) as shown in FIG. 203*a*. According to an embodiment, if the angle between the direction z of the screen and the opposite direction w of the view is more than the predetermined reference, i.e., in case the direction z of the screen is not similar to the opposite direction w of the view, the control module E201 may control the display so that the content is not displayed on the screen. According to an embodiment, in case the direction z of the screen is not similar to the opposite direction w of the view, the control module E201 may power off the screen or operate the electronic device as a low power device or control the display to output on the screen other content, e.g., clock, screen saver, weather information, or lock screen image, instead of the content.

According to an embodiment, in case the direction z of the screen is similar to the opposite direction w of the view, the control module E201 may determine whether to output content on the screen through the display based on the security level of the content. For example, such context is assumed that it is not easy for the user wearing the electronic device to identify the content. In case the content has a high security level, for example, in case the content is personal information, health information, or information on the caller of an incoming call, the control module E201 may control the display to abstain from displaying the content. By contrast, in case the content has a low security level, for example, in case the content is weather or time, the control module E201 may control the display to display the content. According to an embodiment, for low-security level contents, the control module E201 may always display them on the screen through the display regardless of the user's current state.

As mentioned above, the contents may have security levels divided into two grades or more. According to an embodiment, a security level may be previously determined for each content, and the security level of each content may be determined by the control module E201.

According to an embodiment, the control module E201 may control the display to output only contents with a particular level or more of security level or less than the particular level in case the direction z of the screen is similar to the opposite direction w of the view.

Further, referring to FIG. 203*a*, the control module E201 may determine that the screen of the electronic device E101 is in a horizontally longer shape with respect to the x and y axis of the coordinate system G51 shown in FIG. 203(*b*). Further, the contents outputted through the screen of FIG. 203*a*(*a*) and (*c*) may have a horizontally longer shape or may be arranged and displayed in the horizontally longer shape. Referring to FIG. 203(*b*), the y axis of the coordinate system G51 is in the direction of a virtual line that vertically meets two longer edges of the four edges of the screen on the screen surface (e.g., the central point of the screen surface), and the x axis is in the direction of a line perpendicular to the y axis on the screen surface (e.g., the central point on the screen surface). The control module E201 may determine the direction z of the screen (e.g., the direction where the screen faces or norm vector on the screen surface) using the point where the x axis and the y axis meet. Here, the control module E201 may determine that the opposite direction w of the user's view is closer to the y axis than the x axis. For example, the control module E201 may determine that the current pose of the user wearing the electronic device is the pose under the state where the horizontal edge of the screen is longer under the movement of the user's arm or wrist or the direction of the y axis of the electronic device is similar to the direction of the gravity or its opposite direction. Accordingly, the control module E201 may control the display so that the content is outputted in a horizontally long shape.

FIG. 203*b*(*a*) shows an example in which the user wears the electronic device E101 on his right hand G01, and FIG. 203*b*(*c*) shows an example in which the user wears the electronic device E101 on his left hand G02. Further, FIG. 203*b*(*b*) shows the view direction G12 incident onto the screen of the electronic device E101 and the coordinate system G52 in case the user wears the electronic device on his right hand G01.

Referring to FIG. 203*b*, for the user, the screen of the electronic device E101 is in a vertically longer shape with respect to the x axis and y axis of the coordinate system G52. Further, the contents outputted through the screen of FIG. 203*b*(*a*) and (*c*) may have a vertically longer shape or may be arranged and displayed in the vertically longer shape. As described above, in case the direction z of the screen is identical or similar to the opposite direction w of the view, although the vertical edge of the screen is longer than the horizontal edge, the control module E201 may control the display so that the contents are outputted in the horizontal direction (e.g., from left to right or from right to left). That is, the control module E201 may adjust the layout so that the contents fit the vertically longer screen and control the display so that the contents are arranged and outputted in row units. According to another embodiment, the control module E201 may control the display so that the contents are outputted in a vertical direction, i.e., from above to down. For example, the letters may be arranged and outputted vertically (sorted in column units) like the way in, e.g., ancient books.

According to an embodiment, the direction in which the contents are arranged on the screen (e.g., the horizontal direction, vertical direction, left-to-right direction, or upper-lower direction) may be determined by the user input. The user input may be user's manipulation, e.g., selection of menu, selection of button, or selection of icon. The way to arrange the contents by the user input may be information preset and stored in the electronic device, and the control module E201 may control the display so that the contents may be outputted in the way of arrangement according to the user input. According to an embodiment, the way to arrange contents may be varied according to the user input. For example, the user may enable the control module E201 to adjust the way to arrange contents by entering which hand the user wears the electronic device to the electronic device. In case the screen displaying contents is shaped as a square or rectangle, if the user's hand wearing the electronic device is determined, the control module E201 may designate one of the four edges of the screen, as a reference for outputting the content. Thus, the way to arrange contents may be determined.

According to an embodiment, one or more sensors previously provided in the electronic device may sense the pose of the electronic device, specifically the screen, and generate pose information (hereinafter, "screen pose information") accordingly. For example, the electronic device may be pitched, yawed, or rolled, and one or more sensors previously provided in the electronic device may sense the poses. At this time, the screen included in the electronic device may also be pitched, yawed, or rolled. The screen pose information represents information indicating the pose the screen currently makes. The control module E201 may determine or vary the way to arrange contents or whether to output contents based on the screen pose information. For example, the control module E201 may determine the direction z of the screen based on sensing data measured by the acceleration sensor or gyro sensor provided from the electronic device. Further, the control module E201 may determine the way to arrange contents, such as displaying contents in the horizontal mode or landscape mode or in the vertical mode or portrait mode depending on the direction z of the screen.

According to an embodiment, the one or more sensors may sense the movement of the electronic device and generate movement information (hereinafter, device movement information) accordingly. For example, the electronic device may be tilted or rotated, and the one or more sensors may sense the movement of the electronic device. The movement information represents information on various movements generated from the electronic device. The control module E201 may determine or vary the way to arrange contents or whether to output contents based on the device movement information.

According to an embodiment, the control module E201 may determine or vary the way to arrange contents or whether to output contents based on the angle between the user's eyes and the screen (e.g., the angle between the direction −w where the view faces the screen and the direction z where the screen faces).

According to an embodiment, the opposite direction w of the user's view may be determined based on a separate embedded sensor (e.g., the camera, IR camera, or view tracing device). For example, the electronic device may include a camera device (not shown) facing in the same direction as the screen and may analyze the area including the user's eyes or facial area in the image inputted through the camera to determine whether the user's view or face faces the screen. For example, the control module E201 may extract the user's eye area, face area, or eyeball area from the image captured for the user's face or eye. The control module E201 may determine the opposite direction w of the user's view based on one or more of the eye area, face area, or eyeball area. At this time, the control module E201 may determine the opposite direction w of the user's view based on the shape or area of each of the eye area, face area, or eyeball area.

According to an embodiment, the pose information on the user's face (hereinafter, face pose information) may be identified based on the face image or eye image. For example, the control module E201 may be aware of the arranged shape of each of the elements constituting the user's face, such as eyes, nose, and mouth, through the face image and may be aware of the shape or relative position of each eye through the eye image. The control module E201 may sense the face pose information, e.g., one or more of the orientation of the user's face or eyeball, based on the information.

According to an embodiment, the control module E201 may determine the device pose information or screen pose information based on the face pose information and may determine the way to arrange contents through the screen based on the device pose information or screen pose information. That is, the control module E201 may determine the orientation or device pose information of the camera module previously provided in the electronic device using the face pose information. Further, the control module E201 may also determine the orientation of the camera module or screen pose information using the face pose information.

According to an embodiment, the opposite direction w of the user's view may be determined based on the information indicating the movement or pose (e.g., pitch, yaw, or roll) of the electronic device, e.g., device pose information or screen pose information. Further, the information indicating the movement or pose of the electronic device may be sensed or determined using one or more of the acceleration sensor, gyro sensor, and geo-magnetic sensor.

FIGS. 203*a* and 203*b* correspond to examples in which the user looks down to the wrist where the electronic device E101 is worn. In FIGS. 203*a* and 203*b*, the direction z of the screen of the electronic device E101 faces in the opposite direction of the ground or in a similar direction to the opposite direction of the ground. The electronic device E101 determines the information indicating the movement or pose of the electronic device E101 using at least one of the above-described sensors. Subsequently, the electronic device E101 may determine the direction where the screen faces, i.e., the direction z of the screen, based on the information indicating the movement or pose of the electronic device E101. Subsequently, the electronic device E101 may perform control so that, if the direction z of the screen is within a predetermined reference angle (e.g., 45°) from the opposite direction of the ground (not shown), the contents are displayed through the display.

According to another embodiment, in case the direction z of the screen faces the ground, it may be predicted that the user cannot identify the screen. If the angle between the direction z of the screen and the orientated direction of the ground (not shown) is within a predetermined reference angle (e.g., 45°), the control module E201 of the electronic device may perform control so that the contents are not outputted on the screen of the display.

According to an embodiment, the movement or pose of the screen may be sensed using one or more sensors to determine the direction where the contents displayed on the screen are arranged. For example, the control module E201 may control the display so that the contents may be displayed on the screen in the horizontal mode or landscape mode in which the horizontal line is longer than the vertical line or the vertical mode or portrait mode in which the vertical line is longer than the horizontal line.

FIG. 203*c*(*a*) shows an example in which the user wears the electronic device E101 on his right hand G01, and FIG. 203*c*(*c*) shows an example in which the user wears the electronic device E101 on his left hand G02. Further, FIG. 203*c*(*b*) shows the view direction G13 incident onto the screen of the electronic device E101 and the coordinate system G53 in case the user wears the electronic device E101 on his right hand G01.

Referring to FIG. 203*c*, the electronic device E101 remains worn on the user's right hand G01 or left hand G02. In case the electronic device E101 is worn on the user's right hand G01 or left hand G02, the direction w facing the user's eyes (the opposite direction of the view's direction G13, when referring to the coordinate system G53, is not similar or opposite to the direction z of the screen included in the display, i.e., the direction in which the display faces. For example, the direction z of the screen shown in FIG. 203*c* may be not similar or opposite to the opposite direction w of the view depending on the state where the user wears the electronic device.

If the direction z of the screen is opposite to the opposite direction w of the view or the angle between the direction z of screen and the opposite direction w of the view is not less than a predetermined reference angle (e.g., 30°) and the direction z of the screen is not similar to the opposite direction w of the view, the control module E201 may control the display so that the contents are not outputted on the screen. In case the direction z of the screen is opposite or not similar to the opposite direction w of the view, this may mean that the direction of the user's view is identical or similar to the direction z of the screen. Accordingly, although contents are outputted on the screen, the user may not identify the contents. In the above case, the control module E201 may prevent waste of power that may occur when the screen remains powered on by preventing the display from outputting the content on the screen or turning off the screen.

According to an embodiment, the control module may determine the direction z of the screen of the electronic device worn on the user who is on the move based on the sensing data obtained from, e.g., the acceleration sensor or gyro sensor. The following Table 11 represents parameters available for the control module E201 to determine the direction z of the screen. The parameters may be stored in the memory 130.

The following Table 11 assumes that the electronic device is a wearable device implemented in a bracelet or wrist watch-type wearable on the user's wrist. In case the electronic device is implemented as a wearable device as above, the control module E201 may determine the direction z of the screen and the user's body portion (e.g., left wrist, right wrist, portion adjacent to the back of a hand, or position adjacent to a palm) wearing the electronic device by referring to Table 11 below.

According to an embodiment, after first wearing the electronic device, the user may move with the electronic device on. In particular, if the user does such exercise as to rotate or tilt his wrist, the electronic device may sense the direction of exercise in which the user may smoothly do the exercise to determine the user's body portion where the electronic device is worn.

For example, it is assumed as shown in FIG. 203*b* that the electronic device is worn at an adjacent position, such as the back of the left wrist. At this time, the display z of the screen in which the content is displayed is assumed to be the opposite direction of the ground. When the user moves or does exercise so that his palm faces up, i.e., the direction z of the screen in the electronic device faces the ground, the user may easily tilt counterclockwise the left wrist where the electronic device is worn. However, it is not easy for the user to tilt clockwise his left wrist wearing the electronic device so that the direction z of the screen of the electronic device faces the ground or does exercise, and its resultant rotation angle is relatively restricted as well. This comes from a human being's exercise capability per body portion, and the electronic device may determine the position on the body portion where the electronic device is worn or candidate position by sensing the direction of smooth exercise after the user wears the electronic device.

In case it is not known which hand the electronic device is worn, the control module E201 may determine in pair candidate positions for wearing the electronic device according to the movement of the wrist. According to another embodiment, as shown in Table 11, the control module E201 may determine one candidate position where the electronic device is worn based on the tendency where most people tend to let their back of hand face in the opposite direction of the ground (e.g., the tendency of determining the main direction of the screen embedded in the electronic device worn on the wrist).

TABLE 11

| Main direction (z) of screen of electronic device | smooth rotational direction of electronic device upon wrist tilting exercise | orientation direction (z) of screen after wrist tilting exercise | smooth rotational direction upon subsequent tilting exercise while wrist is tilted | determined position where electronic device is mounted |
|---|---|---|---|---|
| opposite direction of the ground | counterclockwise (clockwise direction is relatively limited) | direction of the ground | clockwise (counterclockwise direction is relatively limited) | position adjacent to the back of left wrist |
| opposite direction of the ground | clockwise (counterclockwise direction is relatively limited) | direction of the ground | counterclockwise (clockwise direction is relatively limited) | position adjacent to the back of right wrist |
| direction of the ground | counterclockwise (clockwise direction is relatively limited) | opposite direction of the ground | clockwise (counterclockwise direction is relatively limited) | position adjacent to palm of left wrist |
| direction of the ground | clockwise (counterclockwise direction is relatively limited) | opposite direction of the ground | counterclockwise (clockwise direction is relatively limited) | position adjacent to palm of right wrist |

Figure 203D:
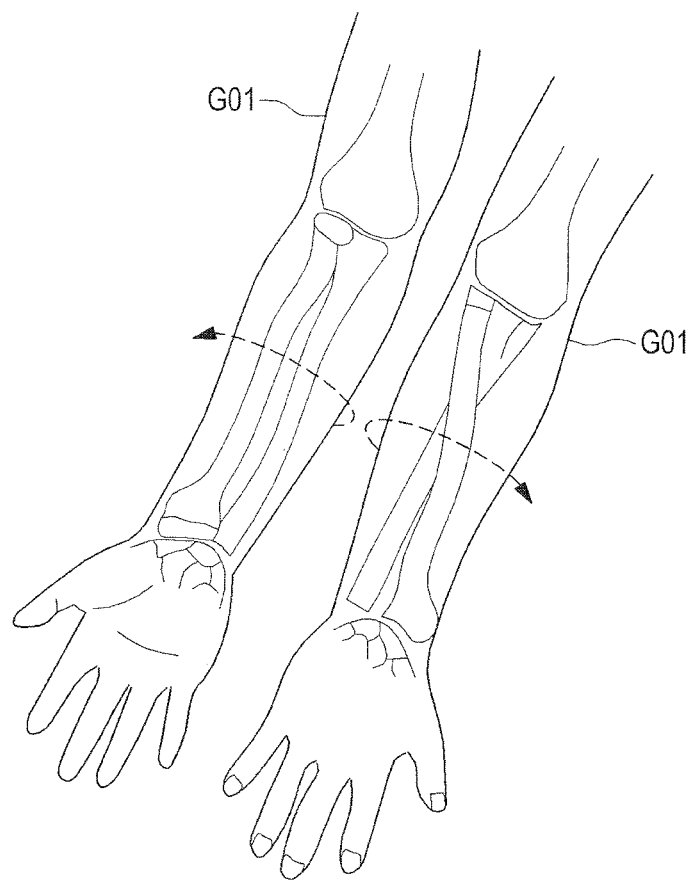

FIG. 203d is a view illustrating an example in which the user's right arm where the electronic device is worn is viewed from above. Referring to FIG. 203d and Table 11, the user may turn his wrist clockwise so that the user's palm is rotated to be viewed while the back of the right hand of the user wearing the electronic device implemented as a wearable device faces up (the state where the screen of the electronic device faces in the opposite direction of the ground), i.e., in order for the user to allow the direction z of the screen of the electronic device to face the ground by supination.

Thereafter, in order for the user to turn the wrist with the user's right palm facing up (the state where the screen faces the ground) so that the user's wrist is viewed, that is, in order for the user to do pronation so that the screen of the electronic device faces in the opposite direction of the ground, the user may turn the wrist counterclockwise.

One or more sensors included in the sensor module of the electronic device, e.g., the acceleration sensor or gyro sensor, may obtain the slope or acceleration of the electronic device that is moved when the user twists his wrist or turns his arm as shown in FIG. 203d. The control module E201 may determine whether the electronic device is attached to the user's body using the directivity of the rotational movement in the electronic device caused by the user's movement and the main direction z of the screen. Further, the control module E201 may determine the position where the electronic device is worn using the directivity of the rotational movement in the electronic device and the direction z of the screen.

FIGS. 204a and 204b are views illustrating an example in which the electronic device E101 displays content on the screen G150 through the display according to an embodiment. In particular, FIGS. 204a and 204b are views illustrating contents receivable by the user wearing the electronic device E101 implemented as a wearable device from the electronic device E101.

Referring to FIG. 204a, the direction z of the screen G150 included in the display of the electronic device E101 is not consistent with the opposite direction w of the user's view. Further, the angle between the opposite direction w of the user's view and the direction z of the screen G150 is A°. That is, the screen G150 is in the state turned by A° counterclockwise with respect to the opposite display w of the view. Referring to FIG. 204a, the opposite direction w of the view faces to the left of the screen G150. Accordingly, it may be shown that the user's view is inclined to the left of the screen G150. As described above, in case the user's view is inclined to a portion of the screen G150, the control module E201 may control the display so that the contents are displayed inclined to the side where the view is inclined. Referring to FIG. 204a, since the user's view is inclined to the left, the control module E201 may control the display so that the contents are displayed inclined to the left of the screen G150. In FIGS. 204a and 204b, the content displayed on the screen G150 through the display is current time, "7:06." As shown in FIG. 204a, if the user's view faces from the left side of the electronic device to the screen G150 of the electronic device, the control module E210 may control the display so that "7:06" is displayed inclined to the left with the right side of the screen G150 emptied.

Also in FIG. 204b, the direction z of the screen G150 of the electronic device E101 is not consistent with the opposite direction w of the user's view. Further, the angle between the opposite direction w of the user's view and the direction z of the screen G150 is B°. That is, the screen G150 is in the state turned by B° clockwise with respect to the opposite display w of the view. Referring to FIG. 204b, the opposite direction w of the view faces to the right of the screen G150. Accordingly, it may be shown that the user's view is inclined to the right of the screen G150. As described above, in case the user's view is inclined to a portion of the screen G150, the control module E201 may control the display so that the contents are displayed inclined to the side where the view is inclined. Referring to FIG. 204b, since the user's view is inclined to the right, the control module E201 may control the display so that the contents are displayed inclined to the right of the screen G150. In FIGS. 204a and 204b, the content displayed on the screen G150 through the display is current time, "7:06." As shown in FIG. 204a, if the user's view comes to the screen G150 of the electronic device from the right side of the electronic device, the control module E210 may control the display so that "7:06" is displayed inclined to the right with the left side of the screen G150 emptied.

According to an embodiment, the display may display the UI displayed on the screen in the horizontal direction or vertical direction under the control of the control module E201. Hereinafter, the UI displayed in the horizontal direction is referred to as a horizontal UI, and the UI displayed in the vertical direction is referred to as a vertical UI. The display may switch the UI displayed on the screen from the horizontal UI to the vertical UI or from the vertical UI to the horizontal UI under the control of the control module E201.

The switch between the horizontal UI and vertical UI may be predicted utilizing a user profile previously stored in the electronic device, such as a pre-stored exercise range of the user's body. After the user wears the electronic device, the control module E201 may compare the user's profile previously stored with the exercise range of the current body activity to determine the UI displayed on the screen. At this time, the control module E201 may determine whether to display the horizontal UI or vertical UI on the screen.

According to another embodiment, the electronic device may determine the UI displayed on the screen according to a user input. At this time, the control module E201 may determine whether to display the horizontal UI or vertical UI on the screen according to the user input. The user input may include an input for selecting a virtual button, an input for selecting an icon, or an input of a physical button, such as a hard key.

According to an embodiment, the control module E201 may sense a movement input (e.g., a motion input or gesture input) entered through the electronic device using the motion sensor. The control module E201 may compare the movement input sensed using the motion sensor with movement data previously stored in the memory 130 to change the UI even when the similarity is not less than a reference value. At this time, the control module E201 may control the display to change the horizontal UI into the vertical UI or change the vertical UI into the horizontal UI and display the same.

For example, the user wearing the electronic device implemented as a wearable device may change the direction of the UI displayed on the screen by tilting his head or wrist or shaking the wrist. For example, the user may make a gesture with a preset particular angle, particular direction, or particular speed, and the electronic device may perform motion recognition on the gesture. The control module E201 may change the direction of the UI displayed on the screen depending on the result of the motion recognition. As another example, the user may change the direction of the UI by making a large circle with his arm with the electronic device worn on the arm or tilting the hand with the electronic device on the wrist or finger.

According to an embodiment, the control module E201 may switch the horizontal UI into the vertical UI or the vertical UI into the horizontal UI based on the state and type of the user's exercise. That is, the display may automatically change UIs and display the same depending on the state or type of the user's exercise. The control module E201 may determine the state or type of the user's exercise using at least one sensor included in the electronic device, e.g., one or more of the motion sensor, location sensor, or bio sensor.

For example, the horizontal UI in a normal situation where the user does not exercise, the horizontal UI in case the exercise is biking, and the vertical UI in case the exercise is running may be provided to the user. That is, upon detecting a signal strength not more than a predetermined reference through the acceleration sensor or if the heart rate is not more than a predetermined reference, the control module E201 may determine that the use is not doing exercise. If the user's movement is sensed by the acceleration sensor, and the signal pattern measured by the acceleration sensor is similar to running by a predetermined reference or more, the control module E201 may determine that the user is running.

As another example, if the signal pattern measured by the acceleration sensor provided in the electronic device worn on the wrist is a pattern in which the user is not running but moves left or right, and the user's travel distance measured by the GPS sensor is a predetermined distance or more, the control module E201 may determine that the user's state is in a state of riding the bicycle. That is, the control module E201 may sense context information, such as location or travel speed, using the acceleration sensor or gyro sensor and may determine whether to display the horizontal UI or vertical UI on the screen using data outputted from the sensors. Further, the control module E201 may control the display to change the horizontal UI into the vertical UI or change the vertical UI into the horizontal UI and display the same using the data outputted from the sensors.

As an example, the user may desire UIs with different directions in the company or home, frequently visiting coffee shop, bus or subway. If the travel speed measured using the GPS sensor or positioning sensor included in the electronic device is a predetermined reference or more or the user is determined to stand still on a road, the control module E201 may determine that the user is on the move using a vehicle or public transportation. Further, the control module E201 may determine whether the user is driving a car using the acceleration sensor or gyro sensor.

According to an embodiment, the electronic device may determine whether the user is indoor or outdoor by receiving and measuring the sound around the user through an audio device, such as the microphone. For example, if there is high surrounding noise, the user is highly likely to be in a busy place, such as an outside place or to use the public transportation. If it is a bus or subway under such determination condition, the control module E201 may display letters in a smaller font or images in a reduced size when running an application, such as message, personal schedule, or diary. By doing so, the electronic device may reduce exposure of the user's privacy and protect the user's privacy. If the user is determined to be behind the wheel or be indoor alone, such as home or office under the determination condition, the control module E201 may control the display to enlarge and display the letters or image. Further, the control module E201 may analyze the location information of the electronic device, determine the location of the electronic device, i.e., whether the user is indoor or outdoor, and control the display to display the horizontal UI or vertical UI according to the result of determination.

According to another embodiment, in case the user puts more weight on readability, although the user is in a bus or subway, the control module E201 may enlarge and display the letter font or image when running an application, such as message, personal schedule, or diary.

When determining what space the user is located in, the control module E201 may use the illumination sensor, temperature sensor, or pressure sensor included in the electronic device. That is, the control module E201 may determine the space where the user is located using data outputted through the illumination sensor, temperature sensor, or pressure sensor. Further, the control module E201 may control the operation of the electronic device depending on the space where the user is located. For example, in case the illuminance is high, the control module E201 may determine that it is shiny outside, and the control module E201 may additionally adjust the screen brightness of the electronic device.

FIG. 205 is a view illustrating another example of a method of displaying content by an electronic device according to an embodiment.

Figures 205A, 205B:
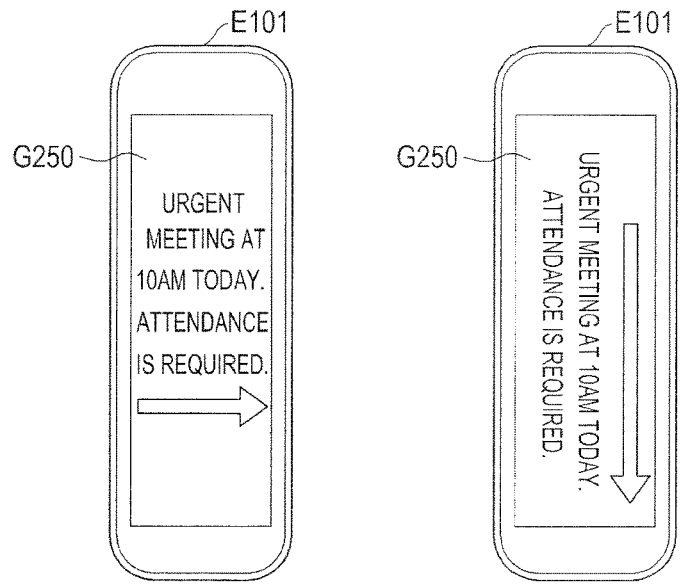

FIG. 205(a) shows the electronic device E101 running the horizontal writing mode and including the screen of the display where contents from the user are inputted in the horizontal direction (from left to right). The content G250 inputted through the screen of the display from the user in FIG. 205(a) is text saying "Urgent meeting at LOAM today. Attendance is required." According to an embodiment, the electronic device may support writing horizontally in the horizontal writing mode and may receive letters from the user in the horizontal direction.

FIG. 205(a) shows the electronic device E101 running the vertical writing mode and including the screen of the display where contents from the user are inputted in the vertical direction (from above to down). The content inputted through the display from the user in FIG. 205(b) is text saying "Urgent meeting at LOAM today. Attendance is required." According to an embodiment, the electronic device may support writing vertically in the vertical writing mode and may receive letters from the user in the vertical direction.

As described above, the electronic device may receive contents from the user as well as output contents in the horizontal or vertical direction of the display. According to an embodiment, the electronic device may receive contents (e.g., text or images) from the user through a virtual keypad or handwriting recognition. Further, the horizontal writing mode as shown in FIG. 205(a) and the vertical writing mode as shown in FIG. 205(b) may be performed in parallel. For example, contents may be displayed or inputted on an upper end of the display in the horizontal writing mode. Contents may be displayed or inputted on a lower end of the display in the vertical writing mode.

Figure 205C:
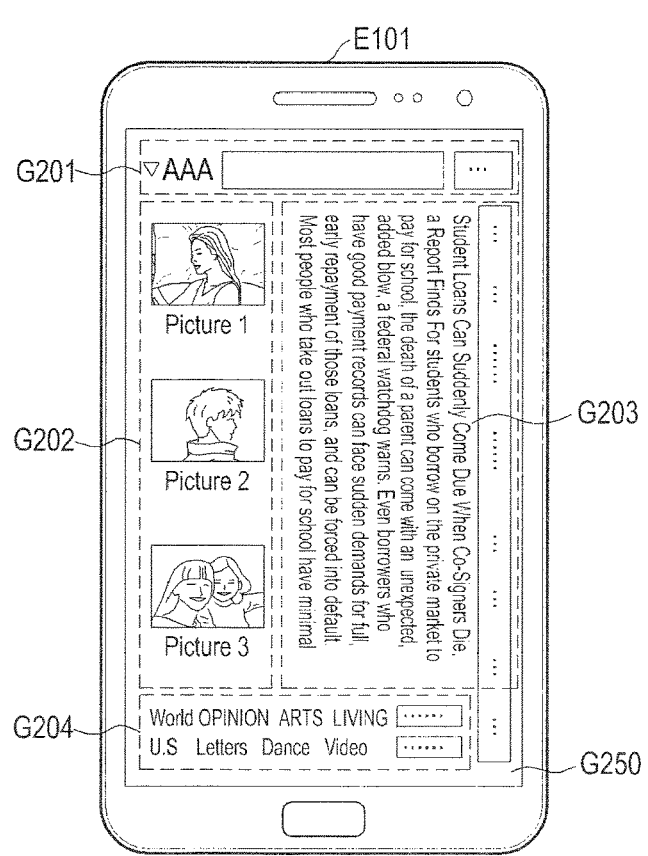

FIG. 205(c) shows the electronic device E101 outputting the content G250 in the horizontal and vertical direction through the display. Referring to FIG. 205(c), the electronic device E101 runs the horizontal writing mode for a portion of the display and the vertical writing mode for the rest of the display. Among the contents G201, G202, G203, and G204 displayed on the display, the first content G201, the second content G202, and the fourth content G204 are outputted in the horizontal direction (from left to right) according to the horizontal writing mode. Further, the third content G203 is outputted in the vertical direction (from above to down) according to the vertical writing mode. As shown in FIG. 205(c), the horizontal writing mode and the vertical writing mode may be performed in parallel on one screen, and this may apply to input of contents as well as output of contents.

According to an embodiment, in case of providing a screen image including various contents, such as a web browser screen, to the user, the horizontal area in the layout constituting the screen image, where the name of search engine (e.g., NAVER) and the search window are arranged, the vertical area where the body and pictures are arranged, and a lower horizontal area where other contents are arranged may have the contents arranged in the form of horizontal writing or vertical writing depending on the shape of the areas. According to an embodiment, the control module E201 may recognize the vertical mode or horizontal mode using the tilt information on the screen included in the display. The control module E201 may select the writing mode in which more information may be displayed of the horizontal writing and vertical writing using the tilt information or determine the shape of areas configuring the layout of the screen image, and control the display so that the contents are arranged in the corresponding area in the horizontal writing if the corresponding area is longer horizontally and are arranged in the corresponding area in the vertical writing if the corresponding area is longer vertically.

FIG. 206 is a view illustrating another example of a method of displaying content by an electronic device according to an embodiment.

Referring to FIG. 206, the electronic device may display content in a color requiring less power consumption or its similar color. According to an embodiment, the electronic device may display an edit window G302 to receive content from the user or display the edit window G302 for editing the content.

According to an embodiment, the control module E201 may adjust the font or color for saving electric current depending on the remaining battery and charged state. In case the electronic device is implemented as a wearable device or mobile device, the battery capability may be limited by the characteristics of the device. Accordingly, the control module E201 may control the operation of the electronic device to minimize power consumption due to running various operations of the electronic device.

For example, if the remaining battery of the electronic device is less than 30%, the control module E201 may configure the screen image so that the display including the screen may be driven only with smaller power in order to minimize the power consumption. For example, the control module E201 may configure the screen image in a color that may be implemented with less power and its close color. As an example, in case the screen is a LCD, the control module E201 may configure the background of the screen image in black. As an example, in case the screen is an OLED, the control module E201 may control some OLEDs to output the background in red and convert the shape or color of the remaining portion except for the background, e.g., images or text, into a form that may be easily noticeable to the user. Further, in case only a portion of the screen may light on, such as the OLED, the control module E201 may control the display so that only a portion of the screen may light on considering the characteristics of the OLED. For example, the control module E201 may control the display so that an area positioned off the user's view angle of the screen displaying the contents may light off.

According to an embodiment, the control module E201 may control the display including the screen displaying contents depending on the type of exercise. For example, the operation of determining whether the screen is at a position noticeable to the user's eyes or not during exercise may be more easily performed by determining the type of the exercise. For example, swimming has a unique movement pattern per swimming style, and thus, the control module E201, if a unique movement pattern is determined to occur as per the style, may determine that the user's exercise is swimming. As another example, for running outdoor, the control module E201 may determine that the exercise is running through arm movement information and travel distance.

According to an embodiment, the electronic device may previously receive the type of exercise from the user. The user may input the type of exercise to the electronic device before starting to exercise.

The control module E201 may obtain a unique pattern of the exercise through the information indicating the exercise, i.e., exercise information. Further, the control module E201 may obtain information on the direction and position where the electronic device is mounted using the user's body exercise range information. The control module E201 may grasp the user's view direction or view position information based on the direction or position of the electronic device. Further, the control module E201 may recognize or estimate the user's view direction or view position information along with the position and direction of the electronic device. The control module E201 may control the display or light off the screen so that information fitting the context, i.e., contents, may be displayed based on the user's view direction, view position information, and position and direction information of the electronic device.

In particular, in case the electronic device automatically recognizes the type of the user's exercise, the control module E201 may control the electronic device to provide the user with necessary information using the user's pose and the position and direction information of the electronic device. For example, the electronic device may provide the user with only information (e.g., coaching information or pose correction) necessary at necessary times. By contrast, if the time is determined to be not necessary for the user, the electronic device may reduce power consumption or display only common information by abstaining from displaying separate information.

FIG. 207 is a view illustrating an example of a method of displaying content by a plurality of electronic devices according to an embodiment. The electronic device E101 and the external electronic device E104, respectively, may be implemented as a host device and companion device, and the electronic device E101 and the external electronic device E104 may interwork with each other. It is assumed in FIG. 207 that the electronic device E101 which is the host device controls the external electronic device E104 which is the companion device.

Referring to FIG. 207, the external electronic device E104 which is the companion device is worn on a wrist of the user G401 and runs an exercise mode under the control of the electronic device E101. Since the external electronic device E104 is worn on the wrist of the user G401, the electronic device E101 may control the sensor module (not shown) of the external electronic device E104 to measure various bio signals of the user G401 (e.g., the blood pressure, blood flow, heart rate, body temperature, respiratory rate, oxygen saturation, heart-lung sound, or blood sugar of the user G401) or travel speed, travel acceleration, travel direction or slope of the external electronic device E104. The electronic device E101 may determine the direction of the display of the external electronic device E104 or the current state of the user G401 based on the sensor value measured through the sensor module of the external electronic device E104. The electronic device E101 may determine the content to be displayed on the display according to the direction of the display of the external electronic device E104 or the current state of the user G401. Further, the electronic device E101 may transmit the content to be displayed on the display of the external electronic device E104 to the external electronic device E104, and the external electronic device E104 may display the content received from the electronic device E101.

The electronic device E101 may sense that the user G401 is doing exercise through the sensor value measured by the sensor module of the external electronic device E104 and may change the electronic device E101 or external electronic device E104 into the exercise mode. If the exercise mode runs, the electronic device E101 or external electronic device E104 may display content by the exercise mode on the display 190.

It is assumed in FIG. 207 that the electronic device E101 determines that the user G401 is doing exercise based on the sensor value measured through the sensor module of the external electronic device E104. In FIG. 207, the control module E201 of the electronic device E101 switches the operation mode of the electronic device E101 and the external electronic device E104 both into the exercise mode. Accordingly, the type of exercise (running), calorie consumption (234 Kcal), travel distance (6.2 km), pulse rate (95), and exercise duration (00:28:30) are being displayed on the display of the external electronic device E104. Further, contents as per the exercise mode may also be displayed on the electronic device E101 which is the host device and is interworking with the external electronic device E104. Further, the operation mode (exercise mode) of the electronic device E101, calorie consumption (234 Kcal), travel distance (6.2 km), heart rate (95), and exercise duration (00:28:30) are being displayed on the display of the electronic device E101.

Here, the contents displayed on the display of the external electronic device E104 may be contents transmitted from the electronic device. Further, the external electronic device E104 may continuously measure bio signals of the user G401 using the sensor module under the control of the electronic device E101 and transfer sensor values measured by the sensor module to the electronic device E101.

Each of the aforementioned components of the electronic device may include one or more parts, and a name of the part may vary with a type of the electronic device. The electronic device in accordance with various embodiments of the present disclosure may include at least one of the aforementioned components, omit some of them, or include other additional component(s). Some of the components may be combined into an entity, but the entity may perform the same functions as the components may do.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of Application Specific Integrated Circuit (ASIC) chips, Field Programmable Gate Arrays (FPGAs), or Programmable Logic Arrays (PLAs) that perform some operations, which have already been known or will be developed in the future.

At least a part of the device (e.g., modules or their functions) or method (e.g., operations) may be implemented as instructions stored in a computer-readable storage medium e.g., in the form of a programming module. The instructions, when executed by one or more processor (e.g., the processor 120 or 210), may enable the processor to carry out a corresponding function. The computer-readable storage medium may be e.g., a memory (e.g., the memory 130). At least a part of the programming module may be implemented (e.g., run) by e.g., the processor 120. At least a part of the programming module may include e.g., a module, program, routine, set of instructions, process, or the like for performing one or more functions.

The computer-readable storage medium may include a hardware device configured to store and perform program instructions (e.g., programming module), such as magnetic media such as hard discs, floppy discs, and magnetic tapes, optical media such as compact disc read only memories (CD-ROMs) and digital versatile discs (DVDs), magneto-optical media such as floptical disks, read only memories (ROMs), random access memories (RAMs), flash memories, and/or the like. Examples of the program instructions may include not only machine language codes but also high-level language codes which are executable by various computing means using an interpreter. The aforementioned hardware devices may be configured to operate as one or more software modules to carry out exemplary embodiments of the present disclosure, and vice versa.

Modules or programming modules in accordance with various embodiments of the present disclosure may include at least one or more of the aforementioned components, omit some of them, or further include other additional components. Operations performed by modules, programming modules or other components in accordance with various embodiments of the present disclosure may be carried out sequentially, simultaneously, repeatedly, or heuristically. Furthermore, some of the operations may be performed in a different order, or omitted, or include other additional operation(s).

According to an embodiment, the terms "comprise" and/or "comprising" as herein used specify the presence of disclosed functions, operations, or components, but do not preclude the presence or addition of one or more other functions, operations, or components. It will be further understood that the terms "comprise" and/or "have," when used in this specification, specify the presence of stated features, integers, steps, operations, elements, and/or components, but do not preclude the presence or addition of one or more other features, integers, steps, operations, elements, components, and/or groups thereof.

As used herein, the term "and/or" includes any and all combinations of one or more of the associated listed items. For examples, "A or B" may include A, or include B, or include both A and B.

Ordinal numbers as herein used, such as "first", "second", etc., may modify various components of various embodiments, but do not limit those components. For example, these terms do not limit the order and/or importance of the components. These terms are only used to distinguish one component from another. For example, a first component may be denoted a second component, and vice versa without departing from the scope of the present disclosure.

While the inventive concept has been shown and described with reference to exemplary embodiments thereof, it will be apparent to those of ordinary skill in the art that various changes in form and detail may be made thereto without departing from the spirit and scope of the inventive concept as defined by the following claims.

The invention claimed is:

1. An electronic device, comprising:
   at least one sensor;
   at least one processor; and
   a memory connected with the at least one processor, wherein the memory stores instructions that, when executed by the at least one processor, cause the at least one processor to:
      identify a change in a state of the electronic device based on a preset condition,
      in response to the identifying of the change in the state of the electronic device based on the preset condition, obtain first bio information about a user via the at least one sensor,
      change a period of obtaining bio information via the at least one sensor based on a difference between the obtained first bio information and previous bio information,
      identify at least one service associated with the first bio information among a plurality of services supported by the electronic device, and
      provide the identified at least one service.

2. The electronic device of claim 1, wherein the first bio information includes at least one of the user's identification information, body information, emotion information, health information, disease information, exercise information, stress information, or sleep information.

3. The electronic device of claim 1, wherein the preset condition includes at least one of a movement of the electronic device according to a preset gesture, a location movement of the electronic device to a preset area, or a switch between a sleep state of the electronic device and a wakeup state.

4. The electronic device of claim 1, wherein the instructions further cause the at least one processor to obtain additional bio information about the user periodically according to the changed period.

5. The electronic device of claim 1, wherein the instructions further cause the at least one processor to:
   determine user association information associated with the first bio information among pre-stored user association information,
   wherein at least one service corresponding to the determined user association information and the first bio information is determined from among the plurality of services, and
   wherein the user association information includes at least one of information on the user, information on the electronic device, or information on an ambient environment of the electronic device.

6. The electronic device of claim 1, wherein the identified at least one service is at least one of varying a user interface, user authentication, exercise coaching, recommending information, providing information, restricting access to a preset content, function, or service, or varying a setting of the electronic device.

7. The electronic device of claim 1,
   wherein the first bio information includes the user's age, and
   wherein the identified at least one service changes a current user interface currently displayed into a user interface according to the user's age.

8. The electronic device of claim 1,
   wherein the first bio information includes the user's age, and
   wherein the identified at least one service includes at least one of changing a guidance voice of the electronic device, changing a voice volume, restricting access to a preset content or service, providing an alert feedback, or recommending information.

9. The electronic device of claim 1, wherein the instructions further cause the at least one processor to:
   compare the first bio information with a preset value, and
   output at least one alarm signal according to a difference between the first bio information and the preset value,
   wherein the at least one alarm signal is at least one of a visual signal, an audible signal, or a tactile signal.

10. The electronic device of claim 1, wherein the instructions further cause the at least one processor to:
   compare the first bio information with a preset value, and
   output at least one alarm signal according to a difference between the first bio information and the preset value, wherein if a difference between the first bio information and the preset value is larger than a threshold, a strength of the at least one alarm signal, type of the at least one alarm signal, count of outputting the at least one alarm signal, or period of obtaining the bio information increases.

11. The electronic device of claim 1, wherein the instructions further cause the at least one processor to:
obtain the user's movement or location information, and
authenticate the user based on the first bio information and the movement or location information.

12. The electronic device of claim 1, wherein the instructions further cause the at least one processor to:
obtain the user's current location, and
authenticate the user based on the first bio information and the current location.

13. The electronic device of claim 1, wherein the instructions further cause the at least one processor to:
obtain the user's exercise strength or activity type, and
authenticate the user based on the first bio information and one of the exercise strength and the activity type.

14. The electronic device of claim 1, wherein the instructions further cause the at least one processor to:
compare the first bio information with a preset first value to authenticate the user,
when a difference between the first bio information and the preset first value is not more than a threshold, obtain second bio information about the user different from the first bio information, and
compare the second bio information with a preset second value to authenticate the user.

15. The electronic device of claim 1, wherein the instructions further cause the at least one processor to:
detect an event,
authenticate the user based on the first bio information,
search a database stored in the electronic device or a first external device for an event identical to the detected event, and
control the electronic device, the first external device, or a second external device based on control information stored in the database corresponding to the searched event,
wherein the control information comprises at least one of an adjustment of a volume of the electronic device, the first external device or the second external device, varying a user interface, varying a brightness, or varying a channel.

16. The electronic device of claim 1, wherein the instructions further cause the at least one processor to:
detect an event,
authenticate the user based on the first bio information,
detect the user's control information associated with the event, and
store information on the event and the control information in a database of the electronic device or an external device.

17. The electronic device of claim 1, wherein the instructions further cause the at least one processor to:
compare the first bio information with a preset value,
obtain user association information according to a difference between the first bio information and the preset value, and
store the first bio information and the user association information in a database of the electronic device or an external device,
wherein the user association information includes at least one of an image, a video, an audio, a location, a time, or weather.

18. The electronic device of claim 1, wherein the instructions further cause the at least one processor to:
determine a category where the first bio information belongs among a plurality of preset categories, and
store information on the category and content being currently played in a database of the electronic device or an external device.

19. The electronic device of claim 1, wherein the instructions further cause the at least one processor to:
detect an event,
determine bio information corresponding to the detected event, and
determine at least one service corresponding to the determined bio information among the plurality of services supported by the electronic device.

20. The electronic device of claim 19, wherein the instructions further cause the at least one processor to:
search a database stored in the electronic device or an external device for an event identical to the detected event, and
determine that stored bio information stored in the database corresponding to the searched event is the bio information corresponding to the detected event.

21. The electronic device of claim 19, wherein the instructions further cause the at least one processor to:
determine control information of an external device corresponding to the determined bio information, and
transmit the control information through a transceiver to the external device.

22. The electronic device of claim 19, wherein the instructions further cause the at least one processor to:
search a database stored in the electronic device or external device for an area where the electronic device is located, and
determine that stored bio information stored in the database corresponding to the searched area is the bio information corresponding to the detected event.

* * * * *